United States Patent
Wang et al.

(10) Patent No.: US 11,591,355 B2
(45) Date of Patent: Feb. 28, 2023

(54) CD73 INHIBITORS AND USES THEREOF

(71) Applicant: Peloton Therapeutics, Inc., Kenilworth, NJ (US)

(72) Inventors: Bin Wang, Dallas, TX (US); Hanbiao Yang, San Diego, CA (US); Karl Bedke, Oceanside, CA (US); Paul Wehn, Dallas, TX (US); James P. Rizzi, Aurora, CO (US)

(73) Assignee: Peloton Therapeutics Inc., Kenilworth, NJ (US)

( * ) Notice: Subject to any disclaimer, the term of this patent is extended or adjusted under 35 U.S.C. 154(b) by 105 days.

(21) Appl. No.: 17/338,802

(22) Filed: Jun. 4, 2021

(65) Prior Publication Data

US 2021/0317150 A1 Oct. 14, 2021

Related U.S. Application Data

(62) Division of application No. 16/498,338, filed as application No. PCT/US2018/025079 on Mar. 29, 2018, now abandoned.

(60) Provisional application No. 62/648,625, filed on Mar. 27, 2018, provisional application No. 62/526,265, filed on Jun. 28, 2017, provisional application No. 62/480,093, filed on Mar. 31, 2017.

(51) Int. Cl.
*C07F 9/6561* (2006.01)

(52) U.S. Cl.
CPC ........ *C07F 9/65616* (2013.01); *C07F 9/6561* (2013.01)

(58) Field of Classification Search
CPC ..... C07H 19/23; C07H 19/167; C07F 9/6561; C07F 9/65616
See application file for complete search history.

(56) References Cited

U.S. PATENT DOCUMENTS

| | | | |
|---|---|---|---|
| 2010/0204182 A1 | 8/2010 | Mueller et al. | |
| 2017/0044202 A1* | 2/2017 | Ware | A61P 31/12 |
| 2020/0222441 A1* | 7/2020 | Debien | A61P 37/08 |

FOREIGN PATENT DOCUMENTS

| | | |
|---|---|---|
| WO | 2015164573 A1 | 10/2015 |
| WO | 2015177351 A1 | 11/2015 |
| WO | 2018067424 A1 | 4/2018 |
| WO | 2018208727 A1 | 11/2018 |
| WO | 2019090111 A1 | 5/2019 |

OTHER PUBLICATIONS

U.S. Appl. No. 16/498,338, filed Mar. 4, 2020.

* cited by examiner

*Primary Examiner* — Valerie Rodriguez-Garcia
(74) *Attorney, Agent, or Firm* — Eric A. Meade; John C. Todaro

(57) ABSTRACT

The present disclosure provides compounds of Formula (II)

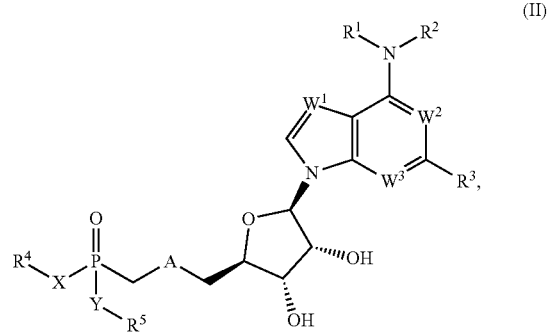

wherein $R^1$, $R^2$, $R^3$, $R^4$, $R^5$, $W^1$, $W^2$, $W^3$, X, Y, and A are as described herein. The disclosed compounds modulate CD73 activity. The present disclosure also provides, pharmaceutical compositions containing these compounds, and methods of using these compounds for treating diseases associated with CD73 activity.

25 Claims, No Drawings

CD73 INHIBITORS AND USES THEREOF

CROSS-REFERENCE

This application is a divisional of U.S. application Ser. No. 16/498,338, filed Sep. 26, 2019 which is the U.S. National Phase application of PCT/US2018/025079, filed Mar. 29, 2018, which claims the benefit of U.S. Provisional Application No. 62/480,093, filed Mar. 31, 2017; U.S. Provisional Application No. 62/526,265, filed Jun. 28, 2017; and U.S. Provisional Application No. 62/648,625, filed Mar. 27, 2018, each incorporated herein by reference in its entirety.

BACKGROUND OF THE INVENTION

The immune system plays a critical role in the identification and elimination of neoplastic cells. Tumor cells use various mechanisms for evading the immune-mediated destruction of tumor cells. Among those pathways, adenosine has been identified as a highly effective inhibitor of effector T cell function, and the enzyme CD73 (ecto-5'-nucleotidase, NT5E) has been identified as the enzyme responsible for generating adenosine.

As tumor cells undergo cell death as a result of metabolic or hypoxic stress, they release intracellular stores of ATP into the extracellular space. CD39 and CD73 are two ecto-enzymes that work together in a two-step reaction to convert pro-inflammatory ATP into immunosuppressive adenosine. CD39 hydrolyzes ATP into AMP, which is further hydrolyzed by CD73 into adenosine. Adenosine binds A2A receptors on T cells and activates an intracellular signaling cascade leading to the suppression of T cell activation and function. Activation of A2A receptors inhibits IFNg production, as well as cytotoxic killing by CD8+ cells, and also promotes the differentiation of CD4+ cells into T-regulatory cells (Jin, et al. (2010) Cancer Res. 70:2245-55). Adenosine can also inhibit differentiation and function of dendritic cells, as well as proliferation and cytolytic function of NK cells (Hoskin, et. al. (2008) Int J Oncol 32:527-35). Activation of A2A receptors on tumor cells has also been suggested to promote tumor cell metastasis (Beavis et al. (2013) Proc Natl Acad Sci USA 110:14711-14716).

CD73 is expressed primarily in endothelial cells and a subset of hematopoietic cells. CD73 expression has been observed in tumor cells in leukemia, bladder cancer, glioma, glioblastoma, lung cancer, ovarian cancer, melanoma, prostate cancer, thyroid cancer, esophageal cancer and breast cancer. CD73 expression in non-small-cell lung cancer and triple-negative breast cancer is a prognostic marker for lower survival rate (Inoue, et al. (2017) Oncotarget 5:8738-8751; and Loi, et al. (2013) Proc Natl Acad Sci USA 110:11091-11096). In the mouse, knock-down using siRNA or overexpression of CD73 on mouse tumor cells can modulate tumor growth and metastasis (Beavis et al. (2013) Proc Natl Acad Sci USA 110:14711-14716; Stagg et al. (2010) Cancer Res. 71:2892-2900; and Jin et al. (2010) Cancer Res. 70: 2245-55). CD73 plays a key role in promoting tumor growth in the tumor microenvironment, as CD73−/− mice are protected from transplanted and spontaneous tumors (Stagg et al. (2010) Cancer Res. 71:2892-2900). Inhibition of CD73 has been proposed as a therapeutic approach for the treatment of cancer, and antibodies to CD73 have been reported to inhibit tumor growth by restoring immune response to the tumors (Hay, et al. (2016) Oncoimmunology; 5 (8):e1208875).

SUMMARY OF THE INVENTION

A better understanding of the complex interactions between the immune system and tumors has allowed for the identification of key molecules that govern the tumor immune evasion. These findings have revitalized interest in cancer immunotherapeutics designed to overcome these checkpoint mechanisms. There is a need in the art for novel CD73 small molecule inhibitors. The present disclosure addresses this need by providing CD73 inhibitors as described herein.

In certain aspects, the present disclosure provides a compound of Formula (III):

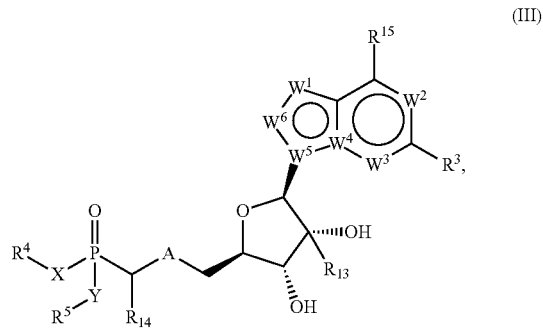

(III)

or a pharmaceutically acceptable salt thereof, wherein:

$W^1$ is selected from N, $NR^8$, $CR^6$, and S;

$W^2$ and $W^3$ are each independently selected from N and $CR^6$;

$W^4$ and $W^5$ are each independently selected from N and C;

$W^6$ is selected from N, $CR^6$, and S;

wherein at least one of $W^1$, $W^2$, $W^3$, $W^4$, $W^5$, and $W^6$ is N, and provided that:

when $W^1$, $W^2$, $W^3$, $W^5$, and $W^6$ are N, $W^4$ is not N; and when either $W^1$ or $W^6$ is S, the other is $CR^6$;

$R^{15}$ is selected from $-NR^1R^2$, $-OR^1$, $-SR^1$ and $-CN$; and $C_{3-12}$ membered carbocycle and 3- to 12-membered heterocycle, each of which is optionally substituted with one or more $R^7$;

$R^1$ is selected from hydrogen; and $C_{1-6}$ alkyl and $C_{3-12}$ carbocycle, each of which is optionally substituted with one or more $R^7$;

$R^2$ is selected from $C_{1-6}$ alkyl, $C_{3-12}$ carbocycle, 3- to 12-membered heterocycle and benzyl, each of which is optionally substituted with one or more $R^7$; or $R^1$ and $R^2$ are taken together with the nitrogen atom to which they are attached to form a 3- to 12-membered heterocycle, optionally substituted with one or more $R^7$;

$R^3$ is selected from hydrogen, halogen, cyano, $-N(R^8)_2$ and $-OR^1$; and $C_{1-6}$ alkyl, $C_{2-10}$ alkenyl, $C_{2-10}$ alkynyl, $C_{3-12}$ carbocycle, 3- to 12-membered heterocycle and benzyl, each of which is optionally substituted with one or more $R^7$;

A is selected from $-O-$, $-S-$, $-S(=O)-$ and $-S(=O)_2-$;

X and Y are independently selected from $-O-$ and $-NR^8-$;

$R^4$ and $R^5$ are independently selected from:

hydrogen; and $C_{1-6}$ alkyl, phenyl, and 3- to 12-membered heterocycle, each of which is independently optionally substituted at each occurrence with one or more substituents selected from halogen, —$NO_2$, —CN, —$OR^8$, —$SR^8$, —$N(R^8)_2$, —$NR^9R^{10}$, —$S(=O)R^8$, —$S(=O)_2R^8$, —$S(=O)_2N(R^8)_2$, —$S(=O)_2NR^9R^{10}$, —$NR^8S(=O)_2R^8$, —$NR^8S(=O)_2N(R^8)_2$, —$NR^8S(=O)_2NR^9R^{10}$, —S—S—$R^8$, —S—C(O)$R^8$, —C(O)$R^8$, —C(O)O$R^8$, —OC(O)$R^8$, —OC(O)O$R^8$, —OC(O)N($R^8$)$_2$, —OC(O)N$R^9R^{10}$, —N$R^8$C(O)$R^8$, —N$R^8$C(O)O$R^8$, —N$R^8$C(O)N($R^8$)$_2$, —N$R^8$C(O)N$R^9R^{10}$, —C(O)N($R^8$)$_2$, —C(O)N$R^9R^{10}$, —P(O)(O$R^8$)$_2$, —P(O)($R^8$)$_2$, —OP(O)(O$R^8$)$_2$, =O, =S, =N($R^8$), $C_{3-12}$ carbocycle, and 3- to 12-membered heterocycle; or $R^4$ and $R^5$ are taken together with the atoms to which they are attached to form a 3- to 12-membered heterocycle, optionally substituted with one or more $R^7$;

$R^6$ is selected from hydrogen, halogen and cyano; and $C_{1-6}$ alkyl, optionally substituted with one or more $R^7$;

$R^7$ is independently selected at each occurrence from:

halogen, —$NO_2$, —CN, —$OR^8$, —$SR^8$, —$N(R^8)_2$, —$NR^9R^{10}$, —$S(=O)R^8$, —$S(=O)_2R^8$, —$S(=O)_2N(R^8)_2$, —$S(=O)_2NR^9R^{10}$, —$NR^8S(=O)_2R^8$, —$NR^8S(=O)_2N(R^8)_2$, —$NR^8S(=O)_2NR^9R^{10}$, —C(O)$R^8$, —C(O)O$R^8$, —OC(O)$R^8$, —OC(O)O$R^8$, —OC(O)N($R^8$)$_2$, —OC(O)N$R^9R^{10}$, —N$R^8$C(O)$R^8$, —N$R^8$C(O)O$R^8$, —N$R^8$C(O)N($R^8$)$_2$, —N$R^8$C(O)N$R^9R^{10}$, —C(O)N($R^8$)$_2$, —C(O)N$R^9R^{10}$, —P(O)(O$R^8$)$_2$, —P(O)($R^8$)$_2$, =O, =S, and =N($R^8$);

$C_{1-10}$ alkyl, $C_{2-10}$ alkenyl, and $C_{2-10}$ alkynyl, each of which is independently optionally substituted at each occurrence with one or more substituents selected from halogen, —$NO_2$, —CN, —$OR^8$, —$SR^8$, —$N(R^8)_2$, —$NR^9R^{10}$, —$S(=O)R^8$, —$S(=O)_2R^8$, —$S(=O)_2N(R^8)_2$, —$S(=O)_2NR^9R^{10}$, —$NR^8S(=O)_2R^8$, —$NR^8S(=O)_2N(R^8)_2$, —$NR^8S(=O)_2NR^9R^{10}$, —C(O)$R^8$, —C(O)O$R^8$, —OC(O)$R^8$, —OC(O)O$R^8$, —OC(O)N($R^8$)$_2$, —OC(O)N$R^9R^{10}$, —N$R^8$C(O)$R^8$, —N$R^8$C(O)O$R^8$, —N$R^8$C(O)N($R^8$)$_2$, —N$R^8$C(O)N$R^9R^{10}$, —C(O)N($R^8$)$_2$, —C(O)N$R^9R^{10}$, —P(O)(O$R^8$)$_2$, —P(O)($R^8$)$_2$, =O, =S, =N($R^8$), $C_{3-12}$ carbocycle, and 3- to 12-membered heterocycle; and $C_{3-12}$ carbocycle and 3- to 12-membered heterocycle, wherein each $C_{3-12}$ carbocycle and 3- to 12-membered heterocycle in $R^7$ is independently optionally substituted with one or more substituents selected from halogen, —$NO_2$, —CN, —$OR^8$, —$SR^8$, —$N(R^8)_2$, —$NR^9R^{10}$, —$S(=O)R^8$, —$S(=O)_2R^8$, —$S(=O)_2N(R^8)_2$, —$S(=O)_2NR^9R^{10}$, —$NR^8S(=O)_2R^8$, —$NR^8S(=O)_2N(R^8)_2$, —$NR^8S(=O)_2NR^9R^{10}$, —C(O)$R^8$, —C(O)O$R^8$, —OC(O)$R^8$, —OC(O)O$R^8$, —OC(O)N($R^8$)$_2$, —OC(O)N$R^9R^{10}$, —N$R^8$C(O)$R^8$, —N$R^8$C(O)O$R^8$, —N$R^8$C(O)N($R^8$)$_2$, —N$R^8$C(O)N$R^9R^{10}$, —C(O)N($R^8$)$_2$, —C(O)N$R^9R^{10}$, —P(O)(O$R^8$)$_2$, —P(O)($R^8$)$_2$, =O, =S, =N($R^8$), $C_{1-6}$ alkyl, $C_{1-6}$ haloalkyl, $C_{2-6}$ alkenyl, and $C_{2-6}$ alkynyl;

$R^8$ is independently selected at each occurrence from hydrogen; and $C_{1-20}$ alkyl, $C_{2-20}$ alkenyl, $C_{2-20}$ alkynyl, 1- to 6-membered heteroalkyl, $C_{3-12}$ carbocycle, and 3- to 12-membered heterocycle, each of which is optionally substituted by halogen, —CN, —$NO_2$, —$NH_2$, —$NHCH_3$, —$NHCH_2CH_3$, =O, —OH, —$OCH_3$, —$OCH_2CH_3$, $C_{3-12}$ carbocycle, or 3- to 6-membered heterocycle;

$R^9$ and $R^{10}$ are taken together with the nitrogen atom to which they are attached to form a heterocycle, optionally substituted with one or more $R^7$;

$R^{13}$ is selected from hydrogen and $C_{1-6}$ alkyl; and $R^{14}$ is selected from hydrogen and $R^7$.

In some embodiments, for a compound of Formula (III), $W^5$ is N. In some embodiments, $W^5$ is C. In some embodiments, one of $W^1$ or $W^6$ is S. In some embodiments, $W^4$ is N. In some embodiments, $R^{13}$ is hydrogen. In some embodiments, $R^{14}$ is selected from hydrogen and phenyl. In some embodiments, $R^{15}$ is —$NR^1R^2$. In some embodiments, A is —O—. In some embodiments, A is selected from —S—, —S(=O)— and —S(=O)$_2$—.

In certain aspects, the present disclosure provides a compound of Formula (II):

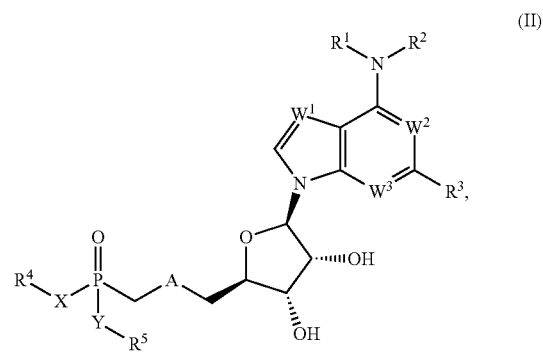

(II)

or a pharmaceutically acceptable salt thereof, wherein:

$W^1$, $W^2$ and $W^3$ are each independently selected from N and $CR^6$, wherein at least one of $W^1$, $W^2$ and $W^3$ is N;

$R^1$ is selected from hydrogen; and $C_{1-6}$ alkyl and $C_{3-12}$ carbocycle, each of which is optionally substituted with one or more $R^7$;

$R^2$ is selected from $C_{1-6}$ alkyl, $C_{3-12}$ carbocycle, 3- to 12-membered heterocycle and benzyl, each of which is optionally substituted with one or more $R^7$; or $R^1$ and $R^2$ are taken together with the nitrogen atom to which they are attached to form a 3- to 12-membered heterocycle, optionally substituted with one or more $R^7$;

$R^3$ is selected from hydrogen, halogen and cyano; and $C_{1-6}$ alkyl, $C_{3-12}$ carbocycle, 3- to 12-membered heterocycle and benzyl, each of which is optionally substituted with one or more $R^7$;

A is selected from —S—, —S(=O)— and —S(=O)$_2$—;

X and Y are independently selected from —O— and —$NR^8$—;

$R^4$ and $R^5$ are independently selected from:

hydrogen; and $C_{1-6}$ alkyl and phenyl, each of which is independently optionally substituted at each occurrence with one or more substituents selected from halogen, —$NO_2$, —CN, —$OR^8$, —$SR^8$, —$N(R^8)_2$, —$NR^9R^{10}$, —$S(=O)R^8$, —$S(=O)_2R^8$, —$S(=O)_2N(R^8)_2$, —$S(=O)_2NR^9R^{10}$, —$NR^8S(=O)_2R^8$, —$NR^8S(=O)_2N(R^8)_2$, —$NR^8S(=O)_2NR^9R^{10}$, —S—S—$R^8$, —S—C(O)$R^8$, —C(O)$R^8$, —C(O)O$R^8$, —OC(O)$R^8$, —OC(O)O$R^8$, —OC(O)N($R^8$)$_2$, —OC(O)N$R^9R^{10}$, —N$R^8$C(O)$R^8$, —N$R^8$C(O)O$R^8$, —N$R^8$C(O)N($R^8$)$_2$, —N$R^8$C(O)N$R^9R^{10}$, —C(O)N($R^8$)$_2$, —C(O)N$R^9R^{10}$, —P(O)(O$R^8$)$_2$, —P(O)($R^8$)$_2$, —OP(O)(O$R^8$)$_2$, =O, =S, =N($R^8$), $C_{3-12}$ carbocycle, and 3- to 12-membered heterocycle;

$R^6$ is selected from hydrogen, halogen and cyano; and $C_{1-6}$ alkyl, optionally substituted with one or more $R^7$;

R⁷ is independently selected at each occurrence from:
halogen, —NO₂, —CN, —OR⁸, —SR⁸, —N(R⁸)₂, —NR⁹R¹⁰, —S(=O)R⁸, —S(=O)₂R⁸, —S(=O)₂N(R⁸)₂, —S(=O)₂NR⁹R¹⁰, —NR⁸S(=O)₂R⁸, —NR⁸S(=O)₂N(R⁸)₂, —NR⁸S(=O)₂NR⁹R¹⁰, —C(O)R⁸, —C(O)OR⁸, —OC(O)R⁸, —OC(O)OR⁸, —OC(O)N(R⁸)₂, —OC(O)NR⁹R¹⁰, —NR⁸C(O)R⁸, —NR⁸C(O)OR⁸, —NR⁸C(O)N(R⁸)₂, —NR⁸C(O)NR⁹R¹⁰, —C(O)N(R⁸)₂, —C(O)NR⁹R¹⁰, —P(O)(OR⁸)₂, —P(O)(R⁸)₂, =O, =S, and =N(R⁸);

C₁₋₁₀ alkyl, C₂₋₁₀ alkenyl, and C₂₋₁₀ alkynyl, each of which is independently optionally substituted at each occurrence with one or more substituents selected from halogen, —NO₂, —CN, —OR⁸, —SR⁸, —N(R⁸)₂, —NR⁹R¹⁰, —S(=O)R⁸, —S(=O)₂R⁸, —S(=O)₂N(R⁸)₂, —S(=O)₂NR⁹R¹⁰, —NR⁸S(=O)₂R⁸, —NR⁸S(=O)₂N(R⁸)₂, —NR⁸S(=O)₂NR⁹R¹⁰, —C(O)R⁸, —C(O)OR⁸, —OC(O)R⁸, —OC(O)OR⁸, —OC(O)N(R⁸)₂, —OC(O)NR⁹R¹⁰, —NR⁸C(O)R⁸, —NR⁸C(O)OR⁸, —NR⁸C(O)N(R⁸)₂, —NR⁸C(O)NR⁹R¹⁰, —C(O)N(R⁸)₂, —C(O)NR⁹R¹⁰, —P(O)(OR⁸)₂, —P(O)(R⁸)₂, =O, =S, =N(R⁸), $C_{3-12}$ carbocycle, and 3- to 12-membered heterocycle; and $C_{3-12}$ carbocycle and 3- to 12-membered heterocycle, wherein each $C_{3-12}$ carbocycle and 3- to 12-membered heterocycle in R⁷ is independently optionally substituted with one or more substituents selected from halogen, —NO₂, —CN, —OR⁸, —SR⁸, —N(R⁸)₂, —NR⁹R¹⁰, —S(=O)R⁸, —S(=O)₂R⁸, —S(=O)₂N(R⁸)₂, —S(=O)₂NR⁹R¹⁰, —NR⁸S(=O)₂R⁸, —NR⁸S(=O)₂N(R⁸)₂, —NR⁸S(=O)₂NR⁹R¹⁰, —C(O)R⁸, —C(O)OR⁸, —OC(O)R⁸, —OC(O)OR⁸, —OC(O)N(R⁸)₂, —OC(O)NR⁹R¹⁰, —NR⁸C(O)R⁸, —NR⁸C(O)OR⁸, —NR⁸C(O)N(R⁸)₂, —NR⁸C(O)NR⁹R¹⁰, —C(O)N(R⁸)₂, —C(O)NR⁹R¹⁰, —P(O)(OR⁸)₂, —P(O)(R⁸)₂, =O, =S, =N(R⁸), $C_{1-6}$ alkyl, $C_{1-6}$ haloalkyl, $C_{2-6}$ alkenyl, and $C_{2-6}$ alkynyl;

R⁸ is independently selected at each occurrence from hydrogen; and $C_{1-20}$ alkyl, $C_{2-20}$ alkenyl, $C_{2-20}$ alkynyl, 1- to 6-membered heteroalkyl, $C_{3-12}$ carbocycle, and 3- to 12-membered heterocycle, each of which is optionally substituted by halogen, —CN, —NO₂, —NH₂, —NHCH₃, —NHCH₂CH₃, =O, —OH, —OCH₃, —OCH₂CH₃, $C_{3-12}$ carbocycle, or 3- to 6-membered heterocycle; and R⁹ and R¹⁰ are taken together with the nitrogen atom to which they are attached to form a heterocycle, optionally substituted with one or more R⁷.

In certain aspects, the present disclosure provides a compound of Formula (I):

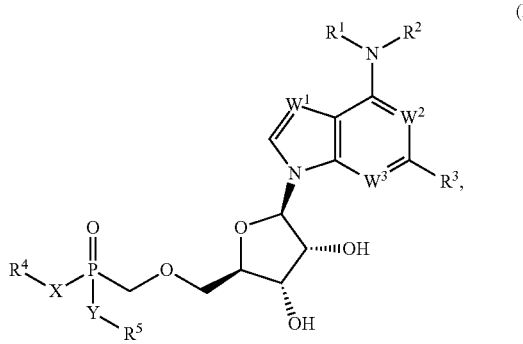

(I)

or a pharmaceutically acceptable salt thereof, wherein:
W¹, W² and W³ are each independently selected from N and CR⁶, wherein at least one of W¹, W² and W³ is N;

R¹ is selected from hydrogen; and $C_{1-6}$ alkyl and $C_{3-12}$ carbocycle, each of which is optionally substituted with one or more R⁷;

R² is selected from $C_{1-6}$ alkyl, $C_{3-12}$ carbocycle, 3- to 12-membered heterocycle and benzyl, each of which is optionally substituted with one or more R⁷; or R¹ and R² are taken together with the nitrogen atom to which they are attached to form a 3- to 12-membered heterocycle, optionally substituted with one or more R⁷;

R³ is selected from halogen and cyano; and $C_{1-6}$ alkyl, $C_{3-12}$ carbocycle, 3- to 12-membered heterocycle and benzyl, each of which is optionally substituted with one or more R⁷;

X and Y are independently selected from —O— and —NR⁸—;

R⁴ and R⁵ are independently selected from:
hydrogen; and
$C_{1-6}$ alkyl and phenyl, each of which is independently optionally substituted at each occurrence with one or more substituents selected from halogen, —NO₂, —CN, —OR⁸, —SR⁸, —N(R⁸)₂, —NR⁹R¹⁰, —S(=O)R⁸, —S(=O)₂R⁸, —S(=O)₂N(R⁸)₂, —S(=O)₂NR⁹R¹⁰, —NR⁸S(=O)₂R⁸, —NR⁸S(=O)₂N(R⁸)₂, —NR⁸S(=O)₂NR⁹R¹⁰, —S—S—R⁸, —S—C(O)R⁸, —C(O)R⁸, —C(O)OR⁸, —OC(O)R⁸, —OC(O)OR⁸, —OC(O)N(R⁸)₂, —OC(O)NR⁹R¹⁰, —NR⁸C(O)R⁸, —NR⁸C(O)OR⁸, —NR⁸C(O)N(R⁸)₂, —NR⁸C(O)NR⁹R¹⁰, —C(O)N(R⁸)₂, —C(O)NR⁹R¹⁰, —P(O)(OR⁸)₂, —P(O)(R⁸)₂, —OP(O)(OR⁸)₂, =O, =S, =N(R⁸), $C_{3-12}$ carbocycle, and 3- to 12-membered heterocycle;

R⁶ is selected from hydrogen, halogen and cyano; and $C_{1-6}$ alkyl, optionally substituted with one or more R⁷;

R⁷ is independently selected at each occurrence from:
halogen, —NO₂, —CN, —OR⁸, —SR⁸, —N(R⁸)₂, —NR⁹R¹⁰, —S(=O)R⁸, —S(=O)₂R⁸, —S(=O)₂N(R⁸)₂, —S(=O)₂NR⁹R¹⁰, —NR⁸S(=O)₂R⁸, —NR⁸S(=O)₂N(R⁸)₂, —NR⁸S(=O)₂NR⁹R¹⁰, —C(O)R⁸, —C(O)OR⁸, —OC(O)R⁸, —OC(O)OR⁸, —OC(O)N(R⁸)₂, —OC(O)NR⁹R¹⁰, —NR⁸C(O)R⁸, —NR⁸C(O)OR⁸, —NR⁸C(O)N(R⁸)₂, —NR⁸C(O)NR⁹R¹⁰, —C(O)N(R⁸)₂, —C(O)NR⁹R¹⁰, —P(O)(OR⁸)₂, —P(O)(R⁸)₂, =O, =S, and =N(R⁸);

C₁₋₁₀ alkyl, C₂₋₁₀ alkenyl, and C₂₋₁₀ alkynyl, each of which is independently optionally substituted at each occurrence with one or more substituents selected from halogen, —NO₂, —CN, —OR⁸, —SR⁸, —N(R⁸)₂, —NR⁹R¹⁰, —S(=O)R⁸, —S(=O)₂R⁸, —S(=O)₂N(R⁸)₂, —S(=O)₂NR⁹R¹⁰, —NR⁸S(=O)₂R⁸, —NR⁸S(=O)₂N(R⁸)₂, —NR⁸S(=O)₂NR⁹R¹⁰, —C(O)R⁸, —C(O)OR⁸, —OC(O)R⁸, —OC(O)OR⁸, —OC(O)N(R⁸)₂, —OC(O)NR⁹R¹⁰, —NR⁸C(O)R⁸, —NR⁸C(O)OR⁸, —NR⁸C(O)N(R⁸)₂, —NR⁸C(O)NR⁹R¹⁰, —C(O)N(R⁸)₂, —C(O)NR⁹R¹⁰, —P(O)(OR⁸)₂, —P(O)(R⁸)₂, =O, =S, =N(R⁸), $C_{3-12}$ carbocycle, and 3- to 12-membered heterocycle; and $C_{3-12}$ carbocycle and 3- to 12-membered heterocycle, wherein each $C_{3-12}$ carbocycle and 3- to 12-membered heterocycle in R⁷ is independently optionally substituted with one or more substituents selected from halogen, —NO₂, —CN, —OR⁸, —SR⁸, —N(R⁸)₂, —NR⁹R¹⁰, —S(=O)R⁸, —S(=O)₂R⁸, —S(=O)₂N(R⁸)₂, —S(=O)₂NR⁹R¹⁰, —NR⁸S(=O)₂R⁸, —NR⁸S(=O)₂N(R⁸)₂, —NR⁸S(=O)₂NR⁹R¹⁰, —C(O)R⁸, —C(O)OR⁸, —OC(O)R⁸, —OC(O)OR⁸, —OC(O)N(R⁸)₂, —OC(O)NR⁹R¹⁰, —NR⁸C(O)R⁸, —NR⁸C(O)OR⁸, —NR⁸C(O)N(R⁸)₂, —NR⁸C(O)NR⁹R¹⁰, —C(O)N(R⁸)₂, —C(O)NR⁹R¹⁰, —P(O)(OR⁸)₂, —P(O)(R⁸)₂, =O, =S, =N(R⁸), $C_{1-6}$ alkyl, $C_{1-6}$ haloalkyl, $C_{2-6}$ alkenyl, and $C_{2-6}$ alkynyl;

R⁸ is independently selected at each occurrence from hydrogen; and $C_{1-20}$ alkyl, $C_{2-20}$ alkenyl, $C_{2-20}$ alkynyl, 1- to 6-membered heteroalkyl, C$_{3-12}$ carbocycle, and 3- to 12-membered heterocycle, each of which is optionally substituted by halogen, —CN, —NO$_2$, —NH$_2$, —NHCH$_3$, —NHCH$_2$CH$_3$, =O, —OH, —OCH$_3$, —OCH$_2$CH$_3$, C$_{3-12}$ carbocycle, or 3- to 6-membered heterocycle; and R$^9$ and R$^{10}$ are taken together with the nitrogen atom to which they are attached to form a heterocycle, optionally substituted with one or more R$^7$.

In some embodiments, for a compound of Formula (I), (II) or (III), R$^1$ and R$^2$ are taken together with the nitrogen atom to which they are attached to form a 3- to 12-membered heterocycle, optionally substituted with one or more R$^7$. In some embodiments, R$^1$ and R$^2$ are taken together with the nitrogen atom to which they are attached to form a 3- to 12-membered heterocycle, optionally substituted with one or more substituents independently selected from halogen, —CN, C$_{1-4}$ alkyl, C$_{1-3}$ haloalkyl, —OH and —NH$_2$. In some embodiments, R$^1$ and R$^2$ are taken together with the nitrogen atom to which they are attached to form optionally substituted 3- to 7-membered monocyclic heterocycloalkyl or optionally substituted 5- to 12-membered fused bicyclic heterocycloalkyl.

In some embodiments, for a compound of Formula (I), (II) or (III), R$^2$ is selected from C$_{1-6}$ alkyl, C$_{3-12}$ carbocycle, 3- to 12-membered heterocycle and benzyl, each of which is optionally substituted with one or more substituents independently selected from halogen, —CN, C$_{1-4}$ alkyl, C$_{1-3}$ haloalkyl, —OH and —NH$_2$. In some embodiments, R$^2$ is benzyl, optionally substituted with one or more R$^7$. In some embodiments, R$^2$ is benzyl, optionally substituted with one or more substituents independently selected from halogen, —CN, C$_{1-4}$ alkyl, C$_{1-3}$ haloalkyl, —OH and —NH$_2$.

In certain aspects, the present disclosure provides a compound of Formula (III-A) or (III-B):

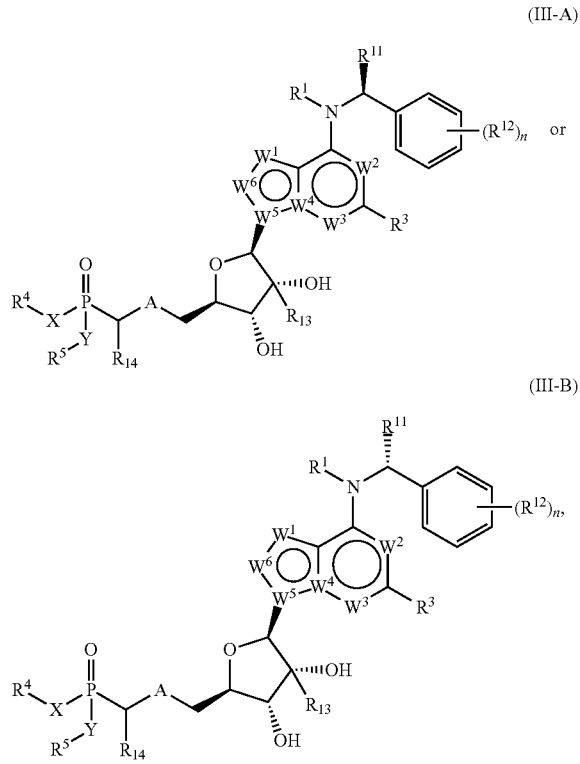

or a pharmaceutically acceptable salt thereof, wherein:
W$^1$ is selected from N, NR$^8$, CR$^6$, and S;
W$^2$ and W$^3$ are each independently selected from N and CR$^6$;
W$^4$ and W$^5$ are each independently selected from N and C;
W$^6$ is selected from N, CR$^6$, and S;
wherein at least one of W$^1$, W$^2$, W$^3$, W$^4$, W$^5$, and W$^6$ is N, and provided that: when W$^1$, W$^2$, W$^3$, W$^5$, and W$^6$ are N, W$^4$ is not N; and
when either W$^1$ or W$^6$ is S, the other is CR$^6$;
R$^1$ is selected from hydrogen; and C$_{1-6}$ alkyl and C$_{3-12}$ carbocycle, each of which is optionally substituted with one or more R$^7$;
R$^3$ is selected from hydrogen, halogen, cyano, —N(R$^8$)$_2$ and —OR$^8$; and C$_{1-6}$ alkyl, C$_{2-10}$ alkenyl, C$_{2-10}$ alkynyl, C$_{3-12}$ carbocycle, 3- to 12-membered heterocycle and benzyl, each of which is optionally substituted with one or more R$^7$;
A is selected from —O—, —S—, —S(=O)— and —S(=O)$_2$—;
X and Y are independently selected from —O— and —NR$^8$—;
R$^4$ and R$^5$ are independently selected from:
hydrogen; and
C$_{1-6}$ alkyl, phenyl, and 3- to 12-membered heterocycle, each of which is independently optionally substituted at each occurrence with one or more substituents selected from halogen, —NO$_2$, —CN, —OR$^8$, —SR$^8$, —N(R$^8$)$_2$, —NR$^9$R$^{10}$, —S(=O)R$^8$, —S(=O)$_2$R$^8$, —S(=O)$_2$N(R$^8$)$_2$, —S(=O)$_2$NR$^9$R$^{10}$, —NR$^8$S(=O)$_2$R$^8$, —NR$^8$S(=O)$_2$N(R$^8$)$_2$, —NR$^8$S(=O)$_2$NR$^9$R$^{10}$, —S—S—R$^8$, —S—C(O)R$^8$, —C(O)R$^8$, —C(O)OR$^8$, —OC(O)R$^8$, —OC(O)OR$^8$, —OC(O)N(R$^8$)$_2$, —OC(O)NR$^9$R$^{10}$, —NR$^8$C(O)R$^8$, —NR$^8$C(O)OR$^8$, —NR$^8$C(O)N(R$^8$)$_2$, —NR$^8$C(O)NR$^9$R$^{10}$, —C(O)N(R$^8$)$_2$, —C(O)NR$^9$R$^{10}$, —P(O)(OR$^8$)$_2$, —P(O)(R$^8$)$_2$, —OP(O)(OR$^8$)$_2$, =O, =S, =N(R$^8$), C$_{3-12}$ carbocycle, and 3- to 12-membered heterocycle; or
R$^4$ and R$^5$ are taken together with the atoms to which they are attached to form a 3- to 12-membered heterocycle, optionally substituted with one or more R$^7$;
R$^6$ is selected from hydrogen, halogen and cyano; and C$_{1-6}$ alkyl, optionally substituted with one or more R$^7$;
R$^7$ is independently selected at each occurrence from:
halogen, —NO$_2$, —CN, —OR$^8$, —SR$^8$, —N(R$^8$)$_2$, —NR$^9$R$^{10}$, —S(=O)R$^8$, —S(=O)$_2$R$^8$, —S(=O)$_2$N(R$^8$)$_2$, —S(=O)$_2$NR$^9$R$^{10}$, —NR$^8$S(=O)$_2$R$^8$, —NR$^8$S(=O)$_2$N(R$^8$)$_2$, —NR$^8$S(=O)$_2$NR$^9$R$^{10}$, —C(O)R$^8$, —C(O)OR$^8$, —OC(O)R$^8$, —OC(O)OR$^8$, —OC(O)N(R$^8$)$_2$, —OC(O)NR$^9$R$^{10}$, —NR$^8$C(O)R$^8$, —NR$^8$C(O)OR$^8$, —NR$^8$C(O)N(R$^8$)$_2$, —NR$^8$C(O)NR$^9$R$^{10}$, —C(O)N(R$^8$)$_2$, —C(O)NR$^9$R$^{10}$, —P(O)(OR$^8$)$_2$, —P(O)(R$^8$)$_2$, =O, =S, and =N(R$^8$);
C$_{1-10}$ alkyl, C$_{2-10}$ alkenyl, and C$_{2-10}$ alkynyl, each of which is independently optionally substituted at each occurrence with one or more substituents selected from halogen, —NO$_2$, —CN, —OR$^8$, —SR$^8$, —N(R$^8$)$_2$, —NR$^9$R$^{10}$, —S(=O)R$^8$, —S(=O)$_2$R$^8$, —S(=O)$_2$N(R$^8$)$_2$, —S(=O)$_2$NR$^9$R$^{10}$, —NR$^3$S(=O)$_2$R$^8$, —NR$^8$S(=O)$_2$N(R$^8$)$_2$, —NR$^8$S(=O)$_2$NR$^9$R$^{10}$, —C(O)R$^8$, —C(O)OR$^8$, —OC(O)R$^8$, —OC(O)OR$^8$, —OC(O)N(R$^8$)$_2$, —OC(O)NR$^9$R$^{10}$, —NR$^8$C(O)R$^8$, —NR$^8$C(O)OR$^8$, —NR$^8$C(O)N(R$^8$)$_2$, —NR$^8$C(O)NR$^9$R$^{10}$, —C(O)N(R$^8$)$_2$, —C(O)NR$^9$R$^{10}$, —P(O)(OR$^8$)$_2$, —P(O)(R$^8$)$_2$, =O, =S, =N(R$^8$), C$_{3-12}$ carbocycle, and 3- to 12-membered heterocycle; and
C$_{3-12}$ carbocycle and 3- to 12-membered heterocycle, wherein each C$_{3-12}$ carbocycle and 3- to 12-membered heterocycle in R$^7$ is independently optionally substituted with one or more substituents selected from halogen, —NO$_2$, —CN, —OR$^8$, —SR$^8$, —N(R$^8$)$_2$, —NR⁹R¹⁰, —S(=O)R⁸, —S(=O)₂R⁸, —S(=O)₂N(R⁸)₂, —S(=O)₂NR⁹R¹⁰, —NR⁸S(=O)₂R⁸, —NR⁸S(=O)₂N(R⁸)₂, —NR⁸S(=O)₂NR⁹R¹⁰, —C(O)R⁸, —C(O)OR⁸, —OC(O)R⁸, —OC(O)OR⁸, —OC(O)N(R⁸)₂, —OC(O)NR⁹R¹⁰, —NR⁸C(O)R⁸, —NR⁸C(O)OR⁸, —NR⁸C(O)N(R⁸)₂, —NR⁸C(O)NR⁹R¹⁰, —C(O)N(R⁸)₂, —C(O)NR⁹R¹⁰, —P(O)(OR⁸)₂, —P(O)(R⁸)₂, =O, =S, =N(R⁸), C₁₋₆ alkyl, C₁₋₆ haloalkyl, C₂₋₆ alkenyl, and C₂₋₆ alkynyl;

R⁸ is independently selected at each occurrence from hydrogen; and C₁₋₂₀ alkyl, C₂₋₂₀ alkenyl, C₂₋₂₀ alkynyl, 1- to 6-membered heteroalkyl, C₃₋₁₂ carbocycle, and 3- to 12-membered heterocycle, each of which is optionally substituted by halogen, —CN, —NO₂, —NH₂, —NHCH₃, —NHCH₂CH₃, =O, —OH, —OCH₃, —OCH₂CH₃, C₃₋₁₂ carbocycle, or 3- to 6-membered heterocycle;

R⁹ and R¹⁰ are taken together with the nitrogen atom to which they are attached to form a heterocycle, optionally substituted with one or more R⁷;

R¹³ is selected from hydrogen and C₁₋₆ alkyl;

R¹⁴ is selected from hydrogen and R⁷;

R¹¹ is selected from C₁₋₆ alkyl and C₃₋₁₂ carbocycle, each of which is optionally substituted with one or more R⁷;

R¹² is independently selected at each occurrence from R⁷; and n is an integer from 0 to 3.

In certain aspects, the present disclosure provides a compound of Formula (II-A) or (II-B):

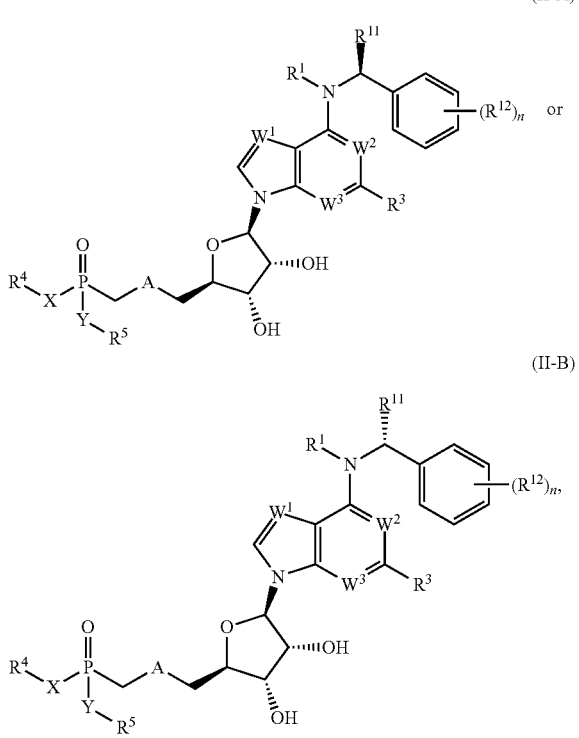

(II-A)

(II-B)

or a pharmaceutically acceptable salt thereof, wherein:
W¹, W² and W³ are each independently selected from N and CR⁶, wherein at least one of W¹, W² and W³ is N;
R¹ is selected from hydrogen; and C₁₋₆ alkyl and C₃₋₁₂ carbocycle, each of which is optionally substituted with one or more R⁷;

R³ is selected from hydrogen, halogen and cyano; and C₁₋₆ alkyl, C₃₋₁₂ carbocycle, 3- to 12-membered heterocycle and benzyl, each of which is optionally substituted with one or more R⁷;

A is selected from —S—, —S(=O)— and —S(=O)₂—;
X and Y are independently selected from —O— and —NR⁸—;
R⁴ and R⁵ are independently selected from:
hydrogen; and
C₁₋₆ alkyl and phenyl, each of which is independently optionally substituted at each occurrence with one or more substituents selected from halogen, —NO₂, —CN, —OR⁸, —SR⁸, —N(R⁸)₂, —NR⁹R¹⁰, —S(=O)R⁸, —S(=O)₂R⁸, —S(=O)₂N(R⁸)₂, —S(=O)₂NR⁹R¹⁰, —NR⁸S(=O)₂R⁸, —NR⁸S(=O)₂N(R⁸)₂, —NR⁸S(=O)₂NR⁹R¹⁰, —S—S—R⁸, —S—C(O)R⁸, —C(O)R⁸, —C(O)OR⁸, —OC(O)R⁸, —OC(O)OR⁸, —OC(O)N(R⁸)₂, —OC(O)NR⁹R¹⁰, —NR⁸C(O)R⁸, —NR⁸C(O)OR⁸, —NR⁸C(O)N(R⁸)₂, —NR⁸C(O)NR⁹R¹⁰, —C(O)N(R⁸)₂, —C(O)NR⁹R¹⁰, —P(O)(OR⁸)₂, —P(O)(R⁸)₂, —OP(O)(OR⁸)₂, =O, =S, =N(R⁸), C₃₋₁₂ carbocycle, and 3- to 12-membered heterocycle;

R⁶ is selected from hydrogen, halogen and cyano; and C₁₋₆ alkyl, optionally substituted with one or more R⁷;

R⁷ is independently selected at each occurrence from:
halogen, —NO₂, —CN, —OR⁸, —SR⁸, —N(R⁸)₂, —NR⁹R¹⁰, —S(=O)R⁸, —S(=O)₂R⁸, —S(=O)₂N(R⁸)₂, —S(=O)₂NR⁹R¹⁰, —NR⁸S(=O)₂R⁸, —NR⁸S(=O)₂N(R⁸)₂, —NR⁸S(=O)₂NR⁹R¹⁰, —C(O)R⁸, —C(O)OR⁸, —OC(O)R⁸, —OC(O)OR⁸, —OC(O)N(R⁸)₂, —OC(O)NR⁹R¹⁰, —NR⁸C(O)R⁸, —NR⁸C(O)OR⁸, —NR⁸C(O)N(R⁸)₂, —NR⁸C(O)NR⁹R¹⁰, —C(O)N(R⁸)₂, —C(O)NR⁹R¹⁰, —P(O)(OR⁸)₂, —P(O)(R⁸)₂, =O, =S, and =N(R⁸);

C₁₋₁₀ alkyl, C₂₋₁₀ alkenyl, and C₂₋₁₀ alkynyl, each of which is independently optionally substituted at each occurrence with one or more substituents selected from halogen, —NO₂, —CN, —OR⁸, —SR⁸, —N(R⁸)₂, —NR⁹R¹⁰, —S(=O)R⁸, —S(=O)₂R⁸, —S(=O)₂N(R⁸)₂, —S(=O)₂NR⁹R¹⁰, —NR⁸S(=O)₂R⁸, —NR⁸S(=O)₂N(R⁸)₂, —NR⁸S(=O)₂NR⁹R¹⁰, —C(O)R⁸, —C(O)OR⁸, —OC(O)R⁸, —OC(O)OR⁸, —OC(O)N(R⁸)₂, —OC(O)NR⁹R¹⁰, —NR⁸C(O)R⁸, —NR⁸C(O)OR⁸, —NR⁸C(O)N(R⁸)₂, —NR⁸C(O)NR⁹R¹⁰, —C(O)N(R⁸)₂, —C(O)NR⁹R¹⁰, —P(O)(OR⁸)₂, —P(O)(R⁸)₂, =O, =S, =N(R⁸), C₃₋₁₂ carbocycle, and 3- to 12-membered heterocycle; and C₃₋₁₂ carbocycle and 3- to 12-membered heterocycle, wherein each C₃₋₁₂ carbocycle and 3- to 12-membered heterocycle in R⁷ is independently optionally substituted with one or more substituents selected from halogen, —NO₂, —CN, —OR⁸, —SR⁸, —N(R⁸)₂, —NR⁹R¹⁰, —S(=O)R⁸, —S(=O)₂R⁸, —S(=O)₂N(R⁸)₂, —S(=O)₂NR⁹R¹⁰, —NR⁸S(=O)₂R⁸, —NR⁸S(=O)₂N(R⁸)₂, —NR⁸S(=O)₂NR⁹R¹⁰, —C(O)R⁸, —C(O)OR⁸, —OC(O)R⁸, —OC(O)OR⁸, —OC(O)N(R⁸)₂, —OC(O)NR⁹R¹⁰, —NR⁸C(O)R⁸, —NR⁸C(O)OR⁸, —NR⁸C(O)N(R⁸)₂, —NR⁸C(O)NR⁹R¹⁰, —C(O)N(R⁸)₂, —C(O)NR⁹R¹⁰, —P(O)(OR⁸)₂, —P(O)(R⁸)₂, =O, =S, =N(R⁸), C₁₋₆ alkyl, C₁₋₆ haloalkyl, C₂₋₆ alkenyl, and C₂₋₆ alkynyl;

R⁸ is independently selected at each occurrence from hydrogen; and C₁₋₂₀ alkyl, C₂₋₂₀ alkenyl, C₂₋₂₀ alkynyl, 1- to 6-membered heteroalkyl, C₃₋₁₂ carbocycle, and 3- to 12-membered heterocycle, each of which is optionally substituted by halogen, —CN, —NO₂, —NH₂, —NHCH₃, —NHCH$_2$CH$_3$, =O, —OH, —OCH$_3$, —OCH$_2$CH$_3$, C$_{3-12}$ carbocycle, or 3- to 6-membered heterocycle;

R$^9$ and R$^{10}$ are taken together with the nitrogen atom to which they are attached to form a heterocycle, optionally substituted with one or more R$^7$;

R$^{11}$ is selected from C$_{1-6}$ alkyl and C$_{3-12}$ carbocycle, each of which is optionally substituted with one or more R$^7$;

R$^{12}$ is independently selected at each occurrence from R$^7$; and n is an integer from 0 to 3.

In certain aspects, the present disclosure provides a compound of Formula (I-A) or (I-B):

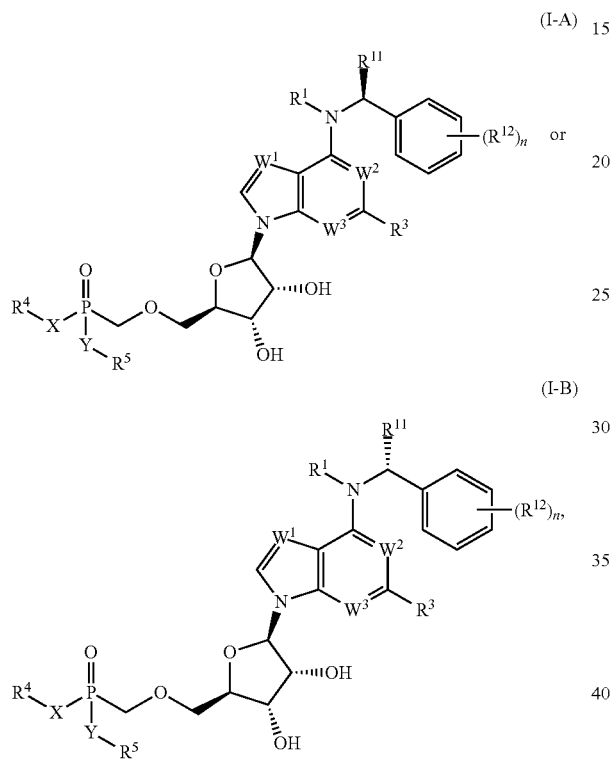

or a pharmaceutically acceptable salt thereof, wherein:

W$^1$, W$^2$ and W$^3$ are each independently selected from N and CR$^6$, wherein at least one of W$^1$, W$^2$ and W$^3$ is N;

R$^1$ is selected from hydrogen; and C$_{1-6}$ alkyl and C$_{3-12}$ carbocycle, each of which is optionally substituted with one or more R$^7$;

R$^3$ is selected from halogen and cyano; and C$_{1-6}$ alkyl, C$_{3-12}$ carbocycle, 3- to 12-membered heterocycle and benzyl, each of which is optionally substituted with one or more R$^7$;

X and Y are independently selected from —O— and —NR$^8$—;

R$^4$ and R$^5$ are independently selected from:
hydrogen; and
C$_{1-6}$ alkyl and phenyl, each of which is independently optionally substituted at each occurrence with one or more substituents selected from halogen, —NO$_2$, —CN, —OR$^8$, —SR$^8$, —N(R$^8$)$_2$, —NR$^9$R$^{10}$, —S(=O)R$^8$, —S(=O)$_2$R$^8$, —S(=O)$_2$N(R$^8$)$_2$, —S(=O)$_2$NR$^9$R$^{10}$, —NR$^8$S(=O)$_2$R$^8$, —NR$^8$S(=O)$_2$N(R$^8$)$_2$, —NR$^8$S(=O)$_2$NR$^9$R$^{10}$, —S—S—R$^8$, —S—C(O)R$^8$, —C(O)R$^8$, —C(O)OR$^8$, —OC(O)R$^8$, —OC(O)OR$^8$, —OC(O)N(R$^8$)$_2$, —OC(O)NR$^9$R$^{10}$, —NR$^8$C(O)R$^8$, —NR$^8$C(O)OR$^8$, —NR$^8$C(O)N(R$^8$)$_2$, —NR$^8$C(O)NR$^9$R$^{10}$, —C(O)N(R$^8$)$_2$, —C(O)NR$^9$R$^{10}$, —P(O)(OR$^8$)$_2$, —P(O)(R$^8$)$_2$, —OP(O)(OR$^8$)$_2$, =O, =S, =N(R$^8$), C$_{3-12}$ carbocycle, and 3- to 12-membered heterocycle;

R$^6$ is selected from hydrogen, halogen and cyano; and C$_{1-6}$ alkyl, optionally substituted with one or more R$^7$;

R$^7$ is independently selected at each occurrence from:
halogen, —NO$_2$, —CN, —OR$^8$, —SR$^8$, —N(R$^8$)$_2$, —NR$^9$R$^{10}$, —S(=O)R$^8$, —S(=O)$_2$R$^8$, —S(=O)$_2$N(R$^8$)$_2$, —S(=O)$_2$NR$^9$R$^{10}$, —NR$^8$S(=O)$_2$R$^8$, —NR$^8$S(=O)$_2$N(R$^8$)$_2$, —NR$^8$S(=O)$_2$NR$^9$R$^{10}$, —C(O)R$^8$, —C(O)OR$^8$, —OC(O)R$^8$, —OC(O)OR$^8$, —OC(O)N(R$^8$)$_2$, —OC(O)NR$^9$R$^{10}$, —NR$^8$C(O)R$^8$, —NR$^8$C(O)OR$^8$, —NR$^8$C(O)N(R$^8$)$_2$, —NR$^8$C(O)NR$^9$R$^{10}$, —C(O)N(R$^8$)$_2$, —C(O)NR$^9$R$^{10}$, —P(O)(OR$^8$)$_2$, —P(O)(R$^8$)$_2$, =O, =S, and =N(R$^8$);

C$_{1-10}$ alkyl, C$_{2-10}$ alkenyl, and C$_{2-10}$ alkynyl, each of which is independently optionally substituted at each occurrence with one or more substituents selected from halogen, —NO$_2$, —CN, —OR$^8$, —SR$^8$, —N(R$^8$)$_2$, —NR$^9$R$^{10}$, —S(=O)R$^8$, —S(=O)$_2$R$^8$, —S(=O)$_2$N(R$^8$)$_2$, —S(=O)$_2$NR$^9$R$^{10}$, —NR$^8$S(=O)$_2$R$^8$, —NR$^8$S(=O)$_2$N(R$^8$)$_2$, —NR$^8$S(=O)$_2$NR$^9$R$^{10}$, —C(O)R$^8$, —C(O)OR$^8$, —OC(O)R$^8$, —OC(O)OR$^8$, —OC(O)N(R$^8$)$_2$, —OC(O)NR$^9$R$^{10}$, —NR$^8$C(O)R$^8$, —NR$^8$C(O)OR$^8$, —NR$^8$C(O)N(R$^8$)$_2$, —NR$^8$C(O)NR$^9$R$^{10}$, —C(O)N(R$^8$)$_2$, —C(O)NR$^9$R$^{10}$, —P(O)(OR$^8$)$_2$, —P(O)(R$^8$)$_2$, =O, =S, =N(R$^8$), C$_{3-12}$ carbocycle, and 3- to 12-membered heterocycle; and C$_{3-12}$ carbocycle and 3- to 12-membered heterocycle, wherein each C$_{3-12}$ carbocycle and 3- to 12-membered heterocycle in R$^7$ is independently optionally substituted with one or more substituents selected from halogen, —NO$_2$, —CN, —OR$^8$, —SR$^8$, —N(R$^8$)$_2$, —NR$^9$R$^{10}$, —S(=O)R$^8$, —S(=O)$_2$R$^8$, —S(=O)$_2$N(R$^8$)$_2$, —S(=O)$_2$NR$^9$R$^{10}$, —NR$^8$S(=O)$_2$R$^8$, —NR$^8$S(=O)$_2$N(R$^8$)$_2$, —NR$^8$S(=O)$_2$NR$^9$R$^{10}$, —C(O)R$^8$, —C(O)OR$^8$, —OC(O)R$^8$, —OC(O)OR$^8$, —OC(O)N(R$^8$)$_2$, —OC(O)NR$^9$R$^{10}$, —NR$^8$C(O)R$^8$, —NR$^8$C(O)OR$^8$, —NR$^8$C(O)N(R$^8$)$_2$, —NR$^8$C(O)NR$^9$R$^{10}$, —C(O)N(R$^8$)$_2$, —C(O)NR$^9$R$^{10}$, —P(O)(OR$^8$)$_2$, —P(O)(R$^8$)$_2$, =O, =S, =N(R$^8$), C$_{1-6}$ alkyl, C$_{1-6}$ haloalkyl, C$_{2-6}$ alkenyl, and C$_{2-6}$ alkynyl;

R$^8$ is independently selected at each occurrence from hydrogen; and C$_{1-20}$ alkyl, C$_{2-20}$ alkenyl, C$_{2-20}$ alkynyl, 1- to 6-membered heteroalkyl, C$_{3-12}$ carbocycle, and 3- to 12-membered heterocycle, each of which is optionally substituted by halogen, —CN, —NO$_2$, —NH$_2$, —NHCH$_3$, —NHCH$_2$CH$_3$, =O, —OH, —OCH$_3$, —OCH$_2$CH$_3$, C$_{3-12}$ carbocycle, or 3- to 6-membered heterocycle;

R$^9$ and R$^{10}$ are taken together with the nitrogen atom to which they are attached to form a heterocycle, optionally substituted with one or more R$^7$;

R$^{11}$ is selected from C$_{1-6}$ alkyl and C$_{3-12}$ carbocycle, each of which is optionally substituted with one or more R$^7$;

R$^{12}$ is independently selected at each occurrence from R$^7$; and n is an integer from 0 to 3.

In some embodiments, for a compound of Formula (I-A), (I-B), (II-A), (II-B), (III-A) or (III-B), R$^{11}$ is C$_{1-4}$ alkyl. In some embodiments, R$^{11}$ is selected from methyl, ethyl, iso-propyl and tert-butyl. In some embodiments, R$^{11}$ is selected from C$_{1-4}$ alkyl and C$_{3-12}$ cycloalkyl, each of which is optionally substituted with one or more R$^7$. In some embodiments, R$^{12}$ is independently selected at each occurrence from halogen, —CN, C$_{1-4}$ alkoxy, C$_{1-4}$ haloalkoxy, C$_{1-4}$ alkyl and C$_{1-4}$ haloalkyl. In some embodiments, R$^{12}$ is independently selected at each occurrence from halogen, —CN, C$_{1-4}$ alkyl and C$_{1-4}$ haloalkyl. In some embodiments, R$^{12}$ is independently selected at each occurrence from F, —CN, —CH$_3$ and —CF$_3$. In some embodiments, n is an integer from 1 to 3.

In certain aspects, the present disclosure provides a compound of Formula (III-C):

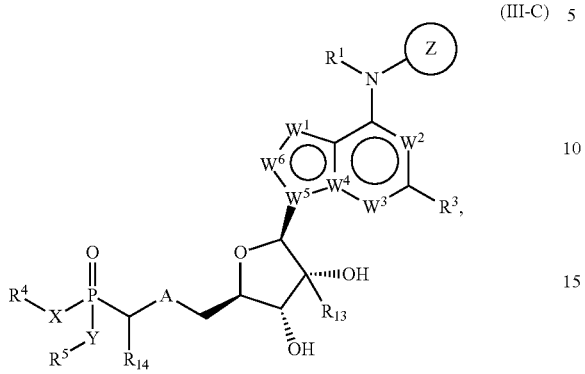

(III-C)

or a pharmaceutically acceptable salt thereof, wherein:
$W^1$ is selected from N, $NR^8$, $CR^6$, and S;
$W^2$ and $W^3$ are each independently selected from N and $CR^6$;
$W^4$ and $W^5$ are each independently selected from N and C;
$W^6$ is selected from N, $CR^6$, and S;
wherein at least one of $W^1$, $W^2$, $W^3$, $W^4$, $W^5$, and $W^6$ is N, and provided that:
when $W^1$, $W^2$, $W^3$, $W^5$, and $W^6$ are N, $W^4$ is not N; and
when either $W^1$ or $W^6$ is S, the other is $CR^6$;
$R^1$ is selected from hydrogen; and $C_{1-6}$ alkyl and $C_{3-12}$ carbocycle, each of which is optionally substituted with one or more $R^7$;
$R^3$ is selected from hydrogen, halogen, cyano, $-N(R^8)_2$ and $-OR^8$; and $C_{1-6}$ alkyl, $C_{2-10}$ alkenyl, $C_{2-10}$ alkynyl, $C_{3-12}$ carbocycle, 3- to 12-membered heterocycle and benzyl, each of which is optionally substituted with one or more $R^7$;
A is selected from $-O-$, $-S-$, $-S(=O)-$ and $-S(=O)_2-$;
X and Y are independently selected from $-O-$ and $-NR^8-$;
$R^4$ and $R^5$ are independently selected from:
hydrogen; and
$C_{1-6}$ alkyl, phenyl, and 3- to 12-membered heterocycle, each of which is independently optionally substituted at each occurrence with one or more substituents selected from halogen, $-NO_2$, $-CN$, $-OR^8$, $-SR^8$, $-N(R^8)_2$, $-NR^9R^{10}$, $-S(=O)R^8$, $-S(=O)_2R^8$, $-S(=O)_2N(R^8)_2$, $-S(=O)_2NR^9R^{10}$, $-NR^8S(=O)_2R^8$, $-NR^8S(=O)_2N(R^8)_2$, $-NR^8S(=O)_2NR^9R^{10}$, $-S-S-R^8$, $-S-C(O)R^8$, $-C(O)R^8$, $-C(O)OR^8$, $-OC(O)R^8$, $-OC(O)OR^8$, $-OC(O)N(R^8)_2$, $-OC(O)NR^9R^{10}$, $-NR^8C(O)R^8$, $-NR^8C(O)OR^8$, $-NR^8C(O)N(R^8)_2$, $-NR^8C(O)NR^9R^{10}$, $-C(O)N(R^8)_2$, $-C(O)NR^9R^{10}$, $-P(O)(OR^8)_2$, $-P(O)(R^8)_2$, $-OP(O)(OR^8)_2$, $=O$, $=S$, $=N(R^8)$, $C_{3-12}$ carbocycle, and 3- to 12-membered heterocycle; or
$R^4$ and $R^5$ are taken together with the atoms to which they are attached to form a 3- to 12-membered heterocycle, optionally substituted with one or more $R^7$;
$R^6$ is selected from hydrogen, halogen and cyano; and $C_{1-6}$ alkyl, optionally substituted with one or more $R^7$;
$R^7$ is independently selected at each occurrence from:
halogen, $-NO_2$, $-CN$, $-OR^8$, $-SR^8$, $-N(R^8)_2$, $-NR^9R^{10}$, $-S(=O)R^8$, $-S(=O)_2R^8$, $-S(=O)_2N(R^8)_2$, $-S(=O)_2NR^9R^{10}$, $-NR^8S(=O)_2R^8$, $-NR^8S(=O)_2N(R^8)_2$, $-NR^8S(=O)_2NR^9R^{10}$, $-C(O)R^8$, $-C(O)OR^8$, $-OC(O)R^8$, $-OC(O)OR^8$, $-OC(O)N(R^8)_2$, $-OC(O)NR^9R^{10}$, $-NR^8C(O)R^8$, $-NR^8C(O)OR^8$, $-NR^8C(O)N(R^8)_2$, $-NR^8C(O)NR^9R^{10}$, $-C(O)N(R^8)_2$, $-C(O)NR^9R^{10}$, $-P(O)(OR^8)_2$, $-P(O)(R^8)_2$, $=O$, $=S$, and $=N(R^8)$;
$C_{1-10}$ alkyl, $C_{2-10}$ alkenyl, and $C_{2-10}$ alkynyl, each of which is independently optionally substituted at each occurrence with one or more substituents selected from halogen, $-NO_2$, $-CN$, $-OR^8$, $-SR^8$, $-N(R^8)_2$, $-NR^9R^{10}$, $-S(=O)R^8$, $-S(=O)_2R^8$, $-S(=O)_2N(R^8)_2$, $-S(=O)_2NR^9R^{10}$, $-NR^8S(=O)_2R^8$, $-NR^8S(=O)_2N(R^8)_2$, $-NR^8S(=O)_2NR^9R^{10}$, $-C(O)R^8$, $-C(O)OR^8$, $-OC(O)R^8$, $-OC(O)OR^8$, $-OC(O)N(R^8)_2$, $-OC(O)NR^9R^{10}$, $-NR^8C(O)R^8$, $-NR^8C(O)OR^8$, $-NR^8C(O)N(R^8)_2$, $-NR^8C(O)NR^9R^{10}$, $-C(O)N(R^8)_2$, $-C(O)NR^9R^{10}$, $-P(O)(OR^8)_2$, $-P(O)(R^8)_2$, $=O$, $=S$, $=N(R^8)$, $C_{3-12}$ carbocycle, and 3- to 12-membered heterocycle; and
$C_{3-12}$ carbocycle and 3- to 12-membered heterocycle, wherein each $C_{3-12}$ carbocycle and 3- to 12-membered heterocycle in $R^7$ is independently optionally substituted with one or more substituents selected from halogen, $-NO_2$, $-CN$, $-OR^8$, $-SR^8$, $-N(R^8)_2$, $-NR^9R^{10}$, $-S(=O)R^8$, $-S(=O)_2R^8$, $-S(=O)_2N(R^8)_2$, $-S(=O)_2NR^9R^{10}$, $-NR^8S(=O)_2R^8$, $-NR^8S(=O)_2N(R^8)_2$, $-NR^8S(=O)_2NR^9R^{10}$, $-C(O)R^8$, $-C(O)OR^8$, $-OC(O)R^8$, $-OC(O)OR^8$, $-OC(O)N(R^8)_2$, $-OC(O)NR^9R^{10}$, $-NR^8C(O)R^8$, $-NR^8C(O)OR^8$, $-NR^8C(O)N(R^8)_2$, $-NR^8C(O)NR^9R^{10}$, $-C(O)N(R^8)_2$, $-C(O)NR^9R^{10}$, $-P(O)(OR^8)_2$, $-P(O)(R^8)_2$, $=O$, $=S$, $=N(R^8)$, $C_{1-6}$ alkyl, $C_{1-6}$ haloalkyl, $C_{2-6}$ alkenyl, and $C_{2-6}$ alkynyl;
$R^8$ is independently selected at each occurrence from hydrogen; and $C_{1-20}$ alkyl, $C_{2-20}$ alkenyl, $C_{2-20}$ alkynyl, 1- to 6-membered heteroalkyl, $C_{3-12}$ carbocycle, and 3- to 12-membered heterocycle, each of which is optionally substituted by halogen, $-CN$, $-NO_2$, $-NH_2$, $-NHCH_3$, $-NHCH_2CH_3$, $=O$, $-OH$, $-OCH_3$, $-OCH_2CH_3$, $C_{3-12}$ carbocycle, or 3- to 6-membered heterocycle;
$R^9$ and $R^{10}$ are taken together with the nitrogen atom to which they are attached to form a heterocycle, optionally substituted with one or more $R^7$;
$R^{13}$ is selected from hydrogen and $C_{1-6}$ alkyl;
$R^{14}$ is selected from hydrogen and $R^7$; and
Z is selected from $C_{3-12}$ cycloalkyl and 3- to 12-membered heterocycloalkyl, each of which is optionally substituted with one or more $R^7$.

In certain aspects, the present disclosure provides a compound of Formula (II-C):

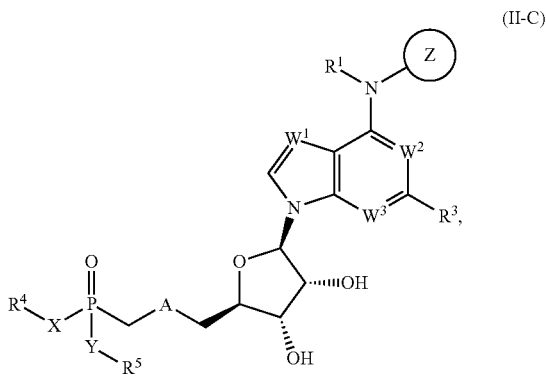

(II-C)

or a pharmaceutically acceptable salt thereof, wherein:
$W^1$, $W^2$ and $W^3$ are each independently selected from N and $CR^6$, wherein at least one of $W^1$, $W^2$ and $W^3$ is N;
$R^1$ is selected from hydrogen; and $C_{1-6}$ alkyl and $C_{3-12}$ carbocycle, each of which is optionally substituted with one or more $R^7$;

R$^3$ is selected from hydrogen, halogen and cyano; and C$_{1-6}$ alkyl, C$_{3-12}$ carbocycle, 3- to 12-membered heterocycle and benzyl, each of which is optionally substituted with one or more R$^7$;

A is selected from —S—, —S(=O)— and —S(=O)$_2$—;

X and Y are independently selected from —O— and —NR$^8$—;

R$^4$ and R$^5$ are independently selected from:

hydrogen; and

C$_{1-6}$ alkyl and phenyl, each of which is independently optionally substituted at each occurrence with one or more substituents selected from halogen, —NO$_2$, —CN, —OR$^8$, —SR$^8$, —N(R$^8$)$_2$, —NR$^9$R$^{10}$, —S(=O)R$^8$, —S(=O)$_2$R$^8$, —S(=O)$_2$N(R$^8$)$_2$, —S(=O)$_2$NR$^9$R$^{10}$, —NR$^8$S(=O)$_2$R$^8$, —NR$^8$S(=O)$_2$N(R$^8$)$_2$, —NR$^8$S(=O)$_2$NR$^9$R$^{10}$, —S—S—R$^8$, —S—C(O)R$^8$, —C(O)R$^8$, —C(O)OR$^8$, —OC(O)R$^8$, —OC(O)OR$^8$, —OC(O)N(R$^8$)$_2$, —OC(O)NR$^9$R$^{10}$, —NR$^8$C(O)R$^8$, —NR$^8$C(O)OR$^8$, —NR$^8$C(O)N(R$^8$)$_2$, —NR$^8$C(O)NR$^9$R$^{10}$, —C(O)N(R$^8$)$_2$, —C(O)NR$^9$R$^{10}$, —P(O)(OR$^8$)$_2$, —P(O)(R$^8$)$_2$, —OP(O)(OR$^8$)$_2$, =O, =S, =N(R$^8$), C$_{3-12}$ carbocycle, and 3- to 12-membered heterocycle;

R$^6$ is selected from hydrogen, halogen and cyano; and C$_{1-6}$ alkyl, optionally substituted with one or more R$^7$;

R$^7$ is independently selected at each occurrence from:

halogen, —NO$_2$, —CN, —OR$^8$, —SR$^8$, —N(R$^8$)$_2$, —NR$^9$R$^{10}$, —S(=O)R$^8$, —S(=O)$_2$R$^8$, —S(=O)$_2$N(R$^8$)$_2$, —S(=O)$_2$NR$^9$R$^{10}$, —NR$^8$S(=O)$_2$R$^8$, —NR$^8$S(=O)$_2$N(R$^8$)$_2$, —NR$^8$S(=O)$_2$NR$^9$R$^{10}$, —C(O)R$^8$, —C(O)OR$^8$, —OC(O)R$^8$, —OC(O)OR$^8$, —OC(O)N(R$^8$)$_2$, —OC(O)NR$^9$R$^{10}$, —NR$^8$C(O)R$^8$, —NR$^8$C(O)OR$^8$, —NR$^8$C(O)N(R$^8$)$_2$, —NR$^8$C(O)NR$^9$R$^{10}$, —C(O)N(R$^8$)$_2$, —C(O)NR$^9$R$^{10}$, —P(O)(OR$^8$)$_2$, —P(O)(R$^8$)$_2$, =O, =S, and =N(R$^8$);

C$_{1-10}$ alkyl, C$_{2-10}$ alkenyl, and C$_{2-10}$ alkynyl, each of which is independently optionally substituted at each occurrence with one or more substituents selected from halogen, —NO$_2$, —CN, —OR$^8$, —SR$^8$, —N(R$^8$)$_2$, —NR$^9$R$^{10}$, —S(=O)R$^8$, —S(=O)$_2$R$^8$, —S(=O)$_2$N(R$^8$)$_2$, —S(=O)$_2$NR$^9$R$^{10}$, —NR$^8$S(=O)$_2$R$^8$, —NR$^8$S(=O)$_2$N(R$^8$)$_2$, —NR$^8$S(=O)$_2$NR$^9$R$^{10}$, —C(O)R$^8$, —C(O)OR$^8$, —OC(O)R$^8$, —OC(O)OR$^8$, —OC(O)N(R$^8$)$_2$, —OC(O)NR$^9$R$^{10}$, —NR$^8$C(O)R$^8$, —NR$^8$C(O)OR$^8$, —NR$^8$C(O)N(R$^8$)$_2$, —NR$^8$C(O)NR$^9$R$^{10}$, —C(O)N(R$^8$)$_2$, —C(O)NR$^9$R$^{10}$, —P(O)(OR$^8$)$_2$, —P(O)(R$^8$)$_2$, =O, =S, =N(R$^8$), C$_{3-12}$ carbocycle, and 3- to 12-membered heterocycle; and C$_{3-12}$ carbocycle and 3- to 12-membered heterocycle, wherein each C$_{3-12}$ carbocycle and 3- to 12-membered heterocycle in R$^7$ is independently optionally substituted with one or more substituents selected from halogen, —NO$_2$, —CN, —OR$^8$, —SR$^8$, —N(R$^8$)$_2$, —NR$^9$R$^{10}$, —S(=O)R$^8$, —S(=O)$_2$R$^8$, —S(=O)$_2$N(R$^8$)$_2$, —S(=O)$_2$NR$^9$R$^{10}$, —NR$^8$S(=O)$_2$R$^8$, —NR$^8$S(=O)$_2$N(R$^8$)$_2$, —NR$^8$S(=O)$_2$NR$^9$R$^{10}$, —C(O)R$^8$, —C(O)OR$^8$, —OC(O)R$^8$, —OC(O)OR$^8$, —OC(O)N(R$^8$)$_2$, —OC(O)NR$^9$R$^{10}$, —NR$^8$C(O)R$^8$, —NR$^8$C(O)N(R$^8$)$_2$, —NR$^8$C(O)NR$^9$R$^{10}$, —C(O)N(R$^8$)$_2$, —C(O)NR$^9$R$^{10}$, —P(O)(OR$^8$)$_2$, —P(O)(R$^8$)$_2$, =O, =S, =N(R$^8$), C$_{1-6}$ alkyl, C$_{1-6}$ haloalkyl, C$_{2-6}$ alkenyl, and C$_{2-6}$ alkynyl;

R$^8$ is independently selected at each occurrence from hydrogen; and C$_{1-20}$ alkyl, C$_{2-20}$ alkenyl, C$_{2-20}$ alkynyl, 1- to 6-membered heteroalkyl, C$_{3-12}$ carbocycle, and 3- to 12-membered heterocycle, each of which is optionally substituted by halogen, —CN, —NO$_2$, —NH$_2$, —NHCH$_3$, —NHCH$_2$CH$_3$, =O, —OH, —OCH$_3$, —OCH$_2$CH$_3$, C$_{3-12}$ carbocycle, or 3- to 6-membered heterocycle;

R$^9$ and R$^{10}$ are taken together with the nitrogen atom to which they are attached to form a heterocycle, optionally substituted with one or more R$^7$; and Z is selected from C$_{3-12}$ cycloalkyl and 3- to 12-membered heterocycloalkyl, each of which is optionally substituted with one or more R$^7$.

In certain aspects, the present disclosure provides a compound of Formula (I-C):

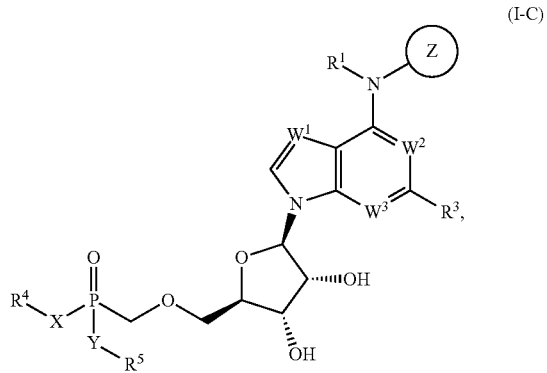

(I-C)

or a pharmaceutically acceptable salt thereof, wherein:

W$^1$, W$^2$ and W$^3$ are each independently selected from N and CR$^6$, wherein at least one of W$^1$, W$^2$ and W$^3$ is N;

R$^1$ is selected from hydrogen; and C$_{1-6}$ alkyl and C$_{3-12}$ carbocycle, each of which is optionally substituted with one or more R$^7$;

R$^3$ is selected from halogen and cyano; and C$_{1-6}$ alkyl, C$_{3-12}$ carbocycle, 3- to 12-membered heterocycle and benzyl, each of which is optionally substituted with one or more R$^7$;

X and Y are independently selected from —O— and —NR$^8$—;

R$^4$ and R$^5$ are independently selected from:

hydrogen; and

C$_{1-6}$ alkyl and phenyl, each of which is independently optionally substituted at each occurrence with one or more substituents selected from halogen, —NO$_2$, —CN, —OR$^8$, —SR$^8$, —N(R$^8$)$_2$, —NR$^9$R$^{10}$, —S(=O)R$^8$, —S(=O)$_2$R$^8$, —S(=O)$_2$N(R$^8$)$_2$, —S(=O)$_2$NR$^9$R$^{10}$, —NR$^8$S(=O)$_2$R$^8$, —NR$^8$S(=O)$_2$N(R$^8$)$_2$, —NR$^8$S(=O)$_2$NR$^9$R$^{10}$, —S—S—R$^8$, —S—C(O)R$^8$, —C(O)R$^8$, —C(O)OR$^8$, —OC(O)R$^8$, —OC(O)OR$^8$, —OC(O)N(R$^8$)$_2$, —OC(O)NR$^9$R$^{10}$, —NR$^8$C(O)R$^8$, —NR$^8$C(O)OR$^8$, —NR$^8$C(O)N(R$^8$)$_2$, —NR$^8$C(O)NR$^9$R$^{10}$, —C(O)N(R$^8$)$_2$, —C(O)NR$^9$R$^{10}$, —P(O)(OR$^8$)$_2$, —P(O)(R$^8$)$_2$, —OP(O)(OR$^8$)$_2$, =O, =S, =N(R$^8$), C$_{3-12}$ carbocycle, and 3- to 12-membered heterocycle;

R$^6$ is selected from hydrogen, halogen and cyano; and C$_{1-6}$ alkyl, optionally substituted with one or more R$^7$;

R$^7$ is independently selected at each occurrence from:

halogen, —NO$_2$, —CN, —OR$^8$, —SR$^8$, —N(R$^8$)$_2$, —NR$^9$R$^{10}$, —S(=O)R$^8$, —S(=O)$_2$R$^8$, —S(=O)$_2$N(R$^8$)$_2$, —S(=O)$_2$NR$^9$R$^{10}$, —NR$^8$S(=O)$_2$R$^8$, —NR$^8$S(=O)$_2$N(R$^8$)$_2$, —NR$^8$S(=O)$_2$NR$^9$R$^{10}$, —C(O)R$^8$, —C(O)OR$^8$, —OC(O)R$^8$, —OC(O)OR$^8$, —OC(O)N(R$^8$)$_2$, —OC(O)NR$^9$R$^{10}$, —NR$^8$C(O)R$^8$, —NR$^8$C(O)N(R$^8$)$_2$, —NR$^8$C(O)NR$^9$R$^{10}$, —C(O)N(R$^8$)$_2$, —C(O)NR$^9$R$^{10}$, —P(O)(OR$^8$)$_2$, —P(O)(R$^8$)$_2$, =O, =S, and =N(R$^8$);

$C_{1-10}$ alkyl, $C_{2-10}$ alkenyl, and $C_{2-10}$ alkynyl, each of which is independently optionally substituted at each occurrence with one or more substituents selected from halogen, —$NO_2$, —CN, —$OR^8$, —$SR^8$, —$N(R^8)_2$, —$NR^9R^{10}$, —$S(=O)R^8$, —$S(=O)_2R^8$, —$S(=O)_2N(R^8)_2$, —$S(=O)_2NR^9R^{10}$, —$NR^8S(=O)_2R^8$, —$NR^8S(=O)_2N(R^8)_2$, —$NR^8S(=O)_2NR^9R^{10}$, —$C(O)R^8$, —$C(O)OR^8$, —$OC(O)R^8$, —$OC(O)OR^8$, —$OC(O)N(R^8)_2$, —$OC(O)NR^9R^{10}$, —$NR^8C(O)R^8$, —$NR^8C(O)OR^8$, —$NR^8C(O)N(R^8)_2$, —$NR^8C(O)NR^9R^{10}$, —$C(O)N(R^8)_2$, —$C(O)NR^9R^{10}$, —$P(O)(OR^8)_2$, —$P(O)(R^8)_2$, =O, =S, =$N(R^8)$, $C_{3-12}$ carbocycle, and 3- to 12-membered heterocycle; and $C_{3-12}$ carbocycle and 3- to 12-membered heterocycle, wherein each $C_{3-12}$ carbocycle and 3- to 12-membered heterocycle in $R^7$ is independently optionally substituted with one or more substituents selected from halogen, —$NO_2$, —CN, —$OR^8$, —$SR^8$, —$N(R^8)_2$, —$NR^9R^{10}$, —$S(=O)R^8$, —$S(=O)_2R^8$, —$S(=O)_2N(R^8)_2$, —$S(=O)_2NR^9R^{10}$, —$NR^8S(=O)_2R^8$, —$NR^8S(=O)_2N(R^8)_2$, —$NR^8S(=O)_2NR^9R^{10}$, —$C(O)R^8$, —$C(O)OR^8$, —$OC(O)R^8$, —$OC(O)OR^8$, —$OC(O)N(R^8)_2$, —$OC(O)NR^9R^{10}$, —$NR^8C(O)R^8$, —$NR^8C(O)OR^8$, —$NR^8C(O)N(R^8)_2$, —$NR^8C(O)NR^9R^{10}$, —$C(O)N(R^8)_2$, —$C(O)NR^9R^{10}$, —$P(O)(OR^8)_2$, —$P(O)(R^8)_2$, =O, =S, =$N(R^8)$, $C_{1-6}$ alkyl, $C_{1-6}$ haloalkyl, $C_{2-6}$ alkenyl, and $C_{2-6}$ alkynyl;

$R^8$ is independently selected at each occurrence from hydrogen; and $C_{1-20}$ alkyl, $C_{2-20}$ alkenyl, $C_{2-20}$ alkynyl, 1- to 6-membered heteroalkyl, $C_{3-12}$ carbocycle, and 3- to 12-membered heterocycle, each of which is optionally substituted by halogen, —CN, —$NO_2$, —$NH_2$, —$NHCH_3$, —$NHCH_2CH_3$, =O, —OH, —$OCH_3$, —$OCH_2CH_3$, $C_{3-12}$ carbocycle, or 3- to 6-membered heterocycle;

$R^9$ and $R^{10}$ are taken together with the nitrogen atom to which they are attached to form a heterocycle, optionally substituted with one or more $R^7$; and Z is selected from $C_{3-12}$ cycloalkyl and 3- to 12-membered heterocycloalkyl, each of which is optionally substituted with one or more $R^7$.

In some embodiments, for a compound of Formula (I-C), (II-C) or (III-C), Z is selected from $C_{3-12}$ monocyclic cycloalkyl or $C_{5-12}$ fused bicyclic cycloalkyl, each of which is optionally substituted with one or more $R^7$. In some embodiments, Z is $C_{5-12}$ fused bicyclic cycloalkyl, optionally substituted with one or more $R^7$. In some embodiments, Z is substituted with one or more substituents independently selected from halogen, —CN, $C_{1-4}$ alkyl and $C_{1-3}$ haloalkyl.

In some embodiments, for a compound of Formula (I), (I-A), (I-B), (I-C), (II), (II-A), (II-B), (II-C), (III), (III-A), (III-B) or (III-C), $R^1$ is selected from hydrogen and —$CH_3$.

In some embodiments, for a compound of Formula (I), (I-A), (I-B), (I-C), (II), (II-A), (II-B), (II-C), (III), (III-A), (III-B) or (III-C), $W^3$ is N. In some embodiments, $W^2$ is N or CH. In some embodiments, $W^2$ is N. In some embodiments, $W^1$ is N or CH. In some embodiments, $W^1$ is N. In some embodiments, $W^1$ is N or CH, $W^2$ is N and $W^3$ is N.

In some embodiments, for a compound of Formula (I), (I-A), (I-B), (I-C), (II), (II-A), (II-B), (II-C), (III), (III-A), (III-B) or (III-C), $R^3$ is selected from halogen and cyano; and $C_{1-6}$ alkyl, $C_{3-12}$ carbocycle, 3- to 12-membered heterocycle and benzyl, each of which is optionally substituted with one or more $R^7$. In some embodiments, $R^3$ is selected from hydrogen, halogen, —CN, $C_{1-3}$ alkyl and $C_{1-3}$ haloalkyl. In some embodiments, $R^3$ is selected from —CN, $C_{1-3}$ alkyl and $C_{1-3}$ haloalkyl. In some embodiments, $R^3$ is selected from —Cl and —CN.

In some embodiments, for a compound of Formula (I), (I-A), (I-B), (I-C), (II), (II-A), (II-B), (II-C), (III), (III-A), (III-B) or (III-C), at least one of $R^4$ and $R^5$ is $C_{1-6}$ alkyl, optionally substituted at each occurrence with one or more substituents selected from halogen, —$OR^8$, —S—S—$R^8$, —S—C(O)$R^8$, —OC(O)$R^8$, —OC(O)$OR^8$ and —$P(O)(OR^8)_2$. In some embodiments, $R^4$ and $R^5$ are independently selected from $C_{1-6}$ alkyl, optionally substituted at each occurrence with one or more substituents selected from halogen, —$OR^8$, —S—S—$R^8$, —S—C(O)$R^8$, —OC(O)$R^8$, —OC(O)$OR^8$ and —$P(O)(OR^8)_2$. In some embodiments, $R^4$ and $R^5$ are independently selected from hydrogen and $C_{1-6}$ alkyl, wherein the $C_{1-6}$ alkyl is optionally substituted at each occurrence with one or more substituents selected from halogen, —$OR^8$, —S—S—$R^8$, —S—C(O)$R^8$, —OC(O)$R^8$, —OC(O)$OR^8$ and —$P(O)(OR^8)_2$. In some embodiments, $R^4$ and $R^5$ are independently selected from —$CH_2OC(O)R^8$ and —$CH_2OC(O)OR^8$. In some embodiments, $R^4$ and $R^5$ are independently selected from —$CH_2OC(O)C(CH_3)_3$, —$CH_2OC(O)OCH(CH_3)_2$, —$CH_2OC(O)CH_3$, —$CH_2CH_2$—S—S—$(CH_2)_2OH$ and —$CH_2CH_2$—S—C(O)$CH_3$. In some embodiments, $R^4$ is phenyl, optionally substituted with —$OR^8$; $R^5$ is $C_{1-6}$ alkyl substituted with one or more substituents selected from —OC(O)$R^8$, —C(O)$OR^8$, and —OC(O)$OR^8$; and $R^8$ is $C_{1-6}$ alkyl.

In some embodiments, for a compound of Formula (I), (I-A), (I-B), (I-C), (II), (II-A), (II-B), (II-C), (III), (III-A), (III-B) or (III-C), X and Y are each —O—. In some embodiments, one of X and Y is —O— and the other one of X and Y is —$NR^8$—. In some embodiments, —X—$R^4$ and —Y—$R^5$ are each —OH.

In some embodiments, for a compound of Formula (I), (I-A), (I-B), (I-C), (II), (II-A), (II-B), (II-C), (III), (III-A), (III-B) or (III-C), $W_1$ is selected from N and $CR^6$; $W^2$ is selected from N and CH; $W^3$ is N; $R^1$ is selected from hydrogen and $C_{1-4}$ alkyl; $R^3$ is selected from halogen and cyano; and $R^6$ is selected from hydrogen, halogen, cyano and $C_{1-4}$ alkyl. In some embodiments, $W^1$ is selected from N and $CR^6$; $W^2$ is selected from N and CH; $W^3$ is N; $R^1$ is selected from hydrogen and $C_{1-4}$ alkyl; $R^3$ is selected from halogen and cyano; and $R^6$ is selected from halogen, cyano and $C_{1-4}$ alkyl.

In some embodiments, for a compound of Formula (III), (III-A), (III-B) or (III-C), $R^3$ is selected from optionally substituted $C_2$-alkynyl and —$OR^8$. In some embodiments, $R^3$ is selected from

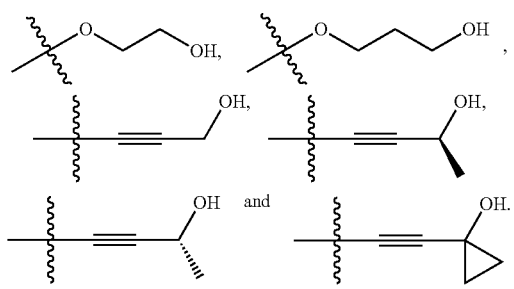

In some embodiments, for a compound of Formula (III), (III-A), (III-B) or (III-C), $W^1$ is selected from N and $CR^6$; $W^2$ is selected from N and CH; $W^3$ is N; $W^4$ is C; $W^5$ is N; $W^6$ is CH; $R^1$ is selected from hydrogen and $C_{1-4}$ alkyl; $R^3$ is selected from halogen and cyano; and $R^6$ is selected from hydrogen, halogen, cyano and $C_{1-4}$ alkyl. In some embodiments, $W^1$ is CH; $W^2$ is N; $W^3$ is N; $W^4$ is C; $W^5$ is N; $W^6$ is CH; $R^1$ is selected from hydrogen; $R^2$ is $C_{3-12}$ carbocycle; and $R^3$ is selected from optionally substituted $C_2$-alkynyl and —$OR^8$.

In certain aspects, the present disclosure provides a substantially pure stereoisomer of a compound of Formula (I), (I-A), (I-B), (I-C), (II), (II-A), (II-B), (II-C), (III), (III-A), (III-B) or (III-C). In some embodiments, the stereoisomer is provided in at least 90% diastereomeric excess.

In certain aspects, the present disclosure provides a compound selected from Table 1.

In certain aspects, the present disclosure provides a pharmaceutical composition comprising a compound or salt described herein, such as a compound of Formula (I), (I-A), (I-B3), (I-C), (II), (II-A), (II-B3), (II-C), (III), (III-A), (III-B3) or (III-C), and a pharmaceutically acceptable carrier or diluent.

In certain aspects, the present disclosure provides a method of inhibiting CD73-catalyzed hydrolysis of adenosine monophosphate, comprising contacting CD73 with an effective amount of a compound described herein, such as a compound of Formula (I), (I-A), (I-B), (I-C), (II), (II-A), (II-B), (II-C), (III), (III-A), (III-B) or (III-C). The contacting may comprise contacting a cell that expresses CD73. The contacting may take place in vivo.

INCORPORATION BY REFERENCE

All publications, patents and patent applications mentioned in this specification are herein incorporated by reference to the same extent as if each individual publication, patent or patent application was specifically and individually indicated to be incorporated by reference.

DETAILED DESCRIPTION OF THE INVENTION

While preferred embodiments of the present invention have been shown and described herein, it will be obvious to those skilled in the art that such embodiments are provided by way of example only. Numerous variations, changes and substitutions will now occur to those skilled in the art without departing from the invention. It should be understood that various alternatives to the embodiments of the invention described herein may be employed in practicing the invention. It is intended that the appended claims define the scope of the invention and that methods and structures within the scope of these claims and their equivalents be covered thereby.

Unless defined otherwise, all technical and scientific terms used herein have the same meaning as is commonly understood by one of skill in the art to which this invention belongs.

As used in the specification and claims, the singular form "a", "an" and "the" include plural references unless the context clearly dictates otherwise.

The term "$C_{x-y}$" or "$C_x$—$C_y$" when used in conjunction with a chemical moiety, such as alkyl, alkenyl, or alkynyl is meant to include groups that contain from x to y carbons in the chain. For example, the term "$C_{x-y}$ alkyl" refers to substituted or unsubstituted saturated hydrocarbon groups, including straight-chain alkyl and branched-chain alkyl groups that contain from x to y carbons in the chain.

"Alkyl" refers to substituted or unsubstituted saturated hydrocarbon groups, including straight-chain alkyl and branched-chain alkyl groups. An alkyl group may contain from one to twelve carbon atoms (e.g., $C_{1-12}$ alkyl), such as one to eight carbon atoms ($C_{1-8}$ alkyl) or one to six carbon atoms ($C_{1-6}$ alkyl). Exemplary alkyl groups include methyl, ethyl, n-propyl, isopropyl, n-butyl, isobutyl, sec-butyl, tert-butyl, pentyl, isopentyl, neopentyl, hexyl, septyl, octyl, nonyl, and decyl. An alkyl group is attached to the rest of the molecule by a single bond. Unless stated otherwise specifically in the specification, an alkyl group is optionally substituted by one or more substituents such as those substituents described herein.

"Haloalkyl" refers to an alkyl group that is substituted by one or more halogens. Exemplary haloalkyl groups include trifluoromethyl, difluoromethyl, trichloromethyl, 2,2,2-trifluoroethyl, 1,2-difluoroethyl, 3-bromo-2-fluoropropyl, and 1,2-dibromoethyl.

"Alkenyl" refers to substituted or unsubstituted hydrocarbon groups, including straight-chain or branched-chain alkenyl groups containing at least one double bond. An alkenyl group may contain from two to twelve carbon atoms (e.g., $C_{2-12}$ alkenyl). Exemplary alkenyl groups include ethenyl (i.e., vinyl), prop-1-enyl, but-1-enyl, pent-1-enyl, penta-1,4-dienyl, and the like. Unless stated otherwise specifically in the specification, an alkenyl group is optionally substituted by one or more substituents such as those substituents described herein.

"Alkynyl" refers to substituted or unsubstituted hydrocarbon groups, including straight-chain or branched-chain alkynyl groups containing at least one triple bond. An alkynyl group may contain from two to twelve carbon atoms (e.g., $C_{2-12}$ alkynyl). Exemplary alkynyl groups include ethynyl, propynyl, butynyl, pentynyl, hexynyl, and the like. Unless stated otherwise specifically in the specification, an alkynyl group is optionally substituted by one or more substituents such as those substituents described herein.

"Alkylene" or "alkylene chain" refers to substituted or unsubstituted divalent saturated hydrocarbon groups, including straight-chain alkylene and branched-chain alkylene groups that contain from one to twelve carbon atoms. Exemplary alkylene groups include methylene, ethylene, propylene, and n-butylene. Similarly, "alkenylene" and "alkynylene" refer to alkylene groups, as defined above, which comprise one or more carbon-carbon double or triple bonds, respectively. The points of attachment of the alkylene, alkenylene or alkynylene chain to the rest of the molecule can be through one carbon or any two carbons within the chain. Unless stated otherwise specifically in the specification, an alkylene, alkenylene, or alkynylene group is optionally substituted by one or more substituents such as those substituents described herein.

"Heteroalkyl", "heteroalkenyl" and "heteroalkynyl" refer to substituted or unsubstituted alkyl, alkenyl and alkynyl groups which respectively have one or more skeletal chain atoms selected from an atom other than carbon, e.g., O, N, P, Si, S or combinations thereof, and wherein the nitrogen, phosphorus, and sulfur atoms may optionally be oxidized and the nitrogen heteroatom may optionally be quaternized. If given, a numerical range refers to the chain length in total. For example, a 3- to 8-membered heteroalkyl has a chain length of 3 to 8 atoms. Connection to the rest of the molecule may be through either a heteroatom or a carbon in the heteroalkyl, heteroalkenyl or heteroalkynyl chain. Unless stated otherwise specifically in the specification, a heteroalkyl, heteroalkenyl, or heteroalkynyl group is optionally substituted by one or more substituents such as those substituents described herein.

"Heteroalkylene", "heteroalkenylene" and "heteroalkynylene" refer to substituted or unsubstituted alkylene, alkenylene and alkynylene groups which respectively have one or more skeletal chain atoms selected from an atom other than carbon, e.g., O, N, P, Si, S or combinations thereof, and wherein the nitrogen, phosphorus, and sulfur atoms may optionally be oxidized and the nitrogen heteroatom may optionally be quaternized. The points of attachment of the heteroalkylene, heteroalkenylene or heteroalkynylene chain to the rest of the molecule can be through either one heteroatom or one carbon, or any two heteroatoms, any two carbons, or any one heteroatom and any one carbon in the heteroalkyl, heteroalkenyl or heteroalkynyl chain. Unless stated otherwise specifically in the specification, a heteroalkylene, heteroalkenylene, or heteroalkynylene group is optionally substituted by one or more substituents such as those substituents described herein.

"Carbocycle" refers to a saturated, unsaturated or aromatic ring in which each atom of the ring is a carbon atom. Carbocycle may include 3- to 10-membered monocyclic rings, 6- to 12-membered bicyclic rings, and 6- to 12-membered bridged rings. Each ring of a bicyclic carbocycle may be selected from saturated, unsaturated, and aromatic rings. In some embodiments, the carbocycle is an aryl. In some embodiments, the carbocycle is a cycloalkyl. In some embodiments, the carbocycle is a cycloalkenyl. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, are included in the definition of carbocyclic. Exemplary carbocycles include cyclopentyl, cyclohexyl, cyclohexenyl, adamantyl, phenyl, indanyl, and naphthyl. Unless stated otherwise specifically in the specification, a carbocycle is optionally substituted by one or more substituents such as those substituents described herein.

"Heterocycle" refers to a saturated, unsaturated or aromatic ring comprising one or more heteroatoms. Exemplary heteroatoms include N, O, Si, P, B, and S atoms. Heterocycles include 3- to 10-membered monocyclic rings, 6- to 12-membered bicyclic rings, and 6- to 12-membered bridged rings. Each ring of a bicyclic heterocycle may be selected from saturated, unsaturated, and aromatic rings. The heterocycle may be attached to the rest of the molecule through any atom of the heterocycle, valence permitting, such as a carbon or nitrogen atom of the heterocycle. In some embodiments, the heterocycle is a heteroaryl. In some embodiments, the heterocycle is a heterocycloalkyl. In an exemplary embodiment, a heterocycle, e.g., pyridyl, may be fused to a saturated or unsaturated ring, e.g., cyclohexane, cyclopentane, or cyclohexene. Exemplary heterocycles include pyrrolidinyl, pyrrolyl, imidazolyl, pyrazolyl, triazolyl, piperidinyl, pyridinyl, pyrimidinyl, pyridazinyl, pyrazinyl, thiophenyl, oxazolyl, thiazolyl, morpholinyl, indazolyl, indolyl, and quinolinyl. Unless stated otherwise specifically in the specification, a heterocycle is optionally substituted by one or more substituents such as those substituents described herein.

"Heteroaryl" refers to a 3- to 12-membered aromatic ring that comprises at least one heteroatom wherein each heteroatom may be independently selected from N, O, and S. As used herein, the heteroaryl ring may be selected from monocyclic or bicyclic and fused or bridged ring systems wherein at least one of the rings in the ring system is aromatic, i.e., it contains a cyclic, delocalized (4n+2) π-electron system in accordance with the Hückel theory. The heteroatom(s) in the heteroaryl may be optionally oxidized. One or more nitrogen atoms, if present, are optionally quaternized. The heteroaryl may be attached to the rest of the molecule through any atom of the heteroaryl, valence permitting, such as a carbon or nitrogen atom of the heteroaryl. Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-TH-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pridinyl, and thiophenyl (i.e. thienyl). Unless stated otherwise specifically in the specification, a heteroaryl is optionally substituted by one or more substituents such as those substituents described herein.

The term "substituted" refers to moieties having substituents replacing a hydrogen on one or more carbons or heteroatoms of the structure. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this disclosure, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, a carbocycle, a heterocycle, a cycloalkyl, a heterocycloalkyl, an aromatic and heteroaromatic moiety. In some embodiments, substituents may include any substituents described herein, for example: halogen, hydroxy, oxo (=O), thioxo (=S), cyano (—CN), nitro (—NO$_2$), imino (=N—H), oximo (=N—OH), hydrazino (=N—NH$_2$), —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$R$^a$ (where t is 1 or 2), —R$^b$—S(O)$_t$OR$^a$ (where t is 1 or 2), and —R$^b$—S(O)$_t$N(R$^a$)$_2$ (where t is 1 or 2); and alkyl, alkenyl, alkynyl, aryl, aralkyl, aralkenyl, aralkynyl, cycloalkyl, cycloalkylalkyl, heterocycloalkyl, heterocycloalkylalkyl, heteroaryl, and heteroarylalkyl any of which may be optionally substituted by alkyl, alkenyl, alkynyl, halogen, hydroxy, haloalkyl, haloalkenyl, haloalkynyl, oxo (=O), thioxo (=S), cyano (—CN), nitro (—NO$_2$), imino (=N—H), oximo (=N—OH), hydrazine (=N—NH$_2$), —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$R$^a$ (where t is 1 or 2), —R$^b$—S(O)$_t$OR$^a$ (where t is 1 or 2) and —R$^b$—S(O)$_t$N(R$^a$)$_2$ (where t is 1 or 2); wherein each R$^a$ is independently selected from hydrogen, alkyl, cycloalkyl, cycloalkylalkyl, aryl, aralkyl, heterocycloalkyl, heterocycloalkylalkyl, heteroaryl, or heteroarylalkyl, wherein each R$^a$, valence permitting, may be optionally substituted with alkyl, alkenyl, alkynyl, halogen, haloalkyl, haloalkenyl, haloalkynyl, oxo (=O), thioxo (=S), cyano (—CN), nitro (—NO$_2$), imino (=N—H), oximo (=N—OH), hydrazine (=N—NH$_2$), —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$R$^a$ (where t is 1 or 2), —R$^b$—S(O)$_t$OR$^a$ (where t is 1 or 2) and —R$^b$—S(O)$_t$N(R$^a$)$_2$ (where t is 1 or 2); and wherein each R$^b$ is independently selected from a direct bond or a straight or branched alkylene, alkenylene, or alkynylene chain, and each R$^c$ is a straight or branched alkylene, alkenylene or alkynylene chain. In some embodiments, a substituent is selected from R$^7$ as defined herein below.

It will be understood by those skilled in the art that substituents can themselves be substituted, if appropriate. Unless specifically stated as "unsubstituted," references to chemical moieties herein are understood to include substituted variants. For example, reference to a "heteroaryl" group or moiety implicitly includes both substituted and unsubstituted variants.

Where substituent groups are specified by their conventional chemical formulae, written from left to right, they equally encompass the chemically identical substituents that would result from writing the structure from right to left, e.g., —CH$_2$O— is equivalent to —OCH$_2$—.

"Optional" or "optionally" means that the subsequently described event of circumstances may or may not occur, and that the description includes instances where the event or circumstance occurs and instances in which it does not. For example, "optionally substituted aryl" means that the aryl group may or may not be substituted and that the description includes both substituted aryl groups and aryl groups having no substitution.

Compounds of the present disclosure also include crystalline and amorphous forms of those compounds, pharmaceutically acceptable salts, and active metabolites of these compounds having the same type of activity, including, for example, polymorphs, pseudopolymorphs, solvates, hydrates, unsolvated polymorphs (including anhydrates), conformational polymorphs, and amorphous forms of the compounds, as well as mixtures thereof.

The compounds described herein may exhibit their natural isotopic abundance, or one or more of the atoms may be artificially enriched in a particular isotope having the same atomic number, but an atomic mass or mass number different from the atomic mass or mass number predominantly found in nature. All isotopic variations of the compounds of the present disclosure, whether radioactive or not, are encompassed within the scope of the present disclosure. For example, hydrogen has three naturally occurring isotopes, denoted $^1$H (protium), $^2$H (deuterium), and $^3$H (tritium). Protium is the most abundant isotope of hydrogen in nature. Enriching for deuterium may afford certain therapeutic advantages, such as increased in vivo half-life and/or exposure, or may provide a compound useful for investigating in vivo routes of drug elimination and metabolism. Isotopically-enriched compounds may be prepared by conventional techniques well known to those skilled in the art.

"Isomers" are different compounds that have the same molecular formula. "Stereoisomers" are isomers that differ only in the way the atoms are arranged in space. "Enantiomers" are a pair of stereoisomers that are non superimposable mirror images of each other. A 1:1 mixture of a pair of enantiomers is a "racemic" mixture. The term "(±)" is used to designate a racemic mixture where appropriate. "Diastereoisomers" or "diastereomers" are stereoisomers that have at least two asymmetric atoms but are not mirror images of each other. The absolute stereochemistry is specified according to the Cahn-Ingold-Prelog R-S system. When a compound is a pure enantiomer, the stereochemistry at each chiral carbon can be specified by either R or S. Resolved compounds whose absolute configuration is unknown can be designated (+) or (−) depending on the direction (dextro- or levorotatory) in which they rotate plane polarized light at the wavelength of the sodium D line. Certain compounds described herein contain one or more asymmetric centers and can thus give rise to enantiomers, diastereomers, and other stereoisomeric forms, the asymmetric centers of which can be defined, in terms of absolute stereochemistry, as (R)- or (S)-. The present chemical entities, pharmaceutical compositions and methods are meant to include all such possible stereoisomers, including racemic mixtures, optically pure forms, mixtures of diastereomers and intermediate mixtures. Optically active (R)- and (S)-isomers can be prepared using chiral synthons or chiral reagents, or resolved using conventional techniques. The optical activity of a compound can be analyzed via any suitable method, including but not limited to chiral chromatography and polarimetry, and the degree of predominance of one stereoisomer over the other isomer can be determined.

Chemical entities having carbon-carbon double bonds or carbon-nitrogen double bonds may exist in Z- or E-form (or cis- or trans-form). Furthermore, some chemical entities may exist in various tautomeric forms. Unless otherwise specified, chemical entities described herein are intended to include all Z-, E- and tautomeric forms as well.

Isolation and purification of the chemical entities and intermediates described herein can be effected, if desired, by any suitable separation or purification procedure such as, for example, filtration, extraction, crystallization, column chromatography, thin-layer chromatography or thick-layer chromatography, or a combination of these procedures. Specific illustrations of suitable separation and isolation procedures can be had by reference to the examples herein below. However, other equivalent separation or isolation procedures can also be used.

When stereochemistry is not specified, certain small molecules described herein include, but are not limited to, when possible, their isomers, such as enantiomers and diastereomers, mixtures of enantiomers, including racemates, mixtures of diastereomers, and other mixtures thereof, to the extent they can be made by one of ordinary skill in the art by routine experimentation. In those situations, the single enantiomers or diastereomers, i.e., optically active forms, can be obtained by asymmetric synthesis or by resolution of the racemates or mixtures of diastereomers. Resolution of the racemates or mixtures of diastereomers, if possible, can be accomplished, for example, by conventional methods such as crystallization in the presence of a resolving agent, or chromatography, using, for example, a chiral high-pressure liquid chromatography (HPLC) column. Furthermore, a mixture of two enantiomers enriched in one of the two can be purified to provide further optically enriched form of the major enantiomer by recrystallization and/or trituration. In addition, such certain small molecules include Z- and E-forms (or cis- and trans-forms) of certain small molecules with carbon-carbon double bonds or carbon-nitrogen double bonds. Where certain small molecules described herein exist in various tautomeric forms, the term "certain small molecule" is intended to include all tautomeric forms of the certain small molecule.

The term "salt" or "pharmaceutically acceptable salt" refers to salts derived from a variety of organic and inorganic counter ions well known in the art. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. In some embodiments, the pharmaceutically acceptable base addition salt is chosen from ammonium, potassium, sodium, calcium, and magnesium salts.

"Pharmaceutically acceptable carrier, diluent or excipient" includes without limitation any adjuvant, carrier, excipient, glidant, sweetening agent, diluent, preservative, dye, colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

The term "effective amount" or "therapeutically effective amount" refers to that amount of a compound described herein that is sufficient to affect the intended application, including but not limited to disease treatment, as defined below. The therapeutically effective amount may vary depending upon the intended treatment application (in vivo), or the subject and disease condition being treated, e.g., the weight and age of the subject, the severity of the disease condition, the manner of administration and the like, which can readily be determined by one of ordinary skill in the art. The term also applies to a dose that will induce a particular response in target cells, e.g., reduction of platelet adhesion and/or cell migration. The specific dose will vary depending on the particular compounds chosen, the dosing regimen to be followed, whether it is administered in combination with other compounds, timing of administration, the tissue to which it is administered, and the physical delivery system in which it is carried.

As used herein, "treatment" or "treating" refers to an approach for obtaining beneficial or desired results with respect to a disease, disorder, or medical condition including but not limited to a therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the subject, notwithstanding that the subject may still be afflicted with the underlying disorder. In certain embodiments, for prophylactic benefit, the compositions are administered to a subject at risk of developing a particular disease, or to a subject reporting one or more of the physiological symptoms of a disease, even though a diagnosis of this disease may not have been made.

A "therapeutic effect," as that term is used herein, encompasses a therapeutic benefit and/or a prophylactic benefit as described above. A prophylactic effect includes delaying or eliminating the appearance of a disease or condition, delaying or eliminating the onset of symptoms of a disease or condition, slowing, halting, or reversing the progression of a disease or condition, or any combination thereof.

The term "co-administration," "administered in combination with," and their grammatical equivalents, as used herein, encompass administration of two or more agents to an animal, including humans, so that both agents and/or their metabolites are present in the subject at the same time. Co-administration includes simultaneous administration in separate compositions, administration at different times in separate compositions, or administration in a composition in which both agents are present.

The terms "antagonist" and "inhibitor" are used interchangeably, and they refer to a compound having the ability to inhibit a biological function (e.g., activity, expression, binding, protein-protein interaction) of a target protein or enzyme (e.g., CD73). Accordingly, the terms "antagonist" and "inhibitor" are defined in the context of the biological role of the target protein. While preferred antagonists herein specifically interact with (e.g., bind to) the target, compounds that inhibit a biological activity of the target protein by interacting with other members of the signal transduction pathway of which the target protein is a member are also specifically included within this definition. A preferred biological activity inhibited by an antagonist is associated with the development, growth, or spread of a tumor.

The term "agonist" as used herein refers to a compound having the ability to initiate or enhance a biological function of a target protein, whether by inhibiting the activity or expression of the target protein. Accordingly, the term "agonist" is defined in the context of the biological role of the target polypeptide. While preferred agonists herein specifically interact with (e.g., bind to) the target, compounds that initiate or enhance a biological activity of the target polypeptide by interacting with other members of the signal transduction pathway of which the target polypeptide is a member are also specifically included within this definition.

"Signal transduction" is a process during which stimulatory or inhibitory signals are transmitted into and within a cell to elicit an intracellular response. A modulator of a signal transduction pathway refers to a compound which modulates the activity of one or more cellular proteins mapped to the same specific signal transduction pathway. A modulator may augment (agonist) or suppress (antagonist) the activity of a signaling molecule.

An "anti-cancer agent", "anti-tumor agent" or "chemotherapeutic agent" refers to any agent useful in the treatment of a neoplastic condition. One class of anti-cancer agents comprises chemotherapeutic agents. "Chemotherapy" means the administration of one or more chemotherapeutic drugs and/or other agents to a cancer patient by various methods, including intravenous, oral, intramuscular, intraperitoneal, intravesical, subcutaneous, transdermal, buccal, or inhalation or in the form of a suppository.

The term "cell proliferation" refers to a phenomenon by which the cell number has changed as a result of division. This term also encompasses cell growth by which the cell morphology has changed (e.g., increased in size) consistent with a proliferative signal.

The term "selective inhibition" or "selectively inhibit" refers to the ability of a biologically active agent to preferentially reduce the target signaling activity as compared to off-target signaling activity, via direct or indirect interaction with the target.

"Subject" refers to an animal, such as a mammal, for example a human. The methods described herein can be useful in both human therapeutics and veterinary applications. In some embodiments, the subject is a mammal, and in some embodiments, the subject is human. "Mammal" includes humans and both domestic animals such as laboratory animals and household pets (e.g., cats, dogs, swine, cattle, sheep, goats, horses, rabbits), and non-domestic animals such as wildlife and the like.

"Prodrug" is meant to indicate a compound that may be converted under physiological conditions or by solvolysis to a biologically active compound described herein (e.g., compound of Formula (I), (I-A), (I-B), (I-C), (II), (II-A), (II-B), (II-C), (III), (III-A), (III-B) or (III-C)). Thus, the term "prodrug" refers to a precursor of a biologically active compound that is pharmaceutically acceptable. In some aspects, a prodrug is inactive when administered to a subject but is converted in vivo to an active compound, for example, by hydrolysis. In some aspects, a prodrug has reduced activity compared to that of the parent compound. The prodrug compound often offers advantages of oral bioavailability, solubility, tissue compatibility or delayed release in a mammalian organism (see, e.g., Bundgard, H., Design of Prodrugs (1985), pp. 7-9, 21-24 (Elsevier, Amsterdam); Higuchi, T., et al., "Pro-drugs as Novel Delivery Systems," (1987) A.C.S. Symposium Series, Vol. 14; and Bioreversible Carriers in Drug Design, ed. Edward B. Roche, American Pharmaceutical Association and Pergamon Press) each of which is incorporated in full by reference herein. The term "prodrug" is also meant to include any covalently bonded carriers, which release the active compound in vivo when such prodrug is administered to a mammalian subject. Prodrugs of an active compound, as described herein, are typically prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a mammalian subject, cleaves to form a free hydroxy, free amino or free mercapto group, respectively. Examples of prodrugs include, but are not limited to, acetate, formate and benzoate derivatives of a hydroxy functional group, or acetamide, formamide and benzamide derivatives of an amine functional group in the active compound and the like.

The term "in vivo" refers to an event that takes place in a subject's body.

The term "in vitro" refers to an event that takes places outside of a subject's body. For example, an in vitro assay encompasses any assay run outside of a subject. In vitro assays encompass cell-based assays in which cells alive or dead are employed. In vitro assays also encompass a cell-free assay in which no intact cells are employed.

The disclosure is also meant to encompass the in vivo metabolic products of the disclosed compounds. Such products may result from, for example, the oxidation, reduction, hydrolysis, amidation, esterification, and the like of the administered compound, primarily due to enzymatic processes. Accordingly, the disclosure includes compounds produced by a process comprising administering a compound of this disclosure to a mammal for a period of time sufficient to yield a metabolic product thereof. Such products are typically identified by administering a radiolabeled compound of the disclosure in a detectable dose to an animal, such as rat, mouse, guinea pig, monkey, or to human, allowing sufficient time for metabolism to occur, and isolating its conversion products from the urine, blood or other biological samples.

The chemical naming protocol and structure diagrams used herein are a modified form of the I.U.P.A.C. nomenclature system, using ChemDraw Professional 15.1 or OpenEye Scientific Software's mol2nam application. For complex chemical names employed herein, a substituent group is typically named before the group to which it attaches. For example, cyclopropylethyl comprises an ethyl backbone with a cyclopropyl substituent. Except as described below, all bonds are identified in the chemical structure diagrams herein, except for all bonds on some carbon atoms, which are assumed to be bonded to sufficient hydrogen atoms to complete the valency.

The present disclosure provides compounds that are capable of selectively binding to and/or modulating CD73. In some embodiments, the compounds modulate CD73 by binding to or interacting with one or more amino acids. The binding of these compounds may disrupt the ability of CD73 to hydrolyze adenosine monophosphate (AMP).

In certain aspects, the present disclosure provides a compound of Formula (I):

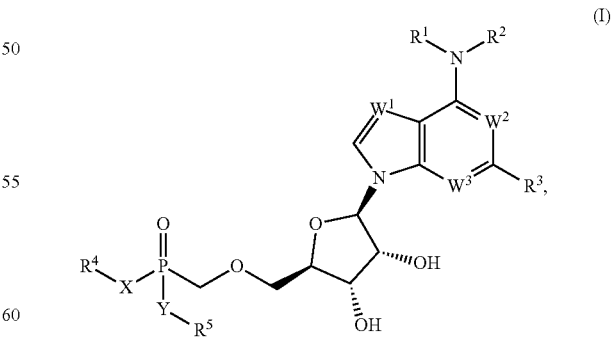

(I)

or a pharmaceutically acceptable salt thereof, wherein:
$W^1$, $W^2$ and $W^3$ are each independently selected from N and $CR^6$, wherein at least one of $W^1$, $W^2$ and $W^3$ is N;
$R^1$ is selected from hydrogen; and $C_{1-6}$ alkyl and $C_{3-12}$ carbocycle, each of which is optionally substituted with one or more $R^7$;

$R^2$ is selected from $C_{1-6}$ alkyl, $C_{3-12}$ carbocycle, 3- to 12-membered heterocycle and benzyl, each of which is optionally substituted with one or more $R^7$; or $R^1$ and $R^2$ are taken together with the nitrogen atom to which they are attached to form a 3- to 12-membered heterocycle, optionally substituted with one or more $R^7$;

$R^3$ is selected from halogen and cyano; and $C_{1-6}$ alkyl, $C_{3-12}$ carbocycle, 3- to 12-membered heterocycle and benzyl, each of which is optionally substituted with one or more $R^7$;

X and Y are independently selected from —O— and —NR$^8$—;

$R^4$ and $R^5$ are independently selected from:
hydrogen; and
$C_{1-6}$ alkyl and phenyl, each of which is independently optionally substituted at each occurrence with one or more substituents selected from halogen, —NO$_2$, —CN, —OR$^8$, —SR$^8$, —N(R$^8$)$_2$, —NR$^9$R$^{10}$, —S(=O)R$^8$, —S(=O)$_2$R$^8$, —S(=O)$_2$N(R$^8$)$_2$, —S(=O)$_2$NR$^9$R$^{10}$, —NR$^8$S(=O)$_2$R$^8$, —NR$^8$S(=O)$_2$N(R$^8$)$_2$, —NR$^8$S(=O)$_2$NR$^9$R$^{10}$, —S—S—R$^8$, —S—C(O)R$^8$, —C(O)R$^8$, —C(O)OR$^8$, —OC(O)R$^8$, —OC(O)OR$^8$, —OC(O)N(R$^8$)$_2$, —OC(O)NR$^9$R$^{10}$, —NR$^8$C(O)R$^8$, —NR$^8$C(O)OR$^8$, —NR$^8$C(O)N(R$^8$)$_2$, —NR$^8$C(O)NR$^9$R$^{10}$, —C(O)N(R$^8$)$_2$, —C(O)NR$^9$R$^{10}$, —P(O)(OR$^8$)$_2$, —P(O)(R$^8$)$_2$, —OP(O)(OR$^8$)$_2$, =O, =S, =N(R$^8$), $C_{3-12}$ carbocycle, and 3- to 12-membered heterocycle;

$R^6$ is selected from hydrogen, halogen and cyano; and $C_{1-6}$ alkyl, optionally substituted with one or more $R^7$;

$R^7$ is independently selected at each occurrence from:
halogen, —NO$_2$, —CN, —OR$^8$, —SR$^8$, —N(R$^8$)$_2$, —NR$^9$R$^{10}$, —S(=O)R$^8$, —S(=O)$_2$R$^8$, —S(=O)$_2$N(R$^8$)$_2$, —S(=O)$_2$NR$^9$R$^{10}$, —NR$^8$S(=O)$_2$R$^8$, —NR$^8$S(=O)$_2$N(R$^8$)$_2$, —NR$^8$S(=O)$_2$NR$^9$R$^{10}$, —C(O)R$^8$, —C(O)OR$^8$, —OC(O)R$^8$, —OC(O)OR$^8$, —OC(O)N(R$^8$)$_2$, —OC(O)NR$^9$R$^{10}$, —NR$^8$C(O)R$^8$, —NR$^8$C(O)OR$^8$, —NR$^8$C(O)N(R$^8$)$_2$, —NR$^8$C(O)NR$^9$R$^{10}$, —C(O)N(R$^8$)$_2$, —C(O)NR$^9$R$^{10}$, —P(O)(OR$^8$)$_2$, —P(O)(R$^8$)$_2$, =O, =S, and =N(R$^8$);

$C_{1-10}$ alkyl, $C_{2-10}$ alkenyl, and $C_{2-10}$ alkynyl, each of which is independently optionally substituted at each occurrence with one or more substituents selected from halogen, —NO$_2$, —CN, —OR$^8$, —SR$^8$, —N(R$^8$)$_2$, —NR$^9$R$^{10}$, —S(=O)R$^8$, —S(=O)$_2$R$^8$, —S(=O)$_2$N(R$^8$)$_2$, —S(=O)$_2$NR$^9$R$^{10}$, —NR$^8$S(=O)$_2$R$^8$, —NR$^8$S(=O)$_2$N(R$^8$)$_2$, —NR$^8$S(=O)$_2$NR$^9$R$^{10}$, —C(O)R$^8$, —C(O)OR$^8$, —OC(O)R$^8$, —OC(O)OR$^8$, —OC(O)N(R$^8$)$_2$, —OC(O)NR$^9$R$^{10}$, —NR$^8$C(O)R$^8$, —NR$^8$C(O)OR$^8$, —NR$^8$C(O)N(R$^8$)$_2$, —NR$^8$C(O)NR$^9$R$^{10}$, —C(O)N(R$^8$)$_2$, —C(O)NR$^9$R$^{10}$, —P(O)(OR$^8$)$_2$, —P(O)(R$^8$)$_2$, =O, =S, =N(R$^8$), $C_{3-12}$ carbocycle, and 3- to 12-membered heterocycle; and $C_{3-12}$ carbocycle and 3- to 12-membered heterocycle, wherein each $C_{3-12}$ carbocycle and 3- to 12-membered heterocycle in $R^7$ is independently optionally substituted with one or more substituents selected from halogen, —NO$_2$, —CN, —OR$^8$, —SR$^8$, —N(R$^8$)$_2$, —NR$^9$R$^{10}$, —S(=O)R$^8$, —S(=O)$_2$R$^8$, —S(=O)$_2$N(R$^8$)$_2$, —S(=O)$_2$NR$^9$R$^{10}$, —NR$^8$S(=O)$_2$R$^8$, —NR$^8$S(=O)$_2$N(R$^8$)$_2$, —NR$^8$S(=O)$_2$NR$^9$R$^{10}$, —C(O)R$^8$, —C(O)OR$^8$, —OC(O)R$^8$, —OC(O)OR$^8$, —OC(O)N(R$^8$)$_2$, —OC(O)NR$^9$R$^{10}$, —NR$^8$C(O)R$^8$, —NR$^8$C(O)OR$^8$, —NR$^8$C(O)N(R$^8$)$_2$, —NR$^8$C(O)NR$^9$R$^{10}$, —C(O)N(R$^8$)$_2$, —C(O)NR$^9$R$^{10}$, —P(O)(OR$^8$)$_2$, —P(O)(R$^8$)$_2$, =O, =S, =N(R$^8$), $C_{1-6}$ alkyl, $C_{1-6}$ haloalkyl, $C_{2-6}$ alkenyl, and $C_{2-6}$ alkynyl;

$R^8$ is independently selected at each occurrence from hydrogen; and $C_{1-20}$ alkyl, $C_{2-20}$ alkenyl, $C_{2-20}$ alkynyl, 1- to 6-membered heteroalkyl, $C_{3-12}$ carbocycle, and 3- to 12-membered heterocycle, each of which is optionally substituted by halogen, —CN, —NO$_2$, —NH$_2$, —NHCH$_3$, —NHCH$_2$CH$_3$, =O, —OH, —OCH$_3$, —OCH$_2$CH$_3$, $C_{3-12}$ carbocycle, or 3- to 6-membered heterocycle; and $R^9$ and $R^{10}$ are taken together with the nitrogen atom to which they are attached to form a heterocycle, optionally substituted with one or more $R^7$.

In some embodiments, for a compound of Formula (I), $R^1$ is selected from hydrogen and $C_{1-6}$ alkyl, wherein the $C_{1-6}$ alkyl is optionally substituted with one or more $R^7$. In some embodiments, $R^1$ is selected from hydrogen and —CH$_3$.

In some embodiments, for a compound of Formula (I), $R^2$ is selected from $C_{1-6}$ alkyl, $C_{3-12}$ carbocycle, 3- to 12-membered heterocycle and benzyl, each of which is optionally substituted with one or more substituents independently selected from halogen, —CN, $C_{1-4}$ alkyl, $C_{1-3}$ haloalkyl, —OH and —NH$_2$. In some embodiments, $R^2$ is benzyl, optionally substituted with one or more $R^7$. In some embodiments, $R^2$ is benzyl, optionally substituted with one or more substituents independently selected from halogen, —CN, $C_{1-4}$ alkyl, $C_{1-3}$ haloalkyl, —OH and —NH$_2$. In some embodiments, $R^2$ is $C_{1-6}$ alkyl or $C_{3-8}$ cycloalkyl, each of which is optionally substituted with one or more substituents independently selected from halogen, —CN, $C_{1-3}$ haloalkyl, —OH, —NH$_2$, optionally substituted phenyl and optionally substituted pyridyl. In some embodiments, $R^2$ is $C_{3-8}$ cycloalkyl, such as cyclopropyl, cyclobutyl, cyclopentyl or cyclohexyl. In some embodiments, $R^2$ is $C_{1-4}$ alkyl, such as methyl, ethyl, propyl, isopropyl, n-butyl, sec-butyl, isobutyl or tert-butyl. In some embodiments, $R^2$ is $C_{1-6}$ alkyl, $C_{3-8}$ cycloalkyl, or benzyl, each of which is optionally substituted with one or more substituents independently selected from halogen, —CN, $C_{1-4}$ alkyl, $C_{1-3}$ haloalkyl, —OH and —NH$_2$.

In some embodiments, for a compound of Formula (I), $R^1$ and $R^2$ are taken together with the nitrogen atom to which they are attached to form a 3- to 12-membered heterocycle, optionally substituted with one or more $R^7$, such as one or more substituents independently selected from halogen, —CN, $C_{1-4}$ alkyl, $C_{1-3}$ haloalkyl, —OH and —NH$_2$. In some embodiments, $R^1$ and $R^2$ are taken together with the nitrogen atom to which they are attached to form an optionally substituted 3- to 7-membered monocyclic heterocycloalkyl or an optionally substituted 5- to 12-membered fused bicyclic heterocycloalkyl. The 3- to 12-membered heterocycle formed by $R^1$, $R^2$ and the nitrogen atom to which they are attached may be selected from

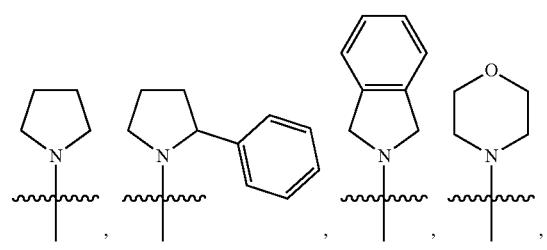

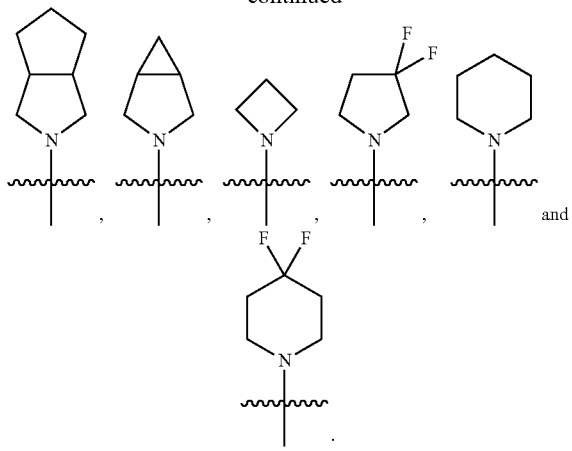

In some embodiments, a compound of Formula (I) is represented by Formula (I-A) or (I-B):

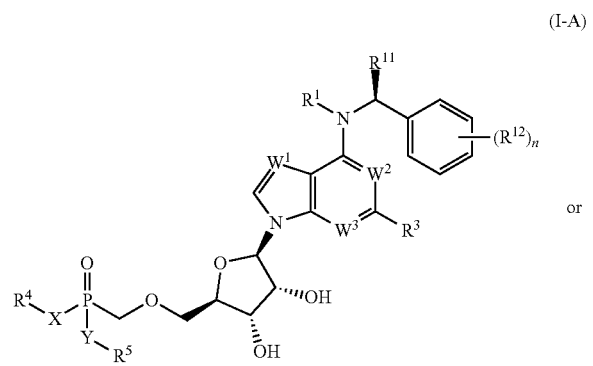

(I-A)

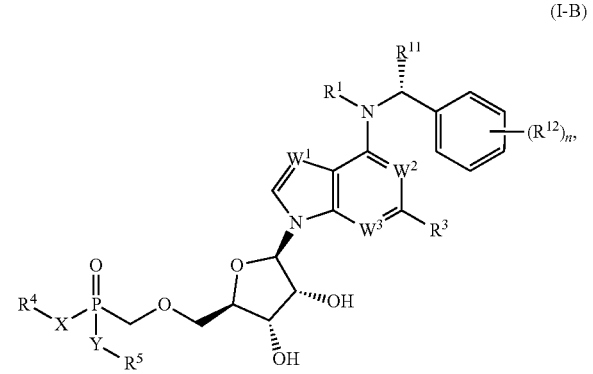

(I-B)

or a pharmaceutically acceptable salt thereof, wherein:
$R^{11}$ is selected from $C_{1-6}$ alkyl and $C_{3-12}$ carbocycle, each of which is optionally substituted with one or more $R^7$;
$R^{12}$ is independently selected at each occurrence from $R^7$; and
n is an integer from 0 to 3.

In some embodiments, for a compound of Formula (I-A) or (I-B), $R^{11}$ is $C_{1-6}$ alkyl, such as $C_{1-4}$ alkyl. In some embodiments, $R^{11}$ is selected from methyl, ethyl, iso-propyl and tert-butyl. In some embodiments, $R^{11}$ is selected from $C_{1-4}$ alkyl and $C_{3-12}$ cycloalkyl, each of which is optionally substituted with one or more $R^7$. In some embodiments, $R^{11}$ is —$CH_3$. In some embodiments, $R^{11}$ is selected from $R^7$.

In some embodiments, for a compound of Formula (I-A) or (I-B), $R^{12}$ is independently selected at each occurrence from halogen, —CN, alkoxy, haloalkoxy, alkyl and haloalkyl. In some embodiments, $R^{12}$ is independently selected at each occurrence from halogen, —CN, $C_{1-4}$ alkoxy, $C_{1-4}$ haloalkoxy, $C_{1-4}$ alkyl and $C_{1-4}$ haloalkyl. In some embodiments, $R^{12}$ is independently selected at each occurrence from halogen, —CN, $C_{1-4}$ alkoxy, $C_{1-4}$ fluoroalkoxy, $C_{1-4}$ alkyl and $C_{1-4}$ haloalkyl. In some embodiments, $R^{12}$ is independently selected at each occurrence from halogen, —CN, $C_{1-4}$ alkyl and $C_{1-3}$ haloalkyl. In some embodiments, $R^{12}$ is independently selected at each occurrence from F, —CN, —$CH_3$ and —$CF_3$. In some embodiments, $R^{12}$ is independently selected at each occurrence from halogen, —CN, —$CH_3$ and —$CF_3$.

In some embodiments, for a compound of Formula (I-A) or (I-B), n is an integer from 1 to 3, such as n is 1.

In some embodiments, for a compound of Formula (I-A) or (I-B):
$R^{11}$ is selected from $C_{1-6}$ alkyl, optionally substituted with one or more $R^7$;
$R^{12}$ is independently selected at each occurrence from halogen, —CN, $C_{1-4}$ alkyl and $C_{1-3}$ haloalkyl; and
n is an integer from 1 to 3.

In some embodiments, for a compound of Formula (I-A) or (I-B):
$R^{11}$ is selected from $C_{1-6}$ alkyl and $C_{3-12}$ carbocycle, each of which is optionally substituted with one or more $R^7$;
$R^{12}$ is independently selected at each occurrence from halogen, —CN, alkoxy, haloalkoxy, alkyl and haloalkyl; and
n is an integer from 0 to 3.

In some embodiments, a compound of Formula (I) is represented by Formula (I-C):

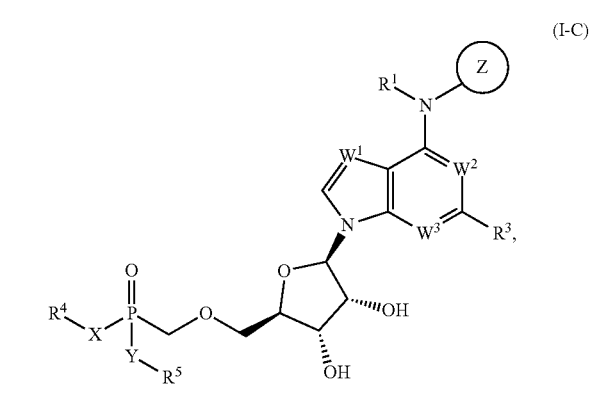

(I-C)

or a pharmaceutically acceptable salt thereof, wherein:
Z is selected from $C_{3-12}$ cycloalkyl and 3- to 12-membered heterocycloalkyl, each of which is optionally substituted with one or more $R^7$.

In some embodiments, for a compound of Formula (I-C), Z is selected from $C_{3-12}$ monocyclic cycloalkyl or $C_{5-12}$ fused bicyclic cycloalkyl, each of which is optionally substituted with one or more $R^7$. In some embodiments, Z is $C_{5-12}$ fused bicyclic cycloalkyl, optionally substituted with one or more $R^7$. In some embodiments, Z is selected from $C_{3-12}$ monocyclic cycloalkyl or $C_{5-12}$ bicyclic cycloalkyl, each of which is optionally substituted with one or more $R^7$. In some embodiments, Z is substituted with one or more substituents independently selected from halogen, —CN, $C_{1-4}$ alkyl and $C_{1-3}$ haloalkyl. In some embodiments, Z is selected from

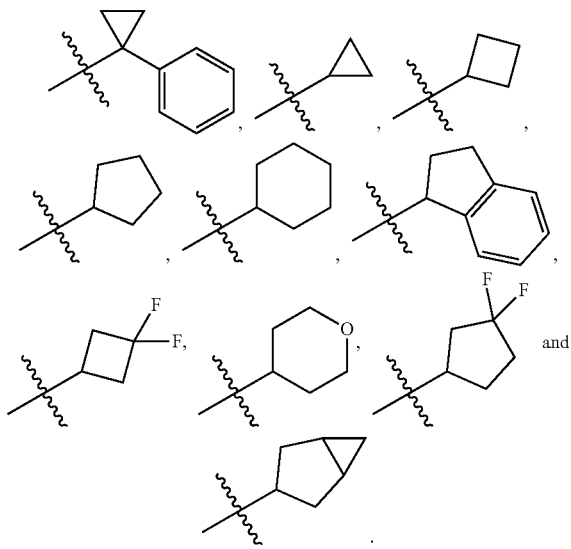

In some embodiments, for a compound of Formula (I), (I-A), (I-B) or (I-C), $R^1$ is selected from hydrogen and $C_{1-6}$ alkyl, wherein the $C_{1-6}$ alkyl is optionally substituted with one or more $R^7$. In some embodiments, $R^1$ is selected from hydrogen and —$CH_3$. In some embodiments, $R^1$ is $C_{1-6}$ alkyl, such as —$CH_3$.

In some embodiments, for a compound of Formula (I), (I-A), (I-B) or (I-C), $W^3$ is N. In some embodiments, $W^2$ is N or CH, such as $W^2$ is N. In some embodiments, $W^1$ is N. In some embodiments, $W^3$ is N and $W^2$ and $W^1$ are independently N or CH. In some embodiments, $W^1$ is CH, $W^2$ is N and $W^3$ is N. In some embodiments, $W^1$ is N, $W^2$ is CH and $W^3$ is N. In some embodiments, $W^1$, $W^2$ and $W^3$ are each N.

In some embodiments, for a compound of Formula (I), (I-A), (I-B) or (I-C), $R^3$ is selected from halogen and cyano; and $C_{1-6}$ alkyl, aryl, heteroaryl and benzyl, each of which is optionally substituted with one or more $R^7$. In some embodiments, $R^3$ is selected from halogen, —CN, $C_{1-3}$ alkyl and $C_{1-3}$ haloalkyl. In some embodiments, $R^3$ is selected from —Cl and —CN.

In some embodiments, for a compound of Formula (I), (I-A), (I-B) or (I-C), at least one of $R^4$ and $R^5$ is $C_{1-6}$ alkyl, optionally substituted at each occurrence with one or more substituents selected from halogen, —$OR^8$, —S—S—$R^8$, —S—C(O)$R^8$, —OC(O)$R^8$, —OC(O)O$R^8$ and —P(O)(O$R^8$)$_2$.

In some embodiments, for a compound of Formula (I), (I-A), (I-B) or (I-C), $R^4$ and $R^5$ are independently selected from $C_{1-6}$ alkyl, optionally substituted at each occurrence with one or more substituents selected from halogen, —$OR^8$, —S—S—$R^8$, —S—C(O)$R^8$, —OC(O)$R^8$, —OC(O)O$R^8$ and —P(O)(O$R^8$)$_2$. In some embodiments, $R^4$ and $R^5$ are independently selected from —$CH_2$OC(O)$R^8$ and —$CH_2$OC(O)O$R^8$. In some embodiments, $R^4$ and $R^5$ are independently selected from —$CH_2$OC(O)C(CH$_3$)$_3$, —$CH_2$OC(O)OCH(CH$_3$)$_2$, —$CH_2$OC(O)CH$_3$, —$CH_2$CH$_2$—S—S—(CH$_2$)$_2$OH and —$CH_2$CH$_2$—S—C(O)CH$_3$.

In some embodiments, for a compound of Formula (I), (I-A), (I-B) or (I-C), $R^4$ is phenyl, optionally substituted with —$OR^8$; $R^5$ is $C_{1-6}$ alkyl substituted with one or more substituents selected from —OC(O)$R^8$, —C(O)O$R^8$, and —OC(O)O$R^8$; and $R^8$ is $C_{1-6}$ alkyl.

In some embodiments, for a compound of Formula (I), (I-A), (I-B) or (I-C), X and Y are each —O—. In some embodiments, one of X and Y is —O— and the other one of X and Y is —$NR^8$—.

In some embodiments, for a compound of Formula (I), (I-A), (I-B) or (I-C): $W^1$ is selected from N and $CR^6$; $W^2$ is selected from N and CH; $W^3$ is N; $R^1$ is selected from hydrogen and $C_{1-4}$ alkyl; $R^3$ is selected from halogen and cyano; and $R^6$ is selected from halogen, cyano and $C_{1-4}$ alkyl.

In some embodiments, for a compound of Formula (I), (I-A), (I-B) or (I-C), —X—$R^4$ and —Y—$R^5$ are each —OH.

In some embodiments, for a compound of Formula (I), (I-A), (I-B) or (I-C), at least one of $R^4$ and $R^5$ is selected from $C_{1-6}$ alkyl, $C_{2-6}$ alkenyl, and $C_{2-6}$ alkynyl, each of which is independently optionally substituted at each occurrence with one or more substituents selected from halogen, —$NO_2$, —CN, —$OR^8$, —$SR^8$, —$N(R^8)_2$, —$NR^9R^{10}$, —S(=O)$R^8$, —S(=O)$_2R^8$, —S(=O)$_2N(R^8)_2$, —S(=O)$_2NR^9R^{10}$, —$NR^8$S(=O)$_2R^8$, —$NR^8$S(=O)$_2N(R^8)_2$, —$NR^8$S(=O)$_2NR^9R^{10}$, —S—S—$R^8$, —S—C(O)$R^8$, —C(O)$R^8$, —C(O)O$R^8$, —OC(O)$R^8$, —OC(O)O$R^8$, —OC(O)N($R^8$)$_2$, —OC(O)N$R^9R^{10}$, —$NR^8$C(O)$R^8$, —$NR^8$C(O)O$R^8$, —$NR^8$C(O)N($R^8$)$_2$, —$NR^8$C(O)N$R^9R^{10}$, —C(O)N($R^8$)$_2$, —C(O)N$R^9R^{10}$, —P(O)(O$R^8$)$_2$, —P(O)($R^8$)$_2$, —OP(O)(O$R^8$)$_2$, =O, =S, =N($R^8$); and $C_{3-12}$ carbocycle, and 3- to 12-membered heterocycle, each of which is independently optionally substituted at each occurrence with one or more substituents selected from halogen, $C_{1-6}$ alkyl, —$OR^8$, —OC(O)$R^8$, and —C(O)$R^8$.

In some embodiments, for a compound of Formula (I), (I-A), (I-B) or (I-C), $R^4$ and $R^5$ are independently selected from $C_{1-6}$ alkyl, $C_{2-6}$ alkenyl, and $C_{2-6}$ alkynyl, each of which is independently optionally substituted at each occurrence with one or more substituents selected from halogen, —$NO_2$, —CN, —$OR^8$, —$SR^8$, —$N(R^8)_2$, —$NR^9R^{10}$, —S(=O)$R^8$, —S(=O)$_2R^8$, —S(=O)$_2N(R^8)_2$, —S(=O)$_2NR^9R^{10}$, —$NR^8$S(=O)$_2R^8$, —$NR^8$S(=O)$_2N(R^8)_2$, —$NR^8$S(=O)$_2NR^9R^{10}$, —S—S—$R^8$, —S—C(O)$R^8$, —C(O)$R^8$, —C(O)O$R^8$, —OC(O)$R^8$, —OC(O)O$R^8$, —OC(O)N($R^8$)$_2$, —OC(O)N$R^9R^{10}$, —$NR^8$C(O)$R^8$, —$NR^8$C(O)O$R^8$, —$NR^8$C(O)N($R^8$)$_2$, —$NR^8$C(O)N$R^9R^{10}$, —C(O)N($R^8$)$_2$, —C(O)N$R^9R^{10}$, —P(O)(O$R^8$)$_2$, —P(O)($R^8$)$_2$, —OP(O)(O$R^8$)$_2$, =O, =S, =N($R^8$); and $C_{3-12}$ carbocycle, and 3- to 12-membered heterocycle, each of which is independently optionally substituted at each occurrence with one or more substituents selected from halogen, $C_{1-6}$ alkyl, —$OR^8$, —OC(O)$R^8$, and —C(O)$R^8$.

In some embodiments, for a compound of Formula (I), (I-A), (I-B) or (I-C), $R^4$ and $R^5$ are independently selected from $C_{1-6}$ alkyl substituted with one or more substituents selected from halogen, —OC(O)$R^8$, —OC(O)O$R^8$, —S—S—$R^8$, —S—C(O)$R^8$, —$OR^8$, and —P(O)(O$R^8$)$_2$. In some embodiments, $R^4$ and $R^5$ are independently selected from hydrogen and $C_{1-6}$ alkyl, wherein each $C_{1-6}$ alkyl is optionally substituted at each occurrence with one or more substituents selected from halogen, —OC(O)$R^8$, —OC(O)O$R^8$, —S—S—$R^8$, —S—C(O)$R^8$, —$OR^8$, and —P(O)(O$R^8$)$_2$. In some embodiments, $R^4$ and $R^5$ are independently selected from $C_{1-6}$ alkyl substituted with one or more substituents selected from —OC(O)$R^8$ and —OC(O)O$R^8$. In some embodiments, $R^4$ and $R^5$ are independently selected from $C_1$ alkyl substituted with one or more substituents selected from —OC(O)$R^8$ and —OC(O)O$R^8$, wherein $R^8$ is $C_{1-6}$ alkyl. In some embodiments, $R^4$ and $R^5$ are independently selected from —CH₂OC(O)C(CH₃)₃, —CH₂OC(O)OCH(CH₃)₂, and —CH₂OC(O)CH₃. In some embodiments, $R^4$ and $R^5$ are each —CH₂OC(O)C(CH₃)₃. In some embodiments, $R^4$ and $R^5$ are each —CH₂OC(O)OCH(CH₃)₂.

In some embodiments, for a compound of Formula (I), (I-A), (I-B) or (I-C), $R^4$ and $R^5$ are independently selected from $C_{1-6}$ alkyl substituted with one or more substituents selected from —S—S—$R^8$, and —S—C(O)$R^8$. In some embodiments, $R^4$ and $R^5$ are independently selected from —CH₂CH₂—S—S—(CH₂)₂OH and —CH₂CH₂—S—C(O)CH₃. In some embodiments, $R^4$ and $R^5$ are each —CH₂CH₂—S—S—(CH₂)₂OH. In some embodiments, $R^4$ and $R^5$ are each —CH₂CH₂—S—C(O)CH₃.

In some embodiments, for a compound of Formula (I), (I-A), (I-B) or (I-C), $R^4$ and $R^5$ are independently selected from $C_{3-12}$ carbocycle, such as phenyl, wherein the $C_{3-12}$ carbocycle is optionally substituted with one or more substituents selected from halogen, $C_{1-6}$ alkyl, —O$R^8$, —OC(O)$R^8$, —C(O)O$R^8$, and —C(O)$R^8$. In some embodiments, $R^4$ and $R^5$ are independently selected from phenyl, wherein the phenyl is optionally substituted with —O$R^8$, such as phenyl substituted with —OCH₂CH₃. In some embodiments, one of $R^4$ and $R^5$ is selected from $C_{3-12}$ carbocycle, such as phenyl and benzyl, and the other of $R^4$ and $R^5$ is selected from $C_{1-6}$ alkyl substituted with one or more substituents selected from —OC(O)$R^8$, —C(O)O$R^8$, and —OC(O)O$R^8$, wherein $R^8$ is $C_{1-6}$ alkyl.

In some embodiments, for a compound of Formula (I), (I-A), (I-B) or (I-C), $R^4$ and $R^5$ are independently selected from hydrogen and $C_{1-6}$ alkylene-O$R^{20}$, wherein $R^{20}$ at each occurrence is independently selected from $C_{7-20}$ alkyl and $C_{7-20}$ alkenyl. In some embodiments, one of $R^4$ or $R^5$ is selected from —$C_{1-3}$alkylene-O—$C_{7-20}$alkyl and —$C_{1-3}$alkylene-O—$C_{7-20}$alkenyl, such as one of $R^4$ or $R^5$ is selected from hexadecyloxypropyl (—CH₂(CH₂)₂O(CH₂)₁₅CH₃), octadecyloxyethyl (—CH₂CH₂O(CH₂)₁₇CH₃), oleyoxyethyl (—CH₂CH₂O(CH₂)₈CH═CH(CH₂)₇CH₃), and oleyoxypropyl (—CH₂(CH₂)₂O(CH₂)₈CH═CH(CH₂)₇CH₃), and the other of $R^4$ and $R^5$ is hydrogen.

In some embodiments, for a compound of Formula (I), (I-A), (I-B) or (I-C), $R^4$ and $R^5$ are taken together with the atoms to which they are attached to form a heterocycle, optionally substituted with one or more $R^7$. In some embodiments, the heterocycle is a 5- or 6-membered heterocycle. In some embodiments, $R^4$ and $R^5$ are taken together with the atoms to which they are attached to form a heterocycle selected from:

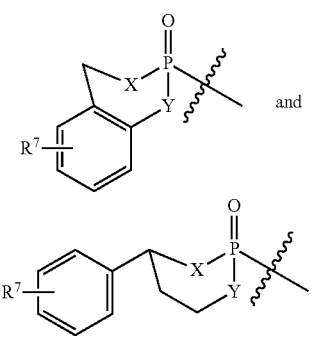

and

In some embodiments, $R^7$ is a halogen.

In some embodiments, for a compound of Formula (I), (I-A), (I-B) or (I-C), X and Y are each —O—. In some embodiments, one of X and Y is —O— and the other one of X and Y is —N($R^8$)—. In some embodiments, at least one of —X—$R^4$ and —Y—$R^5$ comprises an amino acid or an amino acid ester, such as an L-alanine ester, e.g., —NHCH(CH₃)C(O)OCH(CH₃)₂ and —NHCH(CH₃)C(O)OCH₂CH₃. In some embodiments, at least one of —X—$R^4$ and —Y—$R^5$ comprises alanine, serine, phenylalanine, valine, or two or more thereof.

In some embodiments, for a compound of Formula (I), (I-A), (I-B) or (I-C), —X—$R^4$ and —Y—$R^5$ are independently selected from: —OH, —O—CH₃, —O—CH₂CH₃, —O—CH₂-Ph, —O-Ph,

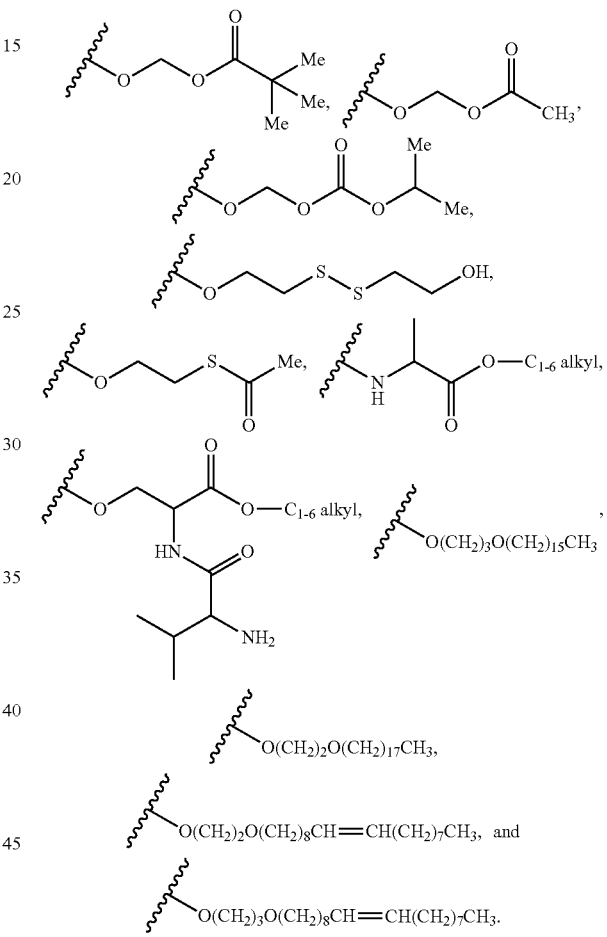

In some embodiments, —X—$R^4$ and —Y—$R^5$ are different, such as —X—$R^4$ is —OH and —Y—$R^5$ is —O(CH₂)₃O(CH₂)₁₅CH₃. In some embodiments, one of —X—$R^4$ and —Y—$R^5$ is —OH, and the other one of —X—$R^4$ and —Y—$R^5$ is selected from

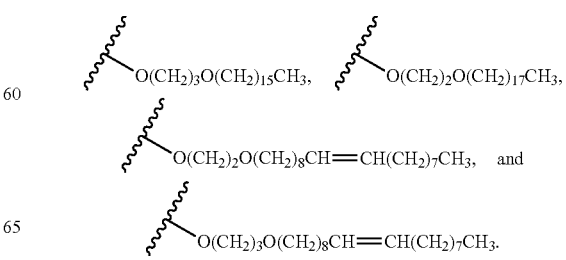

In some embodiments, —X—R⁴ and —Y—R⁵ are selected from the same moieties, for example, —X—R⁴ is

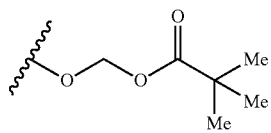 [SMILES: *OCOC(=O)C(C)(C)C]

and —Y—R⁵ is

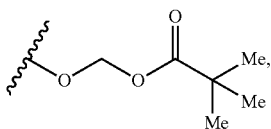 [SMILES: *OCOC(=O)C(C)(C)C]

or —X-R⁴ is

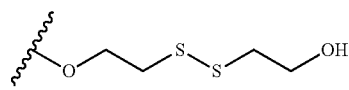 [SMILES: *OCCSSCCO]

and —Y—R⁵ is

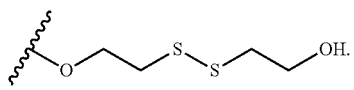 [SMILES: *OCCSSCCO]

In some embodiments, —X—R⁴ and —Y—R⁵ are each —O—CH₃, —O—CH₂CH₃, —O—CH₂Ph, —OPh,

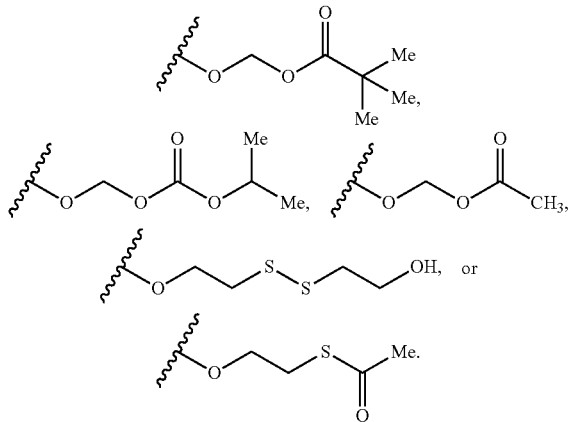

In some embodiments, for a compound of Formula (I), (I-A), (I-B) or (I-C), —X—R⁴ is selected from: —OH, —OCH₃, —OCH₂CH₃, —OCH₂Ph, —OPh,

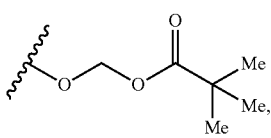

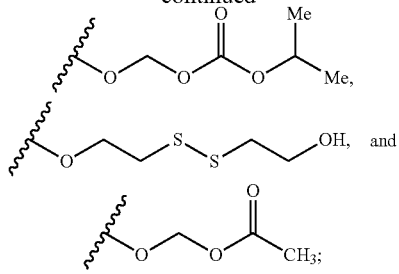

and —Y—R⁵ is selected from —OCH₃, —OCH₂CH₃, —OCH₂Ph, —OPh,

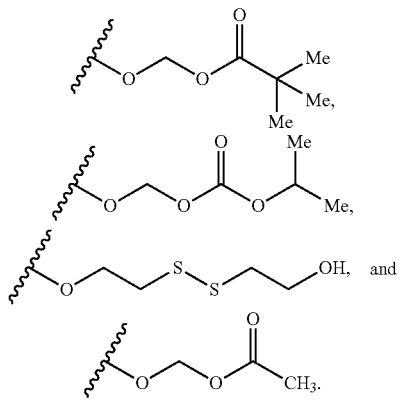

In some embodiments, for a compound of Formula (I), (I-A), (I-B) or (I-C):
W¹ and W² are each independently selected from N and CH, wherein at least one of W¹ and W² is N;
W³ is N;
R¹ is selected from hydrogen and $C_{1-6}$ alkyl; wherein the $C_{1-6}$ alkyl is optionally substituted with one or more R⁷;
R³ is selected from halogen, —CN, $C_{1-3}$ alkyl and $C_{1-3}$ haloalkyl;
X and Y are each —O—; and
R⁴ and R⁵ are each hydrogen.

In some embodiments, for a compound of Formula (I), (I-A), (I-B) or (I-C):
W¹ and W² are CH;
W³ is N;
R¹ is selected from hydrogen and $C_{1-6}$ alkyl; wherein the $C_{1-6}$ alkyl is optionally substituted with one or more R⁷;
R³ is selected from halogen, —CN, $C_{1-3}$ alkyl, aryl, heteroaryl and $C_{1-3}$ haloalkyl;
X and Y are each —O—; and
R⁴ and R⁵ are each hydrogen.

In some embodiments, for a compound of Formula (I), (II-A), (II-B) or (III):
W¹ and W² are each independently selected from N and CH, wherein at least one of W¹ and W² is N;
W³ is N;
R¹ is selected from hydrogen and $C_{1-6}$ alkyl; wherein the $C_{1-6}$ alkyl is optionally substituted with one or more R⁷;
R³ is selected from halogen, —CN, $C_{1-3}$ alkyl and $C_{1-3}$ haloalkyl;
X and Y are independently selected from —O— and —NR⁸—, wherein at least one of X and Y is —O—; and
R⁴ and R⁵ are independently selected from $C_{1-6}$ alkyl substituted with one or more substituents selected from halogen, —OC(O)R⁸, —OC(O)OR⁸, —S—S—R⁸, —S—C(O)R⁸, —OR⁸, and —P(O)(OR⁸)₂.

In some embodiments, for a compound of Formula (I), (I-A), (I-B) or (I-C):

$W^1$ and $W^2$ are CH;
$W^3$ is N;
$R^1$ is selected from hydrogen and $C_{1-6}$ alkyl; wherein the $C_{1-6}$ alkyl is optionally substituted with one or more $R^7$;
$R^3$ is selected from halogen, —CN, $C_{1-3}$ alkyl, aryl, heteroaryl and $C_{1-3}$ haloalkyl;
X and Y are independently selected from —O— and —NR⁸—, wherein at least one of X and Y is —O—; and
$R^4$ and $R^5$ are independently selected from $C_{1-6}$ alkyl substituted with one or more substituents selected from halogen, —OC(O)R⁸, —OC(O)OR⁸, —S—S—R⁸, —S—C(O)R⁸, —OR⁸, and —P(O)(OR⁸)₂.

In some embodiments, for a compound of Formula (I), (I-A), (I-B) or (I-C):

$W^1$ and $W^2$ are each independently selected from N and CH, wherein at least one of $W^1$ and $W^2$ is N;
$W^3$ is N;
$R^1$ is selected from hydrogen and $C_{1-6}$ alkyl; wherein the $C_{1-6}$ alkyl is optionally substituted with one or more $R^7$;
$R^3$ is selected from halogen, —CN, $C_{1-3}$ alkyl and $C_{1-3}$ haloalkyl; and
—X—R⁴ and —Y—R⁵ are independently selected from: —OH, —O—CH₃, —O—CH₂CH₃, —O—CH₂-Ph, —O-Ph,

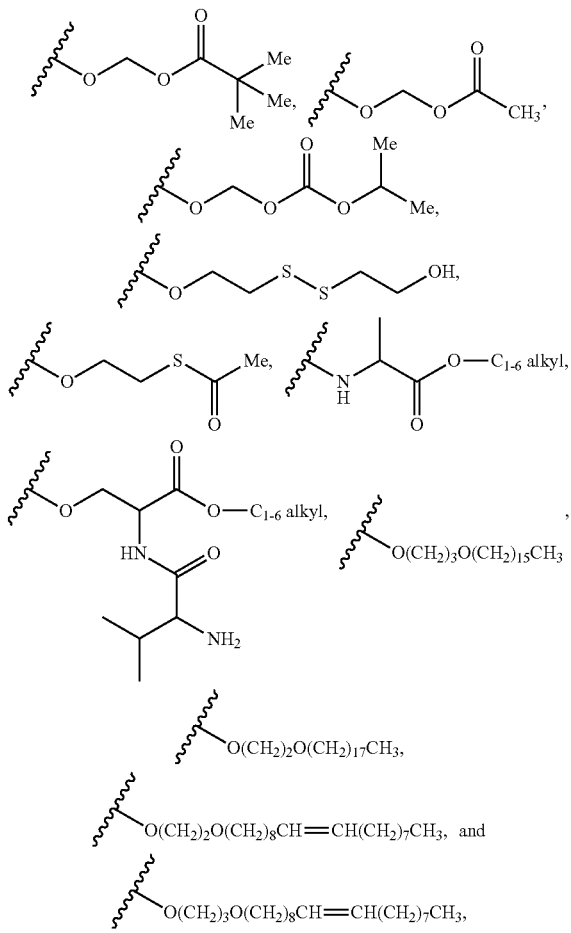

wherein at least one of —X—R⁴ and —Y—R⁵ is not —OH.

In certain aspects, the present disclosure provides a compound of Formula (I-A) or (I-B):

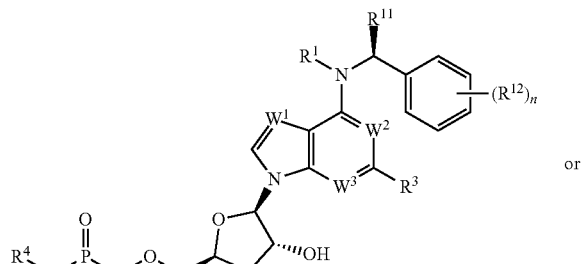

(I-A)

or

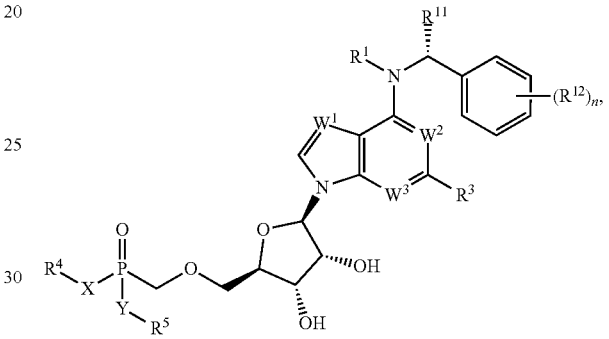

(I-B)

or a pharmaceutically acceptable salt thereof, wherein:

$W^1$, $W^2$ and $W^3$ are each independently selected from N and CH, wherein at least one of $W^1$, $W^2$ and $W^3$ is N;

$R^1$ is selected from hydrogen and $C_{1-6}$ alkyl;

$R^3$ is selected from halogen and cyano;

—X—R⁴ is selected from —OH, —OCH₃, —OCH₂CH₃, —OCH₂Ph, —OPh,

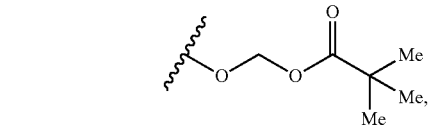

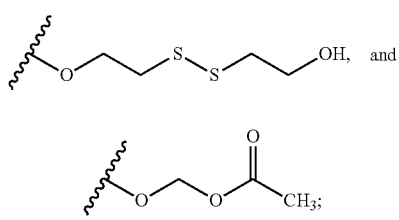

—Y—R⁵ is selected from —OCH₃, —OCH₂CH₃, —OCH₂Ph, —OPh,

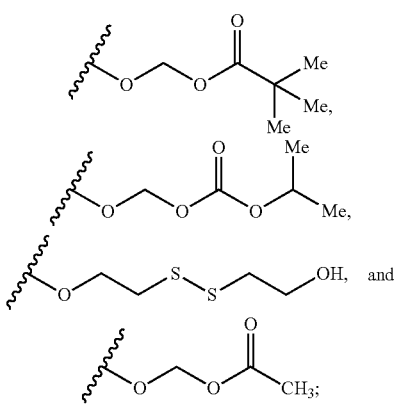

$R^7$ is independently selected at each occurrence from: halogen, —NO$_2$, —CN, —OR$^8$, —SR$^8$, —N(R$^8$)$_2$, —NR$^9$R$^{10}$, —S(=O)R$^8$, —S(=O)$_2$R$^8$, —S(=O)$_2$N(R$^8$)$_2$, —S(=O)$_2$NR$^9$R$^{10}$, —NR$^8$S(=O)$_2$R$^8$, —NR$^8$S(=O)$_2$N(R$^8$)$_2$, —NR$^8$S(=O)$_2$NR$^9$R$^{10}$, —C(O)R$^8$, —C(O)OR$^8$, —OC(O)R$^8$, —OC(O)OR$^8$, —OC(O)N(R$^8$)$_2$, —OC(O)NR$^9$R$^{10}$, —NR$^8$C(O)R$^8$, —NR$^8$C(O)OR$^8$, —NR$^8$C(O)N(R$^8$)$_2$, —NR$^8$C(O)NR$^9$R$^{10}$, —C(O)N(R$^8$)$_2$, —C(O)NR$^9$R$^{10}$, —P(O)(OR$^8$)$_2$, —P(O)(R$^8$)$_2$, =O, =S, and =N(R$^8$);

C$_{1-10}$ alkyl, C$_{2-10}$ alkenyl, and C$_{2-10}$ alkynyl, each of which is independently optionally substituted at each occurrence with one or more substituents selected from halogen, —NO$_2$, —CN, —OR$^8$, —SR$^8$, —N(R$^8$)$_2$, —NR$^9$R$^{10}$, —S(=O)R$^8$, —S(=O)$_2$R$^8$, —S(=O)$_2$N(R$^8$)$_2$, —S(=O)$_2$NR$^9$R$^{10}$, —NR$^8$S(=O)$_2$R$^8$, —NR$^8$S(=O)$_2$N(R$^8$)$_2$, —NR$^8$S(=O)$_2$NR$^9$R$^{10}$, —C(O)R$^8$, —C(O)OR$^8$, —OC(O)R$^8$, —OC(O)OR$^8$, —OC(O)N(R$^8$)$_2$, —OC(O)NR$^9$R$^{10}$, —NR$^8$C(O)R$^8$, —NR$^8$C(O)OR$^8$, —NR$^8$C(O)N(R$^8$)$_2$, —NR$^8$C(O)NR$^9$R$^{10}$, —C(O)N(R$^8$)$_2$, —C(O)NR$^9$R$^{10}$, —P(O)(OR$^8$)$_2$, —P(O)(R$^8$)$_2$, =O, =S, =N(R$^8$), C$_{3-12}$ carbocycle, and 3- to 12-membered heterocycle; and C$_{3-12}$ carbocycle and 3- to 12-membered heterocycle, wherein each C$_{3-12}$ carbocycle and 3- to 12-membered heterocycle in R$^7$ is independently optionally substituted with one or more substituents selected from halogen, —NO$_2$, —CN, —OR$^8$, —SR$^8$, —N(R$^8$)$_2$, —NR$^9$R$^{10}$, —S(=O)R$^8$, —S(=O)$_2$R$^8$, —S(=O)$_2$N(R$^8$)$_2$, —S(=O)$_2$NR$^9$R$^{10}$, —NR$^8$S(=O)$_2$R$^8$, —NR$^8$S(=O)$_2$N(R$^8$)$_2$, —NR$^8$S(=O)$_2$NR$^9$R$^{10}$, —C(O)R$^8$, —C(O)OR$^8$, —OC(O)R$^8$, —OC(O)OR$^8$, —OC(O)N(R$^8$)$_2$, —OC(O)NR$^9$R$^{10}$, —NR$^8$C(O)R$^8$, —NR$^8$C(O)OR$^8$, —NR$^8$C(O)N(R$^8$)$_2$, —NR$^8$C(O)NR$^9$R$^{10}$, —C(O)N(R$^8$)$_2$, —C(O)NR$^9$R$^{10}$, —P(O)(OR$^8$)$_2$, —P(O)(R$^8$)$_2$, =O, =S, =N(R$^8$), C$_{1-6}$ alkyl, C$_{1-6}$ haloalkyl, C$_{2-6}$ alkenyl, and C$_{2-6}$ alkynyl;

R$^8$ is independently selected at each occurrence from hydrogen; and C$_{1-20}$ alkyl, C$_{2-20}$ alkenyl, C$_{2-20}$ alkynyl, 1- to 6-membered heteroalkyl, C$_{3-12}$ carbocycle, and 3- to 12-membered heterocycle, each of which is optionally substituted by halogen, —CN, —NO$_2$, —NH$_2$, —NHCH$_3$, —NHCH$_2$CH$_3$, =O, —OH, —OCH$_3$, —OCH$_2$CH$_3$, C$_{3-12}$ carbocycle, or 3- to 6-membered heterocycle;

R$^9$ and R$^{10}$ are taken together with the nitrogen atom to which they are attached to form a heterocycle, optionally substituted with one or more R$^7$;

R$^{11}$ is selected from C$_{1-6}$ alkyl and C$_{3-12}$ carbocycle, each of which is optionally substituted with one or more R$^7$;

R$^{12}$ is independently selected at each occurrence from halogen, —CN, C$_{1-4}$ alkyl and C$_{1-3}$ haloalkyl; and n is an integer from 0 to 3.

In certain aspects, the present disclosure provides a compound of Formula (I-A) or (I-B):

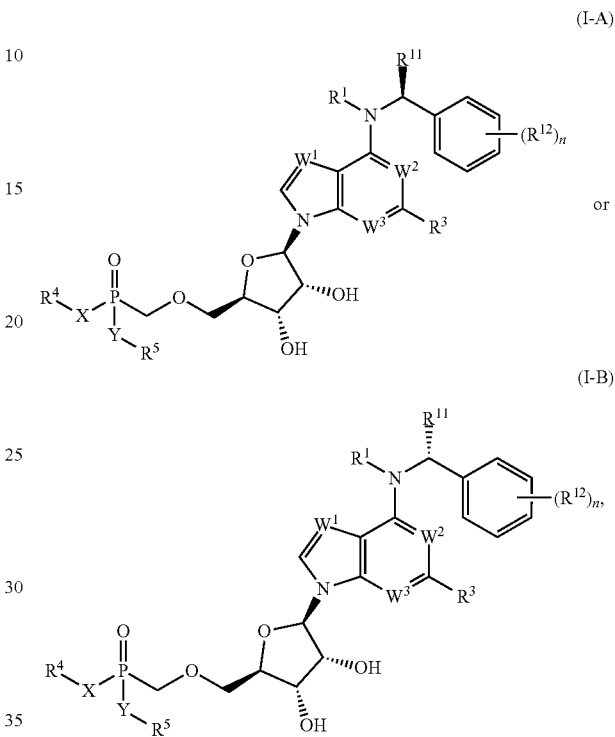

or a pharmaceutically acceptable salt thereof, wherein:

W$^1$, W$^2$ and W$^3$ are each independently selected from N and CH, wherein at least one of W$^1$, W$^2$ and W$^3$ is N;

R$^1$ is selected from hydrogen and C$_{1-6}$ alkyl; wherein the C$_{1-6}$ alkyl is optionally substituted with one or more R$^7$;

R$^3$ is selected from halogen and cyano;

—X—R$^4$ is selected from —OH, —OCH$_3$, —OCH$_2$CH$_3$, —OCH$_2$Ph, —OPh,

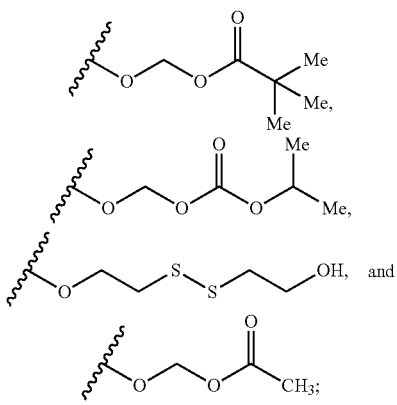

—Y—R$^5$ is selected from —OCH$_3$, —OCH$_2$CH$_3$, —OCH$_2$Ph, —OPh,

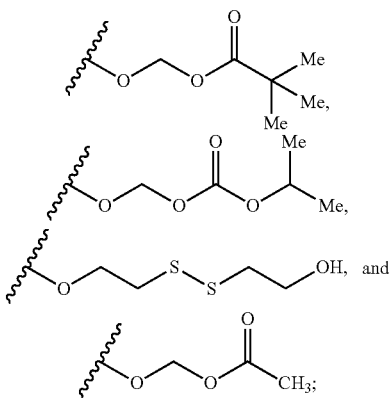

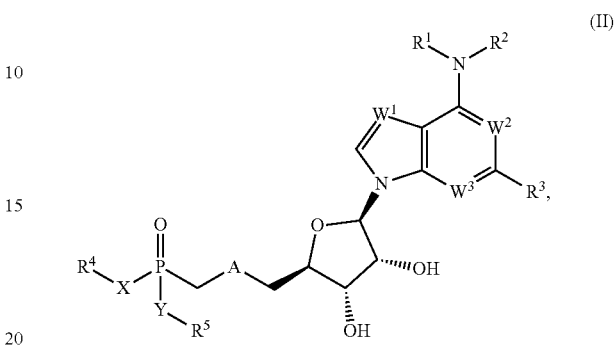

$R^7$ is independently selected at each occurrence from:
halogen, —NO₂, —CN, —OR⁸, —SR⁸, —N(R⁸)₂, —NR⁹R¹⁰, —S(═O)R⁸, —S(═O)₂R⁸, —S(═O)₂N(R⁸)₂, —S(═O)₂NR⁹R¹⁰, —NR⁸S(═O)₂R⁸, —NR⁸S(═O)₂N(R⁸)₂, —NR⁸S(═O)₂NR⁹R¹⁰, —C(O)R⁸, —C(O)OR⁸, —OC(O)R⁸, —OC(O)OR⁸, —OC(O)N(R⁸)₂, —OC(O)NR⁹R¹⁰, —NR⁸C(O)R⁸, —NR⁸C(O)OR⁸, —NR⁸C(O)N(R⁸)₂, —NR⁸C(O)NR⁹R¹⁰, —C(O)N(R⁸)₂, —C(O)NR⁹R¹⁰, —P(O)(OR⁸)₂, —P(O)(R⁸)₂, ═O, ═S, and ═N(R⁸);

$C_{1-10}$ alkyl, $C_{2-10}$ alkenyl, and $C_{2-10}$ alkynyl, each of which is independently optionally substituted at each occurrence with one or more substituents selected from halogen, —NO₂, —CN, —OR⁸, —SR⁸, —N(R⁸)₂, —NR⁹R¹⁰, —S(═O)R⁸, —S(═O)₂R⁸, —S(═O)₂N(R⁸)₂, —S(═O)₂NR⁹R¹⁰, —NR⁸S(═O)₂R⁸, —NR⁸S(═O)₂N(R⁸)₂, —NR⁸S(═O)₂NR⁹R¹⁰, —C(O)R⁸, —C(O)OR⁸, —OC(O)R⁸, —OC(O)OR⁸, —OC(O)N(R⁸)₂, —OC(O)NR⁹R¹⁰, —NR⁸C(O)R⁸, —NR⁸C(O)OR⁸, —NR⁸C(O)N(R⁸)₂, —NR⁸C(O)NR⁹R¹⁰, —C(O)N(R⁸)₂, —C(O)NR⁹R¹⁰, —P(O)(OR⁸)₂, —P(O)(R⁸)₂, ═O, ═S, ═N(R⁸), $C_{3-12}$ carbocycle, and 3- to 12-membered heterocycle; and $C_{3-12}$ carbocycle and 3- to 12-membered heterocycle, wherein each $C_{3-12}$ carbocycle and 3- to 12-membered heterocycle in $R^7$ is independently optionally substituted with one or more substituents selected from halogen, —NO₂, —CN, —OR⁸, —SR⁸, —N(R⁸)₂, —NR⁹R¹⁰, —S(═O)R⁸, —S(═O)₂R⁸, —S(═O)₂N(R⁸)₂, —S(═O)₂NR⁹R¹⁰, —NR⁸S(═O)₂R⁸, —NR⁸S(═O)₂N(R⁸)₂, —NR⁸S(═O)₂NR⁹R¹⁰, —C(O)R⁸, —C(O)OR⁸, —OC(O)R⁸, —OC(O)OR⁸, —OC(O)N(R⁸)₂, —OC(O)NR⁹R¹⁰, —NR⁸C(O)R⁸, —NR⁸C(O)OR⁸, —NR⁸C(O)N(R⁸)₂, —NR⁸C(O)NR⁹R¹⁰, —C(O)N(R⁸)₂, —C(O)NR⁹R¹⁰, —P(O)(OR⁸)₂, —P(O)(R⁸)₂, ═O, ═S, ═N(R⁸), $C_{1-6}$ alkyl, $C_{1-6}$ haloalkyl, $C_{2-6}$ alkenyl, and $C_{2-6}$ alkynyl;

$R^8$ is independently selected at each occurrence from hydrogen; and $C_{1-20}$ alkyl, $C_{2-20}$ alkenyl, $C_{2-20}$ alkynyl, 1- to 6-membered heteroalkyl, $C_{3-12}$ carbocycle, and 3- to 12-membered heterocycle, each of which is optionally substituted by halogen, —CN, —NO₂, —NH₂, —NHCH₃, —NHCH₂CH₃, ═O, —OH, —OCH₃, —OCH₂CH₃, $C_{3-12}$ carbocycle, or 3- to 6-membered heterocycle;

$R^9$ and $R^{10}$ are taken together with the nitrogen atom to which they are attached to form a heterocycle, optionally substituted with one or more $R^7$;

$R^{11}$ is selected from $C_{1-6}$ alkyl and $C_{3-12}$ carbocycle, each of which is optionally substituted with one or more $R^7$;

$R^{12}$ is independently selected at each occurrence from halogen, —CN, $C_{1-4}$ alkyl and $C_{1-3}$ haloalkyl; and n is an integer from 0 to 3.

In certain aspects, the present disclosure provides a compound of Formula (II):

or a pharmaceutically acceptable salt thereof, wherein:

$W^1$, $W^2$ and $W^3$ are each independently selected from N and $CR^6$, wherein at least one of $W^1$, $W^2$ and $W^3$ is N;

$R^1$ is selected from hydrogen; and $C_{1-6}$ alkyl and $C_{3-12}$ carbocycle, each of which is optionally substituted with one or more $R^7$;

$R^2$ is selected from $C_{1-6}$ alkyl, $C_{3-12}$ carbocycle, 3- to 12-membered heterocycle and benzyl, each of which is optionally substituted with one or more $R^7$; or $R^1$ and $R^2$ are taken together with the nitrogen atom to which they are attached to form a 3- to 12-membered heterocycle, optionally substituted with one or more $R^7$;

$R^3$ is selected from hydrogen, halogen and cyano; and $C_{1-6}$ alkyl, $C_{3-12}$ carbocycle, 3- to 12-membered heterocycle and benzyl, each of which is optionally substituted with one or more $R^7$;

A is selected from —S—, —S(═O)— and —S(═O)₂—;

X and Y are independently selected from —O— and —NR⁸—;

$R^4$ and $R^5$ are independently selected from:
hydrogen; and
$C_{1-6}$ alkyl and phenyl, each of which is independently optionally substituted at each occurrence with one or more substituents selected from halogen, —NO₂, —CN, —OR⁸, —SR⁸, —N(R⁸)₂, —NR⁹R¹⁰, —S(═O)R⁸, —S(═O)₂R⁸, —S(═O)₂N(R⁸)₂, —S(═O)₂NR⁹R¹⁰, —NR⁸S(═O)₂R⁸, —NR⁸S(═O)₂N(R⁸)₂, —NR⁸S(═O)₂NR⁹R¹⁰, —S—S—R⁸, —S—C(O)R⁸, —C(O)R⁸, —C(O)OR⁸, —OC(O)R⁸, —OC(O)OR⁸, —OC(O)N(R⁸)₂, —OC(O)NR⁹R¹⁰, —NR⁸C(O)R⁸, —NR⁸C(O)OR⁸, —NR⁸C(O)N(R⁸)₂, —NR⁸C(O)NR⁹R¹⁰, —C(O)N(R⁸)₂, —C(O)NR⁹R¹⁰, —P(O)(OR⁸)₂, —P(O)(R⁸)₂, —OP(O)(OR⁸)₂, ═O, ═S, ═N(R⁸), $C_{3-12}$ carbocycle, and 3- to 12-membered heterocycle;

$R^6$ is selected from hydrogen, halogen and cyano; and $C_{1-6}$ alkyl, optionally substituted with one or more $R^7$;

$R^7$ is independently selected at each occurrence from:
halogen, —NO₂, —CN, —OR⁸, —SR⁸, —N(R⁸)₂, —NR⁹R¹⁰, —S(═O)R⁸, —S(═O)₂R⁸, —S(═O)₂N(R⁸)₂, —S(═O)₂NR⁹R¹⁰, —NR⁸S(═O)₂R⁸, —NR⁸S(═O)₂N(R⁸)₂, —NR⁸S(═O)₂NR⁹R¹⁰, —C(O)R⁸, —C(O)OR⁸, —OC(O)R⁸, —OC(O)OR⁸, —OC(O)N(R⁸)₂, —OC(O)NR⁹R¹⁰, —NR⁸C(O)R⁸, —NR⁸C(O)

—OR⁸, —NR⁸C(O)N(R⁸)₂, —NR⁸C(O)NR⁹R¹⁰, —C(O)N(R⁸)₂, —C(O)NR⁹R¹⁰, —P(O)(OR⁸)₂, —P(O)(R⁸)₂, =O, =S, and =N(R⁸);

C$_{1-10}$ alkyl, C$_{2-10}$ alkenyl, and C$_{2-10}$ alkynyl, each of which is independently optionally substituted at each occurrence with one or more substituents selected from halogen, —NO₂, —CN, —OR⁸, —SR⁸, —N(R⁸)₂, —NR⁹R¹⁰, —S(=O)R⁸, —S(=O)₂R⁸, —S(=O)₂N(R⁸)₂, —S(=O)₂NR⁹R¹⁰, —NR⁸S(=O)₂R⁸, —NR⁸S(=O)₂N(R⁸)₂, —NR⁸S(=O)₂NR⁹R¹⁰, —C(O)R⁸, —C(O)OR⁸, —OC(O)R⁸, —OC(O)OR⁸, —OC(O)N(R⁸)₂, —OC(O)NR⁹R¹⁰, —NR⁸C(O)R⁸, —NR⁸C(O)OR⁸, —NR⁸C(O)N(R⁸)₂, —NR⁸C(O)NR⁹R¹⁰, —C(O)N(R⁸)₂, —C(O)NR⁹R¹⁰, —P(O)(OR⁸)₂, —P(O)(R⁸)₂, =O, =S, =N(R⁸), C$_{3-12}$ carbocycle, and 3- to 12-membered heterocycle; and C$_{3-12}$ carbocycle and 3- to 12-membered heterocycle, wherein each C$_{3-12}$ carbocycle and 3- to 12-membered heterocycle in R⁷ is independently optionally substituted with one or more substituents selected from halogen, —NO₂, —CN, —OR⁸, —SR⁸, —N(R⁸)₂, —NR⁹R¹⁰, —S(=O)R⁸, —S(=O)₂R⁸, —S(=O)₂N(R⁸)₂, —S(=O)₂NR⁹R¹⁰, —NR⁸S(=O)₂R⁸, —NR⁸S(=O)₂N(R⁸)₂, —NR⁸S(=O)₂NR⁹R¹⁰, —C(O)R⁸, —C(O)OR⁸, —OC(O)R⁸, —OC(O)OR⁸, —OC(O)N(R⁸)₂, —OC(O)NR⁹R¹⁰, —NR⁸C(O)R⁸, —NR⁸C(O)OR⁸, —NR⁸C(O)N(R⁸)₂, —NR⁸C(O)NR⁹R¹⁰, —C(O)N(R⁸)₂, —C(O)NR⁹R¹⁰, —P(O)(OR⁸)₂, —P(O)(R⁸)₂, =O, =S, =N(R⁸), C$_{1-6}$ alkyl, C$_{1-6}$ haloalkyl, C$_{2-6}$ alkenyl, and C$_{2-6}$ alkynyl;

R⁸ is independently selected at each occurrence from hydrogen; and C$_{1-20}$ alkyl, C$_{2-20}$ alkenyl, C$_{2-20}$ alkynyl, 1- to 6-membered heteroalkyl, C$_{3-12}$ carbocycle, and 3- to 12-membered heterocycle, each of which is optionally substituted by halogen, —CN, —NO₂, —NH₂, —NHCH₃, —NHCH₂CH₃, =O, —OH, —OCH₃, —OCH₂CH₃, C$_{3-12}$ carbocycle, or 3- to 6-membered heterocycle; and R⁹ and R¹⁰ are taken together with the nitrogen atom to which they are attached to form a heterocycle, optionally substituted with one or more R⁷.

In some embodiments, for a compound of Formula (II), R¹ is selected from hydrogen and C$_{1-6}$ alkyl, wherein the C$_{1-6}$ alkyl is optionally substituted with one or more R⁷. In some embodiments, R is selected from hydrogen and —CH₃.

In some embodiments, for a compound of Formula (II), R² is selected from C$_{1-6}$ alkyl, C$_{3-12}$ carbocycle, 3- to 12-membered heterocycle and benzyl, each of which is optionally substituted with one or more substituents independently selected from halogen, —CN, C$_{1-4}$ alkyl, C$_{1-3}$ haloalkyl, —OH and —NH₂. In some embodiments, R² is benzyl, optionally substituted with one or more R⁷. In some embodiments, R² is benzyl, optionally substituted with one or more substituents independently selected from halogen, —CN, C$_{1-4}$ alkyl, C$_{1-3}$ haloalkyl, —OH and —NH₂. In some embodiments, R² is C$_{1-6}$ alkyl or C$_{3-8}$ cycloalkyl, each of which is optionally substituted with one or more substituents independently selected from halogen, —CN, C$_{1-3}$ haloalkyl, —OH, —NH₂, optionally substituted phenyl and optionally substituted pyridyl. In some embodiments, R² is C$_{3-8}$ cycloalkyl, such as cyclopropyl, cyclobutyl, cyclopentyl or cyclohexyl. In some embodiments, R² is C$_{1-4}$ alkyl, such as methyl, ethyl, propyl, isopropyl, n-butyl, sec-butyl, isobutyl or tert-butyl. In some embodiments, R² is C$_{1-6}$ alkyl, C$_{3-8}$ cycloalkyl, or benzyl, each of which is optionally substituted with one or more substituents independently selected from halogen, —CN, C$_{1-4}$ alkyl, C$_{1-3}$ haloalkyl, —OH and —NH₂.

In some embodiments, for a compound of Formula (II), R¹ and R² are taken together with the nitrogen atom to which they are attached to form a 3- to 12-membered heterocycle, optionally substituted with one or more R⁷, such as one or more substituents independently selected from halogen, —CN, C$_{1-4}$ alkyl, C$_{1-3}$ haloalkyl, —OH and —NH₂. In some embodiments, R¹ and R² are taken together with the nitrogen atom to which they are attached to form an optionally substituted 3- to 7-membered monocyclic heterocycloalkyl or an optionally substituted 5- to 12-membered fused bicyclic heterocycloalkyl. The 3- to 12-membered heterocycle formed by R¹, R² and the nitrogen atom to which they are attached may be selected from

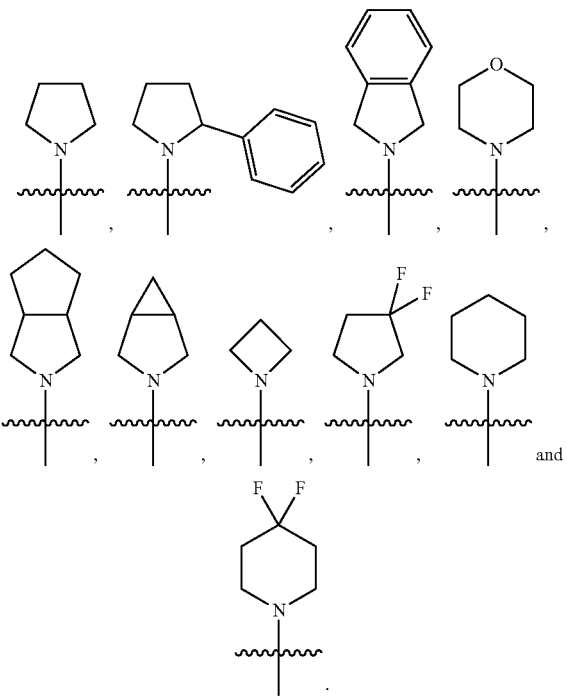

In some embodiments, a compound of Formula (II) is represented by Formula (II-A) or (II-B):

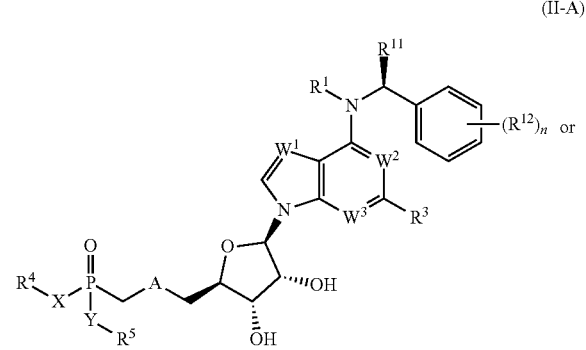

(II-A)

-continued (II-B)

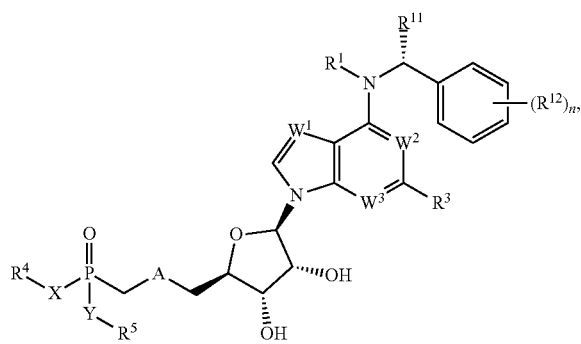

or a pharmaceutically acceptable salt thereof, wherein:

$R^{11}$ is selected from hydrogen, $C_{1-6}$ alkyl and $C_{3-12}$ carbocycle, each of which is optionally substituted with one or more $R^7$;

$R^{12}$ is independently selected at each occurrence from $R^7$; and n is an integer from 0 to 3.

In some embodiments, for a compound of Formula (II-A) or (II-B), $R^{11}$ is selected from $C_{1-6}$ alkyl and $C_{3-12}$ carbocycle, each of which is optionally substituted with one or more $R^7$; $R^{12}$ is independently selected at each occurrence from $R^7$; and n is an integer from 0 to 3.

In some embodiments, for a compound of Formula (II-A) or (II-B), $R^{11}$ is $C_{1-6}$ alkyl, such as $C_{1-4}$ alkyl. In some embodiments, $R^{11}$ is selected from methyl, ethyl, iso-propyl and tert-butyl. In some embodiments, $R^{11}$ is selected from $C_{1-4}$ alkyl and $C_{3-12}$ cycloalkyl, each of which is optionally substituted with one or more $R^7$. In some embodiments, $R^{11}$ is —$CH_3$. In some embodiments, $R^{11}$ is selected from $R^7$.

In some embodiments, for a compound of Formula (II-A) or (II-B), $R^{12}$ is independently selected at each occurrence from halogen, —CN, alkoxy, haloalkoxy, alkyl and haloalkyl. In some embodiments, $R^{12}$ is independently selected at each occurrence from halogen, —CN, $C_{1-4}$ alkoxy, $C_{1-4}$ haloalkoxy, $C_{1-4}$ alkyl and $C_{1-4}$ haloalkyl. In some embodiments, $R^{12}$ is independently selected at each occurrence from halogen, —CN, $C_{1-4}$ alkoxy, $C_{1-4}$ fluoroalkoxy, $C_{1-4}$ alkyl and $C_{1-4}$ haloalkyl. In some embodiments, $R^{12}$ is independently selected at each occurrence from halogen, —CN, $C_{1-4}$ alkyl and $C_{1-3}$ haloalkyl. In some embodiments, $R^{12}$ is independently selected at each occurrence from F, —CN, —$CH_3$ and —$CF_3$. In some embodiments, $R^{12}$ is independently selected at each occurrence from halogen, —CN, —$CH_3$ and —$CF_3$.

In some embodiments, for a compound of Formula (II-A) or (II-B), n is an integer from 1 to 3, such as n is 1.

In some embodiments, for a compound of Formula (II-A) or (II-B):

$R^{11}$ is selected from $C_{1-6}$ alkyl, optionally substituted with one or more $R^7$;

$R^{12}$ is independently selected at each occurrence from halogen, —CN, $C_{1-4}$ alkyl and $C_{1-3}$ haloalkyl; and n is an integer from 1 to 3.

In some embodiments, for a compound of Formula (II-A) or (II-B):

$R^{11}$ is selected from $C_{1-6}$ alkyl and $C_{3-12}$ carbocycle, each of which is optionally substituted with one or more $R^7$;

$R^{12}$ is independently selected at each occurrence from halogen, —CN, alkoxy, haloalkoxy, alkyl and haloalkyl; and n is an integer from 0 to 3.

In some embodiments, a compound of Formula (II) is represented by Formula (II-C):

(II-C)

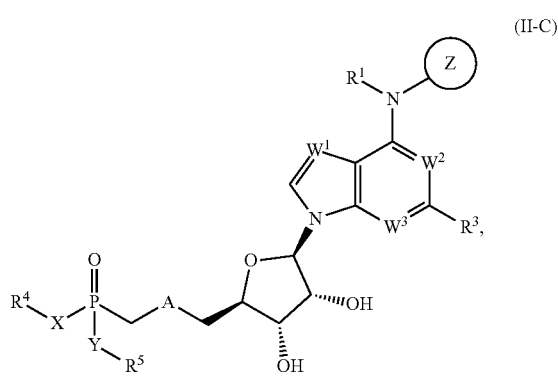

or a pharmaceutically acceptable salt thereof, wherein:

Z is selected from $C_{3-12}$ cycloalkyl and 3- to 12-membered heterocycloalkyl, each of which is optionally substituted with one or more $R^7$.

In some embodiments, for a compound of Formula (II-C), Z is selected from $C_{3-12}$ monocyclic cycloalkyl or $C_{5-12}$ fused bicyclic cycloalkyl, each of which is optionally substituted with one or more $R^7$. In some embodiments, Z is $C_{5-12}$ fused bicyclic cycloalkyl, optionally substituted with one or more $R^7$. In some embodiments, Z is selected from $C_{3-12}$ monocyclic cycloalkyl or $C_{5-12}$ bicyclic cycloalkyl, each of which is optionally substituted with one or more $R^7$. In some embodiments, Z is substituted with one or more substituents independently selected from halogen, —CN, $C_{1-4}$ alkyl and $C_{1-3}$ haloalkyl. In some embodiments, Z is selected from

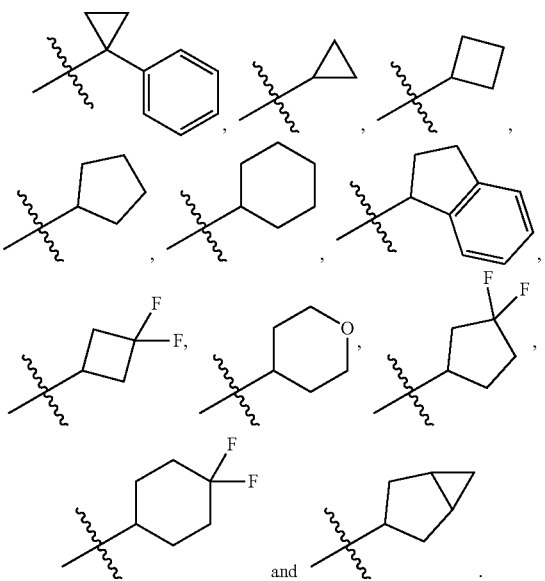

In some embodiments, for a compound of Formula (II), (II-A), (II-B) or (II-C), $R^1$ is selected from hydrogen and $C_{1-6}$ alkyl, wherein the $C_{1-6}$ alkyl is optionally substituted with one or more $R^7$. In some embodiments, $R^1$ is selected from hydrogen and —$CH_3$. In some embodiments, $R^1$ is $C_{1-6}$ alkyl, such as —$CH_3$.

In some embodiments, for a compound of Formula (II), (II-A), (II-B) or (II-C), $W^3$ is N. In some embodiments, $W^2$ is N or CH, such as $W^2$ is N. In some embodiments, $W^1$ is N or CH, such as $W^1$ is N. In some embodiments, $W^1$ is CH. In some embodiments, $W^3$ is N and $W^2$ and $W^1$ are independently N or CH. In some embodiments, $W^1$ is CH, $W^2$ is N and $W^3$ is N. In some embodiments, $W^1$ is N, $W^2$ is CH and $W^3$ is N. In some embodiments, $W^1$, $W^2$ and $W^3$ are each N.

In some embodiments, for a compound of Formula (II), (II-A), (II-B) or (II-C), $R^3$ is selected from hydrogen, halogen and cyano; and $C_{1-6}$ alkyl, aryl, heteroaryl and benzyl, each of which is optionally substituted with one or more $R^7$. In some embodiments, $R^3$ is selected from hydrogen, halogen, —CN, $C_{1-3}$ alkyl and $C_{1-3}$ haloalkyl. In some embodiments, $R^3$ is selected from —H, —Cl and —CN. In some embodiments, $R^3$ is selected from hydrogen, halogen and cyano.

In some embodiments, for a compound of Formula (II), (II-A), (II-B) or (II-C), $R^3$ is selected from halogen and cyano; and $C_{1-6}$ alkyl, aryl, heteroaryl and benzyl, each of which is optionally substituted with one or more $R^7$. In some embodiments, $R^3$ is selected from halogen, —CN, $C_{1-3}$ alkyl and $C_{1-3}$ haloalkyl. In some embodiments, $R^3$ is selected from —Cl and —CN. In some embodiments, $R^3$ is selected from halogen and cyano.

In some embodiments, for a compound of Formula (II), (II-A), (II-B) or (II-C), A is selected from —S—, —S(=O)— and —S(=O)$_2$. In some embodiments, A is selected from —S(=O)— and —S(=O)$_2$. In some embodiments, A is selected from —S— and —S(=O)$_2$. In some embodiments, A is selected from —S— and —S(=O)—. In some embodiments, A is —S—. In some embodiments, A is —S(=O)—. In some embodiments, A is —S(=O)$_2$.

In some embodiments, for a compound of Formula (II), (II-A), (II-B) or (II-C), at least one of $R^4$ and $R^5$ is $C_{1-6}$ alkyl, optionally substituted at each occurrence with one or more substituents selected from halogen, —OR$^8$, —S—S—R$^8$, —S—C(O)R$^8$, —OC(O)R$^8$, —OC(O)OR$^8$ and —P(O)(OR$^8$)$_2$.

In some embodiments, for a compound of Formula (II), (II-A), (II-B) or (II-C), $R^4$ and $R^5$ are independently selected from $C_{1-6}$ alkyl, optionally substituted at each occurrence with one or more substituents selected from halogen, —OR$^8$, —S—S—R$^8$, —S—C(O)R$^8$, —OC(O)R$^8$, —OC(O)OR$^8$ and —P(O)(OR$^8$)$_2$. In some embodiments, $R^4$ and $R^5$ are independently selected from —CH$_2$OC(O)R$^8$ and —CH$_2$OC(O)OR$^8$. In some embodiments, $R^4$ and $R^5$ are independently selected from —CH$_2$OC(O)C(CH$_3$)$_3$, —CH$_2$OC(O)OCH(CH$_3$)$_2$, —CH$_2$OC(O)CH$_3$, —CH$_2$CH$_2$—S—S—(CH$_2$)$_2$OH and —CH$_2$CH$_2$—S—C(O)CH$_3$.

In some embodiments, for a compound of Formula (II), (II-A), (II-B) or (II-C), $R^4$ is phenyl, optionally substituted with —OR$^8$; $R^5$ is $C_{1-6}$ alkyl substituted with one or more substituents selected from —OC(O)R$^8$, —C(O)OR$^8$, and —OC(O)OR$^8$; and $R^8$ is $C_{1-6}$ alkyl.

In some embodiments, for a compound of Formula (II), (II-A), (II-B) or (II-C), X and Y are each —O—. In some embodiments, one of X and Y is —O— and the other one of X and Y is —NR$^8$—.

In some embodiments, for a compound of Formula (II), (II-A), (II-B) or (II-C): $W^1$ is selected from N and CR$^6$; $W^2$ is selected from N and CH; $W^3$ is N; $R^1$ is selected from hydrogen and $C_{1-4}$ alkyl; $R^3$ is selected from halogen and cyano; and $R^6$ is selected from halogen, cyano and $C_{1-4}$ alkyl.

In some embodiments, for a compound of Formula (II), (II-A), (II-B) or (II-C), —X—R$^4$ and —Y—R$^5$ are each —OH.

In some embodiments, for a compound of Formula (II), (II-A), (II-B) or (II-C), at least one of $R^4$ and $R^5$ is selected from $C_{1-6}$ alkyl, $C_{2-6}$ alkenyl, and $C_{2-6}$ alkynyl, each of which is independently optionally substituted at each occurrence with one or more substituents selected from halogen, —NO$_2$, —CN, —OR$^8$, —SR$^8$, —N(R$^8$)$_2$, —NR$^9$R$^{10}$, —S(=O)R$^8$, —S(=O)$_2$R$^8$, —S(=O)$_2$N(R$^8$)$_2$, —S(=O)$_2$NR$^9$R$^{10}$, —NR$^8$S(=O)$_2$R$^8$, —NR$^8$S(=O)$_2$N(R$^8$)$_2$, —NR$^8$S(=O)$_2$NR$^9$R$^{10}$, —S—S—R$^8$, —S—C(O)R$^8$, —C(O)R$^8$, —C(O)OR$^8$, —OC(O)R$^8$, —OC(O)OR$^8$, —OC(O)N(R$^8$)$_2$, —OC(O)NR$^9$R$^{10}$, —NR$^8$C(O)R$^8$, —NR$^8$C(O)OR$^8$, —NR$^8$C(O)N(R$^8$)$_2$, —NR$^8$C(O)NR$^9$R$^{10}$, —C(O)N(R$^8$)$_2$, —C(O)NR$^9$R$^{10}$, —P(O)(OR$^8$)$_2$, —P(O)(R$^8$)$_2$, —OP(O)(OR$^8$)$_2$, =O, =S, =N(R$^8$); and $C_{3-12}$ carbocycle, and 3- to 12-membered heterocycle, each of which is independently optionally substituted at each occurrence with one or more substituents selected from halogen, $C_{1-6}$ alkyl, —OR$^8$, —OC(O)R$^8$, and —C(O)R$^8$.

In some embodiments, for a compound of Formula (II), (II-A), (II-B) or (II-C), $R^4$ and $R^5$ are independently selected from $C_{1-6}$ alkyl, $C_{2-6}$ alkenyl, and $C_{2-6}$ alkynyl, each of which is independently optionally substituted at each occurrence with one or more substituents selected from halogen, —NO$_2$, —CN, —OR$^8$, —SR$^8$, —N(R$^8$)$_2$, —NR$^9$R$^{10}$, —S(=O)R$^8$, —S(=O)$_2$R$^8$, —S(=O)$_2$N(R$^8$)$_2$, —S(=O)$_2$NR$^9$R$^{10}$, —NR$^8$S(=O)$_2$R$^8$, —NR$^8$S(=O)$_2$N(R$^8$)$_2$, —NR$^8$S(=O)$_2$NR$^9$R$^{10}$, —S—S—R$^8$, —S—C(O)R$^8$, —C(O)R$^8$, —C(O)OR$^8$, —OC(O)R$^8$, —OC(O)OR$^8$, —OC(O)N(R$^8$)$_2$, —OC(O)NR$^9$R$^{10}$, —NR$^8$C(O)R$^8$, —NR$^8$C(O)OR$^8$, —NR$^8$C(O)N(R$^8$)$_2$, —NR$^8$C(O)NR$^9$R$^{10}$, —C(O)N(R$^8$)$_2$, —C(O)NR$^9$R$^{10}$, —P(O)(OR$^8$)$_2$, —P(O)(R$^8$)$_2$, —OP(O)(OR$^8$)$_2$, =O, =S, =N(R$^8$); and $C_{3-12}$ carbocycle, and 3- to 12-membered heterocycle, each of which is independently optionally substituted at each occurrence with one or more substituents selected from halogen, $C_{1-6}$ alkyl, —OR$^8$, —OC(O)R$^8$, and —C(O)R$^8$.

In some embodiments, for a compound of Formula (II), (II-A), (II-B) or (II-C), $R^4$ and $R^5$ are independently selected from $C_{1-6}$ alkyl substituted with one or more substituents selected from halogen, —OC(O)R$^8$, —OC(O)OR$^8$, —S—S—R$^8$, —S—C(O)R$^8$, —OR$^8$, and —P(O)(OR$^8$)$_2$. In some embodiments, $R^4$ and $R^5$ are independently selected from hydrogen and $C_{1-6}$ alkyl, wherein each $C_{1-6}$ alkyl is optionally substituted at each occurrence with one or more substituents selected from halogen, —OC(O)R$^8$, —OC(O)OR$^8$, —S—S—R$^8$, —S—C(O)R$^8$, —OR$^8$, and —P(O)(OR$^8$)$_2$. In some embodiments, $R^4$ and $R^5$ are independently selected from $C_{1-6}$ alkyl substituted with one or more substituents selected from —OC(O)R$^8$ and —OC(O)OR$^8$. In some embodiments, $R^4$ and $R^5$ are independently selected from $C_1$ alkyl substituted with one or more substituents selected from —OC(O)R$^8$ and —OC(O)OR$^8$, wherein R$^8$ is $C_{1-6}$ alkyl. In some embodiments, $R^4$ and $R^5$ are independently selected from —CH$_2$OC(O)C(CH$_3$)$_3$, —CH$_2$OC(O)OCH(CH$_3$)$_2$, and —CH$_2$OC(O)CH$_3$. In some embodiments, $R^4$ and $R^5$ are each —CH$_2$OC(O)C(CH$_3$)$_3$. In some embodiments, $R^4$ and $R^5$ are each —CH$_2$OC(O)OCH(CH$_3$)$_2$.

In some embodiments, for a compound of Formula (II), (II-A), (II-B) or (II-C), $R^4$ and $R^5$ are independently selected from $C_{1-6}$ alkyl substituted with one or more substituents selected from —S—S—R$^8$, and —S—C(O)R$^8$. In some embodiments, $R^4$ and $R^5$ are independently selected from —CH$_2$CH$_2$—S—S—(CH$_2$)$_2$OH and —CH$_2$CH$_2$—S—C(O)CH$_3$. In some embodiments, $R^4$ and $R^5$ are each —CH$_2$CH$_2$—S—S—(CH$_2$)$_2$OH. In some embodiments, $R^4$ and $R^5$ are each —CH$_2$CH$_2$—S—C(O)CH$_3$.

In some embodiments, for a compound of Formula (II), (II-A), (II-B) or (II-C), $R^4$ and $R^5$ are independently selected from $C_{3-12}$ carbocycle, such as phenyl, wherein the $C_{3-12}$ carbocycle is optionally substituted with one or more substituents selected from halogen, $C_{1-6}$ alkyl, $-OR^8$, $-OC(O)R^8$, $-C(O)OR^8$, and $-C(O)R^8$. In some embodiments, $R^4$ and $R^5$ are independently selected from phenyl, wherein the phenyl is optionally substituted with $-OR^8$, such as phenyl substituted with $-OCH_2CH_3$. In some embodiments, one of $R^4$ and $R^5$ is selected from $C_{3-12}$ carbocycle, such as phenyl and benzyl, and the other of $R^4$ and $R^5$ is selected from $C_{1-6}$ alkyl substituted with one or more substituents selected from $-OC(O)R^8$, $-C(O)OR^8$, and $-OC(O)OR^8$, wherein $R^8$ is $C_{1-6}$ alkyl.

In some embodiments, for a compound of Formula (II), (II-A), (II-B) or (II-C), $R^4$ and $R^5$ are independently selected from hydrogen and $C_{1-6}$alkylene-$OR^{20}$, wherein $R^{20}$ at each occurrence is independently selected from $C_{7-20}$alkyl and $C_{7-20}$alkenyl. In some embodiments, one of $R^4$ or $R^5$ is selected from $-C_{1-3}$alkylene-O-$C_{7-20}$alkyl and $-C_{1-3}$alkylene-O-$C_{7-20}$alkenyl, such as one of $R^4$ or $R^5$ is selected from hexadecyloxypropyl ($-CH_2(CH_2)_2O(CH_2)_{15}CH_3$), octadecyloxyethyl ($-CH_2CH_2O(CH_2)_{17}CH_3$), oleyoxyethyl ($-CH_2CH_2O(CH_2)_8CH=CH(CH_2)_7CH_3$), and oleyoxypropyl ($-CH_2(CH_2)_2O(CH_2)_8CH=CH(CH_2)_7CH_3$), and the other of $R^4$ and $R^5$ is hydrogen.

In some embodiments, for a compound of Formula (II), (II-A), (II-B) or (II-C), $R^4$ and $R^5$ are taken together with the atoms to which they are attached to form a heterocycle, optionally substituted with one or more $R^7$. In some embodiments, the heterocycle is a 5- or 6-membered heterocycle. In some embodiments, $R^4$ and $R^5$ are taken together with the atoms to which they are attached to form a heterocycle selected from:

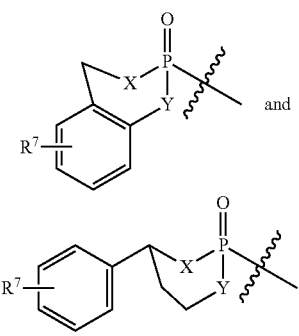

In some embodiments, $R^7$ is a halogen.

In some embodiments, for a compound of Formula (II), (II-A), (II-B) or (II-C), X and Y are each $-O-$. In some embodiments, one of X and Y is $-O-$ and the other one of X and Y is $-N(R^8)-$. In some embodiments, at least one of $-X-R^4$ and $-Y-R^5$ comprises an amino acid or an amino acid ester, such as an L-alanine ester, e.g., $-NHCH(CH_3)C(O)OCH(CH_3)_2$ and $-NHCH(CH_3)C(O)OCH_2CH_3$. In some embodiments, at least one of $-X-R^4$ and $-Y-R^5$ comprises alanine, serine, phenylalanine, valine, or two or more thereof.

In some embodiments, for a compound of Formula (II), (II-A), (II-B) or (II-C), $-X-R^4$ and $-Y-R^5$ are independently selected from:
$-OH$, $-O-CH_3$, $-O-CH_2CH_3$, $-O-CH_2$-Ph, $-O$-Ph,

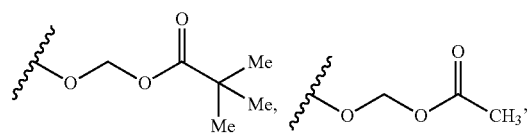

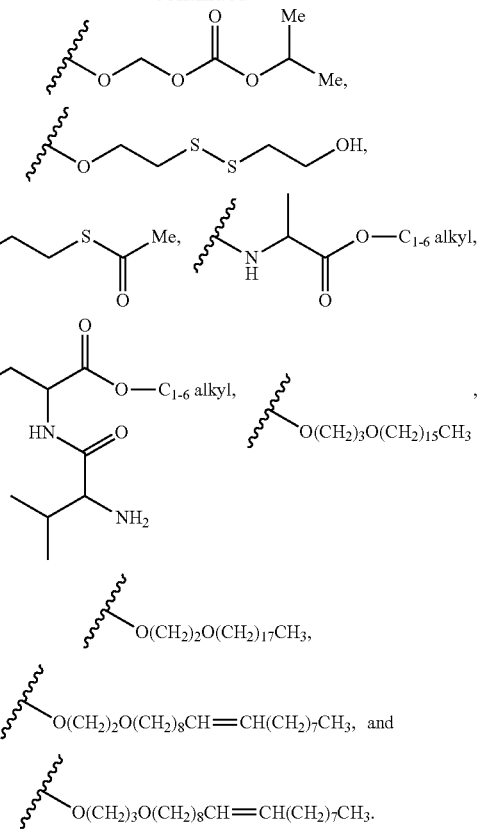

In some embodiments, $-X-R^4$ and $-Y-R^5$ are different, such as $-X-R^4$ is $-OH$ and $-Y-R^5$ is $-O(CH_2)_3O(CH_2)_{15}CH_3$. In some embodiments, one of $-X-R^4$

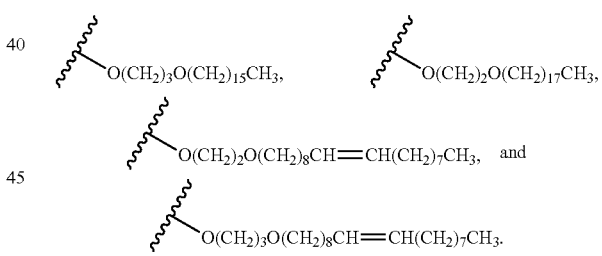

In some embodiments, $-X-R^4$ and $-Y-R^5$ are selected from the same moieties, for example, $-X-R^4$ is

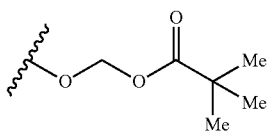 [SMILES: *OCOC(=O)C(C)(C)C]

and $-Y-R^5$ is

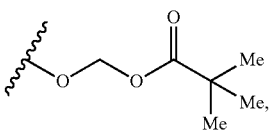 [SMILES: *OCOC(=O)C(C)(C)C]

or —X—R⁴ is

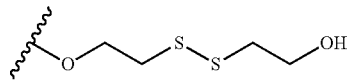 [SMILES: *OCCSSCCO]

and —Y—R⁵ is

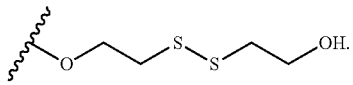 [SMILES: *OCCSSCCO]

In some embodiments, —X—R⁴ and —Y—R⁵ are each —O—CH₃, —O—CH₂CH₃, —O—CH₂Ph, —OPh

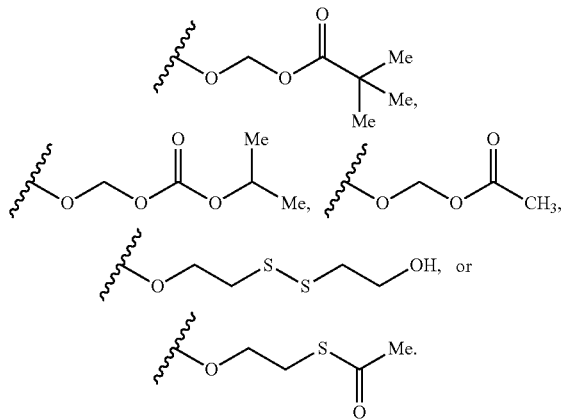

In some embodiments, for a compound of Formula (I), (II-A), (II-B) or (II-C), —X—R⁴ s selected from: —OH, —OCH₃, —OCH₂CH₃, —OCH₂Ph, —OPh,

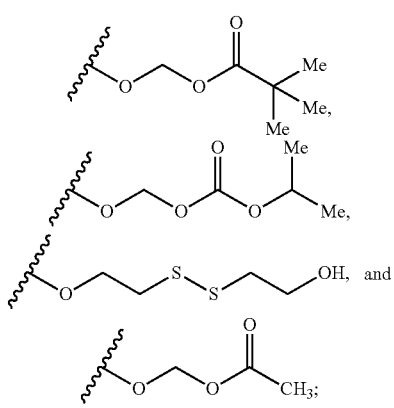

and —Y—R⁵ is selected from —OCH₃, —OCH₂CH₃, —OCH₂Ph, —OPh,

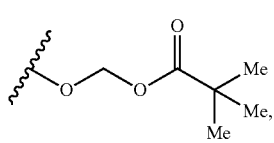

-continued

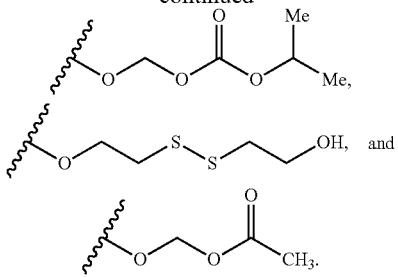

In some embodiments, for a compound of Formula (II), (II-A), (II-B) or (II-C):
$W^1$ and $W^2$ are each independently selected from N and CH, wherein at least one of $W^1$ and $W^2$ is N;
$W^3$ is N;
$R^1$ is selected from hydrogen and $C_{1-6}$ alkyl; wherein the $C_{1-6}$ alkyl is optionally substituted with one or more $R^7$;
$R^3$ is selected from hydrogen, halogen, —CN, $C_{1-3}$ alkyl and $C_{1-3}$ haloalkyl;
X and Y are each —O—; and
$R^4$ and $R^5$ are each hydrogen.

In some embodiments, for a compound of Formula (II), (II-A), (II-B) or (II-C):
$W^1$ and $W^2$ are each independently selected from N and CH, wherein at least one of $W^1$ and $W^2$ is N;
$W^3$ is N;
$R^1$ is selected from hydrogen and $C_{1-6}$ alkyl; wherein the $C_{1-6}$ alkyl is optionally substituted with one or more $R^7$;
$R^3$ is selected from halogen, —CN, $C_{1-3}$ alkyl and $C_{1-3}$ haloalkyl;
X and Y are each —O—; and
$R^4$ and $R^5$ are each hydrogen.

In some embodiments, for a compound of Formula (II), (II-A), (II-B) or (II-C):
$W^1$ and $W^2$ are each independently selected from N and CH, wherein at least one of $W^1$ and $W^2$ is N;
$W^3$ is N;
$R^1$ is selected from hydrogen and $C_{1-6}$ alkyl; wherein the $C_{1-6}$ alkyl is optionally substituted with one or more $R^7$;
$R^3$ is selected from hydrogen, halogen, —CN, $C_{1-3}$ alkyl and $C_{1-3}$ haloalkyl;
X and Y are independently selected from —O— and —NR⁸—, wherein at least one of X and Y is —O—; and
$R^4$ and $R^5$ are independently selected from $C_{1-6}$ alkyl substituted with one or more substituents selected from halogen, —OC(O)R⁸, —OC(O)OR⁸, —S—S—R⁸, —S—C(O)R⁸, —OR⁸, and —P(O)(OR⁸)₂.

In some embodiments, for a compound of Formula (II), (II-A), (II-B) or (II-C):
$W^1$ and $W^2$ are each independently selected from N and CH, wherein at least one of $W^1$ and $W^2$ is N;
$W^3$ is N;
$R^1$ is selected from hydrogen and $C_{1-6}$ alkyl; wherein the $C_{1-6}$ alkyl is optionally substituted with one or more $R^7$;
$R^3$ is selected from halogen, —CN, $C_{1-3}$ alkyl and $C_{1-3}$ haloalkyl;
X and Y are independently selected from —O— and —NR⁸—, wherein at least one of X and Y is —O—; and
$R^4$ and $R^5$ are independently selected from $C_{1-6}$ alkyl substituted with one or more substituents selected from halogen, —OC(O)R⁸, —OC(O)OR⁸, —S—S—R⁸, —S—C(O)R⁸, —OR⁸, and —P(O)(OR⁸)₂.

In some embodiments, for a compound of Formula (II), (II-A), (II-B) or (II-C):

W$^1$ and W$^2$ are each independently selected from N and CH, wherein at least one of W$^1$ and W$^2$ is N;

W$^3$ is N;

R$^1$ is selected from hydrogen and C$_{1-6}$ alkyl; wherein the C$_{1-6}$ alkyl is optionally substituted with one or more R$^7$;

R$^3$ is selected from hydrogen, halogen, —CN, C$_{1-3}$ alkyl and C$_{1-3}$ haloalkyl; and —X—R$^4$ and —Y—R$^5$ are independently selected from: —OH, —O—CH$_3$, —O—CH$_2$CH$_3$, —O—CH$_2$-Ph, —O-Ph,

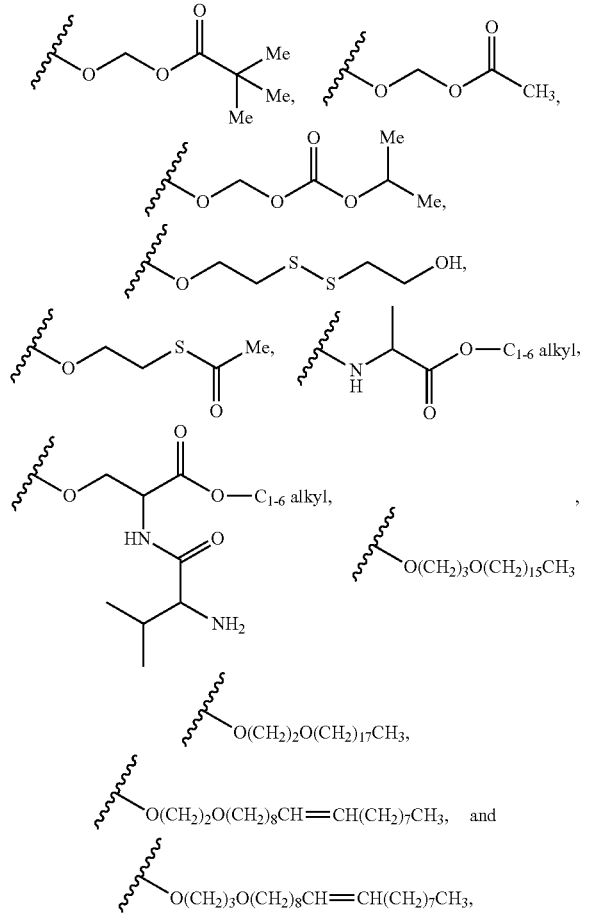

wherein at least one of —X—R$^4$ and —Y—R$^5$ is not —OH.

In certain aspects, the present disclosure provides a compound of Formula (II-A) or (II-B):

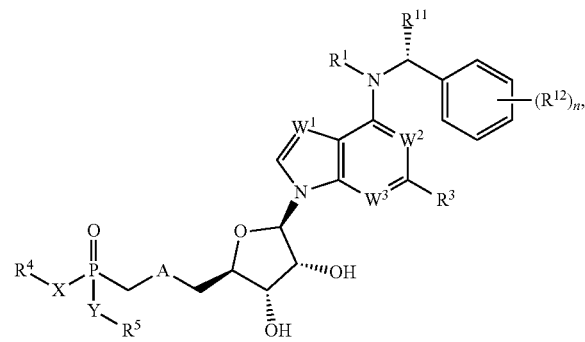

or a pharmaceutically acceptable salt thereof, wherein:

W$^1$, W$^2$ and W$^3$ are each independently selected from N and CH, wherein at least one of W$^1$, W$^2$ and W$^3$ is N;

R$^1$ is selected from hydrogen and C$_{1-6}$ alkyl;

R$^3$ is selected from hydrogen, halogen and cyano;

A is selected from —S—, —S(═O)— and —S(═O)$_2$—;

—X—R$^4$ is selected from —OH, —OCH$_3$, —OCH$_2$CH$_3$, —OCH$_2$Ph, —OPh,

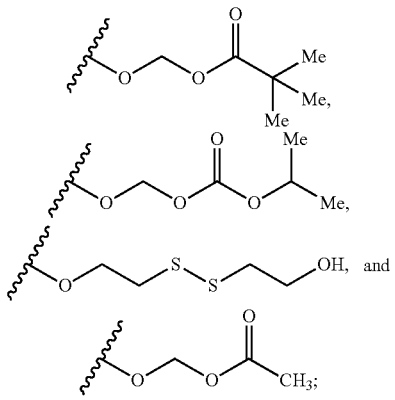

—Y—R$^5$ is selected from —OCH$_3$, —OCH$_2$CH$_3$, —OCH$_2$Ph,

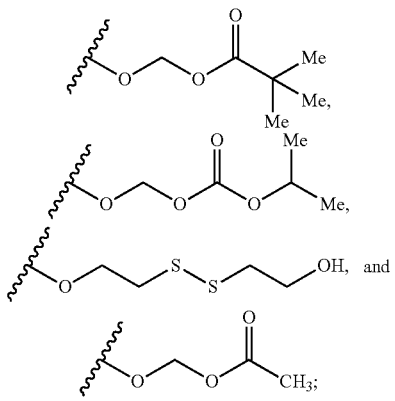

R$^7$ is independently selected at each occurrence from:
halogen, —NO$_2$, —CN, —OR$^8$, —SR$^8$, —N(R$^8$)$_2$, —NR$^9$R$^{10}$, —S(═O)R$^8$, —S(═O)$_2$R$^8$, —S(═O)$_2$N(R$^8$)$_2$, —S(═O)$_2$NR$^9$R$^{10}$, —NR$^8$S(═O)$_2$R$^8$, —NR$^8$S (=O)₂N(R⁸)₂, —NR⁸S(=O)₂NR⁹R¹⁰, —C(O)R⁸, —C(O)OR⁸, —OC(O)R⁸, —OC(O)OR⁸, —OC(O)N(R⁸)₂, —OC(O)NR⁹R¹⁰, —NR⁸C(O)R⁸, —NR⁸C(O)OR⁸, —NR⁸C(O)N(R⁸)₂, —NR⁸C(O)NR⁹R¹⁰, —C(O)N(R⁸)₂, —C(O)NR⁹R¹⁰, —P(O)(OR⁸)₂, —P(O)(R⁸)₂, =O, =S, and =N(R⁸);

C$_{1-10}$ alkyl, C$_{2-10}$ alkenyl, and C$_{2-10}$ alkynyl, each of which is independently optionally substituted at each occurrence with one or more substituents selected from halogen, —NO₂, —CN, —OR⁸, —SR⁸, —N(R⁸)₂, —NR⁹R¹⁰, —S(=O)R⁸, —S(=O)₂R⁸, —S(=O)₂N(R⁸)₂, —S(=O)₂NR⁹R¹⁰, —NR⁸S(=O)₂R⁸, —NR⁸S(=O)₂N(R⁸)₂, —NR⁸S(=O)₂NR⁹R¹⁰, —C(O)R⁸, —C(O)OR⁸, —OC(O)R⁸, —OC(O)OR⁸, —OC(O)N(R⁸)₂, —OC(O)NR⁹R¹⁰, —NR⁸C(O)R⁸, —NR⁸C(O)OR⁸, —NR⁸C(O)N(R⁸)₂, —NR⁸C(O)NR⁹R¹⁰, —C(O)N(R⁸)₂, —C(O)NR⁹R¹⁰, —P(O)(OR⁸)₂, —P(O)(R⁸)₂, =O, =S, =N(R⁸), C$_{3-12}$ carbocycle, and 3- to 12-membered heterocycle; and C$_{3-12}$ carbocycle and 3- to 12-membered heterocycle, wherein each C$_{3-12}$ carbocycle and 3- to 12-membered heterocycle in R⁷ is independently optionally substituted with one or more substituents selected from halogen, —NO₂, —CN, —OR⁸, —SR⁸, —N(R⁸)₂, —NR⁹R¹⁰, —S(=O)R⁸, —S(=O)₂R⁸, —S(=O)₂N(R⁸)₂, —S(=O)₂NR⁹R¹⁰, —NR⁸S(=O)₂R⁸, —NR⁸S(=O)₂N(R⁸)₂, —NR⁸S(=O)₂NR⁹R¹⁰, —C(O)R⁸, —C(O)OR⁸, —OC(O)R⁸, —OC(O)OR⁸, —OC(O)N(R⁸)₂, —OC(O)NR⁹R¹⁰, —NR⁸C(O)R⁸, —NR⁸C(O)OR⁸, —NR⁸C(O)N(R⁸)₂, —NR⁸C(O)NR⁹R¹⁰, —C(O)N(R⁸)₂, —C(O)NR⁹R¹⁰, —P(O)(OR⁸)₂, —P(O)(R⁸)₂, =O, =S, =N(R⁸), C$_{1-6}$ alkyl, C$_{1-6}$ haloalkyl, C$_{2-6}$ alkenyl, and C$_{2-6}$ alkynyl;

R⁸ is independently selected at each occurrence from hydrogen; and C$_{1-20}$ alkyl, C$_{2-20}$ alkenyl, C$_{2-20}$ alkynyl, 1- to 6-membered heteroalkyl, C$_{3-12}$ carbocycle, and 3- to 12-membered heterocycle, each of which is optionally substituted by halogen, —CN, —NO₂, —NH₂, —NHCH₃, —NHCH₂CH₃, =O, —OH, —OCH₃, —OCH₂CH₃, C$_{3-12}$ carbocycle, or 3- to 6-membered heterocycle;

R⁹ and R¹⁰ are taken together with the nitrogen atom to which they are attached to form a heterocycle, optionally substituted with one or more R⁷;

R¹¹ is selected from C$_{1-6}$ alkyl and C$_{3-12}$ carbocycle, each of which is optionally substituted with one or more R⁷;

R¹² is independently selected at each occurrence from halogen, —CN, C$_{1-4}$ alkyl and C$_{1-3}$ haloalkyl; and n is an integer from 0 to 3.

In certain aspects, the present disclosure provides a compound of Formula (II-A) or (II-B):

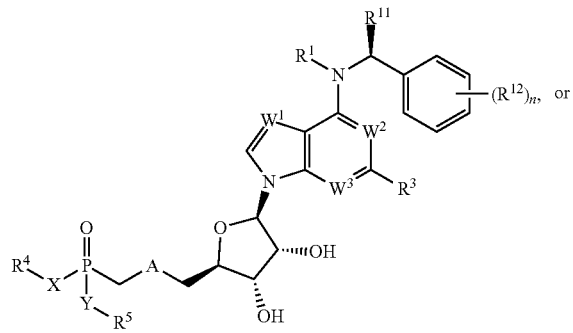

(II-A)

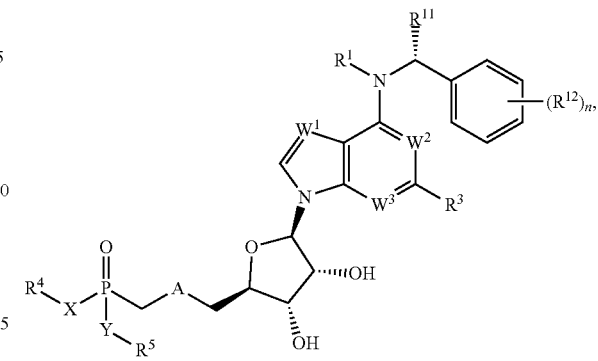

(II-B)

or a pharmaceutically acceptable salt thereof, wherein:
W¹, W² and W³ are each independently selected from N and CH, wherein at least one of W¹, W² and W³ is N;
R¹ is selected from hydrogen and C$_{1-6}$ alkyl; wherein the C$_{1-6}$ alkyl is optionally substituted with one or more R⁷;
R³ is selected from hydrogen, halogen and cyano;
A is selected from —S—, —S(=O)— and —S(=O)₂—;
—X—R⁴ is selected from —OH, —OCH₃, —OCH₂CH₃, —OCH₂Ph, —OPh,

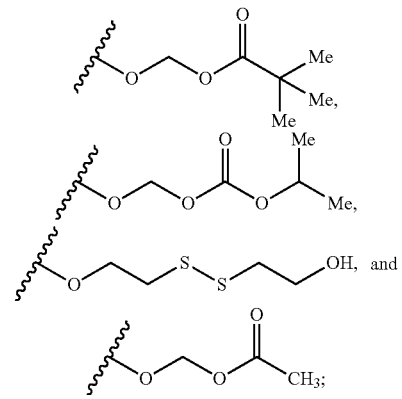

—Y—R⁵ is selected from —OCH₃, —OCH₂CH₃, —OCH₂Ph, —OPh,

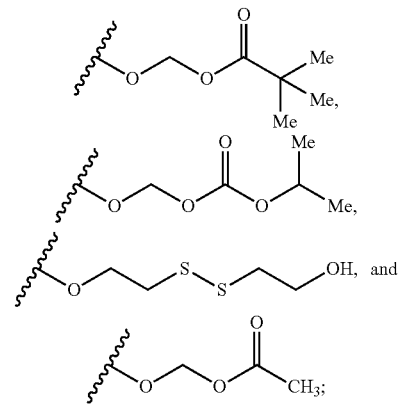

R⁷ is independently selected at each occurrence from:
halogen, —NO₂, —CN, —OR⁸, —SR⁸, —N(R⁸)₂, —NR⁹R¹⁰, —S(=O)R, —S(=O)₂R⁸, —S(=O)₂N(R⁸)₂, —S(=O)₂NR⁹R¹⁰, —NR⁸S(=O)₂R⁸, —NR⁸S(=O)₂N(R⁸)₂, —NR⁸S(=O)₂NR⁹R¹⁰, —C(O)R⁸, —C(O)OR⁸, —OC(O)R⁸, —OC(O)OR⁸, —OC(O)N(R⁸)₂, —OC(O)NR⁹R¹⁰, —NR⁸C(O)R⁸, —NR⁸C(O)OR⁸, —NR⁸C(O)N(R⁸)₂, —NR⁸C(O)NR⁹R¹⁰, —C(O)N(R⁸)₂, —C(O)NR⁹R¹⁰, —P(O)(OR⁸)₂, —P(O)(R⁸)₂, =O, =S, and =N(R⁸);

$C_{1-10}$ alkyl, $C_{2-10}$ alkenyl, and $C_{2-10}$ alkynyl, each of which is independently optionally substituted at each occurrence with one or more substituents selected from halogen, —NO₂, —CN, —OR⁸, —SR⁸, —N(R⁸)₂, —NR⁹R¹⁰, —S(=O)R⁸, —S(=O)₂R⁸, —S(=O)₂N(R⁸)₂, —S(=O)₂NR⁹R¹⁰, —NR⁸S(=O)₂R⁸, —NR⁸S(=O)₂N(R⁸)₂, —NR⁸S(=O)₂NR⁹R¹⁰, —C(O)R⁸, —C(O)OR⁸, —OC(O)R⁸, —OC(O)OR⁸, —OC(O)N(R⁸)₂, —OC(O)NR⁹R¹⁰, —NR⁸C(O)R⁸, —NR⁸C(O)OR⁸, —NR⁸C(O)N(R⁸)₂, —NR⁸C(O)NR⁹R¹⁰, —C(O)N(R⁸)₂, —C(O)NR⁹R¹⁰, —P(O)(OR⁸)₂, —P(O)(R⁸)₂, =O, =S, =N(R⁸), $C_{3-12}$ carbocycle, and 3- to 12-membered heterocycle; and $C_{3-12}$ carbocycle and 3- to 12-membered heterocycle, wherein each $C_{3-12}$ carbocycle and 3- to 12-membered heterocycle in $R^7$ is independently optionally substituted with one or more substituents selected from halogen, —NO₂, —CN, —OR⁸, —SR⁸, —N(R⁸)₂, —NR⁹R¹⁰, —S(=O)R⁸, —S(=O)₂R⁸, —S(=O)₂N(R⁸)₂, —S(=O)₂NR⁹R¹⁰, —NR⁸S(=O)₂R⁸, —NR⁸S(=O)₂N(R⁸)₂, —NR⁸S(=O)₂NR⁹R¹⁰, —C(O)R⁸, —C(O)OR⁸, —OC(O)R⁸, —OC(O)OR⁸, —OC(O)N(R⁸)₂, —OC(O)NR⁹R¹⁰, —NR⁸C(O)R⁸, —NR⁸C(O)OR⁸, —NR⁸C(O)N(R⁸)₂, —NR⁸C(O)NR⁹R¹⁰, —C(O)N(R⁸)₂, —C(O)NR⁹R¹⁰, —P(O)(OR⁸)₂, —P(O)(R⁸)₂, =O, =S, =N(R⁸), $C_{1-6}$ alkyl, $C_{1-6}$ haloalkyl, $C_{2-6}$ alkenyl, and $C_{2-6}$ alkynyl;

$R^8$ is independently selected at each occurrence from hydrogen; and $C_{1-20}$ alkyl, $C_{2-20}$ alkenyl, $C_{2-20}$ alkynyl, 1- to 6-membered heteroalkyl, $C_{3-12}$ carbocycle, and 3- to 12-membered heterocycle, each of which is optionally substituted by halogen, —CN, —NO₂, —NH₂, —NHCH₃, —NHCH₂CH₃, =O, —OH, —OCH₃, —OCH₂CH₃, $C_{3-12}$ carbocycle, or 3- to 6-membered heterocycle;

$R^9$ and $R^{10}$ are taken together with the nitrogen atom to which they are attached to form a heterocycle, optionally substituted with one or more $R^7$;

$R^{11}$ is selected from $C_{1-6}$ alkyl and $C_{3-12}$ carbocycle, each of which is optionally substituted with one or more $R^7$;

$R^{12}$ is independently selected at each occurrence from halogen, —CN, $C_{1-4}$ alkyl and $C_{1-3}$ haloalkyl; and n is an integer from 0 to 3.

In certain aspects, the present disclosure provides a compound of Formula (III):

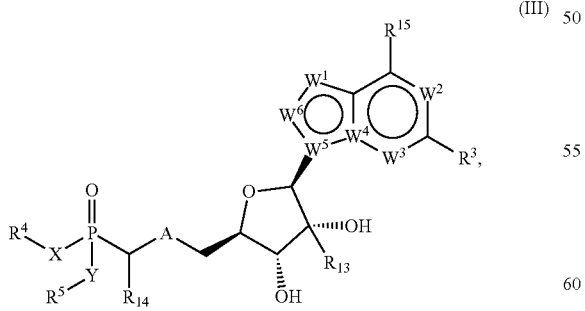

(III)

or a pharmaceutically acceptable salt thereof, wherein:
$W^1$ is selected from N, NR⁸, CR⁶, and S;
$W^2$ and $W^3$ are each independently selected from N and CR⁶;
$W^4$ and $W^5$ are each independently selected from N and C;
$W^6$ is selected from N, CR⁶, and S;

wherein at least one of $W^1$, $W^2$, $W^3$, $W^4$, $W^5$, and $W^6$ is N, and provided that:
when $W^1$, $W^2$, $W^3$, $W^5$, and $W^6$ are N, $W^4$ is not N; and
when either $W^1$ or $W^6$ is S, the other is CR⁶.

$R^{15}$ is selected from —NR¹R², —OR⁸, —SR¹ and —CN; and $C_{3-12}$ membered carbocycle and 3- to 12-membered heterocycle, each of which is optionally substituted with one or more $R^7$;

$R^1$ is selected from hydrogen; and $C_{1-6}$ alkyl and $C_{3-12}$ carbocycle, each of which is optionally substituted with one or more $R^7$;

$R^2$ is selected from $C_{1-6}$ alkyl, $C_{3-12}$ carbocycle, 3- to 12-membered heterocycle and benzyl, each of which is optionally substituted with one or more $R^7$; or $R^1$ and $R^2$ are taken together with the nitrogen atom to which they are attached to form a 3- to 12-membered heterocycle, optionally substituted with one or more $R^7$;

$R^3$ is selected from hydrogen, halogen, cyano, —N(R⁸)₂ and —OR⁸; and $C_{1-6}$ alkyl, $C_{2-10}$ alkenyl, $C_{2-10}$ alkynyl, $C_{3-12}$ carbocycle, 3- to 12-membered heterocycle and benzyl, each of which is optionally substituted with one or more $R^7$;

A is selected from —O—, —S—, —S(=O)— and —S(=O)₂—;

X and Y are independently selected from —O— and —NR⁸—;

$R^4$ and $R^5$ are independently selected from:
hydrogen; and $C_{1-6}$ alkyl, phenyl, and 3- to 12-membered heterocycle, each of which is independently optionally substituted at each occurrence with one or more substituents selected from halogen, —NO₂, —CN, —OR⁸, —SR⁸, —N(R⁸)₂, —NR⁹R¹⁰, —S(=O)R⁸, —S(=O)₂R⁸, —S(=O)₂N(R⁸)₂, —S(=O)₂NR⁹R¹⁰, —NR⁸S(=O)₂R⁸, —NR⁸S(=O)₂N(R⁸)₂, —NR⁸S(=O)₂NR⁹R¹⁰, —S—S—R⁸, —S—C(O)R⁸, —C(O)R⁸, —C(O)OR⁸, —OC(O)R⁸, —OC(O)OR⁸, —OC(O)N(R⁸)₂, —OC(O)NR⁹R¹⁰, —NR⁸C(O)R⁸, —NR⁸C(O)OR⁸, —NR⁸C(O)N(R⁸)₂, —NR⁸C(O)NR⁹R¹⁰, —C(O)N(R⁸)₂, —C(O)NR⁹R¹⁰, —P(O)(OR⁸)₂, —P(O)(R⁸)₂, —OP(O)(OR⁸)₂, =O, =S, =N(R⁸), $C_{3-12}$ carbocycle, and 3- to 12-membered heterocycle; or $R^4$ and $R^5$ are taken together with the atoms to which they are attached to form a 3- to 12-membered heterocycle, optionally substituted with one or more $R^7$;

$R^6$ is selected from hydrogen, halogen and cyano; and $C_{1-6}$ alkyl, optionally substituted with one or more $R^7$;

$R^7$ is independently selected at each occurrence from:
halogen, —NO₂, —CN, —OR⁸, —SR⁸, —N(R⁸)₂, —NR⁹R¹⁰, —S(=O)R⁸, —S(=O)₂R⁸, —S(=O)₂N(R⁸)₂, —S(=O)₂NR⁹R¹⁰, —NR⁸S(=O)₂R⁸, —NR⁸S(=O)₂N(R⁸)₂, —NR⁸S(=O)₂NR⁹R¹⁰, —C(O)R⁸, —C(O)OR⁸, —OC(O)R⁸, —OC(O)OR⁸, —OC(O)N(R⁸)₂, —OC(O)NR⁹R¹⁰, —NR⁸C(O)R⁸, —NR⁸C(O)OR⁸, —NR⁸C(O)N(R⁸)₂, —NR⁸C(O)NR⁹R¹⁰, —C(O)N(R⁸)₂, —C(O)NR⁹R¹⁰, —P(O)(OR⁸)₂, —P(O)(R⁸)₂, =O, =S, and =N(R⁸);

$C_{1-10}$ alkyl, $C_{2-10}$ alkenyl, and $C_{2-10}$ alkynyl, each of which is independently optionally substituted at each occurrence with one or more substituents selected from halogen, —NO₂, —CN, —OR⁸, —SR⁸, —N(R⁸)₂, —NR⁹R¹⁰, —S(=O)R⁸, —S(=O)₂R⁸, —S(=O)₂N(R⁸)₂, —S(=O)₂NR⁹R¹⁰, —NR⁸S(=O)₂R⁸, —NR⁸S(=O)₂N(R⁸)₂, —NR⁸S(=O)₂NR⁹R¹⁰, —C(O)R⁸, —C(O)OR⁸, —OC(O)R⁸, —OC(O)OR⁸, —OC(O)N(R⁸)₂, —OC(O)NR⁹R¹⁰, —NR⁸C(O)R⁸, —NR⁸C(O)OR⁸, —NR⁸C(O)N(R⁸)₂, —NR⁸C(O)NR⁹R¹⁰, —C(O)N(R⁸)₂, —C(O)NR⁹R¹⁰, —P(O)(OR⁸)₂, —P(O)(R⁸)₂, =O, =S, =N(R⁸), $C_{3-12}$ carbocycle, and 3- to 12-membered heterocycle; and $C_{3-12}$ carbocycle and 3- to 12-membered heterocycle,
wherein each $C_{3-12}$ carbocycle and 3- to 12-membered heterocycle in $R^7$ is independently optionally substituted with one or more substituents selected from halogen, —$NO_2$, —CN, —$OR^8$, —$SR^8$, —$N(R^8)_2$, —$NR^9R^{10}$, —S(=O)$R^8$, —S(=O)$_2R^8$, —S(=O)$_2N(R^8)_2$, —S(=O)$_2NR^9R^{10}$, —$NR^8S(=O)_2R^8$, —$NR^8S(=O)_2N(R^8)_2$, —$NR^8S(=O)_2NR^9R^{10}$, —C(O)$R^8$, —C(O)ORB, —OC(O)$R^8$, —OC(O)$OR^8$, —OC(O)N$(R^8)_2$, —OC(O)$NR^9R^{10}$, —$NR^8C(O)R^8$, —$NR^8C(O)OR^8$, —$NR^8C(O)N(R^8)_2$, —$NR^8C(O)NR^9R^{10}$, —C(O)$N(R^8)_2$, —C(O)$NR^9R^{10}$, —P(O)(OR$^8)_2$, —P(O)($R^8)_2$, =O, =S, =N($R^8$), $C_{1-6}$ alkyl, $C_{1-6}$ haloalkyl, $C_{2-6}$ alkenyl, and $C_{2-6}$ alkynyl;

$R^8$ is independently selected at each occurrence from hydrogen; and $C_{1-20}$ alkyl, $C_{2-20}$ alkenyl, $C_{2-20}$ alkynyl, 1- to 6-membered heteroalkyl, $C_{3-12}$ carbocycle, and 3- to 12-membered heterocycle, each of which is optionally substituted by halogen, —CN, —$NO_2$, —$NH_2$, —$NHCH_3$, —$NHCH_2CH_3$, =O, —OH, —$OCH_3$, —$OCH_2CH_3$, $C_{3-12}$ carbocycle, or 3- to 6-membered heterocycle;

$R^9$ and $R^{10}$ are taken together with the nitrogen atom to which they are attached to form a heterocycle, optionally substituted with one or more $R^7$;

$R^{13}$ is selected from hydrogen and $C_{1-6}$ alkyl; and
$R^{14}$ is selected from hydrogen and $R^7$.

In some embodiments, for a compound of Formula (III), one of $W^1$ or $W^6$ is S. In some embodiments, one of $W^1$ or $W^6$ is S and $W^5$ is C. In some embodiments, $W^6$ and $W^5$ are N and $W^1$ is CH. In some embodiments, $W^1$ is NH, $W^6$ is CH, and $W^5$ is C. In some embodiments, $W^1$ is selected from N, NH, $CR^6$ and S.

In some embodiments, a compound of Formula (III) is represented by the structure

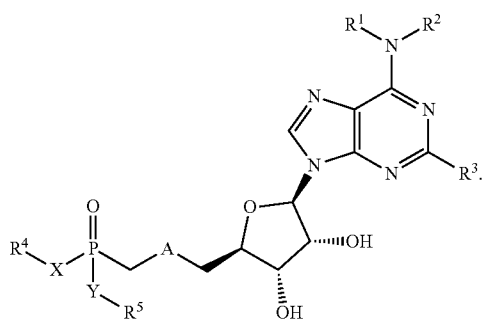

In some embodiments, a compound of Formula (III) is represented by the structure

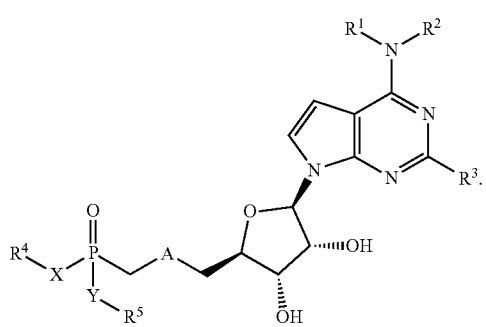

In some embodiments, a compound of Formula (III) is represented by the structure

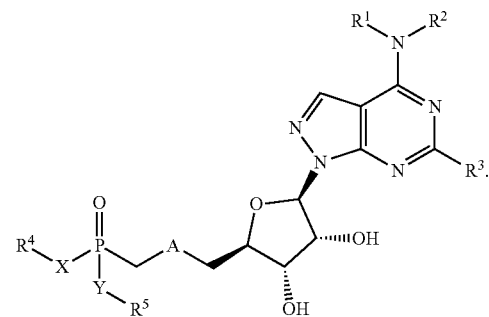

In some embodiments, a compound of Formula (III) is represented by the structure

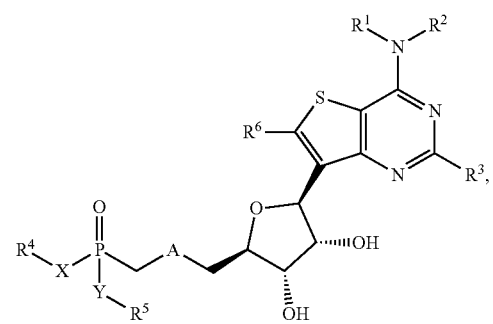

optionally wherein $R^6$ is halogen. In some embodiments, a compound of Formula (III) is represented by the structure

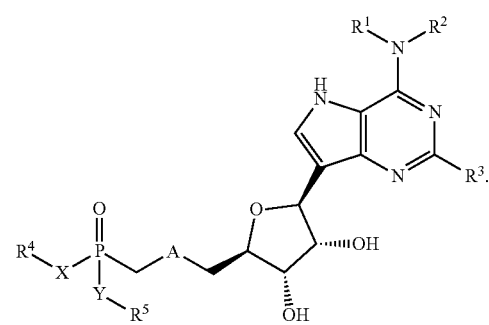

In some embodiments, a compound of Formula (III) is represented by the structure

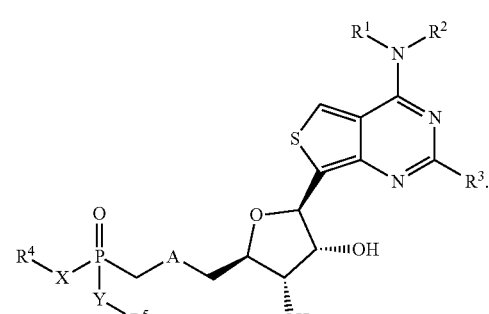

In some embodiments, a compound of Formula (III) is represented by the structure

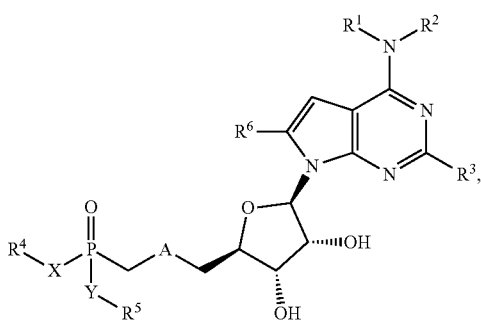

optionally wherein $R^6$ is methyl. In some embodiments, a compound of Formula (III) is represented by the structure

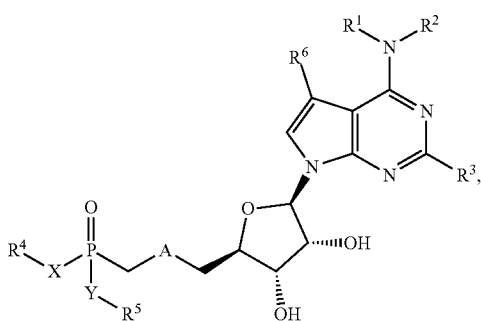

optionally wherein $R^6$ is methyl.

In some embodiments, for a compound of Formula (III), $R^{15}$ is selected from —$OR^1$ and $SR^1$, optionally wherein $R^1$ is selected from $C_{1-6}$ alkyl and $C_{3-12}$ carbocycle. In some embodiments, $R^{15}$ is selected from $C_{3-12}$ carbocycle, such as phenyl or cyclopentyl. In some embodiments, $R^{15}$ is selected from

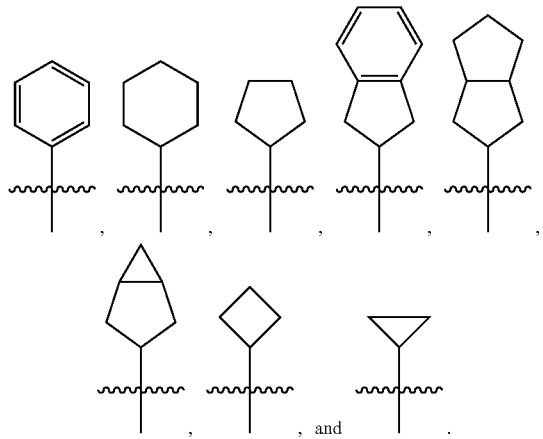

In some embodiments, $R^{15}$ is —$NR^1R^2$.

In some embodiments, for a compound of Formula (III), $R^1$ is selected from hydrogen and $C_{1-6}$ alkyl, wherein the $C_{1-6}$ alkyl is optionally substituted with one or more $R^7$. In some embodiments, $R^1$ is selected from hydrogen and —$CH_3$.

In some embodiments, for a compound of Formula (III), $R^2$ is selected from $C_{1-6}$ alkyl, $C_{3-12}$ carbocycle, 3- to 12-membered heterocycle and benzyl, each of which is optionally substituted with one or more substituents independently selected from halogen, —CN, $C_{1-4}$ alkyl, $C_{1-3}$ haloalkyl, —OH and —$NH_2$. In some embodiments, $R^2$ is benzyl, optionally substituted with one or more $R^7$. In some embodiments, $R^2$ is benzyl, optionally substituted with one or more substituents independently selected from halogen, —CN, $C_{1-4}$ alkyl, $C_{1-3}$ haloalkyl, —OH and —$NH_2$. In some embodiments, $R^2$ is $C_{1-6}$ alkyl or $C_{3-8}$ cycloalkyl, each of which is optionally substituted with one or more substituents independently selected from halogen, —CN, $C_{1-3}$ haloalkyl, —OH, —$NH_2$, optionally substituted phenyl and optionally substituted pyridyl. In some embodiments, $R^2$ is $C_{3-8}$ cycloalkyl, such as cyclopropyl, cyclobutyl, cyclopentyl or cyclohexyl. In some embodiments, $R^2$ is $C_{1-4}$ alkyl, such as methyl, ethyl, propyl, isopropyl, n-butyl, sec-butyl, isobutyl or tert-butyl. In some embodiments, $R^2$ is $C_{1-6}$ alkyl, $C_{3-8}$ cycloalkyl, or benzyl, each of which is optionally substituted with one or more substituents independently selected from halogen, —CN, $C_{1-4}$ alkyl, $C_{1-3}$ haloalkyl, —OH and —$NH_2$.

In some embodiments, for a compound of Formula (III), $R^{15}$ is —$NR^1R^2$ wherein $R^1$ and $R^2$ are taken together with the nitrogen atom to which they are attached to form a 3- to 12-membered heterocycle, optionally substituted with one or more $R^7$, such as one or more substituents independently selected from halogen, —CN, $C_{1-4}$ alkyl, $C_{1-3}$ haloalkyl, —OH and —$NH_2$. In some embodiments, $R^1$ and $R^2$ are taken together with the atom to which they are attached to form an optionally substituted 3- to 7-membered monocyclic heterocycloalkyl or an optionally substituted 5- to 12-membered fused bicyclic heterocycloalkyl. The 3- to 12-membered heterocycle formed by $R^1$, $R^2$ and the nitrogen atom to which they are attached may be selected from

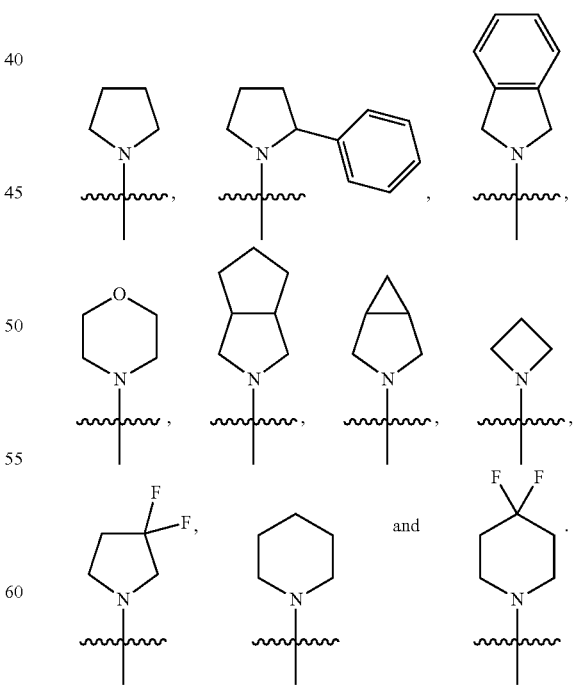

In some embodiments, a compound of Formula (III) is represented by Formula (III-A) or (III-B):

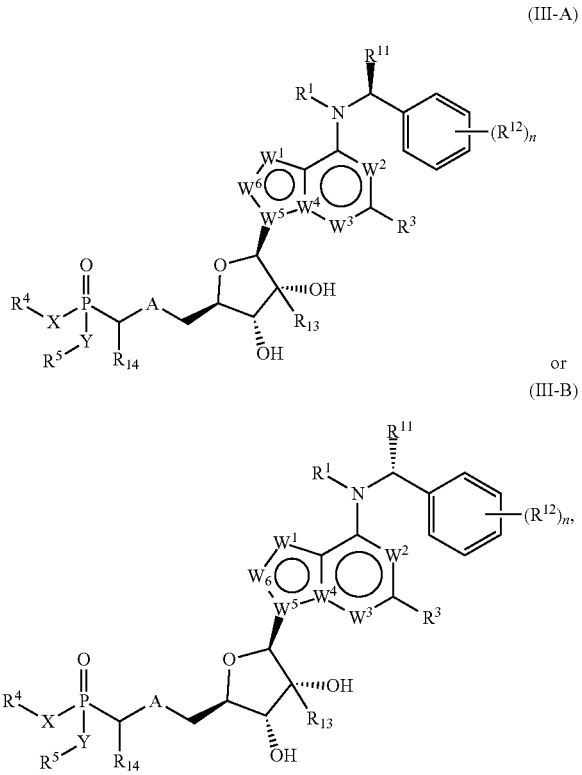

(III-A)

(III-B)

or a pharmaceutically acceptable salt thereof, wherein:

$R^{11}$ is selected from $C_{1-6}$ alkyl and $C_{3-12}$ carbocycle, each of which is optionally substituted with one or more $R^7$;

$R^{12}$ is independently selected at each occurrence from $R^7$; and n is an integer from 0 to 3.

In some embodiments, for a compound of Formula (III-A) or (III-B), $R^{11}$ is selected from $C_{1-6}$ alkyl and $C_{3-12}$ carbocycle, each of which is optionally substituted with one or more $R^7$; $R^{12}$ is independently selected at each occurrence from $R^7$; and n is an integer from 0 to 3.

In some embodiments, for a compound of Formula (III-A) or (III-B), $R^{11}$ is $C_{1-6}$ alkyl, such as $C_{1-4}$ alkyl. In some embodiments, $R^{11}$ is selected from methyl, ethyl, iso-propyl and tert-butyl. In some embodiments, $R^{11}$ is selected from $C_{1-4}$ alkyl and $C_{3-12}$ cycloalkyl, each of which is optionally substituted with one or more $R^7$. In some embodiments, $R^{11}$ is —$CH_3$. In some embodiments, $R^{11}$ is selected from $R^7$.

In some embodiments, for a compound of Formula (III-A) or (III-B), $R^{12}$ is independently selected at each occurrence from halogen, —CN, alkoxy, haloalkoxy, alkyl and haloalkyl. In some embodiments, $R^{12}$ is independently selected at each occurrence from halogen, —CN, $C_{1-4}$ alkoxy, $C_{1-4}$ haloalkoxy, $C_{1-4}$ alkyl and $C_{1-4}$ haloalkyl. In some embodiments, $R^{12}$ is independently selected at each occurrence from halogen, —CN, $C_{1-4}$ alkoxy, $C_{1-4}$ fluoroalkoxy, $C_{1-4}$ alkyl and $C_{1-4}$ haloalkyl. In some embodiments, $R^{12}$ is independently selected at each occurrence from halogen, —CN, $C_{1-4}$ alkyl and $C_{1-3}$ haloalkyl. In some embodiments, $R^{12}$ is independently selected at each occurrence from —F, —CN, —$CH_3$ and —$CF_3$. In some embodiments, $R^{12}$ is independently selected at each occurrence from halogen, —CN, —$CH_3$ and —$CF_3$.

In some embodiments, for a compound of Formula (III-A) or (III-B), n is an integer from 1 to 3, such as n is 1.

In some embodiments, for a compound of Formula (III-A) or (III-B):

$R^{11}$ is selected from $C_{1-6}$ alkyl, optionally substituted with one or more $R^7$;

$R^{12}$ is independently selected at each occurrence from halogen, —CN, $C_{1-4}$ alkyl and $C_{1-3}$ haloalkyl; and n is an integer from 1 to 3.

In some embodiments, for a compound of Formula (III-A) or (III-B):

$R^{11}$ is selected from $C_{1-6}$ alkyl and $C_{3-12}$ carbocycle, each of which is optionally substituted with one or more $R^7$;

$R^{12}$ is independently selected at each occurrence from halogen, —CN, alkoxy, haloalkoxy, alkyl and haloalkyl; and n is an integer from 0 to 3.

In some embodiments, for a compound of Formula (III-A) or (III-B), one of $W^1$ or $W^6$ is S. In some embodiments, one of $W^1$ or $W^6$ is S and $W^5$ is C. In some embodiments, $W^6$ and $W^5$ are N and $W^1$ is CH. In some embodiments, $W^1$ is NH, $W^6$ is CH, and $W^5$ is C.

In some embodiments, a compound of Formula (III) is represented by Formula (III-C):

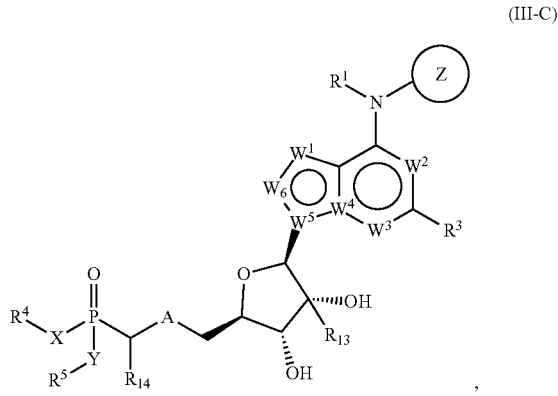

(III-C)

or a pharmaceutically acceptable salt thereof, wherein:

Z is selected from $C_{3-12}$ cycloalkyl and 3- to 12-membered heterocycloalkyl, each of which is optionally substituted with one or more $R^7$.

In some embodiments, for a compound of Formula (III-C), Z is selected from $C_{3-12}$ monocyclic cycloalkyl or $C_{5-12}$ fused bicyclic cycloalkyl, each of which is optionally substituted with one or more $R^7$. In some embodiments, Z is $C_{5-12}$ fused bicyclic cycloalkyl, optionally substituted with one or more $R^7$. In some embodiments, Z is selected from $C_{3-12}$ monocyclic cycloalkyl or $C_{5-12}$ bicyclic cycloalkyl, each of which is optionally substituted with one or more $R^7$. In some embodiments, Z is substituted with one or more substituents independently selected from halogen, —CN, $C_{1-4}$ alkyl and $C_{1-3}$ haloalkyl. In some embodiments, Z is selected from

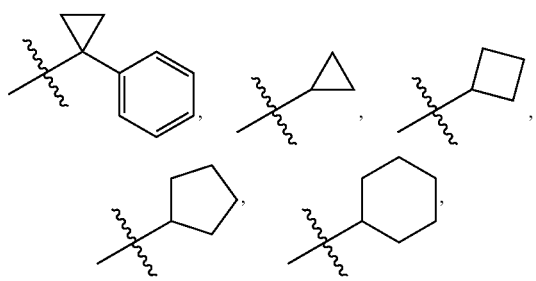

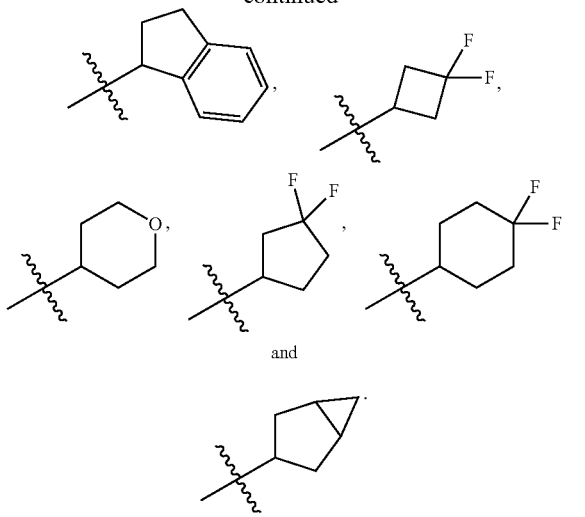

In some embodiments, for a compound of Formula (III), (III-A), (III-B) or (III-C), $R^3$ is $C_2$-alkynyl optionally substituted with one or more $R^7$. In some embodiments, the $C_2$-alkynyl is selected from

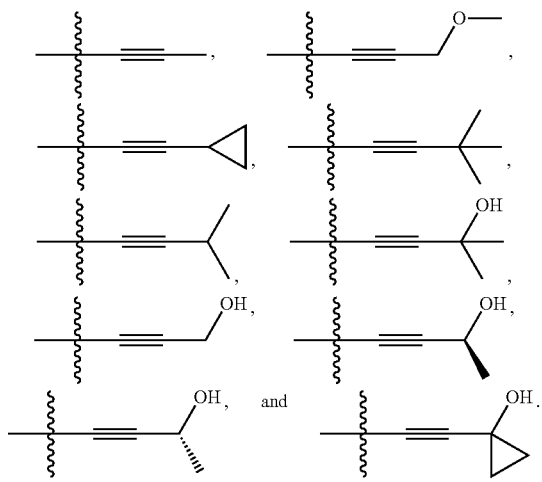

In some embodiments, for a compound of Formula (III), (III-A), (III-B) or (III-C), $R^3$ is $-OR^8$. In some embodiments, $R^3$ is selected from

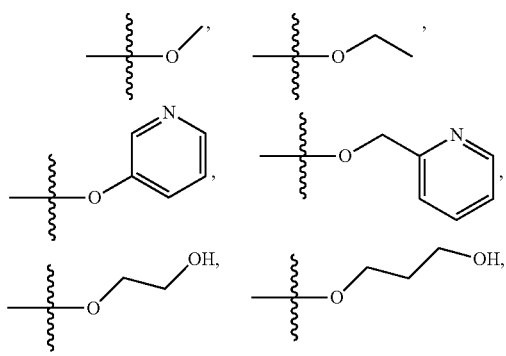

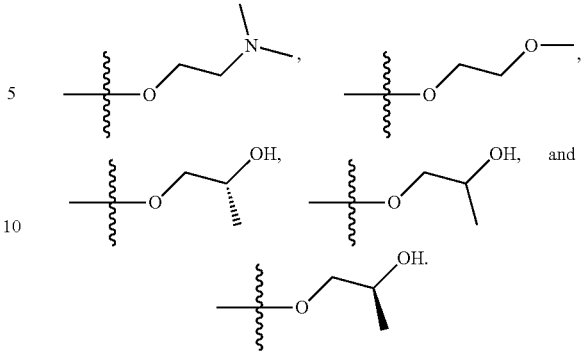

In some embodiments, for a compound of Formula (III), (III-A), (III-B), or (III-C), one of $W^1$ or $W^6$ is S. In some embodiments, one of $W^1$ or $W^6$ is S and $W^5$ is C. In some embodiments, $W^6$ and $W^5$ are N and $W^1$ is CH. In some embodiments, $W^1$ is NH, $W^6$ is CH, and $W^5$ is C.

In some embodiments, for a compound of Formula (III), (III-A), (III-B), or (III-C), $R^1$ is selected from hydrogen and $C_{1-6}$ alkyl, wherein the $C_{1-6}$ alkyl is optionally substituted with one or more $R^7$. In some embodiments, $R^1$ is selected from hydrogen and $-CH_3$. In some embodiments, $R^1$ is $C_{1-6}$ alkyl, such as $-CH_3$.

In some embodiments, for a compound of Formula (III), (III-A), (III-B), or (III-C), $W^3$ is N. In some embodiments, $W^2$ is N or CH, such as $W^2$ is N. In some embodiments, $W^1$ is N or CH, such as $W^1$ is N. In some embodiments, $W^1$ is CH. In some embodiments, $W^3$ is N and $W^2$ and $W^1$ are independently N or CH. In some embodiments, $W^1$ is CH, $W^2$ is N and $W^3$ is N. In some embodiments, $W^1$ is N, $W^2$ is CH and $W^3$ is N. In some embodiments, $W^1$, $W^2$ and $W^3$ are each N. In some embodiments, $W^2$, $W^3$, and $W^5$ are each N. In some embodiments, $W^1$, $W^2$, and $W^3$ are each N. In some embodiments, $W^2$ and $W^3$ are each N and $W^1$ is S. In some embodiments, $W^2$ and $W^3$ are each N and $W^6$ is S. In some embodiments $W^2$, $W^3$, $W^1$, $W^6$ and $W^5$ are each N. In some embodiments, $W^5$ is C. In some embodiments, $W^1$ is NH, $W^2$ is N, $W^3$ is N, $W^4$ is C, $W^5$ is C and $W^6$ is CH. In some embodiments, $W^1$ is S, $W^2$ is N, $W^3$ is N, $W^4$ is C, $W^5$ is C and $W^6$ is CH. In some embodiments, $W^1$ is selected from N, NH, $CR^6$ and S.

In some embodiments, for a compound of Formula (III), (III-A), (III-B), or (III-C), $R^3$ is selected from hydrogen, halogen and cyano; and $C_{1-6}$ alkyl, aryl, heteroaryl and benzyl, each of which is optionally substituted with one or more $R^7$. In some embodiments, $R^3$ is selected from hydrogen, halogen, $-CN$, $C_{1-3}$ alkyl and $C_{1-3}$ haloalkyl. In some embodiments, $R^3$ is selected from $-H$, $-Cl$ and $-CN$. In some embodiments, $R^3$ is selected from hydrogen, halogen and cyano.

In some embodiments, for a compound of Formula (III), (III-A), (III-B), or (III-C), $R^3$ is selected from halogen and cyano; and $C_{1-6}$ alkyl, aryl, heteroaryl and benzyl, each of which is optionally substituted with one or more $R^7$. In some embodiments, $R^3$ is selected from halogen, $-CN$, $C_{1-3}$ alkyl and $C_{1-3}$ haloalkyl. In some embodiments, $R^3$ is selected from $-Cl$ and $-CN$. In some embodiments, $R^3$ is selected from halogen and cyano.

In some embodiments, for a compound of Formula (III), (III-A), (III-B), or (III-C), A is selected from $-O-$, $-S-$, $-S(=O)-$, $-S(=O)_2-$ and $-OP(O)(OH)-$. In some embodiments, A is selected from $-S(=O)-$ and $-S(=O)_2$. In some embodiments, A is selected from $-S-$ and —S(=O)$_2$. In some embodiments, A is selected from —S— and —S(=O)—. In some embodiments, A is —S—. In some embodiments, A is —S(=O)—. In some embodiments, A is —S(=O)$_2$. In some embodiments, A is selected from —OP(O)(OH)— and —O—. In some embodiments, A is —OP(O)(OH)—. In some embodiments, A is —O—. In some embodiments, A is selected from —O—, —S—, —S(=O)— and —S(=O)$_2$—.

In some embodiments, for a compound of Formula (III), (III-A), (III-B), or (III-C), at least one of R$^4$ and R$^5$ is C$_{1-6}$ alkyl, optionally substituted at each occurrence with one or more substituents selected from halogen, —OR$^8$, —S—S—R$^8$, —S—C(O)R$^8$, —OC(O)R$^8$, —OC(O)OR$^8$ and —P(O)(OR$^8$)$_2$.

In some embodiments, for a compound of Formula (III), (III-A), (III-B), or (III-C), R$^4$ and R$^5$ are independently selected from C$_{1-6}$ alkyl, optionally substituted at each occurrence with one or more substituents selected from halogen, —OR$^8$, —S—S—R$^8$, —S—C(O)R$^8$, —OC(O)R$^8$, —OC(O)OR$^8$ and —P(O)(OR$^8$)$_2$. In some embodiments, R$^4$ and R$^5$ are independently selected from —CH$_2$OC(O)R$^8$ and —CH$_2$OC(O)OR$^8$. In some embodiments, R$^4$ and R$^5$ are independently selected from —CH$_2$OC(O)C(CH$_3$)$_3$, —CH$_2$OC(O)OCH(CH$_3$)$_2$, —CH$_2$OC(O)CH$_3$, —CH$_2$CH$_2$—S—S—(CH$_2$)$_2$OH and —CH$_2$CH$_2$—S—C(O)CH$_3$.

In some embodiments, for a compound of Formula (III), (III-A), (III-B), or (III-C), R$^4$ is phenyl, optionally substituted with —OR$^8$; R$^5$ is C$_{1-6}$ alkyl substituted with one or more substituents selected from —OC(O)R$^8$, —C(O)OR$^8$, and —OC(O)OR$^8$; and R$^8$ is C$_{1-6}$ alkyl.

In some embodiments, for a compound of Formula (III), (III-A), (III-B), or (III-C), R$^4$ is a 3- to 12-membered heterocycle. In some embodiments, R$^4$ is a 6-membered heterocycle, such as pyridyl. In some embodiments R$^4$ is pyrimidyl. In some embodiments, R$^4$ and R$^5$ are taken together with the atoms to which they are attached to form a 3- to 12-membered heterocycle, optionally substituted with one or more R$^7$.

In some embodiments, for a compound of Formula (III), (III-A), (III-B), or (III-C), X and Y are each —O—. In some embodiments, one of X and Y is —O— and the other one of X and Y is —NR$^8$—. In some embodiments, one of X and Y is —O— and the other one of X and Y is —NR$^8$, and R$^4$ and R$^5$ are taken together with the atoms to which they are attached to form a 3- to 12-membered heterocycle, such as a 6-membered heterocycle, optionally substituted with one or more R$^7$.

In some embodiments, for a compound of Formula (III), (III-A), (III-B), or (III-C), R$^{14}$ is selected from hydrogen; and C$_{3-12}$ carbocycle and 3- to 12-membered heterocycle each of which is optionally substituted with one or more substituents selected from halogen, —NO$_2$, —CN, —OR$^8$, —SR$^8$, —N(R$^8$)$_2$, —NR$^9$R$^{10}$, —S(=O)R$^8$, —S(=O)$_2$R$^8$, —S(=O)$_2$N(R$^8$)$_2$, —S(=O)$_2$NR$^9$R$^{10}$, —NR$^8$S(=O)$_2$R$^8$, —NR$^8$S(=O)$_2$N(R$^8$)$_2$, —NR$^8$S(=O)$_2$NR$^9$R$^{10}$, —C(O)R$^8$, —C(O)OR$^8$, —OC(O)R$^8$, —OC(O)OR$^8$, —OC(O)N(R$^8$)$_2$, —OC(O)NR$^9$R$^{10}$, —NR$^8$C(O)R$^8$, —NR$^8$C(O)OR$^8$, —NR$^8$C(O)N(R$^8$)$_2$, —NR$^8$C(O)NR$^9$R$^{10}$, —C(O)N(R$^8$)$_2$, —C(O)NR$^9$R$^{10}$, —P(O)(OR$^8$)$_2$, —P(O)(R$^8$)$_2$, =O, =S, =N(R$^8$), C$_{1-6}$ alkyl, C$_{1-6}$ haloalkyl, C$_{2-6}$ alkenyl, and C$_{2-6}$ alkynyl. In some embodiments, R$^{14}$ is phenyl.

In some embodiments, for a compound of Formula (III), (III-A), (III-B), or (III-C), W$^1$ is selected from N and CR$^6$; W$^2$ is selected from N and CH; W$^3$ is N; R$^1$ is selected from hydrogen and C$_{1-4}$ alkyl; R$^3$ is selected from halogen and cyano; and R$^6$ is selected from halogen, cyano and C$_{1-4}$ alkyl.

In some embodiments, for a compound of Formula (III), (III-A), (III-B), or (III-C), —X—R$^4$ and —Y—R$^5$ are each —OH.

In some embodiments, for a compound of Formula (III), (III-A), (III-B), or (III-C), at least one of R$^4$ and R$^5$ is selected from C$_{1-6}$ alkyl, C$_{2-6}$ alkenyl, and C$_{2-6}$ alkynyl, each of which is independently optionally substituted at each occurrence with one or more substituents selected from halogen, —NO$_2$, —CN, —OR$^8$, —SR$^8$, —N(R$^8$)$_2$, —NR$^9$R$^{10}$, —S(=O)R$^8$, —S(=O)$_2$R$^8$, —S(=O)$_2$N(R$^8$)$_2$, —S(=O)$_2$NR$^9$R$^{10}$, —NR$^8$S(=O)$_2$R$^8$, —NR$^8$S(=O)$_2$N(R$^8$)$_2$, —NR$^8$S(=O)$_2$NR$^9$R$^{10}$, —S—S—R$^8$, —S—C(O)R$^8$, —C(O)R$^8$, —C(O)OR$^8$, —OC(O)R$^8$, —OC(O)OR$^8$, —OC(O)N(R$^8$)$_2$, —OC(O)NR$^9$R$^{10}$, —NR$^8$C(O)R$^8$, —NR$^8$C(O)OR$^8$, —NR$^8$C(O)N(R$^8$)$_2$, —NR$^8$C(O)NR$^9$R$^{10}$, —C(O)N(R$^8$)$_2$, —C(O)NR$^9$R$^{10}$, —P(O)(OR$^8$)$_2$, —P(O)(R$^8$)$_2$, —OP(O)(OR$^8$)$_2$, =O, =S, =N(R$^8$); and C$_{3-12}$ carbocycle, and 3- to 12-membered heterocycle, each of which is independently optionally substituted at each occurrence with one or more substituents selected from halogen, C$_{1-6}$ alkyl, —OR$^8$, —OC(O)R$^8$, and —C(O)R$^8$.

In some embodiments, for a compound of Formula (III), (III-A), (III-B), or (III-C), R$^4$ and R$^5$ are independently selected from C$_{1-6}$ alkyl, C$_{2-6}$ alkenyl, and C$_{2-6}$ alkynyl, each of which is independently optionally substituted at each occurrence with one or more substituents selected from halogen, —NO$_2$, —CN, —OR$^8$, —SR$^8$, —N(R$^8$)$_2$, —NR$^9$R$^{10}$, —S(=O)R$^8$, —S(=O)$_2$R$^8$, —S(=O)$_2$N(R$^8$)$_2$, —S(=O)$_2$NR$^9$R$^{10}$, —NR$^8$S(=O)$_2$R$^8$, —NR$^8$S(=O)$_2$N(R$^8$)$_2$, —NR$^8$S(=O)$_2$NR$^9$R$^{10}$, —S—S—R$^8$, —S—C(O)R$^8$, —C(O)R$^8$, —C(O)OR$^8$, —OC(O)R$^8$, —OC(O)OR$^8$, —OC(O)N(R$^8$)$_2$, —OC(O)NR$^9$R$^{10}$, —NR$^8$C(O)R$^8$, —NR$^8$C(O)OR$^8$, —NR$^8$C(O)N(R$^8$)$_2$, —NR$^8$C(O)NR$^9$R$^{10}$, —C(O)N(R$^8$)$_2$, —C(O)NR$^9$R$^{10}$, —P(O)(OR$^8$)$_2$, —P(O)(R$^8$)$_2$, —OP(O)(OR$^8$)$_2$, =O, =S, =N(R$^8$); and C$_{3-12}$ carbocycle, and 3- to 12-membered heterocycle, each of which is independently optionally substituted at each occurrence with one or more substituents selected from halogen, C$_{1-6}$ alkyl, —OR$^8$, —OC(O)R$^8$, and —C(O)R$^8$.

In some embodiments, for a compound of Formula (III), (III-A), (III-B), or (III-C), R$^4$ and R$^5$ are independently selected from C$_{1-6}$ alkyl substituted with one or more substituents selected from halogen, —OC(O)R$^8$, —OC(O)OR$^8$, —S—S—R$^8$, —S—C(O)R$^8$, —OR$^8$, and —P(O)(OR$^8$)$_2$. In some embodiments, R$^4$ and R$^5$ are independently selected from hydrogen and C$_{1-6}$ alkyl, wherein each C$_{1-6}$ alkyl is optionally substituted at each occurrence with one or more substituents selected from halogen, —OC(O)R$^8$, —OC(O)OR$^8$, —S—S—R$^8$, —S—C(O)R$^8$, —OR$^8$, and —P(O)(OR$^8$)$_2$. In some embodiments, R$^4$ and R$^5$ are independently selected from C$_{1-6}$ alkyl substituted with one or more substituents selected from —OC(O)R$^8$ and —OC(O)OR$^8$. In some embodiments, R$^4$ and R$^5$ are independently selected from C$_1$ alkyl substituted with one or more substituents selected from —OC(O)R$^8$ and —OC(O)OR$^8$, wherein R$^8$ is C$_{1-6}$ alkyl. In some embodiments, R$^4$ and R$^5$ are independently selected from —CH$_2$OC(O)C(CH$_3$)$_3$, —CH$_2$OC(O)OCH(CH$_3$)$_2$, and —CH$_2$OC(O)CH$_3$. In some embodiments, R$^4$ and R$^5$ are each —CH$_2$OC(O)C(CH$_3$)$_3$. In some embodiments, R$^4$ and R$^5$ are each —CH$_2$OC(O)OCH(CH$_3$)$_2$.

In some embodiments, for a compound of Formula (III), (III-A), (III-B), or (III-C), R$^4$ and R$^5$ are independently selected from C$_{1-6}$ alkyl substituted with one or more substituents selected from —S—S—R$^8$, and —S—C(O)R$^8$. In some embodiments, $R^4$ and $R^5$ are independently selected from —$CH_2CH_2$—S—S—$(CH_2)_2OH$ and —$CH_2CH_2$—S—$C(O)CH_3$. In some embodiments, $R^4$ and $R^5$ are each —$CH_2CH_2$—S—S—$(CH_2)_{20}H$. In some embodiments, $R^4$ and $R^5$ are each —$CH_2CH_2$—S—$C(O)CH_3$.

In some embodiments, for a compound of Formula (III), (III-A), (III-B), or (III-C), $R^4$ and $R^5$ are independently selected from $C_{3-12}$ carbocycle, such as phenyl, wherein the $C_{3-12}$ carbocycle is optionally substituted with one or more substituents selected from halogen, $C_{1-6}$ alkyl, —$OR^8$, —$OC(O)R^8$, —$C(O)OR^8$, and —$C(O)R^8$. In some embodiments, $R^4$ and $R^5$ are independently selected from phenyl, wherein the phenyl is optionally substituted with —$OR^8$, such as phenyl substituted with —$OCH_2CH_3$. In some embodiments, one of $R^4$ and $R^5$ is selected from $C_{3-12}$ carbocycle, such as phenyl and benzyl, and the other of $R^4$ and $R^5$ is selected from $C_{1-6}$ alkyl substituted with one or more substituents selected from —$OC(O)R^8$, —$C(O)OR^8$, and —$OC(O)OR^8$, wherein $R^8$ is $C_{1-6}$ alkyl.

In some embodiments, for a compound of Formula (III), (III-A), (III-B), or (III-C), $R^4$ and $R^5$ are independently selected from hydrogen and $C_{1-6}$alkylene-$OR^{20}$, wherein $R^{20}$ at each occurrence is independently selected from $C_{7-20}$alkyl and $C_{7-20}$alkenyl. In some embodiments, one of $R^4$ or $R^5$ is selected from —$C_{1-3}$alkylene-O—$C_{7-20}$alkyl and —$C_{1-3}$alkylene-O—$C_{7-20}$alkenyl, such as one of $R^4$ or $R^5$ is selected from hexadecyloxypropyl (—$CH_2(CH_2)_2O(CH_2)_{15}CH_3$), octadecyloxyethyl (—$CH_2CH_2O(CH_2)_{17}CH_3$), oleyoxyethyl (—$CH_2CH_2O(CH_2)_8CH$=$CH(CH_2)_7CH_3$), and oleyoxypropyl (—$CH_2(CH_2)_2O(CH_2)_8CH$=$CH(CH_2)_7CH_3$), and the other of $R^4$ and $R^5$ is hydrogen.

In some embodiments, for a compound of Formula (III), (III-A), (III-B), or (III-C), $R^4$ and $R^5$ are taken together with the atoms to which they are attached to form a heterocycle, optionally substituted with one or more $R^7$. In some embodiments, the heterocycle is a 5- or 6-membered heterocycle. In some embodiments, $R^4$ and $R^5$ are taken together with the atoms to which they are attached to form a heterocycle selected from:

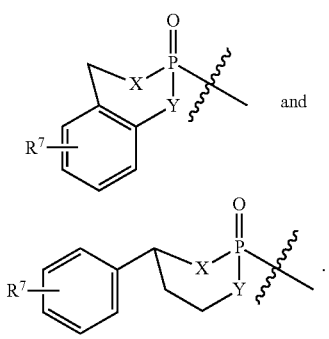

and

.

In some embodiments, $R^7$ is a halogen.

In some embodiments, for a compound of Formula (III), (III-A), (III-B), or (III-C), X and Y are each —O—. In some embodiments, one of X and Y is —O— and the other one of X and Y is —$N(R^8)$—. In some embodiments, at least one of —X—$R^4$ and —Y—$R^5$ comprises an amino acid or an amino acid ester, such as an L-alanine ester, e.g., —NHCH($CH_3$)C(O)OCH($CH_3$)$_2$ and —NHCH($CH_3$)C(O)OCH$_2$CH$_3$. In some embodiments, at least one of —X—$R^4$ and —Y—$R^5$ comprises alanine, serine, phenylalanine, valine, or two or more thereof.

In some embodiments, for a compound of Formula (III), (III-A), (III-B), or (III-C), —X—$R^4$ and —Y—$R^5$ are independently selected from: —OH, —O—$CH_3$, —O—$CH_2CH_3$, —O—$CH_2$-Ph, —O-Ph,

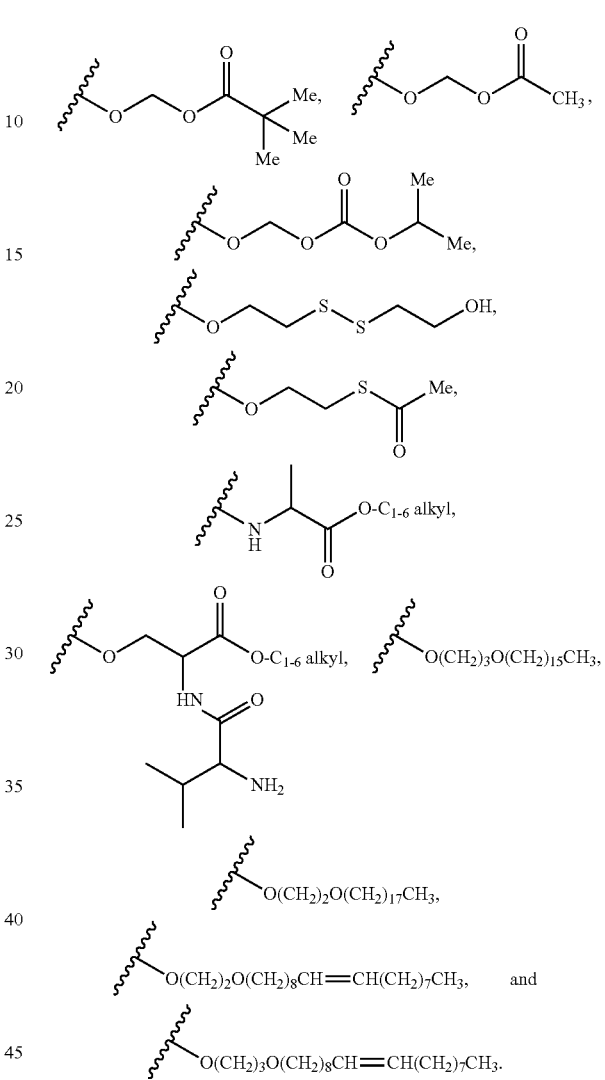

In some embodiments, —X—$R^4$ and —Y—$R^5$ are different, such as —X—$R^4$ is —OH and —Y—$R^5$ is —O(CH$_2$)$_3$O(CH$_2$)$_{15}$CH$_3$. In some embodiments, one of —X—$R^4$ and —Y—$R^5$ is —OH, and the other one of —X—$R^4$ and —Y—$R^5$ is selected from

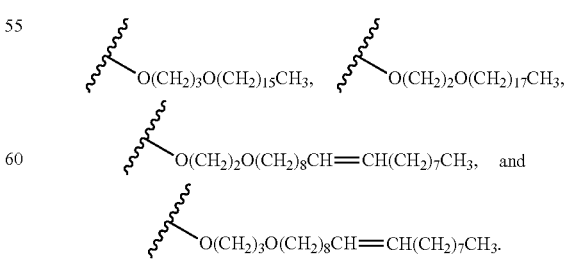

In some embodiments, —X—$R^4$ and —Y—$R^5$ are selected from the same moieties, for example, —X—$R^4$ is

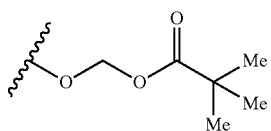 [SMILES: *OCOC(=O)C(C)(C)C]

and —Y—R⁵ is

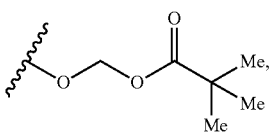 [SMILES: *OCOC(=O)C(C)(C)C]

or —X—R⁴ is

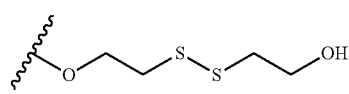 [SMILES: *OCCSSCCO]

and —Y—R⁵ is

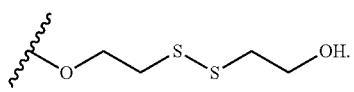 [SMILES: *OCCSSCCO]

In some embodiments, —X—R⁴ and —Y—R⁵ are each —O—CH₃, —O—CH₂CH₃, —O—CH₂Ph, —OPh,

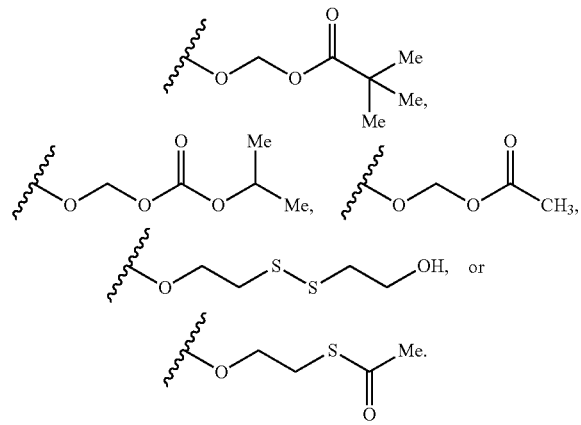

In some embodiments, for a compound of Formula (III), (III-A), (III-B), or (III-C), —X—R⁴ is selected from: —OH, —OCH₃, —OCH₂CH₃, —OCH₂Ph, —OPh,

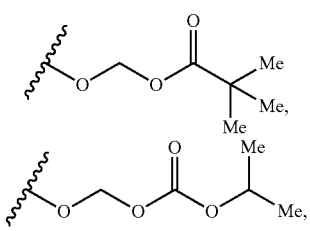

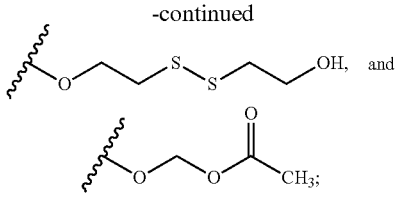

and —Y—R⁵ is selected from —OCH₃, —OCH₂CH₃, —OCH₂Ph, —OPh,

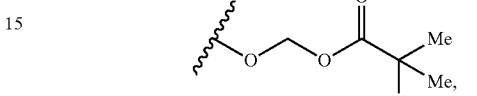

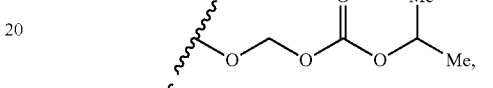

In some embodiments, for a compound of Formula (III), (III-A), (III-B), or (III-C), $W^1$ is selected from N and $CR^6$; $W^2$ is selected from N and CH; $W^3$ is N; $W^4$ is C; $W^5$ is N; $W^6$ is CH; $R^1$ is selected from hydrogen and $C_{1-4}$ alkyl; $R^3$ is selected from halogen and cyano; and $R^6$ is selected from hydrogen, halogen, cyano and $C_{1-4}$ alkyl.

In some embodiments, for a compound of Formula (III), (III-A), (III-B), or (III-C), $W^1$ is CH; $W^2$ is N; $W^3$ is N; $W^4$ is C; $W^5$ is N; $W^6$ is CH; $R^1$ is hydrogen; $R^2$ is $C_{3-12}$ carbocycle; and $R^3$ is selected from a) $C_2$-alkynyl optionally substituted with one or more $R^7$; and b) —$OR^8$.

In some embodiments, for a compound of Formula (III), (III-A), (III-B), or (III-C), —X—R⁴ and —Y—R⁵ are each —OH. In some embodiments, —X—R⁴ and —Y—R⁵ are each —OH and A is —OP(O)(OH)—.

In some embodiments, a compound or salt of Formula (I), (I-A), (I-B), (I-C), (II), (II-A), (II-B), (II-C), (III), (III-A), (III-B) or (III-C) may be a prodrug, e.g., wherein a phosphonic acid in the parent compound is presented as an ester, or carboxylic acid present in the parent compound is presented as an ester. The term "prodrug" is intended to encompass compounds which, under physiologic conditions, are converted into pharmaceutical agents, i.e., parent compound, of the present disclosure. One method for making a prodrug is to include one or more selected moieties which are hydrolyzed under physiologic conditions to reveal the desired molecule. In other embodiments, the prodrug is converted by an enzymatic activity of the host animal such as specific target cells in the host animal. For example, esters or carbonates (e.g., esters or carbonates of alcohols or carboxylic acids and esters of phosphonic acids) are preferred prodrugs of the present disclosure.

Phosphonic acids are typically ionized at physiological pH (6.5-7.4). Molecules containing this group may be highly charged, and thus may have poor oral bioavailability due to poor cell permeability. Prodrugs may overcome poor cell permeability of phosphonic acids to achieve oral bioavailability (see, e.g., Hecker and Erion, J. Med. Chem. 2008, 51, 2328, incorporated herein by reference). One or more cleavable masking group(s) may be attached to a phosphonic acid moiety to mask the charge of the acid at physiological pH, improving the cell permeability and oral bioavailability of the molecule. Upon entering systemic circulation, the masking group(s) are cleaved, releasing the phosphonic acid. Cleavable/masking groups include, but are not limited to: acyloxyalkyl diesters, alkyloxycarbonyloxyalkyl diesters, acyloxyalkyl monoesters, alkyloxycarbonyloxyalkyl monoesters, cyclic 1-aryl-1,3-propanyl esters, phosphonic diamides, phosphonic monoamides, benzyl esters, aryl phosphonamidates, dioxolenones, S-acylthioethyl esters, aryl esters, lipid esters, nitrofuranylmethyl amidates, and cyclosaligenyl prodrugs.

In some embodiments, a compound of Formula (I), (I-A), (I-B), (I-C), (II), (II-A), (II-B), (II-C), (III), (III-A), (III-B) or (III-C) is provided as a substantially pure stereoisomer. The stereoisomer may be provided in at least 90% diastereomeric excess. In some embodiments, a compound of Formula (I), (I-A), (I-B), (I-C), (II), (II-A), (II-B), (II-C), (III), (III-A), (III-B) or (III-C) may have an diastereomeric excess of at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or even higher. In some embodiments, a compound of Formula (I), (I-A), (I-B), (I-C), (II), (II-A), (II-B), (II-C), (III), (III-A), (III-B) or (III-C) may have an diastereomeric excess of about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99%.

The chemical entities described herein can be synthesized according to one or more illustrative schemes herein and/or techniques known in the art. Materials used herein are either commercially available or prepared by synthetic methods generally known in the art. These schemes are not limited to the compounds listed in the examples or by any particular substituents, which are employed for illustrative purposes. Although various steps are described and depicted in Schemes 1-7, the steps in some cases may be performed in a different order than the order shown in Schemes 1-7. Various modifications to these synthetic reaction schemes may be made and will be suggested to one skilled in the art having referred to the disclosure contained in this Application. Numberings or R groups in each scheme do not necessarily correspond to that of the claims or other schemes or tables herein.

Unless specified to the contrary, the reactions described herein take place at atmospheric pressure, generally within a temperature range from −10° C. to 200° C. Further, except as otherwise specified, reaction times and conditions are intended to be approximate, e.g., taking place at about atmospheric pressure within a temperature range of about −10° C. to about 110° C. over a period of about 1 to about 24 hours; reactions left to run overnight average a period of about 16 hours.

In some embodiments, compounds of the invention may be prepared by the following reaction schemes:

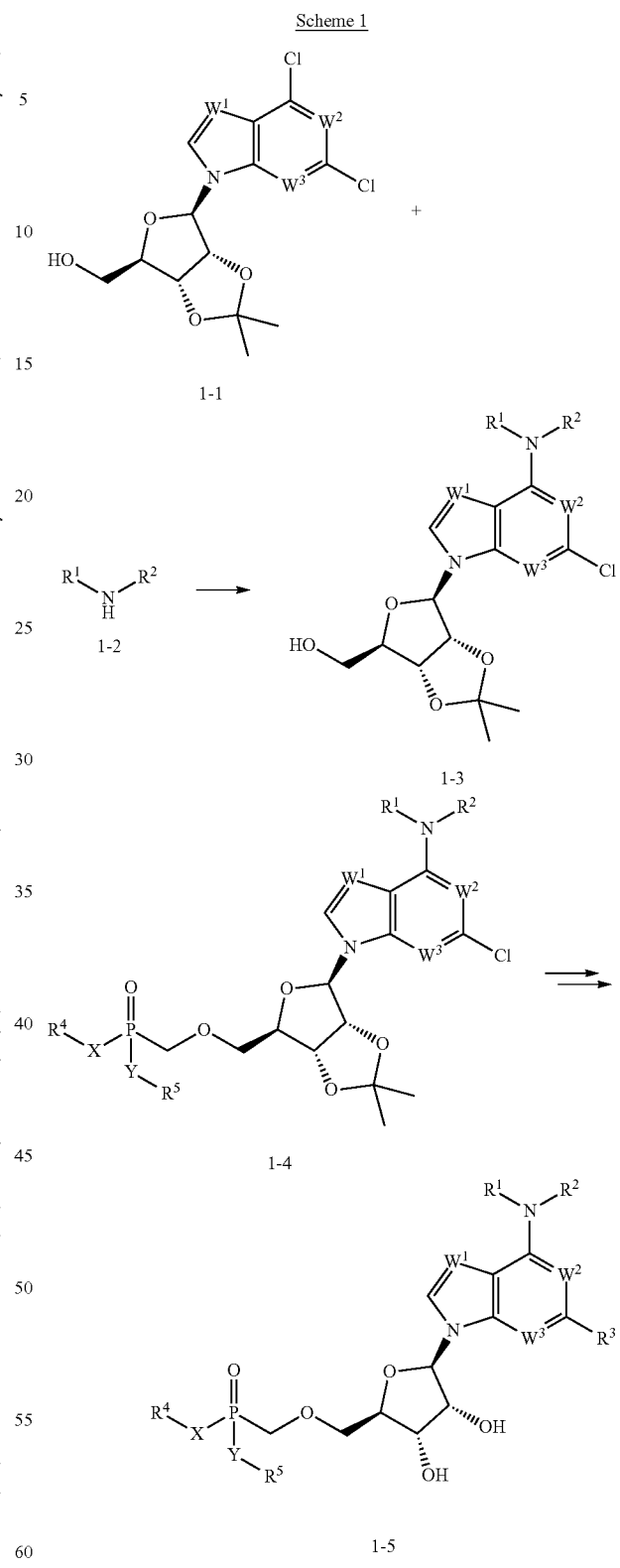

In some embodiments, a compound of Formula 1-5 may be prepared according to steps outlined in Scheme 1. For example, reaction of compound 1-1 with amine 1-2 (e.g., wherein $R^1$ and $R^2$ are alkyl or substituted alkyl) can provide intermediate 1-3. The reaction may be carried out in a suitable organic solvent in the presence of a base. Suitable bases for the reaction include, but are not limited to, organic bases, for example, triethylamine, N,N-diisopropylethylamine, 1,4-diazabicyclo[2.2.2]octane, and inorganic bases, for example, cesium bicarbonate, sodium carbonate, and potassium carbonate. Compound 1-3 may be alkylated with a suitable alkylation reagent to give compound 1-4. Elevated temperature may be needed for the alkylation to occur. The temperature may be in a range of 50° C. to 100° C. Further substitution and hydrolysis of compound 1-4 can be carried out to afford phosphonic acid 1-5.

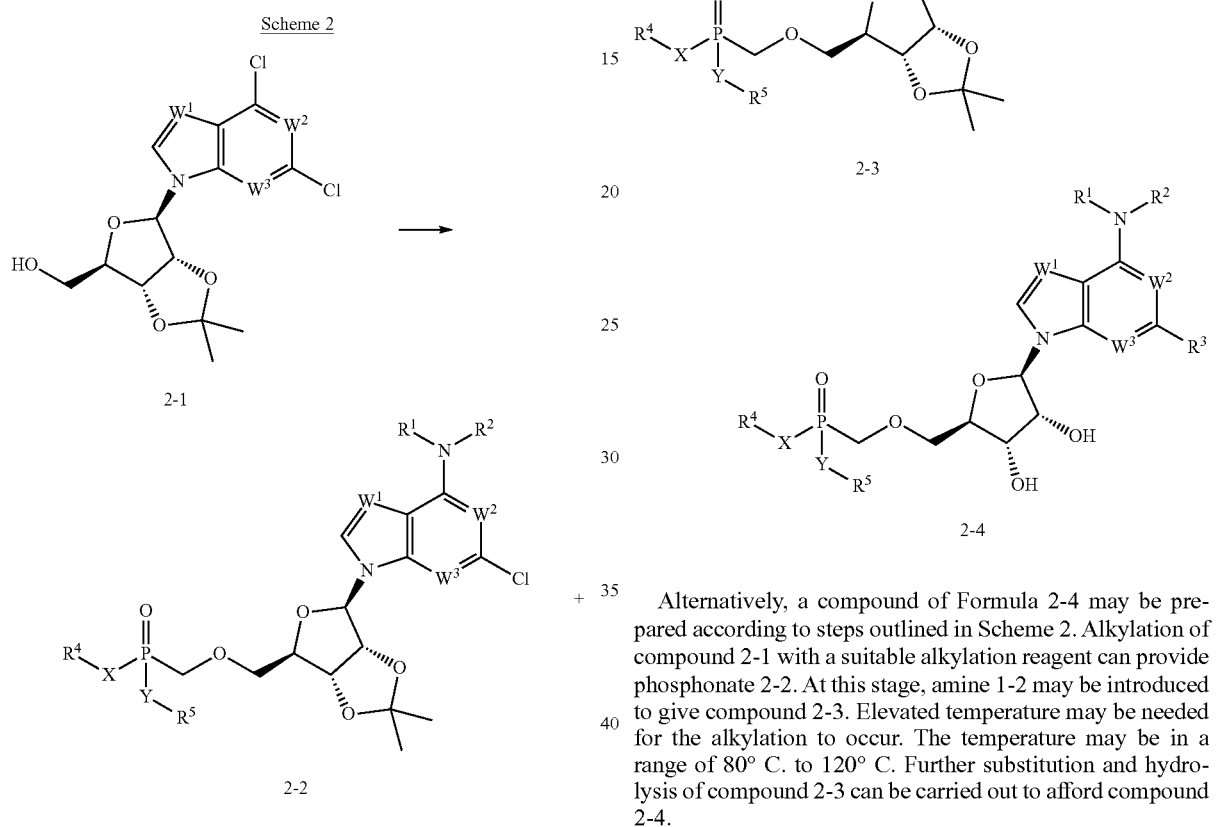

Alternatively, a compound of Formula 2-4 may be prepared according to steps outlined in Scheme 2. Alkylation of compound 2-1 with a suitable alkylation reagent can provide phosphonate 2-2. At this stage, amine 1-2 may be introduced to give compound 2-3. Elevated temperature may be needed for the alkylation to occur. The temperature may be in a range of 80° C. to 120° C. Further substitution and hydrolysis of compound 2-3 can be carried out to afford compound 2-4.

In some embodiments, a compound of Formula 3-8 may be prepared according to steps outlined in Scheme 3. For example, reaction of compound 3-1 with amine 3-2 (e.g., wherein $R^1$ and $R^2$ are independently alkyl or substituted alkyl) can provide intermediate 3-3. The reaction may be carried out in a suitable organic solvent in the presence of a base. Suitable bases for the reaction include, but are not limited to, organic bases, such as triethylamine, N,N-diisopropylethylamine, 1,4-diazabicyclo[2.2.2]octane, and inorganic bases, such as cesium bicarbonate, sodium carbonate, and potassium carbonate. Alcohol 3-3 may be reacted with a suitable sulfonyl chloride to give compound 3-4. The sulfur atom of the linker may be introduced by reacting compound 3-4 with reagent 3-5 in the presence of a base, such as sodium ethoxide, to give thioether 3-6. Oxidation of thioether 3-6 with an oxidation reagent, such as oxone, affords sulfone 3-7. Further substitution and hydrolysis of compound 3-7 can be carried out to afford compound 3-8.

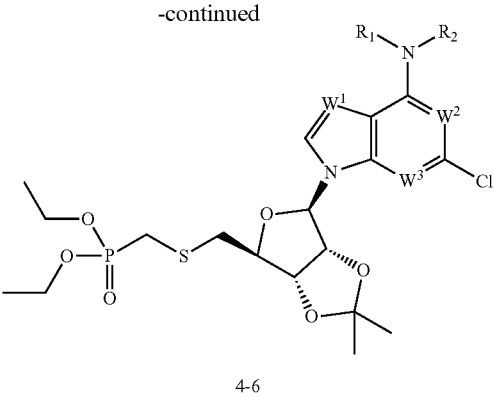

4-6

Alternatively, a compound of Formula 4-6 may be prepared according to steps outlined in Scheme 4. Thioacetate 4-1 may be prepared from compound 4-3 under standard Mitsuobu conditions or by displacing a sulfonate intermediate, e.g., compound 4-4, with potassium thioacetate. Alkylation of compound 4-1 with bromide 4-2 in the presence of a base, such as sodium isopropoxide, can provide phosphonate 4-6.

Scheme 4

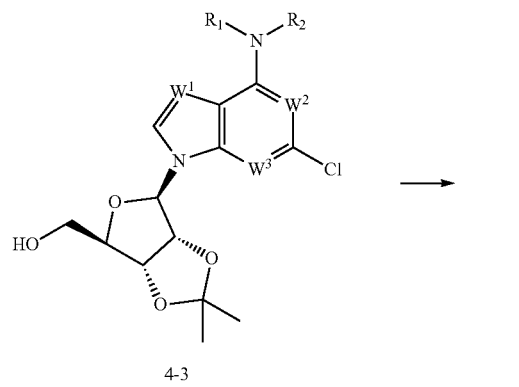

4-3

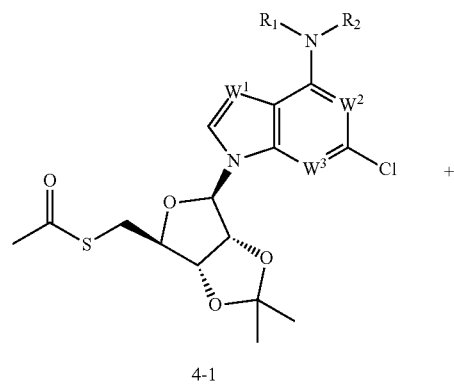

4-1

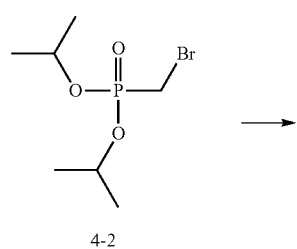

4-2

Scheme 5

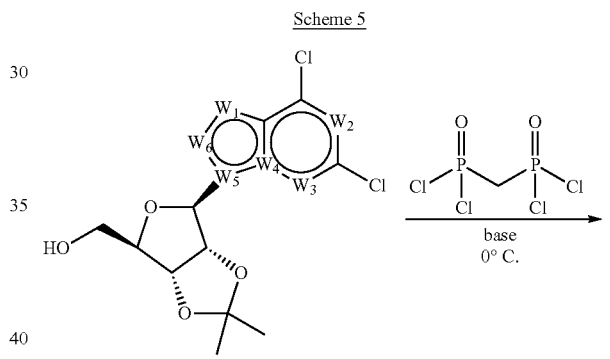

81

-continued

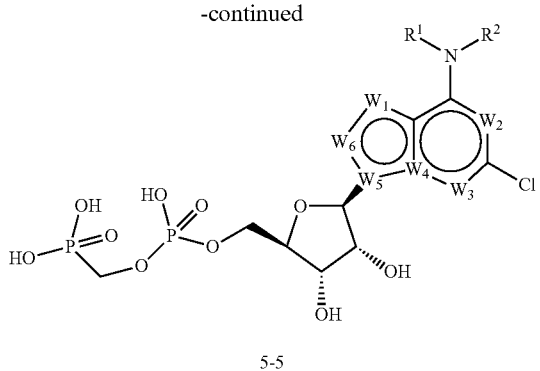

5-5

In some embodiments, a compound of Formula 5-5 may be prepared by the steps outlined in Scheme 5. For example, reaction of 5-1 with P,P'-methylenebis-phosphonic dichloride in the presence of a suitable base can provide intermediate 5-2. Reaction of intermediate 5-2 with amine 5-3 in the presence of base generates intermediate 5-4. Deprotection of 5-4 using strong acid, such as formic acid, yields compound 5-5.

Scheme 6

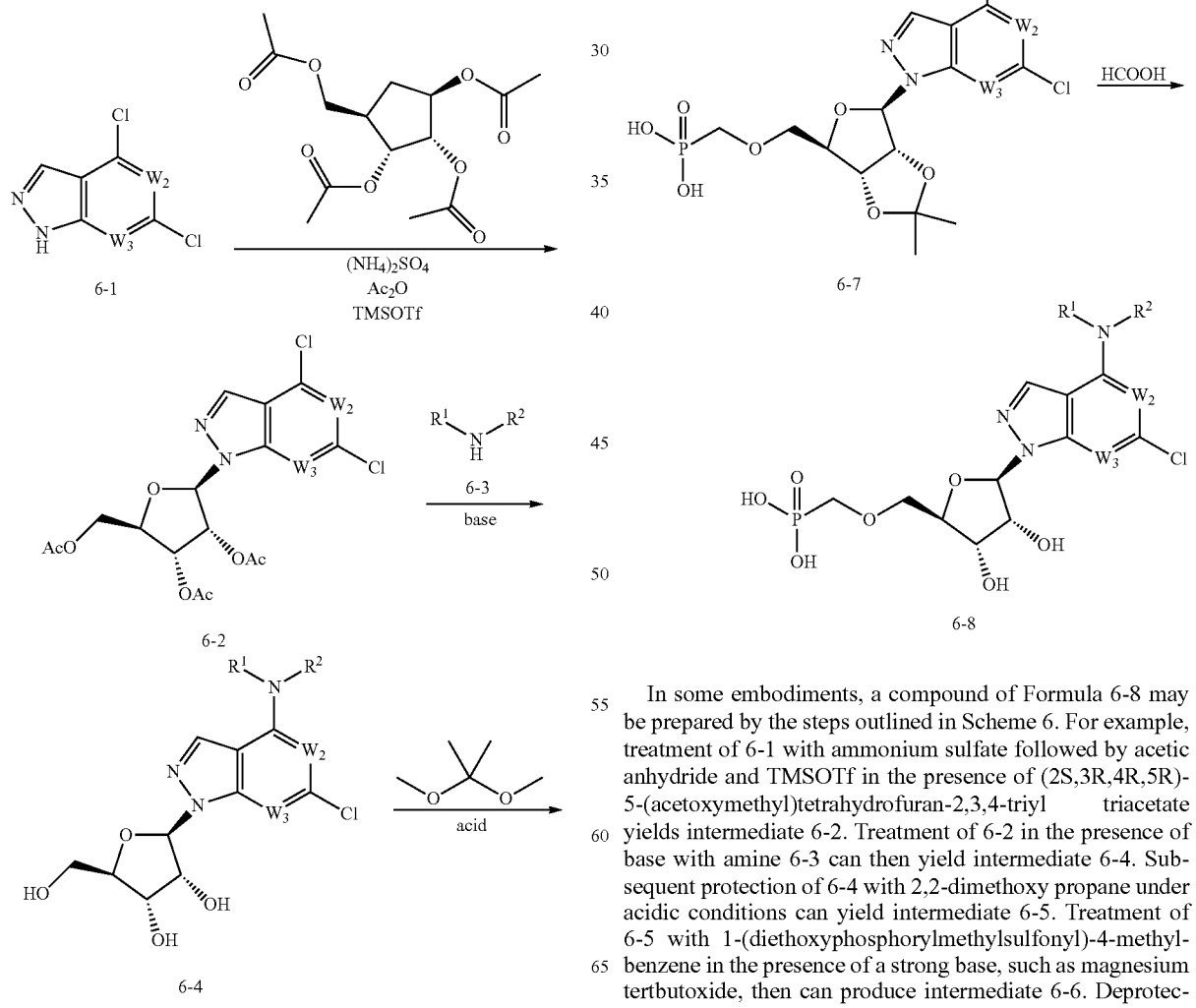

82

-continued

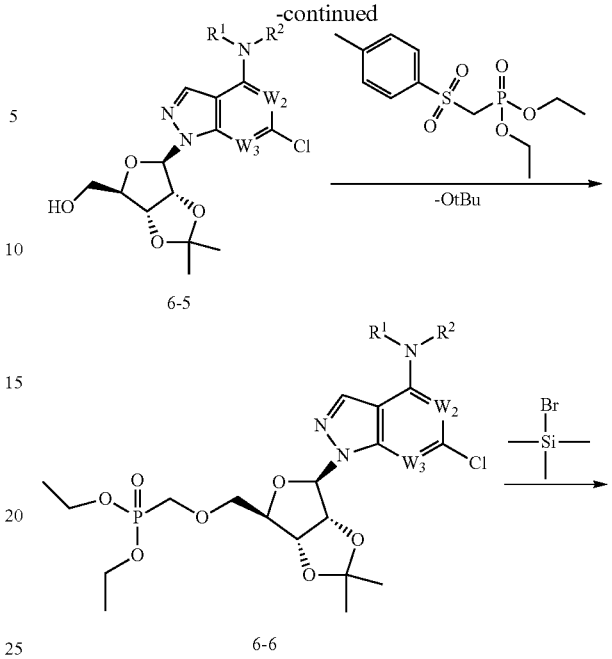

In some embodiments, a compound of Formula 6-8 may be prepared by the steps outlined in Scheme 6. For example, treatment of 6-1 with ammonium sulfate followed by acetic anhydride and TMSOTf in the presence of (2S,3R,4R,5R)-5-(acetoxymethyl)tetrahydrofuran-2,3,4-triyl triacetate yields intermediate 6-2. Treatment of 6-2 in the presence of base with amine 6-3 can then yield intermediate 6-4. Subsequent protection of 6-4 with 2,2-dimethoxy propane under acidic conditions can yield intermediate 6-5. Treatment of 6-5 with 1-(diethoxyphosphorylmethylsulfonyl)-4-methylbenzene in the presence of a strong base, such as magnesium tertbutoxide, then can produce intermediate 6-6. Deprotection of the phosphonate hydroxyls of 6-6 using bromotrimethysilane can produce intermediate 6-7. Finally, deprotection of the ribose hydroxyls in strong acid, such as formic acid, can yield compound 6-8.

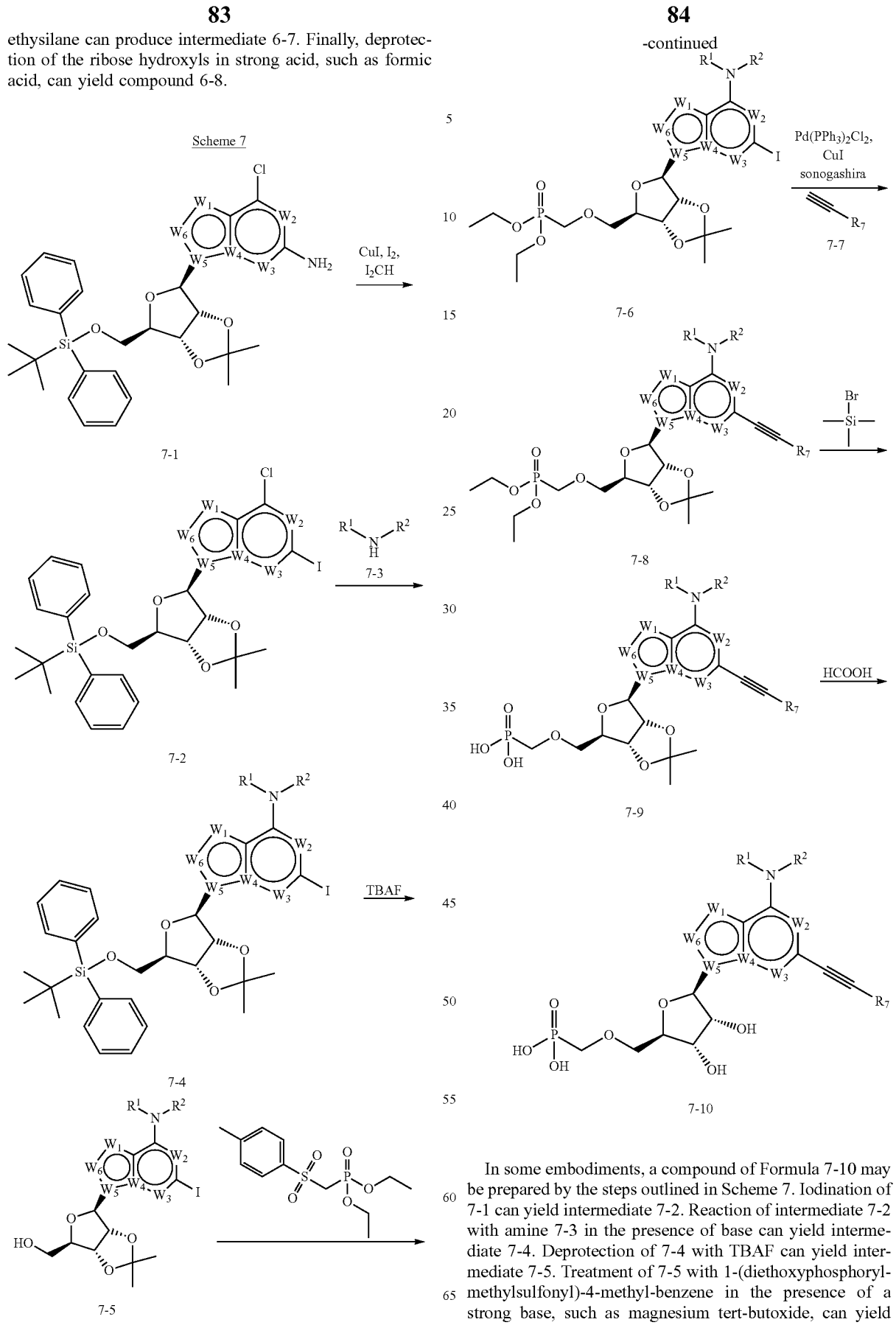

In some embodiments, a compound of Formula 7-10 may be prepared by the steps outlined in Scheme 7. Iodination of 7-1 can yield intermediate 7-2. Reaction of intermediate 7-2 with amine 7-3 in the presence of base can yield intermediate 7-4. Deprotection of 7-4 with TBAF can yield intermediate 7-5. Treatment of 7-5 with 1-(diethoxyphosphoryl-methylsulfonyl)-4-methyl-benzene in the presence of a strong base, such as magnesium tert-butoxide, can yield compound 7-6. Treatment of 7-6 under Sonogashira coupling conditions with alkyne 7-7 can then yield intermediate 7-8. Deprotection of the phosphonate hydroxyls of 7-8 with bromotrimethylsilane can produce intermediate 7-9. Finally, deprotection with a strong acid, such as formic acid, yields compound 7-10.

In some embodiments, a compound of the present invention, for example a compound of a formula given in Table 1, is synthesized according to one of the general routes outlined in Schemes 1-7, Examples 1-22 or by methods generally known in the art.

TABLE 1

| No. | Structure | m/z | IUPAC Name |
|---|---|---|---|
| 1 | 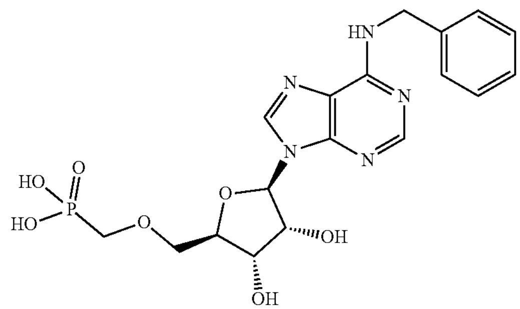 [SMILES: O=P(O)(O)COC[C@H]1O[C@@H](n2cnc3c(NCc4ccccc4)ncnc32)[C@H](O)[C@@H]1O] | [M + H]$^+$: 450; [M − H]$^−$: 452 | [(2R,3S,4R,5R)-5-[6-(benzylamino)purin-9-yl]-3,4-dihydroxy-tetrahydrofuran-2-yl]methoxymethyl-phosphonic acid |
| 2 | 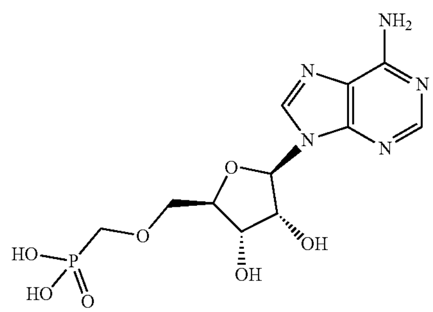 [SMILES: Nc1ncnc2c1ncn2[C@@H]1O[C@H](COCP(=O)(O)O)[C@@H](O)[C@H]1O] | [M + H]$^+$: 362; [M − H]$^−$: 360 | [(2R,3S,4R,5R)-5-(6-aminopurin-9-yl)-3,4-dihydroxy-tetrahydrofuran-2-yl]methoxymethyl-phosphonic acid |
| 3 | 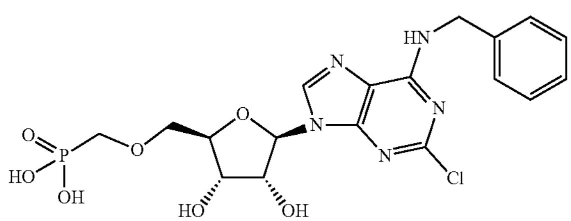 [SMILES: O=P(O)(O)COC[C@H]1O[C@@H](n2cnc3c(NCc4ccccc4)nc(Cl)nc32)[C@H](O)[C@@H]1O] | [M − H]$^−$: 484 | [(2R,3S,4R,5R)-5-[6-(benzylamino)-2-chloro-purin-9-yl]-3,4-dihydroxy-tetrahydrofuran-2-yl]methoxymethyl-phosphonic acid |
| 4 | 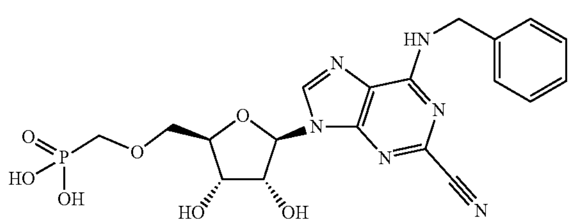 [SMILES: N#Cc1nc(NCc2ccccc2)c2ncn([C@@H]3O[C@H](COCP(=O)(O)O)[C@@H](O)[C@H]3O)c2n1] | [M − H]$^−$: 475 | [(2R,3S,4R,5R)-5-[6-(benzylamino)-2-cyano-purin-9-yl]-3,4-dihydroxy-tetrahydrofuran-2-yl]methoxymethyl-phosphonic acid |
| 5 | 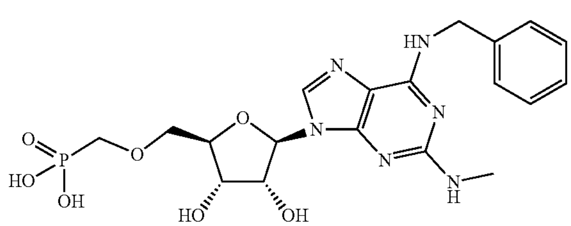 [SMILES: CNc1nc(NCc2ccccc2)c2ncn([C@@H]3O[C@H](COCP(=O)(O)O)[C@@H](O)[C@H]3O)c2n1] | [M + H]$^+$: 481; [M − H]$^−$: 479 | [(2R,3S,4R,5R)-5-[6-(benzylamino)-2-(methylamino)purin-9-yl]-3,4-dihydroxy-tetrahydrofuran-2-yl]methoxymethyl-phosphonic acid |

TABLE 1-continued

| No. | Structure | m/z | IUPAC Name |
|---|---|---|---|
| 6 | 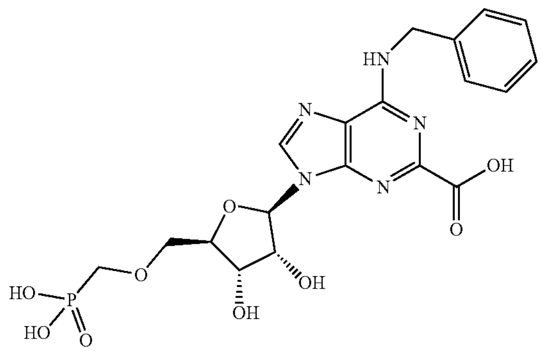 [SMILES: O=C(O)c1nc(NCc2ccccc2)c2ncn([C@@H]3O[C@H](COCP(=O)(O)O)[C@@H](O)[C@H]3O)c2n1] | [M + H]⁺: 496; [M − H]⁻: 494 | 6-(benzylamino)-9-[(2R,3R,4S,5R)-3,4-dihydroxy-5-(phosphonomethoxymethyl)tetrahydrofuran-2-yl]purine-2-carboxylic acid |
| 7 | 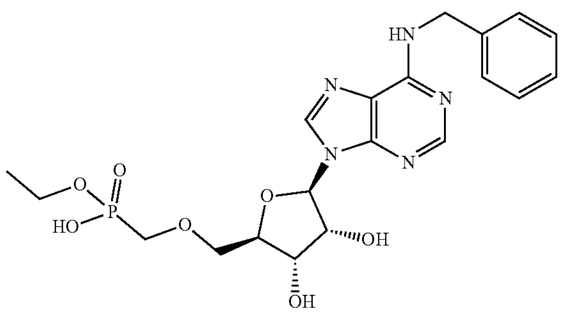 [SMILES: CCOP(=O)(O)COC[C@H]1O[C@@H](n2cnc3c(NCc4ccccc4)ncnc32)[C@H](O)[C@@H]1O] | [M + H]⁺: 480; [M − H]⁻: 478 | [(2R,3S,4R,5R)-5-[6-(benzylamino)purin-9-yl]-3,4-dihydroxy-tetrahydrofuran-2-yl]-methoxymethyl-ethoxy-phosphinic acid |
| 8 | 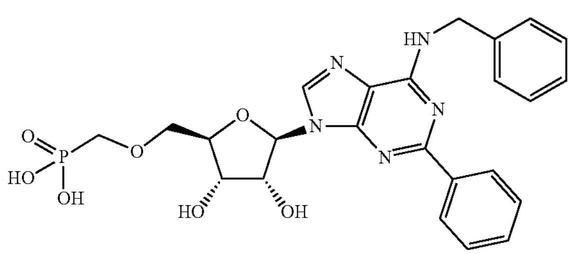 [SMILES: O=P(O)(O)COC[C@H]1O[C@@H](n2cnc3c(NCc4ccccc4)nc(-c4ccccc4)nc32)[C@H](O)[C@@H]1O] | [M − H]⁻: 526 | [(2R,3S,4R,5R)-5-[6-(benzylamino)-2-phenyl-purin-9-yl]-3,4-dihydroxy-tetrahydrofuran-2-yl]methoxymethyl-phosphonic acid |
| 9 | 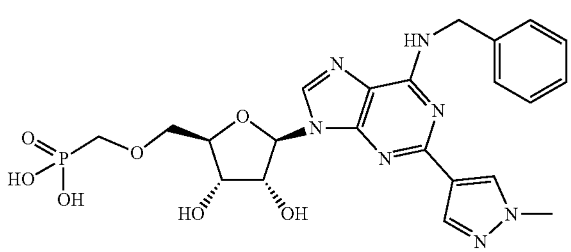 [SMILES: Cn1cc(-c2nc(NCc3ccccc3)c3ncn([C@@H]4O[C@H](COCP(=O)(O)O)[C@@H](O)[C@H]4O)c3n2)cn1] | [M + H]⁺: 532; [M − H]⁻: 530 | [(2R,3S,4R,5R)-5-[6-(benzylamino)-2-(1-methylpyrazol-4-yl)-purin-9-yl]-3,4-dihydroxy-tetrahydrofuran-2-yl]methoxymethylphosphonic acid |
| 10 | 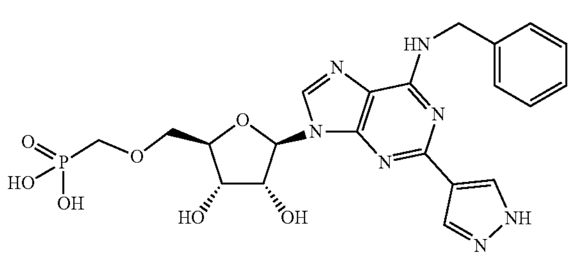 [SMILES: O=P(O)(O)COC[C@H]1O[C@@H](n2cnc3c(NCc4ccccc4)nc(-c4cn[nH]c4)nc32)[C@H](O)[C@@H]1O] | [M + H]⁺: 518; [M − H]⁻: 516 | [(2R,3S,4R,5R)-5-[6-(benzylamino)-2-(1H-pyrazol-4-yl)purin-9-yl]-3,4-dihydroxy-tetrahydrofuran-2-yl]methoxymethylphosphonic acid |

TABLE 1-continued

| No. | Structure | m/z | IUPAC Name |
|---|---|---|---|
| 11 | 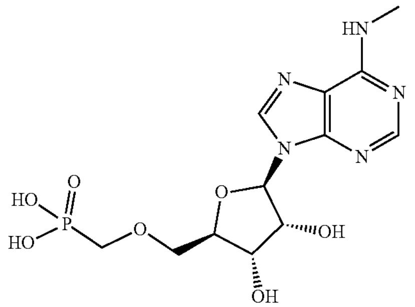 [SMILES: CNc1ncnc2c1ncn2[C@@H]1O[C@H](COCP(=O)(O)O)[C@@H](O)[C@H]1O] | [M + H]+: 376; [M − H]−: 374 | [(2R,3S,4R,5R)-3,4-dihydroxy-5-[6-(methylamino)purin-9-yl]tetrahydrofuran-2-yl]methoxymethyl-phosphonic acid |
| 12 | 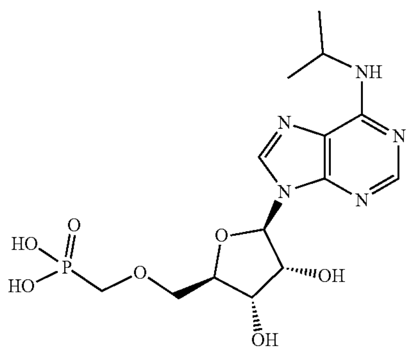 [SMILES: CC(C)Nc1ncnc2c1ncn2[C@@H]1O[C@H](COCP(=O)(O)O)[C@@H](O)[C@H]1O] | [M + H]+: 404; [M − H]−: 402 | [(2R,3S,4R,5R)-3,4-dihydroxy-5-[6-(iso-propylamino)purin-9-yl]tetrahydrofuran-2-yl]methoxymethyl-phosphonic acid |
| 13 | 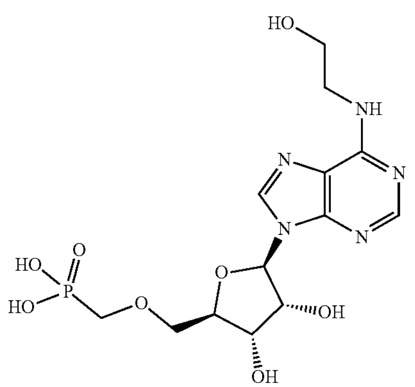 [SMILES: O=P(O)(O)COC[C@H]1O[C@@H](n2cnc3c(NCCO)ncnc32)[C@H](O)[C@@H]1O] | [M + H]+: 406; [M − H]−: 404 | [(2R,3S,4R,5R)-3,4-dihydroxy-5-[6-(2-hydroxyethylamino)-purin-9-yl]tetrahydro-furan-2-yl]methoxy-methylphosphonic acid |
| 14 | 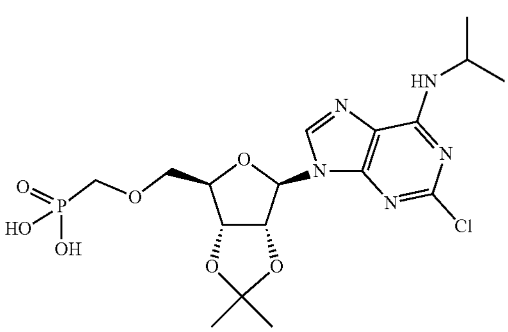 [SMILES: CC(C)Nc1nc(Cl)nc2c1ncn2[C@@H]1O[C@H](COCP(=O)(O)O)[C@H]2OC(C)(C)O[C@H]21] | | [(3aR,4R,6R,6aR)-4-[2-chloro-6-(isopropyl-amino)purin-9-yl]-2,2-dimethyl-3a,4,6,6a-tetrahydrofuro[3,4-d][1,3]dioxol-6-yl]-methoxymethylphos-phonic acid |

TABLE 1-continued

| No. | Structure | m/z | IUPAC Name |
|---|---|---|---|
| 15 | 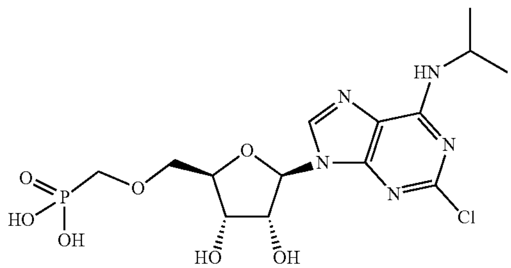 [SMILES: CC(C)Nc1nc(Cl)nc2c1ncn2[C@@H]1O[C@H](COCP(=O)(O)O)[C@@H](O)[C@H]1O] | [M + H]⁺: 438; [M − H]⁻: 436 | [(2R,3S,4R,5R)-5-[2-chloro-6-(isopropyl-amino)purin-9-yl]-3,4-dihydroxy-tetra-hydrofuran-2-yl]-methoxymethylphos-phonic acid |
| 16 | 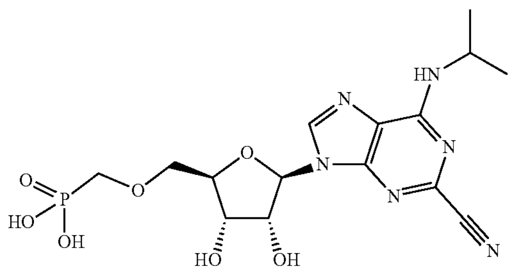 [SMILES: CC(C)Nc1nc(C#N)nc2c1ncn2[C@@H]1O[C@H](COCP(=O)(O)O)[C@@H](O)[C@H]1O] | [M + H]⁺: 429; [M − H]⁻: 427 | [(2R,3S,4R,5R)-5-[2-cyano-6-(isopropyl-amino)purin-9-yl]-3,4-dihydroxy-tetrahydrofuran-2-yl]methoxymethyl-phosphonic acid |
| 17 | 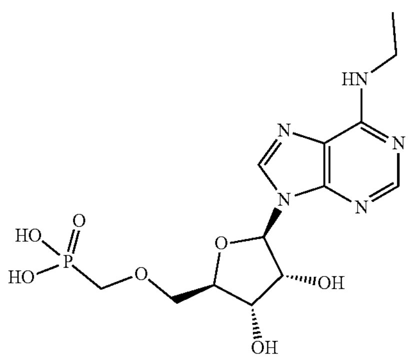 [SMILES: CCNc1ncnc2c1ncn2[C@@H]1O[C@H](COCP(=O)(O)O)[C@@H](O)[C@H]1O] | [M + H]⁺: 390; [M − H]⁻: 388 | [(2R,3S,4R,5R)-5-[6-(ethylamino)purin-9-yl]-3,4-dihydroxy-tetrahydrofuran-2-yl]-methoxymethylphos-phonic acid |
| 18 | 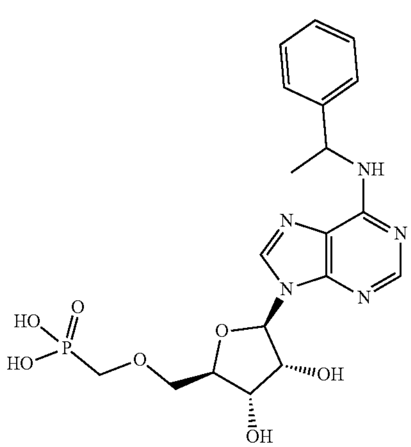 [SMILES: CC(Nc1ncnc2c1ncn2[C@@H]1O[C@H](COCP(=O)(O)O)[C@@H](O)[C@H]1O)c1ccccc1] | [M + H]⁺: 466; [M − H]⁻: 464 | [(2R,3S,4R,5R)-3,4-dihydroxy-5-[6-(1-phenylethylamino)-purin-9-yl]tetrahydro-furan-2-yl]methoxy-methylphosphonic acid |

TABLE 1-continued

| No. | Structure | m/z | IUPAC Name |
|---|---|---|---|
| 19 | 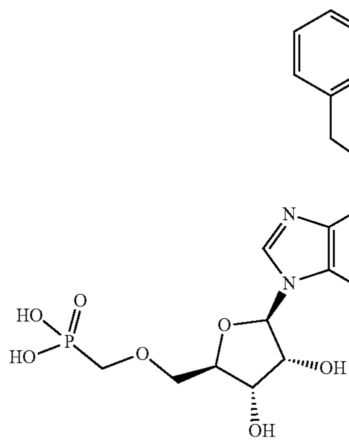 | [M + H]⁺: 453; [M − H]⁻: 451 | [(2R,3S,4R,5R)-3,4-dihydroxy-5-[6-(2-pyridylmethylamino)-purin-9-yl]tetrahydro-furan-2-yl]methoxy-methylphosphonic acid |
| 20 | 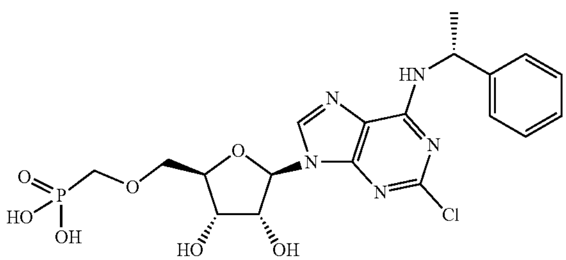 [SMILES: C[C@@H](Nc1nc(Cl)nc2c1ncn2[C@@H]1O[C@H](COCP(=O)(O)O)[C@@H](O)[C@H]1O)c1ccccc1] | [M + H]⁺: 500; [M − H]⁻: 498 | [(2R,3S,4R,5R)-5-[2-chloro-6-[[(1R)-1-phenylethyl]amino]-purin-9-yl]-3,4-dihydroxy-tetrahydro-furan-2-yl]methoxy-methylphosphonic acid |
| 21 | 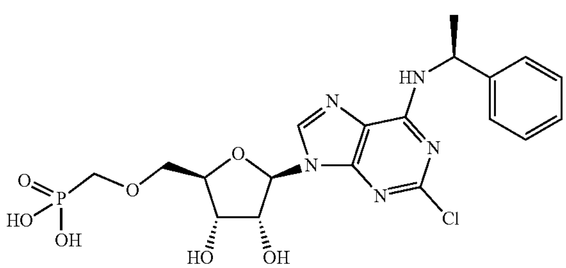 [SMILES: C[C@H](Nc1nc(Cl)nc2c1ncn2[C@@H]1O[C@H](COCP(=O)(O)O)[C@@H](O)[C@H]1O)c1ccccc1] | [M + H]⁺: 500; [M − H]⁻: 498 | [(2R,3S,4R,5R)-5-[2-chloro-6-[[(1S)-1-phenylethyl]amino]-purin-9-yl]-3,4-dihydroxy-tetrahydro-furan-2-yl]methoxy-methylphosphonic acid |
| 22 | 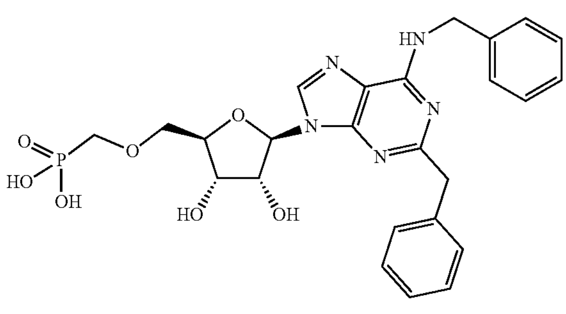 [SMILES: O=P(O)(O)COC[C@H]1O[C@@H](n2cnc3c(NCc4ccccc4)nc(Cc4ccccc4)nc32)[C@H](O)[C@@H]1O] | [M + H]⁺: 542; [M − H]⁻: 540 | [(2R,3S,4R,5R)-5-[2-benzyl-6-(benzyl-amino)purin-9-yl]-3,4-dihydroxy-tetrahydro-furan-2-yl]methoxy-methylphosphonic acid |
| 23 | 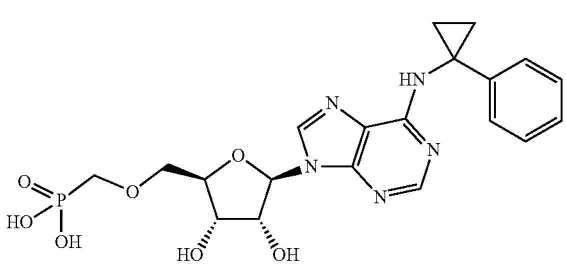 [SMILES: O=P(O)(O)COC[C@H]1O[C@@H](n2cnc3c(NC4(c5ccccc5)CC4)ncnc32)[C@H](O)[C@@H]1O] | [M + H]⁺: 478; [M − H]⁻: 476 | [(2R,3S,4R,5R)-3,4-dihydroxy-5-[6-[(1-phenylcyclopropyl)-amino]purin-9-yl]-tetrahydrofuran-2-yl]-methoxymethylphosphonic acid |

TABLE 1-continued

| No. | Structure | m/z | IUPAC Name |
|---|---|---|---|
| 24 | 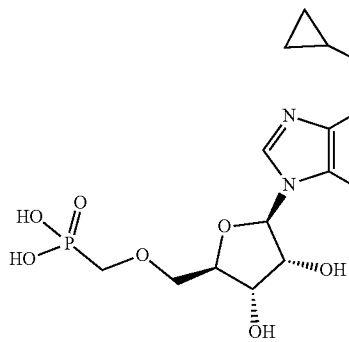 | [M + H]⁺: 402; [M − H]⁻: 400 | [(2R,3S,4R,5R)-5-[6-(cyclopropylamino)-purin-9-yl]-3,4-dihydroxy-tetrahydro-furan-2-yl]methoxy-methylphosphonic acid |
| 25 | 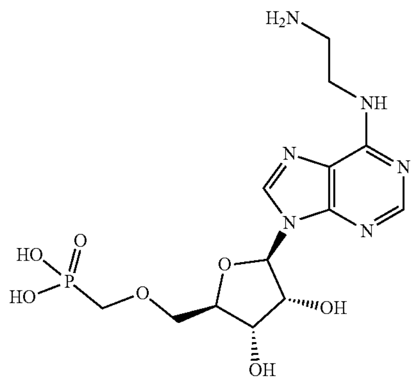 [SMILES: NCCNc1ncnc2c1ncn2[C@@H]1O[C@H](COCP(=O)(O)O)[C@@H](O)[C@H]1O] | [M + H]⁺: 405; [M − H]⁻: 403 | [(2R,3S,4R,5R)-5-[6-(2-aminoethylamino)-purin-9-yl]-3,4-dihydroxy-tetrahydro-furan-2-yl]methoxy-methylphosphonic acid |
| 26 | 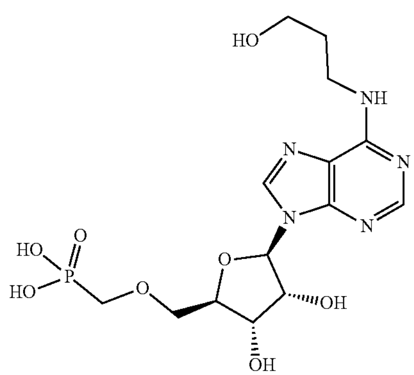 [SMILES: O=P(O)(O)COC[C@H]1O[C@@H](n2cnc3c(NCCCO)ncnc32)[C@H](O)[C@@H]1O] | [M + H]⁺: 420; [M − H]⁻: 418 | [(2R,3S,4R,5R)-3,4-dihydroxy-5-[6-(3-hydroxypropylamino)-purin-9-yl]tetrahydro-furan-2-yl]methoxy-methylphosphonic acid |
| 27 | 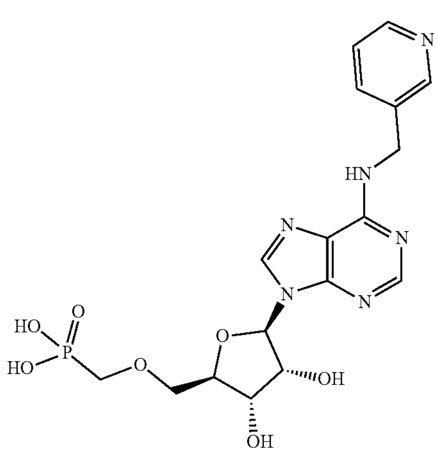 [SMILES: O=P(O)(O)COC[C@H]1O[C@@H](n2cnc3c(NCc4cccnc4)ncnc32)[C@H](O)[C@@H]1O] | [M + H]⁺: 453; [M − H]⁻: 451 | [(2R,3S,4R,5R)-3,4-dihydroxy-5-[6-(3-pyridylmethylamino)-purin-9-yl]tetrahydro-furan-2-yl]methoxy-methylphosphonic acid |

TABLE 1-continued

| No. | Structure | m/z | IUPAC Name |
|---|---|---|---|
| 28 | 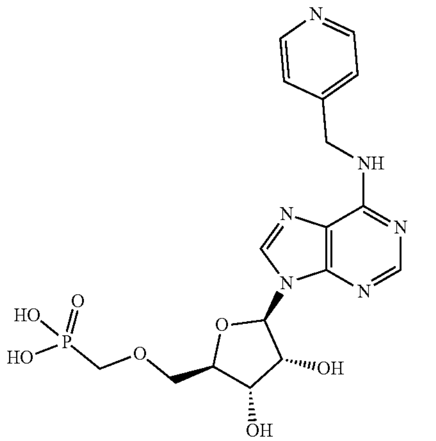 [SMILES: O=P(O)(O)COC[C@H]1O[C@@H](n2cnc3c(NCc4ccncc4)ncnc32)[C@H](O)[C@@H]1O] | [M − H]⁻: 451 | [(2R,3S,4R,5R)-3,4-dihydroxy-5-[6-(4-pyridylmethylamino)-purin-9-yl]tetrahydro-furan-2-yl]methoxy-methylphosphonic acid |
| 29 | 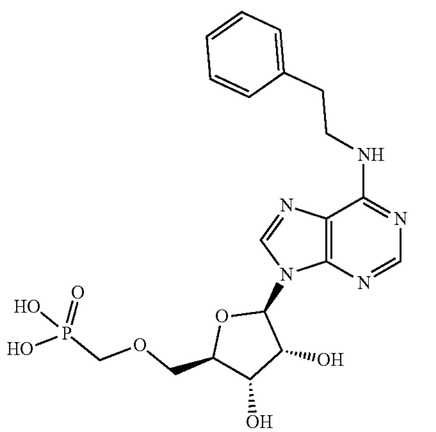 [SMILES: O=P(O)(O)COC[C@H]1O[C@@H](n2cnc3c(NCCc4ccccc4)ncnc32)[C@H](O)[C@@H]1O] | [M + H]⁺: 466; [M − H]⁻: 464 | [(2R,3S,4R,5R)-3,4-dihydroxy-5-[6-(2-phenylethylamino)-purin-9-yl]tetrahydro-furan-2-yl]methoxy-methylphosphonic acid |
| 30 | 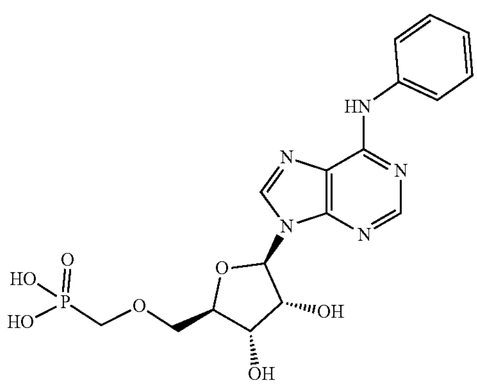 [SMILES: O=P(O)(O)COC[C@H]1O[C@@H](n2cnc3c(Nc4ccccc4)ncnc32)[C@H](O)[C@@H]1O] | [M + H]⁺: 438; [M − H]⁻: 436 | [(2R,3S,4R,5R)-5-(6-anilinopurin-9-yl)-3,4-dihydroxy-tetrahydro-furan-2-yl]methoxy-methylphosphonic acid |
| 31 | 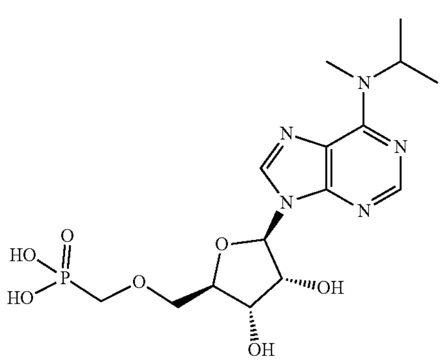 [SMILES: CC(C)N(C)c1ncnc2c1ncn2[C@@H]1O[C@H](COCP(=O)(O)O)[C@@H](O)[C@H]1O] | [M + H]⁺: 418; [M − H]⁻: 416 | [(2R,3S,4R,5R)-3,4-dihydroxy-5-[6-[isopropyl(methyl)-amino]purin-9-yl]-tetrahydrofuran-2-yl]-methoxymethyl phosphonic acid |

TABLE 1-continued

| No. | Structure | m/z | IUPAC Name |
|---|---|---|---|
| 32 | 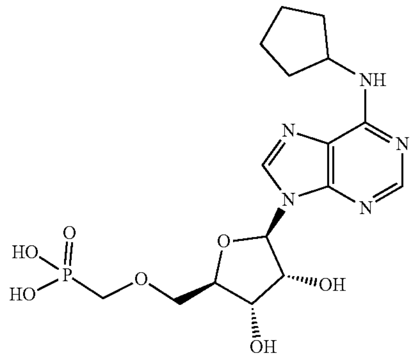 [SMILES: O=P(O)(O)COC[C@H]1O[C@@H](n2cnc3c(NC4CCCC4)ncnc32)[C@H](O)[C@@H]1O] | [M + H]⁺: 430; [M − H]⁻: 428 | [(2R,3S,4R,5R)-5-[6-(cyclopentylamino)-purin-9-yl]-3,4-dihydroxy-tetrahydro-furan-2-yl]methoxy-methylphosphonic acid |
| 33 | 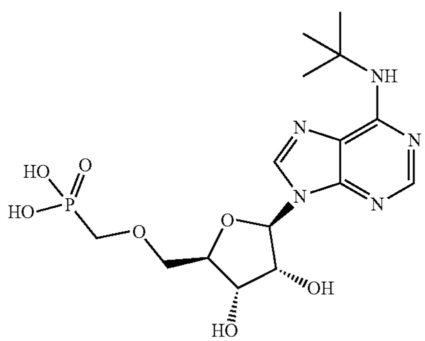 [SMILES: CC(C)(C)Nc1ncnc2c1ncn2[C@@H]1O[C@H](COCP(=O)(O)O)[C@@H](O)[C@H]1O] | [M + H]⁺: 418; [M − H]⁻: 416 | [(2R,3S,4R,5R)-5-[6-(tert-butylamino)purin-9-yl]-3,4-dihydroxy-tetrahydrofuran-2-yl]-methoxymethylphos-phonic acid |
| 34 | 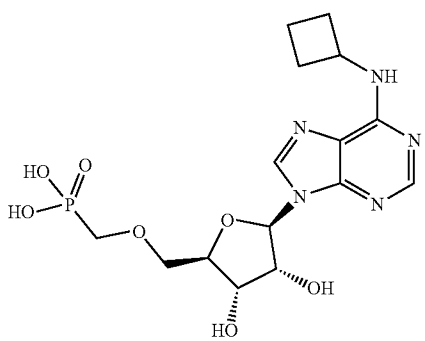 [SMILES: O=P(O)(O)COC[C@H]1O[C@@H](n2cnc3c(NC4CCC4)ncnc32)[C@H](O)[C@@H]1O] | [M + H]⁺: 416; [M − H]⁻: 414 | [(2R,3S,4R,5R)-5-[6-(cyclobutylamino)-purin-9-yl]-3,4-dihydroxy-tetrahydro-furan-2-yl]methoxy-methylphosphonic acid |
| 35 | 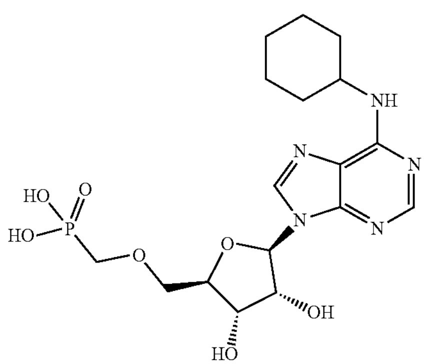 [SMILES: O=P(O)(O)COC[C@H]1O[C@@H](n2cnc3c(NC4CCCCC4)ncnc32)[C@H](O)[C@@H]1O] | [M + H]⁺: 444; [M − H]⁻: 442 | [(2R,3S,4R,5R)-5-[6-(cyclohexylamino)-purin-9-yl]-3,4-dihydroxy-tetrahydro-furan-2-yl]methoxy-methylphosphonic acid |

TABLE 1-continued

| No. | Structure | m/z | IUPAC Name |
|---|---|---|---|
| 36 | 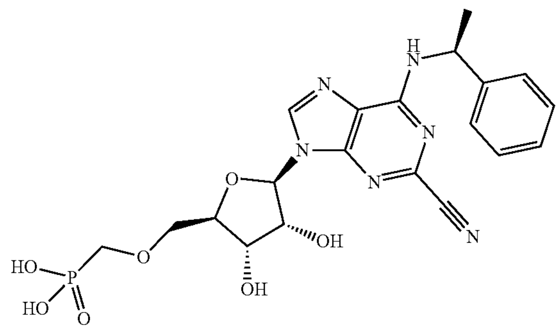 [SMILES: C[C@H](Nc1nc(C#N)nc2c1ncn2[C@@H]1O[C@H](COCP(=O)(O)O)[C@@H](O)[C@H]1O)c1ccccc1] | [M + H]⁺: 491; [M − H]⁻: 489 | [(2R,3S,4R,5R)-5-[2-cyano-6-[[(1S)-1-phenylethyl]amino]-purin-9-yl]-3,4-dihydroxy-tetrahydro-furan-2-yl]methoxy-methylphosphonic acid |
| 37 | 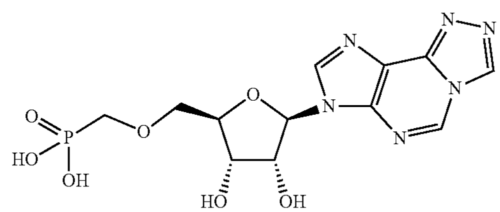 [SMILES: O=P(O)(O)COC[C@H]1O[C@@H](n2cnc3c2ncn2cnnc32)[C@H](O)[C@@H]1O] | | [(2R,3S,4R,5R)-3,4-dihydroxy-5-([1,2,4]-triazolo[3,4-f]purin-7-yl)tetrahydrofuran-2-yl]methoxymethyl-phosphonic acid |
| 38 | 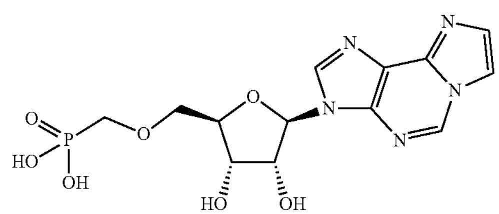 [SMILES: O=P(O)(O)COC[C@H]1O[C@@H](n2cnc3c2ncn2ccnc32)[C@H](O)[C@@H]1O] | | [(2R,3S,4R,5R)-3,4-dihydroxy-5-imidazo-[2,1-f]-purin-3-yl-tetrahydrofuran-2-yl]methoxymethyl-phosphonic acid |
| 39 | 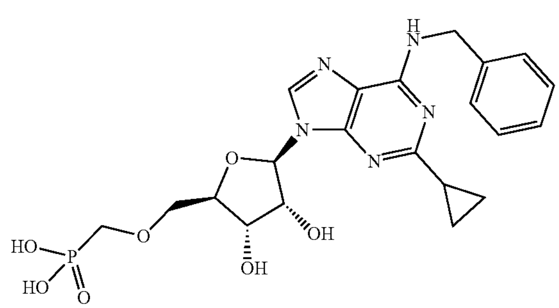 [SMILES: O=P(O)(O)COC[C@H]1O[C@@H](n2cnc3c(NCc4ccccc4)nc(C4CC4)nc32)[C@H](O)[C@@H]1O] | [M + H]⁺: 492; [M − H]⁻: 490 | [(2R,3S,4R,5R)-5-[6-(benzylamino)-2-cyclopropyl-purin-9-yl]-3,4-dihydroxy-tetrahydrofuran-2-yl]-methoxymethyl phosphonic acid |
| 40 | 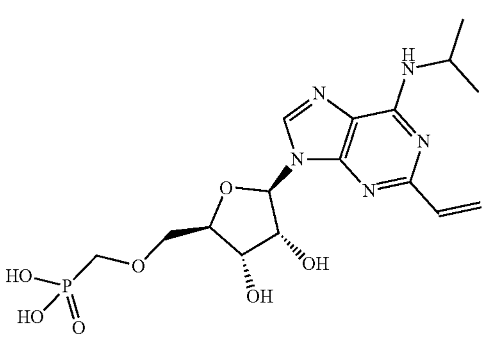 [SMILES: C=Cc1nc(NC(C)C)c2ncn([C@@H]3O[C@H](COCP(=O)(O)O)[C@@H](O)[C@H]3O)c2n1] | [M + H]⁺: 430; [M − H]⁻: 428 | [(2R,3S,4R,5R)-3,4-dihydroxy-5-[6-(iso-propylamino)-2-vinyl-purin-9-yl]tetrahydro-furan-2-yl]methoxy-methylphosphonic acid |

TABLE 1-continued

| No. | Structure | m/z | IUPAC Name |
|---|---|---|---|
| 41 | 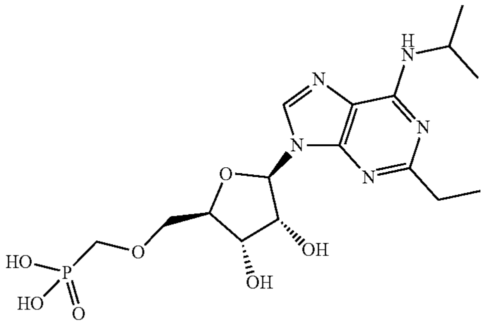 [SMILES: CCc1nc(NC(C)C)c2ncn([C@@H]3O[C@H](COCP(=O)(O)O)[C@@H](O)[C@H]3O)c2n1] | [M − H]⁻: 430 | [(2R,3S,4R,5R)-5-[2-ethyl-6-(isopropyl-amino)purin-9-yl]-3,4-dihydroxy-tetrahydro-furan-2-yl]methoxy-methylphosphonic acid |
| 42 | 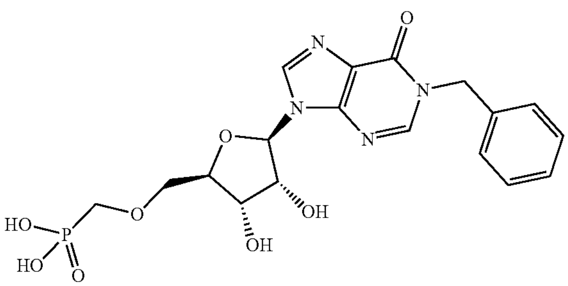 [SMILES: O=c1c2ncn([C@@H]3O[C@H](COCP(=O)(O)O)[C@@H](O)[C@H]3O)c2ncn1Cc1ccccc1] | | [(2R,3S,4R,5R)-5-(1-benzyl-6-oxo-purin-9-yl)-3,4-dihydroxy-tetrahydrofuran-2-yl]-methoxymethylphos-phonic acid |
| 43 | 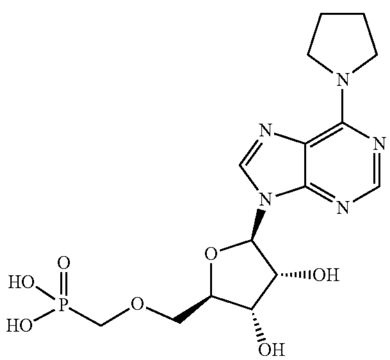 [SMILES: O=P(O)(O)COC[C@H]1O[C@@H](n2cnc3c(N4CCCC4)ncnc32)[C@H](O)[C@@H]1O] | [M + H]⁺: 416; [M − H]⁻: 414 | [(2R,3S,4R,5R)-3,4-dihydroxy-5-(6-pyrrolidin-1-ylpurin-9-yl)tetrahydrofuran-2-yl]methoxymethyl-phosphonic acid |
| 44 | 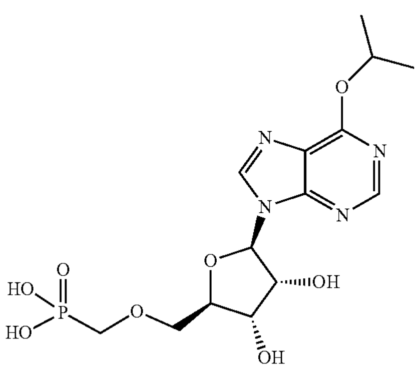 [SMILES: CC(C)Oc1ncnc2c1ncn2[C@@H]1O[C@H](COCP(=O)(O)O)[C@@H](O)[C@H]1O] | [M + H]⁺: 405; [M − H]⁻: 403 | [(2R,3S,4R,5R)-3,4-dihydroxy-5-(6-iso-propoxypurin-9-yl)-tetrahydrofuran-2-yl]-methoxymethylphos-phonic acid |

TABLE 1-continued

| No. | Structure | m/z | IUPAC Name |
|---|---|---|---|
| 45 | 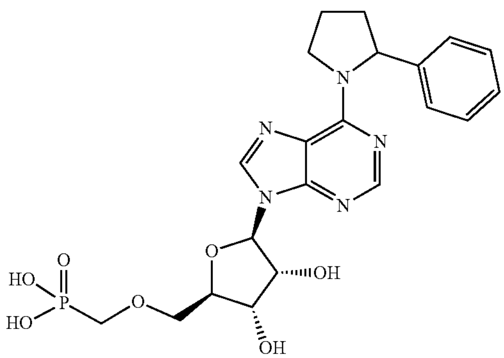 [SMILES: O=P(O)(O)COC[C@H]1O[C@@H](n2cnc3c(N4CCCC4c4ccccc4)ncnc32)[C@H](O)[C@@H]1O] | [M + H]⁺: 492; [M − H]⁻: 490 | [(2R,3S,4R,5R)-3,4-dihydroxy-5-[6-(2-phenylpyrrolidin-1-yl)-purin-9-yl]tetrahydro-furan-2-yl]methoxy-methylphosphonic acid |
| 46 | 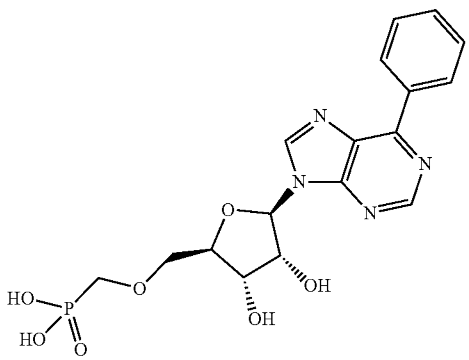 [SMILES: O=P(O)(O)COC[C@H]1O[C@@H](n2cnc3c(-c4ccccc4)ncnc32)[C@H](O)[C@@H]1O] | [M + H]⁺: 432; [M − H]⁻: 421 | [(2R,3S,4R,5R)-3,4-dihydroxy-5-(6-phenyl-purin-9-yl)tetrahydro-furan-2-yl]methoxy-methylphosphonic acid |
| 47 | 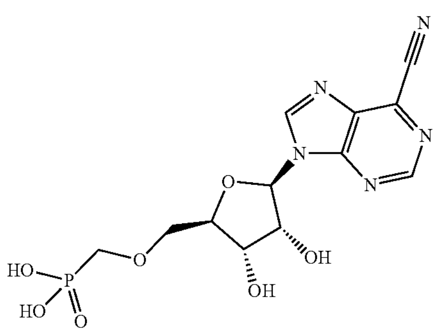 [SMILES: N#Cc1ncnc2c1ncn2[C@@H]1O[C@H](COCP(=O)(O)O)[C@@H](O)[C@H]1O] | [M + H]⁺: 372; [M − H]⁻: 370 | [(2R,3S,4R,5R)-5-(6-cyanopurin-9-yl)-3,4-dihydroxy-tetrahydro-furan-2-yl]methoxy-methylphosphonic acid |
| 48 | 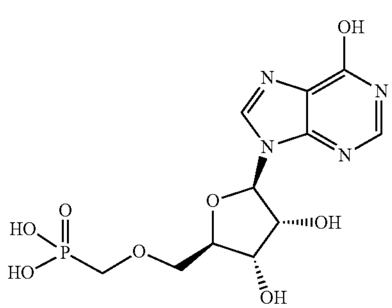 [SMILES: O=P(O)(O)COC[C@H]1O[C@@H](n2cnc3c(O)ncnc32)[C@H](O)[C@@H]1O] | [M − H]⁻: 361 | [(2R,3S,4R,5R)-3,4-dihydroxy-5-(6-hydroxypurin-9-yl)-tetrahydrofuran-2-yl]-methoxymethylphos-phonic acid |

TABLE 1-continued

| No. | Structure | m/z | IUPAC Name |
|---|---|---|---|
| 49 | 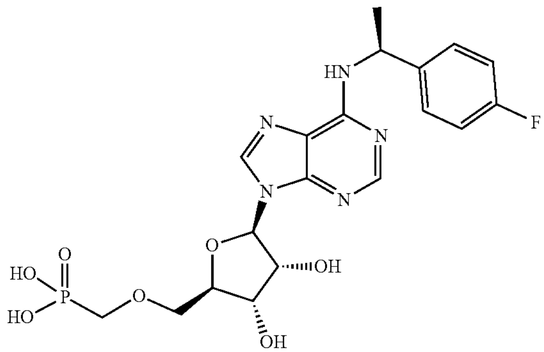 [SMILES: C[C@H](Nc1ncnc2c1ncn2[C@@H]1O[C@H](COCP(=O)(O)O)[C@@H](O)[C@H]1O)c1ccc(F)cc1] | [M + H]⁺: 484; [M − H]⁻: 482 | [(2R,3S,4R,5R)-5-[6-[[(1S)-1-(4-fluoro-phenyl)ethyl]amino]-purin-9-yl]-3,4-dihydroxy-tetrahydro-furan-2-yl]methoxy-methylphosphonic acid |
| 50 | 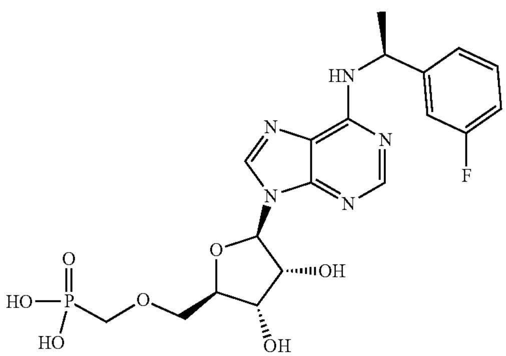 [SMILES: C[C@H](Nc1ncnc2c1ncn2[C@@H]1O[C@H](COCP(=O)(O)O)[C@@H](O)[C@H]1O)c1cccc(F)c1] | [M + H]⁺: 484; [M − H]⁻: 482 | [(2R,3S,4R,5R)-5-[6-[[(1S)-1-(3-fluoro-phenyl)ethyl]amino]-purin-9-yl]-3,4-dihydroxy-tetrahydro-furan-2-yl]methoxy-methylphosphonic acid |
| 51 | 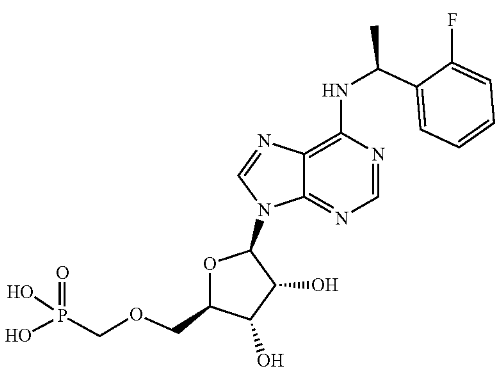 [SMILES: C[C@H](Nc1ncnc2c1ncn2[C@@H]1O[C@H](COCP(=O)(O)O)[C@@H](O)[C@H]1O)c1ccccc1F] | [M + H]⁺: 484; [M − H]⁻: 482 | [(2R,3S,4R,5R)-5-[6-[[(1S)-1-(2-fluoro-phenyl)ethyl]amino]-purin-9-yl]-3,4-dihydroxy-tetrahydro-furan-2-yl]methoxy-methylphosphonic acid |
| 52 | 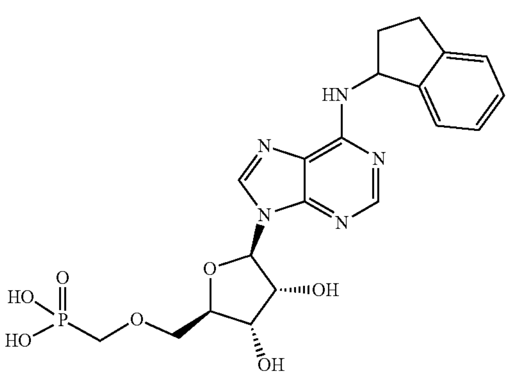 [SMILES: O=P(O)(O)COC[C@H]1O[C@@H](n2cnc3c(NC4CCc5ccccc54)ncnc32)[C@H](O)[C@@H]1O] | [M + H]⁺: 478; [M − H]⁻: 476 | [(2R,3S,4R,5R)-3,4-dihydroxy-5-[6-(indan-1-ylamino)purin-9-yl]-tetrahydrofuran-2-yl]-methoxymethylphos-phonic acid |

TABLE 1-continued

| No. | Structure | m/z | IUPAC Name |
|---|---|---|---|
| 53 | 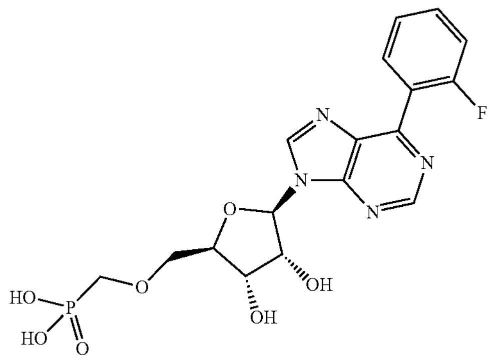 [SMILES: O=P(O)(O)COC[C@H]1O[C@@H](n2cnc3c(-c4ccccc4F)ncnc32)[C@H](O)[C@@H]1O] | [M + H]⁺: 441; [M − H]⁻: 439 | [(2R,3S,4R,5R)-5-[6-(2-fluorophenyl)purin-9-yl]-3,4-dihydroxy-tetrahydrofuran-2-yl]methoxymethyl-phosphonic acid |
| 54 | 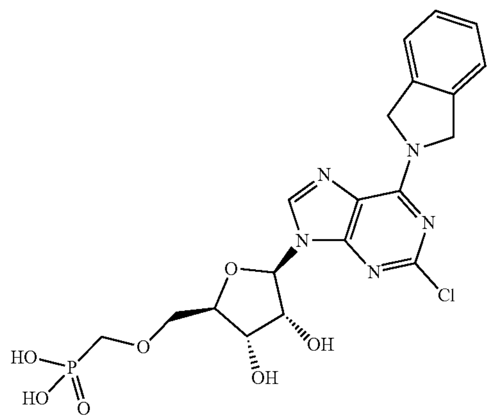 [SMILES: O=P(O)(O)COC[C@H]1O[C@@H](n2cnc3c(N4Cc5ccccc5C4)nc(Cl)nc32)[C@H](O)[C@@H]1O] | [M + H]⁺: 498; [M − H]⁻: 496 | [(2R,3S,4R,5R)-5-(2-chloro-6-isoindolin-2-yl-purin-9-yl)-3,4-dihydroxy-tetrahydrofuran-2-yl]methoxymethylphosphonic acid |
| 55 | 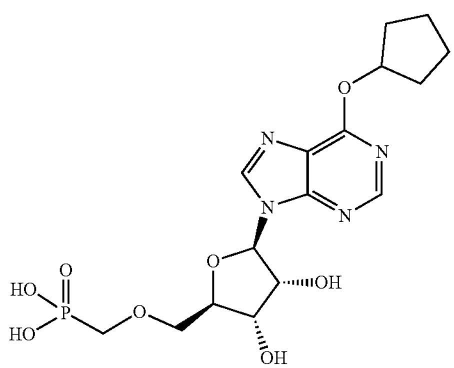 [SMILES: O=P(O)(O)COC[C@H]1O[C@@H](n2cnc3c(OC4CCCC4)ncnc32)[C@H](O)[C@@H]1O] | [M + H]⁺: 431; [M − H]⁻: 429 | [(2R,3S,4R,5R)-5-[6-(cyclopentoxy)purin-9-yl]-3,4-dihydroxy-tetrahydrofuran-2-yl]-methoxymethylphosphonic acid |
| 56 | 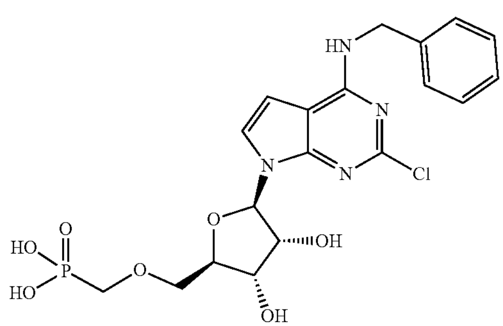 [SMILES: O=P(O)(O)COC[C@H]1O[C@@H](n2ccc3c(NCc4ccccc4)nc(Cl)nc32)[C@H](O)[C@@H]1O] | [M + H]⁺: 485; [M − H]⁻: 483 | [(2R,3S,4R,5R)-5-[4-(benzylamino)-2-chloro-pyrrolo[2,3-d]-pyrimidin-7-yl]-3,4-dihydroxy-tetrahydrofuran-2-yl]methoxymethylphosphonic acid |

TABLE 1-continued

| No. | Structure | m/z | IUPAC Name |
| --- | --- | --- | --- |
| 57 | 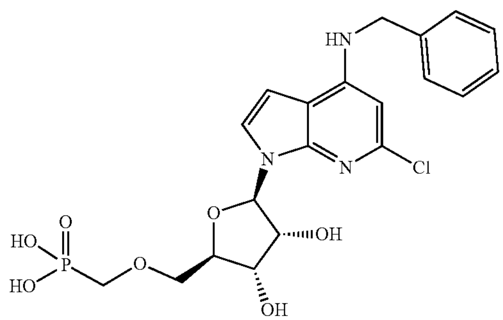 [SMILES: O=P(O)(O)COC[C@H]1O[C@@H](n2ccc3c(NCc4ccccc4)cc(Cl)nc32)[C@H](O)[C@@H]1O] | [M + H]+: 485;<br>[M − H]−: 483 | [(2R,3S,4R,5R)-5-[7-(benzylamino)-5-chloro-imidazo[4,5-b]-pyridin-3-yl]-3,4-dihydroxy-tetrahydro-furan-2-yl]methoxy-methylphosphonic acid |
| 58 | 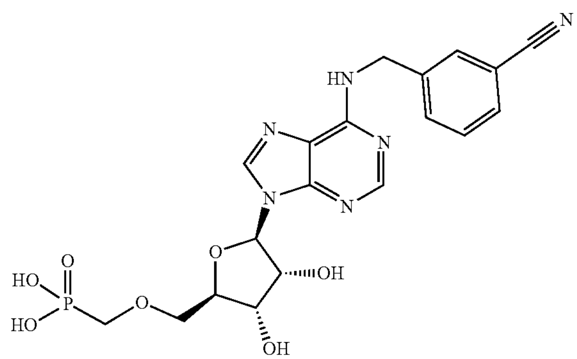 [SMILES: N#Cc1cccc(CNc2ncnc3c2ncn3[C@@H]2O[C@H](COCP(=O)(O)O)[C@@H](O)[C@H]2O)c1] | [M + H]+: 477;<br>[M − H]−: 475 | [(2R,3S,4R,5R)-5-[6-[(3-cyanophenyl)-methylamino]purin-9-yl]-3,4-dihydroxy-tetrahydrofuran-2-yl]-methoxymethylphosphonic acid |
| 59 | 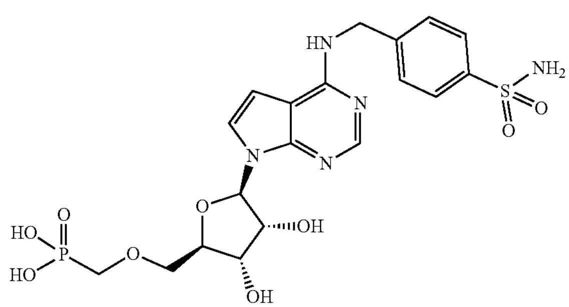 [SMILES: NS(=O)(=O)c1ccc(CNc2ncnc3c2ccn3[C@@H]2O[C@H](COCP(=O)(O)O)[C@@H](O)[C@H]2O)cc1] | [M + H]+: 531;<br>[M − H]−: 529 | [(2R,3S,4R,5R)-3,4-dihydroxy-5-[6-[(4-sulfamoylphenyl)-methylamino]purin-9-yl]tetrahydrofuran-2-yl]methoxymethyl-phosphonic acid |
| 60 | 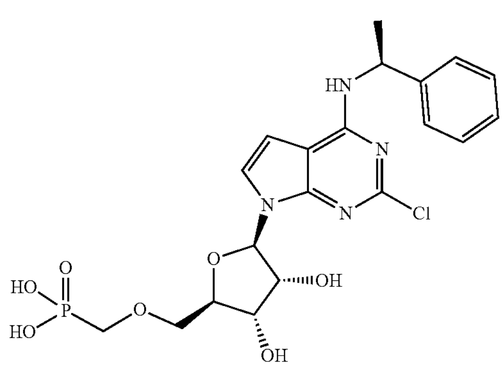 [SMILES: C[C@H](Nc1nc(Cl)nc2c1ccn2[C@@H]1O[C@H](COCP(=O)(O)O)[C@@H](O)[C@H]1O)c1ccccc1] | [M + H]+: 499;<br>[M − H]−: 497 | [(2R,3S,4R,5R)-5-[2-chloro-4-[[(1S)-1-phenylethyl]amino]-pyrrolo[2,3-d]-pyrimidin-7-yl]-3,4-dihydroxy-tetrahydro-furan-2-yl]methoxy-methylphosphonic acid |

TABLE 1-continued

| No. | Structure | m/z | IUPAC Name |
|---|---|---|---|
| 61 | 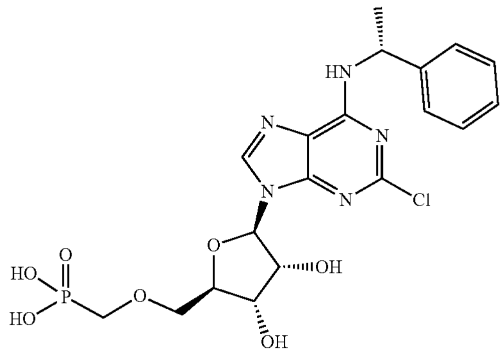 [SMILES: C[C@@H](Nc1nc(Cl)nc2c1ncn2[C@@H]1O[C@H](COCP(=O)(O)O)[C@@H](O)[C@H]1O)c1ccccc1] | [M + H]⁺: 499; [M − H]⁻: 497 | [(2R,3S,4R,5R)-5-[2-chloro-4-[[(1R)-1-phenylethyl]amino]-pyrrolo[2,3-d]-pyrimidin-7-yl]-3,4-dihydroxy-tetrahydro-furan-2-yl]methoxy-methylphosphonic acid |
| 62 | 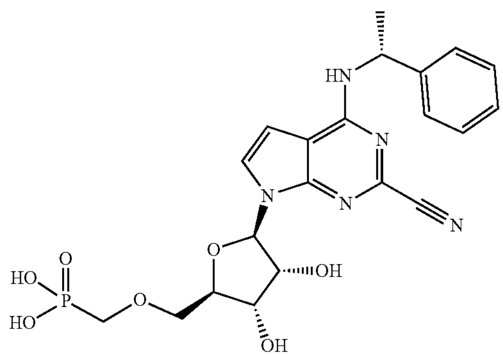 [SMILES: C[C@@H](Nc1nc(C#N)nc2c1ccn2[C@@H]1O[C@H](COCP(=O)(O)O)[C@@H](O)[C@H]1O)c1ccccc1] | [M + H]⁺: 490; [M − H]⁻: 488 | [(2R,3S,4R,5R)-5-[2-cyano-4-[[(1R)-1-phenylethyl]amino]-pyrrolo[2,3-d]-pyrimidin-7-yl]-3,4-dihydroxy-tetrahydro-furan-2-yl]methoxy-methylphosphonic acid |
| 63 | 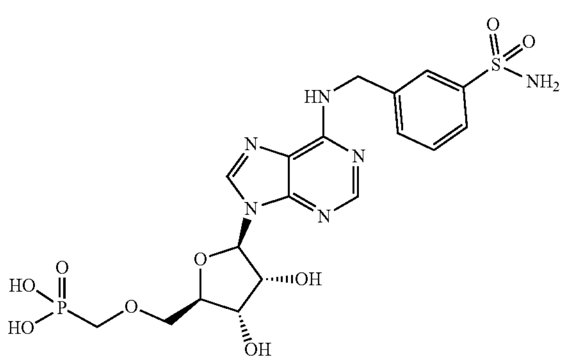 [SMILES: NS(=O)(=O)c1cccc(CNc2ncnc3c2ncn3[C@@H]2O[C@H](COCP(=O)(O)O)[C@@H](O)[C@H]2O)c1] | [M − H]⁻: 529 | [(2R,3S,4R,5R)-3,4-dihydroxy-5-[6-[(3-sulfamoylphenyl)-methylamino]purin-9-yl]tetrahydrofuran-2-yl]methoxymethyl-phosphonic acid |
| 64 | 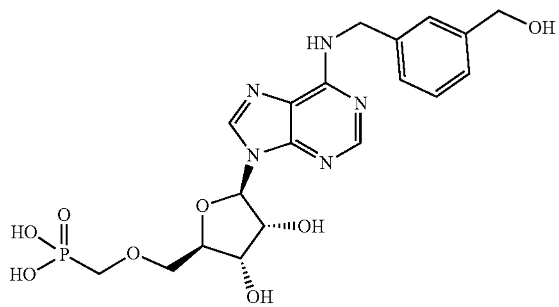 [SMILES: O=P(O)(O)COC[C@H]1O[C@@H](n2cnc3c(NCc4cccc(CO)c4)ncnc32)[C@H](O)[C@@H]1O] | [M + H]⁺: 482 | [(2R,3S,4R,5R)-3,4-dihydroxy-5-[6-[[3-(hydroxymethyl)-phenyl]methylamino]-purin-9-yl]tetrahydro-furan-2-yl]methoxy-methylphosphonic acid |

TABLE 1-continued

| No. | Structure | m/z | IUPAC Name |
|---|---|---|---|
| 65 | 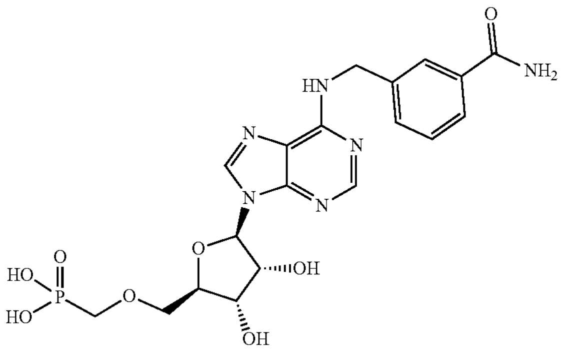 [SMILES: NC(=O)c1cccc(CNc2ncnc3c2ncn3[C@@H]2O[C@H](COCP(=O)(O)O)[C@@H](O)[C@H]2O)c1] | [M + H]⁺: 495; [M − H]⁻: 493 | [(2R,3S,4R,5R)-5-[6-[(3-carbamoylphenyl)-methylamino]purin-9-yl]-3,4-dihydroxy-tetrahydrofuran-2-yl]-methoxymethylphosphonic acid |
| 66 | 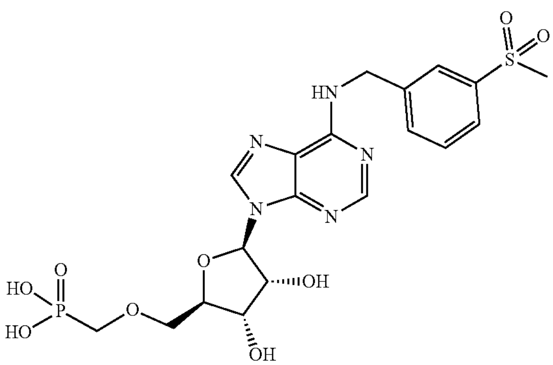 [SMILES: CS(=O)(=O)c1cccc(CNc2ncnc3c2ncn3[C@@H]2O[C@H](COCP(=O)(O)O)[C@@H](O)[C@H]2O)c1] | [M + H]⁺: 530; [M − H]⁻: 528 | [(2R,3S,4R,5R)-3,4-dihydroxy-5-[6-[(3-methylsulfonylphenyl)-methylamino]purin-9-yl]tetrahydrofuran-2-yl]methoxymethyl-phosphonic acid |
| 67 | 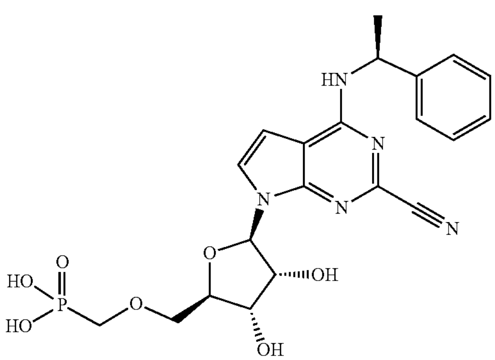 [SMILES: C[C@H](Nc1nc(C#N)nc2c1ccn2[C@@H]1O[C@H](COCP(=O)(O)O)[C@@H](O)[C@H]1O)c1ccccc1] | [M − H]⁻: 488 | [(2R,3S,4R,5R)-5-[2-cyano-4-[[(1S)-1-phenylethyl]amino]-pyrrolo[2,3-d]-pyrimidin-7-yl]-3,4-dihydroxy-tetrahydro-furan-2-yl]methoxy-methylphosphonic acid |
| 68 | 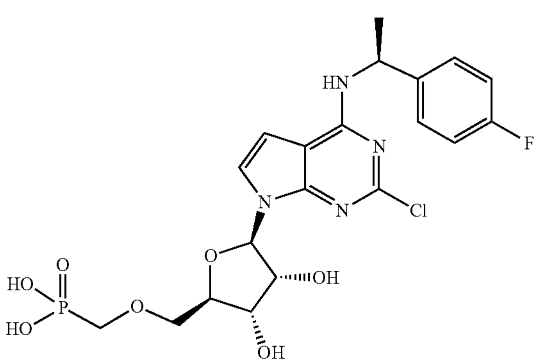 [SMILES: C[C@H](Nc1nc(Cl)nc2c1ccn2[C@@H]1O[C@H](COCP(=O)(O)O)[C@@H](O)[C@H]1O)c1ccc(F)cc1] | [M + H]⁺: 517; [M − H]⁻: 515 | [(2R,3S,4R,5R)-5-[2-chloro-4-[[(1S)-1-(4-fluorophenyl)ethyl]-amino]pyrrolo[2,3-d]-pyrimidin-7-yl]-3,4-dihydroxy-tetrahydro-furan-2-yl]methoxy-methylphosphonic acid |

TABLE 1-continued

| No. | Structure | m/z | IUPAC Name |
|---|---|---|---|
| 69 | 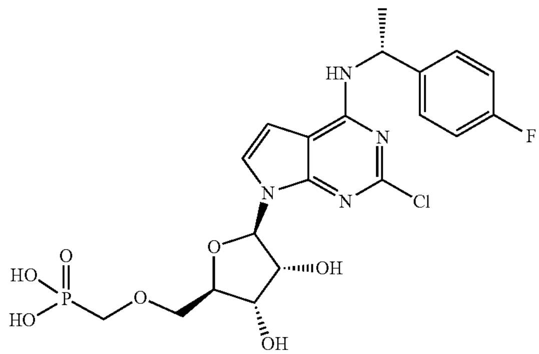 [SMILES: C[C@@H](Nc1nc(Cl)nc2c1ccn2[C@@H]1O[C@H](COCP(=O)(O)O)[C@@H](O)[C@H]1O)c1ccc(F)cc1] | [M + H]⁺: 517; [M − H]⁻: 515 | [(2R,3S,4R,5R)-5-[2-chloro-4-[[(1R)-1-(4-fluorophenyl)ethyl]-amino]pyrrolo[2,3-d]-pyrimidin-7-yl]-3,4-dihydroxy-tetrahydro-furan-2-yl]methoxy-methylphosphonic acid |
| 70 | 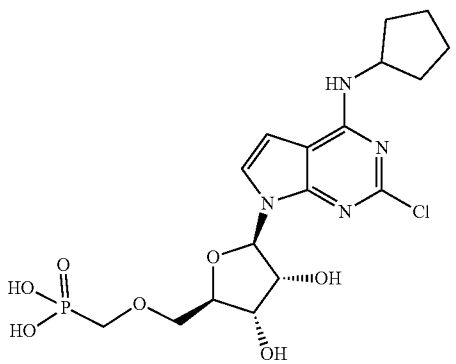 [SMILES: O=P(O)(O)COC[C@H]1O[C@@H](n2ccc3c(NC4CCCC4)nc(Cl)nc32)[C@H](O)[C@@H]1O] | [M + H]⁺: 463; [M − H]⁻: 461 | [(2R,3S,4R,5R)-5-[2-chloro-4-(cyclopentyl-amino)pyrrolo[2,3-d]-pyrimidin-7-yl]-3,4-dihydroxy-tetrahydro-furan-2-yl]methoxy-methylphosphonic acid |
| 71 | 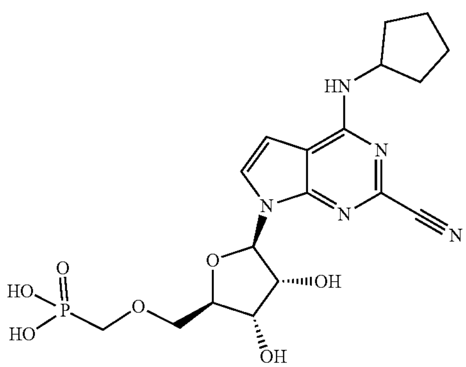 [SMILES: N#Cc1nc(NC2CCCC2)c2ccn([C@@H]3O[C@H](COCP(=O)(O)O)[C@@H](O)[C@H]3O)c2n1] | [M + H]⁺: 454; [M − H]⁻: 452 | [(2R,3S,4R,5R)-5-[2-cyano-4-(cyclopentyl-amino)pyrrolo[2,3-d]-pyrimidin-7-yl]-3,4-dihydroxy-tetrahydro-furan-2-yl]methoxy-methylphosphonic acid |
| 72 | 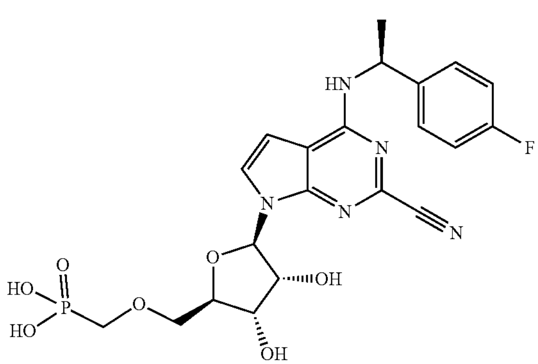 [SMILES: C[C@H](Nc1nc(C#N)nc2c1ccn2[C@@H]1O[C@H](COCP(=O)(O)O)[C@@H](O)[C@H]1O)c1ccc(F)cc1] | [M − H]⁻: 506 | [(2R,3S,4R,5R)-5-[2-cyano-4-[[(1S)-1-(4-fluorophenyl)ethyl]-amino]pyrrolo[2,3-d]-pyrimidin-7-yl]-3,4-dihydroxy-tetrahydro-furan-2-yl]methoxy-methylphosphonic acid |

TABLE 1-continued

| No. | Structure | m/z | IUPAC Name |
|---|---|---|---|
| 73 | 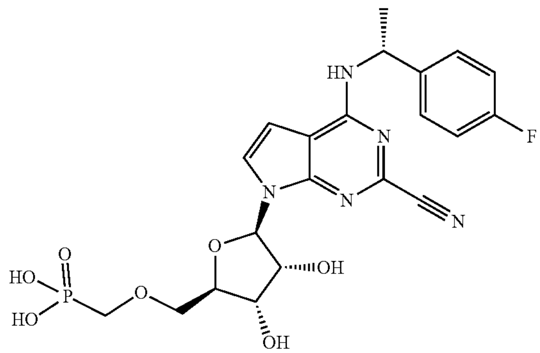 [SMILES: C[C@@H](Nc1nc(C#N)nc2c1ccn2[C@@H]1O[C@H](COCP(=O)(O)O)[C@@H](O)[C@H]1O)c1ccc(F)cc1] | [M + H]⁺: 508; [M − H]⁻: 506 | [(2R,3S,4R,5R)-5-[2-cyano-4-[[(1R)-1-(4-fluorophenyl)ethyl]-amino]pyrrolo[2,3-d]-pyrimidin-7-yl]-3,4-dihydroxy-tetrahydro-furan-2-yl]methoxy-methylphosphonic acid |
| 74 | 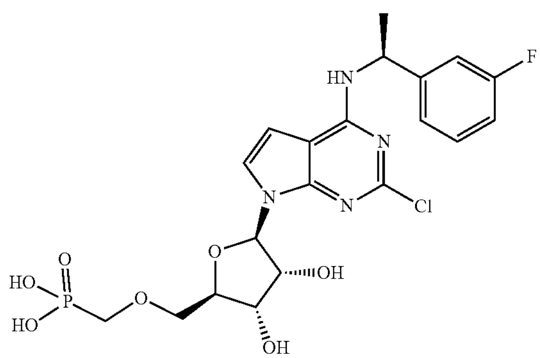 [SMILES: C[C@H](Nc1nc(Cl)nc2c1ccn2[C@@H]1O[C@H](COCP(=O)(O)O)[C@@H](O)[C@H]1O)c1cccc(F)c1] | [M − H]⁻: 515 | [(2R,3S,4R,5R)-5-[2-chloro-4-[[(1S)-1-(3-fluorophenyl)ethyl]-amino]pyrrolo[2,3-d]-pyrimidin-7-yl]-3,4-dihydroxy-tetrahydro-furan-2-yl]methoxy-methylphosphonic acid |
| 75 | 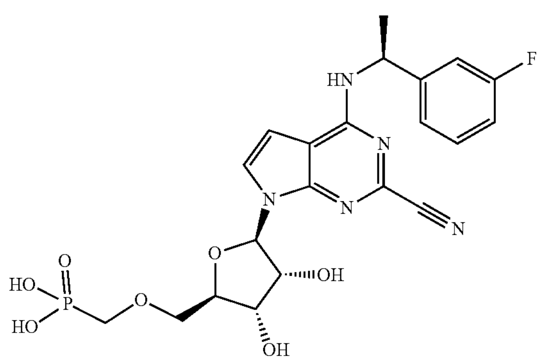 [SMILES: C[C@H](Nc1nc(C#N)nc2c1ccn2[C@@H]1O[C@H](COCP(=O)(O)O)[C@@H](O)[C@H]1O)c1cccc(F)c1] | [M − H]⁻: 506 | [(2R,3S,4R,5R)-5-[2-cyano-4-[[(1S)-1-(3-fluorophenyl)ethyl]-amino]pyrrolo[2,3-d]-pyrimidin-7-yl]-3,4-dihydroxy-tetrahydro-furan-2-yl]methoxy-methylphosphonic acid |
| 76 | 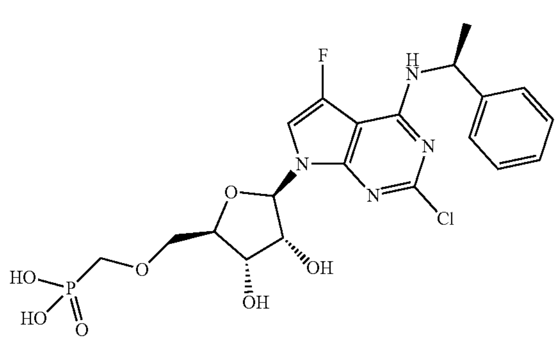 [SMILES: C[C@H](Nc1nc(Cl)nc2c1c(F)cn2[C@@H]1O[C@H](COCP(=O)(O)O)[C@@H](O)[C@H]1O)c1ccccc1] | [M + H]⁺: 517; [M − H]⁻: 515 | [(2R,3S,4R,5R)-5-[2-chloro-5-fluoro-4-[[(1S)-1-phenylethyl]-amino]pyrrolo[2,3-d]-pyrimidin-7-yl]-3,4-dihydroxy-tetrahydro-furan-2-yl]methoxy-methylphosphonic acid |

TABLE 1-continued

| No. | Structure | m/z | IUPAC Name |
|---|---|---|---|
| 77 | 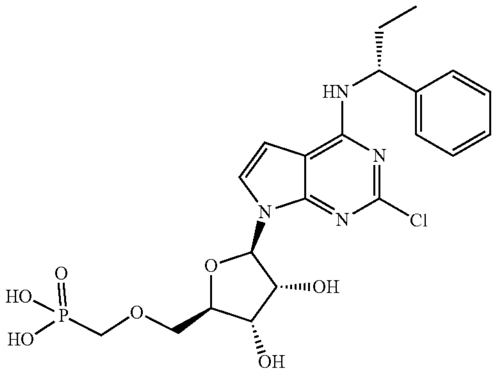 [SMILES: CC[C@@H](Nc1nc(Cl)nc2c1ccn2[C@@H]1O[C@H](COCP(=O)(O)O)[C@@H](O)[C@H]1O)c1ccccc1] | [M + H]⁺: 513; [M − H]⁻: 511 | [(2R,3S,4R,5R)-5-[2-chloro-4-[[(1R)-1-phenylpropyl]amino]-pyrrolo[2,3-d]-pyrimidin-7-yl]-3,4-dihydroxy-tetrahydro-furan-2-yl]methoxy-methylphosphonic acid |
| 78 | 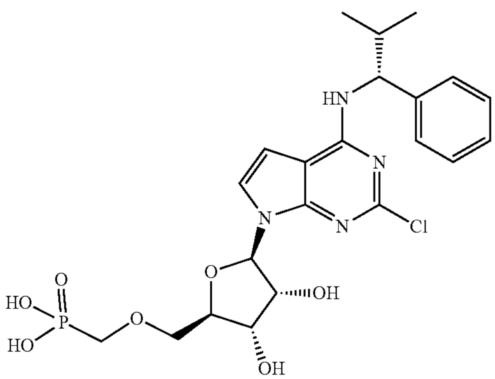 [SMILES: CC(C)[C@@H](Nc1nc(Cl)nc2c1ccn2[C@@H]1O[C@H](COCP(=O)(O)O)[C@@H](O)[C@H]1O)c1ccccc1] | [M + H]⁺: 527; [M − H]⁻: 525 | [(2R,3S,4R,5R)-5-[2-chloro-4-[[(1R)-2-methyl-1-phenyl-propyl[amino]pyrrolo-[2,3-d]pyrimidin-7-yl]-3,4-dihydroxy-tetra-hydrofuran-2-yl]-methoxymethylphos-phonic acid |
| 79 | 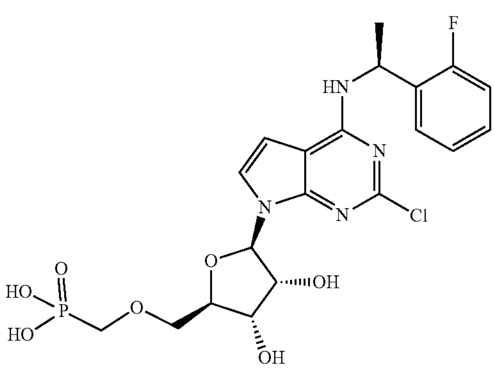 [SMILES: C[C@H](Nc1nc(Cl)nc2c1ccn2[C@@H]1O[C@H](COCP(=O)(O)O)[C@@H](O)[C@H]1O)c1ccccc1F] | [M + H]⁺: 517; [M − H]⁻: 515 | [(2R,3S,4R,5R)-5-[2-chloro-4-[[(1S)-1-(2-fluorophenyl)ethyl]-amino]pyrrolo[2,3-d]-pyrimidin-7-yl]-3,4-dihydroxy-tetrahydro-furan-2-yl]methoxy-methylphosphonic acid |
| 80 | 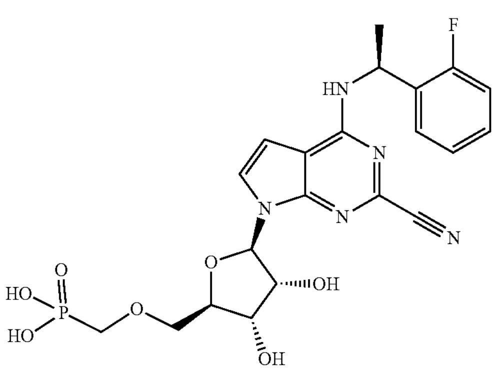 [SMILES: C[C@H](Nc1nc(C#N)nc2c1ccn2[C@@H]1O[C@H](COCP(=O)(O)O)[C@@H](O)[C@H]1O)c1ccccc1F] | [M + H]⁺: 508; [M − H]⁻: 506 | [(2R,3S,4R,5R)-5-[2-cyano-4-[[(1S)-1-(2-fluorophenyl)ethyl]-amino]pyrrolo[2,3-d]-pyrimidin-7-yl]-3,4-dihydroxy-tetrahydro-furan-2-yl]methoxy-methylphosphonic acid |

TABLE 1-continued

| No. | Structure | m/z | IUPAC Name |
|---|---|---|---|
| 81 | 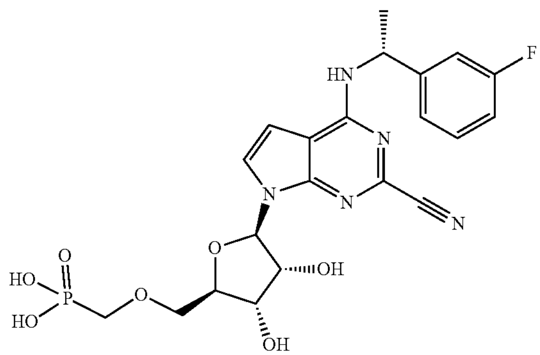 [SMILES: C[C@@H](Nc1nc(C#N)nc2c1ccn2[C@@H]1O[C@H](COCP(=O)(O)O)[C@@H](O)[C@H]1O)c1cccc(F)c1] | [M − H]⁻: 506 | [(2R,3S,4R,5R)-5-[2-cyano-4-[[(1R)-1-(3-fluorophenyl)ethyl]amino]pyrrolo[2,3-d]pyrimidin-7-yl]-3,4-dihydroxy-tetrahydrofuran-2-yl]methoxymethylphosphonic acid |
| 82 | 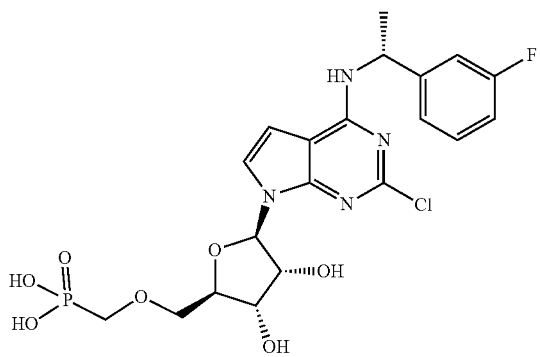 [SMILES: C[C@@H](Nc1nc(Cl)nc2c1ccn2[C@@H]1O[C@H](COCP(=O)(O)O)[C@@H](O)[C@H]1O)c1cccc(F)c1] | [M + H]⁺: 517<br>[M − H]⁻: 515 | [(2R,3S,4R,5R)-5-[2-chloro-4-[[(1R)-1-(3-fluorophenyl)ethyl]amino]pyrrolo[2,3-d]pyrimidin-7-yl]-3,4-dihydroxy-tetrahydrofuran-2-yl]methoxymethylphosphonic acid |
| 83 | 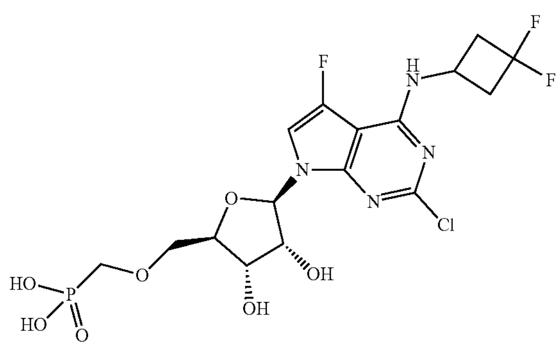 [SMILES: O=P(O)(O)COC[C@H]1O[C@@H](n2cc(F)c3c(NC4CC(F)(F)C4)nc(Cl)nc32)[C@H](O)[C@@H]1O] | [M + H]⁺: 485<br>[M − H]⁻: 483 | [(2R,3S,4R,5R)-5-[2-chloro-4-[(3,3-difluorocyclobutyl)amino]-pyrrolo[2,3-d]-pyrimidin-7-yl]-3,4-dihydroxy-tetrahydrofuran-2-yl]methoxymethylphosphonic acid |
| 84 | 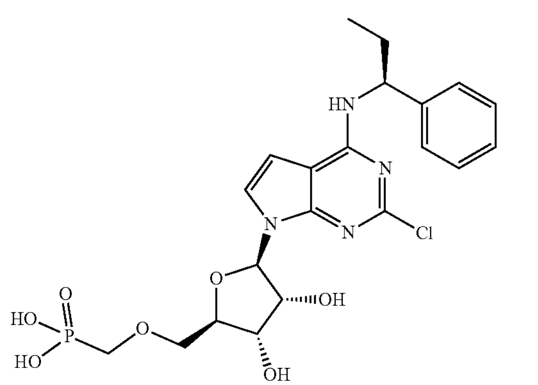 [SMILES: CC[C@H](Nc1nc(Cl)nc2c1ccn2[C@@H]1O[C@H](COCP(=O)(O)O)[C@@H](O)[C@H]1O)c1ccccc1] | [M − H]⁻: 511 | [(2R,3S,4R,5R)-5-[2-chloro-4-[[(1S)-1-phenylpropyl]amino]-pyrrolo[2,3-d]-pyrimidin-7-yl]-3,4-dihydroxy-tetrahydrofuran-2-yl]methoxymethylphosphonic acid |

TABLE 1-continued

| No. | Structure | m/z | IUPAC Name |
|---|---|---|---|
| 85 | 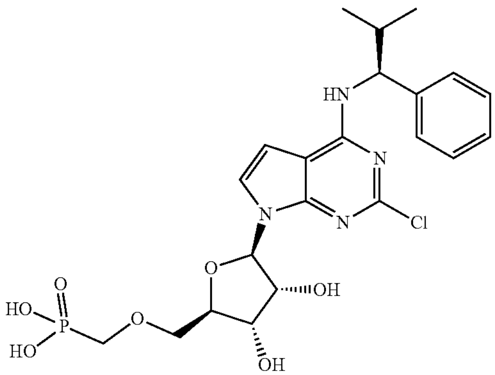 [SMILES: CC(C)[C@H](Nc1nc(Cl)nc2c1ccn2[C@@H]1O[C@H](COCP(=O)(O)O)[C@@H](O)[C@H]1O)c1ccccc1] | [M − H]⁻: 525 | [(2R,3S,4R,5R)-5-[2-chloro-4-[[(1S)-2-methyl-1-phenyl-propyl]amino]pyrrolo-[2,3-d]pyrimidin-7-yl]-3,4-dihydroxy-tetrahydrofuran-2-yl]methoxymethyl-phosphonic acid |
| 86 | 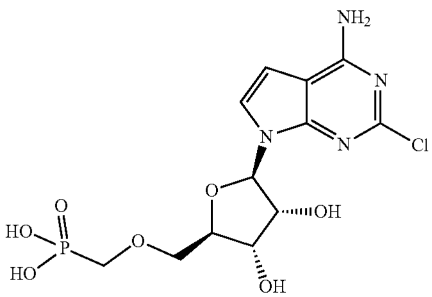 [SMILES: Nc1nc(Cl)nc2c1ccn2[C@@H]1O[C@H](COCP(=O)(O)O)[C@@H](O)[C@H]1O] | [M − H]⁻: 393 | [(2R,3S,4R,5R)-5-(4-amino-2-chloro-pyrrolo[2,3-d]-pyrimidin-7-yl)-3,4-dihydroxy-tetrahydro-furan-2-yl]methoxy-methylphosphonic acid |
| 87 | 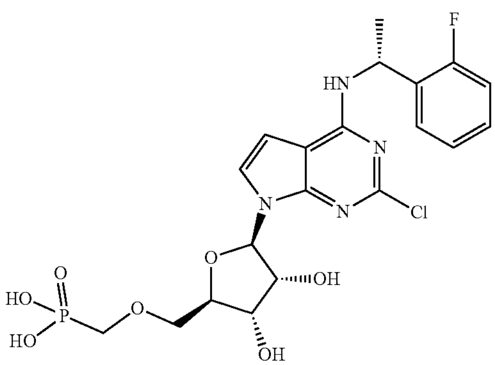 [SMILES: C[C@@H](Nc1nc(Cl)nc2c1ccn2[C@@H]1O[C@H](COCP(=O)(O)O)[C@@H](O)[C@H]1O)c1ccccc1F] | [M − H]⁻: 515 | [(2R,3S,4R,5R)-5-[2-chloro-4-[[(1R)-1-(2-fluorophenyl)ethyl]-amino]pyrrolo[2,3-d]-pyrimidin-7-yl]-3,4-dihydroxy-tetrahydro-furan-2-yl]methoxy-methylphosphonic acid |
| 88 | 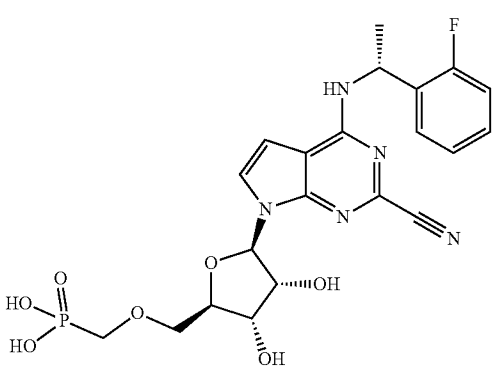 [SMILES: C[C@@H](Nc1nc(C#N)nc2c1ccn2[C@@H]1O[C@H](COCP(=O)(O)O)[C@@H](O)[C@H]1O)c1ccccc1F] | [M + H]⁺: 508<br>[M − H]⁻: 506 | [(2R,3S,4R,5R)-5-[2-cyano-4-[[(1R)-1-(2-fluorophenyl)ethyl]-amino]pyrrolo[2,3-d]-pyrimidin-7-yl]-3,4-dihydroxy-tetrahydro-furan-2-yl]methoxy-methylphosphonic acid |

TABLE 1-continued

| No. | Structure | m/z | IUPAC Name |
|---|---|---|---|
| 89 | 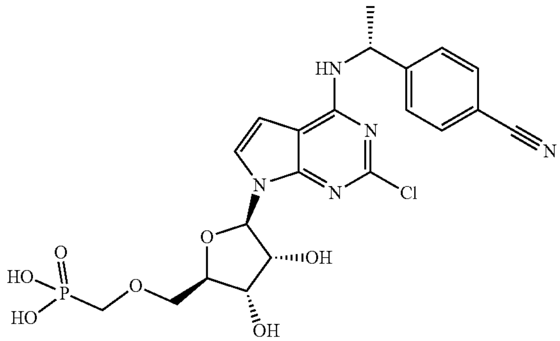 [SMILES: C[C@@H](Nc1nc(Cl)nc2c1ccn2[C@@H]1O[C@H](COCP(=O)(O)O)[C@@H](O)[C@H]1O)c1ccc(C#N)cc1] | [M − H]⁻: 522 | [(2R,3S,4R,5R)-5-[2-chloro-4-[[(1R)-1-(4-cyanophenyl)ethyl]-amino]pyrrolo[2,3-d]-pyrimidin-7-yl]-3,4-dihydroxy-tetrahydro-furan-2-yl]methoxy-methylphosphonic acid |
| 90 | 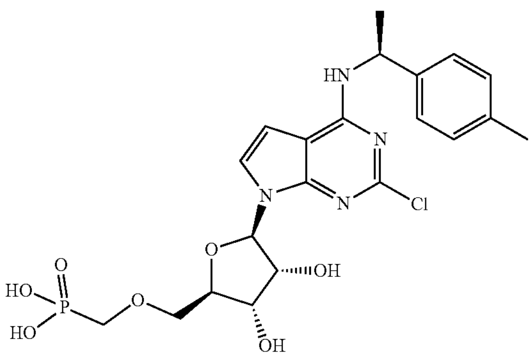 [SMILES: Cc1ccc([C@H](C)Nc2nc(Cl)nc3c2ccn3[C@@H]2O[C@H](COCP(=O)(O)O)[C@@H](O)[C@H]2O)cc1] | [M + H]⁺: 513 | [(2R,3S,4R,5R)-5-[2-chloro-4-[[(1S)-1-(p-tolyl)ethyl]amino]-pyrrolo[2,3-d]-pyrimidin-7-yl]-3,4-dihydroxy-tetrahydro-furan-2-yl]methoxy-methylphosphonic acid |
| 91 | 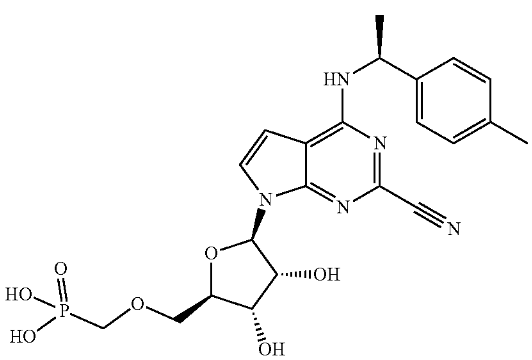 [SMILES: Cc1ccc([C@H](C)Nc2nc(C#N)nc3c2ccn3[C@@H]2O[C@H](COCP(=O)(O)O)[C@@H](O)[C@H]2O)cc1] | [M + H]⁺: 504<br>[M − H]⁻: 502 | [(2R,3S,4R,5R)-5-[2-cyano-4-[[(1S)-1-(p-tolyl)ethyl]amino]-pyrrolo[2,3-d]-pyrimidin-7-yl]-3,4-dihydroxy-tetrahydro-furan-2-yl]methoxy-methylphosphonic acid |
| 92 | 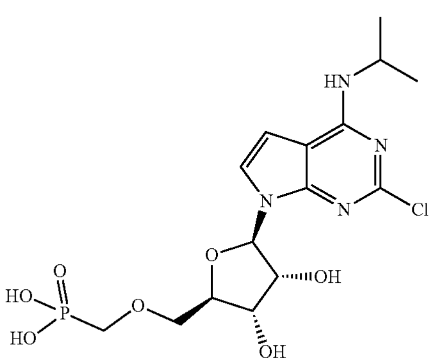 [SMILES: CC(C)Nc1nc(Cl)nc2c1ccn2[C@@H]1O[C@H](COCP(=O)(O)O)[C@@H](O)[C@H]1O] | [M + H]⁺: 437 | [(2R,3S,4R,5R)-5-[2-chloro-4-(isopropyl-amino)pyrrolo[2,3-d]-pyrimidin-7-yl]-3,4-dihydroxy-tetrahydro-furan-2-yl]methoxy-methylphosphonic acid |

TABLE 1-continued

| No. | Structure | m/z | IUPAC Name |
|---|---|---|---|
| 93 | 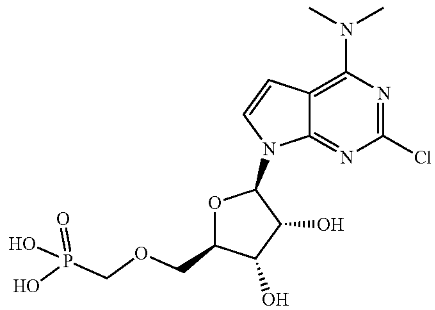 [SMILES: CN(C)c1nc(Cl)nc2c1ccn2[C@@H]1O[C@H](COCP(=O)(O)O)[C@@H](O)[C@H]1O] | [M + H]⁺: 423<br>[M − H]⁻: 421 | [(2R,3S,4R,5R)-5-[2-chloro-4-(dimethyl-amino)pyrrolo[2,3-d]-pyrimidin-7-yl]-3,4-dihydroxy-tetrahydro-furan-2-yl]methoxy-methylphosphonic acid |
| 94 | 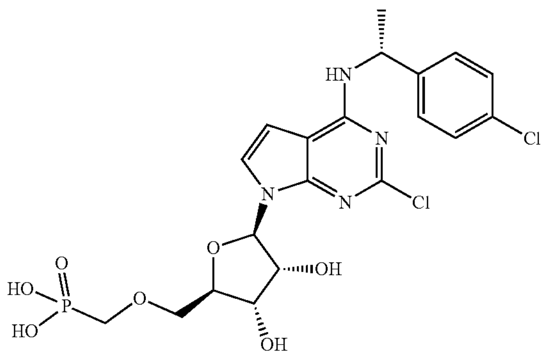 [SMILES: C[C@@H](Nc1nc(Cl)nc2c1ccn2[C@@H]1O[C@H](COCP(=O)(O)O)[C@@H](O)[C@H]1O)c1ccc(Cl)cc1] | [M − H]⁻: 531 | [(2R,3S,4R,5R)-5-[2-chloro-4-[[(1R)-1-(4-chlorophenyl)ethyl]-amino]pyrrolo[2,3-d]-pyrimidin-7-yl]-3,4-dihydroxy-tetrahydro-furan-2-yl]methoxy-methylphosphonic acid |
| 95 | 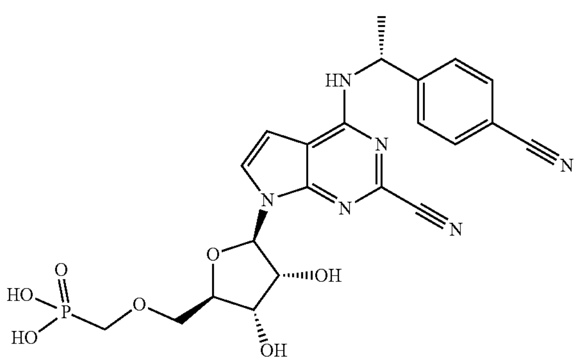 [SMILES: C[C@@H](Nc1nc(C#N)nc2c1ccn2[C@@H]1O[C@H](COCP(=O)(O)O)[C@@H](O)[C@H]1O)c1ccc(C#N)cc1] | [M − H]⁻: 513 | [(2R,3S,4R,5R)-5-[2-cyano-4-[[(1R)-1-(4-cyanophenyl)ethyl]-amino]pyrrolo[2,3-d]-pyrimidin-7-yl]-3,4-dihydroxy-tetrahydro-furan-2-yl]methoxy-methylphosphonic acid |
| 96 | 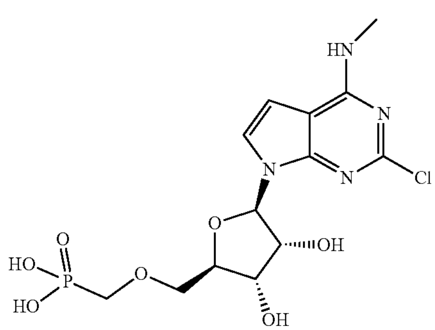 [SMILES: CNc1nc(Cl)nc2c1ccn2[C@@H]1O[C@H](COCP(=O)(O)O)[C@@H](O)[C@H]1O] | [M − H]⁻: 407 | [(2R,3S,4R,5R)-5-[2-chloro-4-(methyl-amino)pyrrolo[2,3-d]-pyrimidin-7-yl]-3,4-dihydroxy-tetrahydro-furan-2-yl]methoxy-methylphosphonic acid |

TABLE 1-continued

| No. | Structure | m/z | IUPAC Name |
|---|---|---|---|
| 97 | 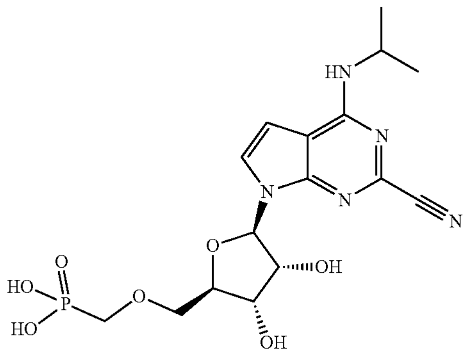 [SMILES: CC(C)Nc1nc(C#N)nc2c1ccn2[C@@H]1O[C@H](COCP(=O)(O)O)[C@@H](O)[C@H]1O] | [M + H]⁺: 428 | [(2R,3S,4R,5R)-5-[2-cyano-4-(isopropyl-amino)pyrrolo[2,3-d]-pyrimidin-7-yl]-3,4-dihydroxy-tetrahydro-furan-2-yl]methoxy-methylphosphonic acid |
| 98 | 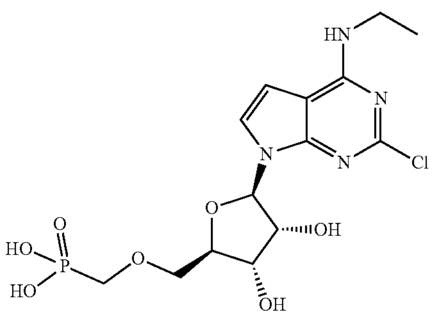 [SMILES: CCNc1nc(Cl)nc2c1ccn2[C@@H]1O[C@H](COCP(=O)(O)O)[C@@H](O)[C@H]1O] | [M + H]⁺: 423 | [(2R,3S,4R,5R)-5-[2-chloro-4-(ethylamino)-pyrrolo[2,3-d]-pyrimidin-7-yl]-3,4-dihydroxy-tetrahydro-furan-2-yl]methoxy-methylphosphonic acid |
| 99 | 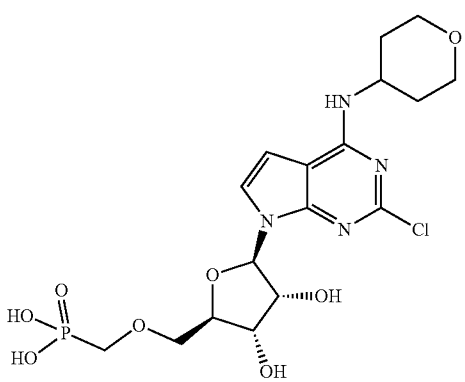 | [M − H]⁻: 477 | [(2R,3S,4R,5R)-5-[2-chloro-4-(tetrahydro-pyran-4-ylamino)-pyrrolo[2,3-d]-pyrimidin-7-yl]-3,4-dihydroxy-tetrahydro-furan-2-yl]methoxy-methylphosphonic acid |
| 100 | 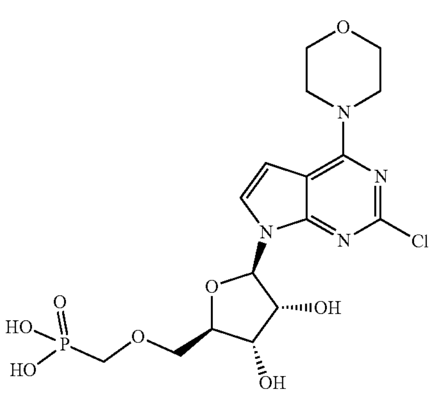 [SMILES: O=P(O)(O)COC[C@H]1O[C@@H](n2ccc3c(N4CCOCC4)nc(Cl)nc32)[C@H](O)[C@@H]1O] | [M + H]⁺: 465<br>[M − H]⁻: 463 | [(2R,3S,4R,5R)-5-(2-chloro-4-morpholino-pyrrolo[2,3-d]-pyrimidin-7-yl)-3,4-dihydroxy-tetrahydro-furan-2-yl]methoxy-methylphosphonic acid |

TABLE 1-continued

| No. | Structure | m/z | IUPAC Name |
|---|---|---|---|
| 101 | 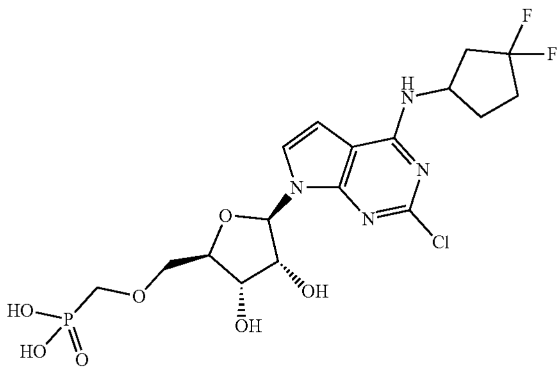 [SMILES: O=P(O)(O)COC[C@H]1O[C@@H](n2ccc3c(NC4CCC(F)(F)C4)nc(Cl)nc32)[C@H](O)[C@@H]1O] | [M + H]⁺: 499; [M − H]⁻: 497 | [(2R,3S,4R,5R)-5-[2-chloro-4-[(3,3-difluoro-cyclopentyl)amino]-pyrrolo[2,3-d]-pyrimidin-7-yl]-3,4-dihydroxy-tetrahydro-furan-2-yl]methoxy-methylphosphonic acid |
| 102 | 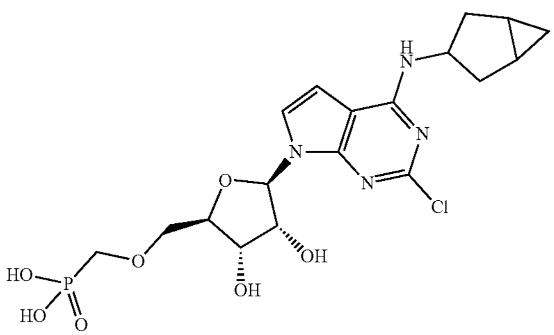 [SMILES: O=P(O)(O)COC[C@H]1O[C@@H](n2ccc3c(NC4CC5CC5C4)nc(Cl)nc32)[C@H](O)[C@@H]1O] | [M + H]⁺: 475; [M − H]⁻: 473 | [(2R,3S,4R,5R)-5-[4-(3-bicyclo[3.1.0]-hexanylamino)-2-chloro-pyrrolo[2,3-d]-pyrimidin-7-yl]-3,4-dihydroxy-tetrahydro-furan-2-yl]methoxy-methylphosphonic acid |
| 103 | 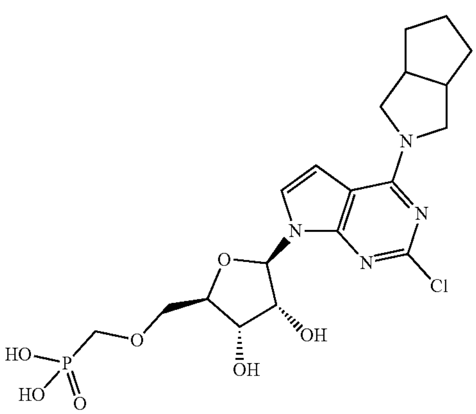 [SMILES: O=P(O)(O)COC[C@H]1O[C@@H](n2ccc3c(N4CC5CCCC5C4)nc(Cl)nc32)[C@H](O)[C@@H]1O] | [M + H]⁺: 489; [M − H]⁻: 487 | [(2R,3S,4R,5R)-5-[4-(3,3a,4,5,6,6a-hexa-hydro-1H-cyclopenta-[c]pyrrol-2-yl)-2-chloro-pyrrolo[2,3-d]-pyrimidin-7-yl]-3,4-dihydroxy-tetrahydro-furan-2-yl]methoxy-methylphosphonic acid |
| 104 | 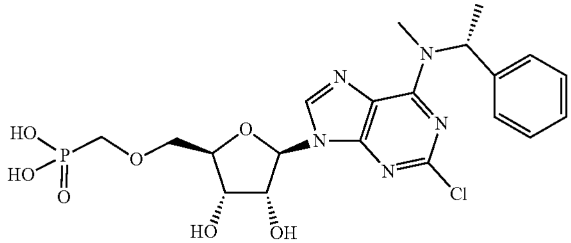 [SMILES: C[C@H](c1ccccc1)N(C)c1nc(Cl)nc2c1ncn2[C@@H]1O[C@H](COCP(=O)(O)O)[C@@H](O)[C@H]1O] | [M + H]⁺: 514; [M − H]⁻: 512 | [(2R,3S,4R,5R)-5-[2-chloro-6-[methyl-[(1R)-1-phenylethyl-[amino]purin-9-yl]-3,4-dihydroxy-tetra-hydrofuran-2-yl]-methoxymethylphos-phonic acid |

TABLE 1-continued

| No. | Structure | m/z | IUPAC Name |
|---|---|---|---|
| 105 | 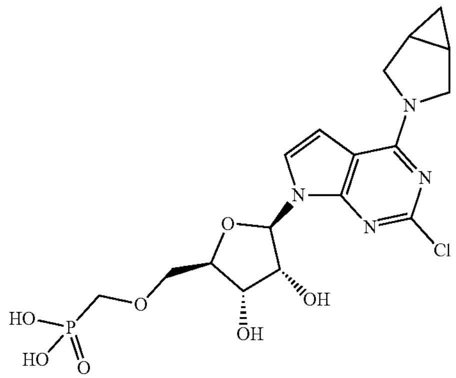 [SMILES: O=P(O)(O)COC[C@H]1O[C@@H](n2ccc3c(N4CC5CC5C4)nc(Cl)nc32)[C@H](O)[C@@H]1O] | [M + H]⁺: 461; [M − H]⁻: 459 | [(2R,3S,4R,5R)-5-[4-(3-azabicyclo[3.1.0]-hexan-3-yl)-2-chloro-pyrrolo[2,3-d]-pyrimidin-7-yl]-3,4-dihydroxy-tetrahydro-furan-2-yl]methoxy-methylphosphonic acid |
| 106 | 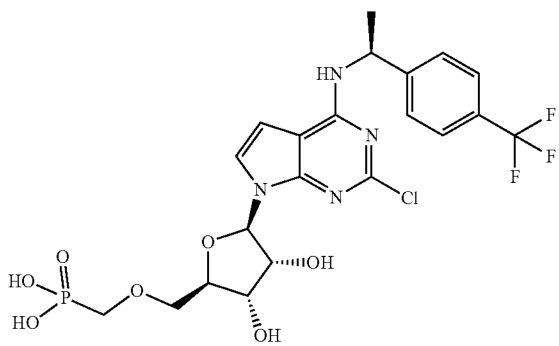 [SMILES: C[C@H](Nc1nc(Cl)nc2c1ccn2[C@@H]1O[C@H](COCP(=O)(O)O)[C@@H](O)[C@H]1O)c1ccc(C(F)(F)F)cc1] | [M − H]⁻: 565 | [(2R,3S,4R,5R)-5-[2-chloro-4-[[(1S)-1-[4-(trifluoromethyl)-phenyl]ethyl]amino]-pyrrolo[2,3-d]-pyrimidin-7-yl]-3,4-dihydroxy-tetrahydro-furan-2-yl]methoxy-methylphosphonic acid |
| 107 | 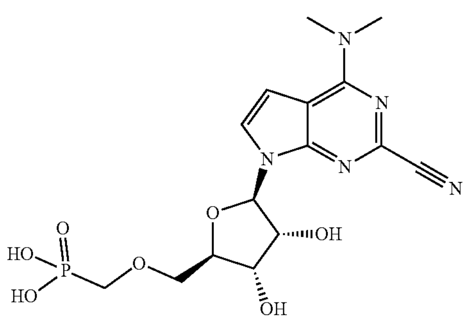 [SMILES: CN(C)c1nc(C#N)nc2c1ccn2[C@@H]1O[C@H](COCP(=O)(O)O)[C@@H](O)[C@H]1O] | [M − H]⁻: 412 | [(2R,3S,4R,5R)-5-[2-cyano-4-(dimethyl-amino)pyrrolo[2,3-d]-pyrimidin-7-yl]-3,4-dihydroxy-tetrahydro-furan-2-yl]methoxy-methylphosphonic acid |
| 108 | 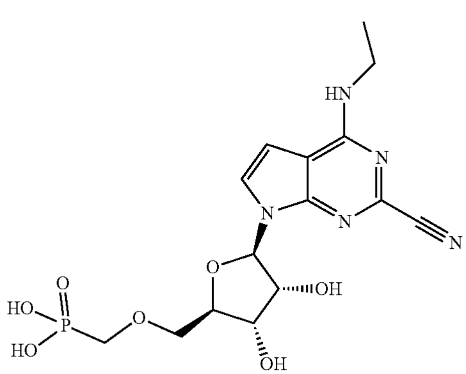 [SMILES: CCNc1nc(C#N)nc2c1ccn2[C@@H]1O[C@H](COCP(=O)(O)O)[C@@H](O)[C@H]1O] | [M − H]⁻: 412 | [(2R,3S,4R,5R)-5-[2-cyano-4-(ethylamino)-pyrrolo[2,3-d]-pyrimidin-7-yl]-3,4-dihydroxy-tetrahydro-furan-2-yl]methoxy-methylphosphonic acid |

TABLE 1-continued

| No. | Structure | m/z | IUPAC Name |
|---|---|---|---|
| 109 | 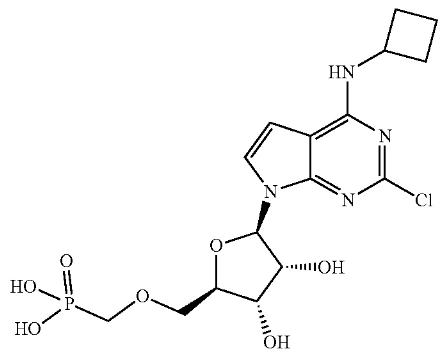 [SMILES: O=P(O)(O)COC[C@H]1O[C@@H](n2ccc3c(NC4CCC4)nc(Cl)nc32)[C@H](O)[C@@H]1O] | [M + H]⁺: 449; [M − H]⁻: 447 | [(2R,3S,4R,5R)-5-[2-chloro-4-(cyclobutyl-amino)pyrrolo[2,3-d]-pyrimidin-7-yl]-3,4-dihydroxy-tetrahydro-furan-2-yl]methoxy-methylphosphonic acid |
| 110 | 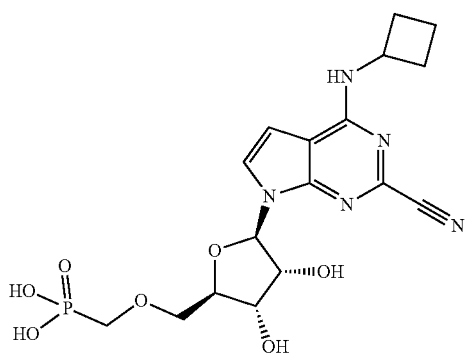 [SMILES: N#Cc1nc(NC2CCC2)c2ccn([C@@H]3O[C@H](COCP(=O)(O)O)[C@@H](O)[C@H]3O)c2n1] | [M + H]⁺: 440; [M − H]⁻: 438 | [(2R,3S,4R,5R)-5-[2-cyano-4-(cyclobutyl-amino)pyrrolo[2,3-d]-pyrimidin-7-yl]-3,4-dihydroxy-tetrahydro-furan-2-yl]methoxy-methylphosphonic acid |
| 111 | 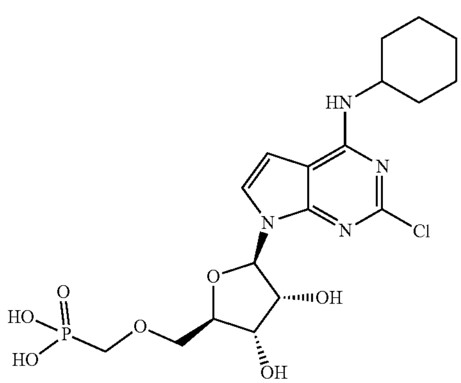 [SMILES: O=P(O)(O)COC[C@H]1O[C@@H](n2ccc3c(NC4CCCCC4)nc(Cl)nc32)[C@H](O)[C@@H]1O] | [M − H]⁻: 475 | [(2R,3S,4R,5R)-5-[2-chloro-4-(cyclohexyl-amino)pyrrolo[2,3-d]-pyrimidin-7-yl]-3,4-dihydroxy-tetrahydro-furan-2-yl]methoxy-methylphosphonic acid |
| 112 | 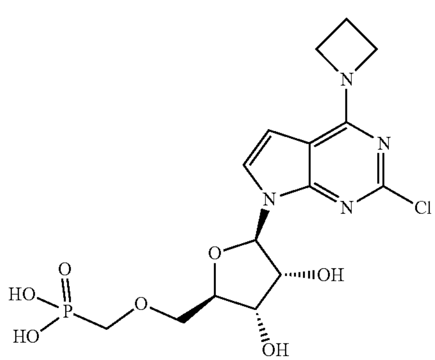 [SMILES: O=P(O)(O)COC[C@H]1O[C@@H](n2ccc3c(N4CCC4)nc(Cl)nc32)[C@H](O)[C@@H]1O] | [M + H]⁺: 435; [M − H]⁻: 433 | [(2R,3S,4R,5R)-5-[4-(azetidin-1-yl)-2-chloro-pyrrolo[2,3-d]-pyrimidin-7-yl]-3,4-dihydroxy-tetrahydro-furan-2-yl]methoxy-methylphosphonic acid |

TABLE 1-continued

| No. | Structure | m/z | IUPAC Name |
|---|---|---|---|
| 113 | 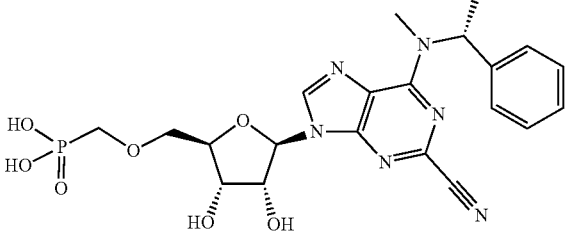 | [M + H]⁺: 505; [M − H]⁻: 503 | [(2R,3S,4R,5R)-5-[2-cyano-6-[methyl-[(1R)-1-phenylethyl-[amino]purin-9-yl]-3,4-dihydroxy-tetrahydrofuran-2-yl]-methoxymethylphosphonic acid |
| 114 | 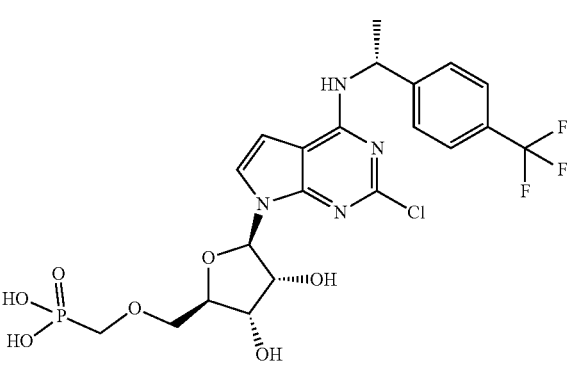 [SMILES: C[C@@H](Nc1nc(Cl)nc2c1ccn2[C@@H]1O[C@H](COCP(=O)(O)O)[C@@H](O)[C@H]1O)c1ccc(C(F)(F)F)cc1] | [M + H]⁺: 567; [M − H]⁻: 565 | [(2R,3S,4R,5R)-5-[2-chloro-4-[[(1R)-1-[4-(trifluoromethyl)-phenyl]ethyl]amino]-pyrrolo[2,3-d]-pyrimidin-7-yl]-3,4-dihydroxy-tetrahydrofuran-2-yl]methoxymethylphosphonic acid |
| 115 | 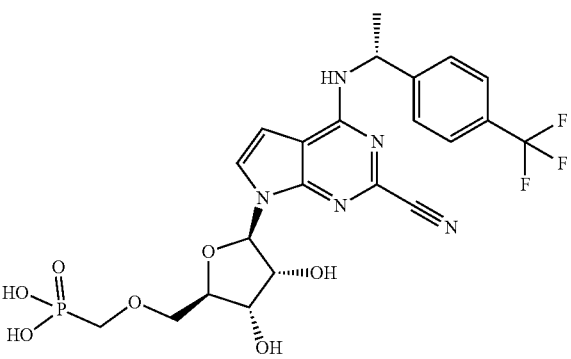 [SMILES: C[C@@H](Nc1nc(C#N)nc2c1ccn2[C@@H]1O[C@H](COCP(=O)(O)O)[C@@H](O)[C@H]1O)c1ccc(C(F)(F)F)cc1] | [M + H]⁺: 558; [M − H]⁻: 556 | [(2R,3S,4R,5R)-5-[2-cyano-4-[[(1R)-1-[4-(trifluoromethyl)-phenyl]ethyl]amino]-pyrrolo[2,3-d]-pyrimidin-7-yl]-3,4-dihydroxy-tetrahydrofuran-2-yl]methoxymethylphosphonic acid |
| 116 | 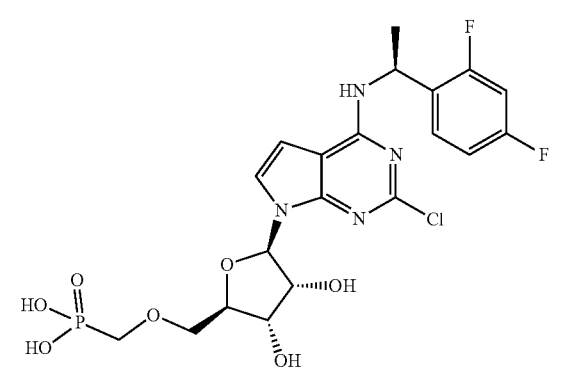 [SMILES: C[C@H](Nc1nc(Cl)nc2c1ccn2[C@@H]1O[C@H](COCP(=O)(O)O)[C@@H](O)[C@H]1O)c1ccc(F)cc1F] | [M + H]⁺: 535; [M − H]⁻: 533 | [(2R,3S,4R,5R)-5-[2-chloro-4-[[(1S)-1-(2,4-difluorophenyl)-ethyl]amino]pyrrolo-[2,3-d]pyrimidin-7-yl]-3,4-dihydroxy-tetrahydrofuran-2-yl]methoxymethyl-phosphonic acid |

TABLE 1-continued

| No. | Structure | m/z | IUPAC Name |
|---|---|---|---|
| 117 | 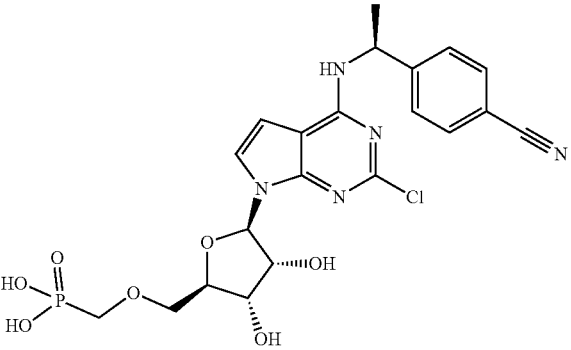 [SMILES: C[C@H](Nc1nc(Cl)nc2c1ccn2[C@@H]1O[C@H](COCP(=O)(O)O)[C@@H](O)[C@H]1O)c1ccc(C#N)cc1] | [M + H]⁺: 524; [M − H]⁻: 522 | [(2R,3S,4R,5R)-5-[2-chloro-4-[[(1S)-1-(4-cyanophenyl)ethyl]-amino]pyrrolo[2,3-d]-pyrimidin-7-yl]-3,4-dihydroxy-tetrahydro-furan-2-yl]methoxy-methylphosphonic acid |
| 118 | 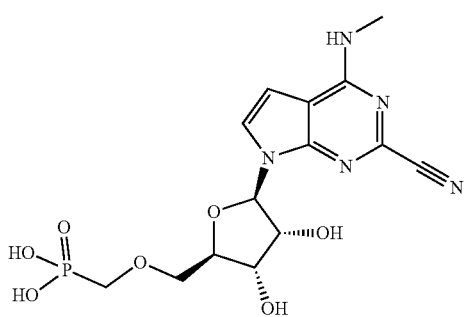 [SMILES: CNc1nc(C#N)nc2c1ccn2[C@@H]1O[C@H](COCP(=O)(O)O)[C@@H](O)[C@H]1O] | [M + H]⁺: 400; [M − H]⁻: 398 | [(2R,3S,4R,5R)-5-[2-cyano-4-(methyl-amino)pyrrolo[2,3-d]-pyrimidin-7-yl]-3,4-dihydroxy-tetrahydro-furan-2-yl]methoxy-methylphosphonic acid |
| 119 | 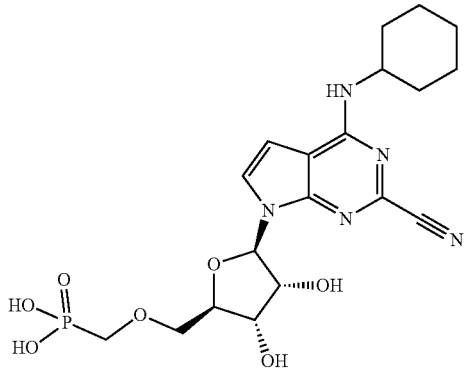 | [M + H]⁺: 468; [M − H]⁻: 466 | [(2R,3S,4R,5R)-5-[2-cyano-4-(cyclohexyl-amino)pyrrolo[2,3-d]-pyrimidin-7-yl]-3,4-dihydroxy-tetrahydro-furan-2-yl]methoxy-methylphosphonic acid |
| 120 | 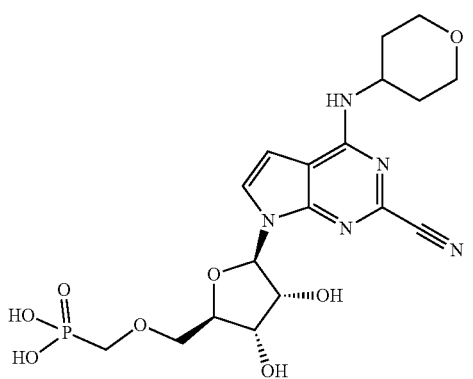 [SMILES: N#Cc1nc(NC2CCOCC2)c2ccn([C@@H]3O[C@H](COCP(=O)(O)O)[C@@H](O)[C@H]3O)c2n1] | [M + H]⁺: 470; [M − H]⁻: 468 | [(2R,3S,4R,5R)-5-[2-cyano-4-(tetrahydro-pyran-4-ylamino)-pyrrolo[2,3-d]-pyrimidin-7-yl]-3,4-dihydroxy-tetrahydro-furan-2-yl]methoxy-methylphosphonic acid |

TABLE 1-continued

| No. | Structure | m/z | IUPAC Name |
|---|---|---|---|
| 121 | 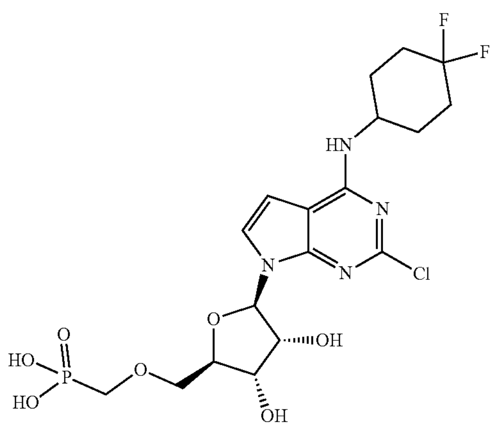 [SMILES: O=P(O)(O)COC[C@H]1O[C@@H](n2ccc3c(NC4CCC(F)(F)CC4)nc(Cl)nc32)[C@H](O)[C@@H]1O] | [M + H]⁺: 513 | [(2R,3S,4R,5R)-5-[2-chloro-4-[(4,4-difluorocyclohexyl)-amino]pyrrolo[2,3-d]-pyrimidin-7-yl]-3,4-dihydroxy-tetrahydro-furan-2-yl]methoxy-methylphosphonic acid |
| 122 | 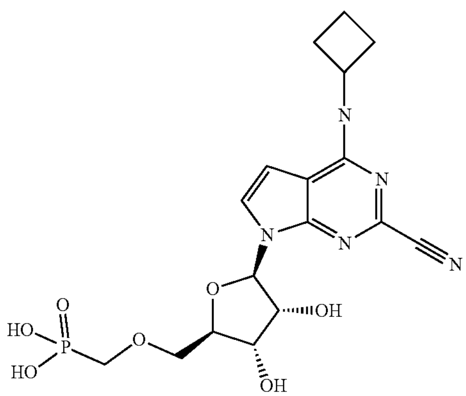 [SMILES: N#Cc1nc(NC2CCC2)c2ccn([C@@H]3O[C@H](COCP(=O)(O)O)[C@@H](O)[C@H]3O)c2n1] | [M − H]⁻: 424 | [(2R,3S,4R,5R)-5-[4-(azetidin-1-yl)-2-cyano-pyrrolo[2,3-d]-pyrimidin-7-yl]-3,4-dihydroxy-tetrahydro-furan-2-yl]methoxy-methylphosphonic acid |
| 123 | 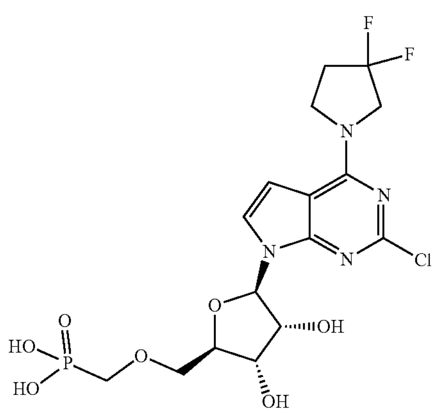 [SMILES: O=P(O)(O)COC[C@H]1O[C@@H](n2ccc3c(N4CCC(F)(F)C4)nc(Cl)nc32)[C@H](O)[C@@H]1O] | [M − H]⁻: 483 | [(2R,3S,4R,5R)-5-[2-chloro-4-(3,3-difluoro-pyrrolidin-1-yl)pyrrolo-[2,3-d]pyrimidin-7-yl]-3,4-dihydroxy-tetrahydrofuran-2-yl]-methoxymethylphos-phonic acid |
| 124 | 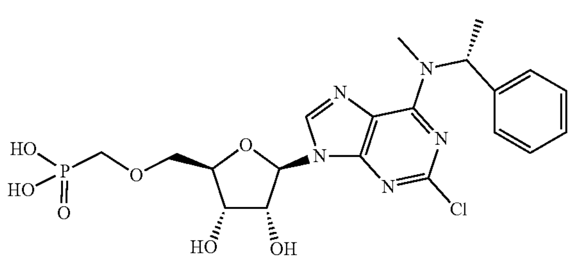 [SMILES: C[C@H](c1ccccc1)N(C)c1nc(Cl)nc2c1ncn2[C@@H]1O[C@H](COCP(=O)(O)O)[C@@H](O)[C@H]1O] | [M + H]⁺: 513; [M − H]⁻: 511 | [(2R,3S,4R,5R)-5-[2-chloro-4-[methyl-[(1R)-1-phenylethyl]-amino]pyrrolo[2,3-d]-pyrimidin-7-yl]-3,4-dihydroxy-tetrahydro-furan-2-yl]methoxy-methylphosphonic acid |

TABLE 1-continued

| No. | Structure | m/z | IUPAC Name |
|---|---|---|---|
| 125 | 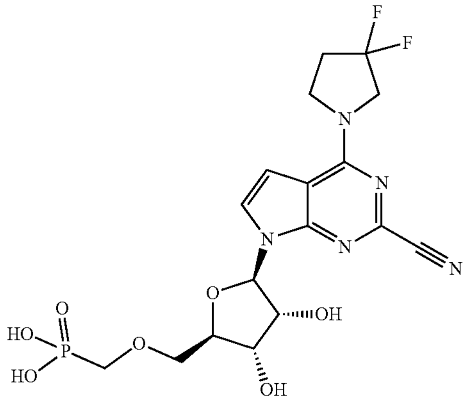 [SMILES: N#Cc1nc(N2CCC(F)(F)C2)c2ccn([C@@H]3O[C@H](COCP(=O)(O)O)[C@@H](O)[C@H]3O)c2n1] | [M + H]⁺: 476;<br>[M − H]⁻: 474 | [(2R,3S,4R,5R)-5-[2-cyano-4-(3,3-difluoropyrrolidin-1-yl)-pyrrolo[2,3-d]-pyrimidin-7-yl]-3,4-dihydroxy-tetrahydro-furan-2-yl]methoxy-methylphosphonic acid |
| 126 | 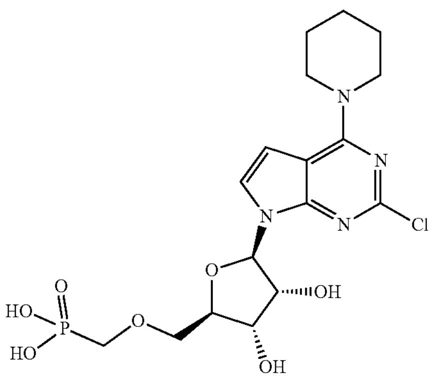 [SMILES: O=P(O)(O)COC[C@H]1O[C@@H](n2ccc3c(N4CCCCC4)nc(Cl)nc32)[C@H](O)[C@@H]1O] | [M + H]⁺: 463;<br>[M − H]⁻: 461 | [(2R,3S,4R,5R)-5-[2-chloro-4-(1-piperidyl)-pyrrolo[2,3-d]-pyrimidin-7-yl]-3,4-dihydroxy-tetrahydro-furan-2-yl]methoxy-methylphosphonic acid |
| 127 | 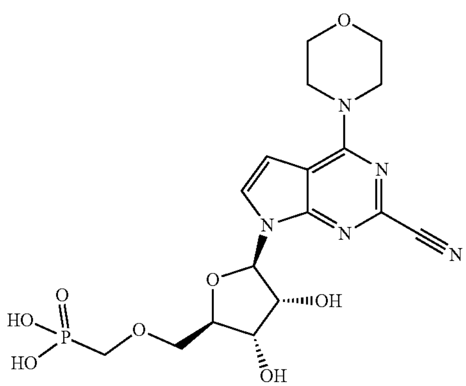 [SMILES: N#Cc1nc(N2CCOCC2)c2ccn([C@@H]3O[C@H](COCP(=O)(O)O)[C@@H](O)[C@H]3O)c2n1] | [M + H]⁺: 456;<br>[M − H]⁻: 454 | [(2R,3S,4R,5R)-5-(2-cyano-4-morpholino-pyrrolo[2,3-d]-pyrimidin-7-yl)-3,4-dihydroxy-tetrahydro-furan-2-yl]methoxy-methylphosphonic acid |
| 128 | 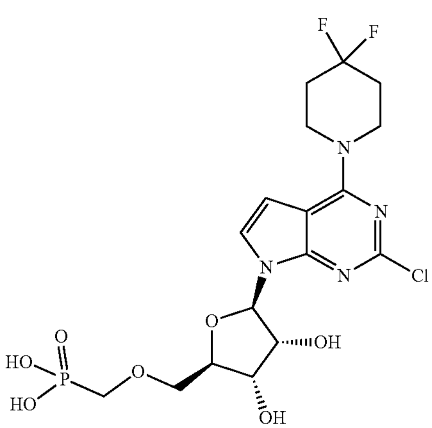 [SMILES: O=P(O)(O)COC[C@H]1O[C@@H](n2ccc3c(N4CCC(F)(F)CC4)nc(Cl)nc32)[C@H](O)[C@@H]1O] | [M − H]⁻: 497 | [(2R,3S,4R,5R)-5-[2-chloro-4-(4,4-difluoro-1-piperidyl)pyrrolo-[2,3-d]pyrimidin-7-yl]-3,4-dihydroxy-tetrahydrofuran-2-yl]-methoxymethylphosphonic acid |

TABLE 1-continued

| No. | Structure | m/z | IUPAC Name |
|---|---|---|---|
| 129 | 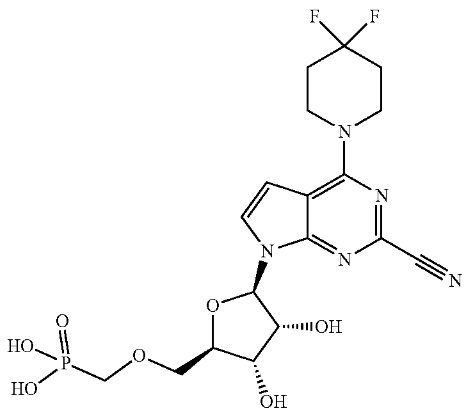 [SMILES: N#Cc1nc(N2CCC(F)(F)CC2)c2ccn([C@@H]3O[C@H](COCP(=O)(O)O)[C@@H](O)[C@H]3O)c2n1] | [M + H]⁺: 490 | [(2R,3S,4R,5R)-5-[2-cyano-4-(4,4-difluoro-1-piperidyl)pyrrolo-[2,3-d]pyrimidin-7-yl]-3,4-dihydroxy-tetrahydrofuran-2-yl]-methoxymethylphosphonic acid |
| 130 | 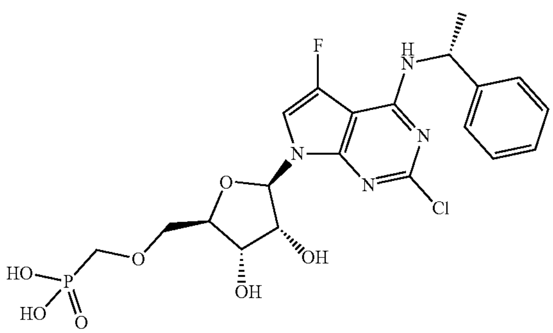 [SMILES: C[C@@H](Nc1nc(Cl)nc2c1c(F)cn2[C@@H]1O[C@H](COCP(=O)(O)O)[C@@H](O)[C@H]1O)c1ccccc1] | [M + H]⁺: 517; [M − H]⁻: 515 | [(2R,3S,4R,5R)-5-[2-chloro-5-fluoro-4-[[(1R)-1-phenylethyl]-amino]pyrrolo[2,3-d]-pyrimidin-7-yl]-3,4-dihydroxy-tetrahydro-furan-2-yl]methoxy-methylphosphonic acid |
| 131 | 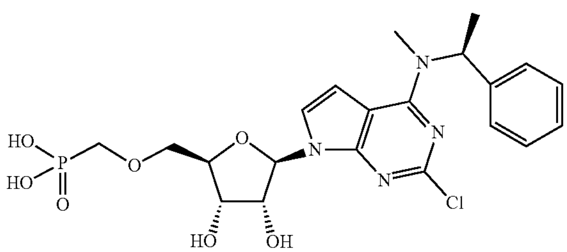 [SMILES: C[C@@H](c1ccccc1)N(C)c1nc(Cl)nc2c1ccn2[C@@H]1O[C@H](COCP(=O)(O)O)[C@@H](O)[C@H]1O] | [M + H]⁺: 513; [M − H]⁻: 511 | [(2R,3S,4R,5R)-5-[2-chloro-4-[methyl-[(1S)-1-phenylethyl]-amino]pyrrolo[2,3-d]-pyrimidin-7-yl]-3,4-dihydroxy-tetrahydro-furan-2-yl]methoxy-methylphosphonic acid |
| 132 | 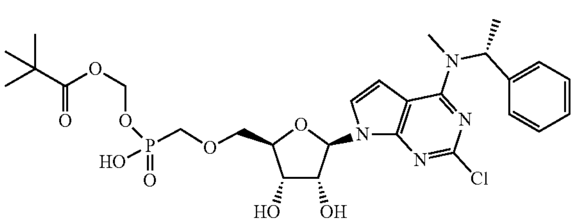 [SMILES: C[C@H](c1ccccc1)N(C)c1nc(Cl)nc2c1ccn2[C@@H]1O[C@H](COCP(=O)(O)OCOC(=O)C(C)(C)C)[C@@H](O)[C@H]1O] | [M + H]⁺: 627; [M − H]⁻: 625 | [(2R,3S,4R,5R)-5-[2-chloro-4-[methyl-[(1R)-1-phenylethyl]-amino]pyrrolo[2,3-d]-pyrimidin-7-yl]-3,4-dihydroxy-tetrahydro-furan-2-yl]methoxy-methyl-(2,2-dimethyl-propanoyloxymethoxy)-phosphinic acid |
| 133 | 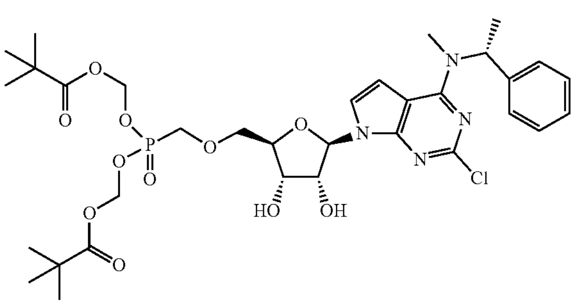 [SMILES: C[C@H](c1ccccc1)N(C)c1nc(Cl)nc2c1ccn2[C@@H]1O[C@H](COCP(=O)(OCOC(=O)C(C)(C)C)OCOC(=O)C(C)(C)C)[C@@H](O)[C@H]1O] | [M + H]⁺: 741 | [[(2R,3S,4R,5R)-5-[2-chloro-4-[methyl-[(1R)-1-phenylethyl]-amino]pyrrolo[2,3-d]-pyrimidin-7-yl]-3,4-dihydroxy-tetrahydro-furan-2-yl]methoxy-methyl-(2,2-dimethyl-propanoyloxymethoxy)-phosphoryl]oxymethyl 2,2-dimethylpropanoate |

TABLE 1-continued

| No. | Structure | m/z | IUPAC Name |
|---|---|---|---|
| 134 | 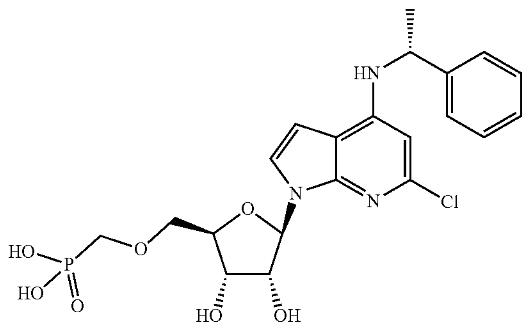 [SMILES: C[C@@H](Nc1cc(Cl)nc2c1ccn2[C@@H]1O[C@H](COCP(=O)(O)O)[C@@H](O)[C@H]1O)c1ccccc1] | [M + H]⁺: 498; [M − H]⁻: 496 | [(2R,3S,4R,5R)-5-[6-chloro-4-[[(1R)-1-phenylethyl]amino]-pyrrolo[2,3-b]pyridin-1-yl]-3,4-dihydroxy-tetrahydrofuran-2-yl]-methoxymethylphosphonic acid |
| 135 | 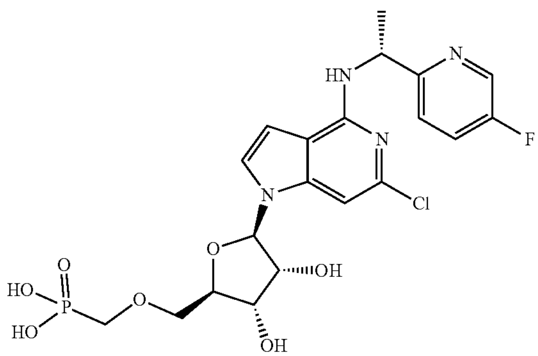 [SMILES: C[C@@H](Nc1nc(Cl)cc2c1ccn2[C@@H]1O[C@H](COCP(=O)(O)O)[C@@H](O)[C@H]1O)c1ccc(F)cn1] | [M − H]⁻: 516 | [(2R,3S,4R,5R)-5-[2-chloro-4-[[(1R)-1-(5-fluoro-2-pyridyl)ethyl]-amino]pyrrolo[2,3-d]-pyrimidin-7-yl]-3,4-dihydroxy-tetrahydro-furan-2-yl]methoxy-methylphosphonic acid |
| 136 | 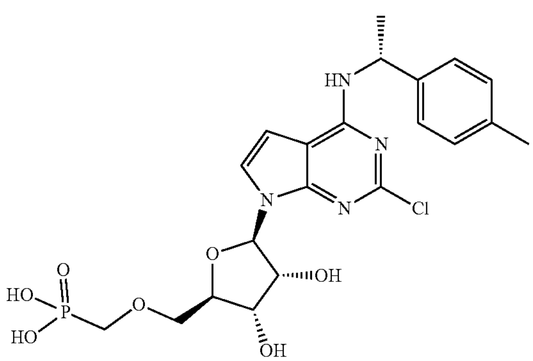 [SMILES: Cc1ccc([C@@H](C)Nc2nc(Cl)nc3c2ccn3[C@@H]2O[C@H](COCP(=O)(O)O)[C@@H](O)[C@H]2O)cc1] | [M + H]⁺: 513; [M − H]⁻: 511 | [(2R,3S,4R,5R)-5-[2-chloro-4-[[(1R)-1-(p-tolyl)ethyl]amino]-pyrrolo[2,3-d]-pyrimidin-7-yl]-3,4-dihydroxy-tetrahydro-furan-2-yl]methoxy-methylphosphonic acid |
| 137 | 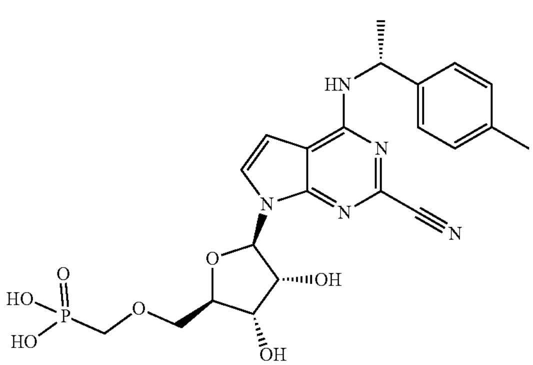 [SMILES: Cc1ccc([C@@H](C)Nc2nc(C#N)nc3c2ccn3[C@@H]2O[C@H](COCP(=O)(O)O)[C@@H](O)[C@H]2O)cc1] | [M − H]⁻: 502 | [(2R,3S,4R,5R)-5-[2-cyano-4-[[(1R)-1-(p-tolyl)ethyl]amino]-pyrrolo[2,3-d]-pyrimidin-7-yl]-3,4-dihydroxy-tetrahydro-furan-2-yl]methoxy-methylphosphonic acid |

TABLE 1-continued

| No. | Structure | m/z | IUPAC Name |
|---|---|---|---|
| 138 | 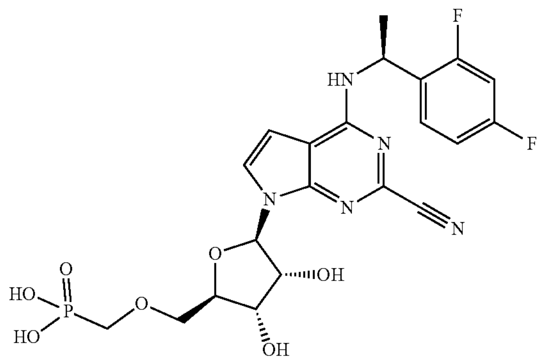 [SMILES: C[C@H](Nc1nc(C#N)nc2c1ccn2[C@@H]1O[C@H](COCP(=O)(O)O)[C@@H](O)[C@H]1O)c1ccc(F)cc1F] | [M − H]⁻: 524 | [(2R,3S,4R,5R)-5-[2-cyano-4-[[(1S)-1-(2,4-difluorophenyl)ethyl]-amino]pyrrolo[2,3-d]-pyrimidin-7-yl]-3,4-dihydroxy-tetrahydro-furan-2-yl]methoxy-methylphosphonic acid |
| 139 | 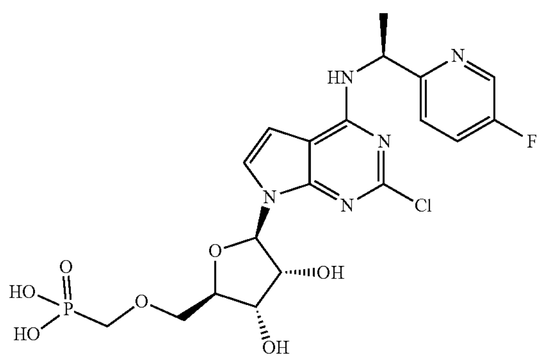 [SMILES: C[C@H](Nc1nc(Cl)nc2c1ccn2[C@@H]1O[C@H](COCP(=O)(O)O)[C@@H](O)[C@H]1O)c1ccc(F)cn1] | [M + H]⁺: 518;<br>[M − H]⁻: 516 | [(2R,3S,4R,5R)-5-[2-chloro-4-[[(1S)-1-(5-fluoro-2-pyridyl)-ethyl]amino]pyrrolo-[2,3-d]pyrimidin-7-yl]-3,4-dihydroxy-tetrahydrofuran-2-yl]-methoxymethylphos-phonic acid |
| 140 | 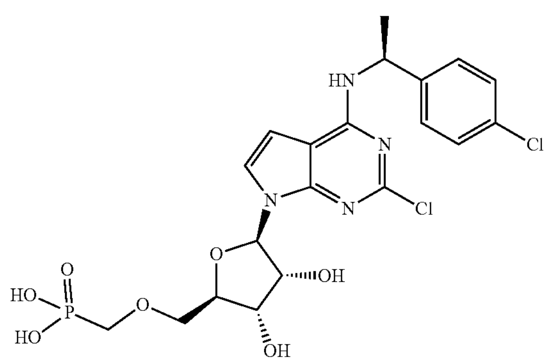 [SMILES: C[C@H](Nc1nc(Cl)nc2c1ccn2[C@@H]1O[C@H](COCP(=O)(O)O)[C@@H](O)[C@H]1O)c1ccc(Cl)cc1] | [M + H]⁺: 533;<br>[M − H]⁻: 531 | [(2R,3S,4R,5R)-5-[2-chloro-4-[[(1S)-1-(4-chlorophenyl)ethyl]-amino]pyrrolo[2,3-d]-pyrimidin-7-yl]-3,4-dihydroxy-tetrahydro-furan-2-yl]methoxy-methylphosphonic acid |
| 141 | 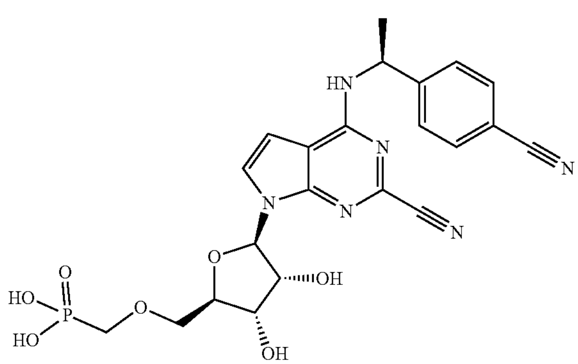 [SMILES: C[C@H](Nc1nc(C#N)nc2c1ccn2[C@@H]1O[C@H](COCP(=O)(O)O)[C@@H](O)[C@H]1O)c1ccc(C#N)cc1] | [M − H]⁻: 513 | [(2R,3S,4R,5R)-5-[2-cyano-4-[[(1S)-1-(4-cyanophenyl)ethyl]-amino]pyrrolo[2,3-d]-pyrimidin-7-yl]-3,4-dihydroxy-tetrahydro-furan-2-yl]methoxy-methylphosphonic acid |

TABLE 1-continued

| No. | Structure | m/z | IUPAC Name |
|---|---|---|---|
| 142 | 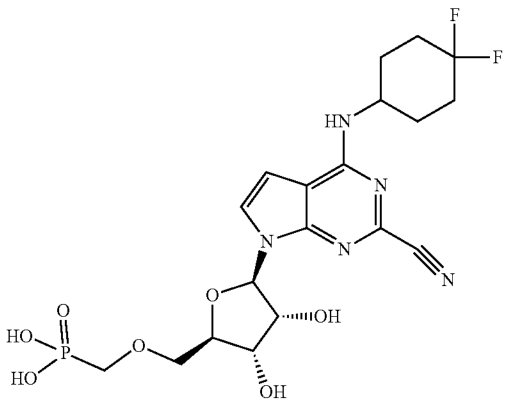 [SMILES: N#Cc1nc(NC2CCC(F)(F)CC2)c2ccn([C@@H]3O[C@H](COCP(=O)(O)O)[C@@H](O)[C@H]3O)c2n1] | [M + H]⁺: 504; [M − H]⁻: 502 | [(2R,3S,4R,5R)-5-[2-cyano-4-[(4,4-difluoro-cyclohexyl)amino]-pyrrolo[2,3-d]-pyrimidin-7-yl]-3,4-dihydroxy-tetrahydro-furan-2-yl]methoxy-methylphosphonic acid |
| 143 | 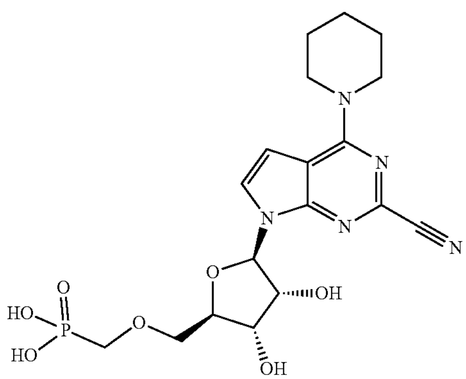 [SMILES: N#Cc1nc(N2CCCCC2)c2ccn([C@@H]3O[C@H](COCP(=O)(O)O)[C@@H](O)[C@H]3O)c2n1] | [M + H]⁺: 454; [M − H]⁻: 452 | [(2R,3S,4R,5R)-5-[2-cyano-4-(1-piperidyl)-pyrrolo[2,3-d]-pyrimidin-7-yl]-3,4-dihydroxy-tetrahydro-furan-2-yl]methoxy-methylphosphonic acid |
| 144 | 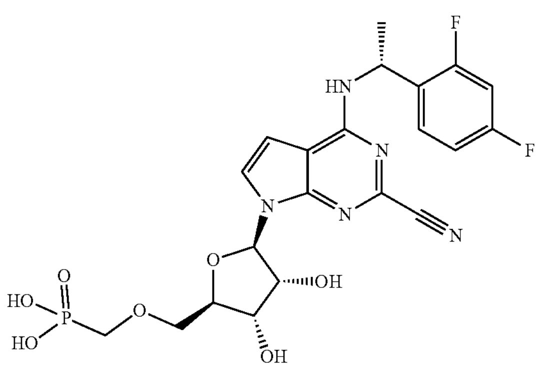 | [M + H]⁺: 535; [M − H]⁻: 533 | [(2R,3S,4R,5R)-5-[2-chloro-4-[[(1R)-1-(2,4-difluorophenyl)-ethyl]amino]pyrrolo-[2,3-d]pyrimidin-7-yl]-3,4-dihydroxy-tetrahydrofuran-2-yl]-methoxymethylphos-phonic acid |
| 145 | 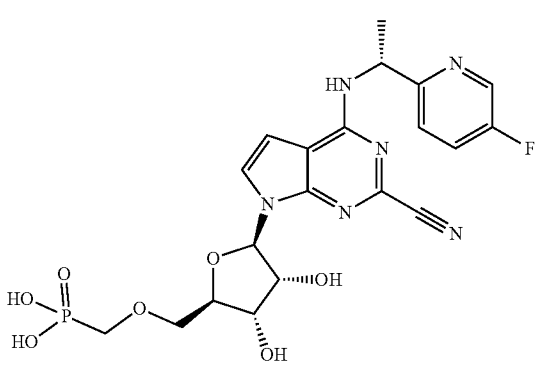 [SMILES: C[C@@H](Nc1nc(C#N)nc2c1ccn2[C@@H]1O[C@H](COCP(=O)(O)O)[C@@H](O)[C@H]1O)c1ccc(F)cn1] | [M − H]⁻: 507 | [(2R,3S,4R,5R)-5-[2-cyano-4-[[(1R)-1-(5-fluoro-2-pyridyl)ethyl]-amino]pyrrolo[2,3-d]-pyrimidin-7-yl]-3,4-dihydroxy-tetrahydro-furan-2-yl]methoxy-methylphosphonic acid |

TABLE 1-continued

| No. | Structure | m/z | IUPAC Name |
|---|---|---|---|
| 146 | 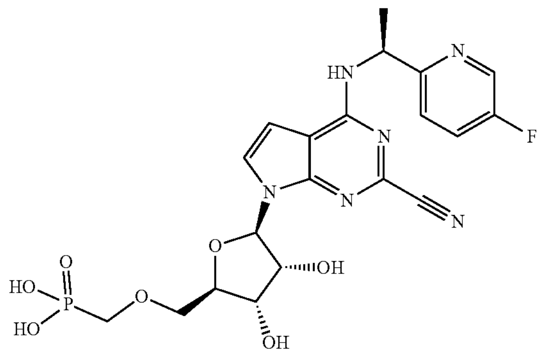 [SMILES: C[C@H](Nc1nc(C#N)nc2c1ccn2[C@@H]1O[C@H](COCP(=O)(O)O)[C@@H](O)[C@H]1O)c1ccc(F)cn1] | [M + H]⁺: 509; [M − H]⁻: 507 | [(2R,3S,4R,5R)-5-[2-cyano-4-[[(1S)-1-(5-fluoro-2-pyridyl)ethylamino]pyrrolo[2,3-d]-pyrimidin-7-yl-3,4-dihydroxy-tetrahydrofuran-2-yl]methoxymethylphosphonic acid |
| 147 | 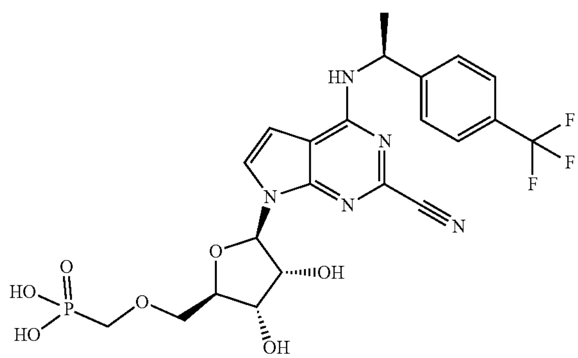 [SMILES: C[C@H](Nc1nc(C#N)nc2c1ccn2[C@@H]1O[C@H](COCP(=O)(O)O)[C@@H](O)[C@H]1O)c1ccc(C(F)(F)F)cc1] | [M − H]⁻: 556 | [(2R,3S,4R,5R)-5-[2-cyano-4-[[(1S)-1-[4-(trifluoromethyl)-phenyl]ethyl]amino]-pyrrolo[2,3-d]-pyrimidin-7-yl]-3,4-dihydroxy-tetrahydrofuran-2-yl]methoxymethylphosphonic acid |
| 148 | 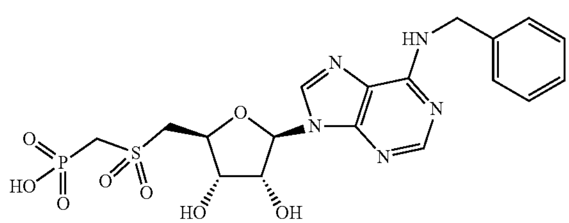 | [M + H]⁺: 500 | [(2S,3S,4R,5R)-5-[6-(benzylamino)purin-9-yl]-3,4-dihydroxy-tetrahydrofuran-2-yl]-methylsulfonylmethylphosphonic acid |
| 149 | 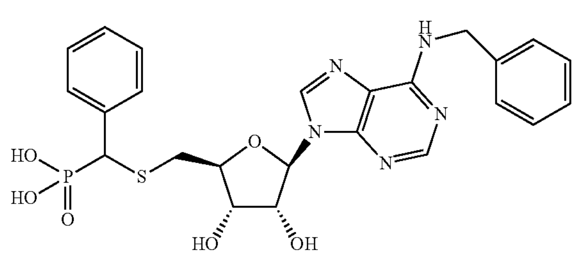 [SMILES: O=P(O)(O)C(SC[C@H]1O[C@@H](n2cnc3c(NCc4ccccc4)ncnc32)[C@H](O)[C@@H]1O)c1ccccc1] | [M + H]⁺: 544; [M − H]⁻: 542 | [[(2S,3S,5R)-5-[6-(benzylamino)purin-9-yl]-3,4-dihydroxy-tetrahydrofuran-2-yl]methylsulfanyl-phenylmethyl]phosphonic acid |
| 150 | 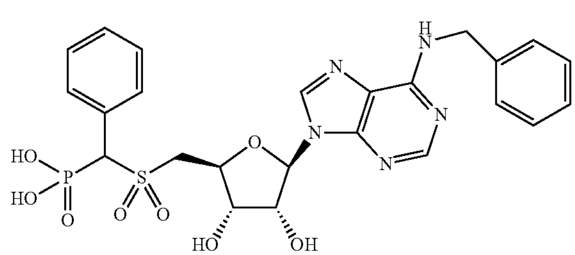 [SMILES: O=P(O)(O)C(c1ccccc1)S(=O)(=O)C[C@H]1O[C@@H](n2cnc3c(NCc4ccccc4)ncnc32)[C@H](O)[C@@H]1O] | [M + H]⁺: 576; [M − H]⁻: 574 | [[(2S,3S,5R)-5-[6-(benzylamino)purin-9-yl]-3,4-dihydroxy-tetrahydrofuran-2-yl]methylsulfonyl-phenylmethyl]phosphonic acid |

TABLE 1-continued

| No. | Structure | m/z | IUPAC Name |
|---|---|---|---|
| 151 | 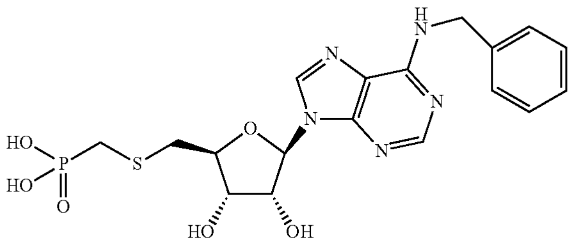 [SMILES: O=P(O)(O)CSC[C@H]1O[C@@H](n2cnc3c(NCc4ccccc4)ncnc32)[C@H](O)[C@@H]1O] | [M + H]⁺: 468; [M − H]⁻: 466 | [(2S,3S,5R)-5-[6-(benzylamino)purin-9-yl]-3,4-dihydroxy-tetrahydrofuran-2-yl]methylsulfanyl-methylphosphonic acid |
| 152 | 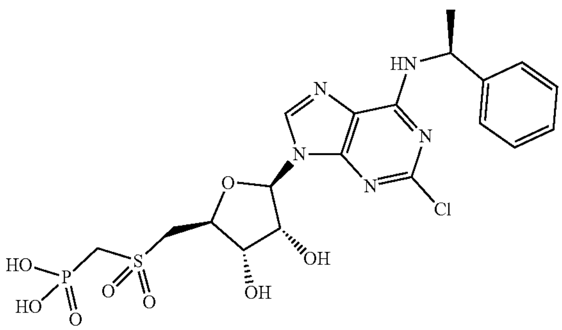 [SMILES: C[C@H](Nc1nc(Cl)nc2c1ncn2[C@@H]1O[C@H](CS(=O)(=O)CP(=O)(O)O)[C@@H](O)[C@H]1O)c1ccccc1] | [M − H]⁻: 546 | [(2S,3S,4R,5R)-5-[2-chloro-6-[[(1S)-1-phenylethyl]amino]-purin-9-yl]-3,4-dihydroxy-tetrahydrofuran-2-yl]methyl-sulfonylmethylphosphonic acid |
| 153 | 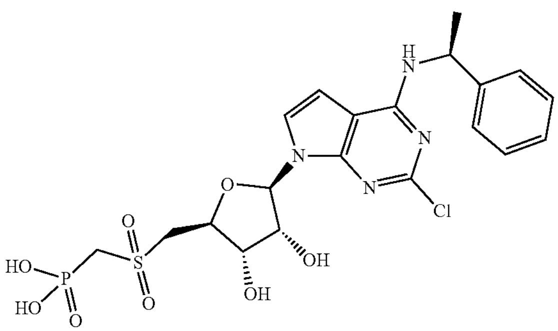 [SMILES: C[C@H](Nc1nc(Cl)nc2c1ccn2[C@@H]1O[C@H](CS(=O)(=O)CP(=O)(O)O)[C@@H](O)[C@H]1O)c1ccccc1] | [M − H]⁻: 545 | [(2S,3S,4R,5R)-5-[2-chloro-4-[[(1S)-1-phenylethyl]amino]-pyrrolo[2,3-d]-pyrimidin-7-yl]-3,4-dihydroxy-tetrahydrofuran-2-yl]methyl-sulfonylmethylphosphonic acid |
| 154 | 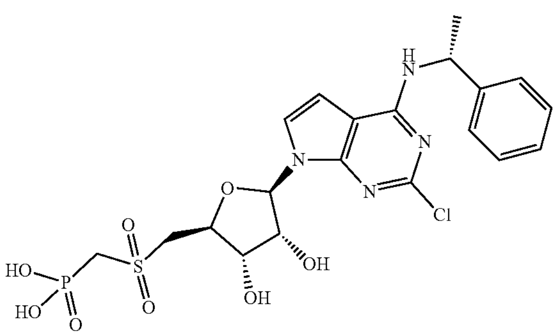 [SMILES: C[C@@H](Nc1nc(Cl)nc2c1ccn2[C@@H]1O[C@H](CS(=O)(=O)CP(=O)(O)O)[C@@H](O)[C@H]1O)c1ccccc1] | [M + H]⁺: 547; [M − H]⁻: 545 | [(2S,3S,4R,5R)-5-[2-chloro-4-[[(1R)-1-phenylethyl]amino]-pyrrolo[2,3-d]-pyrimidin-7-yl]-3,4-dihydroxy-tetrahydrofuran-2-yl]methyl-sulfonylmethylphosphonic acid |
| 155 | 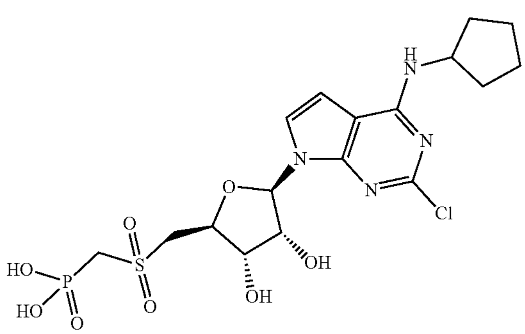 [SMILES: O=P(O)(O)CS(=O)(=O)C[C@H]1O[C@@H](n2ccc3c(NC4CCCC4)nc(Cl)nc32)[C@H](O)[C@@H]1O] | [M + H]⁺: 511; [M − H]⁻: 509 | [(2S,3S,4R,5R)-5-[2-chloro-4-(cyclopentyl-amino)pyrrolo[2,3-d]-pyrimidin-7-yl]-3,4-dihydroxy-tetrahydrofuran-2-yl]methyl-sulfonylmethylphosphonic acid |

TABLE 1-continued

| No. | Structure | m/z | IUPAC Name |
|---|---|---|---|
| 156 | 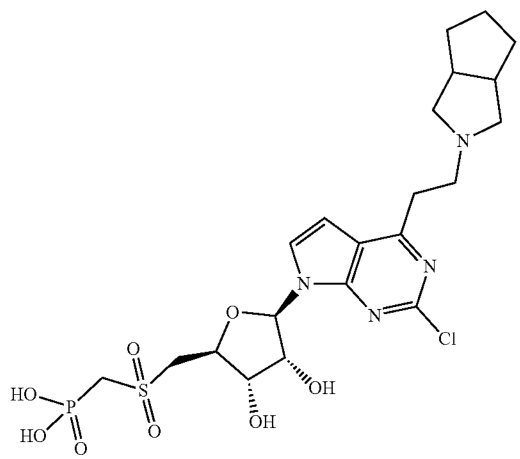 [SMILES: O=P(O)(O)CS(=O)(=O)C[C@H]1O[C@@H](n2ccc3c(CCN4CC5CCCC5C4)nc(Cl)nc32)[C@H](O)[C@@H]1O] | [M + H]⁺: 537; [M − H]⁻: 535 | [(2S,3S,4R,5R)-5-[4-(3,3a,4,5,6,6a-hexahydro-1H-cyclopenta[c]pyrrol-2-yl)-2-chloro-pyrrolo[2,3-d]pyrimidin-7-yl]-3,4-dihydroxy-tetrahydrohydrofuran-2-yl]methylsulfonylmethylphosphonic acid |
| 157 | 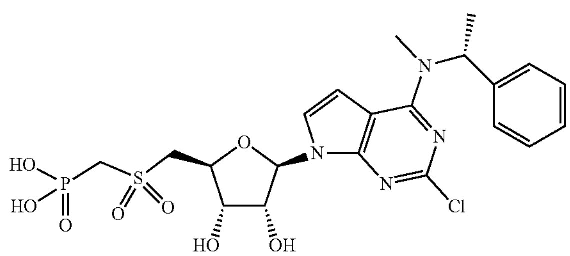 [SMILES: C[C@H](c1ccccc1)N(C)c1nc(Cl)nc2c1ccn2[C@@H]1O[C@H](CS(=O)(=O)CP(=O)(O)O)[C@@H](O)[C@H]1O] | [M + H]⁺: 561; [M − H]⁻: 559 | [(2S,3S,4R,5R)-5-[2-chloro-4-[methyl-[(1R)-1-phenylethyl]-amino]pyrrolo[2,3-d]pyrimidin-7-yl]-3,4-dihydroxy-tetrahydrofuran-2-yl]methylsulfonylmethylphosphonic acid |
| 158 | 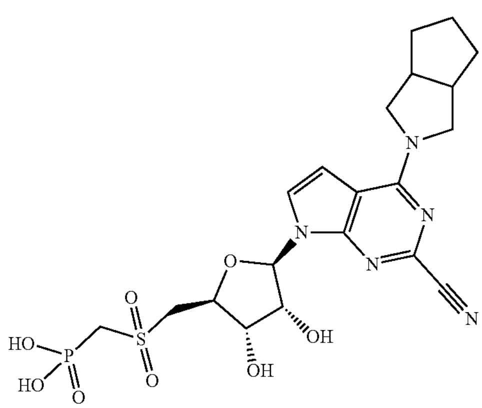 [SMILES: N#Cc1nc(N2CC3CCCC3C2)c2ccn([C@@H]3O[C@H](CS(=O)(=O)CP(=O)(O)O)[C@@H](O)[C@H]3O)c2n1] | [M + H]⁺: 526; [M − H]⁻: 526 | [(2S,3S,4R,5R)-5-[4-(3,3a,4,5,6,6a-hexahydro-1H-cyclopenta[c]pyrrol-2-yl)-2-cyano-pyrrolo[2,3-d]pyrimidin-7-yl]-3,4-dihydroxy-tetrahydrofuran-2-yl]methylsulfonylmethylphosphonic acid |
| 159 | 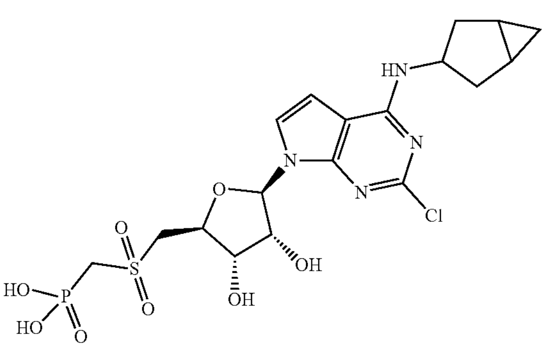 [SMILES: O=P(O)(O)CS(=O)(=O)C[C@H]1O[C@@H](n2ccc3c(NC4CC5CC5C4)nc(Cl)nc32)[C@H](O)[C@@H]1O] | [M + H]⁺: 523; [M − H]⁻: 521 | [(2S,3S,4R,5R)-5-[4-(3-bicyclo[3.1.0]hexanylamino)-2-chloro-pyrrolo[2,3-d]pyrimidin-7-yl]-3,4-dihydroxy-tetrahydrofuran-2-yl]methylsulfonylmethylphosphonic acid |

TABLE 1-continued

| No. | Structure | m/z | IUPAC Name |
|---|---|---|---|
| 160 | 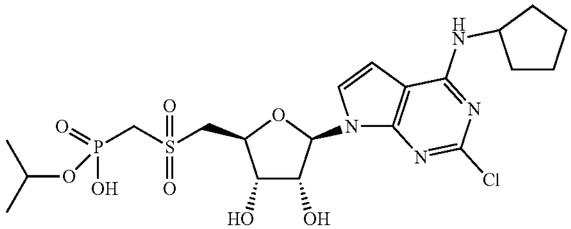 [SMILES: CC(C)OP(=O)(O)CS(=O)(=O)C[C@H]1O[C@@H](n2ccc3c(NC4CCCC4)nc(Cl)nc32)[C@H](O)[C@@H]1O] | [M + H]⁺: 553; [M − H]⁻: 551 | [(2S,3S,4R,5R)-5-[2-chloro-4-(cyclopentylamino)pyrrolo[2,3-d]pyrimidin-7-yl]-3,4-dihydroxy-tetrahydrofuran-2-yl]methylsulfonyl-methyl-isopropoxy-phosphinic acid |
| 161 | 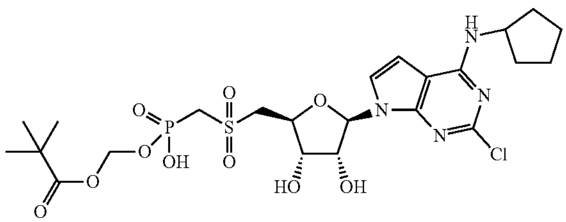 [SMILES: CC(C)(C)C(=O)OCOP(=O)(O)CS(=O)(=O)C[C@H]1O[C@@H](n2ccc3c(NC4CCCC4)nc(Cl)nc32)[C@H](O)[C@@H]1O] | [M + H]⁺: 625; [M − H]⁻: 623 | [(2S,3S,4R,5R)-5-[2-chloro-4-(cyclopentyl-amino)pyrrolo[2,3-d]-pyrimidin-7-yl]-3,4-dihydroxy-tetrahydro-furan-2-yl]methyl-sulfonylmethyl-(2,2-dimethylpropanoyl-oxymethoxy)phosphinic acid |
| 162 | 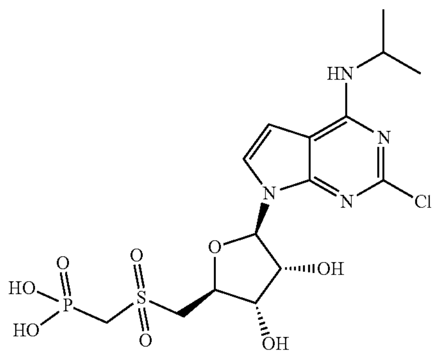 [SMILES: CC(C)Nc1nc(Cl)nc2c1ccn2[C@@H]1O[C@H](CS(=O)(=O)CP(=O)(O)O)[C@@H](O)[C@H]1O] | [M − H]⁻: 483 | [(2S,3S,4R,5R)-5-[2-chloro-4-(isopropyl-amino)pyrrolo[2,3-d]-pyrimidin-7-yl]-3,4-dihydroxy-tetrahydro-furan-2-yl]methyl-sulfonylmethylphos-phonic acid |
| 163 | 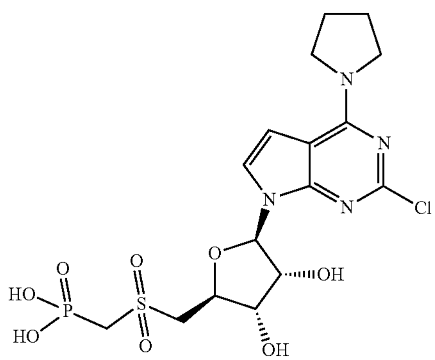 [SMILES: O=P(O)(O)CS(=O)(=O)C[C@H]1O[C@@H](n2ccc3c(N4CCCC4)nc(Cl)nc32)[C@H](O)[C@@H]1O] | [M + H]⁺: 497; [M − H]⁻: 495 | [(2S,3S,4R,5R)-5-(2-chloro-4-pyrrolidin-1-yl-pyrrolo[2,3-d]-pyrimidin-7-yl)-3,4-dihydroxy-tetrahydro-furan-2-yl]methyl-sulfonylmethylphos-phonic acid |
| 164 | 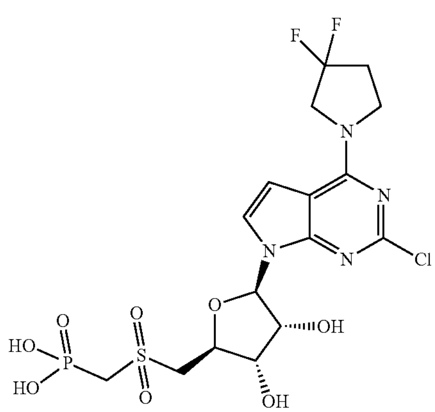 [SMILES: O=P(O)(O)CS(=O)(=O)C[C@H]1O[C@@H](n2ccc3c(N4CCC(F)(F)C4)nc(Cl)nc32)[C@H](O)[C@@H]1O] | [M − H]⁻: 531 | [(2S,3S,4R,5R)-5-[2-chloro-4-(3,3-difluoro-pyrrolidin-1-yl)-pyrrolo[2,3-d]-pyrimidin-7-yl]-3,4-dihydroxy-tetrahydro-furan-2-yl]methyl-sulfonylmethylphos-phonic acid |

TABLE 1-continued

| No. | Structure | m/z | IUPAC Name |
|---|---|---|---|
| 165 | 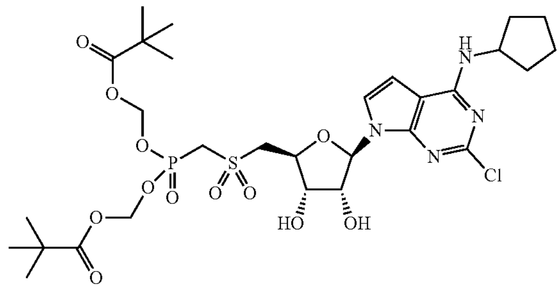 [SMILES: CC(C)(C)C(=O)OCOP(=O)(CS(=O)(=O)C[C@H]1O[C@@H](n2ccc3c(NC4CCCC4)nc(Cl)nc32)[C@H](O)[C@@H]1O)OCOC(=O)C(C)(C)C] | [M + H]⁺: 739 | [[(2S,3S,4R,5R)-5-[2-chloro-4-(cyclopentyl-amino)pyrrolo[2,3-d]-pyrimidin-7-yl]-3,4-dihydroxy-tetrahydro-furan-2-yl]methyl-sulfonylmethyl-(2,2-dimethylpropanoyl-oxymethoxy)phos-phoryl]oxymethyl 2,2-dimethylpropanoate |
| 166 | 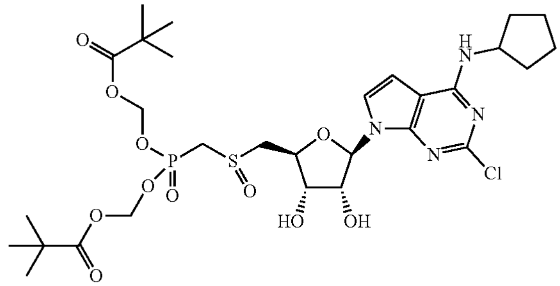 [SMILES: CC(C)(C)C(=O)OCOP(=O)(CS(=O)C[C@H]1O[C@@H](n2ccc3c(NC4CCCC4)nc(Cl)nc32)[C@H](O)[C@@H]1O)OCOC(=O)C(C)(C)C] | [M + H]⁺: 723 | [[(2S,3S,4R,5R)-5-[2-chloro-4-(cyclopentyl-amino)pyrrolo[2,3-d]-pyrimidin-7-yl]-3,4-dihydroxy-tetrahydro-furan-2-yl]methyl-sulfinylmethyl-(2,2-dimethylpropanoyloxy-methoxy)phosphoryl]-oxymethyl 2,2-dimethylpropanoate |
| 167 | 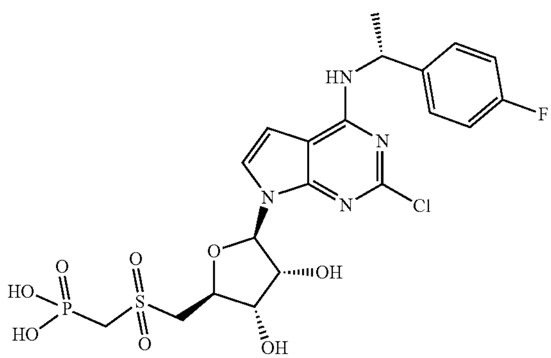 [SMILES: C[C@@H](Nc1nc(Cl)nc2c1ccn2[C@@H]1O[C@H](CS(=O)(=O)CP(=O)(O)O)[C@@H](O)[C@H]1O)c1ccc(F)cc1] | [M + H]⁺: 565; [M − H]⁻: 563 | [(2S,3S,4R,5R)-5-[2-chloro-4-[[(1R)-1-(4-fluorophenyl)ethyl]-amino]pyrrolo[2,3-d]-pyrimidin-7-yl]-3,4-dihydroxy-tetrahydro-furan-2-yl]methyl-sulfonylmethylphos-phonic acid |
| 168 | 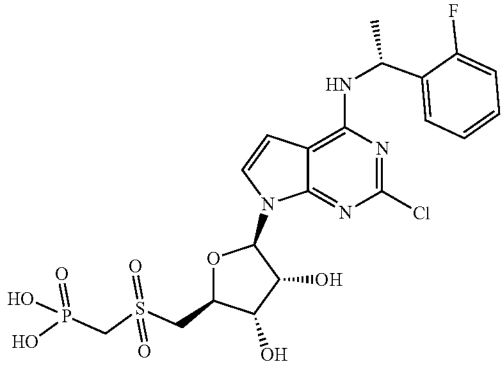 [SMILES: C[C@@H](Nc1nc(Cl)nc2c1ccn2[C@@H]1O[C@H](CS(=O)(=O)CP(=O)(O)O)[C@@H](O)[C@H]1O)c1ccccc1F] | [M − H]⁻: 563 | [(2S,3S,4R,5R)-5-[2-chloro-4-[[(1R)-1-(2-fluorophenyl)ethyl]-amino]pyrrolo[2,3-d]-pyrimidin-7-yl]-3,4-dihydroxy-tetrahydro-furan-2-yl]methyl-sulfonylmethylphos-phonic acid |

TABLE 1-continued

| No. | Structure | m/z | IUPAC Name |
|---|---|---|---|
| 169 | 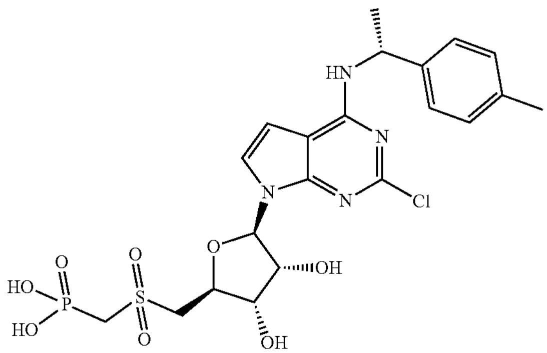 [SMILES: Cc1ccc([C@@H](C)Nc2nc(Cl)nc3c2ccn3[C@@H]2O[C@H](CS(=O)(=O)CP(=O)(O)O)[C@@H](O)[C@H]2O)cc1] | [M − H]⁻: 559 | [(2S,3S,4R,5R)-5-[2-chloro-4-[[(1R)-1-(p-tolyl)ethyl]amino]-pyrrolo[2,3-d]-pyrimidin-7-yl]-3,4-dihydroxy-tetrahydro-furan-2-yl]methyl-sulfonylmethylphosphonic acid |
| 170 | 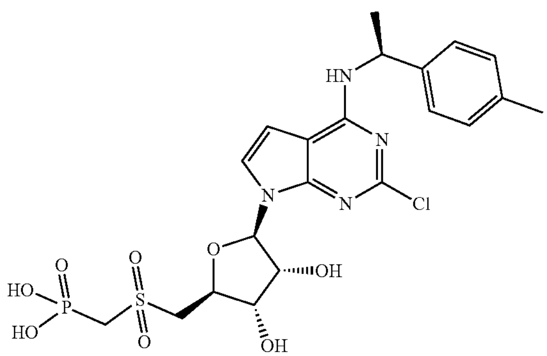 [SMILES: Cc1ccc([C@H](C)Nc2nc(Cl)nc3c2ccn3[C@@H]2O[C@H](CS(=O)(=O)CP(=O)(O)O)[C@@H](O)[C@H]2O)cc1] | [M + H]⁺: 561; [M − H]⁻: 559 | [(2S,3S,4R,5R)-5-[2-chloro-4-[[(1S)-1-(p-tolyl)ethyl]amino]-pyrrolo[2,3-d]-pyrimidin-7-yl]-3,4-dihydroxy-tetrahydro-furan-2-yl]methyl-sulfonylmethylphosphonic acid |
| 171 | 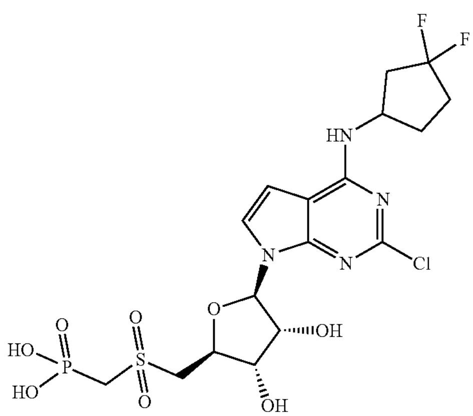 [SMILES: O=P(O)(O)CS(=O)(=O)C[C@H]1O[C@@H](n2ccc3c(NC4CCC(F)(F)C4)nc(Cl)nc32)[C@H](O)[C@@H]1O] | [M − H]⁻: 545 | [(2S,3S,4R,5R)-5-[2-chloro-4-[(3,3-difluoro-cyclopentyl)amino]-pyrrolo[2,3-d]-pyrimidin-7-yl]-3,4-dihydroxy-tetrahydro-furan-2-yl]methyl-sulfonylmethylphosphonic acid |
| 172 | 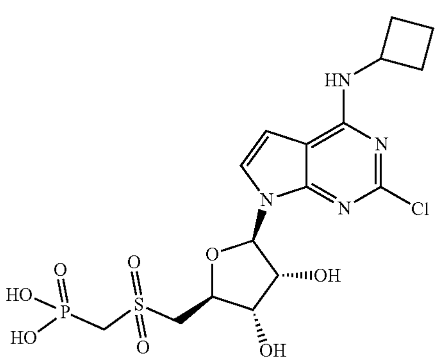 [SMILES: O=P(O)(O)CS(=O)(=O)C[C@H]1O[C@@H](n2ccc3c(NC4CCC4)nc(Cl)nc32)[C@H](O)[C@@H]1O] | [M − H]⁻: 495 | [(2S,3S,4R,5R)-5-[2-chloro-4-(cyclobutyl-amino)pyrrolo[2,3-d]-pyrimidin-7-yl]-3,4-dihydroxy-tetrahydro-furan-2-yl]methyl-sulfonylmethylphosphonic acid |

TABLE 1-continued

| No. | Structure | m/z | IUPAC Name |
|---|---|---|---|
| 173 | 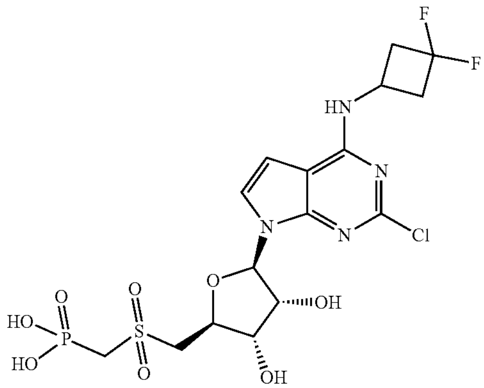 [SMILES: O=P(O)(O)CS(=O)(=O)C[C@H]1O[C@@H](n2ccc3c(NC4CC(F)(F)C4)nc(Cl)nc32)[C@H](O)[C@@H]1O] | [M − H]⁻: 531 | [(2S,3S,4R,5R)-5-[2-chloro-4-[(3,3-difluoro-cyclobutyl)amino]-pyrrolo[2,3-d]-pyrimidin-7-yl]-3,4-dihydroxy-tetrahydro-furan-2-yl]methyl-sulfonylmethylphos-phonic acid |
| 174 | 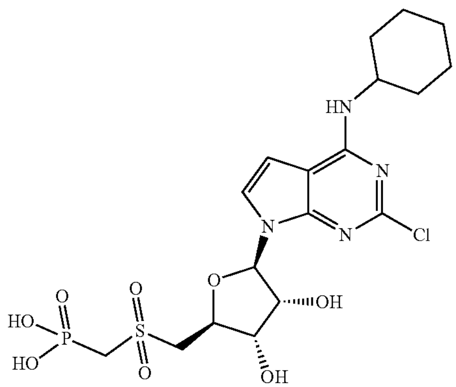 [SMILES: O=P(O)(O)CS(=O)(=O)C[C@H]1O[C@@H](n2ccc3c(NC4CCCCC4)nc(Cl)nc32)[C@H](O)[C@@H]1O] | [M + H]⁺: 525; [M − H]⁻: 523 | [(2S,3S,4R,5R)-5-[2-chloro-4-(cyclohexyl-amino)pyrrolo[2,3-d]-pyrimidin-7-yl]-3,4-dihydroxy-tetrahydro-furan-2-yl]methyl-sulfonylmethylphos-phonic acid |
| 175 | 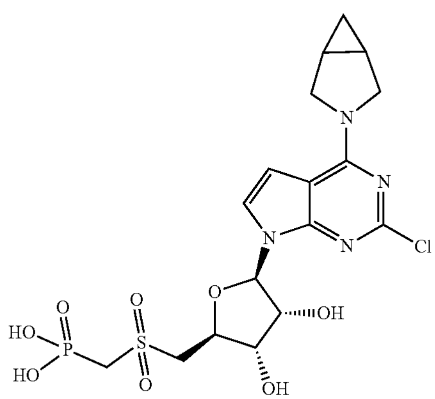 [SMILES: O=P(O)(O)CS(=O)(=O)C[C@H]1O[C@@H](n2ccc3c(N4CC5CC5C4)nc(Cl)nc32)[C@H](O)[C@@H]1O] | [M − H]⁻: 507 | [(2S,3S,4R,5R)-5-[4-(3-azabicyclo[3.1.0]-hexan-3-yl)-2-chloro-pyrrolo[2,3-d]-pyrimidin-7-yl]-3,4-dihydroxy-tetrahydro-furan-2-yl]methyl-sulfonylmethylphos-phonic acid |
| 176 | 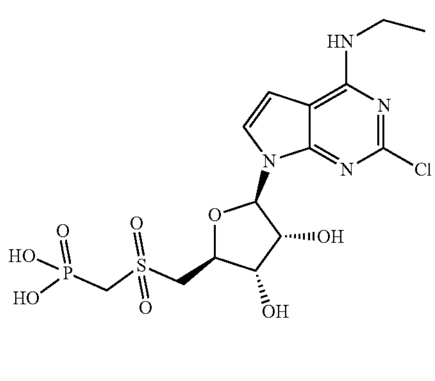 [SMILES: CCNc1nc(Cl)nc2c1ccn2[C@@H]1O[C@H](CS(=O)(=O)CP(=O)(O)O)[C@@H](O)[C@H]1O] | [M − H]⁻: 469 | [(2S,3S,4R,5R)-5-[2-chloro-4-(ethylamino)-pyrrolo[2,3-d]-pyrimidin-7-yl]-3,4-dihydroxy-tetrahydro-furan-2-yl]methyl-sulfonylmethylphos-phonic acid |

TABLE 1-continued

| No. | Structure | m/z | IUPAC Name |
|---|---|---|---|
| 177 | 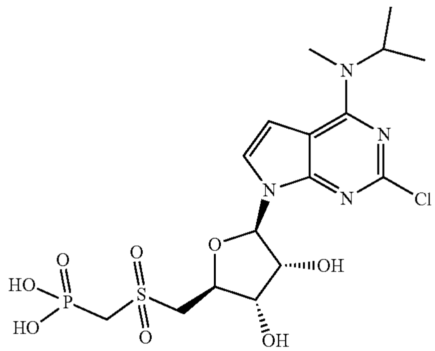 [SMILES: CC(C)N(C)c1nc(Cl)nc2c1ccn2[C@@H]1O[C@H](CS(=O)(=O)CP(=O)(O)O)[C@@H](O)[C@H]1O] | [M + H]⁺: 499; [M – H]⁻: 497 | [(2S,3S,4R,5R)-5-[2-chloro-4-[isopropyl-(methyl)amino]-pyrrolo[2,3-d]-pyrimidin-7-yl]-3,4-dihydroxy-tetrahydro-furan-2-yl]methyl-sulfonylmethylphos-phonic acid |
| 178 | 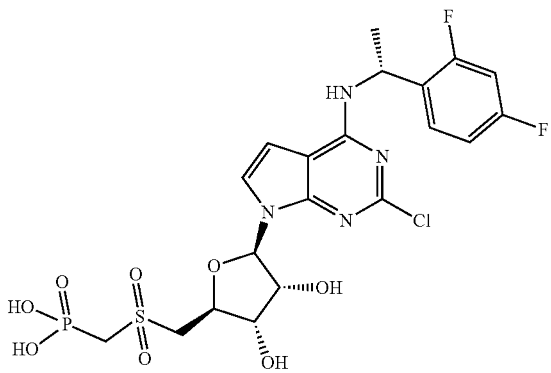 [SMILES: C[C@@H](Nc1nc(Cl)nc2c1ccn2[C@@H]1O[C@H](CS(=O)(=O)CP(=O)(O)O)[C@@H](O)[C@H]1O)c1ccc(F)cc1F] | [M – H]⁻: 581 | [(2S,3S,4R,5R)-5-[2-chloro-4-[[(1R)-1-(2,4-difluorophenyl)ethyl]-amino]pyrrolo[2,3-d]-pyrimidin-7-yl]-3,4-dihydroxy-tetrahydro-furan-2-yl]methyl-sulfonylmethylphos-phonic acid |
| 179 | 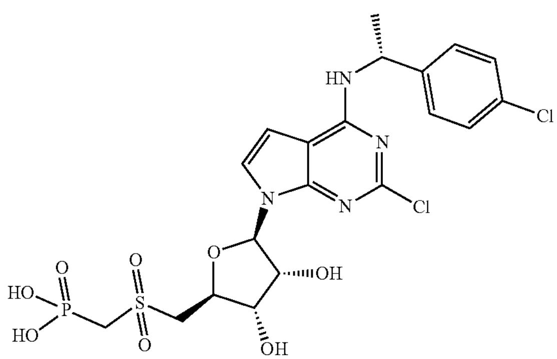 [SMILES: C[C@@H](Nc1nc(Cl)nc2c1ccn2[C@@H]1O[C@H](CS(=O)(=O)CP(=O)(O)O)[C@@H](O)[C@H]1O)c1ccc(Cl)cc1] | [M – H]⁻: 581 | [(2S,3S,4R,5R)-5-[2-chloro-4-[[(1R)-1-(4-chlorophenyl)ethyl]-amino]pyrrolo[2,3-d]-pyrimidin-7-yl]-3,4-dihydroxy-tetrahydro-furan-2-yl]methyl-sulfonylmethylphos-phonic acid |
| 180 | 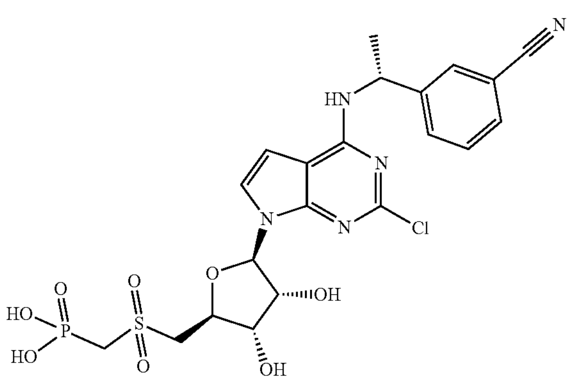 [SMILES: C[C@@H](Nc1nc(Cl)nc2c1ccn2[C@@H]1O[C@H](CS(=O)(=O)CP(=O)(O)O)[C@@H](O)[C@H]1O)c1cccc(C#N)c1] | [M + H]⁺: 572; [M – H]⁻: 570 | [(2S,3S,4R,5R)-5-[2-chloro-4-[[(1R)-1-(3-cyanophenyl)ethyl]-amino]pyrrolo[2,3-d]-pyrimidin-7-yl]-3,4-dihydroxy-tetrahydro-furan-2-yl]methyl-sulfonylmethylphos-phonic acid |

TABLE 1-continued

| No. | Structure | m/z | IUPAC Name |
|---|---|---|---|
| 181 | 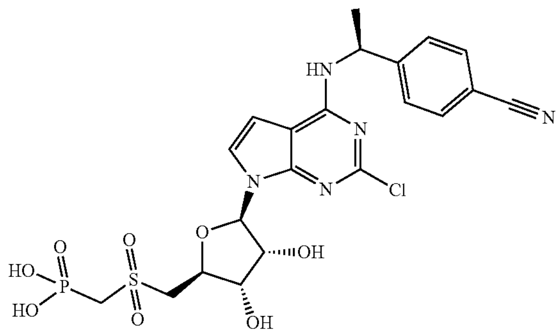 [SMILES: C[C@H](Nc1nc(Cl)nc2c1ccn2[C@@H]1O[C@H](CS(=O)(=O)CP(=O)(O)O)[C@@H](O)[C@H]1O)c1ccc(C#N)cc1] | [M + H]⁺: 572; [M − H]⁻: 570 | [(2S,3S,4R,5R)-5-[2-chloro-4-[[(1S)-1-(4-cyanophenyl)ethyl]-amino]pyrrolo[2,3-d]-pyrimidin-7-yl]-3,4-dihydroxy-tetrahydro-furan-2-yl]methyl-sulfonylmethylphosphonic acid |
| 182 | 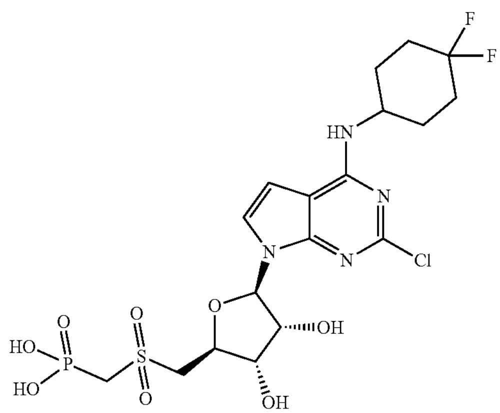 [SMILES: O=P(O)(O)CS(=O)(=O)C[C@H]1O[C@@H](n2ccc3c(NC4CCC(F)(F)CC4)nc(Cl)nc32)[C@H](O)[C@@H]1O] | [M + H]⁺: 561; [M − H]⁻: 559 | [(2S,3S,4R,5R)-5-[2-chloro-4-[(4,4-difluoro-cyclohexyl)amino]-pyrrolo[2,3-d]-pyrimidin-7-yl]-3,4-dihydroxy-tetrahydro-furan-2-yl]methyl-sulfonylmethylphosphonic acid |
| 183 | 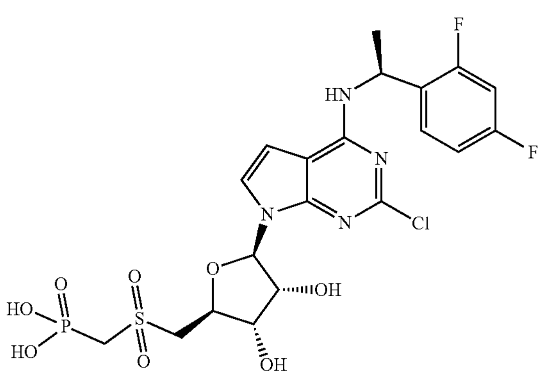 [SMILES: C[C@H](Nc1nc(Cl)nc2c1ccn2[C@@H]1O[C@H](CS(=O)(=O)CP(=O)(O)O)[C@@H](O)[C@H]1O)c1ccc(F)cc1F] | [M + H]⁺: 583; [M − H]⁻: 581 | [(2S,3S,4R,5R)-5-[2-chloro-4-[[(1S)-1-(2,4-difluorophenyl)ethyl]-amino]pyrrolo[2,3-d]-pyrimidin-7-yl]-3,4-dihydroxy-tetrahydro-furan-2-yl]methyl-sulfonylmethylphosphonic acid |
| 184 | 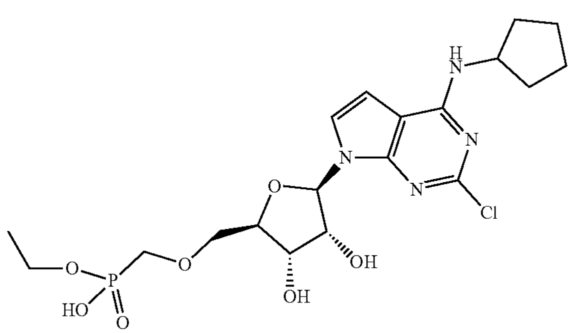 [SMILES: CCOP(=O)(O)COC[C@H]1O[C@@H](n2ccc3c(NC4CCCC4)nc(Cl)nc32)[C@H](O)[C@@H]1O] | [M + H]⁺: 491; [M − H]⁻: 489 | [(2R,3S,4R,5R)-5-[2-chloro-4-(cyclopentyl-amino)pyrrolo[2,3-d]-pyrimidin-7-yl]-3,4-dihydroxy-tetrahydro-furan-2-yl]methoxy-methylethoxy-phosphinic acid |

TABLE 1-continued

| No. | Structure | m/z | IUPAC Name |
|---|---|---|---|
| 185 | 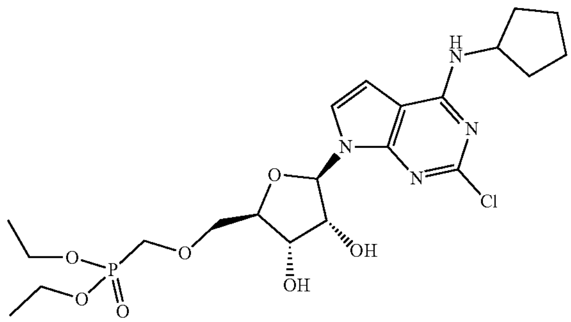 [SMILES: CCOP(=O)(COC[C@H]1O[C@@H](n2ccc3c(NC4CCCC4)nc(Cl)nc32)[C@H](O)[C@@H]1O)OCC] | [M + H]⁺: 519; [M − H]⁻: 517 | (2R,3R,4S,5R)-2-[2-chloro-4-(cyclopentylamino)pyrrolo[2,3-d]pyrimidin-7-yl]-5-(diethoxyphosphorylmethoxymethyl)tetrahydrofuran-3,4-diol |
| 186 | 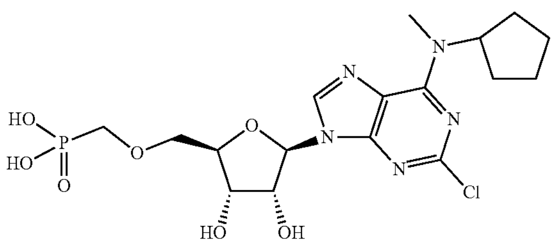 [SMILES: CN(c1nc(Cl)nc2c1ncn2[C@@H]1O[C@H](COCP(=O)(O)O)[C@@H](O)[C@H]1O)C1CCCC1] | [M + H]⁺: 478; [M − H]⁻: 476 | [(2R,3S,4R,5R)-5-[2-chloro-6-[cyclopentyl(methyl)amino]purin-9-yl]-3,4-dihydroxy-tetrahydrofuran-2-yl]-methoxymethylphosphonic acid |
| 187 | 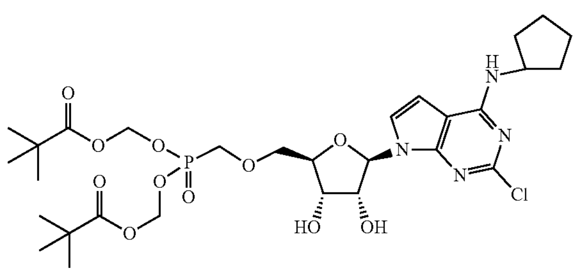 [SMILES: CC(C)(C)C(=O)OCOP(=O)(COC[C@H]1O[C@@H](n2ccc3c(NC4CCCC4)nc(Cl)nc32)[C@H](O)[C@@H]1O)OCOC(=O)C(C)(C)C] | [M + H]⁺: 691; [M − H]⁻: 689 | [[(2R,3S,4R,5R)-5-[2-chloro-4-(cyclopentylamino)pyrrolo[2,3-d]pyrimidin-7-yl]-3,4-dihydroxy-tetrahydrofuran-2-yl]methoxymethyl-(2,2-dimethylpropanoyloxymethoxy)phosphoryl]oxymethyl 2,2-dimethylpropanoate |
| 188 | 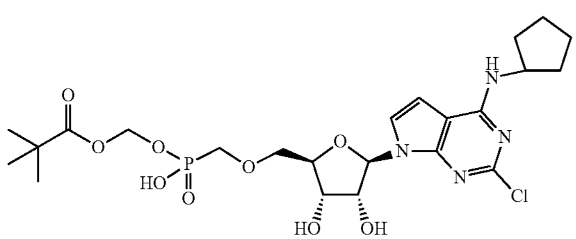 [SMILES: CC(C)(C)C(=O)OCOP(=O)(O)COC[C@H]1O[C@@H](n2ccc3c(NC4CCCC4)nc(Cl)nc32)[C@H](O)[C@@H]1O] | [M + H]⁺: 577; [M − H]⁻: 575 | [(2R,3S,4R,5R)-5-[2-chloro-4-(cyclopentylamino)pyrrolo[2,3-d]pyrimidin-7-yl]-3,4-dihydroxy-tetrahydrofuran-2-yl]methoxymethyl-(2,2-dimethylpropanoyloxymethoxy)phosphinic acid |
| 189 | 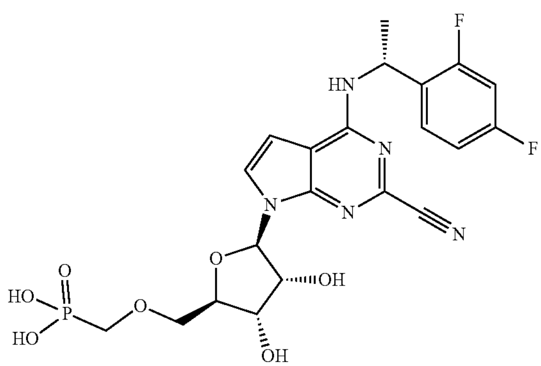 | [M + H]⁺: 535; [M − H]⁻: 533 | [(2R,3S,4R,5R)-5-[2-cyano-4-[[(1R)-1-(2,4-difluorophenyl)ethyl]amino]pyrrolo[2,3-d]pyrimidin-7-yl]-3,4-dihydroxy-tetrahydrofuran-2-yl]methoxymethylphosphonic acid |

TABLE 1-continued

| No. | Structure | m/z | IUPAC Name |
|---|---|---|---|
| 190 | 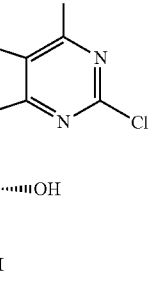 | [M + H]⁺: 449; [M − H]⁻: 447 | [(2R,3S,4R,5R)-5-(2-chloro-4-pyrrolidin-1-yl-pyrrolo[2,3-d]-pyrimidin-7-yl)-3,4-dihydroxy-tetrahydro-furan-2-yl]methoxy-methylphosphonic acid |
| 191 | 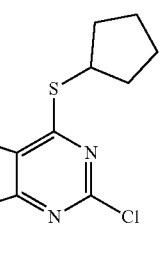 | [M − H]⁻: 486 | [(2R,3S,4R,5R)-5-(2-chloro-4-cyclopentyl-sulfanyl-pyrrolo[2,3-d]-pyrimidin-7-yl)-3,4-dihydroxy-tetrahydro-furan-2-yl]methoxy-methylphosphonic acid |
| 192 | 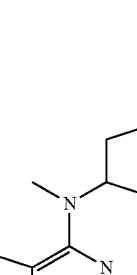 | [M + H]⁺: 477; [M − H]⁻: 475 | [(2R,3S,4R,5R)-5-[2-chloro-4-[cyclopentyl-(methyl)amino]pyrrolo-[2,3-d]pyrimidin-7-yl]-3,4-dihydroxy-tetra-hydrofuran-2-yl]-methoxymethylphos-phonic acid |
| 193 | 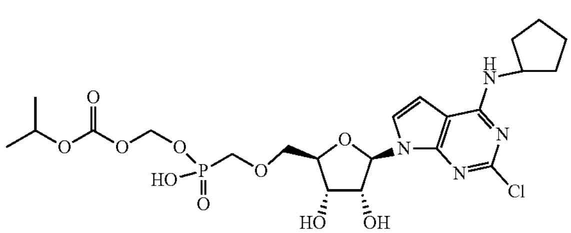 [SMILES: CC(C)OC(=O)OCOP(=O)(O)COC[C@H]1O[C@@H](n2ccc3c(NC4CCCC4)nc(Cl)nc32)[C@H](O)[C@@H]1O] | [M + H]⁺: 579; [M − H]⁻: 577 | [(2R,3S,4R,5R)-5-[2-chloro-4-(cyclopentyl-amino)pyrrolo[2,3-d]-pyrimidin-7-yl]-3,4-dihydroxy-tetrahydro-furan-2-yl]methoxy-methyl-(isopropoxy-carbonyloxymethoxy)-phosphinic acid |
| 194 | 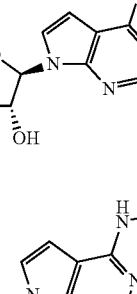 | [M + H]⁺: 563; [M − H]⁻: 561 | [(2R,3S,4R,5R)-5-[2-chloro-4-(cyclopentyl-amino)pyrrolo[2,3-d]-pyrimidin-7-yl]-3,4-dihydroxy-tetrahydro-furan-2-yl]methoxy-methyl-(2-methyl-propanoyloxymeth-oxy)phosphinic acid |

TABLE 1-continued

| No. | Structure | m/z | IUPAC Name |
|---|---|---|---|
| 195 | 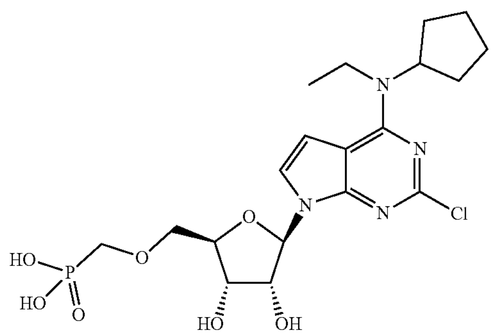 [SMILES: CCN(c1nc(Cl)nc2c1ccn2[C@@H]1O[C@H](COCP(=O)(O)O)[C@@H](O)[C@H]1O)C1CCCC1] | [M − H]⁻: 489 | [(2R,3S,4R,5R)-5-[2-chloro-4-[cyclopentyl-(ethyl)amino]pyrrolo-[2,3-d]pyrimidin-7-yl]-3,4-dihydroxy-tetra-hydrofuran-2-yl]-methoxymethylphos-phonic acid |
| 196 | 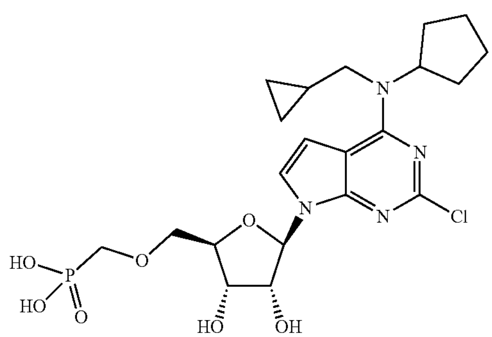 [SMILES: O=P(O)(O)COC[C@H]1O[C@@H](n2ccc3c(N(CC4CC4)C4CCCC4)nc(Cl)nc32)[C@H](O)[C@@H]1O] | [M + H]⁺: 517; [M − H]⁻: 515 | [(2R,3S,4R,5R)-5-[2-chloro-4-[cyclopentyl-(cyclopropylmethyl)-amino]pyrrolo[2,3-d]-pyrimidin-7-yl]-3,4-dihydroxy-tetrahydro-furan-2-yl]methoxy-methylphosphonic acid |
| 197 | 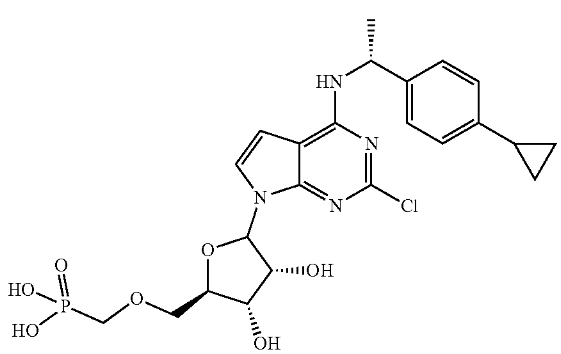 [SMILES: C[C@@H](Nc1nc(Cl)nc2c1ccn2C1O[C@H](COCP(=O)(O)O)[C@@H](O)[C@H]1O)c1ccc(C2CC2)cc1] | [M − H]⁻: 537 | [(2R,3S,4R,5R)-5-[2-chloro-4-[[(1R)-1-(4-cyclopropylphenyl)-ethyl]amino]pyrrolo-[2,3-d]pyrimidin-7-yl]-3,4-dihydroxy-tetra-hydrofuran-2-yl]-methoxymethylphos-phonic acid |
| 198 | 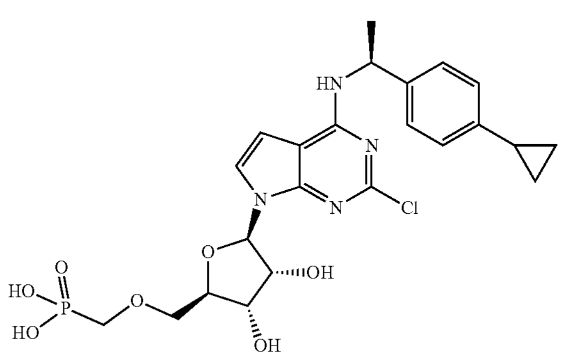 [SMILES: C[C@H](Nc1nc(Cl)nc2c1ccn2[C@@H]1O[C@H](COCP(=O)(O)O)[C@@H](O)[C@H]1O)c1ccc(C2CC2)cc1] | [M − H]⁻: 537 | [(2R,3S,4R,5R)-5-[2-chloro-4-[[(1S)-1-(4-cyclopropylphenyl)-ethyl]amino]pyrrolo-[2,3-d]pyrimidin-7-yl]-3,4-dihydroxy-tetra-hydrofuran-2-yl]-methoxymethylphos-phonic acid |

TABLE 1-continued

| No. | Structure | m/z | IUPAC Name |
|---|---|---|---|
| 199 | 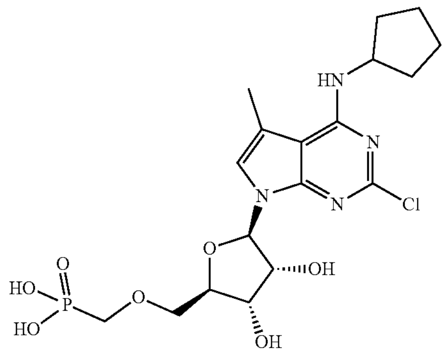 [SMILES: Cc1cn([C@@H]2O[C@H](COCP(=O)(O)O)[C@@H](O)[C@H]2O)c2nc(Cl)nc(NC3CCCC3)c12] | [M − H]⁻: 475 | [(2R,3S,4R,5R)-5-[2-chloro-4-(cyclopentyl-amino)-5-methyl-pyrrolo[2,3-d]-pyrimidin-7-yl]-3,4-dihydroxy-tetrahydro-furan-2-yl]methoxy-methylphosphonic acid |
| 200 | 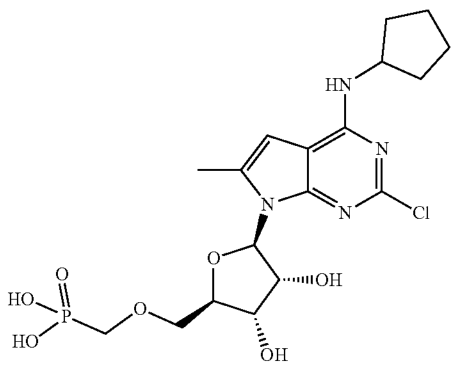 [SMILES: Cc1cc2c(NC3CCCC3)nc(Cl)nc2n1[C@@H]1O[C@H](COCP(=O)(O)O)[C@@H](O)[C@H]1O] | [M − H]⁻: 475 | [(2R,3S,4R,5R)-5-[2-chloro-4-(cyclopentyl-amino)-6-methyl-pyrrolo[2,3-d]-pyrimidin-7-yl]-3,4-dihydroxy-tetrahydro-furan-2-yl]methoxy-methylphosphonic acid |
| 201 | 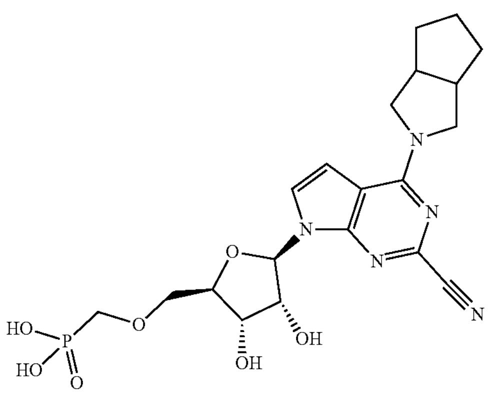 [SMILES: N#Cc1nc(N2CC3CCCC3C2)c2ccn([C@@H]3O[C@H](COCP(=O)(O)O)[C@@H](O)[C@H]3O)c2n1] | [M + H]⁺: 480; [M − H]⁻: 478 | [(2R,3S,4R,5R)-5-[4-(3,3a,4,5,6,6a-hexa-hydro-1H-cyclopenta-[c]pyrrol-2-yl)-2-cyano-pyrrolo[2,3-d]-pyrimidin-7-yl]-3,4-dihydroxy-tetrahydro-furan-2-yl]methoxy-methylphosphonic acid |
| 202 | 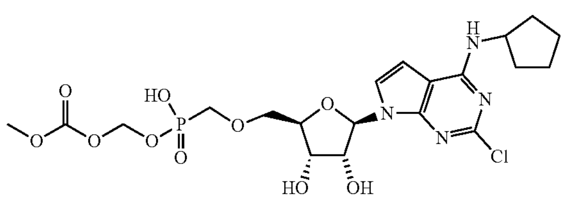 [SMILES: COC(=O)OCOP(=O)(O)COC[C@H]1O[C@@H](n2ccc3c(NC4CCCC4)nc(Cl)nc32)[C@H](O)[C@@H]1O] | [M + H]⁺: 551; [M − H]⁻: 549 | [(2R,3S,4R,5R)-5-[2-chloro-4-(cyclopentyl-amino)pyrrolo[2,3-d]-pyrimidin-7-yl]-3,4-dihydroxy-tetrahydro-furan-2-yl]methoxy-methyl-(methoxy-carbonyloxymethoxy)-phosphinic acid |
| 203 | 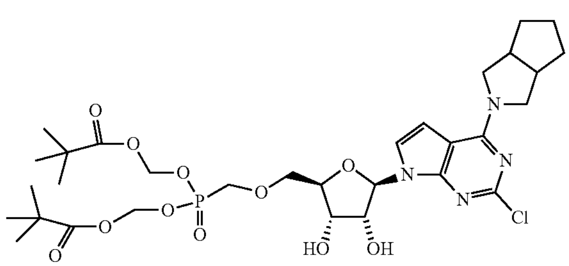 [SMILES: CC(C)(C)C(=O)OCOP(=O)(COC[C@H]1O[C@@H](n2ccc3c(N4CC5CCCC5C4)nc(Cl)nc32)[C@H](O)[C@@H]1O)OCOC(=O)C(C)(C)C] | [M + H]⁺: 717 | [[(2R,3S,4R,5R)-5-[4-(3,3a,4,5,6,6a-hexa-hydro-1H-cyclopenta-[c]pyrrol-2-yl)-2-chloro-pyrrolo[2,3-d]-pyrimidin-7-yl]-3,4-dihydroxy-tetrahydro-furan-2-yl]methoxy-methyl-(2,2-dimethyl-propanoyloxymethoxy)-phosphoryl]oxymethyl 2,2-dimethylpropanoate |

TABLE 1-continued

| No. | Structure | m/z | IUPAC Name |
|---|---|---|---|
| 204 | 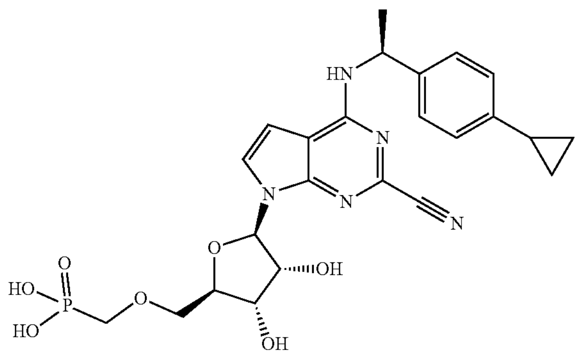 [SMILES: C[C@H](Nc1nc(C#N)nc2c1ccn2[C@@H]1O[C@H](COCP(=O)(O)O)[C@@H](O)[C@H]1O)c1ccc(C2CC2)cc1] | [M − H]⁻: 528 | [(2R,3S,4R,5R)-5-[2-cyano-4-[[(1S)-1-(4-cyclopropylphenyl)-ethyl]amino]pyrrolo-[2,3-d]pyrimidin-7-yl]-3,4-dihydroxy-tetrahydrofuran-2-yl]-methoxymethylphosphonic acid |
| 205 | 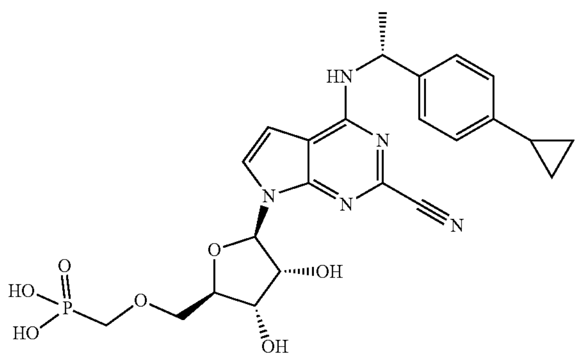 [SMILES: C[C@@H](Nc1nc(C#N)nc2c1ccn2[C@@H]1O[C@H](COCP(=O)(O)O)[C@@H](O)[C@H]1O)c1ccc(C2CC2)cc1] | [M − H]⁻: 528 | [(2R,3S,4R,5R)-5-[2-cyano-4-[[(1R)-1-(4-cyclopropylphenyl)-ethyl]amino]pyrrolo-[2,3-d]pyrimidin-7-yl]-3,4-dihydroxy-tetrahydrofuran-2-yl]-methoxymethylphosphonic acid |
| 206 | 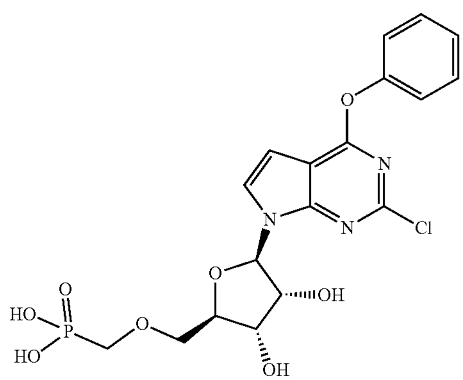 [SMILES: O=P(O)(O)COC[C@H]1O[C@@H](n2ccc3c(Oc4ccccc4)nc(Cl)nc32)[C@H](O)[C@@H]1O] | [M − H]⁻: 470 | [(2R,3S,4R,5R)-5-(2-chloro-4-phenoxy-pyrrolo[2,3-d]-pyrimidin-7-yl)-3,4-dihydroxy-tetrahydrofuran-2-yl]methoxymethylphosphonic acid |
| 207 | 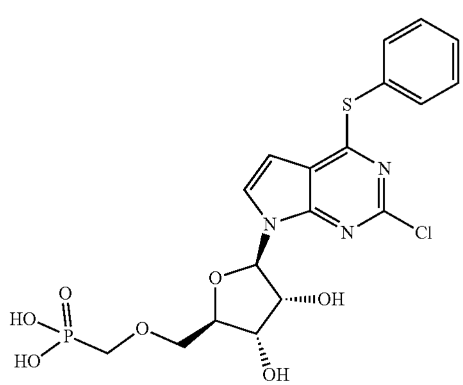 [SMILES: O=P(O)(O)COC[C@H]1O[C@@H](n2ccc3c(Sc4ccccc4)nc(Cl)nc32)[C@H](O)[C@@H]1O] | [M − H]⁻: 486 | [(2R,3S,4R,5R)-5-(2-chloro-4-phenylsulfanyl-pyrrolo[2,3-d]-pyrimidin-7-yl)-3,4-dihydroxy-tetrahydrofuran-2-yl]methoxymethylphosphonic acid |

TABLE 1-continued

| No. | Structure | m/z | IUPAC Name |
|---|---|---|---|
| 208 | 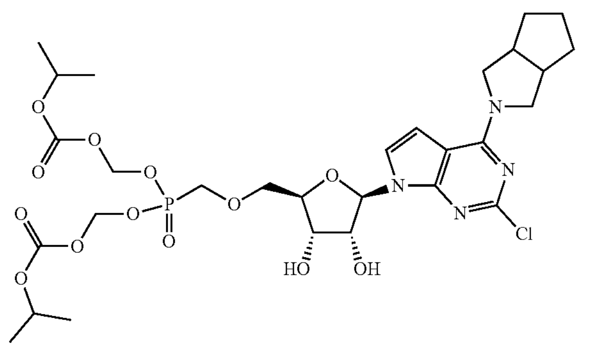 [SMILES: CC(C)OC(=O)OCOP(=O)(COC[C@H]1O[C@@H](n2ccc3c(N4CC5CCCC5C4)nc(Cl)nc32)[C@H](O)[C@@H]1O)OCOC(=O)OC(C)C] | [M + H]⁺: 721 | [[(2R,3S,4R,5R)-5-[4-(3,3a,4,5,6,6a-hexa-hydro-1H-cyclopenta-[c]pyrrol-2-yl)-2-chloro-pyrrolo[2,3-d]-pyrimidin-7-yl]-3,4-dihydroxy-tetrahydro-furan-2-yl]methoxy-methyl-(isopropoxy-carbonyloxymethoxy)-phosphorl]oxymethyl isopropyl carbonate |
| 209 | 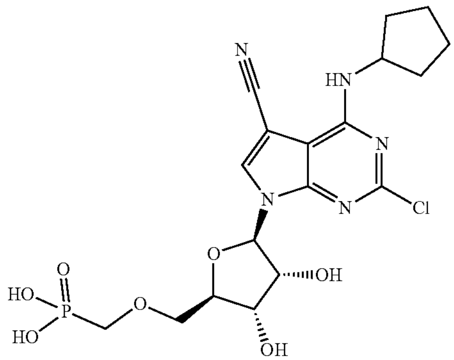 [SMILES: N#Cc1cn([C@@H]2O[C@H](COCP(=O)(O)O)[C@@H](O)[C@H]2O)c2nc(Cl)nc(NC3CCCC3)c12] | [M + H]⁺: 488; [M − H]⁻: 486 | [(2R,3S,4R,5R)-5-[2-chloro-5-cyano-4-(cyclopentylamino)-pyrrolo[2,3-d]-pyrimidin-7-yl]-3,4-dihydroxy-tetrahydro-furan-2-yl]methoxy-methylphosphonic acid |
| 210 | 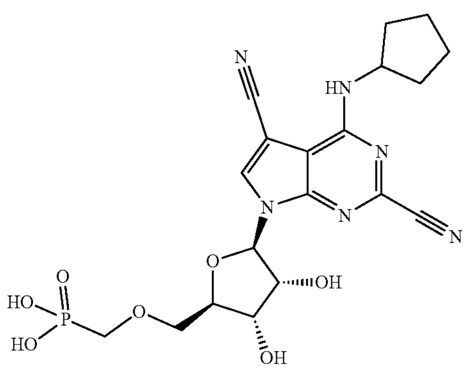 [SMILES: N#Cc1nc(NC2CCCC2)c2c(C#N)cn([C@@H]3O[C@H](COCP(=O)(O)O)[C@@H](O)[C@H]3O)c2n1] | [M − H]⁻: 477 | [(2R,3S,4R,5R)-5-[2,5-dicyano-4-(cyclopentyl-amino)pyrrolo[2,3-d]-pyrimidin-7-yl]-3,4-dihydroxy-tetrahydro-furan-2-yl]methoxy-methylphosphonic acid |
| 211 | 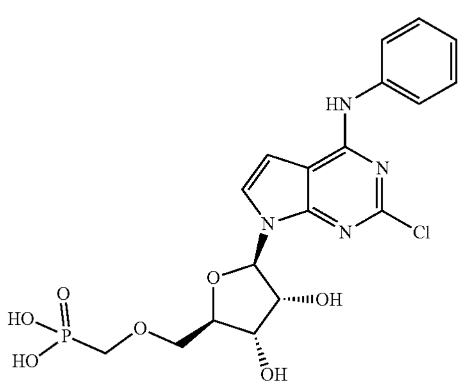 [SMILES: O=P(O)(O)COC[C@H]1O[C@@H](n2ccc3c(Nc4ccccc4)nc(Cl)nc32)[C@H](O)[C@@H]1O] | [M − H]⁻: 469 | [(2R,3S,4R,5R)-5-(4-anilino-2-chloro-pyrrolo[2,3-d]-pyrimidin-7-yl)-3,4-dihydroxy-tetrahydro-furan-2-yl]methoxy-methylphosphonic acid |

TABLE 1-continued

| No. | Structure | m/z | IUPAC Name |
|---|---|---|---|
| 212 | 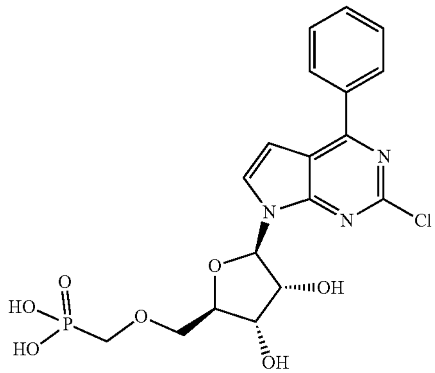 [SMILES: O=P(O)(O)COC[C@H]1O[C@@H](n2ccc3c(-c4ccccc4)nc(Cl)nc32)[C@H](O)[C@@H]1O] | [M − H]⁻: 454 | [(2R,3S,4R,5R)-5-(2-chloro-4-phenyl-pyrrolo[2,3-d]-pyrimidin-7-yl)-3,4-dihydroxy-tetrahydro-furan-2-yl]methoxy-methylphosphonic acid |
| 213 | 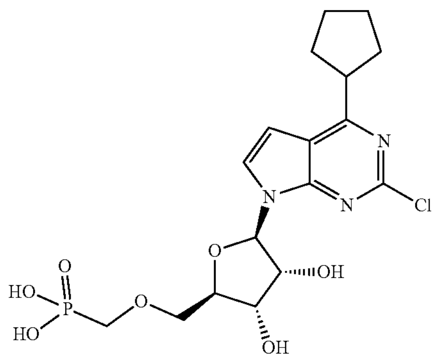 [SMILES: O=P(O)(O)COC[C@H]1O[C@@H](n2ccc3c(C4CCCC4)nc(Cl)nc32)[C@H](O)[C@@H]1O] | [M − H]⁻: 446 | [(2R,3S,4R,5R)-5-(2-chloro-4-cyclopentyl-pyrrolo[2,3-d]-pyrimidin-7-yl)-3,4-dihydroxy-tetrahydro-furan-2-yl]methoxy-methylphosphonic acid |
| 214 | 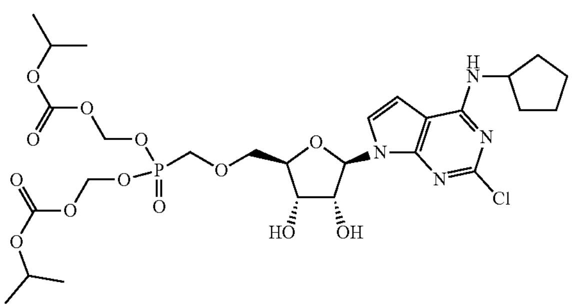 [SMILES: CC(C)OC(=O)OCOP(=O)(COC[C@H]1O[C@@H](n2ccc3c(NC4CCCC4)nc(Cl)nc32)[C@H](O)[C@@H]1O)OCOC(=O)OC(C)C] | [M + H]⁺: 695; [M − H]⁻: 693 | [[(2R,3S,4R,5R)-5-[2-chloro-4-(cyclopentyl-amino)pyrrolo[2,3-d]-pyrimidin-7-yl]-3,4-dihydroxy-tetrahydro-furan-2-yl]methoxy-methyl-(isopropoxy-carbonyloxymethoxy)-phosphoryl]oxymethyl-isopropyl carbonate |
| 215 | 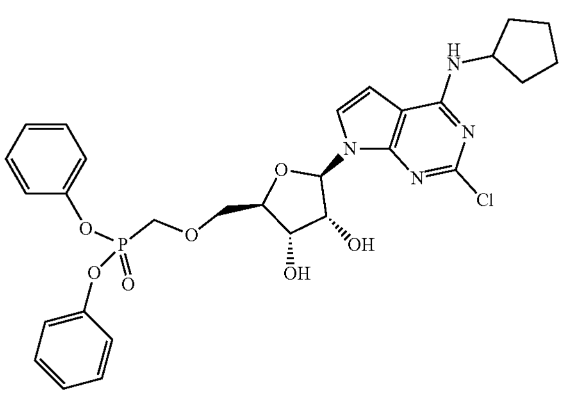 [SMILES: O=P(COC[C@H]1O[C@@H](n2ccc3c(NC4CCCC4)nc(Cl)nc32)[C@H](O)[C@@H]1O)(Oc1ccccc1)Oc1ccccc1] | [M + H]⁺: 615; [M − H]⁻: 613 | (2R,3R,4S,5R)-2-[2-chloro-4-(cyclopentyl-amino)pyrrolo[2,3-d]-pyrimidin-7-yl]-5-(di-phenoxyphosphoryl-methoxymethyl)-tetra-hydrofuran-3,4-diol |

TABLE 1-continued

| No. | Structure | m/z | IUPAC Name |
|---|---|---|---|
| 216 | 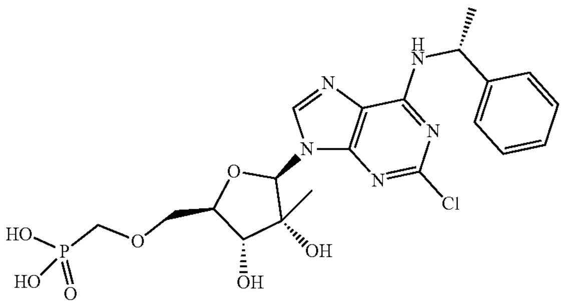 [SMILES: C[C@@H](Nc1nc(Cl)nc2c1ncn2[C@@H]1O[C@H](COCP(=O)(O)O)[C@@H](O)[C@@]1(C)O)c1ccccc1] | [M + H]⁺: 514; [M − H]⁻: 512 | [(2R,3R,4R,5R)-5-[2-chloro-6-[[(1R)-1-phenylethyl]amino]-purin-9-yl]-3,4-dihydroxy-4-methyl-tetrahydrofuran-2-yl]methoxymethyl-phosphonic acid |
| 217 | 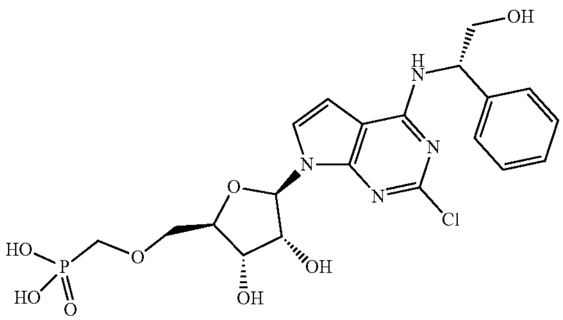 [SMILES: O=P(O)(O)COC[C@H]1O[C@@H](n2ccc3c(N[C@H](CO)c4ccccc4)nc(Cl)nc32)[C@H](O)[C@@H]1O] | [M + H]⁺: 515; [M − H]⁻: 513 | [(2R,3S,4R,5R)-5-[2-chloro-4-[[(1S)-2-hydroxy-1-phenyl-ethyl]amino]pyrrolo-[2,3-d]pyrimidin-7-yl]-3,4-dihydroxy-tetrahydrofuran-2-yl]methoxymethyl-phosphonic acid |
| 218 | 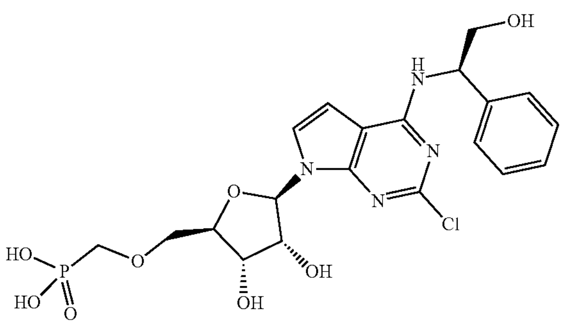 [SMILES: O=P(O)(O)COC[C@H]1O[C@@H](n2ccc3c(N[C@@H](CO)c4ccccc4)nc(Cl)nc32)[C@H](O)[C@@H]1O] | [M + H]⁺: 515; [M − H]⁻: 513 | [(2R,3S,4R,5R)-5-[2-chloro-4-[[(1R)-2-hydroxy-1-phenyl-ethyl]amino]pyrrolo-[2,3-d]pyrimidin-7-yl]-3,4-dihydroxy-tetra-hydrofuran-2-yl]-methoxymethylphos-phonic acid |
| 219 | 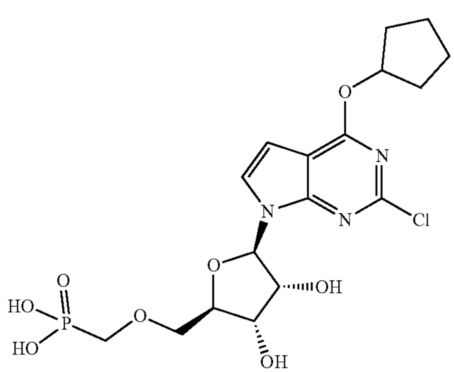 [SMILES: O=P(O)(O)COC[C@H]1O[C@@H](n2ccc3c(OC4CCCC4)nc(Cl)nc32)[C@H](O)[C@@H]1O] | [M + H]⁺: 464; [M − H]⁻: 462 | [(2R,3S,4R,5R)-5-[2-chloro-4-(cyclo-pentoxy)pyrrolo[2,3-d]-pyrimidin-7-yl]-3,4-dihydroxy-tetrahydro-furan-2-yl]methoxy-methylphosphonic acid |
| 220 | 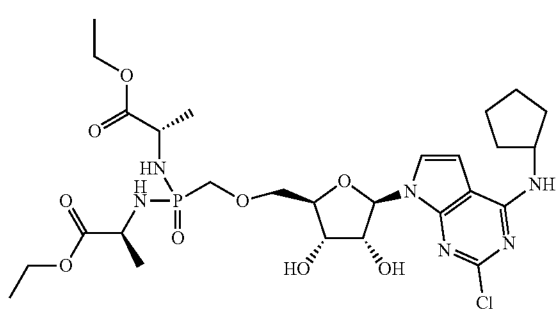 [SMILES: CCOC(=O)[C@H](C)NP(=O)(COC[C@H]1O[C@@H](n2ccc3c(NC4CCCC4)nc(Cl)nc32)[C@H](O)[C@@H]1O)N[C@@H](C)C(=O)OCC] | [M + H]⁺: 661 | ethyl (2S)-2-[[[[(2R,3S,4R,5R)-5-[2-chloro-4-(cyclo-pentylamino)pyrrolo-[2,3-d]pyrimidin-7-yl]-3,4-dihydroxy-tetra-hydrofuran-2-yl]-methoxymethyl-[[(1S)-2-ethoxy-1-methyl-2-oxo-ethyl]amino]-phosphoryl]amino]-propanoate |

TABLE 1-continued

| No. | Structure | m/z | IUPAC Name |
|---|---|---|---|
| 221 | 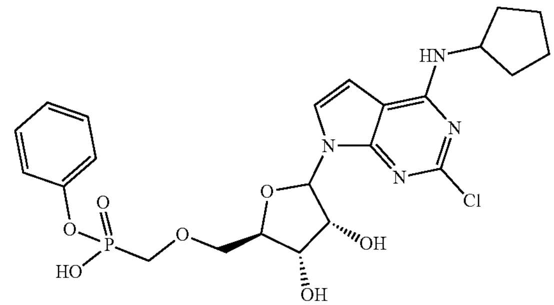 [SMILES: O=P(O)(COC[C@H]1OC(n2ccc3c(NC4CCCC4)nc(Cl)nc32)[C@H](O)[C@@H]1O)Oc1ccccc1] | [M + H]⁺: 539; [M − H]⁻: 537 | [(2R,3S,4R)-5-[2-chloro-4-(cyclopentyl-amino)pyrrolo[2,3-d]-pyrimidin-7-yl]-3,4-dihydroxy-tetrahydro-furan-2-yl]methoxy-methyl-phenoxy-phosphinic acid |
| 222 | 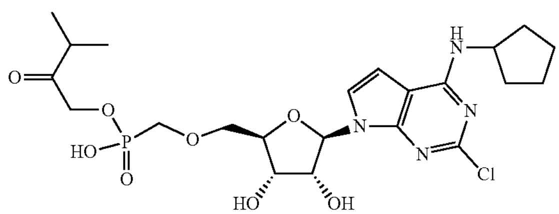 [SMILES: CC(C)C(=O)COP(=O)(O)COC[C@H]1O[C@@H](n2ccc3c(NC4CCCC4)nc(Cl)nc32)[C@H](O)[C@@H]1O] | [M + H]⁺: 547; [M − H]⁻: 545 | [(2R,3S,4R,5R)-5-[2-chloro-4-(cyclopentyl-amino)pyrrolo[2,3-d]-pyrimidin-7-yl]-3,4-dihydroxy-tetrahydro-furan-2-yl]methoxy-methyl-(3-methyl-2-oxo-butoxy)phosphinic acid |
| 223 | 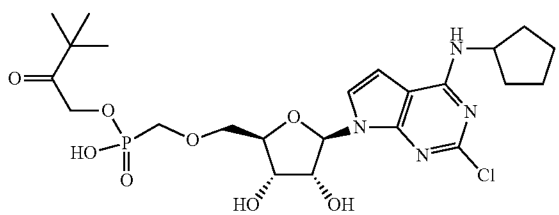 [SMILES: CC(C)(C)C(=O)COP(=O)(O)COC[C@H]1O[C@@H](n2ccc3c(NC4CCCC4)nc(Cl)nc32)[C@H](O)[C@@H]1O] | [M + H]⁺: 561; [M − H]⁻: 559 | [(2R,3S,4R,5R)-5-[2-chloro-4-(cyclopentyl-amino)pyrrolo[2,3-d]-pyrimidin-7-yl]-3,4-dihydroxy-tetrahydro-furan-2-yl]methoxy-methyl-(3,3-dimethyl-2-oxo-butoxy)phosphinic acid |
| 224 | 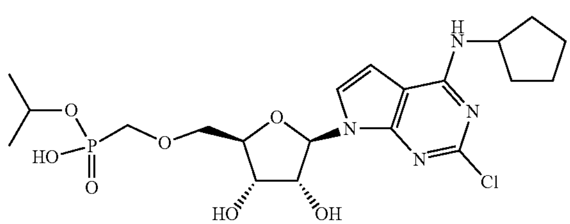 [SMILES: CC(C)OP(=O)(O)COC[C@H]1O[C@@H](n2ccc3c(NC4CCCC4)nc(Cl)nc32)[C@H](O)[C@@H]1O] | [M + H]⁺: 505; [M − H]⁻: 503 | [(2R,3S,4R,5R)-5-[2-chloro-4-(cyclopentyl-amino)pyrrolo[2,3-d]-pyrimidin-7-yl]-3,4-dihydroxy-tetrahydro-furan-2-yl]methoxy-methyl-isopropoxy-phosphinic acid |
| 225 | 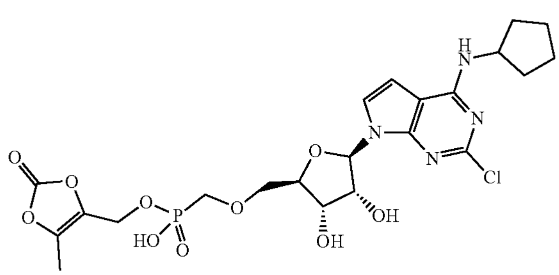 [SMILES: Cc1oc(=O)oc1COP(=O)(O)COC[C@H]1O[C@@H](n2ccc3c(NC4CCCC4)nc(Cl)nc32)[C@H](O)[C@@H]1O] | [M + H]⁺: 575; [M − H]⁻: 573 | [(2R,3S,4R,5R)-5-[2-chloro-4-(cyclopentyl-amino)pyrrolo[2,3-d]-pyrimidin-7-yl]-3,4-dihydroxy-tetrahydro-furan-2-yl]methoxy-methyl-[(5-methyl-2-oxo-1,3-dioxol-4-yl)-methoxy]phosphinic acid |
| 226 | 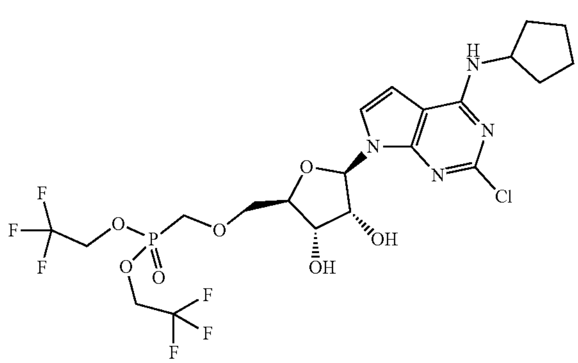 [SMILES: O=P(COC[C@H]1O[C@@H](n2ccc3c(NC4CCCC4)nc(Cl)nc32)[C@H](O)[C@@H]1O)(OCC(F)(F)F)OCC(F)(F)F] | [M + H]⁺: 627; [M − H]⁻: 625 | (2R,3S,4R,5R)-2-[bis(2,2,2-trifluoro-ethoxy)phosphoryl-methoxymethyl]-5-[2-chloro-4-(cyclopentyl-amino)pyrrolo[2,3-d]-pyrimidin-7-yl]tetra-hydrofuran-3,4-diol |

TABLE 1-continued

| No. | Structure | m/z | IUPAC Name |
|---|---|---|---|
| 227 | 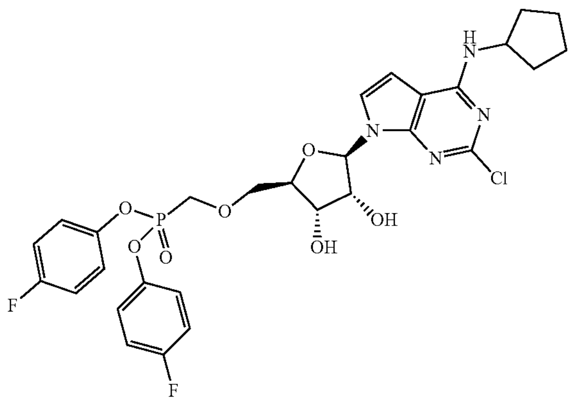 [SMILES: O=P(COC[C@H]1O[C@@H](n2ccc3c(NC4CCCC4)nc(Cl)nc32)[C@H](O)[C@@H]1O)(Oc1ccc(F)cc1)Oc1ccc(F)cc1] | [M + H]⁺: 651; [M − H]⁻: 649 | (2R,3S,4R,5R)-2-[bis (4-fluorophenoxy)-phosphorylmethoxy-methyl]-5-[2-chloro-4-(cyclopentylamino)-pyrrolo[2,3-d]-pyrimidin-7-yl]tetra-hydrofuran-3,4-diol |
| 228 | 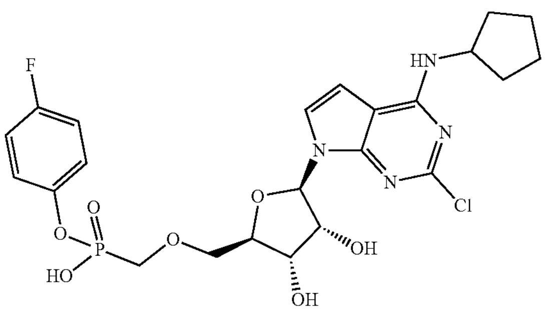 [SMILES: O=P(O)(COC[C@H]1O[C@@H](n2ccc3c(NC4CCCC4)nc(Cl)nc32)[C@H](O)[C@@H]1O)Oc1ccc(F)cc1] | [M + H]⁺: 557; [M − H]⁻: 555 | [(2R,3S,4R,5R)-5-[2-chloro-4-(cyclopentyl-amino)pyrrolo[2,3-d]-pyrimidin-7-yl]-3,4-dihydroxy-tetrahydro-furan-2-yl]methoxy-methyl-(4-fluoro-phenoxy)phosphinic acid |
| 229 | 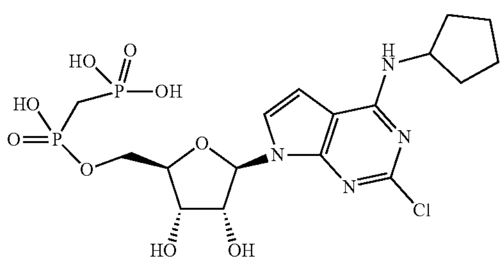 [SMILES: O=P(O)(O)CP(=O)(O)OC[C@H]1O[C@@H](n2ccc3c(NC4CCCC4)nc(Cl)nc32)[C@H](O)[C@@H]1O] | [M + H]⁺: 527; [M − H]⁻: 525 | [[(2R,3S,4R,5R)-5-[2-chloro-4-(cyclopentyl-amino)pyrrolo[2,3-d]-pyrimidin-7-yl]-3,4-dihydroxy-tetrahydro-furan-2-yl]methoxy-hydroxy-phosphoryl]-methylphosphonic acid |
| 230 | 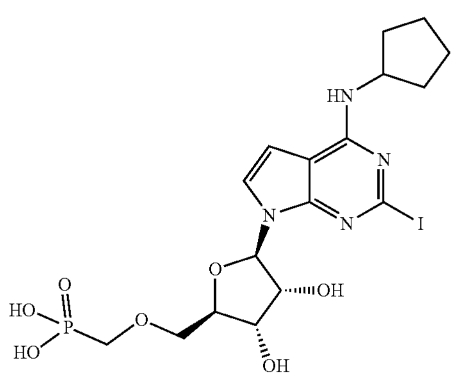 [SMILES: O=P(O)(O)COC[C@H]1O[C@@H](n2ccc3c(NC4CCCC4)nc(I)nc32)[C@H](O)[C@@H]1O] | [M − H]⁻: 553 | [(2R,3S,4R,5R)-5-[4-(cyclopentylamino)-2-iodo-pyrrolo[2,3-d]-pyrimidin-7-yl]-3,4-dihydroxy-tetrahydro-furan-2-yl]methoxy-methylphosphonic acid |

TABLE 1-continued

| No. | Structure | m/z | IUPAC Name |
|---|---|---|---|
| 231 | 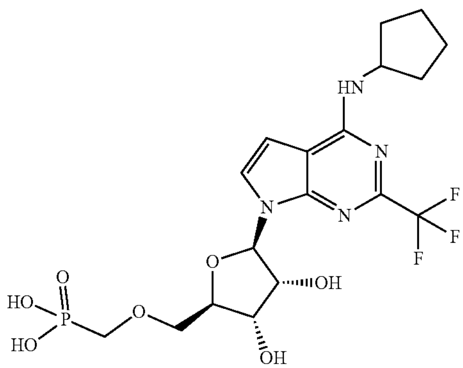 [SMILES: O=P(O)(O)COC[C@H]1O[C@@H](n2ccc3c(NC4CCCC4)nc(C(F)(F)F)nc32)[C@H](O)[C@@H]1O] | [M + H]⁺: 497; [M − H]⁻: 495 | [(2R,3S,4R,5R)-5-[4-(cyclopentylamino)-2-(trifluoromethyl)-pyrrolo[2,3-d]-pyrimidin-7-yl]-3,4-dihydroxy-tetrahydro-furan-2-yl]methoxy-methylphosphonic acid |
| 232 | 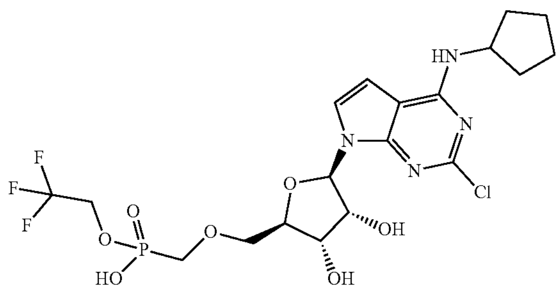 [SMILES: O=P(O)(COC[C@H]1O[C@@H](n2ccc3c(NC4CCCC4)nc(Cl)nc32)[C@H](O)[C@@H]1O)OCC(F)(F)F] | [M + H]⁺: 545; [M − H]⁻: 543 | [(2R,3S,4R,5R)-5-[2-chloro-4-(cyclopentyl-amino)pyrrolo[2,3-d]-pyrimidin-7-yl]-3,4-dihydroxy-tetrahydro-furan-2-yl]methoxy-methyl-(2,2,2-trifluoro-ethoxy)phosphinic acid |
| 233 | 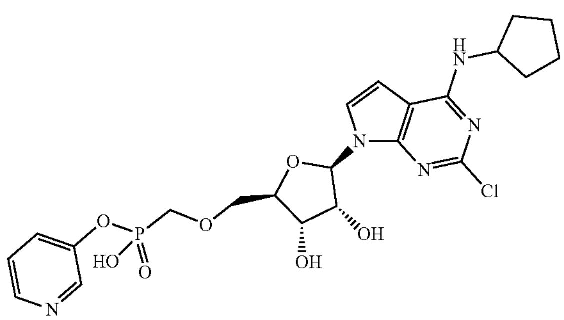 [SMILES: O=P(O)(COC[C@H]1O[C@@H](n2ccc3c(NC4CCCC4)nc(Cl)nc32)[C@H](O)[C@@H]1O)Oc1cccnc1] | [M + H]⁺: 540; [M − H]⁻: 538 | [(2R,3S,4R,5R)-5-[2-chloro-4-(cyclopentyl-amino)pyrrolo[2,3-d]-pyrimidin-7-yl]-3,4-dihydroxy-tetrahydro-furan-2-yl]methoxy-methyl-(3-pyridyloxy)-phosphinic acid |
| 234 | 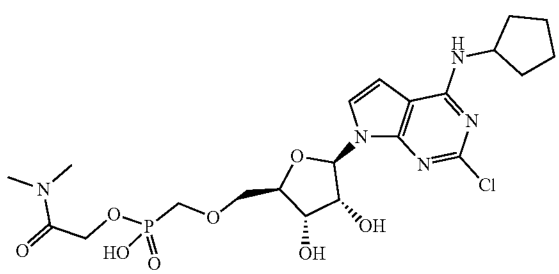 [SMILES: CN(C)C(=O)COP(=O)(O)COC[C@H]1O[C@@H](n2ccc3c(NC4CCCC4)nc(Cl)nc32)[C@H](O)[C@@H]1O] | [M + H]⁺: 548; [M − H]⁻: 546 | [(2R,3S,4R,5R)-5-[2-chloro-4-(cyclopentyl-amino)pyrrolo[2,3-d]-pyrimidin-7-yl]-3,4-dihydroxy-tetrahydro-furan-2-yl]methoxy-methyl-[2-(dimethyl-amino)-2-oxo-ethoxy]-phosphinic acid |
| 235 | 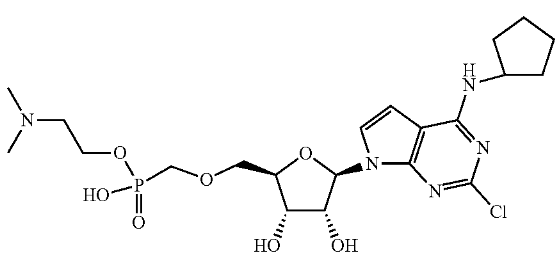 [SMILES: CN(C)CCOP(=O)(O)COC[C@H]1O[C@@H](n2ccc3c(NC4CCCC4)nc(Cl)nc32)[C@H](O)[C@@H]1O] | [M + H]⁺: 534; [M − H]⁻: 532 | [(2R,3S,4R,5R)-5-[2-chloro-4-(cyclopentyl-amino)pyrrolo[2,3-d]-pyrimidin-7-yl]-3,4-dihydroxy-tetrahydro-furan-2-yl]methoxy-methyl-[2-(dimethyl-amino)ethoxy]phos-phinic acid |

TABLE 1-continued

| No. | Structure | m/z | IUPAC Name |
|---|---|---|---|
| 236 | 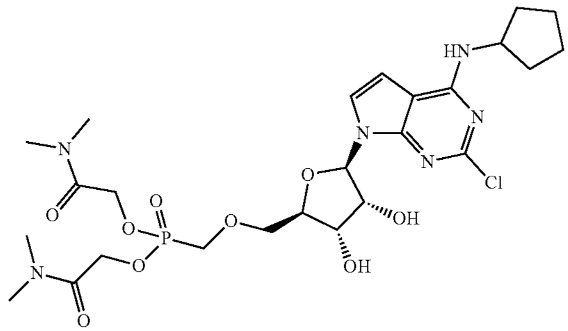 [SMILES: CN(C)C(=O)COP(=O)(COC[C@H]1O[C@@H](n2ccc3c(NC4CCCC4)nc(Cl)nc32)[C@H](O)[C@@H]1O)OCC(=O)N(C)C] | [M + H]⁺: 633 | 2-[[(2R,3S,4R,5R)-5-[2-chloro-4-(cyclopentylamino)pyrrolo[2,3-d]pyrimidin-7-yl]-3,4-dihydroxy-tetrahydrofuran-2-yl]-methoxymethyl-[2-(dimethylamino)-2-oxo-ethoxy]phosphoryl]oxy-N,N-dimethyl-acetamide |
| 237 | 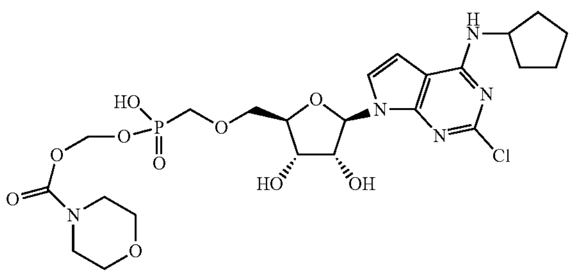 [SMILES: O=C(OCOP(=O)(O)COC[C@H]1O[C@@H](n2ccc3c(NC4CCCC4)nc(Cl)nc32)[C@H](O)[C@@H]1O)N1CCOCC1] | [M + H]⁺: 606;<br>[M − H]⁻: 604 | [(2R,3S,4R,5R)-5-[2-chloro-4-(cyclopentylamino)pyrrolo[2,3-d]-pyrimidin-7-yl]-3,4-dihydroxy-tetrahydrofuran-2-yl]methoxymethyl-(morpholine-4-carbonyloxymethoxy)phosphinic acid |
| 238 | 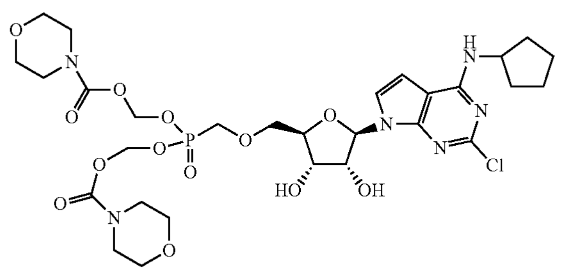 [SMILES: O=C(OCOP(=O)(COC[C@H]1O[C@@H](n2ccc3c(NC4CCCC4)nc(Cl)nc32)[C@H](O)[C@@H]1O)OCOC(=O)N1CCOCC1)N1CCOCC1] | [M + H]⁺: 749;<br>[M − H]⁻: 747 | [[(2R,3S,4R,5R)-5-[2-chloro-4-(cyclopentylamino)pyrrolo[2,3-d]-pyrimidin-7-yl]-3,4-dihydroxy-tetrahydrofuran-2-yl]methoxymethyl-(morpholine-4-carbonyloxymethoxy)phosphoryl]oxymethyl morpholine-4-carboxylate |
| 239 | 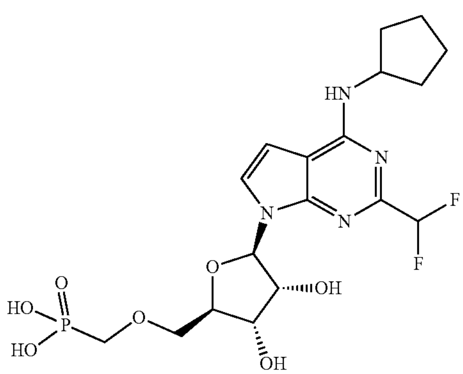 [SMILES: O=P(O)(O)COC[C@H]1O[C@@H](n2ccc3c(NC4CCCC4)nc(C(F)F)nc32)[C@H](O)[C@@H]1O] | [M + H]⁺: 479;<br>[M − H]⁻: 477 | [(2R,3S,4R,5R)-5-[4-(cyclopentylamino)-2-(difluoromethyl)pyrrolo[2,3-d]pyrimidin-7-yl]-3,4-dihydroxy-tetrahydrofuran-2-yl]-methoxymethylphosphonic acid |
| 240 | 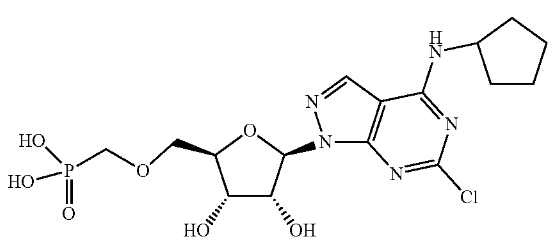 [SMILES: O=P(O)(O)COC[C@H]1O[C@@H](n2ncc3c(NC4CCCC4)nc(Cl)nc32)[C@H](O)[C@@H]1O] | [M − H]⁻: 462 | [(2R,3S,4R,5R)-5-[6-chloro-4-(cyclopentylamino)pyrazolo[3,4-d]-pyrimidin-1-yl]-3,4-dihydroxy-tetrahydrofuran-2-yl]methoxymethylphosphonic acid |

TABLE 1-continued

| No. | Structure | m/z | IUPAC Name |
|---|---|---|---|
| 241 | 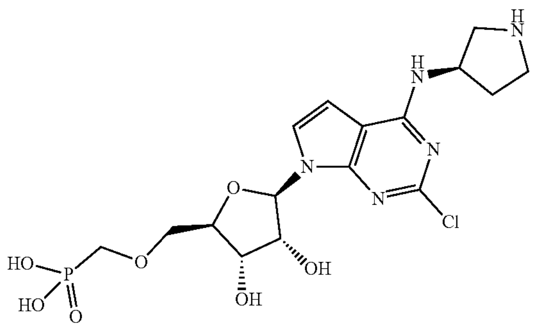 [SMILES: O=P(O)(O)COC[C@H]1O[C@@H](n2ccc3c(N[C@@H]4CCNC4)nc(Cl)nc32)[C@H](O)[C@@H]1O] | [M + H]⁺: 464; [M − H]⁻: 462 | [(2R,3S,4R,5R)-5-[2-chloro-4-[[(3R)-pyrrolidin-3-yl]amino]-pyrrolo[2,3-d]pyrimidin-7-yl]-3,4-dihydroxy-tetrahydrofuran-2-yl]-methoxymethylphosphonic acid |
| 242 | 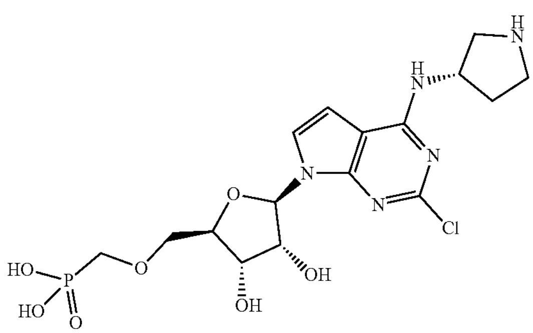 [SMILES: O=P(O)(O)COC[C@H]1O[C@@H](n2ccc3c(N[C@H]4CCNC4)nc(Cl)nc32)[C@H](O)[C@@H]1O] | [M + H]⁺: 464; [M − H]⁻: 462 | [(2R,3S,4R,5R)-5-[2-chloro-4-[[(3S)-pyrrolidin-3-yl]-amino]pyrrolo[2,3-d]-pyrimidin-7-yl]-3,4-dihydroxy-tetrahydro-furan-2-yl]methoxy-methylphosphonic acid |
| 243 | 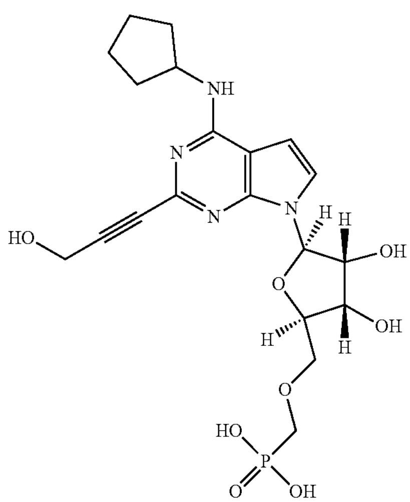 [SMILES: O=P(O)(O)COC[C@H]1O[C@@H](n2ccc3c(NC4CCCC4)nc(C#CCO)nc32)[C@H](O)[C@@H]1O] | [M + H]⁺: 483; [M − H]⁻: 481 | [(2R,3S,4R,5R)-5-[4-(cyclopentylamino)-2-(3-hydroxyprop-1-ynyl)pyrrolo[2,3-d]-pyrimidin-7-yl]-3,4-dihydroxy-tetrahydro-furan-2-yl]methoxy-methylphosphonic acid |

TABLE 1-continued

| No. | Structure | m/z | IUPAC Name |
|---|---|---|---|
| 244 | 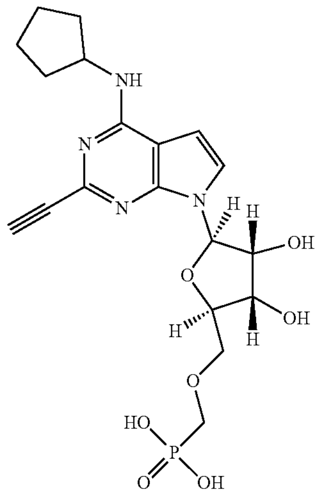 [SMILES: C#Cc1nc(NC2CCCC2)c2ccn([C@@H]3O[C@H](COCP(=O)(O)O)[C@@H](O)[C@H]3O)c2n1] | [M + H]⁺: 453; [M − H]⁻: 451 | [(2R,3S,4R,5R)-5-[4-(cyclopentylamino)-2-ethynyl-pyrrolo[2,3-d]-pyrimidin-7-yl]-3,4-dihydroxy-tetrahydro-furan-2-yl]methoxy-methylphosphonic acid |
| 245 | 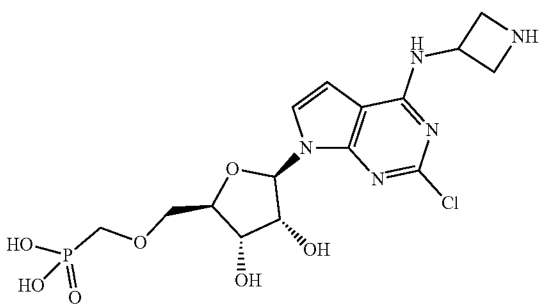 [SMILES: O=P(O)(O)COC[C@H]1O[C@@H](n2ccc3c(NC4CNC4)nc(Cl)nc32)[C@H](O)[C@@H]1O] | [M + H]⁺: 450 | [(2R,3S,4R,5R)-5-[4-(azetidin-3-ylamino)-2-chloro-pyrrolo[2,3-d]pyrimidin-7-yl]-3,4-dihydroxy-tetrahydro-furan-2-yl]methoxy-methylphosphonic acid |
| 246 | 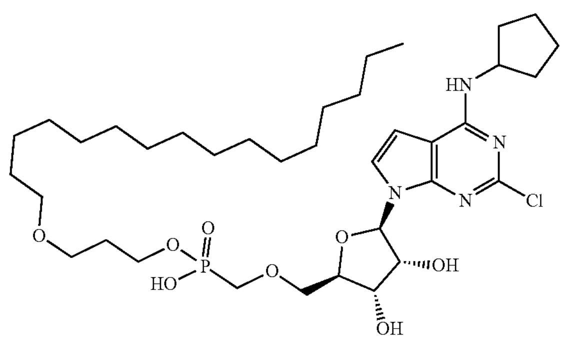 [SMILES: CCCCCCCCCCCCCCCCOCCCOP(=O)(O)COC[C@H]1O[C@@H](n2ccc3c(NC4CCCC4)nc(Cl)nc32)[C@H](O)[C@@H]1O] | [M + H]⁺: 745 | [(2R,3S,4R,5R)-5-[2-chloro-4-(cyclopentyl-amino)pyrrolo[2,3-d]-pyrimidin-7-yl]-3,4-dihydroxy-tetrahydro-furan-2-yl]methoxy-methyl-(3-hexadecoxy-propoxy)phosphinic acid |
| 247 | 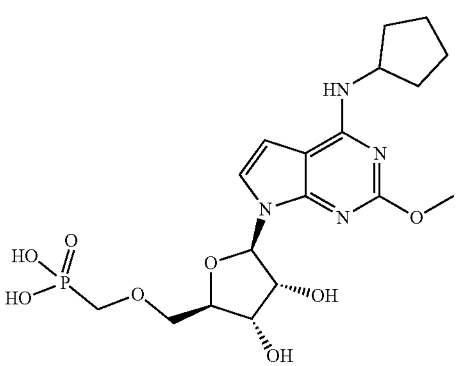 [SMILES: COc1nc(NC2CCCC2)c2ccn([C@@H]3O[C@H](COCP(=O)(O)O)[C@@H](O)[C@H]3O)c2n1] | [M + H]⁺: 459; [M − H]⁻: 457 | [(2R,3S,4R,5R)-5-[4-(cyclopentylamino)-2-methoxy-pyrrolo[2,3-d]pyrimidin-7-yl]-3,4-dihydroxy-tetrahydro-furan-2-yl]methoxy-methylphosphonic acid |

TABLE 1-continued

| No. | Structure | m/z | IUPAC Name |
|---|---|---|---|
| 248 | 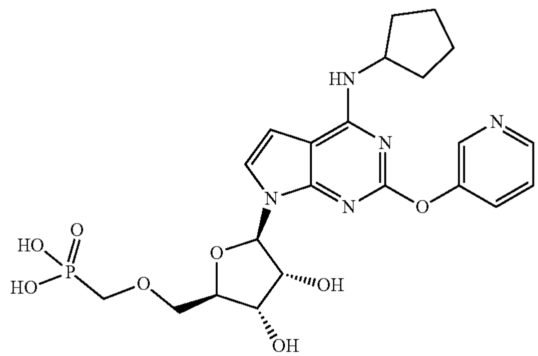 [SMILES: O=P(O)(O)COC[C@H]1O[C@@H](n2ccc3c(NC4CCCC4)nc(Oc4cccnc4)nc32)[C@H](O)[C@@H]1O] | [M + H]⁺: 522; [M − H]⁻: 520 | [(2R,3S,4R,5R)-5-[4-(cyclopentylamino)-2-(3-pyridyloxy)pyrrolo-[2,3-d]pyrimidin-7-yl]-3,4-dihydroxy-tetra-hydrofuran-2-yl]meth-oxymethylphosphonic acid |
| 249 | 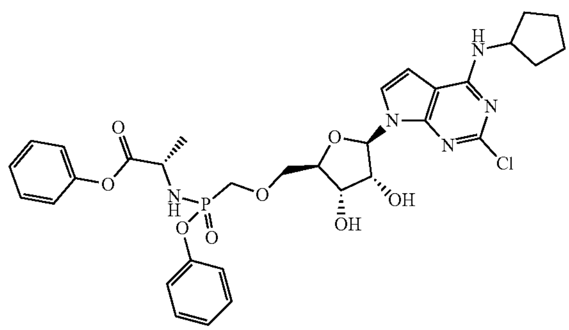 [SMILES: C[C@H](NP(=O)(COC[C@H]1O[C@@H](n2ccc3c(NC4CCCC4)nc(Cl)nc32)[C@H](O)[C@@H]1O)Oc1ccccc1)C(=O)Oc1ccccc1] | [M + H]⁺: 686 | phenyl (2S)-2-[[[(2R,3S,4R,5R)-5-[2-chloro-4-(cyclopentyl-amino)pyrrolo-[2,3-d]-pyrimidin-7-yl]-3,4-dihydroxy-tetrahydro-furan-2-yl]methoxy-methyl-phenoxy-phosphoryl]amino]-propanoate |
| 250 | 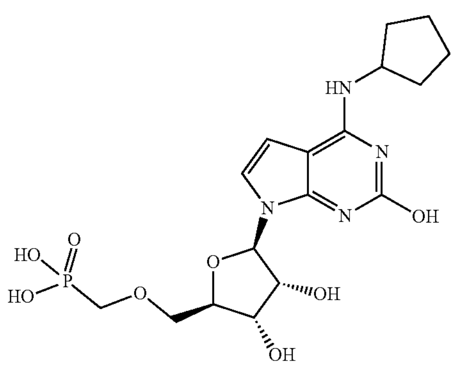 [SMILES: O=P(O)(O)COC[C@H]1O[C@@H](n2ccc3c(NC4CCCC4)nc(O)nc32)[C@H](O)[C@@H]1O] | [M + H]⁺: 445 | [(2R,3S,4R,5R)-5-[4-(cyclopentylamino)-2-hydroxy-pyrrolo[2,3-d]pyrimidin-7-yl]-3,4-dihydroxy-tetrahydro-furan-2-yl]methoxy-methylphosphonic acid |
| 251 | 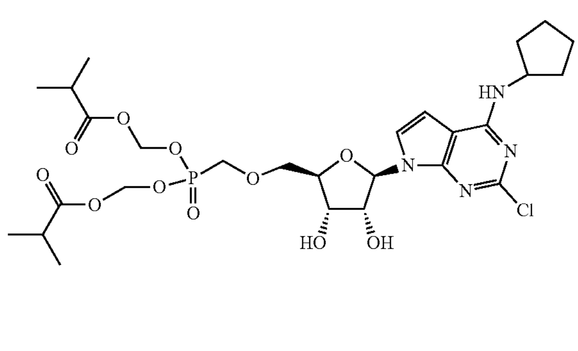 [SMILES: CC(C)C(=O)OCOP(=O)(COC[C@H]1O[C@@H](n2ccc3c(NC4CCCC4)nc(Cl)nc32)[C@H](O)[C@@H]1O)OCOC(=O)C(C)C] | [M + H]⁺: 663; [M − H]⁻: 661 | [[(2R,3S,4R,5R)-5-[2-chloro-4-(cyclopentyl-amino)pyrrolo[2,3-d]-pyrimidin-7-yl]-3,4-dihydroxy-tetrahydro-furan-2-yl]methoxy-methyl-(2-methyl-propanoyloxymethoxy)-phosphoryl]oxymethyl 2-methylpropanoate |

TABLE 1-continued

| No. | Structure | m/z | IUPAC Name |
|---|---|---|---|
| 252 | 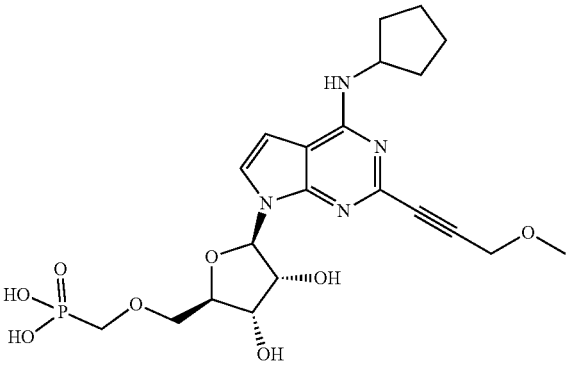 [SMILES: COCC#Cc1nc(NC2CCCC2)c2ccn([C@@H]3O[C@H](COCP(=O)(O)O)[C@@H](O)[C@H]3O)c2n1] | [M + H]⁺: 497 | [(2R,3S,4R,5R)-5-[4-(cyclopentylamino)-2-(3-methoxyprop-1-ynyl)pyrrolo[2,3-d]-pyrimidin-7-yl]-3,4-dihydroxy-tetrahydro-furan-2-yl]methoxy-methylphosphonic acid |
| 253 | 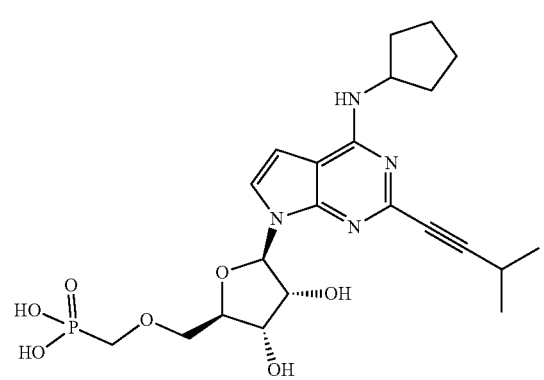 [SMILES: CC(C)C#Cc1nc(NC2CCCC2)c2ccn([C@@H]3O[C@H](COCP(=O)(O)O)[C@@H](O)[C@H]3O)c2n1] | [M + H]⁺: 495 | [(2R,3S,4R,5R)-5-[4-(cyclopentylamino)-2-(3-methylbut-1-ynyl)pyrrolo[2,3-d]-pyrimidin-7-yl]-3,4-dihydroxy-tetrahydro-furan-2-yl]methoxy-methylphosphonic acid |
| 254 | 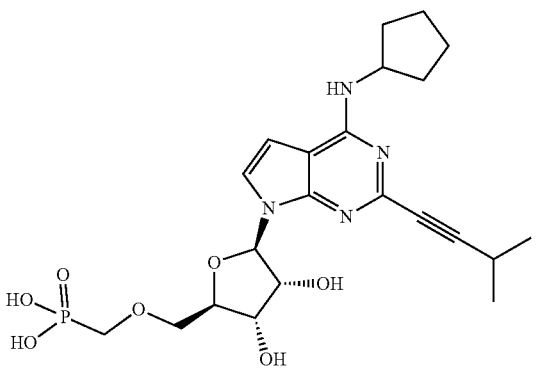 | [M + H]⁺: 509 | [(2R,3S,4R,5R)-5-[4-(cyclopentylamino)-2-(3,3-dimethylbut-1-ynyl)pyrrolo[2,3-d]-pyrimidin-7-yl]-3,4-dihydroxy-tetrahydro-furan-2-yl]methoxy-methylphosphonic acid |
| 255 | 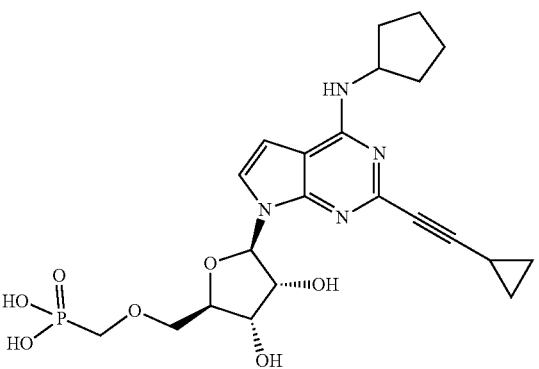 [SMILES: O=P(O)(O)COC[C@H]1O[C@@H](n2ccc3c(NC4CCCC4)nc(C#CC4CC4)nc32)[C@H](O)[C@@H]1O] | [M + H]⁺: 493 | [(2R,3S,4R,5R)-5-[4-(cyclopentylamino)-2-(2-cyclopropyl-ethynyl)pyrrolo[2,3-d]-pyrimidin-7-yl]-3,4-dihydroxy-tetrahydro-furan-2-yl]methoxy-methylphosphonic acid |

TABLE 1-continued

| No. | Structure | m/z | IUPAC Name |
|---|---|---|---|
| 256 | 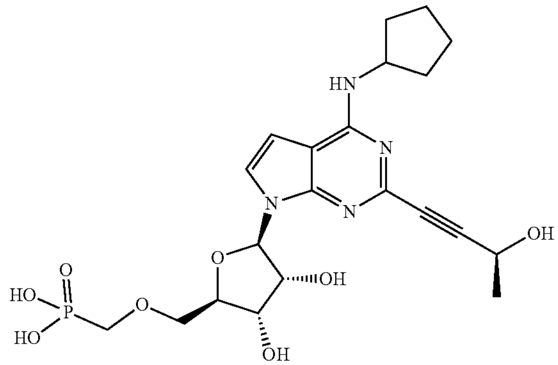 [SMILES: C[C@H](O)C#Cc1nc(NC2CCCC2)c2ccn([C@@H]3O[C@H](COCP(=O)(O)O)[C@@H](O)[C@H]3O)c2n1] | [M + H]⁺: 498 | [(2R,3S,4R,5R)-5-[4-(cyclopentylamino)-2-[(3S)-3-hydroxybut-1-ynyl]pyrrolo[2,3-d]pyrimidin-7-yl]-3,4-dihydroxy-tetrahydrofuran-2-yl]methoxymethylphosphonic acid |
| 257 | 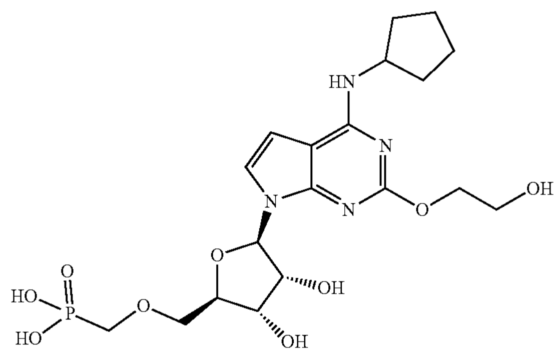 [SMILES: O=P(O)(O)COC[C@H]1O[C@@H](n2ccc3c(NC4CCCC4)nc(OCCO)nc32)[C@H](O)[C@@H]1O] | [M + H]⁺: 489; [M − H]⁻: 487 | [(2R,3S,4R,5R)-5-[4-(cyclopentylamino)-2-(2-hydroxyethoxy)-pyrrolo[2,3-d]-pyrimidin-7-yl]-3,4-dihydroxy-tetrahydrofuran-2-yl]methoxymethylphosphonic acid |
| 258 | 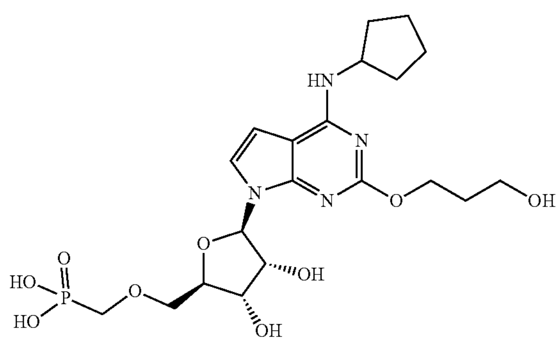 [SMILES: O=P(O)(O)COC[C@H]1O[C@@H](n2ccc3c(NC4CCCC4)nc(OCCCO)nc32)[C@H](O)[C@@H]1O] | [M + H]⁺: 503; [M − H]⁻: 501 | [(2R,3S,4R,5R)-5-[4-(cyclopentylamino)-2-(3-hydroxypropoxy)-pyrrolo[2,3-d]pyrimidin-7-yl]-3,4-dihydroxy-tetrahydrofuran-2-yl]-methoxymethylphosphonic acid |
| 259 | 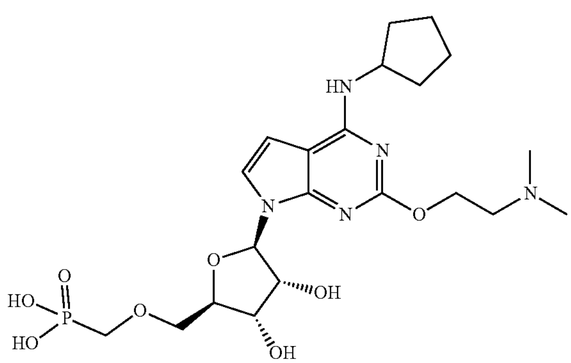 [SMILES: CN(C)CCOc1nc(NC2CCCC2)c2ccn([C@@H]3O[C@H](COCP(=O)(O)O)[C@@H](O)[C@H]3O)c2n1] | [M + H]⁺: 516 | [(2R,3S,4R,5R)-5-[4-(cyclopentylamino)-2-[2-(dimethylamino)-ethoxy]pyrrolo[2,3-d]-pyrimidin-7-yl]-3,4-dihydroxy-tetrahydrofuran-2-yl]methoxymethylphosphonic acid |

TABLE 1-continued

| No. | Structure | m/z | IUPAC Name |
|---|---|---|---|
| 260 | 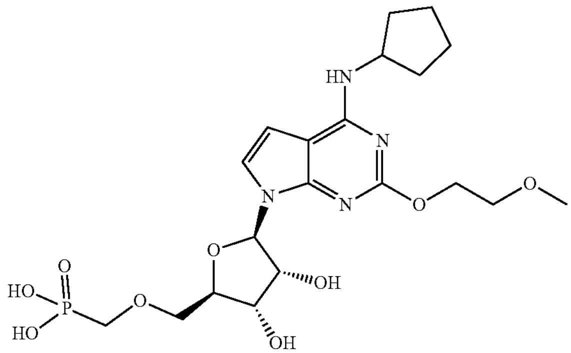 [SMILES: COCCOc1nc(NC2CCCC2)c2ccn([C@@H]3O[C@H](COCP(=O)(O)O)[C@@H](O)[C@H]3O)c2n1] | [M + H]⁺: 503; [M − H]⁻: 501 | [(2R,3S,4R,5R)-5-[4-(cyclopentylamino)-2-(2-methoxyethoxy)-pyrrolo[2,3-d]-pyrimidin-7-yl]-3,4-dihydroxy-tetrahydro-furan-2-yl]methoxy-methylphosphonic acid |
| 261 | 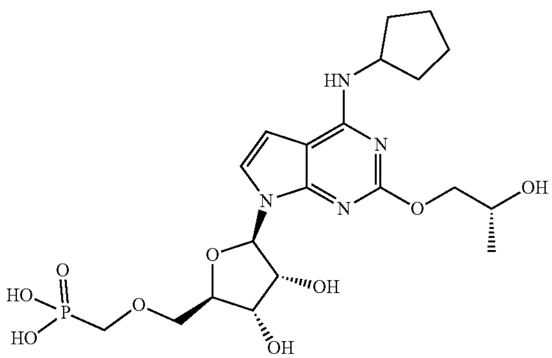 | [M + H]⁺: 503; [M − H]⁻: 501 | [(2R,3S,4R,5R)-5-[4-(cyclopentylamino)-2-[(2R)-2-hydroxy-propoxy]pyrrolo[2,3-d]pyrimidin-7-yl]-3,4-dihydroxy-tetrahydro-furan-2-yl]methoxy-methylphosphonic acid |
| 262 | 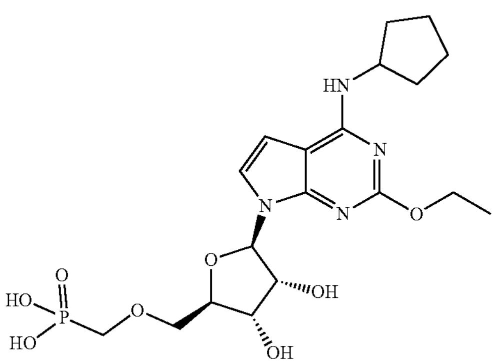 | [M + H]⁺: 473; [M − H]⁻: 471 | [(2R,3S,4R,5R)-5-[4-(cyclopentylamino)-2-ethoxy-pyrrolo[2,3-d]-pyrimidin-7-yl]-3,4-dihydroxy-tetrahydro-furan-2-yl]methoxy-methylphosphonic acid |
| 263 | 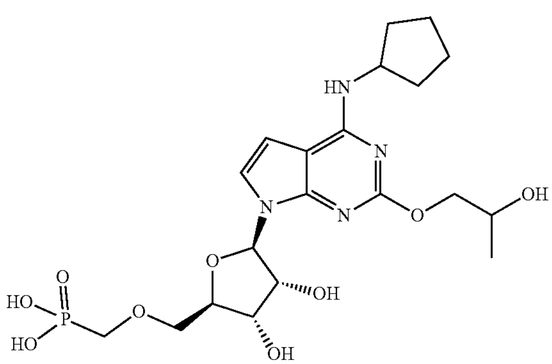 [SMILES: C[C@@H](O)COc1nc(NC2CCCC2)c2ccn([C@@H]3O[C@H](COCP(=O)(O)O)[C@@H](O)[C@H]3O)c2n1] | [M + H]⁺: 503; [M − H]⁻: 501 | [(2R,3S,4R,5R)-5-[4-(cyclopentylamino)-2-(2-hydroxypropoxy)-pyrrolo[2,3-d]pyrimidin-7-yl]-3,4-dihydroxy-tetrahydrofuran-2-yl]-methoxymethylphosphonic acid |

TABLE 1-continued

| No. | Structure | m/z | IUPAC Name |
|---|---|---|---|
| 264 | 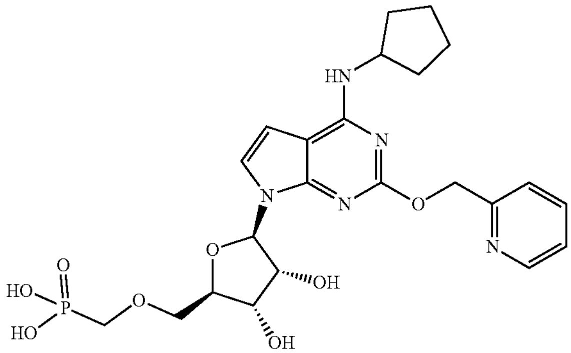 [SMILES: O=P(O)(O)COC[C@H]1O[C@@H](n2ccc3c(NC4CCCC4)nc(OCc4ccccn4)nc32)[C@H](O)[C@@H]1O] | [M + H]⁺: 536;<br>[M − H]⁻: 534 | [(2R,3S,4R,5R)-5-[4-(cyclopentylamino)-2-(2-pyridylmethoxy)-pyrrolo[2,3-d]pyrimidin-7-yl]-3,4-dihydroxy-tetrahydrofuran-2-yl]-methoxymethylphosphonic acid |
| 265 | 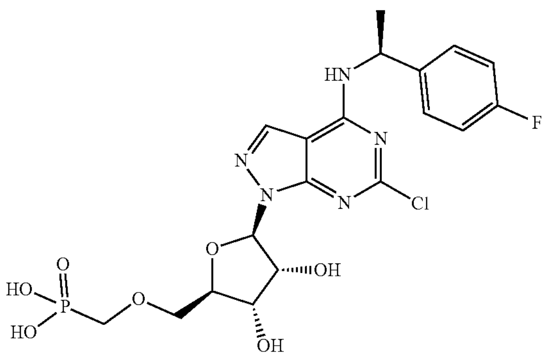 [SMILES: C[C@H](Nc1nc(Cl)nc2c1cnn2[C@@H]1O[C@H](COCP(=O)(O)O)[C@@H](O)[C@H]1O)c1ccc(F)cc1] | [M − H]⁻: 516 | [(2R,3S,4R,5R)-5-[6-chloro-4-[[(1S)-1-(4-fluorophenyl)ethyl]amino]pyrazolo[3,4-d]-pyrimidin-1-yl]-3,4-dihydroxy-tetrahydrofuran-2-yl]methoxymethylphosphonic acid |
| 266 | 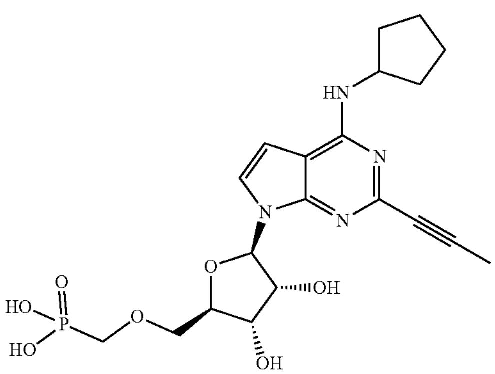 [SMILES: CC#Cc1nc(NC2CCCC2)c2ccn([C@@H]3O[C@H](COCP(=O)(O)O)[C@@H](O)[C@H]3O)c2n1] | [M + H]⁺: 467 | [(2R,3S,4R,5R)-5-[4-(cyclopentylamino)-2-prop-1-ynyl-pyrrolo-[2,3-d]pyrimidin-7-yl]-3,4-dihydroxy-tetrahydrofuran-2-yl]-methoxymethylphosphonic acid |
| 267 | 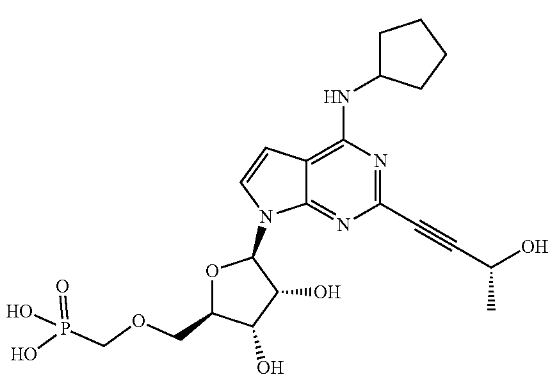 [SMILES: C[C@@H](O)C#Cc1nc(NC2CCCC2)c2ccn([C@@H]3O[C@H](COCP(=O)(O)O)[C@@H](O)[C@H]3O)c2n1] | [M + H]⁺: 497 | [(2R,3S,4R,5R)-5-[4-(cyclopentylamino)-2-[(3R)-3-hydroxybut-1-ynyl]pyrrolo[2,3-d]-pyrimidin-7-yl]-3,4-dihydroxy-tetrahydrofuran-2-yl]methoxymethylphosphonic acid |

TABLE 1-continued

| No. | Structure | m/z | IUPAC Name |
|---|---|---|---|
| 268 | 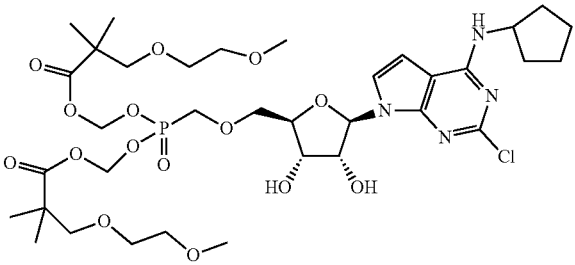 [SMILES: COCCOCC(C)(C)C(=O)OCOP(=O)(COC[C@H]1O[C@@H](n2ccc3c(NC4CCCC4)nc(Cl)nc32)[C@H](O)[C@@H]1O)OCOC(=O)C(C)(C)COCCOC] | | [[(2R,3S,4R,5R)-5-[2-chloro-4-(cyclopentyl-amino)pyrrolo[2,3-d]-pyrimidin-7-yl]-3,4-dihydroxy-tetrahydro-furan-2-yl]methoxy-methyl-[[3-(2-methoxy-ethoxy)-2,2-dimethyl-propanoyl]oxymethoxy]-phosphoryl]oxymethyl 3-(2-methoxyethoxy)-2,2-dimethylpropanoate |
| 269 | 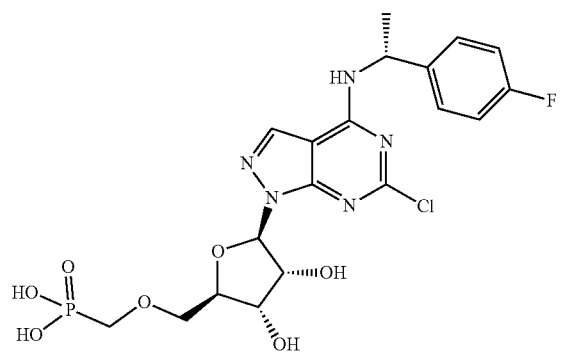 [SMILES: C[C@@H](Nc1nc(Cl)nc2c1cnn2[C@@H]1O[C@H](COCP(=O)(O)O)[C@@H](O)[C@H]1O)c1ccc(F)cc1] | [M − H]⁻: 516 | [(2R,3S,4R,5R)-5-[6-chloro-4-[[(1R)-1-(4-fluorophenyl)ethyl]-amino]pyrazolo[3,4-d]-pyrimidin-1-yl]-3,4-dihydroxy-tetrahydro-furan-2-yl]methoxy-methylphosphonic acid |
| 270 | 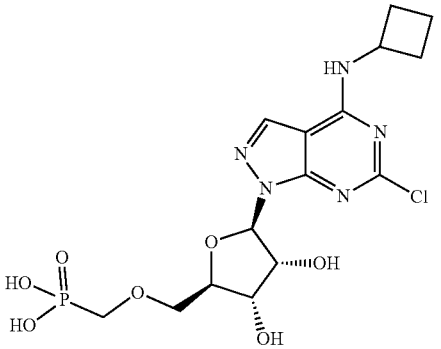 [SMILES: O=P(O)(O)COC[C@H]1O[C@@H](n2ncc3c(NC4CCC4)nc(Cl)nc32)[C@H](O)[C@@H]1O] | [M − H]⁻: 448 | [(2R,3S,4R,5R)-5-[6-chloro-4-(cyclobutyl-amino)pyrazolo[3,4-d]-pyrimidin-1-yl]-3,4-dihydroxy-tetrahydro-furan-2-yl]methoxy-methylphosphonic acid |
| 271 | 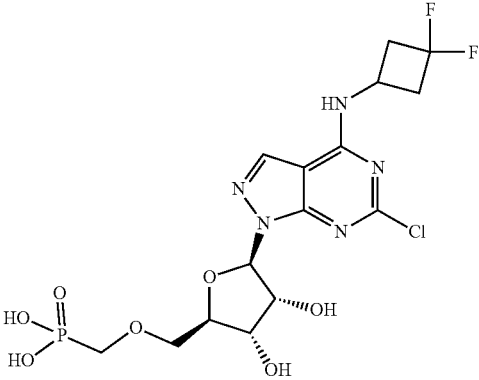 [SMILES: O=P(O)(O)COC[C@H]1O[C@@H](n2ncc3c(NC4CC(F)(F)C4)nc(Cl)nc32)[C@H](O)[C@@H]1O] | [M − H]⁻: 484 | [(2R,3S,4R,5R)-5-[6-chloro-4-[(3,3-difluoro-cyclobutyl)amino]-pyrazolo[3,4-d]-pyrimidin-1-yl]-3,4-dihydroxy-tetrahydro-furan-2-yl]methoxy-methylphosphonic acid |

TABLE 1-continued

| No. | Structure | m/z | IUPAC Name |
|---|---|---|---|
| 272 | 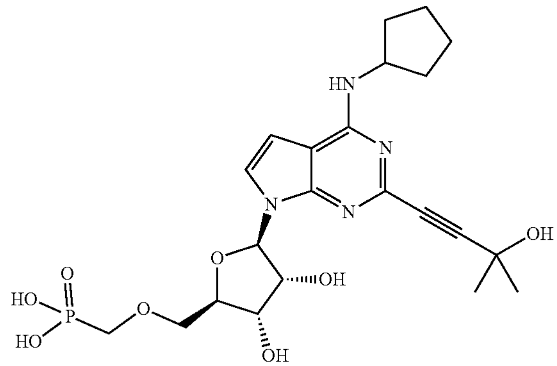 [SMILES: CC(C)(O)C#Cc1nc(NC2CCCC2)c2ccn([C@@H]3O[C@H](COCP(=O)(O)O)[C@@H](O)[C@H]3O)c2n1] | [M + H]+: 511; [M − H]−: 509 | [(2R,3S,4R,5R)-5-[4-(cyclopentylamino)-2-(3-hydroxy-3-methyl-but-1-ynyl)pyrrolo[2,3-d]pyrimidin-7-yl]-3,4-dihydroxy-tetrahydro-furan-2-yl]methoxy-methylphosphonic acid |
| 273 | 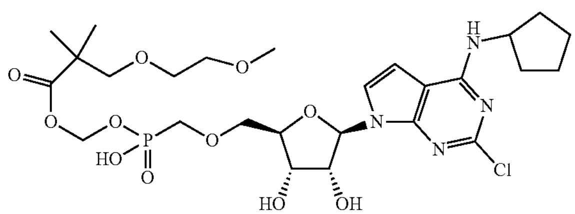 [SMILES: COCCOCC(C)(C)C(=O)OCOP(=O)(O)COC[C@H]1O[C@@H](n2ccc3c(NC4CCCC4)nc(Cl)nc32)[C@H](O)[C@@H]1O] | [M + H]+: 651; [M − H]−: 649 | [(2R,3S,4R,5R)-5-[2-chloro-4-(cyclopentyl-amino)pyrrolo[2,3-d]-pyrimidin-7-yl]-3,4-dihydroxy-tetrahydro-furan-2-yl]methoxy-methyl-[[3-(2-methoxy-ethoxy)-2,2-dimethyl-propanoyl]oxymethoxy]-phosphinic acid |
| 274 | 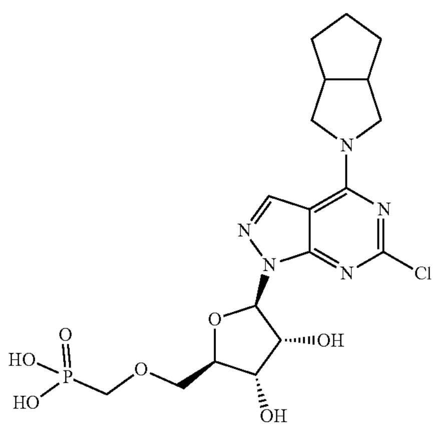 [SMILES: O=P(O)(O)COC[C@H]1O[C@@H](n2ncc3c(N4CC5CCCC5C4)nc(Cl)nc32)[C@H](O)[C@@H]1O] | [M − H]−: 488 | [(2R,3S,4R,5R)-5-[4-(3,3a,4,5,6,6a-hexa-hydro-1H-cyclopenta-[c]pyrrol-2-yl)-6-chloro-pyrazolo[3,4-d]-pyrimidin-1-yl]-3,4-dihydroxy-tetrahydro-furan-2-yl]methoxy-methylphosphonic acid |
| 275 | 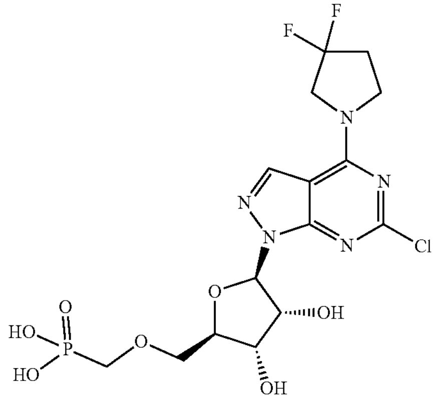 [SMILES: O=P(O)(O)COC[C@H]1O[C@@H](n2ncc3c(N4CCC(F)(F)C4)nc(Cl)nc32)[C@H](O)[C@@H]1O] | [M − H]−: 484 | [(2R,3S,4R,5R)-5-[6-chloro-4-(3,3-difluoro-pyrrolidin-1-yl)-pyrazolo[3,4-d]-pyrimidin-1-yl]-3,4-dihydroxy-tetrahydro-furan-2-yl]methoxy-methylphosphonic acid |

TABLE 1-continued

| No. | Structure | m/z | IUPAC Name |
| --- | --- | --- | --- |
| 276 | 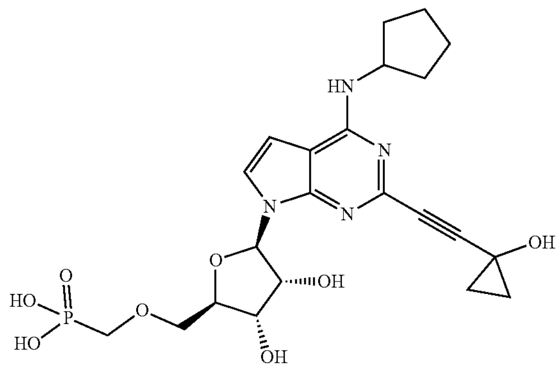 [SMILES: O=P(O)(O)COC[C@H]1O[C@@H](n2ccc3c(NC4CCCC4)nc(C#CC4(O)CC4)nc32)[C@H](O)[C@@H]1O] | [M − H]⁻: 508 | [(2R,3S,4R,5R)-5-[4-(cyclopentylamino)-2-[2-(1-hydroxycyclopropyl)ethynyl]pyrrolo-[2,3-d]pyrimidin-7-yl]-3,4-dihydroxy-tetrahydrofuran-2-yl]-methoxymethylphosphonic acid |
| 277 | 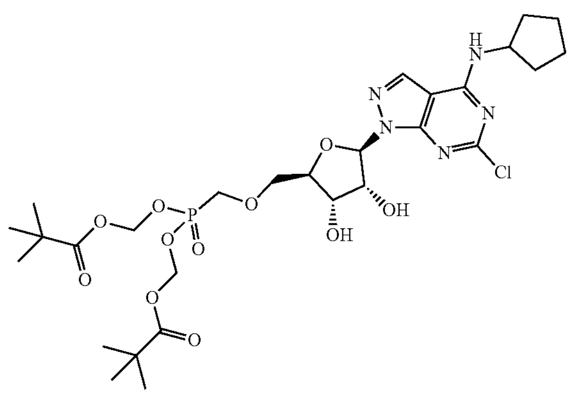 [SMILES: CC(C)(C)C(=O)OCOP(=O)(COC[C@H]1O[C@@H](n2ncc3c(NC4CCCC4)nc(Cl)nc32)[C@H](O)[C@@H]1O)OCOC(=O)C(C)(C)C] | [M + H]⁺: 692 | [[(2R,3S,4R,5R)-5-[6-chloro-4-(cyclopentyl-amino)pyrazolo[3,4-d]-pyrimidin-1-yl]-3,4-dihydroxy-tetrahydro-furan-2-yl]methoxy-methyl-(2,2-dimethyl-propanoyloxymethoxy)-phosphoryl]oxymethyl 2,2-dimethylpropanoate |
| 278 | 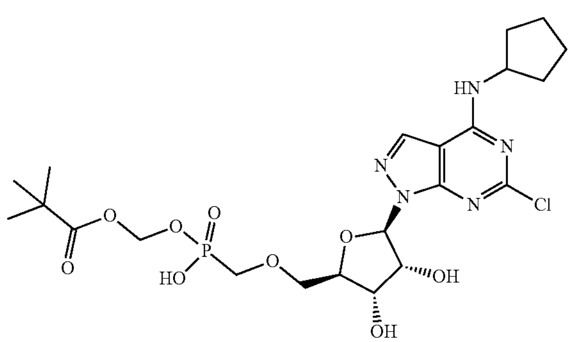 [SMILES: CC(C)(C)C(=O)OCOP(=O)(O)COC[C@H]1O[C@@H](n2ncc3c(NC4CCCC4)nc(Cl)nc32)[C@H](O)[C@@H]1O] | [M − H]⁻: 576 | [(2R,3S,4R,5R)-5-[6-chloro-4-(cyclopentyl-amino)pyrazolo[3,4-d]-pyrimidin-1-yl]-3,4-dihydroxy-tetrahydro-furan-2-yl]methoxy-methyl-(2,2-dimethyl-propanoyloxymethoxy)-phosphinic acid |
| 279 | 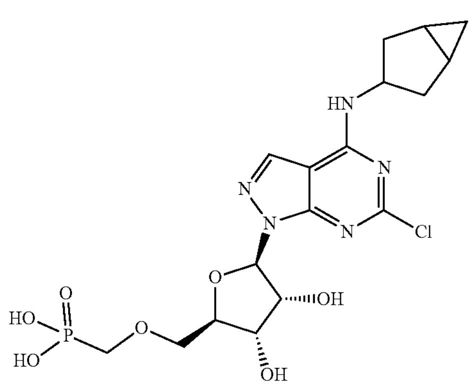 [SMILES: O=P(O)(O)COC[C@H]1O[C@@H](n2ncc3c(NC4CC5CC5C4)nc(Cl)nc32)[C@H](O)[C@@H]1O] | [M − H]⁻: 474 | [(2R,3S,4R,5R)-5-[4-(3-bicyclo[3.1.0]hexa-nylamino)-6-chloro-pyrazolo[3,4-d]-pyrimidin-1-yl]-3,4-dihydroxy-tetrahydro-furan-2-yl]methoxy-methylphosphonic acid |

TABLE 1-continued

| No. | Structure | m/z | IUPAC Name |
|---|---|---|---|
| 280 | 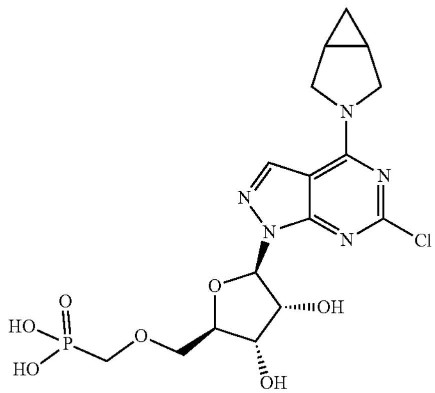 [SMILES: O=P(O)(O)COC[C@H]1O[C@@H](n2ncc3c(N4CC5CC5C4)nc(Cl)nc32)[C@H](O)[C@@H]1O] | [M − H]⁻: 460 | [(2R,3S,4R,5R)-5-[4-(3-azabicyclo[3.1.0]-hexan-3-yl)-6-chloro-pyrazolo[3,4-d]-pyrimidin-1-yl]-3,4-dihydroxy-tetrahydro-furan-2-yl]methoxy-methylphosphonic acid |
| 281 | 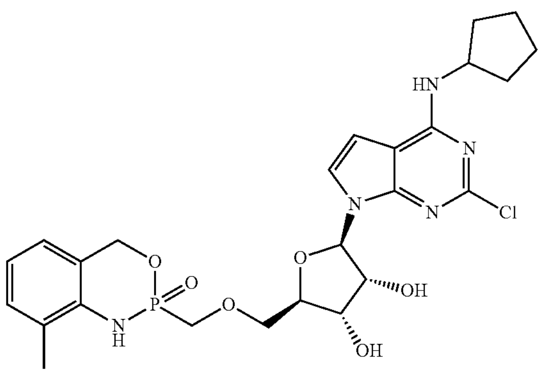 [SMILES: Cc1cccc2c1NP(=O)(COC[C@H]1O[C@@H](n3ccc4c(NC5CCCC5)nc(Cl)nc43)[C@H](O)[C@@H]1O)OC2] | [M + H]⁺: 564 | (2R,3R,4S,5R)-2-[2-chloro-4-(cyclopentyl-amino)pyrrolo[2,3-d]-pyrimidin-7-yl]-5-[(8-methyl-2-oxo-1,4-dihydro-3,1,2$l^{5}-benzoxazaphosphinin-2-yl)methoxymethyl]-tetrahydrofuran-3,4-diol |
| 282 | 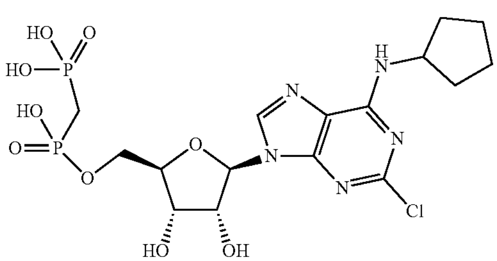 [SMILES: O=P(O)(O)CP(=O)(O)OC[C@H]1O[C@@H](n2cnc3c(NC4CCCC4)nc(Cl)nc32)[C@H](O)[C@@H]1O] | [M + H]⁺: 564 | [[(2R,3S,4R,5R)-5-[2-chloro-6-(cyclopentyl-amino)purin-9-yl]-3,4-dihydroxy-tetrahydro-furan-2-yl]methoxy-hydroxy-phosphoryl]-methylphosphonic acid |
| 283 | 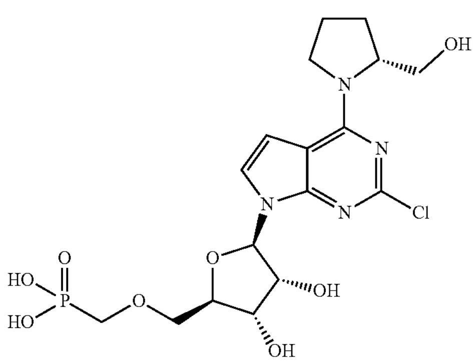 [SMILES: O=P(O)(O)COC[C@H]1O[C@@H](n2ccc3c(N4CCC[C@@H]4CO)nc(Cl)nc32)[C@H](O)[C@@H]1O] | [M + H]⁺: 479; [M − H]⁻: 477 | [(2R,3S,4R,5R)-5-[2-chloro-4-[(2R)-2-(hydroxymethyl)-pyrrolidin-1-yl]-pyrrolo[2,3-d]-pyrimidin-7-yl]-3,4-dihydroxy-tetrahydro-furan-2-yl]methoxy-methylphosphonic acid |

TABLE 1-continued

| No. | Structure | m/z | IUPAC Name |
|---|---|---|---|
| 284 | 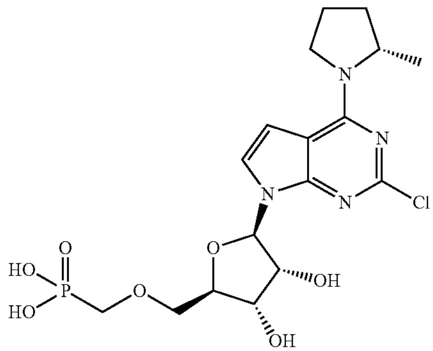 [SMILES: C[C@H]1CCCN1c1nc(Cl)nc2c1ccn2[C@@H]1O[C@H](COCP(=O)(O)O)[C@@H](O)[C@H]1O] | [M + H]⁺: 463; [M − H]⁻: 461 | [(2R,3S,4R,5R)-5-[2-chloro-4-[(2S)-2-methylpyrrolidin-1-yl]pyrrolo[2,3-d]-pyrimidin-7-yl]-3,4-dihydroxy-tetrahydro-furan-2-yl]methoxy-methylphosphonic acid |
| 285 | 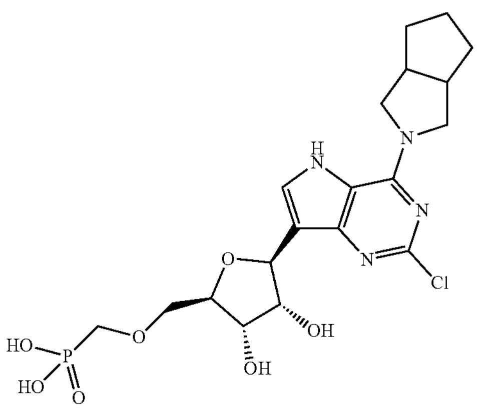 [SMILES: O=P(O)(O)COC[C@H]1O[C@@H](c2c[nH]c3c(N4CC5CCCC5C4)nc(Cl)nc23)[C@H](O)[C@@H]1O] | [M + H]⁺: 489 | [(2R,3S,4R,5S)-5-[4-(3,3a,4,5,6,6a-hexa-hydro-1H-cyclopenta-[c]pyrrol-2-yl)-2-chloro-5H-pyrrolo-[3,2-d]pyrimidin-7-yl]-3,4-dihydroxy-tetrahydrofuran-2-yl]-methoxymethylphos-phonic acid |
| 286 | 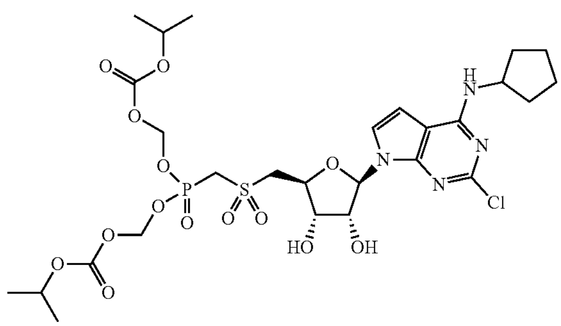 [SMILES: CC(C)OC(=O)OCOP(=O)(CS(=O)(=O)C[C@H]1O[C@@H](n2ccc3c(NC4CCCC4)nc(Cl)nc32)[C@H](O)[C@@H]1O)OCOC(=O)OC(C)C] | [M + H]⁺: 743 | [[(2S,3S,4R,5R)-5-[2-chloro-4-(cyclopentyl-amino)pyrrolo[2,3-d]-pyrimidin-7-yl]-3,4-dihydroxy-tetrahydro-furan-2-yl]methyl-sulfonylmethyl-(iso-propoxycarbonyloxy-methoxy)phosphoryl]-oxymethyl isopropyl carbonate |
| 287 | 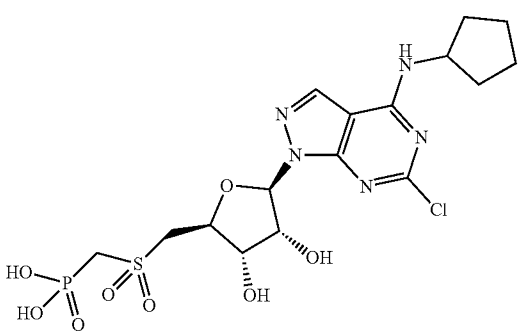 [SMILES: O=P(O)(O)CS(=O)(=O)C[C@H]1O[C@@H](n2ncc3c(NC4CCCC4)nc(Cl)nc32)[C@H](O)[C@@H]1O] | [M + H]⁺: 512; [M − H]⁻: 510 | [(2S,3S,4R,5R)-5-[6-chloro-4-(cyclopentyl-amino)pyrazolo[3,4-d]-pyrimidin-1-yl]-3,4-dihydroxy-tetrahydro-furan-2-yl]methyl-sulfonylmethylphos-phonic acid |

TABLE 1-continued

| No. | Structure | m/z | IUPAC Name |
|---|---|---|---|
| 288 | 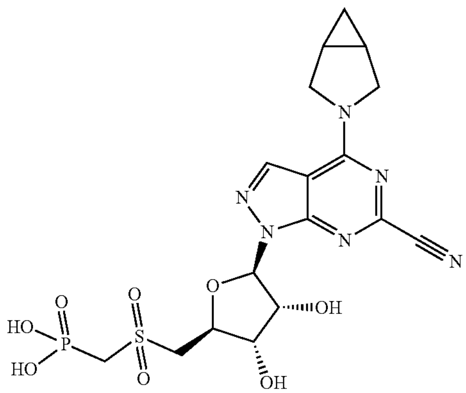 [SMILES: N#Cc1nc(N2CC3CC3C2)c2cnn([C@@H]3O[C@H](CS(=O)(=O)CP(=O)(O)O)[C@@H](O)[C@H]3O)c2n1] | [M − H]⁻: 499 | [(2S,3S,4R,5R)-5-[4-(3-azabicyclo[3.1.0]-hexan-3-yl)-6-cyano-pyrazolo[3,4-d]-pyrimidin-1-yl]-3,4-dihydroxy-tetrahydro-furan-2-yl]methyl-sulfonylmethylphos-phonic acid |
| 289 | 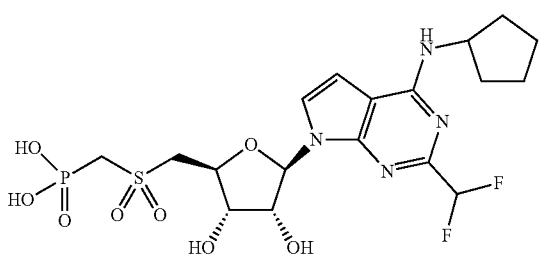 [SMILES: O=P(O)(O)CS(=O)(=O)C[C@H]1O[C@@H](n2ccc3c(NC4CCCC4)nc(C(F)F)nc32)[C@H](O)[C@@H]1O] | [M − H]⁻: 525 | [(2S,3S,4R,5R)-5-[4-(cyclopentylamino)-2-(difluoromethyl)-pyrrolo[2,3-d]-pyrimidin-7-yl]-3,4-dihydroxy-tetrahydro-furan-2-yl]methyl-sulfonylmethylphos-phonic acid |
| 290 | 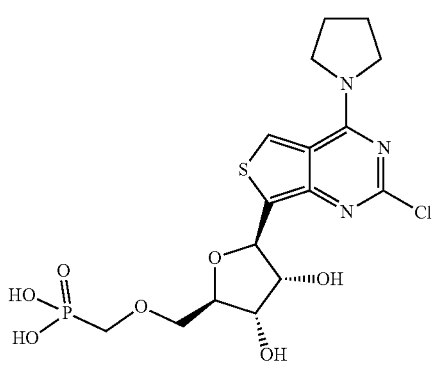 | [M − H]⁻: 446 | [(2R,3S,4R,5R)-5-(2-chloro-4-pyrrolidin-1-yl-thieno[3,4-d]-pyrimidin-7-yl)-3,4-dihydroxy-tetrahydro-furan-2-yl]methoxy-methylphosphonic acid |
| 291 | 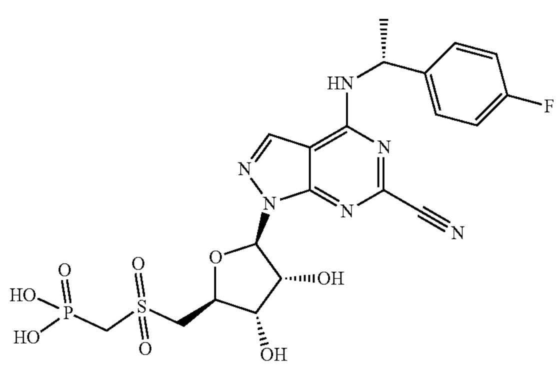 [SMILES: C[C@@H](Nc1nc(C#N)nc2c1cnn2[C@@H]1O[C@H](CS(=O)(=O)CP(=O)(O)O)[C@@H](O)[C@H]1O)c1ccc(F)cc1] | [M − H]⁻: 555 | [(2S,3S,4R,5R)-5-[6-cyano-4-[[(1R)-1-(4-fluorophenyl)ethyl]-amino]pyrazolo[3,4-d]-pyrimidin-1-yl]-3,4-dihydroxy-tetrahydro-furan-2-yl]methyl-sulfonylmethylphos-phonic acid |

TABLE 1-continued

| No. | Structure | m/z | IUPAC Name |
|---|---|---|---|
| 292 | 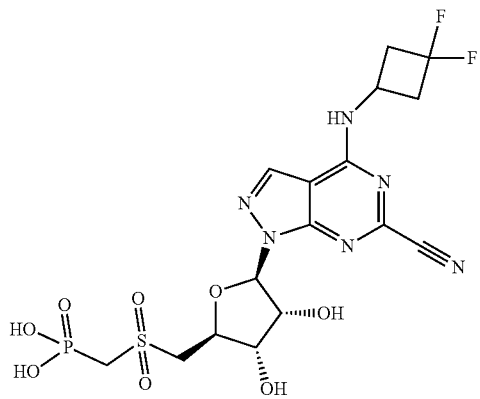 [SMILES: N#Cc1nc(NC2CC(F)(F)C2)c2cnn([C@@H]3O[C@H](CS(=O)(=O)CP(=O)(O)O)[C@@H](O)[C@H]3O)c2n1] | [M − H]⁻: 523 | [(2S,3S,4R,5R)-5-[6-cyano-4-[(3,3-difluoro-difluorocyclobutyl)-amino]pyrazolo[3,4-d]-pyrimidin-1-yl]-3,4-dihydroxy-tetrahydro-furan-2-yl]methyl-sulfonylmethylphos-phonic acid |
| 293 | 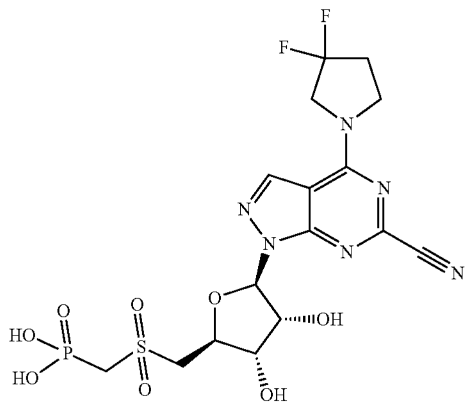 [SMILES: N#Cc1nc(N2CCC(F)(F)C2)c2cnn([C@@H]3O[C@H](CS(=O)(=O)CP(=O)(O)O)[C@@H](O)[C@H]3O)c2n1] | [M − H]⁻: 523 | [(2S,3S,4R,5R)-5-[6-cyano-4-(3,3-difluoro-pyrrolidin-1-yl)-pyrazolo[3,4-d]-pyrimidin-1-yl]-3,4-dihydroxy-tetrahydro-furan-2-yl]methyl-sulfonylmethylphos-phonic acid |
| 294 | 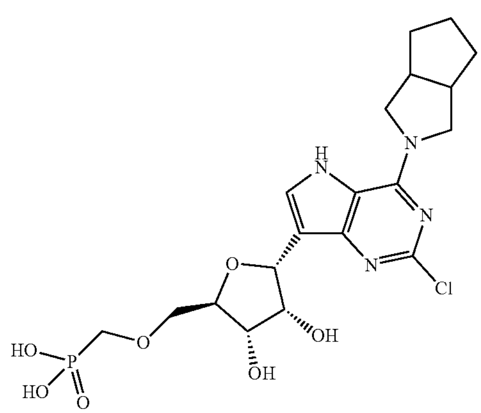 [SMILES: O=P(O)(O)COC[C@H]1O[C@H](c2c[nH]c3c(N4CC5CCCC5C4)nc(Cl)nc23)[C@H](O)[C@@H]1O] | [M + H]⁺: 489; [M − H]⁻: 487 | [(2R,3S,4R,5R)-5-[4-(3,3a,4,5,6,6a-hexa-hydro-1H-cyclopenta-[c]pyrrol-2-yl)-2-chloro-5H-pyrrolo[3,2-d]pyrimidin-7-yl]-3,4-dihydroxy-tetrahydro-furan-2-yl]methoxy-methylphosphonic acid |
| 295 | 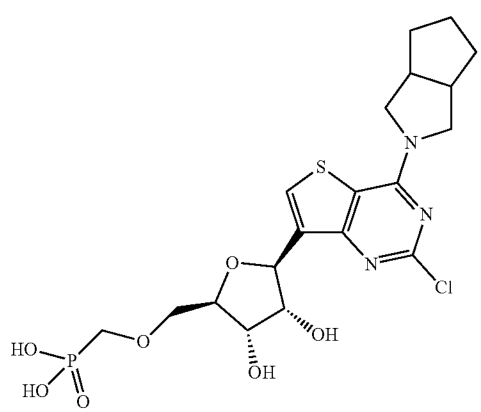 [SMILES: O=P(O)(O)COC[C@H]1O[C@@H](c2csc3c(N4CC5CCCC5C4)nc(Cl)nc23)[C@H](O)[C@@H]1O] | [M + H]⁺: 506; [M − H]⁻: 504 | [(2R,3S,4R,5S)-5-[4-(3,3a,4,5,6,6a-hexa-hydro-1H-cyclopenta-[c]pyrrol-2-yl)-2-chloro-thieno[3,2-d]-pyrimidin-7-yl]-3,4-dihydroxy-tetrahydro-furan-2-yl]methoxy-methylphosphonic acid |

TABLE 1-continued

| No. | Structure | m/z | IUPAC Name |
|---|---|---|---|
| 296 | 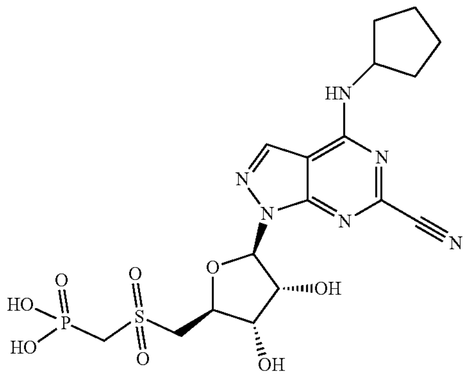 [SMILES: N#Cc1nc(NC2CCCC2)c2cnn([C@@H]3O[C@H](CS(=O)(=O)CP(=O)(O)O)[C@@H](O)[C@H]3O)c2n1] | [M + H]⁺: 503; [M − H]⁻: 501 | [(2S,3S,4R,5R)-5-[6-cyano-4-(cyclopentyl-amino)pyrazolo[3,4-d]-pyrimidin-1-yl]-3,4-dihydroxy-tetrahydro-furan-2-yl]methyl-sulfonylmethylphos-phonic acid |
| 297 | 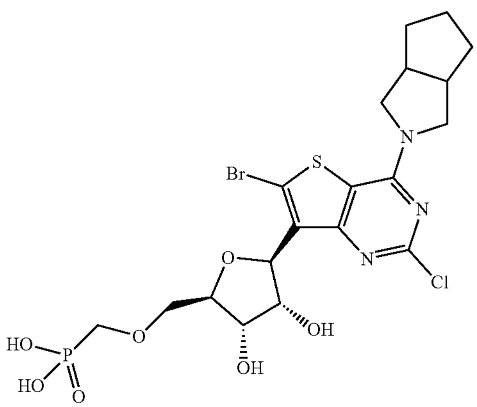 [SMILES: O=P(O)(O)COC[C@H]1O[C@@H](c2c(Br)sc3c(N4CC5CCCC5C4)nc(Cl)nc23)[C@H](O)[C@@H]1O] | [M + H]⁺: 586 | [(2R,3S,4R,5S)-5-[4-(3,3a,4,5,6,6a-hexa-hydro-1H-cyclopenta-[c]pyrrol-2-yl)-6-bromo-2-chloro-thieno[3,2-d]-pyrimidin-7-yl]-3,4-dihydroxy-tetrahydro-furan-2-yl]methoxy-methylphosphonic acid |
| 298 | 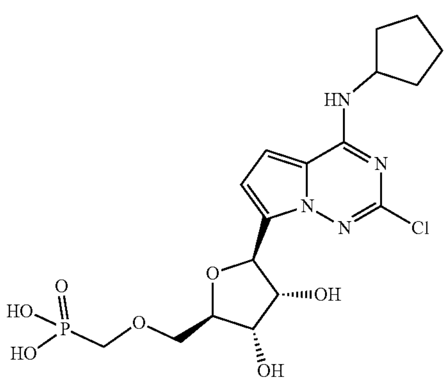 [SMILES: O=P(O)(O)COC[C@H]1O[C@@H](c2ccc3c(NC4CCCC4)nc(Cl)nn23)[C@H](O)[C@@H]1O] | [M − H]⁻: 461 | [(2R,3S,4R,5S)-5-[2-chloro-4-(cyclopentyl-amino)pyrrolo[2,1-f]-[1,2,4]triazin-7-yl]-3,4-dihydroxy-tetrahydro-furan-2-yl]methoxy-methylphosphonic acid |
| 299 | 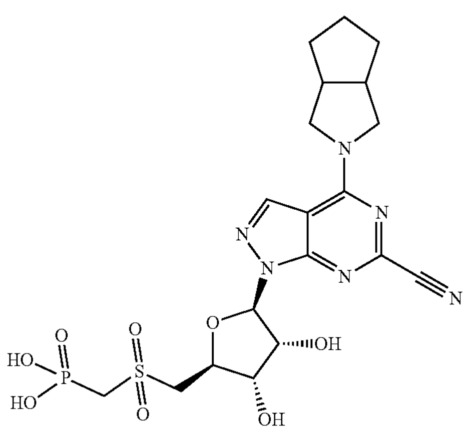 [SMILES: N#Cc1nc(N2CC3CCCC3C2)c2cnn([C@@H]3O[C@H](CS(=O)(=O)CP(=O)(O)O)[C@@H](O)[C@H]3O)c2n1] | [M − H]⁻: 527 | [(2S,3S,4R,5R)-5-[4-(3,3a,4,5,6,6a-hexa-hydro-1H-cyclopenta-[c]pyrrol-2-yl)-6-cyano-pyrazolo[3,4-d]-pyrimidin-1-yl]-3,4-dihydroxy-tetrahydro-furan-2-yl]methyl-sulfonylmethylphos-phonic acid |

TABLE 1-continued

| No. | Structure | m/z | IUPAC Name |
|---|---|---|---|
| 300 | 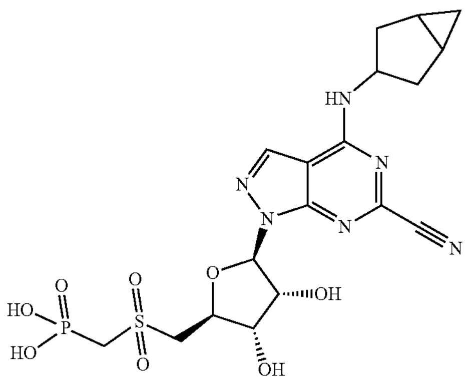 [SMILES: N#Cc1nc(NC2CC3CC3C2)c2cnn([C@@H]3O[C@H](CS(=O)(=O)CP(=O)(O)O)[C@@H](O)[C@H]3O)c2n1] | [M − H]⁻: 513 | [(2S,3S,4R,5R)-5-[4-(3-bicyclo[3.1.0]-hexanylamino)-6-cyano-pyrazolo[3,4-d]-pyrimidin-1-yl]-3,4-dihydroxy-tetrahydro-furan-2-yl]methyl-sulfonylmethylphosphonic acid |
| 301 | 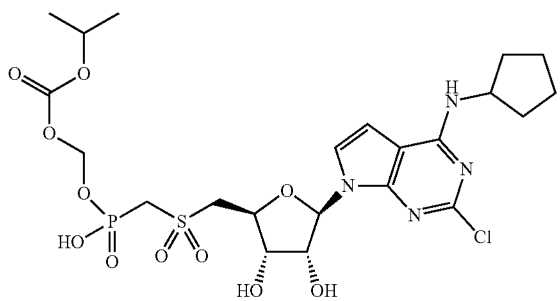 [SMILES: CC(C)OC(=O)OCOP(=O)(O)CS(=O)(=O)C[C@H]1O[C@@H](n2ccc3c(NC4CCCC4)nc(Cl)nc32)[C@H](O)[C@@H]1O] | [M + H]⁺: 627; [M − H]⁻: 625 | [(2S,3S,4R,5R)-5-[2-chloro-4-(cyclopentyl-amino)pyrrolo[2,3-d]-pyrimidin-7-yl]-3,4-dihydroxy-tetrahydro-furan-2-yl]methyl-sulfonylmethyl-(isopropoxycarbonyl-oxymethoxy)phosphinic acid |
| 302 | 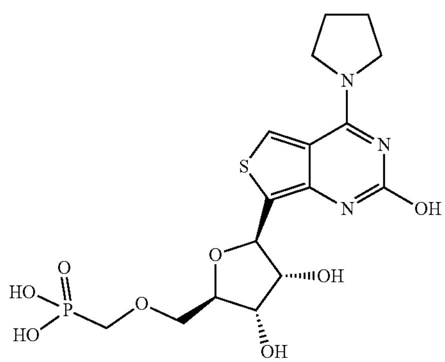 [SMILES: O=P(O)(O)COC[C@H]1O[C@@H](c2scc3c(N4CCCC4)nc(O)nc23)[C@H](O)[C@@H]1O] | [M − H]⁻: 446 | [(2R,3S,4R,5R)-3,4-dihydroxy-5-(2-hydroxy-4-pyrrolidin-1-yl-thieno[3,4-d]-pyrimidin-7-yl)tetra-hydrofuran-2-yl]-methoxymethylphosphonic acid |
| 303 | 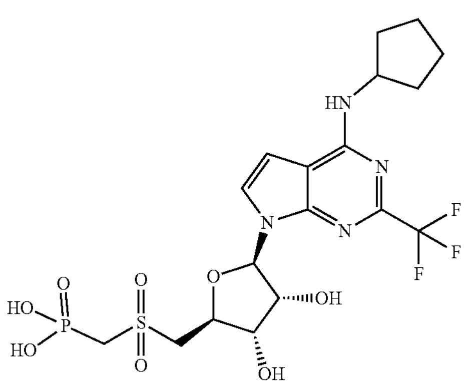 [SMILES: O=P(O)(O)CS(=O)(=O)C[C@H]1O[C@@H](n2ccc3c(NC4CCCC4)nc(C(F)(F)F)nc32)[C@H](O)[C@@H]1O] | [M + H]⁺: 545 | [(2S,3S,4R,5R)-5-[4-(cyclopentylamino)-2-(trifluoromethyl)-pyrrolo[2,3-d]-pyrimidin-7-yl]-3,4-dihydroxy-tetrahydro-furan-2-yl]methyl-sulfonylmethylphosphonic acid |

TABLE 1-continued

| No. | Structure | m/z | IUPAC Name |
|---|---|---|---|
| 304 | 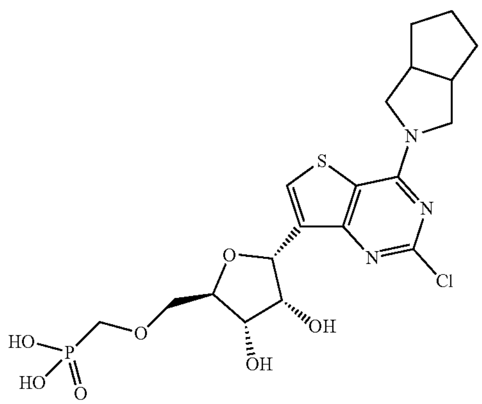 [SMILES: O=P(O)(O)COC[C@H]1O[C@H](c2csc3c(N4CC5CCCC5C4)nc(Cl)nc23)[C@H](O)[C@@H]1O] | [M + H]⁺: 506 | [(2R,3S,4R,5R)-5-[4-(3,3a,4,5,6,6a-hexa-hydro-1H-cyclopenta-[c]pyrrol-2-yl)-2-chloro-thieno[3,2-d]-pyrimidin-7-yl]-3,4-dihydroxy-tetrahydro-furan-2-yl]methoxy-methylphosphonic acid |
| 305 | 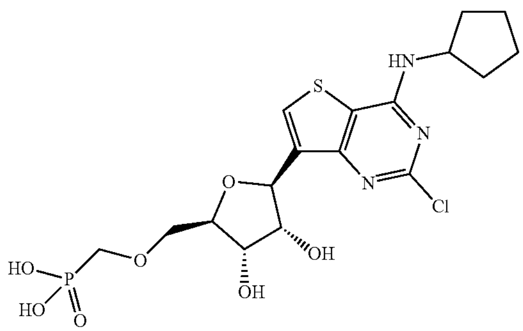 [SMILES: O=P(O)(O)COC[C@H]1O[C@@H](c2csc3c(NC4CCCC4)nc(Cl)nc23)[C@H](O)[C@@H]1O] | [M + H]⁺: 480 | [(2R,3S,4R,5S)-5-[2-chloro-4-(cyclopentyl-amino)thieno[3,2-d]-pyrimidin-7-yl]-3,4-dihydroxy-tetrahydro-furan-2-yl]methoxy-methylphosphonic acid |
| 306 | 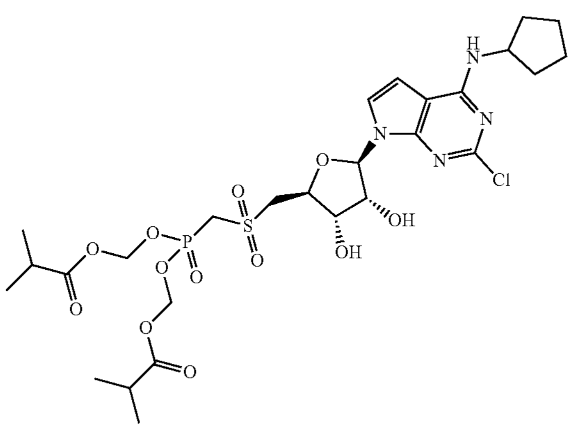 [SMILES: CC(C)C(=O)OCOP(=O)(CS(=O)(=O)C[C@H]1O[C@@H](n2ccc3c(NC4CCCC4)nc(Cl)nc32)[C@H](O)[C@@H]1O)OCOC(=O)C(C)C] | [M + H]⁺: 711 | [[(2S,3S,4R,5R)-5-[2-chloro-4-(cyclopentyl-amino)pyrrolo[2,3-d]-pyrimidin-7-yl]-3,4-dihydroxy-tetrahydro-furan-2-yl]methyl-sulfonylmethyl-(2-methylpropanoyloxy-methoxy)phosphoryl]-oxymethyl 2-methyl-propanoate |
| 307 | 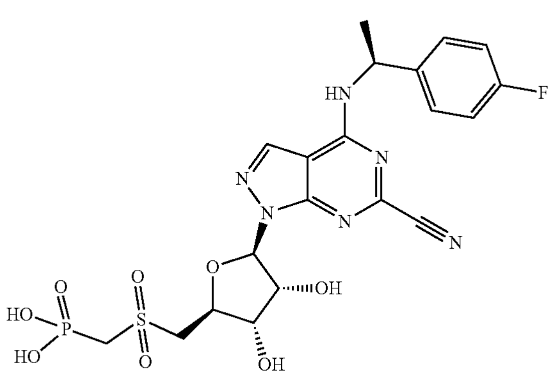 [SMILES: C[C@H](Nc1nc(C#N)nc2c1cnn2[C@@H]1O[C@H](CS(=O)(=O)CP(=O)(O)O)[C@@H](O)[C@H]1O)c1ccc(F)cc1] | [M − H]⁻: 555 | [(2S,3S,4R,5R)-5-[6-cyano-4-[[(1S)-1-(4-fluorophenyl)ethyl]-amino]pyrazolo[3,4-d]pyrimidin-1-yl]-3,4-dihydroxy-tetrahydro-furan-2-yl]methyl-sulfonylmethylphos-phonic acid |

TABLE 1-continued

| No. | Structure | m/z | IUPAC Name |
|---|---|---|---|
| 308 | 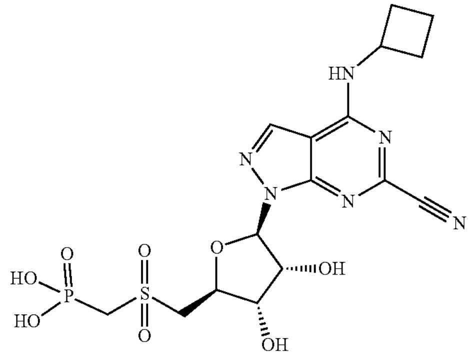 [SMILES: N#Cc1nc(NC2CCC2)c2cnn([C@@H]3O[C@H](CS(=O)(=O)CP(=O)(O)O)[C@@H](O)[C@H]3O)c2n1] | [M − H]⁻: 487 | [(2S,3S,4R,5R)-5-[6-cyano-4-(cyclobutyl-amino)pyrazolo[3,4-d]-pyrimidin-1-yl]-3,4-dihydroxy-tetrahydro-furan-2-yl]methyl-sulfonylmethylphos-phonic acid |

Method of Use: In one aspect, the present invention provides a method for treating a proliferative disorder in a subject in need thereof, comprising administering to said subject a CD73 inhibitor. In some embodiments, the proliferative disorder is a cancer condition. In some further embodiments, said cancer condition is a cancer selected from the group consisting of leukemia, bladder cancer, glioma, glioblastoma, lung cancer, ovarian cancer, melanoma, prostate cancer, thyroid cancer, esophageal cancer, non-small cell lung cancer and breast cancer.

In a further embodiment, the present invention provides a method of treating a cancer condition, wherein the CD73 inhibitor is effective in one or more of inhibiting proliferation of cancer cells, inhibiting metastasis of cancer cells, reducing severity or incidence of symptoms associated with the presence of cancer cells, promoting an immune response to tumor cells, and suppressing hydrolysis of adenosine monophosphate into adensosine. In some embodiments, said method comprises administering to the cancer cells a therapeutically effective amount of a CD73 inhibitor. In some embodiments, the administration takes place in vitro. In other embodiments, the administration takes place in vivo.

As used herein, a therapeutically effective amount of a CD73 inhibitor refers to an amount sufficient to effect the intended application, including but not limited to, disease treatment, as defined herein. Also contemplated in the subject methods is the use of a sub-therapeutic amount of a CD73 inhibitor for treating an intended disease condition.

The amount of the CD73 inhibitor administered may vary depending upon the intended application (in vitro or in vivo), or the subject and disease condition being treated, e.g., the weight and age of the subject, the severity of the disease condition, the manner of administration and the like, which can readily be determined by one of ordinary skill in the art.

Measuring inhibition of biological effects of CD73 can comprise performing an assay on a biological sample, such as a sample from a subject. Any of a variety of samples may be selected, depending on the assay. Examples of samples include, but are not limited to blood samples (e.g. blood plasma or serum), exhaled breath condensate samples, bronchoalveolar lavage fluid, sputum samples, urine samples, and tissue samples.

A subject being treated with a CD73 inhibitor may be monitored to determine the effectiveness of treatment, and the treatment regimen may be adjusted based on the subject's physiological response to treatment. For example, if inhibition of a biological effect of CD73 inhibition is above or below a threshold, the dosing amount or frequency may be decreased or increased, respectively. The methods can further comprise continuing the therapy if the therapy is determined to be efficacious. The methods can comprise maintaining, tapering, reducing, or stopping the administered amount of a compound in the therapy if the therapy is determined to be efficacious. The methods can comprise increasing the administered amount of a compound in the therapy if it is determined not to be efficacious. Alternatively, the methods can comprise stopping therapy if it is determined not to be efficacious. In some embodiments, treatment with a CD73 inhibitor is discontinued if inhibition of the biological effect is above or below a threshold, such as in a lack of response or an adverse reaction. The biological effect may be a change in any of a variety of physiological indicators.

In general, a CD73 inhibitor is a compound that inhibits one or more biological effects of CD73. Examples of biological effects of CD73 include, but are not limited to, production of adenosine and suppression of T cell activation. Such biological effects may be inhibited by about or more than about 10%, 20%, 30%, 40%, 50%, 60%, 70%, 80%, 90%, 95%, or more.

In some other embodiments, the subject methods are useful for treating a disease condition associated with CD73. Any disease condition that results directly or indirectly from an abnormal activity or expression level of CD73 can be an intended disease condition. In some embodiments, the disease condition is a proliferative disorder, such as described herein, including but not limited to cancer. A role of CD73 in tumorigenesis and tumor progression has been implicated in many human cancers. Constitutive activation of CD73 is emerging as a common theme in diverse human cancers, consequently agents that target CD73 have therapeutic value.

The data presented in the Examples herein below demonstrate the anti-cancer effects of a CD73 inhibitor. As such, the subject method is particularly useful for treating a proliferative disorder, such as a neoplastic condition. Non-limiting examples of such conditions include but are not limited to acanthoma, acinic cell carcinoma, acoustic neuroma, acral lentiginous melanoma, acrospiroma, acute eosinophilic leukemia, acute lymphoblastic leukemia, acute megakaryoblastic leukemia, acute monocytic leukemia, acute myeloblastic leukemia with maturation, acute myeloid dendritic cell leukemia, acute myeloid leukemia, acute promyelocytic leukemia, adamantinoma, adenocarcinoma, adenoid cystic carcinoma, adenoma, adenomatoid odontogenic tumor, adrenocortical carcinoma, adult T-cell leukemia, aggressive NK-cell leukemia, AIDS-related cancers, AIDS-related lymphoma, alveolar soft part sarcoma, ameloblastic fibroma, anal cancer, anaplastic large cell lymphoma, anaplastic thyroid cancer, angioimmunoblastic T-cell lymphoma, angiomyolipoma, angiosarcoma, appendix cancer, astrocytoma, atypical teratoid rhabdoid tumor, basal cell carcinoma, basal-like carcinoma, B-cell leukemia, B-cell lymphoma, bellini duct carcinoma, biliary tract cancer, bladder cancer, blastoma, bone cancer, bone tumor, brain stem glioma, brain tumor, breast cancer, brenner tumor, bronchial tumor, bronchioloalveolar carcinoma, brown tumor, Burkitt's lymphoma, carcinoid tumor, carcinoma, carcinosarcoma, Castleman's disease, central nervous system embryonal tumor, cerebellar astrocytoma, cerebral astrocytoma, cervical cancer, cholangiocarcinoma, chondroma, chondrosarcoma, chordoma, choriocarcinoma, choroid plexus papilloma, chronic lymphocytic leukemia, chronic monocytic leukemia, chronic myelogenous leukemia, chronic myeloproliferative disorder, chronic neutrophilic leukemia, clear cell renal cell carcinoma, clear-cell tumor, colon cancer, colorectal cancer, craniopharyngioma, cutaneous T-cell lymphoma, dermatofibrosarcoma protuberans, dermoid cyst, desmoplastic small round cell tumor, diffuse large B cell lymphoma, dysembryoplastic neuroepithelial tumor, embryonal carcinoma, endodermal sinus tumor, endometrial cancer, endometrial uterine cancer, endometrioid tumor, enteropathy-associated T-cell lymphoma, ependymoblastoma, ependymoma, epithelioid sarcoma, erythroleukemia, esophageal cancer, esthesioneuroblastoma, Ewing's sarcoma, extracranial germ cell tumor, extragonadal germ cell tumor, extrahepatic bile duct cancer, extramammary Paget's disease, fallopian tube cancer, fibroma, fibrosarcoma, follicular lymphoma, follicular thyroid cancer, gallbladder cancer, ganglioglioma, ganglioneuroma, gastric cancer, gastric lymphoma, gastrointestinal cancer, gastrointestinal carcinoid tumor, gastrointestinal stromal tumor, germ cell tumor, germinoma, gestational choriocarcinoma, gestational trophoblastic tumor, giant cell tumor of bone, glioblastoma multiforme, glioma, gliomatosis cerebri, *glomus* tumor, glucagonoma, gonadoblastoma, granulosa cell tumor, hairy cell leukemia, head and neck cancer, heart cancer, hemangioblastoma, hemangiopericytoma, hemangiosarcoma, hematological malignancy, hepatocellular carcinoma, hepatosplenic T-cell lymphoma, Hodgkin lymphoma, hypopharyngeal cancer, hypothalamic glioma, inflammatory breast cancer, intraocular melanoma, islet cell carcinoma, juvenile myelomonocytic leukemia, Kaposi's sarcoma, kidney cancer, klatskin tumor, krukenberg tumor, laryngeal cancer, lentigo maligna melanoma, leukemia, lip and oral cavity cancer, liposarcoma, lung cancer, luteoma, lymphangioma, lymphangiosarcoma, lymphoepithelioma, lymphoid leukemia, lymphoma, macroglobulinemia, malignant fibrous histiocytoma, malignant glioma, malignant mesothelioma, malignant peripheral nerve sheath tumor, malignant rhabdoid tumor, malignant triton tumor, malt lymphoma, mantle cell lymphoma, mast cell leukemia, mediastinal germ cell tumor, mediastinal tumor, medullary thyroid cancer, medulloblastoma, medulloepithelioma, melanoma, meningioma, merkel cell carcinoma, mesothelioma, metastatic squamous neck cancer with occult primary, metastatic urothelial carcinoma, mixed mullerian tumor, monocytic leukemia, mouth cancer, mucinous tumor, multiple endocrine neoplasia syndrome, multiple myeloma, mycosis fungoides, myelodysplastic disease, myeloid leukemia, myeloid sarcoma, myeloproliferative disease, myxoma, nasal cavity cancer, nasopharyngeal cancer, neoplasm, neurinoma, neuroblastoma, neurofibroma, neuroma, nodular melanoma, non-Hodgkin lymphoma, non-melanoma skin cancer, non-small cell lung cancer, ocular oncology, oligoastrocytoma, oligodendroglioma, oncocytoma, optic nerve sheath meningioma, oral cancer, oropharyngeal cancer, osteosarcoma, ovarian cancer, ovarian epithelial cancer, ovarian germ cell tumor, ovarian low malignant potential tumor, pancoast tumor, pancreatic cancer, papillary thyroid cancer, papillomatosis, paraganglioma, paranasal sinus cancer, parathyroid cancer, penile cancer, perivascular epithelioid cell tumor, pharyngeal cancer, pheochromocytoma, pineal parenchymal tumor of intermediate differentiation, pineoblastoma, pituicytoma, pituitary adenoma, pituitary tumor, plasma cell neoplasm, pleuropulmonary blastoma, polyembryoma, precursor T-lymphoblastic lymphoma, primitive neuroectodermal tumor, prostate cancer, pseudomyxoma peritonei, rectal cancer, renal cell carcinoma, retinoblastoma, rhabdomyoma, rhabdomyosarcoma, Richter's transformation, sacrococcygeal teratoma, salivary gland cancer, sarcoma, schwannomatosis, sebaceous gland carcinoma, secondary neoplasm, seminoma, serous tumor, Sertoli-Leydig cell tumor, sex cord-stromal tumor, sezary syndrome, signet ring cell carcinoma, skin cancer, small blue round cell tumor, small cell carcinoma, small cell lung cancer, small cell lymphoma, small intestine cancer, soft tissue sarcoma, somatostatinoma, soot wart, spinal tumor, splenic marginal zone lymphoma, squamous cell carcinoma, stomach cancer, superficial spreading melanoma, supratentorial primitive neuroectodermal tumor, surface epithelial-stromal tumor, synovial sarcoma, T-cell acute lymphoblastic leukemia, T-cell large granular lymphocyte leukemia, T-cell leukemia, T-cell lymphoma, T-cell prolymphocytic leukemia, teratoma, terminal lymphatic cancer, testicular cancer, thecoma, throat cancer, thymic carcinoma, thymoma, thyroid cancer, transitional cell cancer of renal pelvis and ureter, transitional cell carcinoma, urachal cancer, urethral cancer, urogenital neoplasm, uterine sarcoma, uveal melanoma, vaginal cancer, verner morrison syndrome, verrucous carcinoma, visual pathway glioma, vulvar cancer, Waldenstrom's macroglobulinemia, Warthin's tumor, Wilms' tumor or any combination thereof.

In some embodiments, the methods of administering a CD73 inhibitor described herein are applied to the treatment of cancers of the adrenal glands, blood, bone marrow, brain, breast, cervix, colon, head and neck, kidney, liver, lung, ovary, pancreas, plasma cells, rectum, retina, skin, spine, throat or any combination thereof.

Certain embodiments contemplate a human subject such as a subject that has been diagnosed as having or being at risk for developing or acquiring a proliferative disorder condition. Certain other embodiments contemplate a non-human subject, for example a non-human primate such as a macaque, chimpanzee, gorilla, vervet, orangutan, baboon or other non-human primate, including such non-human subjects that can be known to the art as preclinical models. Certain other embodiments contemplate a non-human subject that is a mammal, for example, a mouse, rat, rabbit, pig, sheep, horse, bovine, goat, gerbil, hamster, guinea pig or other mammal. There are also contemplated other embodiments in which the subject or biological source can be a non-mammalian vertebrate, for example, another higher vertebrate, or an avian, amphibian or reptilian species, or another subject or biological source. In certain embodiments of the present invention, a transgenic animal is utilized. A transgenic animal is a non-human animal in which one or more of the cells of the animal includes a nucleic acid that is non-endogenous (i.e., heterologous) and is present as an extrachromosomal element in a portion of its cell or stably integrated into its germ line DNA (i.e., in the genomic sequence of most or all of its cells).

Therapeutic Efficacy: In some embodiments, therapeutic efficacy is measured based on an effect of treating a proliferative disorder, such as cancer. In general, therapeutic efficacy of the methods and compositions of the invention, with regard to the treatment of a proliferative disorder (e.g. cancer, whether benign or malignant), may be measured by the degree to which the methods and compositions promote inhibition of tumor cell proliferation, the inhibition of tumor vascularization, the eradication of tumor cells, the reduction in the rate of growth of a tumor, and/or a reduction in the size of at least one tumor. Several parameters to be considered in the determination of therapeutic efficacy are discussed herein. The proper combination of parameters for a particular situation can be established by the clinician. The progress of the inventive method in treating cancer (e.g., reducing tumor size or eradicating cancerous cells) can be ascertained using any suitable method, such as those methods currently used in the clinic to track tumor size and cancer progress. The primary efficacy parameter used to evaluate the treatment of cancer by the inventive method and compositions preferably is a reduction in the size of a tumor. Tumor size can be figured using any suitable technique, such as measurement of dimensions, or estimation of tumor volume using available computer software, such as FreeFlight software developed at Wake Forest University that enables accurate estimation of tumor volume. Tumor size can be determined by tumor visualization using, for example, CT, ultrasound, SPECT, spiral CT, MRI, photographs, and the like. In embodiments where a tumor is surgically resected after completion of the therapeutic period, the presence of tumor tissue and tumor size can be determined by gross analysis of the tissue to be resected, and/or by pathological analysis of the resected tissue.

In some desirable embodiments, the growth of a tumor is stabilized (i.e., one or more tumors do not increase more than 1%, 5%, 10%, 15%, or 20% in size, and/or do not metastasize) as a result of the inventive method and compositions. In some embodiments, a tumor is stabilized for at least about 1, 2, 3, 4, 5, 6, 7, 8, 9, 10, 11, 12, or more weeks. In some embodiments, a tumor is stabilized for at least about 1, 2, 3, 4, 5, 6, 7, 8, 9, 10, 11, 12, or more months. In some embodiments, a tumor is stabilized for at least about 1, 2, 3, 4, 5, 6, 7, 8, 9, 10, or more years. Preferably, the inventive method reduces the size of a tumor at least about 5% (e.g., at least about 10%, 15%, 20%, or 25%). More preferably, tumor size is reduced at least about 30% (e.g., at least about 35%, 40%, 45%, 50%, 55%, 60%, or 65%). Even more preferably, tumor size is reduced at least about 70% (e.g., at least about 75%, 80%, 85%, 90%, or 95%). Most preferably, the tumor is completely eliminated, or reduced below a level of detection. In some embodiments, a subject remains tumor free (e.g. in remission) for at least about 1, 2, 3, 4, 5, 6, 7, 8, 9, 10, 11, 12, or more weeks following treatment. In some embodiments, a subject remains tumor free for at least about 1, 2, 3, 4, 5, 6, 7, 8, 9, 10, 11, 12, or more months following treatment. In some embodiments, a subject remains tumor free for at least about 1, 2, 3, 4, 5, 6, 7, 8, 9, 10, or more years after treatment.

In some embodiments, the efficacy of the inventive method in reducing tumor size can be determined by measuring the percentage of necrotic (i.e., dead) tissue of a surgically resected tumor following completion of the therapeutic period. In some further embodiments, a treatment is therapeutically effective if the necrosis percentage of the resected tissue is greater than about 20% (e.g., at least about 30%, 40%, 50%, 60%, 70%, 80%, 90%, or 100%), more preferably about 90% or greater (e.g., about 90%, 95%, or 100%). Most preferably, the necrosis percentage of the resected tissue is 100%, that is, no tumor tissue is present or detectable.

The efficacy of the inventive method can be determined by a number of secondary parameters. Examples of secondary parameters include, but are not limited to, detection of new tumors, detection of tumor antigens or markers (e.g., CEA, PSA, or CA-125), biopsy, surgical downstaging (i.e., conversion of the surgical stage of a tumor from unresectable to resectable), PET scans, survival, disease progression-free survival, time to disease progression, quality of life assessments such as the Clinical Benefit Response Assessment, and the like, all of which can point to the overall progression (or regression) of cancer in a human. Biopsy is particularly useful in detecting the eradication of cancerous cells within a tissue. Radioimmunodetection (RAID) is used to locate and stage tumors using serum levels of markers (antigens) produced by and/or associated with tumors ("tumor markers" or "tumor-associated antigens"), and can be useful as a pre-treatment diagnostic predicate, a post-treatment diagnostic indicator of recurrence, and a post-treatment indicator of therapeutic efficacy. Examples of tumor markers or tumor-associated antigens that can be evaluated as indicators of therapeutic efficacy include, but are not limited to, carcinembryonic antigen (CEA), prostate-specific antigen (PSA), CA-125, CA19-9, ganglioside molecules (e.g., GM2, GD2, and GD3), MART-1, heat shock proteins (e.g., gp96), sialyl Tn (STn), tyrosinase, MUC-1, HER-2/neu, c-erb-B2, KSA, PSMA, p53, RAS, EGF-R, VEGF, MAGE, and gp100. Other tumor-associated antigens are known in the art. RAID technology in combination with endoscopic detection systems also can efficiently distinguish small tumors from surrounding tissue (see, for example, U.S. Pat. No. 4,932,412).

In additional desirable embodiments, the treatment of cancer in a human patient in accordance with the inventive method is evidenced by one or more of the following results: (a) the complete disappearance of a tumor (i.e., a complete response), (b) about a 25% to about a 50% reduction in the size of a tumor for at least four weeks after completion of the therapeutic period as compared to the size of the tumor before treatment, (c) at least about a 50% reduction in the size of a tumor for at least four weeks after completion of the therapeutic period as compared to the size of the tumor before the therapeutic period, and (d) at least a 2% decrease (e.g., about a 5%, 10%, 20%, 30%, 40%, 50%, 60%, 70%, 80% or 90% decrease) in a specific tumor-associated antigen level at about 4-12 weeks after completion of the therapeutic period as compared to the tumor-associated antigen level before the therapeutic period. While at least a 2% decrease in a tumor-associated antigen level is preferred, any decrease in the tumor-associated antigen level is evidence of treatment of a cancer in a patient by the inventive method. For example, with respect to unresectable, locally advanced pancreatic cancer, treatment can be evidenced by at least a 10% decrease in the CA19-9 tumor-associated antigen level at 4-12 weeks after completion of the therapeutic period as compared to the CA19-9 level before the therapeutic period. Similarly, with respect to locally advanced rectal cancer, treatment can be evidenced by at least a 10% decrease in the CEA tumor-associated antigen level at 4-12 weeks after completion of the therapeutic period as compared to the CEA level before the therapeutic period.

With respect to quality of life assessments, such as the Clinical Benefit Response Criteria, the therapeutic benefit of the treatment in accordance with the invention can be evidenced in terms of pain intensity, analgesic consumption, and/or the Karnofsky Performance Scale score. The treatment of cancer in a human patient alternatively, or in addition, is evidenced by (a) at least a 50% decrease (e.g., at least a 60%, 70%, 80%, 90%, or 100% decrease) in pain intensity reported by a patient, such as for any consecutive four week period in the 12 weeks after completion of treatment, as compared to the pain intensity reported by the patient before treatment, (b) at least a 50% decrease (e.g., at least a 60%, 70%, 80%, 90%, or 100% decrease) in analgesic consumption reported by a patient, such as for any consecutive four week period in the 12 weeks after completion of treatment as compared to the analgesic consumption reported by the patient before treatment, and/or (c) at least a 20 point increase (e.g., at least a 30 point, 50 point, 70 point, or 90 point increase) in the Kamofsky Performance Scale score reported by a patient, such as for any consecutive four week period in the 12 weeks after completion of the therapeutic period as compared to the Kamofsky Performance Scale score reported by the patient before the therapeutic period.

The treatment of a proliferative disorder (e.g. cancer, whether benign or malignant) in a human patient desirably is evidenced by one or more (in any combination) of the foregoing results, although alternative or additional results of the referenced tests and/or other tests can evidence treatment efficacy.

In some embodiments, tumor size is reduced as a result of the inventive method preferably without significant adverse events in the subject. Adverse events are categorized or "graded" by the Cancer Therapy Evaluation Program (CTEP) of the National Cancer Institute (NCI), with Grade 0 representing minimal adverse side effects and Grade 4 representing the most severe adverse events. Desirably, the inventive method is associated with minimal adverse events, e.g. Grade 0, Grade 1, or Grade 2 adverse events, as graded by the CTEP/NCI. However, as discussed herein, reduction of tumor size, although preferred, is not required in that the actual size of tumor may not shrink despite the eradication of tumor cells. Eradication of cancerous cells is sufficient to realize a therapeutic effect. Likewise, any reduction in tumor size is sufficient to realize a therapeutic effect.

Detection, monitoring and rating of various cancers in a human are further described in Cancer Facts and Figures 2001, American Cancer Society, New York, N.Y., and International Patent Application WO 01/24684. Accordingly, a clinician can use standard tests to determine the efficacy of the various embodiments of the inventive method in treating cancer. However, in addition to tumor size and spread, the clinician also may consider quality of life and survival of the patient in evaluating efficacy of treatment.

In some embodiments, administration of a CD73 inhibitor provides improved therapeutic efficacy. Improved efficacy may be measured using any method known in the art, including but not limited to those described herein. In some embodiments, the improved therapeutic efficacy is an improvement of at least about 10%, 20%, 30%, 40%, 50%, 60%, 70%, 75%, 80%, 90%, 95%, 100%, 110%, 120%, 150%, 200%, 300%, 400%, 500%, 600%, 700%, 1000% or more, using an appropriate measure (e.g. tumor size reduction, duration of tumor size stability, duration of time free from metastatic events, duration of disease-free survival).

Improved efficacy may also be expressed as fold improvement, such as at least about 2-fold, 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, 100-fold, 1000-fold, 10000-fold or more, using an appropriate measure (e.g. tumor size reduction, duration of tumor size stability, duration of time free from metastatic events, duration of disease-free survival).

Pharmaceutical compositions: A composition of the present disclosure may be formulated in any suitable pharmaceutical formulation. A pharmaceutical composition of the present disclosure typically contains an active ingredient (e.g., a compound of Formulas (I), (II-A), (II-B), (III), or a pharmaceutically acceptable salt and/or coordination complex thereof), and one or more pharmaceutically acceptable excipients, carriers, including but not limited to, inert solid diluents and fillers, diluents, sterile aqueous solution and various organic solvents, permeation enhancers, solubilizers and adjuvants. A composition of the present disclosure may be formulated in any suitable pharmaceutical formulation. In some embodiments, the pharmaceutical acceptable carriers, excipients are selected from water, alcohol, glycerol, chitosan, alginate, chondroitin, Vitamin E, mineral oil, and dimethyl sulfoxide (DMSO).

Pharmaceutical formulations may be provided in any suitable form, which may depend on the route of administration. In some embodiments, the pharmaceutical composition disclosed herein can be formulated in dosage form for administration to a subject. In some embodiments, the pharmaceutical composition is formulated for oral, intravenous, intraarterial, aerosol, parenteral, buccal, topical, transdermal, rectal, intramuscular, subcutaneous, intraosseous, intranasal, intrapulmonary, transmucosal, inhalation, and/or intraperitoneal administration. In some embodiments, the dosage form is formulated for oral intervention administration. For example, the pharmaceutical composition can be formulated in the form of a pill, a tablet, a capsule, an inhaler, a liquid suspension, a liquid emulsion, a gel, or a powder. In some embodiments, the pharmaceutical composition can be formulated as a unit dosage in liquid, gel, semi-liquid, semi-solid, or solid form.

The amount of each compound administered will be dependent on the mammal being treated, the severity of the disorder or condition, the rate of administration, the disposition of the compound and the discretion of the prescribing physician. However, an effective dosage may be in the range of about 0.001 to about 100 mg per kg body weight per day, in single or divided doses. In some instances, dosage levels below the lower limit of the aforesaid range may be more than adequate, while in other cases still larger doses may be employed without causing any harmful side effect, e.g., by dividing such larger doses into several small doses for administration throughout the day.

In some embodiments, the disclosure provides a pharmaceutical composition comprising an amount of a CD73 inhibitor formulated for administration to a subject in need thereof. In some embodiments, the pharmaceutical composition comprises between about 0.0001-500 g, 0.001-250 g, 0.01-100 g, 0.1-50 g, or 1-10 g of CD73 inhibitor. In some embodiments, the pharmaceutical composition comprises about or more than about 0.0001 g, 0.001 g, 0.01 g, 0.1, 0.5 g, 1 g, 2 g, 3 g, 4 g, 5 g, 6 g, 7 g, 8 g, 9 g,10 g, 15 g, 20 g, 25 g, 50 g, 100 g, 200 g, 250 g, 300 g, 350 g, 400 g, 450 g, 500 g, or more of a CD73 inhibitor. In some embodiments, the pharmaceutical composition comprises between 0.001-2 g of a CD73 inhibitor in a single dose. In some embodiments, the pharmaceutical composition comprises an amount between about 50-150 g of a CD73 inhibitor. In some embodiments, the therapeutic amount can be an amount between about 0.001-0.1 g of a CD73 inhibitor. In some embodiments, the therapeutic amount can be an amount between about 0.01-30 g of a CD73 inhibitor.

In some embodiments, a therapeutically effective amount of CD73 inhibitor, which can be a daily amount administered over the course of a period of treatment, can sufficiently provide any one or more of the therapeutic effects described herein. As an example, the therapeutic effective amount can be in the range of about 0.001-1000 mg/kg body weight, 0.01-500 mg/kg body weight, 0.01-100 mg/kg body weight, 0.01-30 mg/kg body weight, 0.1-200 mg/kg body weight, 3-200 mg/kg body weight, 5-500 mg/kg body weight, 10-100 mg/kg body weight, 10-1000 mg/kg body weight, 50-200 mg/kg body weight, 100-1000 mg/kg body weight, 200-500 mg/kg body weight, 250-350 mg/kg body weight, or 300-600 mg/kg body weight of a CD73 inhibitor. In some embodiments, the therapeutic amount can be about or more than about 0.001 mg/kg body weight, 0.01 mg/kg body weight, 0.1 mg/kg body weight, 0.5 mg/kg body weight, 1 mg/kg body weight, 2 mg/kg body weight, 3 mg/kg body weight, 4 mg/kg body weight, 5 mg/kg body weight, 6 mg/kg body weight, 7 mg/kg body weight, 8 mg/kg body weight, 9 mg/kg body weight, 10 mg/kg body weight, 15 mg/kg body weight, 20 mg/kg body weight, 25 mg/kg body weight, 50 mg/kg body weight, 100 mg/kg body weight, 200 mg/kg body weight, 250 mg/kg body weight, 300 mg/kg body weight, 350 mg/kg body weight, 400 mg/kg body weight, 450 mg/kg body weight, 500 mg/kg body weight, 600 mg/kg body weight, 800 mg/kg body weight, 1000 mg/kg body weight, or more of a CD73 inhibitor. In some embodiments, the effective amount is at least about 0.01 mg/kg body weight of a CD73 inhibitor. In some embodiments, the effective amount is an amount between about 0.01-30 mg/kg body weight of a CD73 inhibitor. In some embodiments, the therapeutic amount can be an amount between about 50-150 mg/kg body weight of a CD73 inhibitor.

In some embodiments, the composition is provided in one or more unit doses. For example, the composition can be administered in 1, 2, 3, 4, 5, 6, 7, 14, 30, 60, or more doses. Such amount can be administered each day, for example in individual doses administered once, twice, or three or more times a day. However, dosages stated herein on a per day basis should not be construed to require administration of the daily dose each and every day. For example, if one of the agents is provided in a suitably slow-release form, two or more daily dosage amounts can be administered at a lower frequency, e.g., as a depot every second day to once a month or even longer. Most typically and conveniently for the subject, a CD73 inhibitor can be administered once a day, for example in the morning, in the evening or during the day.

The unit doses can be administered simultaneously or sequentially. The composition can be administered for an extended treatment period. Illustratively, the treatment period can be at least about one month, for example at least about 3 months, at least about 6 months or at least about 1 year. In some cases, administration can continue for substantially the remainder of the life of the subject.

In some embodiments, the CD73 inhibitor can be administered as part of a therapeutic regimen that comprises administering one or more second agents (e.g. 1, 2, 3, 4, 5, or more second agents), either simultaneously or sequentially with the CD73 inhibitor. When administered sequentially, the CD73 inhibitor may be administered before or after the one or more second agents. When administered simultaneously, the CD73 inhibitor and the one or more second agents may be administered by the same route (e.g. injections to the same location; tablets taken orally at the same time), by a different route (e.g. a tablet taken orally while receiving an intravenous infusion), or as part of the same combination (e.g. a solution comprising a CD73 inhibitor and one or more second agents).

A combination treatment according to the invention may be effective over a wide dosage range. For example, in the treatment of adult humans, dosages from 0.01 to 1000 mg, from 0.5 to 100 mg, from 1 to 50 mg per day, and from 5 to 40 mg per day are examples of dosages that may be used. The exact dosage will depend upon the agent selected, the route of administration, the form in which the compound is administered, the subject to be treated, the body weight of the subject to be treated, and the preference and experience of the attending physician.

Pharmaceutical composition for oral administration: In some embodiments, the disclosure provides a pharmaceutical composition for oral administration containing at least one compound of the present disclosure and a pharmaceutical excipient suitable for oral administration. The composition may be in the form of a solid, liquid, gel, semi-liquid, or semi-solid. In some embodiments, the composition further comprises a second agent.

In some embodiments, the invention provides a solid pharmaceutical composition for oral administration containing: (i) a CD73 inhibitor; and (ii) a pharmaceutical excipient suitable for oral administration. In some embodiments, the composition further contains: (iii) a third agent or even a fourth agent. In some embodiments, each compound or agent is present in a therapeutically effective amount. In other embodiments, one or more compounds or agents is present in a sub-therapeutic amount, and the compounds or agents act synergistically to provide a therapeutically effective pharmaceutical composition.

Pharmaceutical compositions of the disclosure suitable for oral administration can be presented as discrete dosage forms, such as hard or soft capsules, cachets, troches, lozenges, or tablets, or liquids or aerosol sprays each containing a predetermined amount of an active ingredient as a powder or in granules, a solution, or a suspension in an aqueous or non-aqueous liquid, an oil-in-water emulsion, or a water-in-oil liquid emulsion, or dispersible powders or granules, or syrups or elixirs. Such dosage forms can be prepared by any of the methods of pharmacy, which typically include the step of bringing the active ingredient(s) into association with the carrier. In general, the composition are prepared by uniformly and intimately admixing the active ingredient(s) with liquid carriers or finely divided solid carriers or both, and then, if necessary, shaping the product into the desired presentation. For example, a tablet can be prepared by compression or molding, optionally with one or more accessory ingredients. Compressed tablets can be prepared by compressing in a suitable machine the active ingredient(s) in a free-flowing form such as powder or granules, optionally mixed with an excipient such as, but not limited to, a binder, a lubricant, an inert diluent, and/or a surface active or dispersing agent. Molded tablets can be made by molding in a suitable machine a mixture of the powdered compound moistened with an inert liquid diluent.

This disclosure further encompasses anhydrous pharmaceutical composition and dosage forms comprising an active ingredient, since water can facilitate the degradation of some compounds. For example, water may be added (e.g., 5%) in the pharmaceutical arts as a means of simulating long-term storage in order to determine characteristics such as shelflife or the stability of formulations over time. Anhydrous pharmaceutical compositions and dosage forms of the disclosure can be prepared using anhydrous or low moisture containing ingredients and low moisture or low humidity conditions. Pharmaceutical compositions and dosage forms of the disclosure which contain lactose can be made anhydrous if substantial contact with moisture and/or humidity during manufacturing, packaging, and/or storage is expected. An anhydrous pharmaceutical composition may be prepared and stored such that its anhydrous nature is maintained. Accordingly, anhydrous compositions may be packaged using materials known to prevent exposure to water such that they can be included in suitable formulary kits. Examples of suitable packaging include, but are not limited to, hermetically sealed foils, plastic or the like, unit dose containers, blister packs, and strip packs.

An active ingredient can be combined in an intimate admixture with a pharmaceutical carrier according to conventional pharmaceutical compounding techniques. The carrier can take a wide variety of forms depending on the form of preparation desired for administration. In preparing the composition for an oral dosage form, any of the usual pharmaceutical media can be employed as carriers, such as, for example, water, glycols, oils, alcohols, flavoring agents, preservatives, coloring agents, and the like in the case of oral liquid preparations (such as suspensions, solutions, and elixirs) or aerosols; or carriers such as starches, sugars, micro-crystalline cellulose, diluents, granulating agents, lubricants, binders, and disintegrating agents can be used in the case of oral solid preparations, in some embodiments without employing the use of lactose. For example, suitable carriers include powders, capsules, and tablets, with the solid oral preparations. If desired, tablets can be coated by standard aqueous or nonaqueous techniques.

Binders suitable for use in pharmaceutical composition and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, microcrystalline cellulose, and mixtures thereof.

Examples of suitable fillers for use in the pharmaceutical composition and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof.

Disintegrants may be used in the composition of the disclosure to provide tablets that disintegrate when exposed to an aqueous environment. Too much of a disintegrant may produce tablets which may disintegrate in the bottle. Too little may be insufficient for disintegration to occur and may alter the rate and extent of release of the active ingredient(s) from the dosage form. A sufficient amount of disintegrant that is neither too little nor too much to detrimentally alter the release of the active ingredient(s) may be used to form the dosage forms of the compounds disclosed herein. The amount of disintegrant used may vary based upon the type of formulation and mode of administration, and may be readily discernible to those of ordinary skill in the art. About 0.5 to about 15 weight percent of disintegrant, or about 1 to about 5 weight percent of disintegrant, may be used in the pharmaceutical composition. Disintegrants that can be used to form pharmaceutical composition and dosage forms of the disclosure include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums or mixtures thereof.

Lubricants which can be used to form pharmaceutical composition and dosage forms of the disclosure include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethylaureate, agar, or mixtures thereof. Additional lubricants include, for example, a syloid silica gel, a coagulated aerosol of synthetic silica, or mixtures thereof. A lubricant can optionally be added, in an amount of less than about 1 weight percent of the pharmaceutical composition.

When aqueous suspensions and/or elixirs are desired for oral administration, the active ingredient therein may be combined with various sweetening or flavoring agents, coloring matter or dyes and, if so desired, emulsifying and/or suspending agents, together with such diluents as water, ethanol, propylene glycol, glycerin and various combinations thereof.

The tablets can be uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Surfactant which can be used to form pharmaceutical composition and dosage forms of the disclosure include, but are not limited to, hydrophilic surfactants, lipophilic surfactants, and mixtures thereof. That is, a mixture of hydrophilic surfactants may be employed, a mixture of lipophilic surfactants may be employed, or a mixture of at least one hydrophilic surfactant and at least one lipophilic surfactant may be employed.

A suitable hydrophilic surfactant may generally have an HLB value of at least 10, while suitable lipophilic surfactants may generally have an HLB value of or less than about 10. An empirical parameter used to characterize the relative hydrophilicity and hydrophobicity of non-ionic amphiphilic compounds is the hydrophilic-lipophilic balance ("HLB" value). Surfactants with lower HLB values are more lipophilic or hydrophobic, and have greater solubility in oils, while surfactants with higher HLB values are more hydrophilic, and have greater solubility in aqueous solutions. Hydrophilic surfactants are generally considered to be those compounds having an HLB value greater than about 10, as well as anionic, cationic, or zwitterionic compounds for which the HLB scale is not generally applicable. Similarly, lipophilic (i.e., hydrophobic) surfactants are compounds having an HLB value equal to or less than about 10. However, HLB value of a surfactant is merely a rough guide generally used to enable formulation of industrial, pharmaceutical and cosmetic emulsions.

Hydrophilic surfactants may be either ionic or non-ionic. Suitable ionic surfactants include, but are not limited to, alkylammonium salts; fusidic acid salts; fatty acid derivatives of amino acids, oligopeptides, and polypeptides; glyceride derivatives of amino acids, oligopeptides, and polypeptides; lecithins and hydrogenated lecithins; lysolecithins and hydrogenated lysolecithins; phospholipids and derivatives thereof; lysophospholipids and derivatives thereof; carnitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and mixtures thereof.

Within the aforementioned group, ionic surfactants include, by way of example: lecithins, lysolecithin, phospholipids, lysophospholipids and derivatives thereof; carnitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and mixtures thereof.

Ionic surfactants may be the ionized forms of lecithin, lysolecithin, phosphatidylcholine, phosphatidylethanolamine, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine, lactylic esters of fatty acids, stearoyl-2-lactylate, stearoyl lactylate, succinylated monoglycerides, mono/diacetylated tartaric acid esters of mono/diglycerides, citric acid esters of mono/diglycerides, cholylsarcosine, caproate, caprylate, caprate, laurate, myristate, palmitate, oleate, ricinoleate, linoleate, linolenate, stearate, lauryl sulfate, teracecyl sulfate, docusate, lauroyl carnitines, palmitoyl carnitines, myristoyl carnitines, and salts and mixtures thereof.

Hydrophilic non-ionic surfactants may include, but not limited to, alkylglucosides; alkylmaltosides; alkylthioglucosides; lauryl macrogolglycerides; polyoxyalkylene alkyl ethers such as polyethylene glycol alkyl ethers; polyoxyalkylene alkylphenols such as polyethylene glycol alkyl phenols; polyoxyalkylene alkyl phenol fatty acid esters such as polyethylene glycol fatty acids monoesters and polyethylene glycol fatty acids diesters; polyethylene glycol glycerol fatty acid esters; polyglycerol fatty acid esters; polyoxyalkylene sorbitan fatty acid esters such as polyethylene glycol sorbitan fatty acid esters; hydrophilic transesterification products of a polyol with at least one member of the group of glycerides, vegetable oils, hydrogenated vegetable oils, fatty acids, and sterols; polyoxyethylene sterols, derivatives, and analogues thereof; polyoxyethylated vitamins and derivatives thereof; polyoxyethylene-polyoxypropylene block copolymers; and mixtures thereof; polyethylene glycol sorbitan fatty acid esters and hydrophilic transesterification products of a polyol with at least one member of the group of triglycerides, vegetable oils, and hydrogenated vegetable oils. The polyol may be glycerol, ethylene glycol, polyethylene glycol, sorbitol, propylene glycol, pentaerythritol, or a saccharide.

Other hydrophilic-non-ionic surfactants include, without limitation, PEG-10 laurate, PEG-12 laurate, PEG-20 laurate, PEG-32 laurate, PEG-32 dilaurate, PEG-12 oleate, PEG-15 oleate, PEG-20 oleate, PEG-20 dioleate, PEG-32 oleate, PEG-200 oleate, PEG-400 oleate, PEG-15 stearate, PEG-32 distearate, PEG-40 stearate, PEG-100 stearate, PEG-20 dilaurate, PEG-25 glyceryl trioleate, PEG-32 dioleate, PEG-20 glyceryl laurate, PEG-30 glyceryl laurate, PEG-20 glyceryl stearate, PEG-20 glyceryl oleate, PEG-30 glyceryl oleate, PEG-30 glyceryl laurate, PEG-40 glyceryl laurate, PEG-40 palm kernel oil, PEG-50 hydrogenated castor oil, PEG-40 castor oil, PEG-35 castor oil, PEG-60 castor oil, PEG-40 hydrogenated castor oil, PEG-60 hydrogenated castor oil, PEG-60 corn oil, PEG-6 caprate/caprylate glycerides, PEG-8 caprate/caprylate glycerides, polyglyceryl-10 laurate, PEG-30 cholesterol, PEG-25 phyto sterol, PEG-30 soya sterol, PEG-20 trioleate, PEG-40 sorbitan oleate, PEG-80 sorbitan laurate, polysorbate 20, polysorbate 80, POE-9 lauryl ether, POE-23 lauryl ether, POE-10 oleyl ether, POE-20 oleyl ether, POE-20 stearyl ether, tocopheryl PEG-100 succinate, PEG-24 cholesterol, polyglyceryl-10 oleate, Tween 40, Tween 60, sucrose monostearate, sucrose monolaurate, sucrose monopalmitate, PEG 10-100 nonyl phenol series, PEG 15-100 octyl phenol series, and poloxamers.

Suitable lipophilic surfactants include, by way of example only: fatty alcohols; glycerol fatty acid esters; acetylated glycerol fatty acid esters; lower alcohol fatty acids esters; propylene glycol fatty acid esters; sorbitan fatty acid esters; polyethylene glycol sorbitan fatty acid esters; sterols and sterol derivatives; polyoxyethylated sterols and sterol derivatives; polyethylene glycol alkyl ethers; sugar esters; sugar ethers; lactic acid derivatives of mono- and di-glycerides; hydrophobic transesterification products of a polyol with at least one member of the group of glycerides, vegetable oils, hydrogenated vegetable oils, fatty acids and sterols; oil-soluble vitamins/vitamin derivatives; and mixtures thereof. Within this group, preferred lipophilic surfactants include glycerol fatty acid esters, propylene glycol fatty acid esters, and mixtures thereof, or are hydrophobic transesterification products of a polyol with at least one member of the group of vegetable oils, hydrogenated vegetable oils, and triglycerides.

In one embodiment, the composition may include a solubilizer to ensure good solubilization and/or dissolution of the compound of the present disclosure and to minimize precipitation of the compound of the present disclosure. This can be especially important for composition for non-oral use, e.g., composition for injection. A solubilizer may also be added to increase the solubility of the hydrophilic drug and/or other components, such as surfactants, or to maintain the composition as a stable or homogeneous solution or dispersion.

Examples of suitable solubilizers include, but are not limited to, the following: alcohols and polyols, such as ethanol, isopropanol, butanol, benzyl alcohol, ethylene glycol, propylene glycol, butanediols and isomers thereof, glycerol, pentaerythritol, sorbitol, mannitol, transcutol, dimethyl isosorbide, polyethylene glycol, polypropylene glycol, polyvinylalcohol, hydroxypropyl methylcellulose and other cellulose derivatives, cyclodextrins and cyclodextrin derivatives; ethers of polyethylene glycols having an average molecular weight of about 200 to about 6000, such as tetrahydrofurfuryl alcohol PEG ether (glycofurol) or methoxy PEG; amides and other nitrogen-containing compounds such as 2-pyrrolidone, 2-piperidone, ε-caprolactam, N-alkylpyrrolidone, N-hydroxyalkylpyrrolidone, N-alkylpiperidone, N-alkylcaprolactam, dimethylacetamide and polyvinylpyrrolidone; esters such as ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, ε-caprolactone and isomers thereof, δ-valerolactone and isomers thereof, β-butyrolactone and isomers thereof, and other solubilizers known in the art, such as dimethyl acetamide, dimethyl isosorbide, N-methyl pyrrolidones, monooctanoin, diethylene glycol monoethyl ether, and water.

Mixtures of solubilizers may also be used. Examples include, but not limited to, triacetin, triethylcitrate, ethyl oleate, ethyl caprylate, dimethylacetamide, N-methylpyrrolidone, N-hydroxyethylpyrrolidone, polyvinylpyrrolidone, hydroxypropyl methylcellulose, hydroxypropyl cyclodextrins, ethanol, polyethylene glycol 200-100, glycofurol, transcutol, propylene glycol, and dimethyl isosorbide. Particularly preferred solubilizers include sorbitol, glycerol, triacetin, ethyl alcohol, PEG-400, glycofurol and propylene glycol.

The amount of solubilizer that can be included is not particularly limited. The amount of a given solubilizer may be limited to a bioacceptable amount, which may be readily determined by one of skill in the art. In some circumstances, it may be advantageous to include amounts of solubilizers far in excess of bioacceptable amounts, for example to maximize the concentration of the drug, with excess solubilizer removed prior to providing the composition to a patient using conventional techniques, such as distillation or evaporation. If present, the solubilizer can be in a weight ratio of 10%, 25%, 50%, 100%, or up to about 200% by weight, based on the combined weight of the drug, and other excipients. If desired, very small amounts of solubilizer may also be used, such as 5%, 2%, 1% or even less. Typically, the solubilizer may be present in an amount of about 1% to about 100%, more typically about 5% to about 25% by weight.

The composition can further include one or more pharmaceutically acceptable additives and excipients. Such additives and excipients include, without limitation, detackifiers, anti-foaming agents, buffering agents, polymers, antioxidants, preservatives, chelating agents, viscomodulators, tonicifiers, flavorants, colorants, odorants, opacifiers, suspending agents, binders, fillers, plasticizers, lubricants, and mixtures thereof.

In addition, an acid or a base may be incorporated into the composition to facilitate processing, to enhance stability, or for other reasons. Examples of pharmaceutically acceptable bases include amino acids, amino acid esters, ammonium hydroxide, potassium hydroxide, sodium hydroxide, sodium hydrogen carbonate, aluminum hydroxide, calcium carbonate, magnesium hydroxide, magnesium aluminum silicate, synthetic aluminum silicate, synthetic hydrocalcite, magnesium aluminum hydroxide, diisopropylethylamine, ethanolamine, ethylenediamine, triethanolamine, triethylamine, triisopropanolamine, trimethylamine, tris(hydroxymethyl) aminomethane (TRIS) and the like. Also suitable are bases that are salts of a pharmaceutically acceptable acid, such as acetic acid, acrylic acid, adipic acid, alginic acid, alkanesulfonic acid, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid, and the like. Salts of polyprotic acids, such as sodium phosphate, disodium hydrogen phosphate, and sodium dihydrogen phosphate can also be used. When the base is a salt, the cation can be any convenient and pharmaceutically acceptable cation, such as ammonium, alkali metals, alkaline earth metals, and the like. Example may include, but not limited to, sodium, potassium, lithium, magnesium, calcium and ammonium.

Suitable acids are pharmaceutically acceptable organic or inorganic acids. Examples of suitable inorganic acids include hydrochloric acid, hydrobromic acid, hydriodic acid, sulfuric acid, nitric acid, boric acid, phosphoric acid, and the like. Examples of suitable organic acids include acetic acid, acrylic acid, adipic acid, alginic acid, alkanesulfonic acids, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid and the like.

Pharmaceutical composition for injection: In some embodiments, the disclosure provides a pharmaceutical composition for injection containing a compound of the present disclosure and a pharmaceutical excipient suitable for injection. Components and amounts of agents in the composition are as described herein.

The forms in which the novel composition of the present disclosure may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Aqueous solutions in saline are also conventionally used for injection. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, for the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating the compound of the present disclosure in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, certain desirable methods of preparation are vacuum-drying and freeze-drying techniques which yield a powder of the active ingredient plus any additional desired ingredient from a previously sterile-filtered solution thereof.

Other pharmaceutical compositions: Pharmaceutical compositions may also be prepared from composition described herein and one or more pharmaceutically acceptable excipients suitable for transdermal, inhalative, sublingual, buccal, rectal, intraosseous, intraocular, intranasal, epidural, or intraspinal administration. Preparations for such pharmaceutical composition are well-known in the art. See, e.g., See, e.g., Anderson, Philip O.; Knoben, James E.; Troutman, William G, eds., Handbook of Clinical Drug Data, Tenth Edition, McGraw-Hill, 2002; Pratt and Taylor, eds., Principles of Drug Action, Third Edition, Churchill Livingston, N.Y., 1990; Katzung, ed., Basic and Clinical Pharmacology, Ninth Edition, McGraw Hill, 2003; Goodman and Gilman, eds., The Pharmacological Basis of Therapeutics, Tenth Edition, McGraw Hill, 2001; Remingtons Pharmaceutical Sciences, 20th Ed., Lippincott Williams & Wilkins., 2000; Martindale, The Extra Pharmacopoeia, Thirty-Second Edition (The Pharmaceutical Press, London, 1999); all of which are incorporated by reference herein in their entirety.

The compounds of the present invention can also be administered in the form of liposomes. As is known in the art, liposomes are generally derived from phospholipids or other lipid substances. Liposomes are formed by mono- or multilamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and phosphatidyl cholines (lecithins), both natural and synthetic. Methods to form liposomes are known in the art. See, for example, Prescott, Ed., "Methods in Cell Biology", Volume XIV, ISBN: 978-0-12-564114-2, Academic Press, New York, N.W., p. 33 (1976) and Medina, Zhu, and Kairemo, "Targeted liposomal drug delivery in cancer", Current Pharm. Des. 10: 2981-2989, 2004. For additional information regarding drug formulation and administration, see "Remington: The Science and Practice of Pharmacy," Lippincott Williams & Wilkins, Philadelphia, ISBN-10: 0781746736, 21$^{st}$ Edition (2005).

The invention also provides kits. The kits may include a CD73 inhibitor and one or more additional agents in suitable packaging with written material that can include instructions for use, discussion of clinical studies, listing of side effects, and the like. Such kits may also include information, such as scientific literature references, package insert materials, clinical trial results, and/or summaries of these and the like, which indicate or establish the activities and/or advantages of the composition, and/or which describe dosing, administration, side effects, drug interactions, or other information useful to the health care provider. Such information may be based on the results of various studies, for example, studies using experimental animals involving in vivo models and studies based on human clinical trials. The kit may further contain another agent. In some embodiments, the compound of the present invention and the agent are provided as separate compositions in separate containers within the kit. In some embodiments, the compound of the present invention and the agent are provided as a single composition within a container in the kit. Suitable packaging and additional articles for use (e.g., measuring cup for liquid preparations, foil wrapping to minimize exposure to air, and the like) are known in the art and may be included in the kit. Kits described herein can be provided, marketed and/or promoted to health providers, including physicians, nurses, pharmacists, formulary officials, and the like. Kits may also, in some embodiments, be marketed directly to the consumer.

Combination therapies: The present invention also provides methods for further combination therapies in which, in addition to a CD73 inhibitor, one or more second agents known to modulate other pathways, or other components of the same pathway, or even overlapping sets of target proteins is used, or a pharmaceutically acceptable salt, ester, prodrug, solvate, hydrate or derivative thereof. In one aspect, such therapy includes but is not limited to the combination of the composition comprising a CD73 inhibitor as described herein with one or more of other CD73 inhibitors as described herein, chemotherapeutic agents, therapeutic antibodies, and radiation treatment, to provide, where desired, a synergistic or additive therapeutic effect.

Second agents useful in the methods of the invention include any agent capable of modulating a target molecule, either directly or indirectly. Non-limiting examples of target molecules modulated by second agents include enzymes, enzyme substrates, products of transitions, antibodies, antigens, membrane proteins, nuclear proteins, cytosolic proteins, mitochondrial proteins, lysosomal proteins, scaffold proteins, lipid rafts, phosphoproteins, glycoproteins, membrane receptors, G-protein-coupled receptors, nuclear receptors, protein tyrosine kinases, protein serine/threonine kinases, phosphatases, proteases, hydrolases, lipases, phospholipases, ligases, reductases, oxidases, synthases, transcription factors, ion channels, RNA, DNA, RNAse, DNAse, phospholipids, sphingolipids, nuclear receptors, ion channel proteins, nucleotide-binding proteins, calcium-binding proteins, chaperones, DNA binding proteins, RNA binding proteins, scaffold proteins, tumor suppressors, cell cycle proteins, and histones.

Second agents may target one or more signaling molecules including but not limited to the following: 4EPB-1, 5-lipoxygenase, A1, Ab1, Acetyl-CoAa Carboxylase, actin, adaptor/scaffold proteins, adenylyl cyclase receptors, adhesion molecules, AFT, Akt1, Akt2, Akt3, ALK, AMPKs, APC/C, ARaf, Arf-GAPs, Arfs, ASK, ASKI, asparagine hydroxylase FIH transferases, ATF2, ATF-2, ATM, ATP citrate lyase, ATR, Auroras, B cell adaptor for PI3-kinase (BCAP), Bad, Bak, Bax, Bcl-2, Bcl-B, Bcl-w, Bcl-XL, Bid, Bik, Bim, BLNK, Bmf, BMP receptors, Bok, BRAF, Btk, Bub, cadherins, CaMKs, Casein kinases, Caspase 2, Caspase 3, Caspase 6, Caspase 7, Caspase 8, Caspase 9, caspases, catenins, cathepsins, caveolins, Cb1, CBP/P300 family, CD45, CDCl25 phosphatases, Cdc42, Cdk 1, Cdk 2, Cdk 4, Cdk 6, Cdk 7, Cdks, CENPs, Chk1, Chk2, CLKs, Cot, cRaf, CREB, Crk, CrkL, Csk, Cyclin A, Cyclin B, Cyclin D, Cyclin E, Db1, deacetylases, DLK, DNA methyl transferases, DNA-PK, Dok, Dual Specificity phosphatases (DUSPs), E2Fs, eg5/KSP, Egr-1, eIF4E-binding protein, Elk, elongation factors, endosomal sorting complex required for transport (ESCRT) proteins, Eph receptors, Erks, esterases, Ets, Eyes absent (EYA) tyrosine phosphatases, FAK, Fas associated death domain (FADD), FGF receptors, Fgr, focal adhesion kinase, fodrin, Fos, FOXO, Fyn, GAD, Grb2, Grb2 associated binder (GAB), GSK3a, GSK30, H-Ras, H3K27, Hdm, HER receptors, HIFs, histone acetylases, histone deacetylases, Histone H3K4 demethylases, HMGA, Hrk, Hsp27, Hsp70, Hsp90 s, hydrolases, hydroxylases, IAPs, IGF receptors, IKKs, IL-2, IL-4, IL-6, IL-8, ILK, Immunoglobulin-like adhesion molecules, initiation factors, inositol phosphatases, Insulin receptor, integrins, interferon α, interferon β, IRAKs, Jak1, Jak2, Jak3, JHDM2A, Jnks, K-Ras, Kit receptor, KSR, LAR phosphatase, LAT, Lck, Lim kinase, LKB-1, Low molecular weight tyrosine phosphatase, Lyn, MAP kinase phosphatases (MKPs), MAPKAPKs, MARKs, Mcl-1, Mek 1, Mek 2, MEKKs, MELK, Met receptor, metabolic enzymes, metalloproteinases, MKK3/6, MKK4/7, MLKs, MNKs, molecular chaperones, Mos, mTOR, multi-drug resistance proteins, muscarinic receptors, Myc, MyD88, myosin, myosin binding proteins, myotubularins, MYST family, Myt 1, N-Ras, Nck, NFAT, NIK, nitric oxide synthase, Non receptor tyrosine phosphatases (NPRTPs), Noxa, nucleoside transporters, p130CAS, p14Arf, p16, p21CIP, p27KIP, p38 s, p53, p70S6 Kinase, p90Rsks, PAKs, paxillin, PDGF receptors, PDKI, P-Glycoprotein, phopsholipases, phosphoinositide kinases, PI3-Kinase class 1, Pim1, Pim2, Pim3, *Pini* prolyl isomerase, PKAs, PKCs, PKR, potassium channels, PP1, PP2A, PP2B, PP2C, PP5, PRK, Prks, prolyl-hydroxylases PHD-1, prostaglandin synthases, pS6, PTEN, Puma, RABs, Rac, Ran, Ras-GAP, Rb, Receptor protein tyrosine phosphatases (RPTPs), Rel-A (p65-NFKB), Ret, RHEB, Rho, Rho-GAPs, RIP, RNA polymerase, ROCK 1, ROCK 2, SAPK/JNK1,2,3, SCF ubiquitination ligase complex, selectins, separase, serine phosphatases, SGK1, SGK2, SGK3, Shc, SHIPs, SHPs, sirtuins, SLAP, Slingshot phosphatases (SSH), Smac, SMADs, small molecular weight GTPases, sodium channels, Sos, Spi, sphingomyelinases, sphingosine kinases, Src, SRFs, STAT1, STAT3, STAT4, STAT5, STAT6, suppressors of cytokine signaling (SOCs), Syk, T-bet, T-Cell leukemia family, TCFs, TGFβ receptors, Tiam, TIE1, TIE2, topoisomerases, Tp1, TRADD, TRAF2, Trk receptors, TSC1,2, tubulin, Tyk2, ubiquitin proteases, urokinase-type plasminogen activator (uPA) and uPA receptor (uPAR) system, UTX, Vav, VEGF receptors, vesicular protein sorting (Vsps), VHL, Weel, WT-1, WT-1, XIAP, Yes, ZAP70, β-adrenergic receptors and β-catenin.

In one aspect, this invention also relates to methods and pharmaceutical compositions for inhibiting abnormal cell growth in a mammal which comprises an amount of a CD73 inhibitor, or a pharmaceutically acceptable salt, ester, prodrug, solvate, hydrate or derivative thereof, in combination with an amount of an anti-cancer agent (e.g., a chemotherapeutic agent). Many chemotherapeutics are presently known in the art and can be used in combination with the compounds of the invention.

In some embodiments, the chemotherapeutic is selected from mitotic inhibitors, alkylating agents, anti-metabolites, intercalating antibiotics, growth factor inhibitors, cell cycle inhibitors, enzymes, topoisomerase inhibitors, biological response modifiers, anti-hormones, angiogenesis inhibitors, immunotherapeutic agents, proapoptotic agents, and anti-androgens. Non-limiting examples are chemotherapeutic agents, cytotoxic agents, and non-peptide small molecules such as Tykerb/Tyverb (lapatinib), Gleevec (Imatinib Mesylate), Velcade (bortezomib), Casodex (bicalutamide), Iressa (gefitinib), and Adriamycin as well as a host of chemotherapeutic agents. Non-limiting examples of chemotherapeutic agents include 2,2',2"-trichlorotriethylamine; 2-ethylhydrazide; aceglatone; aldophosphamide glycoside; alkyl sulfonates such as busulfan, improsulfan and piposulfan; alkylating agents such as thiotepa and cyclosphosphamide (CYTOXAN™); aminolevulinic acid; amsacrine; anti-adrenals such as aminoglutethimide, mitotane, trilostane; antibiotics such as anthracyclins, actinomycins and bleomycins including aclacinomysins, actinomycin, anthramycin, azaserine, bleomycins, cactinomycin, calicheamicin, carabicin, carminomycin, carzinophilin, Casodex™, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); arabinoside ("Ara-C"); aziridines such as benzodopa, carboquone, meturedopa, and uredopa; bestrabucil; bisantrene; capecitabine; cyclophosphamide; dacarbazine; defofamine; demecolcine; diaziquone; edatraxate; elformithine; elliptinium acetate; esperamicins; ethylenimines and methylamelamines including altretamine, triethylenemelamine, trietylenephosphoramide, triethylenethiophosphaoramide and trimethylolomelamine; etoglucid; folic acid analogues such as denopterin, methotrexate, pteropterin, trimetrexate; folic acid replenisher such as frolinic acid; gacytosine; gallium nitrate; gemcitabine; hydroxyurea; lentinan; lonidamine; mannomustine; mitobronitol; mitoguazone; mitolactol; mitoxantrone; mopidamol; nitracrine; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosoureas; nitrosoureas such as carmustine, chlorozotocin, fotemustine, lomustine, nimustine, ranimustine; oxazaphosphorines; pentostatin; phenamet; pipobroman; pirarubicin; podophyllinic acid; procarbazine; PSK®; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, androgens such as calusterone, dromostanolone propionate, epitiostanol, mepitiostane, testolactone; razoxane; retinoic acid; sizofiran; spirogermanium; taxanes, e.g., paclitaxel (TAXOL™, Bristol-Myers Squibb Oncology, Princeton, N.J.) and docetaxel (TAXOTERE™, Rhone-Poulenc Rorer, Antony, France); tenuazonic acid; thiotepa; triazenes; triaziquone; urethan; vindesine; and pharmaceutically acceptable salts, acids or derivatives of any of the above. Also included as suitable chemotherapeutic cell conditioners are anti-hormonal agents that act to regulate or inhibit hormone action on tumors such as anti-estrogens including for example tamoxifen (Nolvadex™), raloxifene, aromatase inhibiting 4 (5)-imidazoles, 4-hydroxytamoxifen, trioxifene, keoxifene, LY 117018, onapristone, and toremifene (Fareston); and anti-androgens such as flutamide, nilutamide, bicalutamide, leuprolide, and goserelin; chlorambucil; gemcitabine; 6-thioguanine; mercaptopurine; methotrexate; platinum or platinum analogs and complexes such as cisplatin and carboplatin; anti-microtubule such as diterpenoids, including paclitaxel and docetaxel, or *Vinca* alkaloids including vinblastine, vincristine, vinflunine, vindesine, and vinorelbine; etoposide (VP-16); ifosfamide; mitomycin C; mitoxantrone; vincristine; vinorelbine; navelbine; novantrone; teniposide; daunomycin; aminopterin; xeloda; ibandronate; topoisomerase I and II inhibitors including camptothecins (e.g., camptothecin-11), topotecan, irinotecan, and epipodophyllotoxins; topoisomerase inhibitor RFS 2000; epothilone A or B; difluoromethylornithine (DMFO); histone deacetylase inhibitors; compounds which induce cell differentiation processes; gonadorelin agonists; methionine aminopeptidase inhibitors; compounds targeting/decreasing a protein or lipid kinase activity; compounds which target, decrease or inhibit the activity of a protein or lipid phosphatase; anti-androgens; bisphosphonates; biological response modifiers; antiproliferative antibodies; heparanase inhibitors; inhibitors of Ras oncogenic isoforms; telomerase inhibitors; proteasome inhibitors; compounds used in the treatment of hematologic malignancies; compounds which target, decrease or inhibit the activity of Flt-3; Hsp90 inhibitors; temozolomide (TEMODAL®); Hsp90 inhibitors such as 17-AAG (17-allylaminogeldanamycin, NSC330507), 17-DMAG (17-dimethylaminoethylamino-17-demethoxy-geldanamycin, NSC707545), IPI-504, CNF1010, CNF2024, CNF1010 from Conforma Therapeutics; temozolomide (TEMODAL®); kinesin spindle protein inhibitors, such as SB715992 or SB743921 from GlaxoSmithKline, or pentamidine/chlorpromazine from CombinatoRx; MEK inhibitors such as ARRY142886 from Array PioPharma, AZD6244 from AstraZeneca, PD181461 or PD0325901 from Pfizer, leucovorin, EDG binders, antileukemia compounds, ribonucleotide reductase inhibitors, S-adenosylmethionine decarboxylase inhibitors, antiproliferative antibodies or other chemotherapeutic compounds. Where desired, the compounds or pharmaceutical composition of the present invention can be used in combination with commonly prescribed anti-cancer drugs such as Herceptin®, Avastin®, Erbitux®, Rituxan®, Taxol®, Arimidex®, Taxotere®, and Velcade®.

This invention further relates to a method for using the compounds or pharmaceutical composition in combination with other tumor treatment approaches, including surgery, ionizing radiation, photodynamic therapy, or implants, e.g., with corticosteroids, hormones, or used as radiosensitizers.

One such approach may be, for example, radiation therapy in inhibiting abnormal cell growth or treating the proliferative disorder in the mammal. Techniques for administering radiation therapy are known in the art, and these techniques can be used in the combination therapy described herein. The administration of the compound of the invention in this combination therapy can be determined as described herein.

Radiation therapy can be administered through one of several methods, or a combination of methods, including without limitation external-beam therapy, internal radiation therapy, implant radiation, stereotactic radiosurgery, systemic radiation therapy, radiotherapy and permanent or temporary interstitial brachytherapy. The term "brachytherapy," as used herein, refers to radiation therapy delivered by a spatially confined radioactive material inserted into the body at or near a tumor or other proliferative tissue disease site. The term is intended without limitation to include exposure to radioactive isotopes (e.g., At-211, I-131, I-125, Y-90, Re-186, Re-188, Sm-153, Bi-212, P-32, and radioactive isotopes of Lu). Suitable radiation sources for use as a cell conditioner of the present invention include both solids and liquids. By way of non-limiting example, the radiation source can be a radionuclide, such as I-125, I-131, Yb-169, Ir-192 as a solid source, I-125 as a solid source, or other radionuclides that emit photons, beta particles, gamma radiation, or other therapeutic rays. The radioactive material can also be a fluid made from any solution of radionuclide(s), e.g., a solution of I-125 or I-131, or a radioactive fluid can be produced using a slurry of a suitable fluid containing small particles of solid radionuclides, such as Au-198, Y-90. Moreover, the radionuclide(s) can be embodied in a gel or radioactive micro spheres.

Without being limited by any theory, the compounds of the present invention can render abnormal cells more sensitive to treatment with radiation for purposes of killing and/or inhibiting the growth of such cells. Accordingly, this invention further relates to a method for sensitizing abnormal cells in a mammal to treatment with radiation, which comprises administering to the mammal an amount of a CD73 inhibitor or a pharmaceutically acceptable salt, ester, prodrug, solvate, hydrate or derivative thereof, which is effective in sensitizing abnormal cells to treatment with radiation. The amount of the compound in this method can be determined according to the means for ascertaining effective amounts of such compounds described herein.

Further therapeutic agents that can be combined with a subject compound may be found in Goodman and Gilman's "The Pharmacological Basis of Therapeutics" Tenth Edition edited by Hardman, Limbird and Gilman or the Physician's Desk Reference, both of which are incorporated herein by reference in their entirety.

In some embodiments, the compositions and methods further comprise administering, separately or simultaneously one or more additional agents (e.g. 1, 2, 3, 4, 5, or more). Additional agents can include those useful in wound healing. Non-limiting examples of additional agents include antibiotics (e.g. Aminoglycosides, Cephalosporins, Chloramphenicol, Clindamycin, Erythromycins, Fluoroquinolones, Macrolides, Azolides, Metronidazole, Penicillin's, Tetracycline's, Trimethoprim-sulfamethoxazole, Vancomycin), steroids (e.g. Andranes (e.g. Testosterone), Cholestanes (e.g. Cholesterol), Cholic acids (e.g. Cholic acid), Corticosteroids (e.g. Dexamethasone), Estraenes (e.g. Estradiol), Pregnanes (e.g. Progesterone), narcotic and non-narcotic analgesics (e.g. Morphine, Codeine, Heroin, Hydromorphone, Levorphanol, Meperidine, Methadone, Oxydone, Propoxyphene, Fentanyl, Methadone, Naloxone, Buprenorphine, Butorphanol, Nalbuphine, Pentazocine), chemotherapy (e.g. anti-cancer drugs such as but not limited to Altretamine, Asparaginase, Bleomycin, Busulfan, Carboplatin, Carmustine, Chlorambucil, Cisplatin, Cladribine, Cyclophosphamide, Cytarabine, Dacarbazine, Diethylstilbesterol, Ethinyl estradiol, Etoposide, Floxuridine, Fludarabine, Fluorouracil, Flutamide, Goserelin, Hydroxyurea, Idarubicin, Ifosfamide, Leuprolide, Levamisole, Lomustine, Mechlorethamine, Medroxyprogesterone, Megestrol, Melphalan, Mercaptopurine, Methotrexate, Mitomycin, Mitotane, Mitoxantrone, Paclitaxel, pentastatin, Pipobroman, Plicamycin, Prednisone, Procarbazine, Streptozocin, Tamoxifen, Teniposide, Vinblastine, Vincristine), anti-inflammatory agents (e.g. Alclofenac; Alclometasone Dipropionate; Algestone Acetonide; alpha Amylase; Amcinafal; Amcinafide; Amfenac Sodium; Amiprilose Hydrochloride; Anakinra; Anirolac; Anitrazafen; Apazone; Balsalazide Disodium; Bendazac; Benoxaprofen; Benzydamine Hydrochloride; Bromelains; Broperamole; Budesonide; Carprofen; Ciclprofen; Cintazone; Cliprofen; Clobetasol Propionate; Clobetasone Butyrate; Clopirac; Cloticasone Propionate; Cormethasone Acetate; Cortodoxone; Decanoate; Deflazacort; Delatestryl; Depo-Testosterone; Desonide; Desoximetasone; Dexamethasone Dipropionate; Diclofenac Potassium; Diclofenac Sodium; Diflorasone Diacetate; Diflumidone Sodium; Diflunisal; Difluprednate; Diftalone; Dimethyl Sulfoxide; Drocinonide; Endrysone; Enlimomab; Enolicam Sodium; Epirizole; Etodolac; Etofenamate; Felbinac; Fenamole; Fenbufen; Fenclofenac; Fenclorac; Fendosal; Fenpipalone; Fentiazac; Flazalone; Fluazacort; Flufenamic Acid; Flumizole; Flunisolide Acetate; Flunixin; Flunixin Meglumine; Fluocortin Butyl; Fluorometholone Acetate; Fluquazone; Flurbiprofen; Fluretofen; Fluticasone Propionate; Furaprofen; Furobufen; Halcinonide; Halobetasol Propionate; Halopredone Acetate; Ibufenac; Ibuprofen; Ibuprofen Aluminum; Ibuprofen Piconol; Ilonidap; Indomethacin; Indomethacin Sodium; Indoprofen; Indoxole; Intrazole; Isoflupredone Acetate; Isoxepac; Isoxicam; Ketoprofen; Lofemizole Hydrochloride; Lomoxicam; Loteprednol Etabonate; Meclofenamate Sodium; Meclofenamic Acid; Meclorisone Dibutyrate; Mefenamic Acid; Mesalamine; Meseclazone; Mesterolone; Methandrostenolone; Methenolone; Methenolone Acetate; Methylprednisolone Suleptanate; Morniflumate; Nabumetone; Nandrolone; Naproxen; Naproxen Sodium; Naproxol; Nimazone; Olsalazine Sodium; Orgotein; Orpanoxin; Oxandrolane; Oxaprozin; Oxyphenbutazone; Oxymetholone; Paranyline Hydrochloride; Pentosan Polysulfate Sodium; Phenbutazone Sodium Glycerate; Pirfenidone; Piroxicam; Piroxicam Cinnamate; Piroxicam Olamine; Pirprofen; Prednazate; Prifelone; Prodolic Acid; Proquazone; Proxazole; Proxazole Citrate; Rimexolone; Romazarit; Salcolex; Salnacedin; Salsalate; Sanguinarium Chloride; Seclazone; Sermetacin; Stanozolol; Sudoxicam; Sulindac; Suprofen; Talmetacin; Talniflumate; Talosalate; Tebufelone; Tenidap; Tenidap Sodium; Tenoxicam; Tesicam; Tesimide; Testosterone; Testosterone Blends; Tetrydamine; Tiopinac; Tixocortol Pivalate; Tolmetin; Tolmetin Sodium; Triclonide; Triflumidate;

Zidometacin; Zomepirac Sodium), or anti-histaminic agents (e.g. Ethanolamines (like diphenhydrmine carbinoxamine), Ethylenediamine (like tripelennamine pyrilamine), Alkylamine (like chlorpheniramine, dexchlorpheniramine, brompheniramine, triprolidine), other anti-histamines like astemizole, loratadine, fexofenadine, Bropheniramine, Clemastine, Acetaminophen, Pseudoephedrine, Triprolidine).

EXAMPLES

Preparative thin layer chromatography (PTLC) separations described herein were typically performed on 20×20 cm plates (500 micron thick silica gel).

Chromatographic purifications were typically performed using Biotage Isolera One automated systems running Biotage Isolera One 2.0.6 software (Biotage LLC, Charlotte, N.C.). Flow rates were the default values specified for the particular column in use. Reverse phase chromatography was performed using elution gradients of water and acetonitrile on KP-C18-HS Flash+ columns (Biotage LLC) of various sizes. Typical loading was between 1:50 and 1:1000 crude sample: RP $SiO_2$ by weight. Normal phase chromatography was performed using elution gradients of various solvents (e.g. hexane, ethyl acetate, methylene chloride, methanol, acetone, chloroform, MTBE, etc.). The columns were SNAP Cartridges containing KP-SIL or SNAP Ultra (25 μm spherical particles) of various sizes (Biotage LLC). Typical loading was between 1:10 to 1:150 crude sample: $SiO_2$ by weight. Alternatively, silica gel chromatography was performed on a Biotage Horizon flash chromatography system.

$^1$H NMR analyses of intermediates and exemplified compounds were typically performed on an Agilent Technologies 400/54 or Bruker Ascend™ 400 spectrometer (operating at 400 MHz) at 298° K following standard operating procedure suggested by manufacturer. Reference frequency was set using TMS as an internal standard. Typical deuterated solvents were utilized as indicated in the individual examples.

LCMS analysis were typically performed using one of the two conditions listed below:

(1) LCMS spectra were taken on an Agilent Technologies 1260 Infinity coupled to 6120 Quadrupole spectrometer. The mobile phase for the LC was acetontrile (A) and water (B) with 0.01% formic acid, and the eluent gradient was from 5-95% A in 6.0 min, 60-95% A in 5.0 min, 80-100% A in 5.0 min and 85-100% A in 10 min using a SBC18 50 mm×4.6 mmx 2.7 μm capillary column. Mass spectra (MS) were measured by electrospray ion-mass spectroscopy (ESI). All temperatures are in degrees Celsius unless otherwise noted.

(2) LCMS analysis of intermediates and exemplified compounds was performed on an Agilent Technologies 1200 Series HPLC system coupled to an Agilent Technologies 6150 Quadrapole LC/MS detector. Analytes were detected by UV absorbance at 220 and 254 nm. Analyte ions were detected by mass spectrometry in both negative and positive modes (110-800 amu scan range, API-ES ionization). A long HPLC method was run on a Phenomenex© Kinetex 2.6 μC18 100 Å, 30×3.00 mm column. The column temperature was set at 40° C. UV absorptions were detected at 220 and 254 nm. Samples were prepared as a solution in about 1:1 (v/v) acetonitrile:water mixture. Flow rate was about 0.80 mL/minute. Elution solvents were acetonitrile and water each containing 0.1% formic acid. In a typical run, a linear gradient starting with 5% acetonitrile and 95% water and ending with 95% acetonitrile and 5% water over 12 minutes was carried out. At the end of each run, the column was washed with 95% acetonitrile and 5% water for 2 minutes.

Typically, analytical HPLC mass spectrometry conditions were as follows:

LC1: Column: SB-C18 50 mm×4.6 mmx 2.7 μm; Temperature: 50° C.; Eluent: 5:95 v/v acetonitrile/water+0.01% formic acid in 6 min; Flow Rate: 1.5 mL/min; Injection 5 μL; Detection: PDA, 200-600 nm; MS: mass range 150-750 amu; positive ion electrospray ionization.

LC2: Column: SB-C18 50 mm×4.6 mmx 2.7 μm; Temperature: 50° C.; Eluent: 5:95 to 95:5 v/v acetonitrile/water+ 0.05% TFA over 3.00 min; Flow Rate: 1.5 mE/min; Injection 5 μL; Detection: PDA, 200-600 nm; MS: mass range 150-750 amu; positive ion electrospray ionization.

LC3: Column: SB-C18 50 mm×4.6 mmx 2.7 μm; Temperature: 50° C.; Eluent: 10:90 to 98:2 v acetonitrile/water+ 0.05% TFA over 3.75 min; Flow Rate: 1.0 mL/min; Injection 10 μL; Detection: PDA, 200-600 nm; MS: mass range 150-750 amu; positive ion electrospray ionization.

Preparative HPLC were carried out with one of the two conditions listed below:

Condition 1: GILSON Preparative HPLC System; Column: SHISEIDO CAPCELL PAK, MG; C18, 20 mm×250 mm, 5 μm; Mobile phase: Water+0.1% trifluoroacetic acid; ACN+0.10% trifluoroacetic acid; Method: 15 minutes gradient elution; Initial organic: 10%; Final organic: 80%; UV1: 240; UV2: 230; Flow: 15 ml/min.

Condition 2: GILSON Preparative HPLC System; Column: SunFire® Prep C18 OBD™ 5 uM, 19 mm×150 mm; Mobile phase: Water+0.1% trifluoroacetic acid; ACN+0.1% trifluoroacetic acid; Method: 20 minutes gradient elution; Initial organic: 10%; Final organic: 80%; UV1: 220; UV2: 254; Flow: 15 ml/min.

Compound names were generated with ChemDraw Professional 15.1 or OpenEye Scientific Software's mol2nam application.

Example 1: Synthesis of [(2R,3S,4R,5R)-3,4-dihydroxy-5-[6-(1-phenylethylamino)purin-9-yl]tetrahydrofuran-2-yl]methoxymethylphosphonic acid (Compound 18)

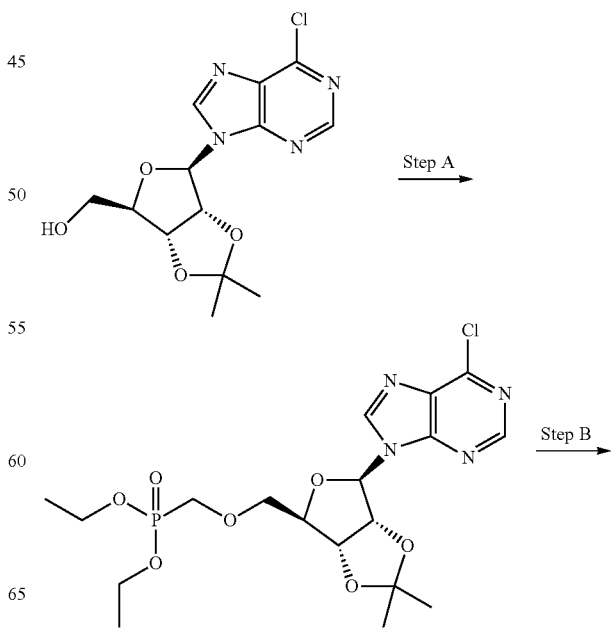

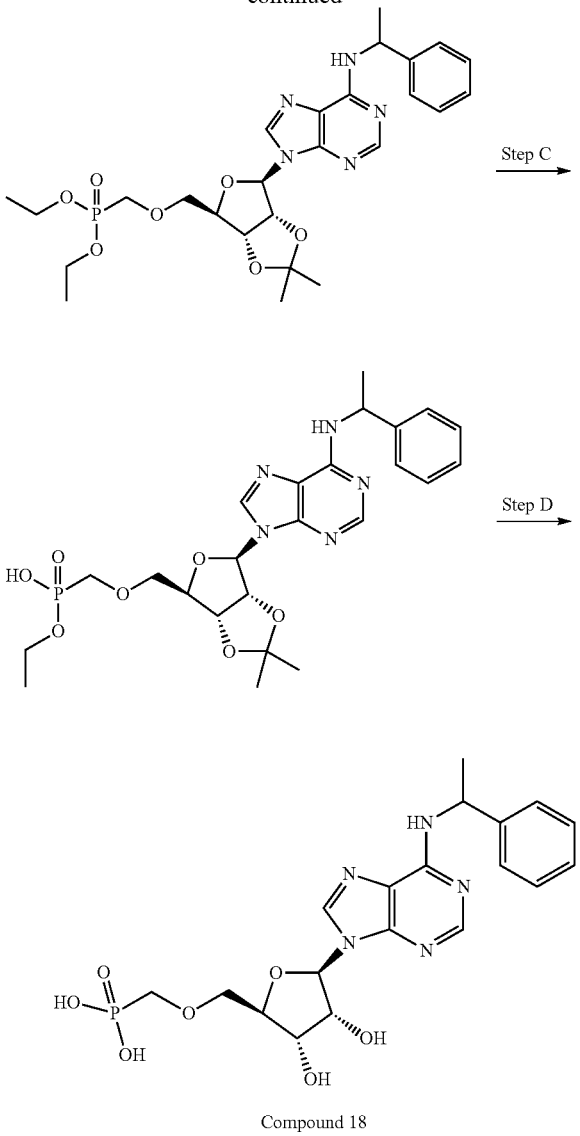

Compound 18

Step A: A mixture of ((3aR,4R,6R,6aR)-6-(6-chloro-9H-purin-9-yl)-2,2-dimethyltetrahydrofuro[3,4-d][1,3]dioxol-4-yl)methanol (1.09 g, 3.34 mmol), (diethoxyphosphoryl)methyl 4-methylbenzenesulfonate (1.29 g, 4.0 mmol) and magnesium 2-methylpropan-2-olate (0.74 g, 4.34 mmol) in DMSO (15 mL) was stirred at 50° C. for 18 hours. After cooling to ambient temperature, water (10 mL) and 1:1 MTBE/ethyl acetate (20 mL) were added. The mixture was passed through a short pad of celite. The organic layer was separated, washed with brine, dried (sodium sulfate), filtered and concentrated under reduced pressure. The residue obtained was purified by flash chromatography on silica gel 10:1 ethyl acetate/methanol to give diethyl ((((3aR,4R,6R,6aR)-6-(6-chloro-9H-purin-9-yl)-2,2-dimethyltetrahydrofuro[3,4-d][1,3]dioxol-4-yl)methoxy)methyl)phosphonate (1.27 g, 80%) as solid. LCMS ESI (+) m/z 477 (M+H)

Step B: 1-Phenylethyl amine (80.0 mg, 0.66 mmol) was added to diethyl ((((3aR,4R,6R,6aR)-6-(6-chloro-9H-purin-9-yl)-2,2-dimethyltetrahydrofuro[3,4-d][1,3]dioxol-4-yl)methoxy)methyl)phosphonate (40.0 mg, 0.08 mmol) in absolute ethanol (2 mL). The mixture was stirred at 45° C.

overnight. The mixture was concentrated under reduced pressure and purified by preparative TLC to give diethyl ((((3aR,4R,6R,6aR)-2,2-dimethyl-6-(6-((1-phenylethyl)amino)-9H-purin-9-yl)tetrahydrofuro[3,4-d][1,3]dioxol-4-yl)methoxy)methyl)phosphonate (40 mg, 85%).

Step C: To a mixture of diethyl ((((3aR,4R,6R,6aR)-2,2-dimethyl-6-(6-((1-phenylethyl)amino)-9H-purin-9-yl)tetrahydrofuro[3,4-d][1,3]dioxol-4-yl)methoxy)methyl)phosphonate (40.0 mg, 0.07 mmol) in dichloromethane (4 mL) were added 2, 6-Lutidine (160.0 mg, 1.49 mmol) and bromotrimethylsilane (240.0 mg, 1.57 mmol). The reaction mixture was stirred at room temperature overnight. The reaction mixture was concentrated under reduced pressure. The residue was co-evaporated with MeCN twice, then purified by reverse phase HPLC (0.1% HCOOH, 25% to 65% MeCN/H$_2$O over 15 min) to give the product ((((3aR,4R,6R,6aR)-2,2-dimethyl-6-(6-((1-phenylethyl)amino)-9H-purin-9-yl)tetrahydrofuro[3,4-d][1,3]dioxol-4-yl)methoxy)methyl)phosphonic acid (28.0 mg, 78%) as solid.

Step D: A solution of [(3aR,4R,6R,6aR)-2,2-dimethyl-4-[6-(1-phenylethylamino)purin-9-yl]-3a,4,6,6a-tetrahydrofuro[3,4-d][1,3]dioxol-6-yl]methoxymethylphosphonic acid (28.0 mg, 0.06 mmol) in 80% HCOOH aqueous solution (3 mL) was stirred at ambient temperature for 2 hours. The mixture was concentrated under reduced pressure and the residue obtained was purified by reverse phase HPLC (0.1% HCOOH, 20 to 60% MeCN/H$_2$O over 15 min) to afford [(2R,3S,4R,5R)-3,4-dihydroxy-5-[6-(1-phenylethylamino)purin-9-yl]tetrahydrofuran-2-yl]methoxymethylphosphonic acid (20.0 mg, 78%) as solid. LCMS ESI (−) m/z 464 (M−H)

Example 2: Synthesis of [(2R,3S,4R,5R)-3,4-dihydroxy-5-(6-isopropoxypurin-9-yl)tetrahydrofuran-2-yl]methoxymethylphosphonic acid (Compound 44)

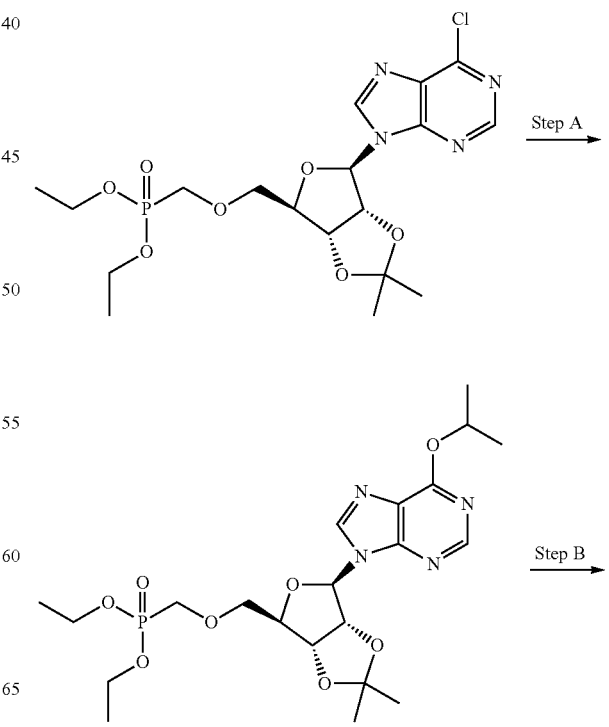

257
-continued

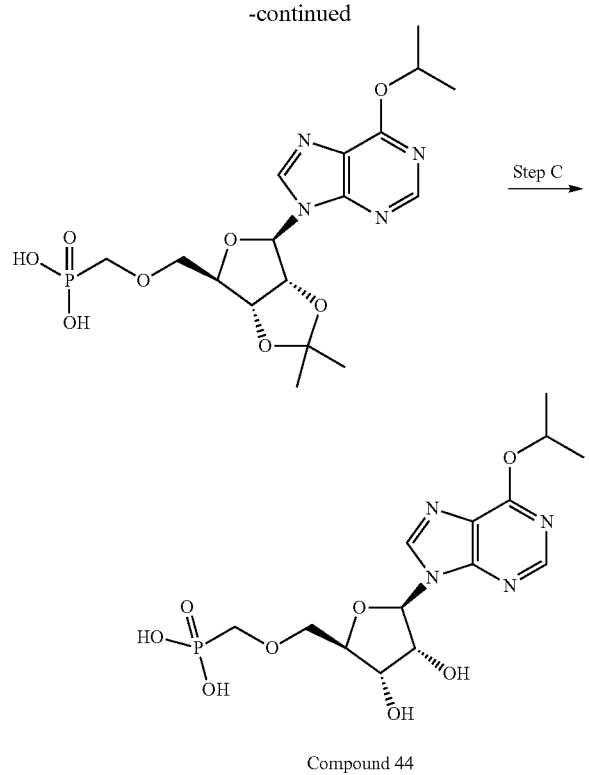

Compound 44

Step A: To a solution of 2-Propanol (5 mL) was added 60% NaH (12.6 mg 0.31 mmol) at 0° C. After 30 min at 0° C., diethyl ((((3aR,4R,6R,6aR)-6-(6-chloro-9H-purin-9-yl)-2,2-dimethyltetrahydrofuro[3,4-d][1,3]dioxol-4-yl)methoxy)methyl)phosphonate (40.0 mg, 0.08 mmol) was added. The reaction mixture was stirred at 0° C. for 0 minutes, water (10 mL) and ethyl acetate (10 mL) were added. The organic layer was separated, dried (sodium sulfate), filtered and concentrated under reduced pressure. The residue obtained was purified by column chromatography on silica gel to give diethyl ((((3aR,4R,6R,6aR)-6-(6-isopropoxy-9H-purin-9-yl)-2,2-dimethyltetrahydrofuro[3,4-d][1,3]dioxol-4-yl)methoxy)methyl)phosphonate (33 mg, 63%) as oil.

Step B: To a solution of diethyl diethyl ((((3aR,4R,6R,6aR)-6-(6-isopropoxy-9H-purin-9-yl)-2,2-dimethyltetrahydrofuro[3,4-d][1,3]dioxol-4-yl)methoxy)methyl)phosphonate (33 mg, 0.05 mmol), 2,6-Lutidine (113 mg, 1.05 mmol) in dichloromethane (2 mL) was added bromotrimethylsilane (161.5 mg, 1.05 mmol). The reaction mixture was stirred at room temperature overnight. The reaction mixture was concentrated under reduced pressure. The residue was co-evaporated with MeCN twice to give [(3aR,4R,6R,6aR)-4-(6-isopropoxypurin-9-yl)-2,2-dimethyl-3a,4,6,6a-tetrahydrofuro[3,4-d][1,3]dioxol-6-yl]methoxymethylphosphonic acid (40 mg) which was used directly in the next step.

Step C: A solution of [(3aR,4R,6R,6aR)-4-(6-isopropoxypurin-9-yl)-2,2-dimethyl-3a,4,6,6a-tetrahydrofuro[3,4-d][1,3]dioxol-6-yl]methoxymethylphosphonic acid (40 mg) in 80% HCOOH aqueous solution (3 mL) was stirred at ambient temperature for 2 hours. The mixture was concentrated under reduced pressure and the residue obtained was purified by reverse phase HPLC (0.1% HCOOH, 20 to 60% MeCN/H$_2$O over 15 min) to afford [(2R,3S,4R,5R)-3,4-dihydroxy-5-(6-isopropoxypurin-9-yl)tetrahydrofuran-2-yl]

258 methoxymethylphosphonic acid (9 mg, 82%) as solid. LCMS ESI (−) m/z 403 (M−H)

Example 3: Synthesis of [(2R,3S,4R,5R)-3,4-dihydroxy-5-(6-phenylpurin-9-yl)tetrahydrofuran-2-yl]methoxymethylphosphonic acid (Compound 46)

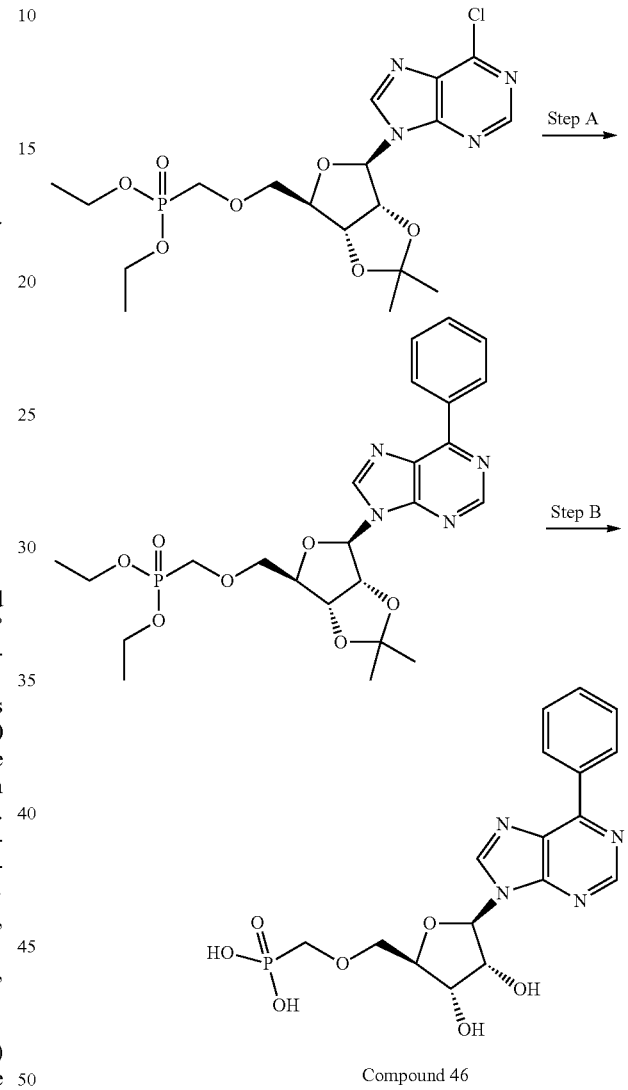

Compound 46

Step A: A mixture of diethyl ((((3aR,4R,6R,6aR)-6-(6-chloro-9H-purin-9-yl)-2,2-dimethyltetrahydrofuro[3,4-d][1,3]dioxol-4-yl)methoxy)methyl)phosphonate (0.05 g, 0.10 mmol), Phenylboronic acid (0.03 g, 0.21 mmol) and Dichloro[1;1'-bis(diphenylphosphino)ferrocene]palladium (II) dichloromethane adduct (0.01 g, 0.01 mmol) in 1,4-Dioxane (2 mL) and Water (0.50 mL) was stirred at 100° C. for 8 hours. After cooled to ambient temperature, water (10 mL) and 1:1 MTBE/ethyl acetate (20 mL) were added. The mixture was passed through a short pad of celite. The organic layer was separated, washed with brine, dried (sodium sulfate), filtered and concentrated under reduced pressure. The residue obtained was purified by reverse phase purification (Biotage Isolera One unit, Biotage@SNAP Ultra C18 30 g column, 20-90% CH$_3$CN/water, 10 CV) to give diethyl (((((2R,3S,4R,5R)-3,4-dihydroxy-5-(6-phenyl-9H-purin-9-yl)tetrahydrofuran-2-yl)methoxy)methyl)phosphonate (0.034 g, 62%) as oil. LCMS ESI (+) m/z 519 (M+H)

Step B: To a solution of diethyl (((((2R,3S,4R,5R)-3,4-dihydroxy-5-(6-phenyl-9H-purin-9-yl)tetrahydrofuran-2-yl)methoxy)methyl)phosphonate (0.03 g, 0.07 mmol) in Dichloromethane (2 mL) was added 2,6-Lutidine (0.04 mL, 0.33 mmol) and trimethyl bromosilane (0.04 mL, 0.33 mmol) at ambient temperature. The reaction mixture was stirred at this temperature for 5 hours. The reaction mixture was concentrated under reduced pressure. The residue was co-evaporated with methanol three times to give a light yellow solid. Formic acid (80% v/v) (2 mL) was added. The reaction mixture was stirred at ambient temperature for 3 hours. Solvent was removed under reduced pressure. The residue was purified by reverse phase HPLC (5-60% CH$_3$CN/water (0.1% TFA)) to give [(2R,3S,4R,5R)-3,4-dihydroxy-5-(6-phenylpurin-9-yl)tetrahydrofuran-2-yl]methoxymethylphosphonic acid (0.024 g, 68%) as TFA salts. LCMS ESI (−) m/z 421 (M−H).

Example 4: Synthesis of (((((2R,3S,4R,5R)-5-(2-chloro-6-(((S)-1-phenylethyl)amino)-9H-purin-9-yl)-3,4-dihydroxytetrahydrofuran-2-yl)methoxy)methyl)phosphonic acid (Compound 21)

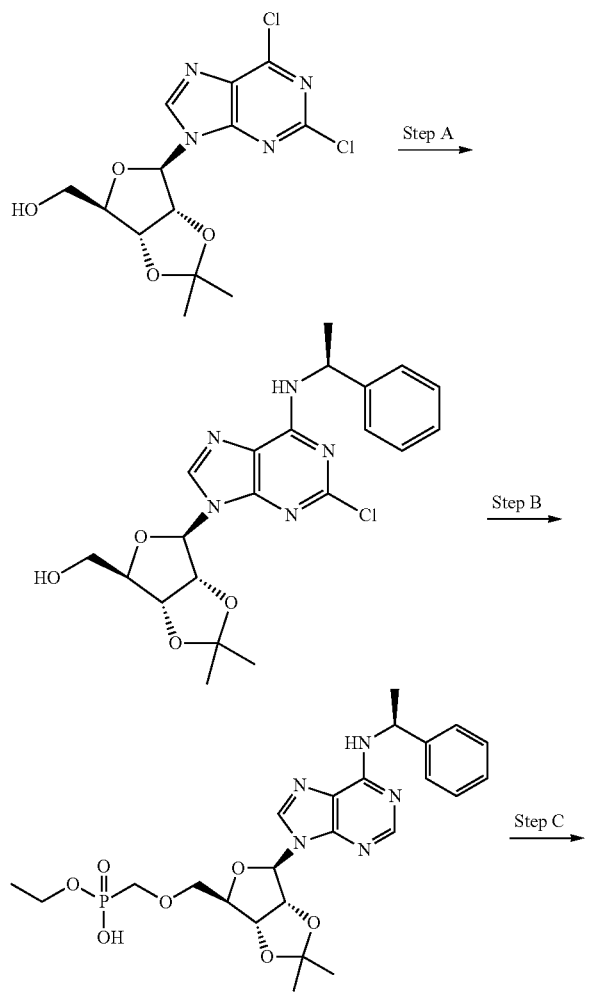

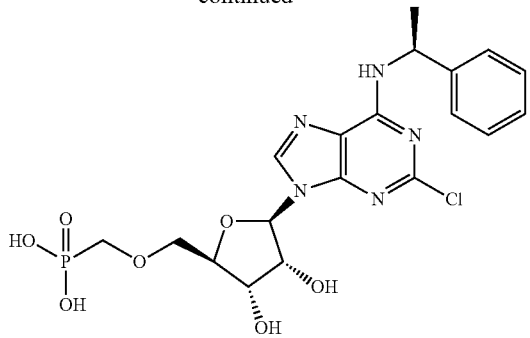

Compound 21

Step A: A mixture of [(3aR,4R,6R,6aR)-4-(2,6-dichloropurin-9-yl)-2,2-dimethyl-3a,4,6,6a-tetrahydrofuro[3,4-d][1,3]dioxol-6-yl]methanol (0.21 g, 0.57 mmol) and N,N-Diisopropylethylamine (0.15 mL, 0.85 mmol) in 2-propanol (2 mL) was added (S)-(−)-1-Phenylethylamine (0.09 g, 0.74 mmol) at ambient temperature. The mixture was stirred at ambient temperature for 18 hours. Water (20 mL) and ethyl acetate (10 mL) were added. The organic layer was separated, washed with brine, dried (sodium sulfate), filtered and concentrated under reduced pressure. The residue obtained was purified by flash chromatography on silica gel ethyl acetate to give [(3aR,4R,6R,6aR)-4-[2-chloro-6-[[(1S)-1-phenylethyl]amino]purin-9-yl]-2,2-dimethyl-3a,4,6,6a-tetrahydrofuro[3,4-d][1,3]dioxol-6-yl]methanol (0.25 g, 98% yield) as solid. LCMS ESI (+) m/z 446 (M+H)

Step B: A mixture of [(3aR,4R,6R,6aR)-4-[2-chloro-6-[[(1S)-1-phenylethyl]amino]purin-9-yl]-2,2-dimethyl-3a,4,6,6a-tetrahydrofuro[3,4-d][1,3]dioxol-6-yl]methanol (0.25 g, 0.56 mmol), diethoxyphosphoryl)methyl 4-methylbenzenesulfonate (0.27 g, 0.84 mmol) and magnesium 2-methylpropan-2-olate (0.21 g, 1.23 mmol) in Dimethyl sulfoxide (4 mL) was stirred at 50° C. for 18 hours. After cooled to ambient temperature, water (10 mL) and 1:1 MTBE/ethyl acetate (20 mL) were added. The mixture was passed through a short pad of celite. The organic layer was separated, washed with brine, dried (sodium sulfate), filtered and concentrated under reduced pressure. The residue obtained was purified by flash chromatography on silica gel 10:1 ethyl acetate/methanol to give diethyl (((((3aR,4R,6R,6aR)-6-(2-chloro-6-(((S)-1-phenylethyl)amino)-9H-purin-9-yl)-2,2-dimethyltetrahydrofuro[3,4-d][1,3]dioxol-4-yl)methoxy)methyl)phosphonate (0.22 g, 65%) as solid. LCMS ESI (+) m/z 596 (M+H)

Step C: To a solution of (((((3aR,4R,6R,6aR)-6-(2-chloro-6-(((S)-1-phenylethyl)amino)-9H-purin-9-yl)-2,2-dimethyltetrahydrofuro[3,4-d][1,3]dioxol-4-yl)methoxy)methyl) phosphonate (0.07 g, 0.12 mmol) in Dichloromethane (3 mL) was added 2,6-Lutidine (0.07 mL, 0.61 mmol) and bromotrimethylsilane (0.08 mL, 0.61 mmol) at ambient temperature. The reaction mixture was stirred at this temperature for 18 hours. The reaction mixture was concentrated under reduced pressure. The residue was co-evaporated with methanol three times to give a light yellow solid. It was dissolved in 80% formic acid (1 mL) and stirred at ambient temperature for 6 hours. The reaction mixture was concentrated under reduced pressure. The residue was dissolved in water (0.5 mL) and Lithium hydroxide monohydrate (1.79 mg, 0.04 mmol) was added. It was stirred at ambient temperature for 2 hours. It was purified directly by preparative reverse phase HPLC (10-80% CH₃CN/water (0.1% TFA)) to give (((((2R,3S,4R,5R)-5-(2-chloro-6-(((S)-1-phenylethyl)amino)-9H-purin-9-yl)-3,4-dihydroxytetrahydrofuran-2-yl)methoxy)methyl)phosphonic acid (0.022 g, 36% yield) as TFA salt. LCMS ESI (−) m/z 498 (M−H).

Example 5: Synthesis of [(2R,3S,4R,5R)-5-[2-cyano-6-[[(1S)-1-phenylethyl]amino]purin-9-yl]-3,4-dihydroxy-tetrahydrofuran-2-yl]methoxymethylphosphonic acid; 2,2,2-trifluoroacetic acid (Compound 36)

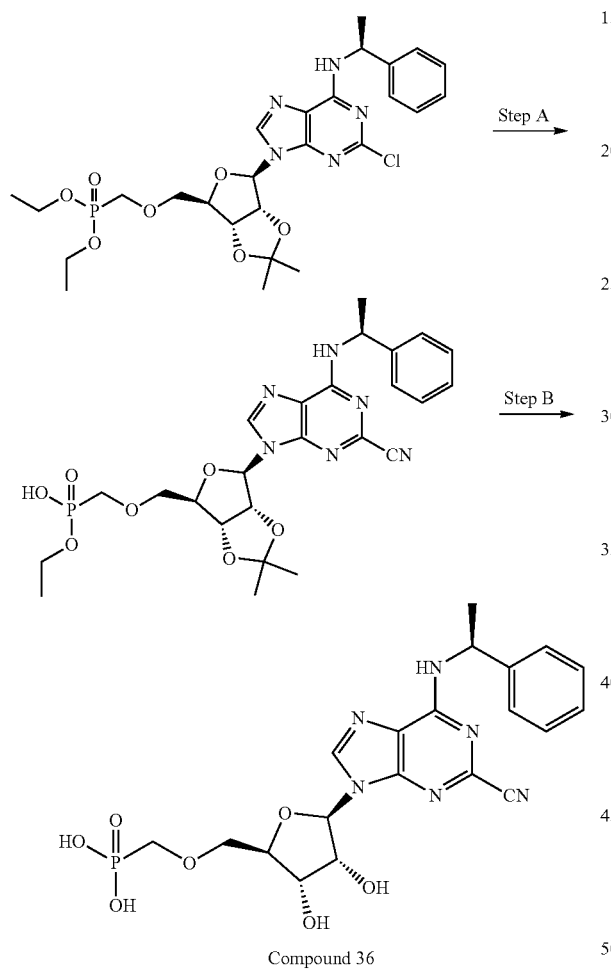

Compound 36

Step A: A mixture of (((((3aR,4R,6R,6aR)-6-(2-chloro-6-(((S)-1-phenylethyl)amino)-9H-purin-9-yl)-2,2-dimethyl-tetrahydrofuro[3,4-d][1,3]dioxol-4-yl)methoxy)methyl) phosphonate (0.16 g, 0.27 mmol) and Sodium Cyanide (0.07 g, 1.33 mmol) in Dimethyl sulfoxide (2 mL) was heated at Microwave at 150° C. for 1 hour and 170° C. for another hour. It was directly purified by reverse phase column (Biotage Isolera One unit, Biotage@SNAP Ultra C18 60 g column, 0-100% CH₃CN/water, 10 CV) to give [(3aR,4R,6R,6aR)-4-[2-cyano-6-[[(1S)-1-phenylethyl]amino]purin-9-yl]-2,2-dimethyl-3a,4,6,6a-tetrahydrofuro[3,4-d][1,3]dioxol-6-yl]methoxymethyl-ethoxy-phosphinic acid (0.064 g, 43% yield) as solid. LCMS ESI (+) m/z 559 (M+H)

Step B: To a solution of [(3aR,4R,6R,6aR)-4-[2-cyano-6-[[(1S)-1-phenylethyl]amino]purin-9-yl]-2,2-dimethyl-3a,4,6,6a-tetrahydrofuro[3,4-d][1,3]dioxol-6-yl]methoxymethyl-ethoxy-phosphinic acid (0.06 g, 0.11 mmol) in Dichloromethane (3 mL) was added 2,6-Lutidine (0.07 mL, 0.57 mmol) and bromotrimethylSilane (0.08 mL, 0.57 mmol) at ambient temperature. The reaction mixture was stirred at this temperature for 18 hours. The reaction mixture was concentrated under reduced pressure. The residue was co-evaporated with methanol three times to give a light yellow solid. Formic acid (80% v/v) (2 mL) was added. The reaction mixture was stirred at ambient temperature for 3 hours. Solvent was removed under reduced pressure. The residue was purified by preparative reverse phase HPLC (10-80% CH₃CN/water (0.1% TFA)) to give [(2R,3S,4R,5R)-5-[2-cyano-6-[[(1S)-1-phenylethyl]amino]purin-9-yl]-3,4-dihydroxy-tetrahydrofuran-2-yl]methoxymethylphosphonic acid; 2,2,2-trifluoroacetic acid (0.041 g, 59%) as TFA salt. LCMS ESI (−) m/z 489 (M−H).

Example 6: Synthesis of [(2R,3S,4R,5R)-5-[6-(benzylamino)-2-phenyl-purin-9-yl]-3,4-dihydroxy-tetrahydrofuran-2-yl]methoxymethylphosphonic acid (Compound 8)

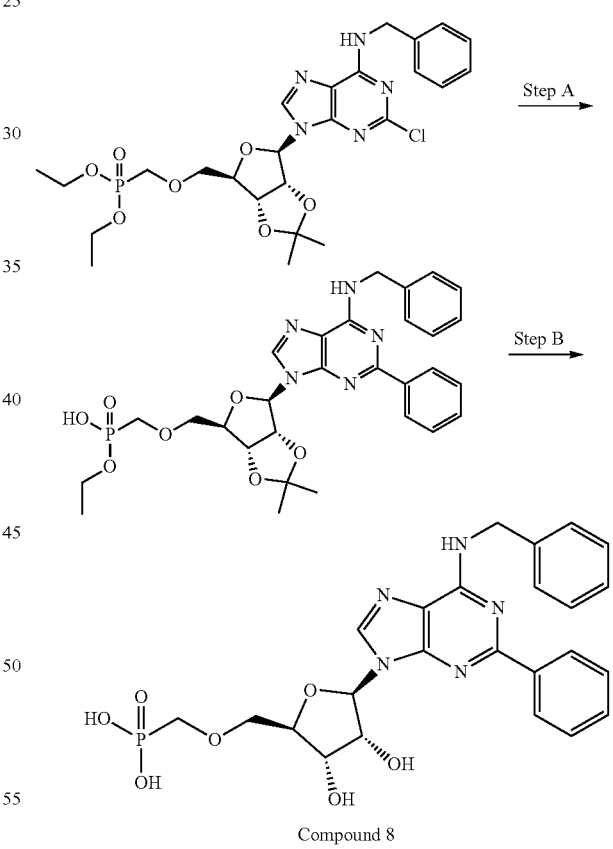

Compound 8

Step A: A mixture of diethyl (((((3aR,4R,6R,6aR)-6-(6-(benzylamino)-2-chloro-9H-purin-9-yl)-2,2-dimethyltetrahydrofuro[3,4-d][1,3]dioxol-4-yl)methoxy)methyl)phosphonate (0.05 g, 0.16 mmol), Phenylboronic acid (0.02 g, 0.17 mmol) and Dichloro[1,1'-bis(diphenylphosphino)ferrocene]palladium (II) dichloromethane adduct (0.01 g, 0.01 mmol) in 1,4-Dioxane (2 mL) and water (0.50 mL) was stirred at 100° C. for 8 hours. After cooled to ambient temperature, water (10 mL) and 1:1 MTBE/ethyl acetate (20 mL) were added. The mixture was passed through a short pad of celite. The organic layer was separated, washed with brine, dried (sodium sulfate), filtered and concentrated under reduced pressure. The residue obtained was purified by flash chromatography on silica gel 10:1 ethyl acetate/methanol to give diethyl ((((3aR,4R,6R,6aR)-6-(6-(benzylamino)-2-phenyl-9H-purin-9-yl)-2,2-dimethyltetrahydrofuro[3,4-d][1,3]dioxol-4-yl)methoxy)methyl) phosphonate (0.048 g, 89%) as solid. LCMS ESI (+) m/z 624 (M+H)

Step B: A mixture of diethyl ((((3aR,4R,6R,6aR)-6-(6-(benzylamino)-2-phenyl-9H-purin-9-yl)-2,2-dimethyltetrahydrofuro[3,4-d][1,3]dioxol-4-yl)methoxy)methyl) phosphonate (0.05 g, 0.08 mmol) and 2, 6-Lutidine (0.09 mL, 0.77 mmol) in Dichloromethane (2 mL) was added bromotrimethylsilane (0.1 mL, 0.77 mmol) at ambient temperature and stirred at room temperature for 18 hours. The reaction mixture was concentrated under reduced pressure. The residue was co-evaporated with methanol three times to give a light yellow solid. 80% formic acid (3 mL) was added and stirred at ambient temperature for 4 hours. Formic acid was removed under reduced pressure. The residue obtained was added 5 mL of saturated sodium bicarbonate and MTBE (10 mL). The aqueous layer was separated and was purified by reverse phase column (Biotage Isolera One unit, Biotage@SNAP Ultra C18 60 g column, 0-80% CH$_3$CN/water, 10 CV) to give [(2R,3S,4R,5R)-5-[6-(benzylamino)-2-phenyl-purin-9-yl]-3,4-dihydroxy-tetrahydrofuran-2-yl]methoxymethylphosphonic acid (0.016 g, 39%) as sodium salts. LCMS ESI (−) m/z 526 (M−H).

Example 7: Synthesis of [(2R,3S,4R,5R)-5-[2-chloro-4-[[(1R)-1-phenylethyl]amino]pyrrolo[2,3-d]pyrimidin-7-yl]-3,4-dihydroxy-tetrahydrofuran-2-yl]methoxymethylphosphonic acid (Compound 61)

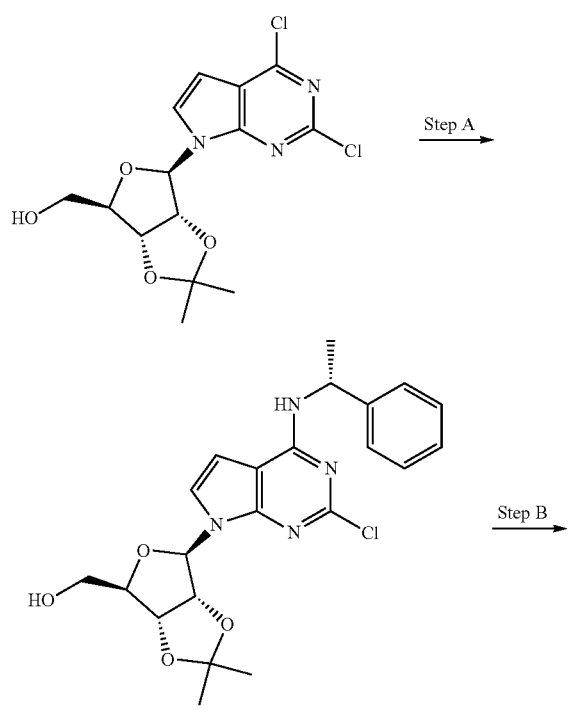

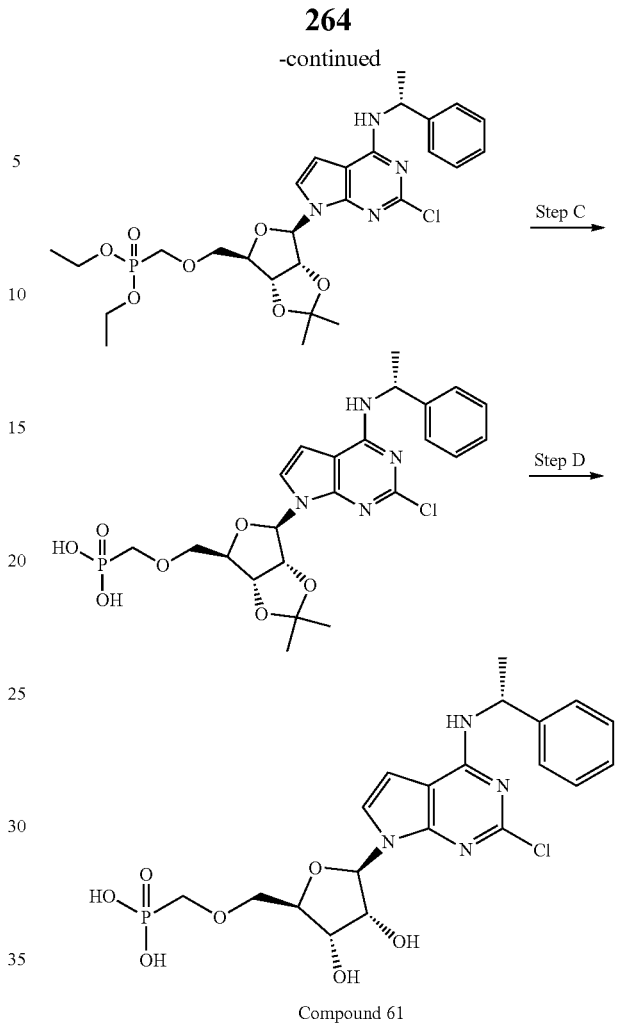

Compound 61

Step A: To a solution of [(3aR,4R,6R,6aR)-4-(2,4-dichloropyrrolo[2,3-d]pyrimidin-7-yl)-2,2-dimethyl-3a,4,6,6a-tetrahydrofuro[3,4-d][1,3]dioxol-6-yl]methanol (0.12 g, 0.33 mmol) in n-butanol (5 mL) was added (R)-(+)-1-Phenylethylamine (0.081 g, 0.67 mmol) and TEA (0.067 g, 0.66 mmol). The mixture was stirred at 100° C. for 16 hours, the solvent was removed under reduced pressure; the residue was partitioned between water and Ethyl acetate. The organic layer was separated, dried (sodium sulfate), filtered and concentrated under reduced pressure. The residue obtained was purified by column chromatography on silica gel 1:1 petroleum ether/ethyl acetate to give [(3aR,4R,6R,6aR)-4-[2-chloro-4-[[(1R)-1-phenylethyl]amino]pyrrolo[2,3-d]pyrimidin-7-yl]-2,2-dimethyl-3a,4,6,6a-tetrahydrofuro[3,4-d][1,3]dioxol-6-yl]methanol (0.13 g, 89%). LCMS ESI (+) m/z 445 (M+H)

Step B: To a solution of [(3aR,4R,6R,6aR)-4-[2-chloro-4-[[(1R)-1-phenylethyl]amino]pyrrolo[2,3-d]pyrimidin-7-yl]-2,2-dimethyl-3a,4,6,6a-tetrahydrofuro[3,4-d][1,3]dioxol-6-yl]methanol (0.13 g, 0.30 mmol) in 1-Methyl-2-pyrrolidone (5 mL) was added 60% sodium hydride (0.060 g, 1.5 mmol) at 10° C., after 5 minutess, (diethoxyphosphoryl)methyl 4-methylbenzenesulfonate (0.19 g, 0.59 mmol) was added, the mixture was stirred at 10° C. for 30 minutes, Ethyl acetate (10 mL) was added, the mixture was cooled to −5° C., then saturated ammonium chloride solution was added. The organic layer was separated, dried (sodium sulfate), filtered and concentrated under reduced pressure.

The residue obtained was purified by Preparative TLC (1:3 petroleum ether/ethyl acetate) to give diethyl (((((3aR,4R,6R,6aR)-6-(2-chloro-6-(((R)-1-phenylethyl)amino)-9H-purin-9-yl)-2,2-dimethyltetrahydrofuro[3,4-d][1,3]dioxol-4-yl)methoxy)methyl)phosphonate (0.045 g, 25%) as solid.

Step C: To a solution of (((((3aR,4R,6R,6aR)-6-(2-chloro-6-(((R)-1-phenylethyl)amino)-9H-purin-9-yl)-2,2-dimethyl-tetrahydrofuro[3,4-d][1,3]dioxol-4-yl)methoxy)methyl)phosphonate (0.020 g, 0.03 mmol) and 2,6-Lutidine (0.12 g, 1.12 mmol) in Dichloromethane (4 mL) was added bromotrimethylsilane (0.18 g, 1.18 mmol) at ambient temperature. The mixture was stirred at ambient temperature overnight. The mixture was concentrated under reduced pressure. The residue was co-evaporated with CH$_3$CN twice to give [(3aR,4R,6R,6aR)-4-[2-chloro-4-[[(1R)-1-phenylethyl]amino]pyrrolo[2,3-d]pyrimidin-7-yl]-2,2-dimethyl-3a,4,6,6a-tetrahydrofuro[3,4-d][1,3]dioxol-6-yl]methoxymethylphosphonic acid which was used directly in the next step without purification.

Step D: A solution of [(3aR,4R,6R,6aR)-4-[2-chloro-4-[[(1R)-1-phenylethyl]amino]pyrrolo[2,3-d]pyrimidin-7-yl]-2,2-dimethyl-3a,4,6,6a-tetrahy drofuro[3,4-d][1,3]dioxol-6-yl]methoxymethylphosphonic acid (0.22 g, 0.04 mmol) in 80% HCOOH (3 mL) was stirred at ambient temperature for 2 hours. The mixture was concentrated under reduced pressure. The residue obtained was purified by reverse phase HPLC (0.1% HCOOH, 20 to 80% MeCN/H$_2$O over 15 min) to give [(2R,3S,4R,5R)-5-[2-chloro-4-[[(1R)-1-phenylethyl]amino]pyrrolo[2,3-d]pyrimidin-7-yl]-3,4-dihydroxy-tetrahydrofuran-2-yl]methoxymethylphosphonic acid (0.006 g, 30%) as solid. LCMS ESI (−) m/z 497 (M−H).

Example 8: Synthesis of [(2R,3S,4R,5R)-5-[2-cyano-4-[[(1R)-1-phenylethyl]amino]pyrrolo[2,3-d]pyrimidin-7-yl]-3,4-dihydroxy-tetrahydrofuran-2-yl]methoxymethylphosphonic acid (Compound 62)

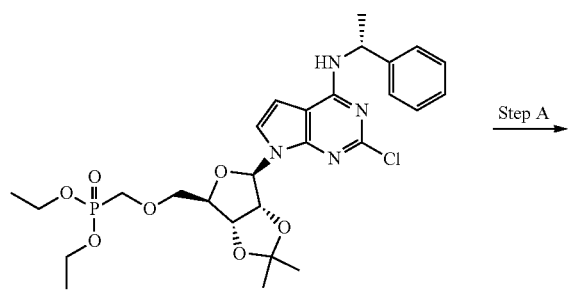

Step A

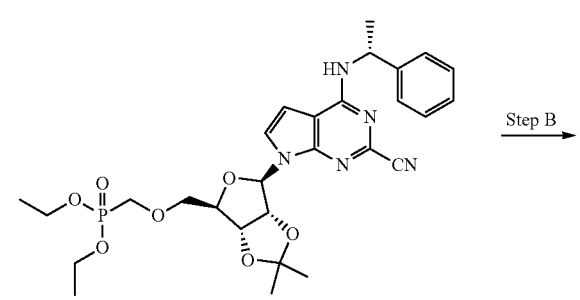

Step B

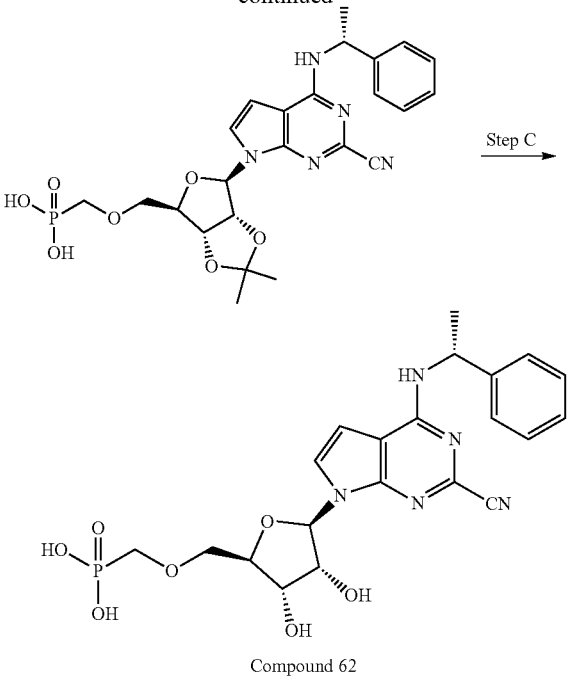

Step C

Compound 62

Step A: To a solution of 7-[(3aR,4R,6R,6aR)-6-(diethoxyphosphorylmethoxymethyl)-2,2-dimethyl-3a,4,6,6a-tetrahydrofuro[3,4-d][1,3]dioxol-4-yl]-2-chloro-N-[(1R)-1-phenylethyl]pyrrolo[2,3-d]pyrimidin-4-amine (0.025 g, 0.04 mmol) in 1-Methyl-2-pyrrolidone (3 mL) was added Zn(CN)$_2$ (0.023 g, 0.2 mmol) and Pd(PPh$_3$)$_4$ (0.046 g, 0.04 mmol) under N2. It was stirred at 180° C. in microwave for 2 hours. The mixture was passed through a pad of celite, washed with ethyl acetate. Water was added; the organic layer was separated, dried (sodium sulfate), filtered and concentrated under reduced pressure. The residue obtained was purified by preparative TLC (1:3 petroleum ether/ethyl acetate) to give 7-[(3aR,4R,6R,6aR)-6-(diethoxyphosphorylmethoxymethyl)-2,2-dimethyl-3a,4,6,6a-tetrahy drofuro [3,4-d][1,3]dioxol-4-yl]-4-[[(1R)-1-phenylethyl]amino]pyrrolo[2,3-d]pyrimidine-2-carbonitrile (0.003 g, 13%).

Step B: To a solution of 7-[(3aR,4R,6R,6aR)-6-(diethoxyphosphorylmethoxymethyl)-2,2-dimethyl-3a,4,6,6a-tetrahy drofuro[3,4-d][1,3]dioxol-4-yl]-4-[[(1R)-1-phenylethyl]amino]pyrrolo[2,3-d]pyrimidine-2-carbonitrile (0.016 g, 0.03 mmol) and 2,6-Lutidine (0.12 g, 1.12 mmol) in Dichloromethane (3 mL) was added bromotrimethylsilane (0.18 g, 1.18 mmol) at ambient temperature. The mixture was stirred at ambient temperature overnight. The mixture was concentrated under reduced pressure. The residue was co-evaporated with CH$_3$CN twice to give [(3aR,4R,6R,6aR)-4-[2-cyano-4-[[(1R)-1-phenylethyl]amino]pyrrolo[2,3-d]pyrimidin-7-yl]-2,2-dimethyl-3a,4,6,6a-tetrahydrofuro[3,4-d][1,3]dioxol-6-yl]methoxymethylphosphonic acid which was used directly in the next step without purification.

Step C: To a solution of [(3aR,4R,6R,6aR)-4-[2-cyano-4-[[(1R)-1-phenylethyl]amino]pyrrolo[2,3-d]pyrimidin-7-yl]-2,2-dimethyl-3a,4,6,6a-tetrahy drofuro[3,4-d][1,3]dioxol-6-yl]methoxymethylphosphonic acid (0.018 g, 0.04 mmol) in 80% HCOOH (3 mL) was stirred at ambient temperature for 2 hours. The mixture was concentrated under reduced pressure. The residue obtained was purified by reverse phase HPLC (0.1% HCOOH, 20 to 80% MeCN/H$_2$O over 15 min) to give [(2R,3S,4R,5R)-5-[2-cyano-4-

[[(1R)-1-phenylethyl]amino]pyrrolo[2,3-d]pyrimidin-7-yl]-3,4-dihydroxy-tetrahydrofuran-2-yl]methoxymethylphosphonic acid (0.003 g, 18%) as solid. LCMS ESI (−) m/z 488 (M−H).

Example 9: Synthesis of ((((2R,3S,4R,5R)-5-(2-chloro-5-fluoro-4-(((S)-1-phenylethyl)amino)-7H-pyrrolo[2,3-d]pyrimidin-7-yl)-3,4-dihydroxytetrahydrofuran-2-yl)methoxy)methyl)phosphonic acid (Compound 76)

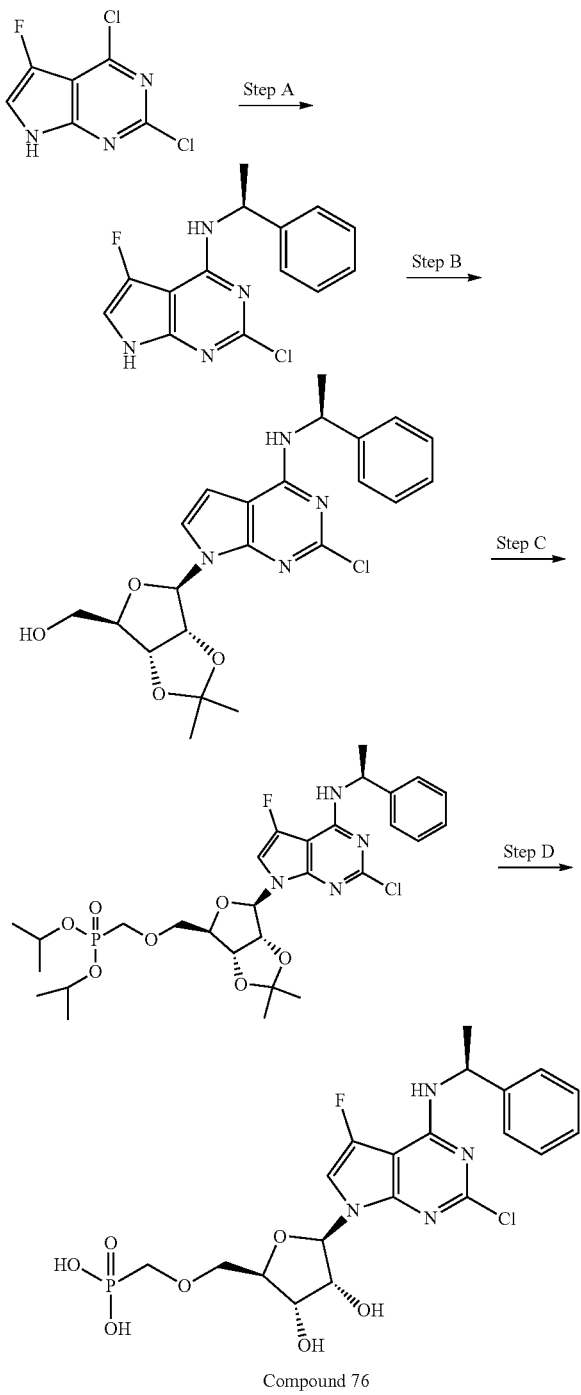

Compound 76

Step A: A mixture of 2,4-dichloro-5-fluoro-7H-pyrrolo[2,3-d]pyrimidine (0.44 g, 2.14 mmol) and N,N-Diisopropylethylamine (0.57 mL, 3.2 mmol) in s-Butanol (5 mL) was added (S)-(−)-1-Phenylethylamine (0.34 g, 2.78 mmol) at ambient temperature. The mixture was stirred at reflux for 3 hours. Solvent was removed under reduced pressure. The residue obtained was purified by flash chromatography on silica gel 1:1 hexane/ethyl acetate to give 2-chloro-5-fluoro-N-[(1S)-1-phenylethyl]-7H-pyrrolo[2,3-d]pyrimidin-4-amine (0.45 g, 72% yield) as solid. LCMS ESI (+) m/z 291 (M+H)

Step B: To a solution of (3aR,6R,6aR)-6-[[tert-butyl(dimethyl)silyl]oxymethyl]-2,2-dimethyl-3a,4,6,6a-tetrahydrofuro[3,4-d][1,3]dioxol-4-ol (0.76 g, 2.5 mmol) and Carbon tetrachloride (0.27 mL, 2.75 mmol) in Tetrahydrofuran (6 mL) was added N,N,N',N',N'',N''-hexamethylphosphanetriamine (0.5 mL, 2.75 mmol) at −30° C. After addition, the mixture was stirred at −30° C. for 1 hour. It was added to a stirred suspension of 2-chloro-5-fluoro-N-[(1S)-1-phenylethyl]-7H-pyrrolo[2,3-d]pyrimidin-4-amine (0.44 g, 1.51 mmol), powdered Potassium Hydroxide (0.17 g, 3.03 mmol) and Tris[2-(2-methoxyethoxy)ethyl]amine (0.58 mL, 0.82 mmol) in Acetonitrile (12 mL) at 0° C. After addition, the reaction mixture was warmed to ambient temperature and stirred at ambient temperature for 18 hours. Saturated ammonium chloride solution (50 mL) and MTBE (50 mL) were added. The organic layer was separated, washed with brine, dried (sodium sulfate), filtered and concentrated under reduced pressure. The residue obtained was purified by flash chromatography on silica gel 5:1 hexane/ethyl acetate to give an oil. It was dissolved in THF (6 mL) and Triethylamine trihydrofluoride (1.23 mL, 7.57 mmol) was added at ambient temperature. The reaction mixture was stirred at ambient temperature for 18 hours. Solvent was removed under reduced pressure. The residue obtained was purified by flash chromatography on silica gel 3:1 DCM/ethyl acetate to give [(3aR,4R,6R,6aR)-4-[2-chloro-5-fluoro-4-[[(1S)-1-phenylethyl]amino]pyrrolo[2,3-d]pyrimidin-7-yl]-2,2-dimethyl-3a,4,6,6a-tetrahydrofuro[3,4-d][1,3]dioxol-6-yl]methanol (0.29 g, 41% yield) as oil. LCMS ESI (+) m/z 463 (M+H)

Step C: A mixture of diisopropyl (bromomethyl)phosphonate (0.18 g, 0.39 mmol) and [(3aR,4R,6R,6aR)-4-[2-chloro-5-fluoro-4-[[(1S)-1-phenylethyl]amino]pyrrolo[2,3-d]pyrimidin-7-yl]-2,2-dimethyl-3a,4,6,6a-tetrahydrofuro[3,4-d][1,3]dioxol-6-yl]methanol (0.10 g, 0.22 mmol) in 1-Methyl-2-pyrrolidone (2 mL) was added 60% Sodium hydride (0.020 g, 0.48 mmol) at ambient temperature. The reaction mixture was stirred at this temperature for 2 hours. 0.5 mL of water was added. It was purified directly by reverse phase column (Biotage Isolera One unit, Biotage@SNAP Ultra C18 30 g column, 20-100% CH$_3$CN/water, 10 CV) to give diisopropyl ((((3aR,4R,6R,6aR)-6-(2-chloro-5-fluoro-4-(((S)-1-phenylethyl)amino)-7H-pyrrolo[2,3-d]pyrimidin-7-yl)-2,2-dimethyltetrahydrofuro[3,4-d][1,3]dioxol-4-yl)methoxy)methyl)phosphonate (0.13 g, 95%) as solid. LCMS ESI (+) m/z 641 (M+H)

Step D: To a solution of diisopropyl ((((3aR,4R,6R,6aR)-6-(2-chloro-5-fluoro-4-(((S)-1-phenylethyl)amino)-7H-pyrrolo[2,3-d]pyrimidin-7-yl)-2,2-dimethyltetrahydrofuro[3,4-d][1,3]dioxol-4-yl)methoxy)methyl)phosphonate (0.13 g, 0.21 mmol) in Dichloromethane (2 mL) was added 2,6-Lutidine (0.25 mL, 2.12 mmol) and bromotrimethylsilane (0.28 mL, 2.12 mmol) at ambient temperature. The reaction mixture was stirred at this temperature for 18 hours. The reaction mixture was concentrated under reduced pressure. The residue was co-evaporated with methanol three times to give a light yellow solid. 80% formic acid (2 mL) was added. The mixture was stirred at ambient temperature for 6 hours. The mixture was concentrated at reduced pressure and co-evaporated with methanol three times to give a thick oil. It was purified by preparative HPLC (10%-95% ACN/H₂O, 0.1% TFA) to give ((((2R,3S,4R,5R)-5-(2-chloro-5-fluoro-4-(((S)-1-phenylethyl)amino)-7H-pyrrolo[2,3-d]pyrimidin-7-yl)-3,4-dihydroxytetrahydrofuran-2-yl)methoxy)methyl)phosphonic acid (0.05 g, 37%) as TFA salts. LCMS ESI (−) m/z 515 (M−H).

Example 10: Synthesis of [(2R,3S,4R,5R)-5-[2-chloro-4-(cyclopentylamino)pyrrolo[2,3-d]pyrimidin-7-yl]-3,4-dihydroxy-tetrahydrofuran-2-yl]methoxymethylphosphonic acid (Compound 70)

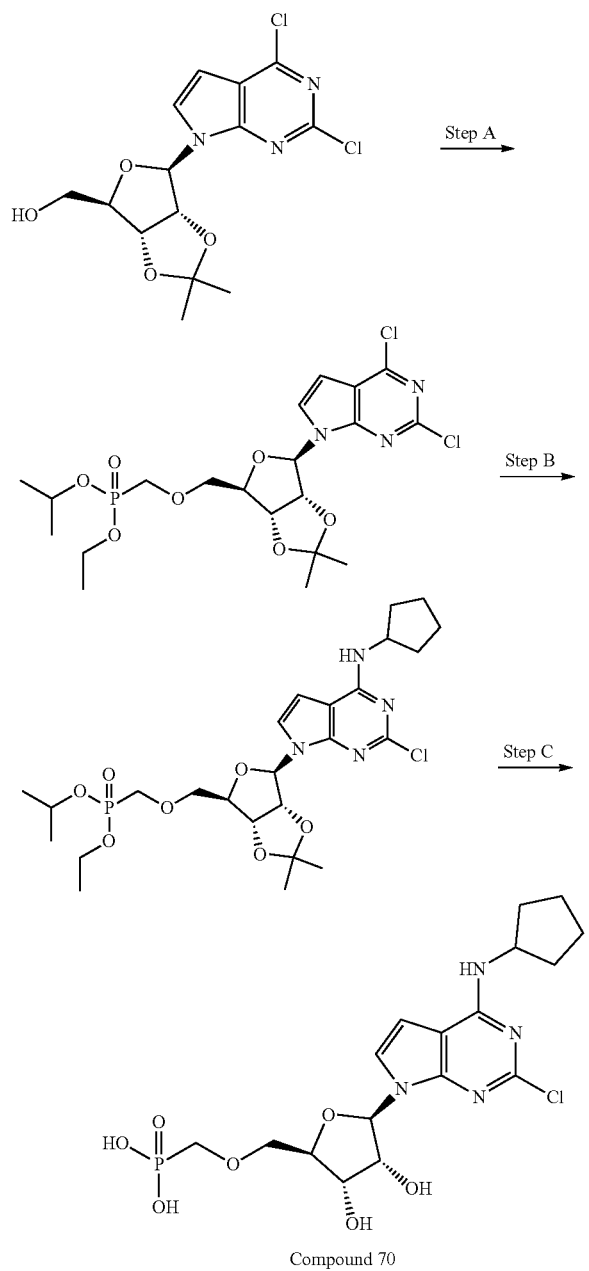

Compound 70

Step A: A mixture of [(3aR,4R,6R,6aR)-4-(2,4-dichloropyrrolo[2,3-d]pyrimidin-7-yl)-2,2-dimethyl-3a,4,6,6a-tetrahydrofuro[3,4-d][1,3]dioxol-6-yl]methanol (0.64 g, 1.78 mmol), diethoxy phosphoryl methyl 4-methylbenzenesulfonate (0.86 g, 2.67 mmol) and magnesium 2-methylpropan-2-olate (0.61 g, 3.55 mmol) in Dimethyl Sulfoxide (10 mL) was heated at 70° C. under nitrogen for 6 hours. After cooled to ambient temperature, the reaction mixture was diluted with saturated ammonium chloride solution (30 mL) and ethyl acetate (30 mL). The organic layer was separated, washed with brine, dried (sodium sulfate), filtered and concentrated under reduced pressure. The residue obtained was purified by reverse phase column (Biotage Isolera One unit, Biotage@SNAP Ultra C18 120 g column, 30-100% CH₃CN/water, 10 CV) to give diethyl ((((3aR,4R,6R,6aR)-6-(2,4-dichloro-7H-pyrrolo[2,3-d]pyrimidin-7-yl)-2,2-dimethyltetrahydrofuro[3,4-d][1,3]dioxol-4-yl)methoxy)methyl)phosphonate (0.30 g, 33%) as solid. LCMS ESI (+) m/z 510 (M+H)

Step B: A mixture of Cyclopentanamine (0.1 g, 1.2 mmol), Et3N (0.17 mL, 1.2 mmol) and ((((3aR,4R,6R,6aR)-6-(2,4-dichloro-7H-pyrrolo[2,3-d]pyrimidin-7-yl)-2,2-dimethyltetrahydrofuro[3,4-d][1,3]dioxol-4-yl)methoxy)methyl)phosphonate (0.31 g, 0.60 mmol) in s-Butanol (5 mL) was stirred at 100° C. overnight. The reaction mixture was concentrated. The residue was purified by flash column chromatography with 1:1 hexane/ethyl acetate to give diethyl ((((3aR,4R,6R,6aR)-6-(2-chloro-4-(cyclopentylamino)-7H-pyrrolo[2,3-d]pyrimidin-7-yl)-2,2-dimethyltetrahydrofuro[3,4-d][1,3]dioxol-4-yl)methoxy)methyl)phosphonate (0.30 g, 89%) as solid. LCMS ESI (+) m/z 559 (M+H)

Step C: To a solution of diethyl ((((3aR,4R,6R,6aR)-6-(2-chloro-4-(cyclopentylamino)-7H-pyrrolo[2,3-d]pyrimidin-7-yl)-2,2-dimethyltetrahydrofuro[3,4-d][1,3]dioxol-4-yl)methoxy)methyl)phosphonate (0.31 g, 0.55 mmol) in Dichloromethane (5 mL) was added 2,6-Lutidine (0.32 mL, 2.73 mmol) and bromotrimethylsilane (0.36 mL, 2.73 mmol) at ambient temperature. The reaction mixture was stirred at this temperature for 18 hours. The reaction mixture was concentrated under reduced pressure. The residue was co-evaporated with methanol three times to give a light yellow solid. 80% formic acid (4 mL) was added. The mixture was stirred at ambient temperature for 6 hours. The mixture was concentrated at reduced pressure and co-evaporated with methanol three times to give a thick oil. 1 N NaOH (4 mL) and MTBE (20 mL) were added. The aqueous phase was isolated and purified directly by reverse phase column (Biotage Isolera One unit, Biotage@SNAP Ultra C18 60 g column, 0-70% CH₃CN/water, 10 CV) to give [(2R,3S,4R,5R)-5-[2-chloro-4-(cyclopentylamino)pyrrolo[2,3-d]pyrimidin-7-yl]-3,4-dihydroxy-tetrahydrofuran-2-yl]methoxymethylphosphonic acid (0.24 g, 95%) as sodium salts. LCMS ESI (−) m/z 461 (M−H).

Example 11: Synthesis of [(2R,3S,4R,5R)-5-[7-(benzylamino)-5-chloro-imidazo[4,5-b]pyridin-3-yl]-3,4-dihydroxy-tetrahydrofuran-2-yl]methoxymethylphosphonic acid (Compound 57)

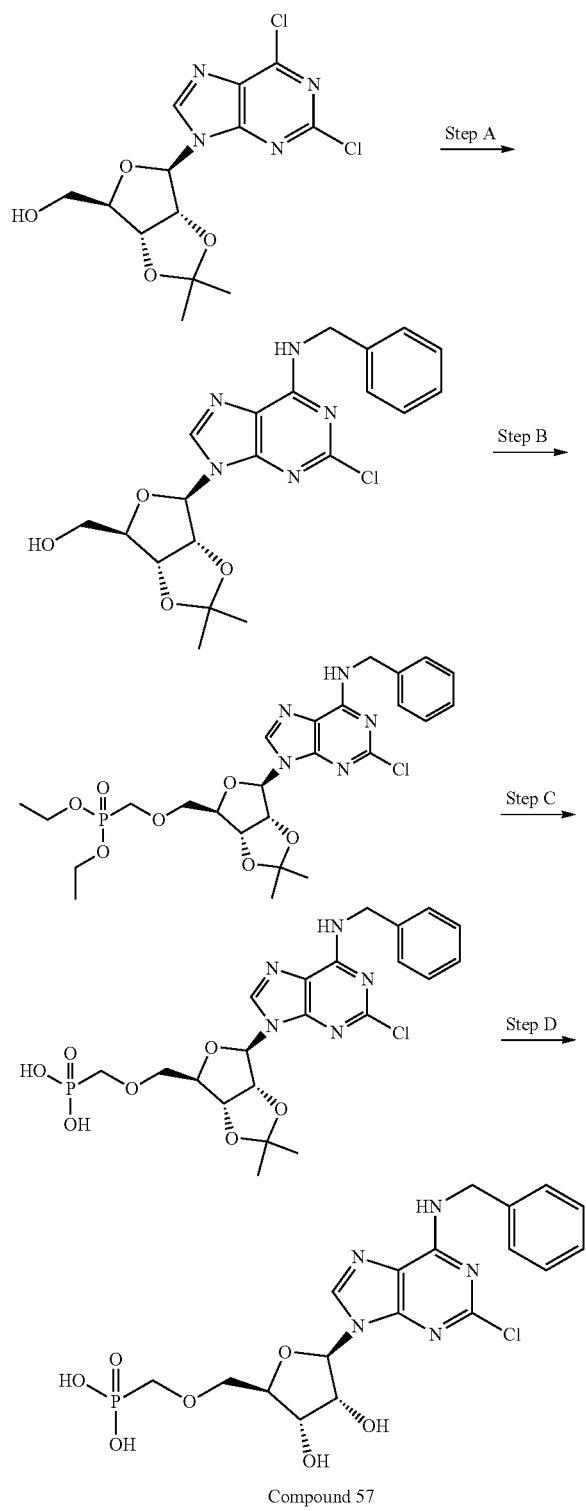

Compound 57

Step A: A solution of [(3aR,4R,6R,6aR)-4-(5,7-dichloro-imidazo[4,5-b]pyridin-3-yl)-2,2-dimethyl-3a,4,6,6a-tetrahydrofuro[3,4-d][1,3]dioxol-6-yl]methanol (115 mg, 0.32 mmol), Benzylamine (54.7 mg, 0.51 mmol) and TEA (64.6 mg, 0.64 mmol) in NMP (6 mL) was stirred at 130° C. in microwave for 3 hours. The mixture was partitioned between water and Ethyl acetate, the organic layer was separated, dried (sodium sulfate), filtered and concentrated under reduced pressure. The residue obtained was purified by Preparative TLC to give [(3aR,4R,6R,6aR)-4-[7-(benzylamino)-5-chloro-imidazo[4,5-b]pyridin-3-yl]-2,2-dimethyl-3a,4,6,6a-tetrahydrofuro[3,4-d][1,3]dioxol-6-yl]methanol (62 mg, 45%).

Step B: To a solution of [(3aR,4R,6R,6aR)-4-[7-(benzylamino)-5-chloro-imidazo[4,5-b]pyridin-3-yl]-2,2-dimethyl-3a,4,6,6a-tetrahydrofuro[3,4-d][1,3]dioxol-6-yl]methanol (50 mg, 0.12 mmol) in NMP (3 mL) was added 60% NaH (9.6 mg, 0.24 mmol) at 10° C. After 10 minutes, diethoxyphosphoryl oxymethyl 4-methylbenzenesulfonate (78.5 mg, 0.23 mmol) was added. The mixture was stirred at 10° C. for an hour. The mixture was quenched with saturated ammonium chloride solution. The residue was partitioned between water and Ethyl acetate, the organic layer was separated, dried (sodium sulfate), filtered, concentrated under reduced pressure. The residue obtained was purified by Preparative TLC 20:1 DCM/MeOH to give diethyl ((((3aR,4R,6R,6aR)-6-(7-(benzylamino)-5-chloro-3H-imidazo[4,5-b]pyridin-3-yl)-2,2-dimethyltetrahydrofuro[3,4-d][1,3]dioxol-4-yl)methoxy)methyl)phosphonate (13 mg, 20%).

Step C: To a solution of diethyl ((((3aR,4R,6R,6aR)-6-(7-(benzylamino)-5-chloro-3H-imidazo[4,5-b]pyridin-3-yl)-2,2-dimethyltetrahydrofuro[3,4-d][1,3]dioxol-4-yl)methoxy)methyl)phosphonate (13 mg, 0.02 mmol) in Dichloromethane (3 mL) was added 2,6-Lutidine (60 mg, 0.56 mmol) and bromotrimethylsilane(90 mg, 0.59 mmol) at ambient temperature. The mixture was stirred at ambient temperature overnight. The mixture was concentrated under reduced pressure and the residue was co-evaporated with CH₃CN twice to give [(3aR,4R,6R,6aR)-4-[7-(benzylamino)-5-chloro-imidazo[4,5-b]pyridin-3-yl]-2,2-dimethyl-3a,4,6,6a-tetrahydrofuro[3,4-d][1,3]dioxol-6-yl]methoxymethylphosphonic acid which was used directly in the next step without purification.

Step D: To a solution of [(3aR,4R,6R,6aR)-4-[7-(benzylamino)-5-chloro-imidazo[4,5-b]pyridin-3-yl]-2,2-dimethyl-3a,4,6,6a-tetrahydrofuro[3,4-d][1,3]dioxol-6-yl]methoxymethyl phosphonic acid (20 mg, 0.04 mmol) in 80% HCOOH (3 mL) was stirred at ambient temperature for 2 hours. The mixture was concentrated under reduced pressure. The residue obtained was purified by reverse phase HPLC (0.1% HCOOH, 20 to 80% MeCN/H₂O over 15 min) [(2R,3S,4R,5R)-5-[7-(benzylamino)-5-chloro-imidazo[4,5-b]pyridin-3-yl]-3,4-dihydroxy-tetrahydrofuran-2-yl]methoxymethylphosphonic acid (3.3 mg, 17%). LCMS ESI (−) m/z 483 (M−H).

Example 12: Synthesis of [(2R,3S,4R,5R)-5-[6-chloro-4-[[(1R)-1-phenylethyl]amino]pyrrolo[2,3-b]pyridin-1-yl]-3,4-dihydroxy-tetrahydrofuran-2-yl]methoxymethylphosphonic acid (Compound 134)

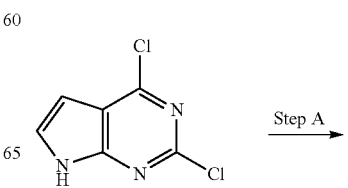

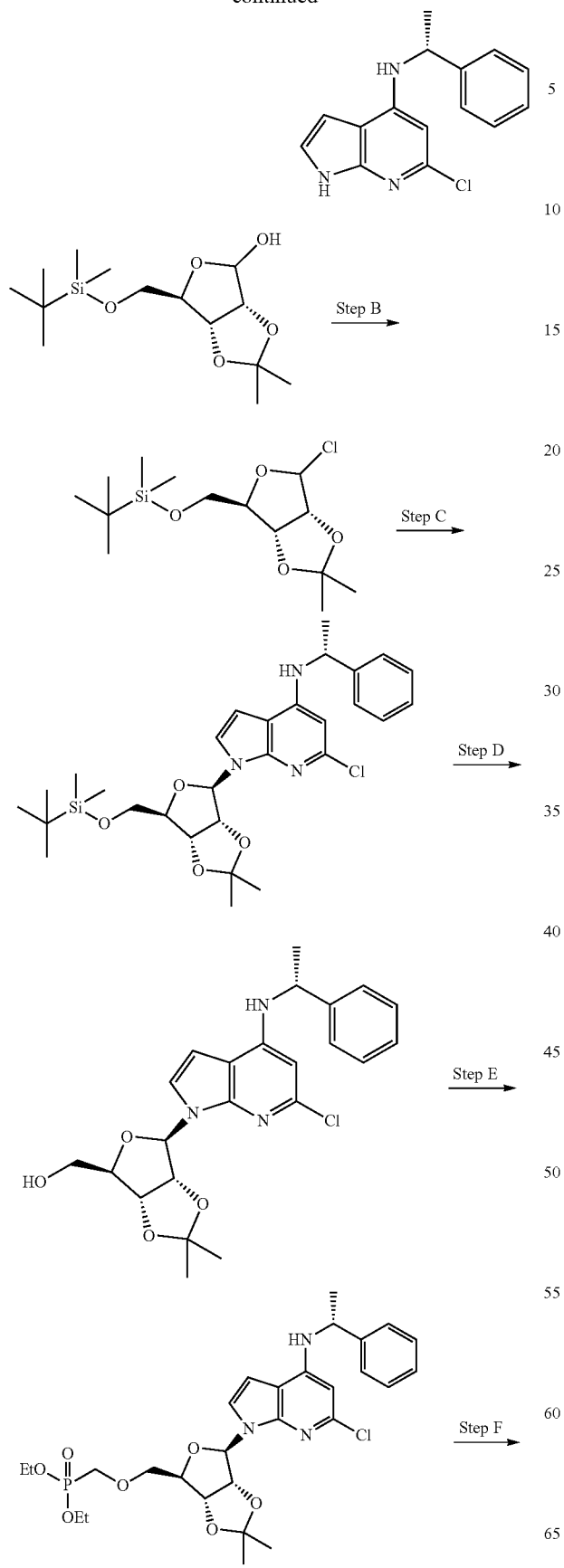

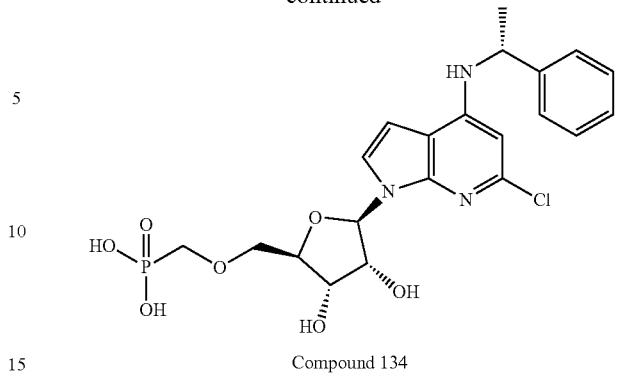

Compound 134

Step A: 46-Dichloro-1H-pyrrolo[2,3b]pyridin (1.0 g, 5.4 mmol) was combined with (R)-(+)-1-phenylethylamine (5.5 mL, 43 mmol) and the mixture was heated in the microwave reactor at 220° C. for 4 hours. The mixture was cooled and washed three times with 10% aqueous citric acid, water, saturated NaCl, dried over $Na_2SO_4$ and concentrated in vacuo. The dark residue was slurried in methylene chloride and the undissolved solids were removed by filtration, washed with methylene chloride then the filtrate was chromatographed on $SiO_2$ (Biotage SNAP 25 g) and eluted with a gradient of ethyl acetate/hexanes. Two isomeric materials eluted from the column. The less polar material was confirmed as the desired product by NMR, (336 mg). LCMS ESI (+) m/z 272.1 (M+H).

Step B: A solution of (3aR,6R,6aR)-6-(((tert-butyldimethylsilyl)oxy)methyl)-2,2-dimethyltetrahydrofuro[3,4-d][1,3]dioxol-4-ol (0.57 g, 1.9 mmol) dissolved in a mixture of carbon tetrachloride (0.2 mL, 2.1 mmol) and THF (3.3 mL) was cooled to −30° C. and treated dropwise with N,N,N,N,N,N-hexamethyl-phosphorus triamide (0.37 mL, 2.1 mmol). The mixture was stirred for 1 hour at −30° C. then a portion was used directly in the next step.

Step C: Potassium hydroxide (0.080 g, 1.5 mmol) was powdered and added to a solution of (R)-6-chloro-N-(1-phenylethyl)-1 □²-pyrrolo[2,3-b]pyridin-4-amine (0.20 g, 0.74 mmol) and 3-[bis[2-(2-methoxyethoxy)ethyl]amino]propan-1-ol; 1-methoxypropane (0.31 mL, 0.88 mmol) dissolved in acetonitrile (3 mL). The resulting suspension was stirred in an ambient temperature bath and treated dropwise with a solution of tert-butyl(((3aR,4R,6aR)-6-chloro-2,2-dimethyltetrahydrofuro[3,4-d][1,3]dioxol-4-yl)methoxy)dimethylsilane (0.31 g, 0.96 mmol) dissolved in THF (1.7 mL) [Step B]. The mixture was stirred at ambient temperature for 14 hours. The reaction was quenched with saturated $NH_4Cl$ (~30 mL) and ethyl acetate. The layers were separated and the organic layer was washed with saturated NaCl, dried over $Na_2SO_4$ and concentrated in vacuo. The crude oil was chromatographed on $SiO_2$ (Biotage SNAP Ultra 10 g) and eluted with a gradient of ethyl acetate/hexanes. Two isomeric products were eluted and the more polar one was identified as the desired product by NMR, (115 mg). LCMS ESI (+) m/z 558.3 (M+H).

Step D: 1-((3aR,4R,6R,6aR)-6-(((tert-butyldimethylsilyl)oxy)methyl)-2,2-dimethyltetrahydrofuro[3,4-d][1,3]dioxol-4-yl)-6-chloro-N—((R)-1-phenylethyl)-1H-pyrrolo[2,3-b]pyridin-4-amine (115 mg, 0.21 mmol) was dissolved in THF (1 mL) and treated with triethylamine trihydrofluoride (0.10 mL, 0.62 mmol). The reaction was stirred at ambient temperature for 6 hours. The mixture was concentrated in vacuo then the crude product was chromatographed on $SiO_2$ (Biotage SNAP 10 g) and eluted with a gradient of ethyl acetate/hexanes, (35 mg). LCMS ESI (+) m/z 444.2 (M+H).

Step E: ((3aR,4R,6R,6aR)-6-(6-chloro-4-(((R)-1-phenylethyl)amino)-1H-pyrrolo[2,3-b]pyridin-1-yl)-2,2-dimethyltetrahydrofuro[3,4-d][1,3]dioxol-4-yl)methanol (35 mg, 0.08 mmol) was dissolved in DMSO (1.4 mL) then treated with (diethoxyphosphoryl)methyl 4-methylbenzenesulfonate (38 mg, 0.12 mmol) and magnesium di-tert-butoxide (37 mg, 0.20 mmol) then the mixture was heated to 70° C. for 14 hours. The reaction was cooled then treated with a mixture of water (5 mL), MtBE (5 mL) and ethyl acetate (5 mL) then stirred for 10 minutes. The mixture was filtered through a pad of celite, then the filtrate was separated and the organic layer was washed twice with saturated NaCl, dried over Na₂SO₄ and concentrated in vacuo. The crude product was chromatographed on SiO₂ (Biotage SNAP 10 g) and eluted with a gradient of ethyl acetate/hexanes, (32 mg). LCMS ESI (+) m/z 594.3 (M+H).

Step F: Diethyl ((((3aR,4R,6R,6aR)-6-(6-chloro-4-(((R)-1-phenylethyl)amino)-1H-pyrrolo[2,3-b]pyridin-1-yl)-2,2-dimethyltetrahydrofuro[3,4-d][1,3]dioxol-4-yl)methoxy)methyl)phosphonate (32 mg, 0.05 mmol) was treated with a pre-mixed solution of formic acid (4 mL) and water (1 mL) then mixture was stirred for 14 hours at ambient temperature. The reaction mixture was concentrated under a stream of nitrogen gas then redissolved and reconcentrated from acetonitrile (~3 mL) five separate times. The resulting oil was dissolved in fresh acetonitrile (0.3 mL) and treated with 2,6-lutidine (0.090 mL, 0.81 mmol) then bromotrimethylsilane (0.11 mL, 0.81 mmol). The reaction mixture was partially insoluble, so additional acetonitrile (0.7 mL) was added and the mixture was stirred at ambient temperature for 14 hours. The mixture was quenched with MeOH (~3 mL) and evaporated using nitrogen gas three times. The crude product was dissolved in MeOH (1 mL) and chromatographed on reversed-phase HPLC [Gilson 271 system] eluting with a gradient of MeCN (modified with 0.1% TFA)/water (modified with 0.1% TFA). The desired product was concentrated using a stream of nitrogen gas to reduce the volume then the remainder was lyophilized to white powder, (9.0 mg). LCMS ESI (+) m/z 498.1 (M+H).

Example 13: Synthesis of ((((((2R,3S,4R,5R)-5-(2-chloro-4-(methyl((R)-1-phenylethyl)amino)-7H-pyrrolo[2,3-d]pyrimidin-7-yl)-3,4-dihydroxytetrahydrofuran-2-yl)methoxy)methyl)(hydroxy) phosphoryl)oxy)methyl pivalate (Compound 132) and ((((((2R,3S,4R,5R)-5-(2-chloro-4-(methyl((R)-1-phenylethyl)amino)-7H-pyrrolo[2,3-d]pyrimidin-7-yl)-3,4-dihydroxytetrahydrofuran-2-yl)methoxy)methyl)phosphoryl)bis(oxy))bis(methylene) bis(2,2-dimethylpropanoate) (Compound 133)

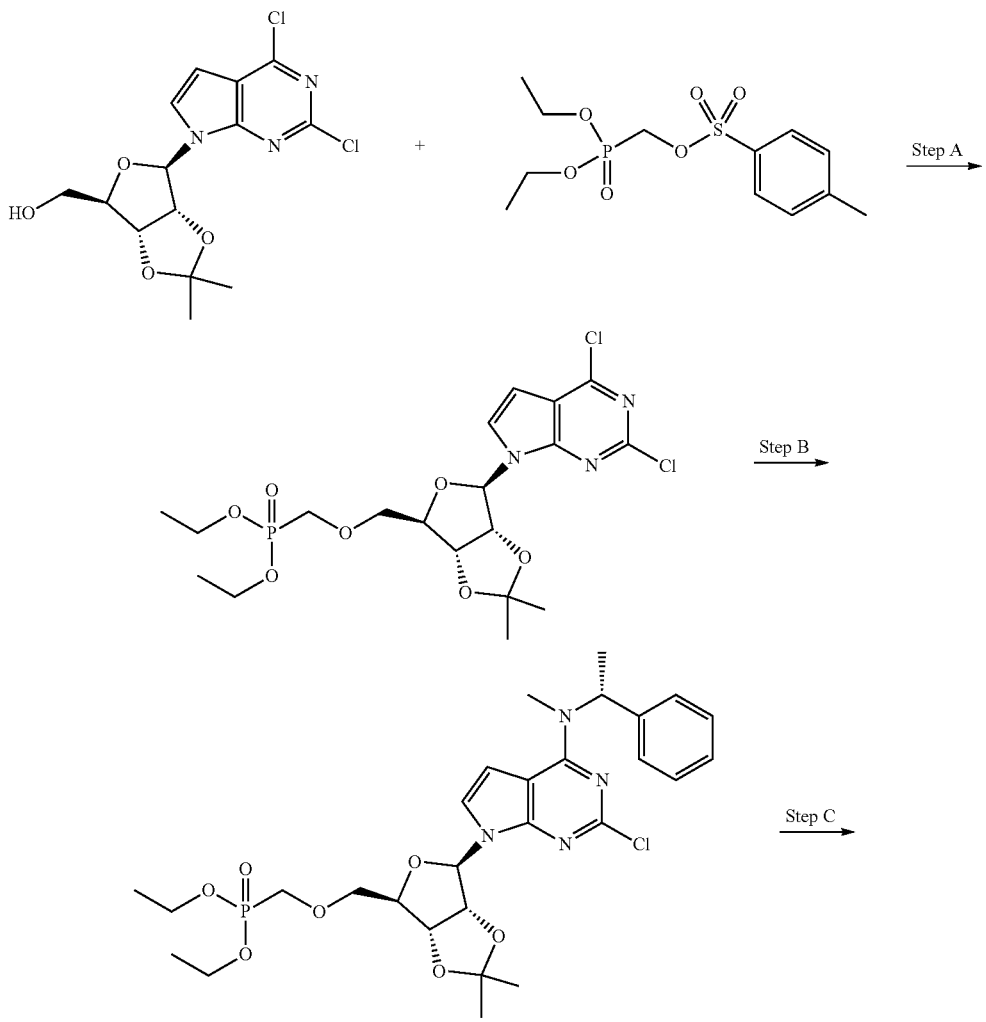

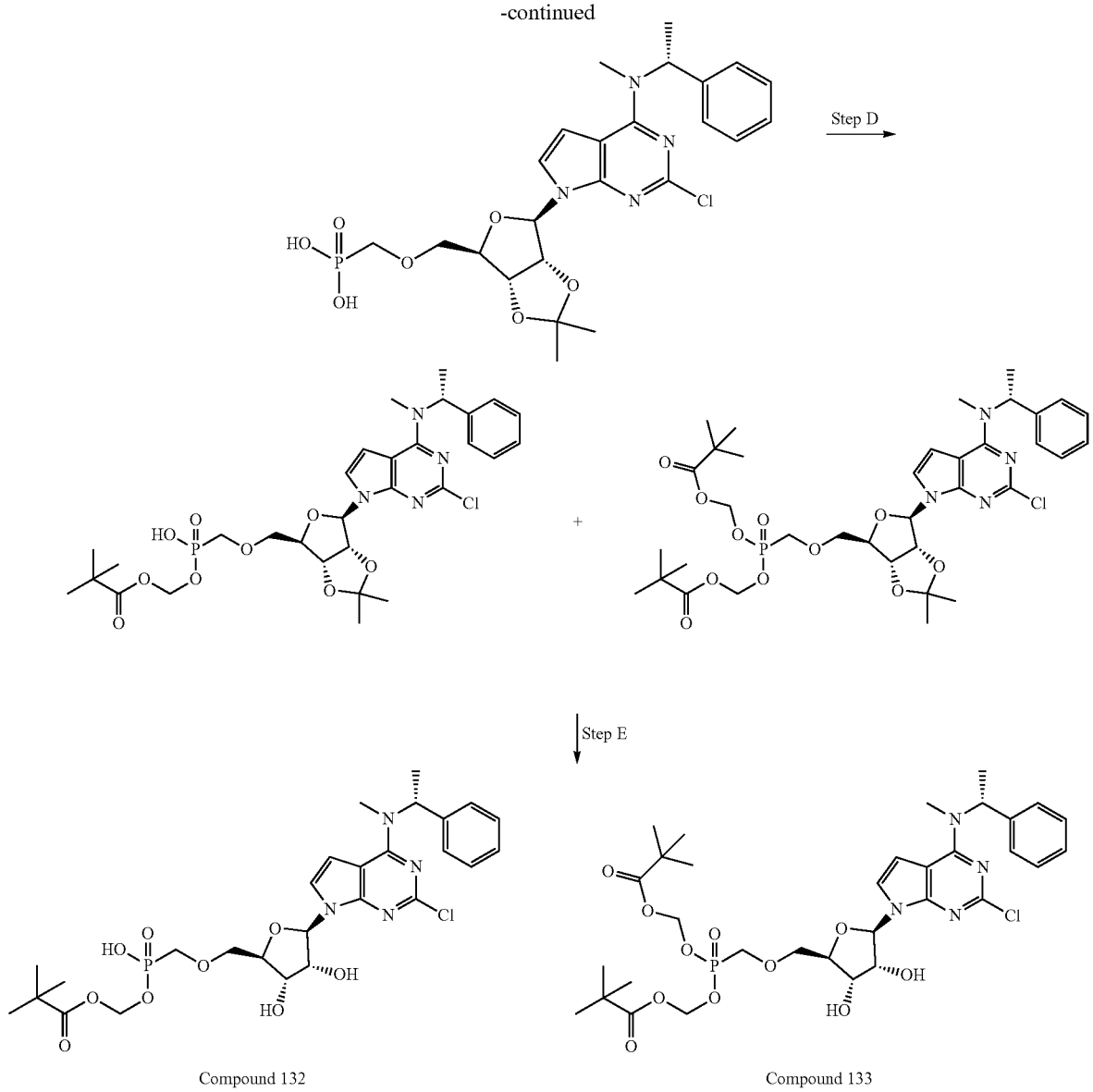

Compound 132

Compound 133

Step A: A mixture of ((3aR,4R,6R,6aR)-6-(2,4-dichloro-7H-pyrrolo[2,3-d]pyrimidin-7-yl)-2,2-dimethyltetrahydrofuro[3,4-d][1,3]dioxol-4-yl)methanol (468 mg, 1.3 mmol), phosphonic acid, P-[[[(4-methylphenyl)sulfonyl]oxy]methyl]-, diethyl ester (628 mg, 1.95 mmol) and ditert-butoxymagnesium (443 mg, 2.6 mmol) in dimethyl sulfoxide (2 mL) was heated at 70° C. under nitrogen overnight. The reaction mixture was diluted with brine and extracted with EtOAc. The organic layer was dried over $Na_2SO_4$, filtered, and concentrated. The residue was purified by flash column chromatography with EtOAc/hexane (10% to 100%) followed by MeOH/EtOAc (0% to 10%) to give diethyl ((((3aR,4R,6R,6aR)-6-(2,4-dichloro-7H-pyrrolo[2,3-d]pyrimidin-7-yl)-2,2-dimethyltetrahydrofuro[3,4-d][1,3]dioxol-4-yl)methoxy)methyl)phosphonate (92 mg, 0.18 mmol, 14% yield). LCMS ESI (+) m/z 510 (M+H).

Step B: A mixture of (R)—N-methyl-1-phenylethan-1-amine (49 mg, 0.36 mmol), $Et_3N$ (0.13 mL, 0.9 mmol) and diethyl ((((3aR,4R,6R,6aR)-6-(2,4-dichloro-7H-pyrrolo[2,3-d]pyrimidin-7-yl)-2,2-dimethyltetrahydrofuro[3,4-d][1,3] dioxol-4-yl)methoxy)methyl)phosphonate (92 mg, 0.18 mmol) in 2-propanol (3 mL) was heated at 100° C. overnight. The reaction mixture was concentrated. The residue was purified by flash column chromatography with EtOAc/hexane (10% to 100%) to give diethyl ((((3aR,4R,6R,6aR)-6-(2-chloro-4-(methyl((R)-1-phenylethyl)amino)-7H-pyrrolo[2,3-d]pyrimidin-7-yl)-2,2-dimethyltetrahydrofuro[3,4-d][1,3]dioxol-4-yl)methoxy)methyl)phosphonate (100 mg, 0.16 mmol, 91% yield). LCMS ESI (+) m/z 609 (M+H).

Step C: To a solution of diethyl ((((3aR,4R,6R,6aR)-6-(2-chloro-4-(methyl((R)-1-phenylethyl)amino)-7H-pyrrolo[2,3-d]pyrimidin-7-yl)-2,2-dimethyltetrahydrofuro[3,4-d][1,3]dioxol-4-yl)methoxy)methyl)phosphonate (77 mg, 0.13 mmol) in acetonitrile (3 mL) was added 2,6-lutidine (0.15 mL, 1.26 mmol) followed by silane, bromotrimethyl-(0.17 mL, 1.26 mmol). The reaction was stirred at room temperature for 6 h and concentrated under reduced pressure. The residue was dissolved in methanol and then concentrated. The process was repeated one more time. The residue was purified by reverse phase flash column chromatography with CH$_3$CN/water (10% to 80%) to give ((((3aR,4R,6R,6aR)-6-(2-chloro-4-(methyl((R)-1-phenylethyl)amino)-7H-pyrrolo[2,3-d]pyrimidin-7-yl)-2,2-dimethyltetrahydrofuro[3,4-d][1,3]dioxol-4-yl)methoxy)methyl)phosphonic acid (54 mg, 0.1 mmol, 77% yield). LCMS ESI (+) m/z 553 (M+H).

Step D: A mixture of iodomethyl 2,2-dimethylpropanoate (0.02 mL, 0.15 mmol), silver oxide (Ag$_2$O) (45 mg, 0.2 mmol) and ((((3aR,4R,6R,6aR)-6-(2-chloro-4-(methyl((R)-1-phenylethyl)amino)-7H-pyrrolo[2,3-d]pyrimidin-7-yl)-2,2-dimethyltetrahydrofuro[3,4-d][1,3]dioxol-4-yl)methoxy)methyl)phosphonic acid (54 mg, 0.1 mmol) in DMF (3 mL) was stirred at 70° C. for 4 h. The reaction mixture was directly purified by reverse phase column chromatography with CH$_3$CN/water (20% to 90%) to give ((((((3aR,4R,6R,6aR)-6-(2-chloro-4-(methyl((R)-1-phenylethyl)amino)-7H-pyrrolo[2,3-d]pyrimidin-7-yl)-2,2-dimethyltetrahydrofuro[3,4-d][1,3]dioxol-4-yl)methoxy)methyl)(hydroxy)phosphoryl)oxy)methyl pivalate (LCMS ESI (+) m/z 667 (M+H)) and ((((((3aR,4R,6R,6aR)-6-(2-chloro-4-(methyl((R)-1-phenylethyl)amino)-7H-pyrrolo[2,3-d]pyrimidin-7-yl)-2,2-dimethyltetrahydrofuro[3,4-d][1,3]dioxol-4-yl)methoxy)methyl)phosphoryl)bis(oxy))bis(methylene) bis(2,2-dimethylpropanoate) (LCMS ESI (+) m/z 781 (M+H)) (yields were not determined; used in the next step).

Step E: A mixture of water (1 mL), formic acid (4 mL) and ((((((3aR,4R,6R,6aR)-6-(2-chloro-4-(methyl((R)-1-phenylethyl)amino)-7H-pyrrolo[2,3-d]pyrimidin-7-yl)-2,2-dimethyltetrahydrofuro[3,4-d][1,3]dioxol-4-yl)methoxy)methyl)(hydroxy)phosphoryl)oxy)methyl pivalate (prepared in step D) was stirred at room temperature for 4 h. The reaction mixture was concentrated with a stream of nitrogen and purified by reverse phase prep HPLC with CH$_3$CN/water (10% to 95% with 1% TFA) to give ((((((2R,3S,4R,5R)-5-(2-chloro-4-(methyl((R)-1-phenylethyl)amino)-7H-pyrrolo[2,3-d]pyrimidin-7-yl)-3,4-dihydroxytetrahydrofuran-2-yl)methoxy)methyl)(hydroxy)phosphoryl)oxy)methyl pivalate (6.4 mg, LCMS ESI (+) m/z 627 (M+H)).

((((((2R,3S,4R,5R)-5-(2-chloro-4-(methyl((R)-1-phenylethyl)amino)-7H-pyrrolo[2,3-d]pyrimidin-7-yl)-3,4-dihydroxytetrahydrofuran-2-yl)methoxy)methyl)phosphoryl)bis(oxy))bis(methylene) bis(2,2-dimethylpropanoate) (4.9 mg, LCMS ESI (+) m/z 741 (M+H)) was prepared similarly.

Example 14: Synthesis of (((((((2S,3S,4R,5R)-5-(2-chloro-4-(cyclopentylamino)-7H-pyrrolo[2,3-d]pyrimidin-7-yl)-3,4-dihydroxytetrahydrofuran-2-yl)methyl)sulfonyl)methyl)phosphoryl)bis(oxy))bis(methylene) bis(2,2-dimethylpropanoate) (Compound 165)

Compound 165

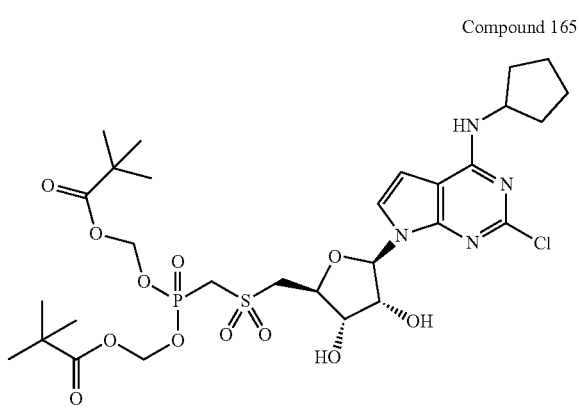 [SMILES: CC(C)(C)C(=O)OCOP(=O)(CS(=O)(=O)C[C@H]1O[C@@H](n2ccc3c(NC4CCCC4)nc(Cl)nc32)[C@H](O)[C@@H]1O)OCOC(=O)C(C)(C)C]

Step A: A mixture of ((3aR,4R,6R,6aR)-6-(2,4-dichloro-7H-pyrrolo[2,3-d]pyrimidin-7-yl)-2,2-dimethyltetrahydrofuro[3,4-d][1,3]dioxol-4-yl)methanol (1.0 g, 2.78 mmol), triethylamine (0.58 mL, 4.16 mmol) and cyclopentanamine (0.47 g, 5.55 mmol) in 2-propanol (12 mL) was heated at 85° C. overnight. Solvent was removed under reduced pressure. The residue was purified by flash chromatography on silica gel with hexane/ethyl acetate (10% to 100%) to give ((3aR,4R,6R,6aR)-6-(2-chloro-4-(cyclopentylamino)-7H-pyrrolo[2,3-d]pyrimidin-7-yl)-2,2-dimethyltetrahydrofuro[3,4-d][1,3]dioxol-4-yl)methanol (0.98 g, 2.4 mmol, 87% yield) as a solid. LCMS ESI (+) m/z 409 (M+H).

Step B: To a solution of thioacetic acid (0.34 mL, 4.8 mmol) and ((3aR,4R,6R,6aR)-6-(2-chloro-4-(cyclopentylamino)-7H-pyrrolo[2,3-d]pyrimidin-7-yl)-2,2-dimethyltetrahydrofuro[3,4-d][1,3]dioxol-4-yl)methanol (982 mg, 2.4 mmol) in anhydrous tetrahydrofuran (12 mL) at 0° C. was added triphenylphosphine (1.89 g, 7.21 mmol) followed by diisopropyl azodicarboxylate (1.41 mL, 7.21 mmol). The ice bath was removed. The reaction was stirred at room temperature overnight. Additional thioacetic acid (0.34 mL, 4.8 mmol), triphenylphosphine (0.945, 3.6 mmol) and diisopropyl azodicarboxylate (1.41 mL, 7.21 mmol) were added. The reaction mixture was stirred at room temperature for another 4 h, diluted with brine and extracted with EtOAc. The organic layer was dried over Na$_2$SO$_4$, filtered, and concentrated. The residue was purified by flash column chromatography with EtOAc/hexane (10% to 80%) to give S-(((3aS,4S,6R,6aR)-6-(2-chloro-4-(cyclopentylamino)-7H-pyrrolo[2,3-d]pyrimidin-7-yl)-2,2-dimethyltetrahydrofuro[3,4-d][1,3]dioxol-4-yl)methyl) ethanethioate (870 mg, 1.86 mmol, 78% yield). LCMS ESI (+) m/z 467 (M+H).

Step C: A solution of S-(((3aS,4S,6R,6aR)-6-(2-chloro-4-(cyclopentylamino)-7H-pyrrolo[2,3-d]pyrimidin-7-yl)-2,2-dimethyltetrahydrofuro[3,4-d][1,3]dioxol-4-yl)methyl) ethanethioate (314 mg, 0.6700 mmol) in 2-propanol (10 mL) was purged with nitrogen for 30 minutes. Isopropoxysodium (110.38 mg, 1.34 mmol) was added. The mixture was stirred at room temperature for 30 minutes. Phosphonic acid, P-(bromomethyl)-, bis(1-methylethyl) ester (348.4 mg, 1.34 mmol) was added. The reaction mixture was stirred at 60° C. for 1 h and then directly purified by flash column chromatography with EtOAc/hexane (10% to 100%) to give diisopropyl (((((3aS,4S,6R,6aR)-6-(2-chloro-4-(cyclopentylamino)-7H-pyrrolo[2,3-d]pyrimidin-7-yl)-2,2-dimethyltetrahydrofuro[3,4-d][1,3]dioxol-4-yl)methyl)thio)methyl)phosphonate (433 mg, 0.72 mmol, quant. yield). LCMS ESI (+) m/z 603 (M+H).

Step D: To a solution of diisopropyl (((((3aS,4S,6R,6aR)-6-(2-chloro-4-(cyclopentylamino)-7H-pyrrolo[2,3-d]pyrimidin-7-yl)-2,2-dimethyltetrahydrofuro[3,4-d][1,3]dioxol-4-yl)methyl)thio)methyl)phosphonate (280 mg, 0.46 mmol) in acetonitrile (5 mL) was added 2,6-lutidine (0.54 mL, 4.64 mmol) followed by bromotrimethylsilane (0.61 mL, 4.64 mmol). The reaction mixture was stirred at room temperature for 4 h and then concentrated under reduced pressure. The residue was dissolved in methanol, and then concentrated. The process was repeated one more time. The residue was purified by reverse phase flash column chromatography with CH$_3$CN/water (10% to 80%) to give (((((3aS,4S,6R,6aR)-6-(2-chloro-4-(cyclopentylamino)-7H-pyrrolo

[2,3-d]pyrimidin-7-yl)-2,2-dimethyltetrahydrofuro[3,4-d] [1,3]dioxol-4-yl)methyl)thio)methyl)phosphonic acid (217 mg, 0.42 mmol, 90% yield). LCMS ESI (+) m/z 519 (M+H).

Step E: A mixture of silver oxide (Ag$_2$O) (549 mg, 2.37 mmol), (((((3aS,4S,6R,6aR)-6-(2-chloro-4-(cyclopentylamino)-7H-pyrrolo[2,3-d]pyrimidin-7-yl)-2,2-dimethyltetrahydrofuro[3,4-d][1,3]dioxol-4-yl)methyl)thio)methyl) phosphonic acid and propanoic acid, 2,2-dimethyl-, iodomethyl ester (0.18 mL, 1.18 mmol) in N,N-dimethylformamide (6 mL) was heated at 75° C. overnight. Additional propanoic acid, 2,2-dimethyl-, iodomethyl ester (0.18 mL, 1.18 mmol) was added and the reaction mixture was stirred at 70° C. for 4 h. After cooling to room temperature, the mixture was diluted with EtOAc and saturated aqueous NaH$_2$PO$_4$, and filtered through celite. The organic layer was separated, dried over Na$_2$SO$_4$, filtered, and concentrated. The residue was purified by reverse phase column chromatography with CH$_3$CN/water (10% to 100%) to give (((((((3aS,4S,6R,6aR)-6-(2-chloro-4-(cyclopentylamino)-7H-pyrrolo[2,3-d]pyrimidin-7-yl)-2,2-dimethyltetrahydrofuro[3,4-d][1,3]dioxol-4-yl)methyl)thio)methyl)phosphoryl)bis(oxy))bis(methylene) bis(2,2-dimethylpropanoate) (98 mg, 0.13 mmol, 33% yield). LCMS ESI (+) m/z 747 (M+H).

Step F: To a solution of (((((((3aS,4S,6R,6aR)-6-(2-chloro-4-(cyclopentylamino)-7H-pyrrolo[2,3-d]pyrimidin-7-yl)-2,2-dimethyltetrahydrofuro[3,4-d][1,3]dioxol-4-yl) methyl)thio)methyl)phosphoryl)bis(oxy))bis(methylene) bis (2,2-dimethylpropanoate) (0.1 g, 0.13 mmol) in acetonitrile (3 mL) and water (1 mL) was added Oxone (0.24 g, 0.79 mmol) at ambient temperature. The mixture was stirred at ambient temperature for 5 hours. Ethyl acetate (20 mL) and water (10 mL) were added. The organic layer was separated, washed with brine, dried (sodium sulfate), filtered, and concentrated under reduced pressure. The residue was purified by column chromatography on silica gel with ethyl acetate/hexane (10% to 100%) to give (((((((3aS,4S,6R,6aR)-6-(2-chloro-4-(cyclopentylamino)-7H-pyrrolo[2,3-d]pyrimidin-7-yl)-2,2-dimethyltetrahydrofuro[3,4-d][1,3]dioxol-4-yl)methyl)sulfonyl)methyl)phosphoryl)bis(oxy))bis (methylene) bis(2,2-dimethylpropanoate) (0.033 g, 0.042 mmol, 32% yield, LCMS ESI (+) m/z 779 (M+H)) and (((((((3aS,4S,6R,6aR)-6-(2-chloro-4-(cyclopentylamino)-7H-pyrrolo[2,3-d]pyrimidin-7-yl)-2,2-dimethyltetrahydrofuro[3,4-d][1,3]dioxol-4-yl)methyl)sulfinyl)methyl)phosphoryl)bis(oxy))bis(methylene) bis(2,2-dimethylpropanoate) (10 mg, 0.013 mmol, 10% yield, LCMS ESI (+) m/z 763 (M+H)).

Step G: A mixture of (((((((3aS,4S,6R,6aR)-6-(2-chloro-4-(cyclopentylamino)-7H-pyrrolo[2,3-d]pyrimidin-7-yl)-2,2-dimethyltetrahydrofuro[3,4-d][1,3]dioxol-4-yl)methyl) sulfonyl)methyl)phosphoryl)bis(oxy))bis(methylene) bis(2,2-dimethylpropanoate) (0.1 g, 0.13 mmol) in water (1 mL) and formic acid (4 mL, 0.13 mmol) was stirred at ambient temperature for 3 hours. The reaction mixture was concentrated with a stream of nitrogen. The residue was purified by preparative HPLC with CH$_3$CN/water (10% to 95% with 1% TFA) to give (((((((2S,3S,4R,5R)-5-(2-chloro-4-(cyclopentylamino)-7H-pyrrolo[2,3-d]pyrimidin-7-yl)-3,4-dihydroxytetrahydrofuran-2-yl)methyl)sulfonyl)methyl)phosphoryl)bis(oxy))bis(methylene) bis(2,2-dimethylpropanoate) (0.032 g, 0.043 mmol, 33% yield). LCMS ESI (+) m/z 739 (M+H).

Example 15: Synthesis of (((((2S,3S,4R,5R)-5-(2-chloro-4-(((R)-1-(2,4-difluorophenyl)ethyl)amino)-7H-pyrrolo[2,3-d]pyrimidin-7-yl)-3,4-dihydroxytetrahydrofuran-2-yl)methyl)sulfonyl)methyl) phosphonic acid (Compound 178)

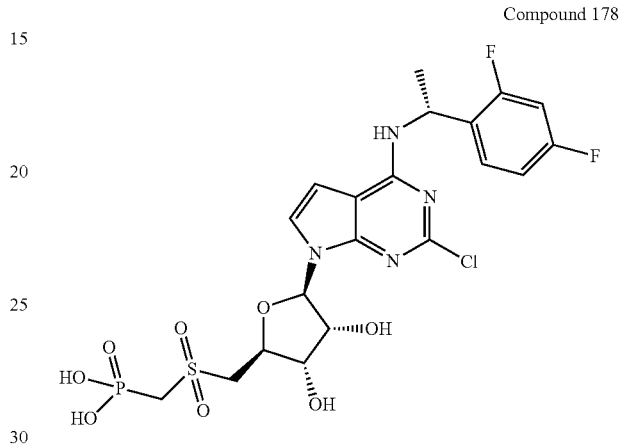

Compound 178

Step A: A mixture of ((3aR,4R,6R,6aR)-6-(2,4-dichloro-7H-pyrrolo[2,3-d]pyrimidin-7-yl)-2,2-dimethyltetrahydrofuro[3,4-d][1,3]dioxol-4-yl)methanol (200 mg, 0.56 mmol), (1R)-1-(2,4-difluorophenyl)ethanamine (131 mg, 0.83 mmol) and Et$_3$N (112 mg, 1.11 mmol) in n-butanol (10 mL) was stirred for 24 h at 100° C. The reaction was concentrated to dryness. The residue was taken up in EtOAc (50 mL). The organic layer was washed with 2×50 mL water then 1×50 mL saturated brine. The organic layer was separated, dried (MgSO$_4$), filtered, and concentrated. The residue was purified by prep-TLC to give ((3aR,4R,6R,6aR)-6-(2-chloro-4-(((R)-1-(2,4-difluorophenyl)ethyl)amino)-7H-pyrrolo[2,3-d]pyrimidin-7-yl)-2,2-dimethyltetrahydrofuro[3,4-d][1,3] dioxol-4-yl)methanol (200 mg, 0.42 mmol, 75% yield) as colorless liquid. LCMS ESI (+) m/z 481 (M+H).

Step B: To solution of ((3aR,4R,6R,6aR)-6-(2-chloro-4-(((R)-1-(2,4-difluorophenyl)ethyl)amino)-7H-pyrrolo[2,3-d]pyrimidin-7-yl)-2,2-dimethyltetrahydrofuro[3,4-d][1,3] dioxol-4-yl)methanol (165 mg, 0.34 mmol) in pyridine (2 mL, 0.34 mmol) at 0° C. was added methanesulfonyl chloride (47 mg, 0.41 mmol) under N2. The mixture was stirred for 2 h at 0° C. The reaction mixture was diluted with EtOAc (30 mL) and the organic layer was washed with 2×30 mL water then 1×30 mL saturated brine. The organic layer was separated, dried (MgSO$_4$), filtered, and concentrated. The residue was purified by prep-TLC to give ((3aR,4R,6R, 6aR)-6-(2-chloro-4-(((R)-1-(2,4-difluorophenyl)ethyl) amino)-7H-pyrrolo[2,3-d]pyrimidin-7-yl)-2,2-dimethyltetrahydrofuro[3,4-d][1,3]dioxol-4-yl)methyl methanesulfonate (180 mg, 0.32 mmol, 94% yield) as a white solid.

Step C: To a mixture of EtONa (65.74 mg, 0.9700 mmol) in DMF (5 mL) was added [amino(diethoxyphosphorylmethylsulfanyl)methylene]ammonium; 4-methylbenzenesulfonate (192.46 mg, 0.4800 mmol) under $N_2$. The mixture was stirred for 1.5 h at room temperature under N2. A solution of ((3aR,4R,6R,6aR)-6-(2-chloro-4-(((R)-1-(2,4-difluorophenyl)ethyl)amino)-7H-pyrrolo[2,3-d]pyrimidin-7-yl)-2,2-dimethyltetrahydrofuro[3,4-d][1,3]dioxol-4-yl) methyl methanesulfonate (180 mg, 0.32 mmol) in DMF (1 mL) was added. The mixture was stirred for 1.5 h at room temperature under N2. The reaction mixture was diluted with EtOAc (60 mL) and washed with 2×60 mL water then 1×60 mL saturated brine. The organic layer was separated, dried ($MgSO_4$), filtered, and concentrated. The residue was purified by prep-TLC to give diethyl (((((3aS,4S,6R,6aR)-6-(2-chloro-4-(((R)-1-(2,4-difluorophenyl)ethyl)amino)-7H-pyrrolo[2,3-d]pyrimidin-7-yl)-2,2-dimethyltetrahydrofuro[3,4-d][1,3]dioxol-4-yl)methyl)thio)methyl) phosphonate (110 mg, 0.17 mmol, 53% yield) as colorless liquid. LCMS ESI (+) m/z 647 (M+H).

Step D: A mixture of diethyl (((((3aS,4S,6R,6aR)-6-(2-chloro-4-(((R)-1-(2,4-difluorophenyl)ethyl)amino)-7H-pyrrolo[2,3-d]pyrimidin-7-yl)-2,2-dimethyltetrahydrofuro[3,4-d][1,3]dioxol-4-yl)methyl)thio)methyl)phosphonate (110 mg, 0.17 mmol) and Oxone (314 mg, 0.51 mmol) in water (2 mL) and acetonitrile (2 mL) was stirred at room temperature for 3.5 h. The reaction mixture was diluted with EtOAc (30 mL). The organic layer was washed with 2×30 mL water, separated, dried ($MgSO_4$), filtered, and concentrated. The residue was purified by prep-TLC to give diethyl (((((3aS,4S,6R,6aR)-6-(2-chloro-4-(((R)-1-(2,4-difluorophenyl)ethyl)amino)-7H-pyrrolo[2,3-d]pyrimidin-7-yl)-2,2-dimethyltetrahydrofuro[3,4-d][1,3]dioxol-4-yl)methyl) sulfonyl)methyl)phosphonate (35 mg, 0.052 mmol, 30% yield) as a white solid. LCMS ESI (+) m/z 679 (M+H).

Step E: A mixture of diethyl (((((3aS,4S,6R,6aR)-6-(2-chloro-4-(((R)-1-(2,4-difluorophenyl)ethyl)amino)-7H-pyrrolo[2,3-d]pyrimidin-7-yl)-2,2-dimethyltetrahydrofuro[3,4-d][1,3]dioxol-4-yl)methyl)sulfonyl)methyl)phosphonate (35 mg, 0.05 mmol), TMSBr (118 mg, 0.77 mmol) and 2,6-lutidine (77 mg, 0.72 mmol) in dichloromethane (2 mL) was stirred at room temperature for 16 h. The reaction mixture was concentrated to dryness and crude (((((3aS,4S,6R,6aR)-6-(2-chloro-4-(((R)-1-(2,4-difluorophenyl)ethyl)amino)-7H-pyrrolo[2,3-d]pyrimidin-7-yl)-2,2-dimethyltetrahydrofuro[3,4-d][1,3]dioxol-4-yl)methyl)sulfonyl)methyl) phosphonic acid (110 mg) was obtained as a white solid. LCMS ESI (−) m/z 621 (M−H).

Step F: A mixture of (((((3aS,4S,6R,6aR)-6-(2-chloro-4-(((R)-1-(2,4-difluorophenyl)ethyl)amino)-7H-pyrrolo[2,3-d]pyrimidin-7-yl)-2,2-dimethyltetrahydrofuro[3,4-d][1,3]dioxol-4-yl)methyl)sulfonyl)methyl)phosphonic acid (crude from Step E) in 80% aqueous formic acid (2 mL, 0.18 mmol) was stirred at room temperature for 2 h. The reaction mixture was concentrated to dryness and the residue was purified by prep-HPLC to give (((((2S,3S,4R,5R)-5-(2-chloro-4-(((R)-1-(2,4-difluorophenyl)ethyl)amino)-7H-pyrrolo[2,3-d]pyrimidin-7-yl)-3,4-dihydroxytetrahydrofuran-2-yl)methyl) sulfonyl)methyl)phosphonic acid (15 mg, 0.026 mmol, 15% yield) as a white solid. LCMS ESI (−) m/z 581 (M−H).

Example 16: Synthesis of (((((2S,3S,4R,5R)-5-(2-chloro-4-(cyclopentylamino)-7H-pyrrolo[2,3-d]pyrimidin-7-yl)-3,4-dihydroxytetrahydrofuran-2-yl) methyl)sulfonyl)methyl)phosphonic acid (Compound 155)

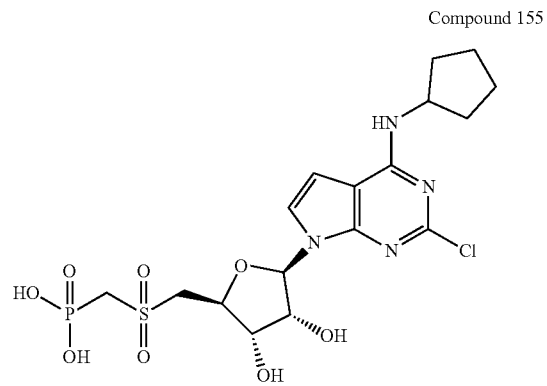 [SMILES: O=P(O)(O)CS(=O)(=O)C[C@H]1O[C@@H](n2ccc3c(NC4CCCC4)nc(Cl)nc32)[C@H](O)[C@@H]1O]

Compound 155

Step A: Preparation of ((3aR,4R,6R,6aR)-6-(2-chloro-4-(cyclopentylamino)-7H-pyrrolo[2,3-d]pyrimidin-7-yl)-2,2-dimethyltetrahydrofuro[3,4-d][1,3]dioxol-4-yl)methanol:
To a mixture of ((3aR,4R,6R,6aR)-6-(2,4-dichloro-7H-pyrrolo[2,3-d]pyrimidin-7-yl)-2,2-dimethyltetrahydrofuro[3,4-d][1,3]dioxol-4-yl)methanol (0.81 g, 2.25 mmol) and DIEA (0.6 mL, 3.38 mmol) in s-butanol (4 mL) was added cyclopentanamine (0.38 g, 4.51 mmol) at ambient temperature. The mixture was stirred at 100° C. in a pressure tube for 4 hours. Solvent was removed under reduced pressure. The residue obtained was purified by flash chromatography on silica gel (3:1 DCM/ethyl acetate) to give ((3aR,4R,6R,6aR)-6-(2-chloro-4-(cyclopentylamino)-7H-pyrrolo[2,3-d]pyrimidin-7-yl)-2,2-dimethyltetrahydrofuro[3,4-d][1,3]dioxol-4-yl)methanol (0.40 g, 43%) as solid. LCMS ESI (−) m/z 407 (M−H).

Step B: Preparation of ((3aR,4R,6R,6aR)-6-(2-chloro-4-(cyclopentylamino)-7H-pyrrolo[2,3-d]pyrimidin-7-yl)-2,2-dimethyltetrahydrofuro[3,4-d][1,3]dioxol-4-yl)methyl methanesulfonate: To a solution of ((3aR,4R,6R,6aR)-6-(2-chloro-4-(cyclopentylamino)-7H-pyrrolo[2,3-d]pyrimidin-7-yl)-2,2-dimethyltetrahydrofuro[3,4-d][1,3]dioxol-4-yl) methanol (0.07 g, 0.17 mmol) in pyridine (2 mL) was added methanesulfonyl chloride (0.01 mL, 0.19 mmol) at 0° C. The reaction mixture was stirred at 0° C. for 2 hours. Saturated sodium bicarbonate solution (10 mL) and MTBE (10 mL) were added. The organic layer was separated, washed with brine, dried (sodium sulfate), filtered and concentrated under reduced pressure to give ((3aR,4R,6R,6aR)-6-(2-chloro-4-(cyclopentylamino)-7H-pyrrolo[2,3-d]pyrimidin-7-yl)-2,2-dimethyltetrahydrofuro[3,4-d][1,3]dioxol-4-yl)methyl methanesulfonate (0.083 g, 100%) as a solid. LCMS ESI (+) m/z 487 (M+H).

Step C: Preparation of S-(((3aS,4S,6R,6aR)-6-(2-chloro-4-(cyclopentylamino)-7H-pyrrolo[2,3-d]pyrimidin-7-yl)-2,2-dimethyltetrahydrofuro[3,4-d][1,3]dioxol-4-yl)methyl) ethanethioate: To a solution of ((3aR,4R,6R,6aR)-6-(2-chloro-4-(cyclopentylamino)-7H-pyrrolo[2,3-d]pyrimidin-7-yl)-2,2-dimethyltetrahydrofuro[3,4-d][1,3]dioxol-4-yl) methanol (0.08 g, 0.17 mmol) in DMF (3 mL) was added tetrabutylammonium bromide (0.01 g, 0.02 mmol) and potassium ethanethioate (0.03 g, 0.26 mmol) at ambient temperature. The reaction mixture was stirred at ambient temperature for 24 hours. Water (10 mL) and MTBE (15 mL) were added. The organic layer was separated, washed with brine, dried (sodium sulfate), filtered and concentrated under reduced pressure. The residue obtained was purified by flash chromatography on silica gel (1:1 hexane/ethyl acetate) to give S-(((3aS,4S,6R,6aR)-6-(2-chloro-4-(cyclopentylamino)-7H-pyrrolo[2,3-d]pyrimidin-7-yl)-2,2-dimethyltetrahydrofuro[3,4-d][1,3]dioxol-4-yl)methyl) ethanethioate (0.07 g, 88%) as a solid. LCMS ESI (+) m/z 467 (M+H).

Step D: Preparation of ((3aS,4S,6R,6aR)-6-(2-chloro-4-(cyclopentylamino)-7H-pyrrolo[2,3-d]pyrimidin-7-yl)-2,2-dimethyltetrahydrofuro[3,4-d][1,3]dioxol-4-yl)methanethiol: To a solution of S-(((3aS,4S,6R,6aR)-6-(2-chloro-4-(cyclopentylamino)-7H-pyrrolo[2,3-d]pyrimidin-7-yl)-2,2-dimethyltetrahydrofuro[3,4-d][1,3]dioxol-4-yl)methyl) ethanethioate (0.07 g, 0.15 mol) was added 7N ammonia in methanol (2.21 mL, 15.5 mmol) at ambient temperature. The reaction mixture was stirred at ambient temperature for 4 hours. Solvent was removed under reduced pressure to give [(3aR,4R,6S,6aS)-4-[2-chloro-6-[[(1S)-1-(4-fluorophenyl)ethyl]amino]purin-9-yl]-2,2-dimethyl-3a,4,6,6a-tetrahydrofuro[3,4-d][1,3]dioxol-6-yl]methanethiol (0.064 g, 100%) as a solid. LCMS ESI (+) m/z 425 (M+H).

Step E: Preparation of diisopropyl (((((3aS,4S,6R,6aR)-6-(2-chloro-4-(cyclopentylamino)-7H-pyrrolo[2,3-d]pyrimidin-7-yl)-2,2-dimethyltetrahydrofuro[3,4-d][1,3]dioxol-4-yl)methyl)thio)methyl)phosphonate: Sodium hydride (60%) (0.01 g, 0.33 mmol) was added to a mixture of [(3aR,4R,6S,6aS)-4-[2-chloro-6-[[(1S)-1-(4-fluorophenyl)ethyl]amino]purin-9-yl]-2,2-dimethyl-3a,4,6,6a-tetrahydrofuro[3,4-d][1,3]dioxol-6-yl]methanethiol (0.06 g, 0.15 mmol) and diisopropyl (bromomethyl)phosphonate (0.08 g, 0.30 mmol) at 0° C. The reaction mixture was stirred at this temperature for 30 minutes. Saturated ammonium chloride solution and MTBE (15 mL) were added. The organic layer was separated, washed with brine, dried (sodium sulfate), filtered and concentrated under reduced pressure. The residue obtained was purified by flash chromatography on silica gel (ethyl acetate) to give diisopropyl (((((3aS,4S,6R,6aR)-6-(2-chloro-4-(cyclopentylamino)-7H-pyrrolo[2,3-d]pyrimidin-7-yl)-2,2-dimethyltetrahydrofuro[3,4-d][1,3]dioxol-4-yl)methyl)thio)methyl)phosphonate (0.053 g, 58%) as an oil. LCMS ESI (−) m/z 601 (M−H).

Step F: Preparation of diisopropyl (((((3aS,4S,6R,6aR)-6-(2-chloro-4-(cyclopentylamino)-7H-pyrrolo[2,3-d]pyrimidin-7-yl)-2,2-dimethyltetrahydrofuro[3,4-d][1,3]dioxol-4-yl)methyl)sulfonyl)methyl)phosphonate: To a solution of diisopropyl (((((3aS,4S,6R,6aR)-6-(2-chloro-4-(cyclopentylamino)-7H-pyrrolo[2,3-d]pyrimidin-7-yl)-2,2-dimethyltetrahydrofuro[3,4-d][1,3]dioxol-4-yl)methyl)thio)methyl)phosphonate (0.05 g, 0.09 mmol) in acetonitrile (3 mL) and water (3 mL) was added Oxone (0.16 g, 0.53 mmol) at ambient temperature. The mixture was stirred at ambient temperature for 5 hours. Ethyl acetate (10 mL) and water (10 mL) were added. The organic layer was separated, washed with brine, dried (sodium sulfate), filtered and concentrated under reduced pressure. The residue obtained was purified chromatography on silica gel (ethyl acetate) to give diisopropyl (((((3aS,4S,6R,6aR)-6-(2-chloro-4-(cyclopentylamino)-7H-pyrrolo[2,3-d]pyrimidin-7-yl)-2,2-dimethyltetrahydrofuro[3,4-d][1,3]dioxol-4-yl)methyl)sulfonyl)methyl)phosphonate (0.013 g, 23%) as a solid. LCMS ESI (−) m/z 633 (M−H).

Step G: Preparation of (((((2S,3S,4R,5R)-5-(2-chloro-4-(cyclopentylamino)-7H-pyrrolo[2,3-d]pyrimidin-7-yl)-3,4-dihydroxytetrahydrofuran-2-yl)methyl)sulfonyl)methyl)phosphonic acid: To a solution of 7 diisopropyl (((((3aS,4S,6R,6aR)-6-(2-chloro-4-(cyclopentylamino)-7H-pyrrolo[2,3-d]pyrimidin-7-yl)-2,2-dimethyltetrahydrofuro[3,4-d][1,3]dioxol-4-yl)methyl)sulfonyl)methyl)phosphonate (0.01 g, 0.02 mmol) in dichloromethane (2 mL) was added 2, 6-Lutidine (0.02 mL, 0.20 mmol) and bromotrimethylsilane (0.03 mL, 0.20 mmol) at ambient temperature. The reaction mixture was stirred at this temperature for 18 hours. The reaction mixture was concentrated under reduced pressure. The residue was co-evaporated with methanol three times to give a light yellow solid. 80% formic acid in water (2 mL) was added. The mixture was stirred at ambient temperature for 6 hours. The mixture was concentrated at reduced pressure and co-evaporated with methanol three times to give a thick oil. It was purified by preparative HPLC (10%-80% ACN/H₂O, 0.1% TFA) to give (((((2S,3S,4R,5R)-5-(2-chloro-4-(cyclopentylamino)-7H-pyrrolo[2,3-d]pyrimidin-7-yl)-3,4-dihydroxytetrahydrofuran-2-yl)methyl)sulfonyl)methyl)phosphonic acid (0.009 g, 70%) as a TFA salt. LCMS ESI (−) m/z 509 (M−H).

Example 17: Synthesis of (((((((2R,3S,4R,5R)-5-(2-chloro-4-(cyclopentylamino)-7H-pyrrolo[2,3-d]pyrimidin-7-yl)-3,4-dihydroxytetrahydrofuran-2-yl)methoxy)(hydroxy)phosphoryl)oxy)methyl) phosphonic acid (Compound 229)

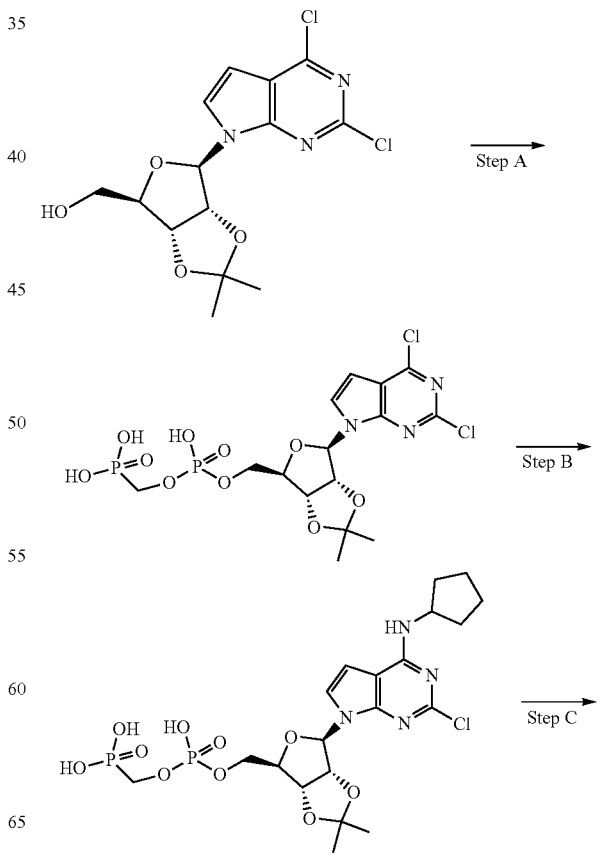

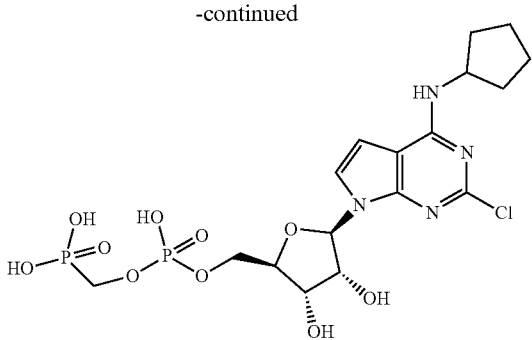

Step A: Preparation of ((((((3aR,4R,6R,6aR)-6-(2,4-dichloro-7H-pyrrolo[2,3-d]pyrimidin-7-yl)-2,2-dimethyltetrahydrofuro[3,4-d][1,3]dioxol-4-yl)methoxy)(hydroxy)phosphoryl)oxy)methyl)phosphonic acid: To a solution of [(3aR,4R,6R,6aR)-4-(2,4-dichloropyrrolo[2,3-d]pyrimidin-7-yl)-2,2-dimethyl-3a,4,6,6a-tetrahydrofuro[3,4-d][1,3]dioxol-6-yl]methanol (0.08 g, 0.21 mmol) and 2,6-lutidine (0.074 mL, 0.64 mmol) in tetrahydrofuran (5 mL) was added a solution of P,P'-methylenebis-phosphonic dichloride (0.08 g, 0.32 mmol) in THF (0.2 mL) at 0° C. The reaction mixture was stirred at 0° C. for 5 hours. Saturated sodium bicarbonate solution (10 mL) and MTBE (30 mL) were added. The aqueous layer was separated and concentrated under reduced pressure. The residue obtained was purified by reverse phase column chromatography with CH$_3$CN/water (0% to 80%) to give [[(3aR,4R,6R,6aR)-4-(2,4-dichloropyrrolo[2,3-d]pyrimidin-7-yl)-2,2-dimethyl-3a,4,6,6a-tetrahydrofuro[3,4-d][1,3]dioxol-6-yl]methoxy-hydroxy-phosphoryl]methylphosphonic acid (0.046 g, 41%) as a solid. LCMS ESI (+) m/z 518 (M+H).

Step B: Preparation of [[(3aR,4R,6R,6aR)-4-(2,4-dichloropyrrolo[2,3-d]pyrimidin-7-yl)-2,2-dimethyl-3a,4,6,6a-tetrahydrofuro[3,4-d][1,3]dioxol-6-yl]methoxy-hydroxy-phosphoryl]methylphosphonic acid: A suspension of [[(3aR,4R,6R,6aR)-4-(2,4-dichloropyrrolo[2,3-d]pyrimidin-7-yl)-2,2-dimethyl-3a,4,6,6a-tetrahydrofuro[3,4-d][1,3]dioxol-6-yl]methoxy-hydroxy-phosphoryl]methylphosphonic acid (0.046 g, 0.08 mmol), cyclopentanamine (0.01 g, 0.16 mmol) and triethylamine (0.02 mL, 0.12 mmol) in s-Butanol (2 mL) was stirred at 100° C. for 4 hours. After cooling to ambient temperature, the solvent was removed under reduced pressure. The residue obtained was purified by preparative reverse phase HPLC (10%-95% ACN/H$_2$O, 0.1% TFA) to give [[(3aR,4R,6R,6aR)-4-[2-chloro-4-(cyclopentylamino)pyrrolo[2,3-d]pyrimidin-7-yl]-2,2-dimethyl-3a,4,6,6a-tetrahydrofuro[3,4-d][1,3]dioxol-6-yl]methoxy-hydroxy-phosphoryl]methylphosphonic acid (0.025 g, 54%) as a solid. LCMS ESI (+) m/z 567 (M+H).

Step C: Preparation of ((((((2R,3S,4R,5R)-5-(2-chloro-4-(cyclopentylamino)-7H-pyrrolo[2,3-d]pyrimidin-7-yl)-3,4-dihydroxytetrahydrofuran-2-yl)methoxy)(hydroxy)phosphoryl)oxy)methyl) phosphonic acid: A solution of [[(3aR,4R,6R,6aR)-4-[2-chloro-4-(cyclopentylamino)pyrrolo[2,3-d]pyrimidin-7-yl]-2,2-dimethyl-3a,4,6,6a-tetrahydrofuro[3,4-d][1,3]dioxol-6-yl]methoxy-hydroxy-phosphoryl]methylphosphonic acid (0.03 g, 0.04 mmol) in 80% formic acid (2 mL) was stirred at ambient temperature for 2 hours. Solvent was removed under reduced pressure. The residue was purified by preparative reverse phase HPLC (10%-95% ACN/H$_2$O, 0.1% TFA) to give [[(2R,3S,4R,5R)-5-[2-chloro-4-(cyclopentylamino)pyrrolo[2,3-d]pyrimidin-7-yl]-3,4-dihydroxy-tetrahydrofuran-2-yl]methoxy-hydroxy-phosphoryl]methylphosphonic acid; 2,2,2-trifluoroacetic acid (0.013 g, 46%) as a solid. LCMS ESI (+) m/z 527 (M+H).

Example 18: Synthesis of (((((2R,3S,4R,5R)-5-(6-chloro-4-(cyclopentylamino)-1H-pyrazolo[3,4-d]pyrimidin-1-yl)-3,4-dihydroxytetrahydrofuran-2-yl)methoxy)methyl)phosphonic acid (Compound 240)

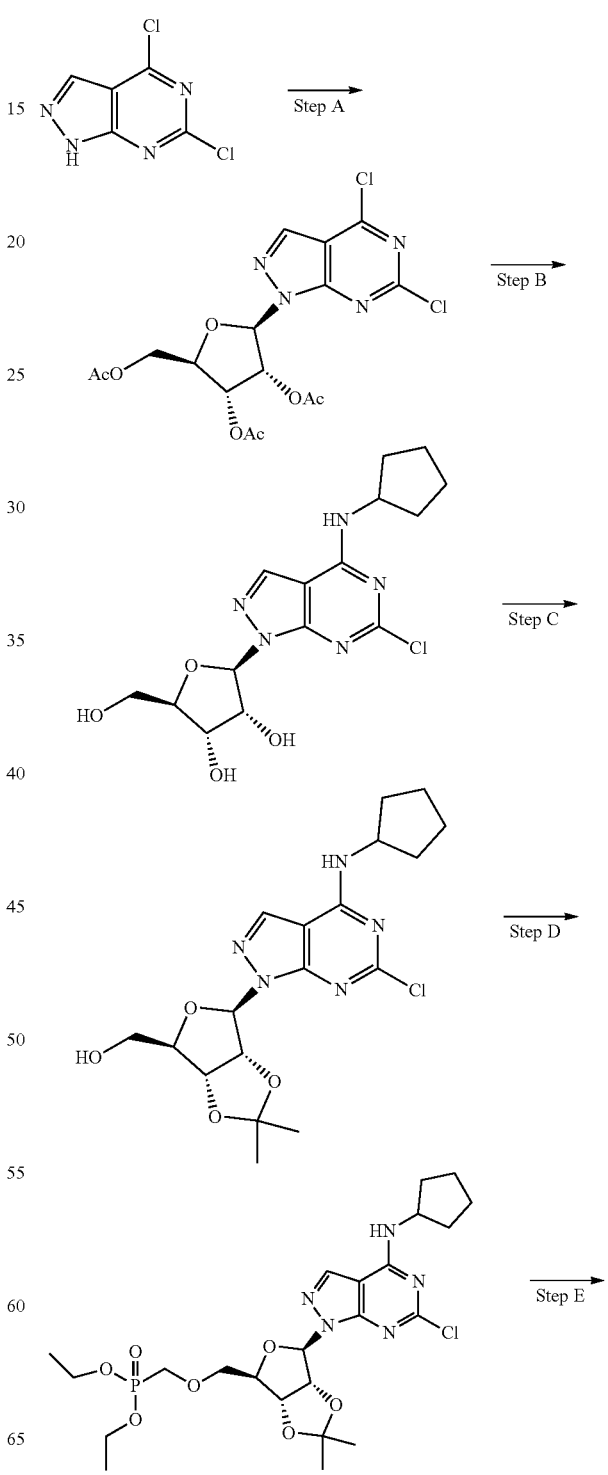

-continued

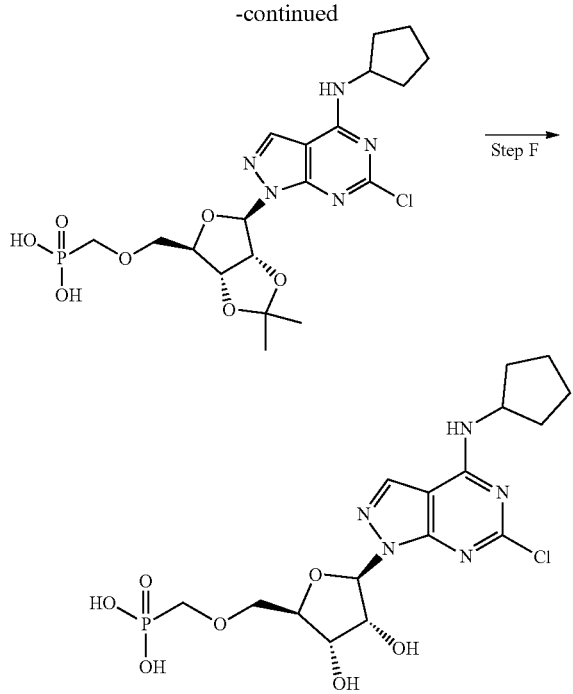

Step F →

Step A: Preparation of (2R,3R,4R,5R)-2-(acetoxymethyl)-5-(4,6-dichloro-1H-pyrazolo[3,4-d]pyrimidin-1-yl)tetrahydrofuran-3,4-diyl diacetate: 4,6-dichloro-1H-pyrazolo[3,4-d]pyrimidine (2.5 g, 13.2 mmol) and ammonium sulfate (19.8 mg, 0.15 mmol) were dissolved in hexamethyldisilane (18 mL). The mixture was warmed to reflux and stirred for 3 hrs. The mixture was then concentrated under reduced pressure. The residue was then taken up in acetic anhydride (36 mL), and (2S,3R,4R,5R)-5-(acetoxymethyl)tetrahydrofuran-2,3,4-triyl triacetate (5.1 g, 15.9 mmol) was added. This mixture was cooled to 0° C. and TMSOTf (3.2 g, 14.6 mmol) was added dropwise. The mixture was warmed to ambient temperature and stirred at ambient temperature overnight. The mixture was then concentrated under reduced pressure. The residue was suspended in ethyl acetate, washed with saturated sodium bicarbonate solution and brine. The organics were dried with sodium sulfate, filtered and concentrated under reduced pressure. The residue was purified by flash column chromatography on silica gel to give [(2R,3R,4R,5R)-3,4-diacetoxy-5-(4,6-dichloro-pyrazolo[3,4-d]pyrimidin-1-yl)tetrahydrofuran-2-yl]methyl acetate (3.3 g, 56%) as a solid.

Step B: Preparation of (2R,3R,4S,5R)-2-(6-chloro-4-(cyclopentylamino)-1H-pyrazolo[3,4-d]pyrimidin-1-yl)-5-(hydroxymethyl)tetrahydrofuran-3,4-diol: To a solution of [(2R,3R,4R,5R)-3,4-diacetoxy-5-(4,6-dichloropyrazolo[3,4-d]pyrimidin-1-yl)tetrahydrofuran-2-yl]methyl acetate (3.3 g, 7.4 mmol) in methanol (16 mL) was added cyclopentanamine (0.66 g, 7.8 mmol) and triethylamine (0.78 g, 7.8 mmol) at 0° C. The mixture was warmed to ambient temperature and stirred at ambient temperature for 4 hours. 7 N ammonium in MeOH (12 mL) was added and the reaction mixture was stirred at ambient temperature for 24 hours. The reaction mixture was concentrated under reduced pressure to give (2R,3R,4S,5R)-2-[6-chloro-4-(cyclopentylamino)pyrazolo[3,4-d]pyrimidin-1-yl]-5-(hydroxymethyl)tetrahydrofuran-3,4-diol (3.0 g, 88%) which was used directly in the next step without purification.

Step C: Preparation of ((3aR,4R,6R,6aR)-6-(6-chloro-4-(cyclopentylamino)-1H-pyrazolo[3,4-d]pyrimidin-1-yl)-2,2-dimethyltetrahydrofuro[3,4-d][1,3]dioxol-4-yl)methanol: A mixture of (2R,3R,4S,5R)-2-[6-chloro-4-(cyclopentylamino)pyrazolo[3,4-d]pyrimidin-1-yl]-5-(hydroxymethyl)tetrahydrofuran-3,4-diol (3.01 g, 8.1 mmol), 2,2-dimethoxypropane (12.7 g, 122.0 mmol), TsOH (2.01 g, 10.6 mmol) in acetone (80 mL) was stirred at ambient temperature for 16 hours. Sodium bicarbonate (0.4 g) and water (200 mL) were added. The mixture was stirred for 1 h and then extracted with ethyl acetate. The organics were separated and dried (MgSO₄), filtered and concentrated under reduced pressure. The residue was purified by flash column chromatography on silica gel to give [(2R,3R,4R,5R)-5-[6-chloro-4-(cyclopentylamino)pyrazolo[3,4-d]pyrimidin-1-yl]-3,4-diethoxytetrahydrofuran-2-yl]methanol (2.3 g, 66%) as a solid.

Step D: Preparation of diethyl ((((3aR,4R,6R,6aR)-6-(6-chloro-4-(cyclopentylamino)-1H-pyrazolo[3,4-d]pyrimidin-1-yl)-2,2-dimethyltetrahydrofuro[3,4-d][1,3]dioxol-4-yl)methoxy)methyl)phosphonate: A mixture of [(3aR,4R,6R,6aR)-4-[6-chloro-4-(cyclopentylamino)pyrazolo[3,4-d]pyrimidin-1-yl]-2,2-dimethyl-3a,4,6,6a-tetrahydrofuro[3,4-d][1,3]dioxol-6-yl]methanol (200.5 mg, 0.49 mmol), 1-(diethoxyphosphorylmethylsulfonyl)-4-methyl-benzene (299.7 mg, 0.98 mmol) and magnesium 2-methylpropan-2-olate (334.6 mg, 1.96 mmol) in DMSO (5 mL) was stirred at 80° C. for 4 hours. After cooling to ambient temperature, saturated ammonium chloride solution (50 mL) and MTBE (30 mL) were added. The organic layer was separated, washed with brine, dried (sodium sulfate), filtered and concentrated under reduced pressure. The residue was purified by flash chromatography on silica gel 10:1 ethyl acetate/methanol to give 1-[(3aR,4R,6R,6aR)-6-(diethoxyphosphorylmethoxymethyl)-2,2-dimethyl-3a,4,6,6a-tetrahydrofuro[3,4-d][1,3]dioxol-4-yl]-6-chloro-N-cyclopentyl-pyrazolo[3,4-d]pyrimidin-4-amine (186 mg, 68%) as a solid.

Step E: Preparation of ((((3aR,4R,6R,6aR)-6-(6-chloro-4-(cyclopentylamino)-1H-pyrazolo[3,4-d]pyrimidin-1-yl)-2,2-dimethyltetrahydrofuro[3,4-d][1,3]dioxol-4-yl)methoxy)methyl)phosphonic acid: To a solution of 1-[(3aR,4R,6R,6aR)-6-(diethoxyphosphorylmethoxymethyl)-2,2-dimethyl-3a,4,6,6a-tetrahy drofuro[3,4-d][1,3]dioxol-4-yl]-6-chloro-N-cyclopentyl-pyrazolo[3,4-d]pyrimidin-4-amine (90.0 mg, 0.16 mmol) and 2,6-lutidine (344.4 mg, 3.2 mmol) in dichloromethane (5 mL) was added bromotrimethylsilane (492.1 mg, 3.2 mmol). The mixture was stirred at ambient temperature overnight. The mixture was concentrated under reduced pressure. The residue was co-evaporated with ACN twice to give [(3aR,4R,6R,6aR)-4-[6-chloro-4-(cyclopentylamino)pyrazolo[3,4-d]pyrimidin-1-yl]-2,2-dimethyl-3a,4,6,6a-tetrahydrofuro[3,4-d][1,3]dioxol-6-yl]methoxymethylphosphonic acid which was used directly in the next step.

Step F: Preparation of (((((2R,3S,4R,5R)-5-(6-chloro-4-(cyclopentylamino)-1H-pyrazolo[3,4-d]pyrimidin-1-yl)-3,4-dihydroxytetrahydrofuran-2-yl)methoxy)methyl)phosphonic acid: A solution of [(3aR,4R,6R,6aR)-4-[6-chloro-4-(cyclopentylamino)pyrazolo[3,4-d]pyrimidin-1-yl]-2,2-dimethyl-3a,4,6,6a-tetrahydrofuro[3,4-d][1,3]dioxol-6-yl]methoxymethylphosphonic acid (90.0 mg, 0.18 mmol) in 80% HCOOH (3 mL) was stirred at ambient temperature for 2 hours. The mixture was concentrated under reduced pressure and purified by preparative reverse phase HPLC (10%-95% ACN/H₂O, 0.1% TFA) to give [(2R,3S,4R,5R)-5-[6-chloro-4-(cyclopentylamino)pyrazolo[3,4-d]pyrimidin-1-yl]-3,4-dihydroxy-tetrahydrofuran-2-yl]methoxymethylphosphonic acid (46 mg, 45%) as a solid. LCMS ESI (+) m/z 462 (M−H).

Example 19: Synthesis of (((((2S,3S,4R,5R)-5-(6-cyano-4-(cyclopentylamino)-1H-pyrazolo[3,4-d]pyrimidin-1-yl)-3,4-dihydroxytetrahydrofuran-2-yl)methyl)sulfonyl)methyl)phosphonic acid (Compound 296)

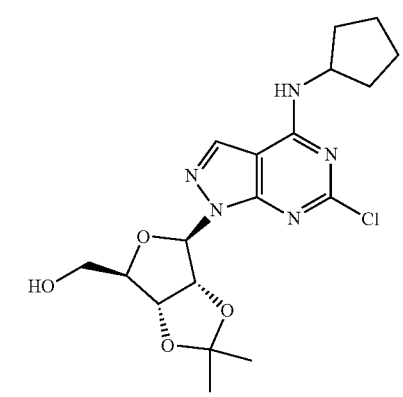

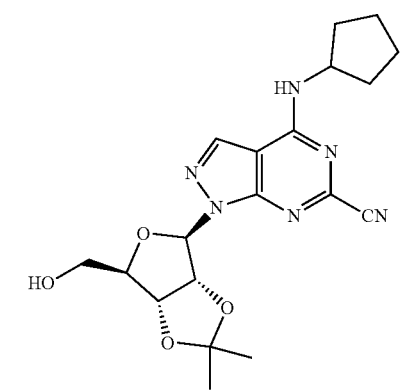

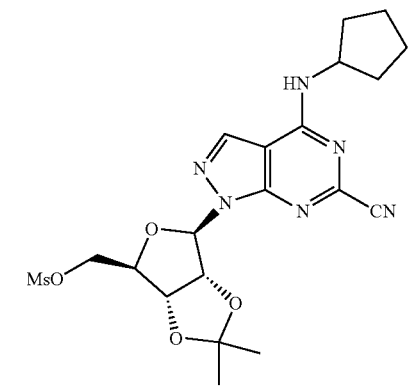

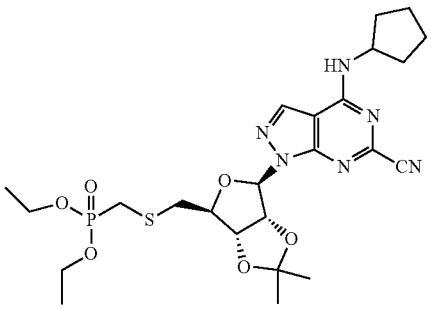

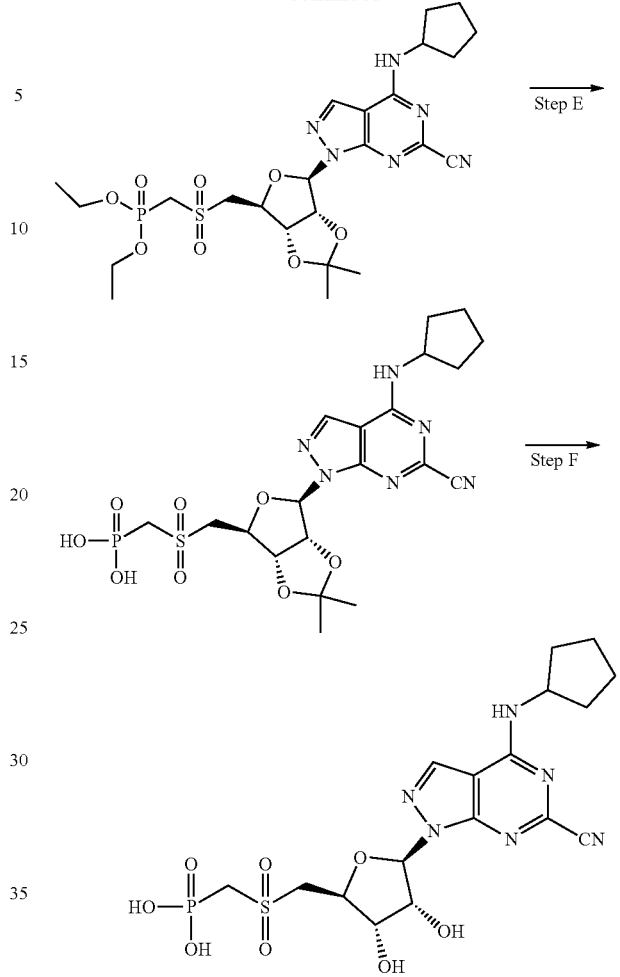

Step A: Preparation of 4-(cyclopentylamino)-1-((3aR,4R,6R,6aR)-6-(hydroxymethyl)-2,2-dimethyltetrahydrofuro[3,4-d][1,3]dioxol-4-yl)-1H-pyrazolo[3,4-d]pyrimidine-6-carbonitrile: A solution of [(3aR,4R,6R,6aR)-4-[6-chloro-4-(cyclopentylamino) pyrazolo[3,4-d]pyrimidin-1-yl]-2,2-dimethyl-3a,4,6,6a-tetrahydrofuro[3,4-d][1,3]dioxol-6-yl] methanol (100.0 mg, 0.24 mmol), zinc cyanide (143.2 mg, 1.22 mmol) and Pd(PPh₃)₄ (281.9 mg, 0.24 mmol) in 1-Methyl-2-pyrrolidone (5 mL) in a sealed tube was stirred at 100° C. under nitrogen for 6 hours. After cooling to ambient temperature, the mixture was diluted with ethyl acetate, filtered through celite and washed with ethyl acetate. The filtrate was washed with brine, dried (Na₂SO₄), filtered and concentrated under reduced pressure. The residue was purified by preparative TLC to give 1-[(3aR,4R,6R,6aR)-6-(hydroxymethyl)-2,2-dimethyl-3a,4,6,6a-tetrahydrofuro[3,4-d][1,3]dioxol-4-yl]-4-(cyclopentylamino)pyrazolo[3,4-d]pyrimidine-6-carbonitrile (90 mg, 92%) as a solid.

Step B: Preparation of ((3aR,4R,6R,6aR)-6-(6-cyano-4-(cyclopentylamino)-1H-pyrazolo[3,4-d]pyrimidin-1-yl)-2,2-dimethyltetrahydrofuro[3,4-d][1,3]dioxol-4-yl)methyl methanesulfonate: To a solution of 1-[(3aR,4R,6R,6aR)-6-(hydroxymethyl)-2,2-dimethyl-3a,4,6,6a-tetrahydrofuro[3,4-d][1,3]dioxol-4-yl]-4-(cyclopentylamino)pyrazolo[3,4-d]pyrimidine-6-carbonitrile (87.9 mg, 0.22 mmol) in pyridine (5 mL) was added methanesulfonyl chloride (37.7 mg, 0.33 mmol) at 0° C., and the resulting mixture was stirred at this temperature for 2 hours. Solvent was removed under reduced pressure. The residue was partitioned between water and ethyl acetate. The organic layer was separated, dried over Na₂SO₄, filtered, concentrated under reduced pressure and purified by preparative TLC to give [(3aR,4R, 6R,6aR)-4-[6-cyano-4-(cyclopentylamino)pyrazolo[3,4-d]pyrimidin-1-yl]-2,2-dimethyl-3a,4,6,6a-tetrahydrofuro[3,4-d][1,3]dioxol-6-yl]methyl methanesulfonate (90 mg, 85%) as a solid.

Step C: Preparation of diethyl (((((3aS,4S,6R,6aR)-6-(6-cyano-4-(cyclopentylamino)-1H-pyrazolo[3,4-d]pyrimidin-1-yl)-2,2-dimethyltetrahydrofuro[3,4-d][1,3]dioxol-4-yl)methyl)thio)methyl)phosphonate: To a solution of NaOEt (38.3 mg, 0.56 mmol) in DMF (4 mL) was added [[amino(diethoxyphosphorylmethylsulfanyl)methylene] ammonium; 4-methylbenzenesulfonate (149.9 mg, 0.38 mmol) under nitrogen at ambient temperature. [(3aR,4R,6R,6aR)-4-[6-cyano-4-(cyclopentylamino)pyrazolo[3,4-d]pyrimidin-1-yl]-2,2-dimethyl-3a,4,6,6a-tetrahydrofuro[3,4-d][1,3]dioxol-6-yl]methyl methanesulfonate (90.0 mg, 0.19 mmol) in DMF (1 mL) was added after 30 minutes. The mixture was stirred at 40° C. for 16 hours. After cooling to ambient temperature, the mixture was dilute with ethyl acetate and water. The organic layer was separated, dried over Na₂SO₄, filtered, and concentrated under reduced pressure. The residue was purified by preparative TLC to give 1-[(3aR,4R,6S,6aS)-6-(diethoxyphosphorylmethylsulfanylmethyl)-2,2-dimethyl-3a,4,6,6a-tetrahydrofuro[3,4-d][1,3]dioxol-4-yl]-4-(cyclopentylamino)pyrazolo[3,4-d]pyrimidine-6-carbonitrile (70 mg, 65%) as a solid.

Step D: Preparation of ((((3aR,4R,6R,6aR)-6-(6-chloro-4-(cyclopentylamino)-1H-pyrazolo[3,4-d]pyrimidin-1-yl)-2,2-dimethyltetrahydrofuro[3,4-d][1,3]dioxol-4-yl)methoxy)methyl)phosphonic acid: To a solution of 1-[(3aR,4R,6S,6aS)-6-(diethoxyphosphorylmethylsulfanylmethyl)-2,2-dimethyl-3a,4,6,6a-tetrahydrofuro[3,4-d][1,3]dioxol-4-yl]-4-(cyclopentylamino)pyrazolo[3,4-d]pyrimidine-6-carbonitrile (70.0 mg, 0.12 mmol) in acetonitrile (3 mL) and water (3 mL) was added Oxone (227.9 mg, 0.37 mmol). The mixture was stirred at ambient temperature for 6 hours and partitioned between water and ethyl acetate. The organic layer was separated, dried over Na₂SO₄, filtered, and concentrated under reduced pressure. The residue was purified by preparative TLC to give 1-[(3aR,4R,6S,6aS)-6-(diethoxyphosphorylmethylsulfonylmethyl)-2,2-dimethyl-3a,4,6,6a-tetrahydrofuro[3,4-d][1,3]dioxol-4-yl]-4-(cyclopentylamino)pyrazolo[3,4-d]pyrimidine-6-carbonitrile (22 mg, 29%) as a solid.

Step E: Preparation of (((((3aS,4S,6R,6aR)-6-(6-cyano-4-(cyclopentylamino)-1H-pyrazolo[3,4-d]pyrimidin-1-yl)-2,2-dimethyltetrahydrofuro[3,4-d][1,3]dioxol-4-yl)methyl)sulfonyl)methyl)phosphonic acid: To a solution of 1-[(3aR,4R,6S,6aS)-6-(diethoxyphosphorylmethylsulfonylmethyl)-2,2-dimethyl-3a,4,6,6a-tetrahydrofuro[3,4-d][1,3]dioxol-4-yl]-4-(cyclopentylamino)pyrazolo[3,4-d]pyrimidine-6-carbonitrile (22.0 mg, 0.04 mmol) and 2,6-lutidine (78.8 mg, 0.74 mmol) in dichloromethane (5 mL) was added bromotrimethylsilane (112.5 mg, 0.74 mmol). The mixture was stirred at ambient temperature overnight and then concentrated under reduced pressure. The residue was co-evaporated with ACN twice to give [(3aR,4R,6S,6aS)-4-[6-cyano-4-(cyclopentylamino)pyrazolo[3,4-d]pyrimidin-1-yl]-2,2-dimethyl-3a,4,6,6a-tetrahydrofuro[3,4-d][1,3]dioxol-6-yl]methylsulfonylmethylphosphonic acid which was used directly in the next step.

Step F: Preparation of (((((2S,3S,4R,5R)-5-(6-cyano-4-(cyclopentylamino)-1H-pyrazolo[3,4-d]pyrimidin-1-yl)-3,4-dihydroxytetrahydrofuran-2-yl)methyl)sulfonyl)methyl)phosphonic acid: A solution of [(3aR,4R,6S,6aS)-4-[6-cyano-4-(cyclopentylamino)pyrazolo[3,4-d]pyrimidin-1-yl]-2,2-dimethyl-3a,4,6,6a-tetrahydrofuro[3,4-d][1,3]dioxol-6-yl]methylsulfonylmethylphosphonic acid (35.0 mg, 0.03 mmol) in 80% HCOOH (3 mL) was stirred at ambient temperature for 2 hours. The mixture was concentrated under reduced pressure and purified by preparative reverse phase HPLC (10%-95% ACN/H₂O, 0.1% TFA) to give [(2S,3S,4R,5R)-5-[6-cyano-4-(cyclopentylamino)pyrazolo[3,4-d]pyrimidin-1-yl]-3,4-dihydroxy-tetrahydrofuran-2-yl]methylsulfonylmethylphosphonic acid (11.5 mg, 88%) as a solid. LCMS ESI (+) m/z 501 (M–H).

Example 20: Synthesis of (((((2R,3S,4R,5S)-5-(2-chloro-4-(hexahydrocyclopenta[c]pyrrol-2 (1H)-yl)-5H-pyrrolo[3,2-d]pyrimidin-7-yl)-3,4-dihydroxytetrahydrofuran-2-yl)methoxy)methyl)phosphonic acid (Compound 285)

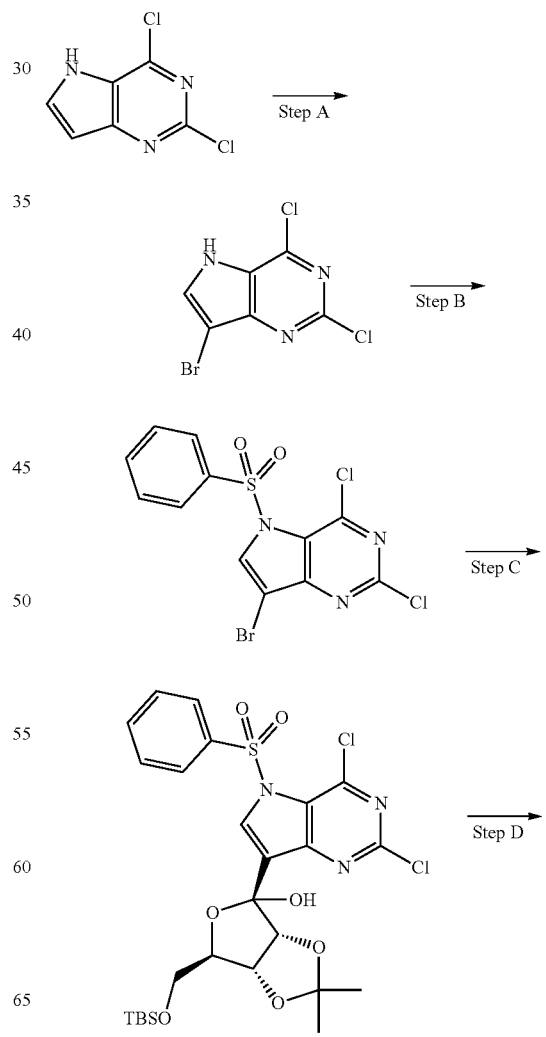

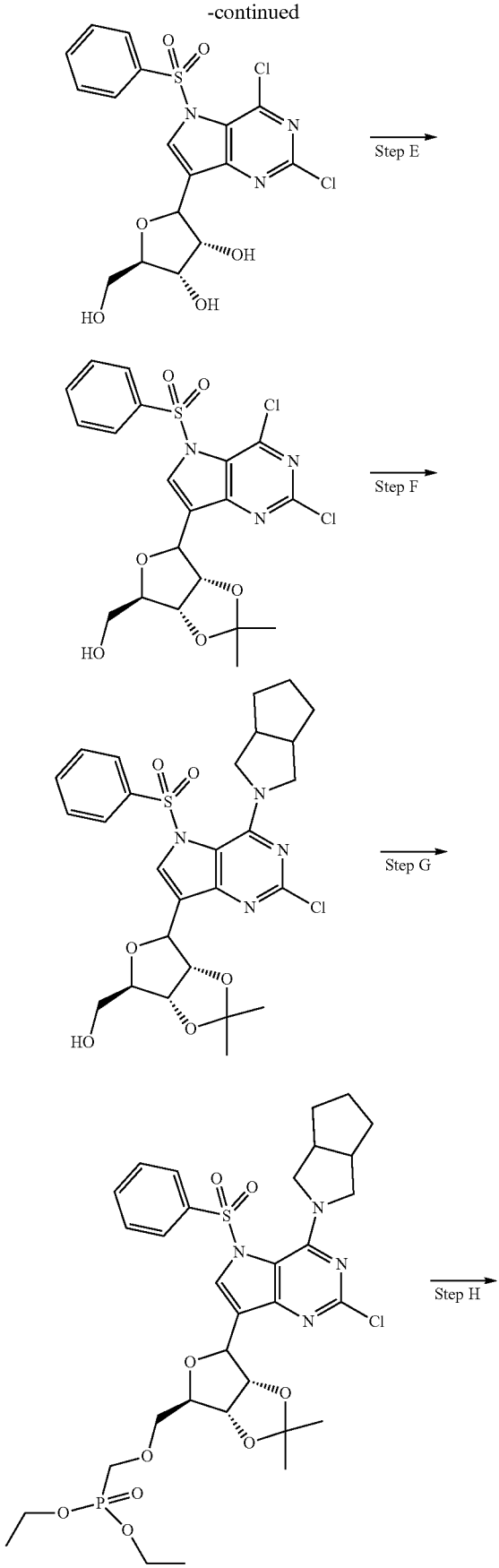

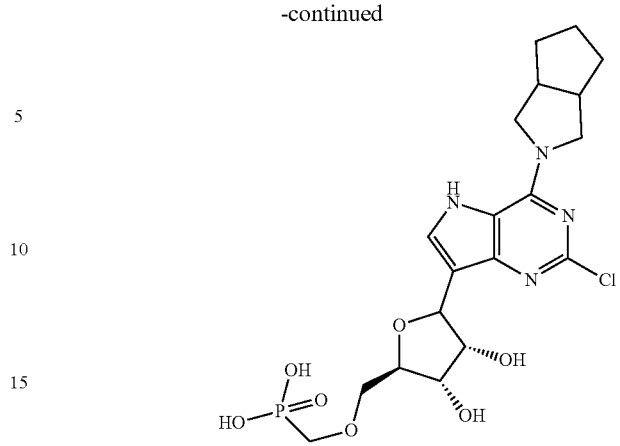

Step A: Preparation of 7-bromo-2,4-dichloro-5H-pyrrolo[3,2-d]pyrimidine: To a solution of, 2,4-dichloro-5H-Pyrrolo[3,2-d]pyrimidine (1.88 g, 10 mmol) in DMF (10 mL) was added N-bromosuccinimide (1.96 g, 11 mmol) at ambient temperature. The mixture was stirred at ambient temperature for 1 hour. Ethyl acetate (20 mL) and saturated sodium bicarbonate solution (20 mL) were added. The organic layer was separated, washed with brine, dried (sodium sulfate), filtered and concentrated under reduced pressure. The residue was purified by flash chromatography on silica gel (1:1 hexane/ethyl acetate) to give 7-bromo-2,4-dichloro-5H-pyrrolo[3,2-d]pyrimidine (2.3 g, 86%) as a solid.

Step B: Preparation of 5-(benzenesulfonyl)-7-bromo-2,4-dichloro-pyrrolo[3,2-d]pyrimidine: To a solution of 7-bromo-2,4-dichloro-5H-pyrrolo[3,2-d]pyrimidine (1.0 g, 3.75 mmol), DIEA (1.0 mL, 5.62 mmol) and 4-(dimethylamino)pyridine (0.05 g, 0.37 mmol) in dichloromethane (30 mL) was added benzenesulfonyl chloride (0.57 mL, 4.5 mmol) at 0° C. The mixture was stirred at 0° C. for 1 hour. Saturated sodium bicarbonate solution (20 mL) was added. The organic layer was separated, washed with brine, dried (sodium sulfate), filtered and concentrated under reduced pressure. The residue obtained was purified by flash chromatography on silica gel (1:1 hexane/DCM) to give 5-(benzenesulfonyl)-7-bromo-2,4-dichloro-pyrrolo[3,2-d]pyrimidine (1.15 g, 75%) as a solid.

Step C: Preparation of (3aR,4S,6R,6aR)-6-(((tert-butyldimethylsilyl)oxy)methyl)-4-(2,4-dichloro-5-(phenylsulfonyl)-5H-pyrrolo[3,2-d]pyrimidin-7-yl)-2,2-dimethyltetrahydrofuro[3,4-d][1,3]dioxol-4-ol: To a solution of (3aR,6R,6aR)-6-[[tert-butyl(dimethyl)silyl]oxymethyl]-2,2-dimethyl-6,6a-dihydro-3aH-furo[3,4-d][1,3]dioxol-4-one (1.28 g, 4.24 mmol) and 5-(benzenesulfonyl)-7-bromo-2,4-dichloro-pyrrolo[3,2-d]pyrimidine (1.15 g, 2.83 mmol) in tetrahydrofuran (20 mL) was added n-butyllithium solution (2.5M in hexane, 1.36 mL, 3.39 mmol) dropwise at −78° C. (30 minutes). After the addition, the mixture was stirred at −78° C. for 2 hours and then quenched with acetic acid (0.26 mL, 4.52 mmol). The resulting mixture was warmed to ambient temperature, diluted with ethyl acetate, and washed with water. The organic layer was separated, washed with brine, dried (sodium sulfate), filtered and concentrated under reduced pressure. The residue was purified by flash chromatography on silica gel (5:1 hexane/ethyl acetate) to give (3aR,4S,6R,6aR)-6-(((tert-butyldimethylsilyl)oxy) methyl)-4-(2,4-dichloro-5-(phenylsulfonyl)-5H-pyrrolo[3,2-d]pyrimidin-7-yl)-2,2-dimethyltetrahydrofuro[3,4-d][1,3]dioxol-4-ol (1.12 g, 31%) as a solid.

Step D: Preparation of (3R,4S,5R)-2-[5-(benzenesulfonyl)-2,4-dichloro-pyrrolo[3,2-d]pyrimidin-7-yl]-5-(hydroxymethyl)tetrahydrofuran-3,4-diol: To a solution of (3aR,6R,6aR)-4-[5-(benzenesulfonyl)-2,4-dichloro-pyrrolo[3,2-d]pyrimidin-7-yl]-6-[[tert-butyl(dimethyl)silyl]oxymethyl]-2,2-dimethyl-6,6a-dihydro-3aH-furo[3,4-d][1,3]dioxol-4-ol (0.67 g, 1.07 mmol) in dichloromethane (10 mL) was added triethylsilane (0.68 mL, 4.26 mmol), then boron trifluoride diethyl etherate (0.39 mL, 3.2 mmol) at ambient temperature. The reaction mixture was stirred at ambient temperature for 18 hours. The reaction mixture was cooled with ice bath and slowly quenched with saturated sodium bicarbonate solution. The organic layer was separated, washed with brine, dried (sodium sulfate), filtered and concentrated under reduced pressure. The residue was purified by flash chromatography on silica gel (ethyl acetate) to give (3R,4S,5R)-2-[5-(benzenesulfonyl)-2,4-dichloro-pyrrolo[3,2-d]pyrimidin-7-yl]-5-(hydroxymethyl)tetrahydrofuran-3,4-diol (1.0 g, 91%) as a solid.

Step E: Preparation of [(3aS,6R,6aR)-4-[5-(benzenesulfonyl)-2,4-dichloro-pyrrolo[3,2-d]pyrimidin-7-yl]-2,2-dimethyl-3a,4,6,6a-tetrahydrofuro[3,4-d][1,3]dioxol-6-yl]methanol: To a solution of (3R,4S,5R)-2-[5-(benzenesulfonyl)-2,4-dichloro-pyrrolo[3,2-d]pyrimidin-7-yl]-5-(hydroxymethyl)tetrahydrofuran-3,4-diol (1.0 g, 2.17 mmol) and 2,2-dimethoxy propane (3.19 mL, 26.1 mmol) in acetone (10 mL) was added 4-methylbenzenesulfonic acid (0.49 g, 2.82 mmol) at ambient temperature. The reaction mixture was stirred at ambient temperature for 2 hours. Solvent was removed under reduce pressure. Water (20 mL) and ethyl acetate (20 mL) were added. The organic layer was separated, washed with brine, dried (sodium sulfate), filtered and concentrated under reduced pressure. The residue was purified by flash chromatography on silica gel 1:1 hexane/ethyl acetate to give [(3aS,6R,6aR)-4-[5-(benzenesulfonyl)-2,4-dichloro-pyrrolo[3,2-d]pyrimidin-7-yl]-2,2-dimethyl-3a,4,6,6a-tetrahydrofuro[3,4-d][1,3]dioxol-6-yl]methanol (0.42 g, 38%) as a solid.

Step F: Preparation of [(3aS,4S,6R,6aR)-4-[4-(3,3a,4,5,6,6a-hexahydro-1H-cyclopenta[c]pyrrol-2-yl)-5-(benzenesulfonyl)-2-chloro-pyrrolo[3,2-d]pyrimidin-7-yl]-2,2-dimethyl-3a,4,6,6a-tetrahydrofuro[3,4-d][1,3]dioxol-6-yl]methanol: A solution of [(3aS,6R,6aR)-4-[5-(benzenesulfonyl)-2,4-dichloro-pyrrolo[3,2-d]pyrimidin-7-yl]-2,2-dimethyl-3a,4,6,6a-tetrahydrofuro[3,4-d][1,3]dioxol-6-yl]methanol (0.42 g, 0.84 mmol), 1,2,3,3a,4,5,6,6a-octahydrocyclopenta[c]pyrrole (0.14 g, 1.26 mmol) and triethylamine (0.23 mL, 1.68 mmol) in s-Butanol (5 mL) was stirred at 80° C. for 1 hour. After cooling to ambient temperature, s-butanol was removed under reduced pressure. Ethyl acetate (20 ml) and water (10 mL) were added. The organic layer was separated, washed with brine, dried (sodium sulfate), filtered and concentrated under reduced pressure. The residue was purified by flash chromatography on silica gel (1:1 hexane/ethyl acetate) to give [(3aS,4S,6R,6aR)-4-[4-(3,3a,4,5,6,6a-hexahydro-1H-cyclopenta[c]pyrrol-2-yl)-5-(benzenesulfonyl)-2-chloro-pyrrolo[3,2-d]pyrimidin-7-yl]-2,2-dimethyl-3a,4,6,6a-tetrahydrofuro[3,4-d][1,3]dioxol-6-yl]methanol (0.148 g, 30%) as a solid.

Step G: Preparation of 7-[(3aS,4S,6R,6aR)-6-(diethoxyphosphorylmethoxymethyl)-2,2-dimethyl-3a,4,6,6a-tetrahydrofuro[3,4-d][1,3]dioxol-4-yl]-4-(3,3a,4,5,6,6a-hexahydro-1H-cyclopenta[c]pyrrol-2-yl)-5-(benzenesulfonyl)-2-chloro-pyrrolo[3,2-d]pyrimidine: A mixture of [(3aS,4S,6R,6aR)-4-[4-(3,3a,4,5,6,6a-hexahydro-1H-cyclopenta[c]pyrrol-2-yl)-5-(benzenesulfonyl)-2-chloro-pyrrolo[3,2-d]pyrimidin-7-yl]-2,2-dimethyl-3a,4,6,6a-tetrahydrofuro[3,4-d][1,3]dioxol-6-yl]methanol (0.12 g, 0.22 mmol), P-[[[(4-methylphenyl)sulfonyl]oxy]methyl]phosphonic acid diethyl ester (0.14 g, 0.43 mmol) and magnesium 2-methylpropan-2-olate (0.15 g, 0.86 mmol) in dimethyl sulfoxide (3 mL) was stirred at 80° C. (bath) for 4 hours. After cooling to ambient temperature, saturated ammonium chloride solution (10 mL) and 1:1 MTBE/ethyl acetate (20 mL) were added. The organic layer was separated, washed with brine, dried (sodium sulfate), filtered and concentrated under reduced pressure. The residue was purified by reverse phase column (Biotage Isolera One unit, Biotage@SNAP Ultra C18 60 g column, 30-100% CH$_3$CN/water, 10 CV) to give 7-[(3aS,4S,6R,6aR)-6-(diethoxyphosphorylmethoxymethyl)-2,2-dimethyl-3a,4,6,6a-tetrahydrofuro[3,4-d][1,3]dioxol-4-yl]-4-(3,3a,4,5,6,6a-hexahydro-1H-cyclopenta[c]pyrrol-2-yl)-5-(benzenesulfonyl)-2-chloro-pyrrolo[3,2-d]pyrimidine (0.044 g, 28%) as an oil.

Step H: Preparation of [(2R,3S,4R,5S)-5-[4-(3,3a,4,5,6,6a-hexahydro-1H-cyclopenta[c]pyrrol-2-yl)-2-chloro-5H-pyrrolo[3,2-d]pyrimidin-7-yl]-3,4-dihydroxy-tetrahydrofuran-2-yl]methoxymethylphosphonic acid: To a solution of 7-[(3aS,4S,6R,6aR)-6-(diethoxyphosphorylmethoxymethyl)-2,2-dimethyl-3a,4,6,6a-tetrahy drofuro[3,4-d][1,3]dioxol-4-yl]-4-(3,3a,4,5,6,6a-hexahydro-1H-cyclopenta[c]pyrrol-2-yl)-5-(benzenesulfonyl)-2-chloro-pyrrolo[3,2-d]pyrimidine (0.040 g, 0.06 mmol) in dichloromethane (2 mL) was added 2,6-lutidine (0.04 mL, 0.30 mmol) and bromotrimethyl silane (0.04 mL, 0.30 mmol) at ambient temperature. The reaction mixture was stirred at this temperature for 18 hours. The reaction mixture was concentrated under reduced pressure. The residue was co-evaporated with methanol three times to give a light yellow solid. The solid was dissolved in 1:1 THF/water (6 mL) and sodium hydroxide (0.07 g, 1.82 mmol) was added. The mixture was stirred at ambient temperature for 1 hour and at 55° C. (bath) for 3 hours. THF and water were removed under reduced pressure. 80% Formic acid in water (3 mL) was added. The resulting mixture was stirred at ambient temperature for 3 hours. Formic acid was removed under reduced pressure. The residue was co-evaporated with methanol three times to give a light yellow solid, which was directly purified by preparative reverse phase HPLC (5%-95% ACN/H$_2$O, 0.1% TFA) to give [(2R,3S,4R,5S)-5-[4-(3,3a,4,5,6,6a-hexahydro-1H-cyclopenta[c]pyrrol-2-yl)-2-chloro-5H-pyrrolo[3,2-d]pyrimidin-7-yl]-3,4-dihydroxy-tetrahydrofuran-2-yl]methoxymethylphosphonic acid (0.007 g, 19%) as a solid. LCMS ESI (+) m/z 489 (M+H).

Example 21: Synthesis of (((((2R,3S,4R,5R)-5-(4-(cyclopentylamino)-2-((1-hydroxycyclopropyl)ethynyl)-7H-pyrrolo[2,3-d]pyrimidin-7-yl)-3,4-dihydroxytetrahydrofuran-2-yl)methoxy)methyl) phosphonic acid (Compound 276)

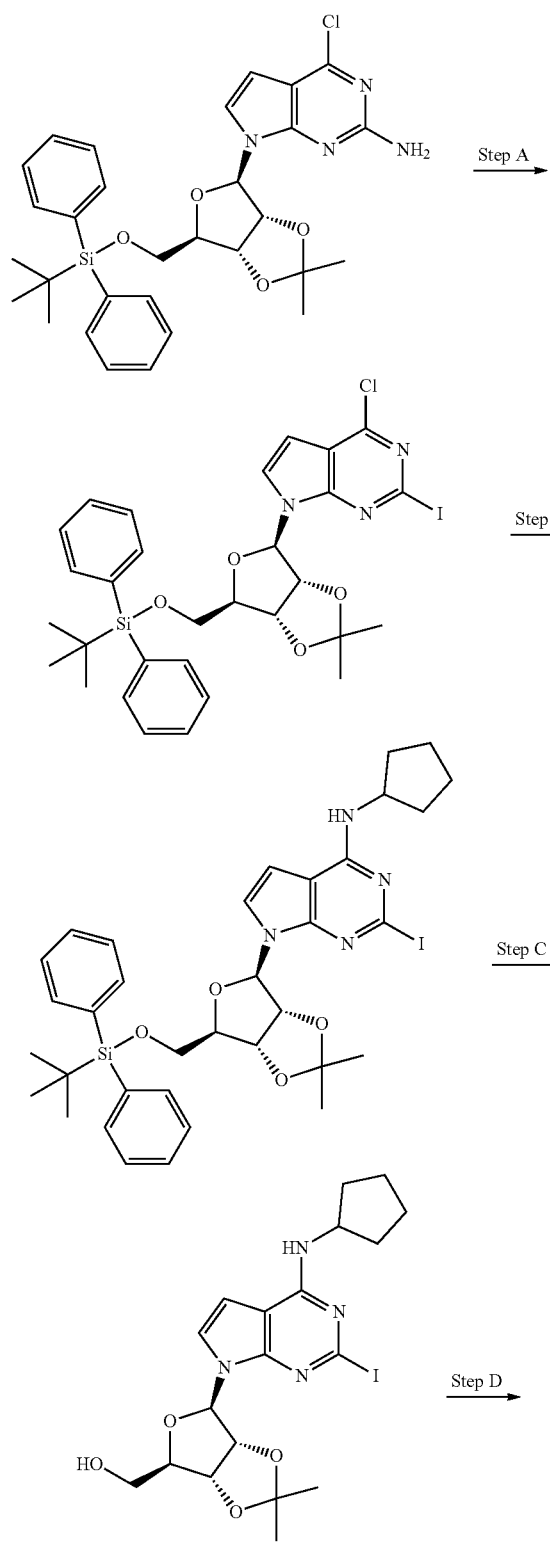

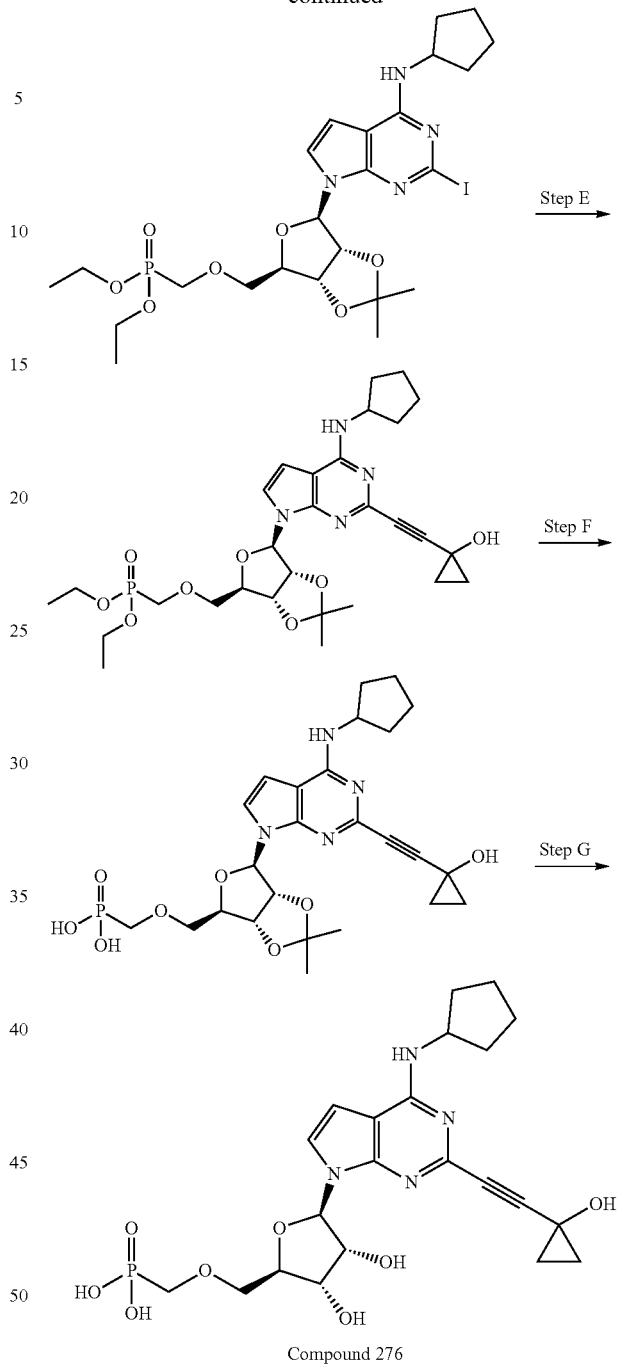

Compound 276

Step A: Isopentyl nitrite (5.2 g, 44.39 mmol) was added to a stirred mixture of 7-((3aR,4R,6R,6aR)-6-(((tert-butyldiphenylsilyl)oxy)methyl)-2,2-dimethyltetrahydrofuro[3,4-d][1,3]dioxol-4-yl)-4-chloro-7H-pyrrolo[2,3-d]pyrimidin-2-amine (8.6 g, 14.85 mmol), CuI (3. g, 15.75 mmol), iodine (4.0 g, 15.76 mmol) and diiodomethane (40 g, 149.3 mmol) in tetrahydrofuran (100 mL) at room temperature. The mixture was then stirred at 80° C. for 45 minutes. The cooled reaction mixture was poured into an aqueous solution of sodium sulphite and extracted with EtOAc. The combined extracts were washed with brine, dried over anhydrous Na$_2$SO$_4$ and the solvent was evaporated. The residue was purified by column chromatography (EtOAc:petroleum ether 1:8) to give 7-((3aR,4R,6R,6aR)-6-(((tert-butyldiphenylsilyl)oxy)methyl)-2,2-dimethyltetrahydrofuro[3,4-d][1,3]dioxol-4-yl)-4-chloro-2-iodo-7H-pyrrolo[2,3-d]pyrimidine (4.0 g, 39%).

Step B: A solution of 7-((3aR,4R,6R,6aR)-6-(((tert-butyldiphenylsilyl)oxy)methyl)-2,2-dimethyltetrahydrofuro[3,4-d][1,3]dioxol-4-yl)-4-chloro-2-iodo-7H-pyrrolo[2,3-d]pyrimidine (1.2 g, 1.7 mmol) and cyclopentanamine (0.5 g, 5.9 mmol) in ethanol (5 mL) was stirred in a sealed tube at 80° C. overnight. The reaction mixture was then concentrated and purified by column chromatography (EtOAc:hexanes 1:8) to give the product 7-((3aR,4R,6R,6aR)-6-(((tert-butyldiphenylsilyl)oxy)methyl)-2,2-dimethyltetrahydrofuro[3,4-d][1,3]dioxol-4-yl)-N-cyclopentyl-2-iodo-7H-pyrrolo[2,3-d]pyrimidin-4-amine (1.1 g, 86%).

Step C: To a solution of 7-((3aR,4R,6R,6aR)-6-(((tert-butyldiphenylsilyl)oxy)methyl)-2,2-dimethyltetrahydrofuro[3,4-d][1,3]dioxol-4-yl)-N-cyclopentyl-2-iodo-7H-pyrrolo[2,3-d]pyrimidin-4-amine (1.3 g, 1.76 mmol) in THF (20 mL) was added a solution of tetrabutylammonium fluoride, 1.0 M in THF (1.91 mL, 1.91 mmol) 0° C. The reaction mixture was stirred at 25° C. for 3 h. The mixture was diluted with EtOAc, washed with brine, then dried (Na$_2$SO$_4$) and filtered before concentration to dryness. The crude residue was purified by column chromatography eluting with 30% EtOAc/hexane to give ((3aR,4R,6R,6aR)-6-(4-(cyclopentylamino)-2-iodo-7H-pyrrolo[2,3-d]pyrimidin-7-yl)-2,2-dimethyltetrahydrofuro[3,4-d][1,3]dioxol-4-yl)methanol (700 mg, 80%) as an off-white solid. LCMS ESI (+) m/z 501, M+H.

Step D: ((3aR,4R,6R,6aR)-6-(4-(cyclopentylamino)-2-iodo-7H-pyrrolo[2,3-d]pyrimidin-7-yl)-2,2-dimethyltetrahydrofuro[3,4-d][1,3]dioxol-4-yl)methanol (85 mg, 0.17 mmol), ditert-butoxymagnesium (65.7 mg, 0.39 mmol) and (diethoxyphosphoryl)methyl 4-methylbenzenesulfonate (130.5 mg, 0.4 mmol) and DMSO (0.6 mL) were successively charged to a 20 mL scintillation vial. The vial was placed in an 80° C. oil bath and aged for 6 hours at this temperature. The cooled reaction mixture was partitioned with EtOAc and saturated aqueous NH$_4$Cl. The aqueous separation was extracted with EtOAc (2×). The combined organic extracts were washed with brine (2×) then dried with Na$_2$SO$_4$, filtered and concentrated to an orange oil. The oil was purified by column chromatography, 10 g SiO2, 5 to 50% (3:1 EtOAc:EtOH (v/v))/hexanes to give diethyl (((3aR,4R,6R,6aR)-6-(4-(cyclopentylamino)-2-iodo-7H-pyrrolo[2,3-d]pyrimidin-7-yl)-2,2-dimethyltetrahydrofuro[3,4-d][1,3]dioxol-4-yl)methoxy)methyl)phosphonate as a tan colored oil. LCMS ESI (+) m/z 651, M+H.

Step E: Pd(PPh$_3$)$_2$C$_{12}$ (8.4 mg, 0.012 mmol) and CuI (4.6 mg, 0.024 mmol) were charged to a vial. A solution of diethyl (((3aR,4R,6R,6aR)-6-(4-(cyclopentylamino)-2-iodo-7H-pyrrolo[2,3-d]pyrimidin-7-yl)-2,2-dimethyltetrahydrofuro[3,4-d][1,3]dioxol-4-yl)methoxy)methyl)phosphonate (40 mg, 0.06 mmol) in 1,4-dioxane (1 mL) was added to the vial, followed by Et$_3$N (15.3 mg, 0.15 mmol). The yellowed orange solution was sparged with argon for 3 minutes, then treated with 1-ethynylcyclopropanol (120 mg, 1.46 mmol), and within a minute had turned a black color. The mixture was stirred at ambient temperature for 90 minutes. The reaction mixture was diluted with ethyl acetate, then filtered over celite. The filtrate was concentrated under reduced pressure, then the residue was purified by column chromatography, 80% EtOAc/hexane, to give diethyl (((3aR,4R,6R,6aR)-6-(4-(cyclopentylamino)-2-((1-hydroxycyclopropyl)ethynyl)-7H-pyrrolo[2,3-d]pyrimidin-7-yl)-2,2-dimethyltetrahydrofuro[3,4-d][1,3]dioxol-4-yl)methoxy)methyl)phosphonate (24 mg, 64% yield).

Step F: To a solution of diethyl (((3aR,4R,6R,6aR)-6-(4-(cyclopentylamino)-2-((1-hydroxycyclopropyl)ethynyl)-7H-pyrrolo[2,3-d]pyrimidin-7-yl)-2,2-dimethyltetrahydrofuro[3,4-d][1,3]dioxol-4-yl)methoxy)methyl)phosphonate (24 mg, 0.04 mmol) and 2,6-lutidine (50 mg, 0.47 mmol) in DCM (5 mL) was added bromotrimethylsilane (70 mg, 0.46 mmol). The mixture was stirred at ambient temperature overnight, then was concentrated under reduced pressure. The residue was coevaporated with CH$_3$CN (2×) to give ((((3aR,4R,6R,6aR)-6-(4-(cyclopentylamino)-2-((1-hydroxycyclopropyl)ethynyl)-7H-pyrrolo[2,3-d]pyrimidin-7-yl)-2,2-dimethyltetrahydrofuro[3,4-d][1,3]dioxol-4-yl)methoxy)methyl)phosphonic acid (28 mg) as a crude product, which was carried forward without further purification.

Step G: A solution of ((((3aR,4R,6R,6aR)-6-(4-(cyclopentylamino)-2-((1-hydroxycyclopropyl)ethynyl)-7H-pyrrolo[2,3-d]pyrimidin-7-yl)-2,2-dimethyltetrahydrofuro[3,4-d][1,3]dioxol-4-yl)methoxy)methyl)phosphonic acid (28 mg, 0.05 mmol) in 80% HCOOH aqueous solution (3 mL) was stirred at ambient temperature for 2 h. The mixture was concentrated under reduced pressure at 30° C., then purified by reverse phase HPLC, 20% to 80% MeCN/H$_2$O with 0.1% TFA, 15 min gradient, to afford (((((2R,3S,4R,5R)-5-(4-(cyclopentylamino)-2-((1-hydroxycyclopropyl)ethynyl)-7H-pyrrolo[2,3-d]pyrimidin-7-yl)-3,4-dihydroxytetrahydrofuran-2-yl)methoxy)methyl)phosphonic acid (5.1 mg, 20% yield) as a white solid. LCMS ESI (+) m/z 508.5, M+H.

Example 22: Synthesis of (((((2R,3S,4R,5R)-5-(4-(cyclopentylamino)-2-(2-hydroxyethoxy)-7H-pyrrolo[2,3-d]pyrimidin-7-yl)-3,4-dihydroxytetrahydrofuran-2-yl)methoxy)methyl)phosphonic acid (Compound 257)

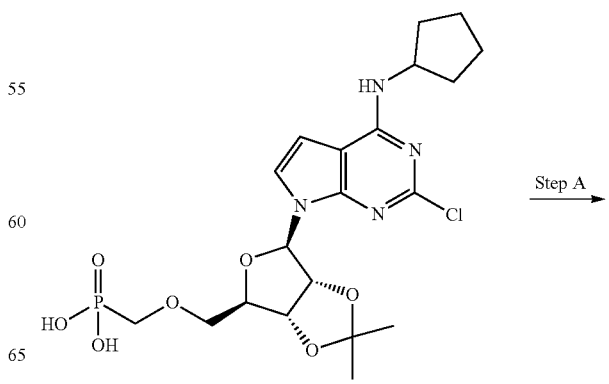

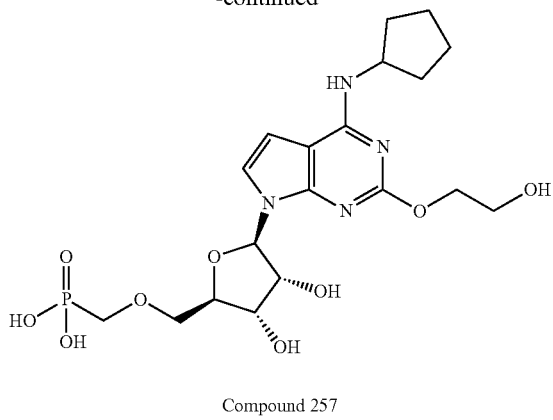

Compound 257

Step A: Sodium hydride (40 mg, 1.67 mmol) was weighed into a vial, then ethylene glycol (0.5 mL, 8.97 mmol) was slowly added, which effervesced and was very exothermic. After the gas evolution had ceased, and the mixture cooled, ((((3aR,4R,6R,6aR)-6-(2-chloro-4-(cyclopentylamino)-7H-pyrrolo[2,3-d]pyrimidin-7-yl)-2,2-dimethyltetrahydrofuro[3,4-d][1,3]dioxol-4-yl)methoxy)methyl)phosphonic acid (20 mg, 0.04 mmol) was added in a single portion. The vial was capped and warmed to 110° C. and stirred for 90 minutes, then was cooled to ambient temperature; the solution was very viscous. The solution was diluted with methanol (0.5 mL), and then treated with 6N aqueous HCl (1.0 mL) and stirred overnight. The solution was purified by HPLC, 5 to 90% MeCN/H$_2$O (with 0.1% TFA) over a 10 minute gradient to give a clear film, ((((3aR,4R,6R,6aR)-6-(4-(cyclopentylamino)-2-(2-hydroxyethoxy)-7H-pyrrolo[2,3-d]pyrimidin-7-yl)-2,2-dimethyltetrahydrofuro[3,4-d][1,3]dioxol-4-yl)methoxy)methyl)phosphonic acid (18.3 mg, 94% yield). LCMS ESI (+) m/z 489, M+H.

Example 23: CD73 Enzyme Assay

Enzyme assays were carried out using an EnzChek® Pyrophosphate Assay Kit (E-6645 Molecular Probes) containing PNP (purine ribonucleoside phosphorylase) at 100 U/mL Stock and MESG (2-amino-6-mercapto-7-methylpurine) at 1 mM Stock. Human CD73 (0.25 nM final concentration in assay), MW 61000 expressed in CHO cells was purchased from R&D Systems.

A compound of the present disclosure (5 µL) was transferred to a 384-well assay plate. Compound was added in a 15 point, 3-fold serial dilution (300 µM to 0.0002 µM) in DMSO. CD73 assay buffer (25 mM HEPES, pH 7.5, 100 mM NaCl, 0.001% Tween-20, 1 uM ZnCl$_2$, 10 units PNP, 0.1 mM MESG, 0.25 nM hCD73) was added and the resulting solution allowed to equilibrate for 10 minutes at room temperature. The enzyme reaction was initiated by adding 20 µL of 125 µM AMP (diluted 10:1 with buffer containing 50% glycerol, 25 mM Tris, pH 7.5, 1 mM ZnCl$_2$) to a final concentration of 25 µM AMP. The plate was immediately placed in a plate reader (Synergy 2 or Spark 10), and a reading taken every minute for 10 to 20 minutes in a kinetic run at 360 nm. The linear portion of the curve was used to determine the observed rate (initial velocity). Low signal controls containing 100 µM adenosine 5'-(α,β-methylene)diphosphate and high signal controls containing no compound were measured for each plate.

IC$_{50}$ values were calculated using Dotmatics template equation for 4-parameter fit. Results are expressed as % inhibition using the following equation:

$$\% \text{ inhibition} = \left(\frac{\text{high control} - \text{sample}}{\text{high control} - \text{low control}}\right) \times 100$$

The IC$_{50}$ of adenosine 5'-(α,β-methylene)diphosphate was 0.050 µM.

Example 24: CD73 Cell-Based Assay

U138 human neuroglioma cells were used in these experiments. U138 cells were obtained from ATCC and cultured in DMEM with 10% FBS. 2500 cells were seeded into 96-well plate with 100 µL of media the day before the experiment. Cells were washed twice with 200 µL of assay buffer (20 mM HEPES, pH 7.4; 137 mM NaCl; 5.4 mM KCl; 1.3 mM CaCl$_2$; 4.2 mM NaHCO$_3$; 1 mg/mL glucose) to remove residual inorganic phosphate. After washing, 100 µL of buffer was added to each well, then 100 µL of a mixture of AMP substrate (200 µM) and diluted compound was added to each well. The cells were incubated at 37° C. (with 5% CO$_2$) for 2 hours. 50 µL of supernatant was transferred to a 96-well assay plate and the concentration of inorganic phosphate was determined using malachite green reagent (R&D System; Cat: DY996).

Table 2 shows biological activities of selected compounds described herein in the enzyme and cell-based assays. Compound numbers correspond to the numbers and structures provided in Table 1 and Examples 1-22.

TABLE 2

| Assay | <10 nM (++++) | ≥10 nM < 100 nM (+++) | ≥100 nM < 1,000 nM (++) | ≥1,000 nM (+) |
|---|---|---|---|---|
| CD73 Cell-Based assay IC$_{50}$ (nM) | 61, 62, 67, 69, 70, 71, 72, 73, 78, 80, 81, 82, 83, 84, 85, 87, 88, 89, 90, 91, 92, 94, 97, 101, 102, 103, 104, 105, 106, 109, 110, 111, 114, 116, 117, 119, | 3, 20, 21, 36, 49, 54, 56, 60, 68, 74, 75, 76, 77, 79, 93, 95, 98, 99, 100, 107, 108, 112, 113, 115, 120, 122, 127, 128, 129, 130, 132, 134, 135, 139, 143, | 4, 15, 16, 18, 32, 43, 52, 57, 86, 96, 160, 184, 188, 207, 209, 211, 222, 248, 254, 283, 297 | 1, 9, 12, 46, 55, 133, 187, 199, 206, 304 |

TABLE 2-continued

| Assay | <10 nM (++++) | ≥10 nM < 100 nM (+++) | ≥100 nM < 1,000 nM (++) | ≥1,000 nM (+) |
|---|---|---|---|---|
| | 121, 123, 124, 125, 126, 131, 136, 137, 138, 140, 141, 142, 144, 147, 154, 155, 156, 157, 158, 159, 161, 164, 167, 168, 169, 170, 171, 172, 173, 174, 177, 178, 179, 180, 181, 182, 183, 189, 190, 192, 194, 195, 196, 197, 198, 201, 204, 205, 229, 230, 240, 243, 244, 252, 253, 255, 256, 257, 258, 261, 263, 266, 267, 269, 270, 271, 272, 274, 275, 276, 279, 280, 285, 287, 289, 290, 291, 292, 294, 295, 296, 298, 299, 300, 307, 308 | 145, 146, 152, 153, 162, 163, 175, 176, 186, 191, 193, 200, 202, 203, 212, 213, 218, 219, 231, 232, 239, 247, 250, 260, 262, 265, 284, 288, 293, 303, 305 | | |
| CD73 Enzyme Assay IC$_{50}$ (nM) | 4, 60, 61, 62, 69, 70, 71, 72, 73, 74, 75, 76, 79, 80, 81, 83, 84, 85, 87, 88, 89, 90, 91, 92, 93, 94, 101, 102, 103, 105, 106, 109, 110, 111, 115, 116, 119, 123, 124, 125, 131, 132, 134, 136, 138, 139, 140, 141, 142, 143, 144, 153, 154, 155, 156, 157, 158, 159, 161, 164, 167, 168, 169, 170, 171, 172, 173, 174, 177, 178, 179, 180, 181, 182, 183, 186, 188, 189, 190, 191, 192, 194, 195, 196, 197, 198, 201, 204, 205, 229, 230, 233, 240, 243, 244, 252, 253, 255, 256, 257, 261, 263, 266, 267, 270, 271, 274, 275, 276, 279, 280, 282, 285, 287, 289, 290, 291, 292, 295, 296, 298, 299, 308 | 15, 16, 20, 21, 36, 49, 54, 56, 67, 68, 77, 78, 82, 95, 97, 98, 99, 100, 104, 107, 108, 112, 113, 114, 117, 121, 122, 126, 127, 128, 129, 130, 137, 147, 152, 162, 163, 175, 176, 193, 200, 202, 206, 212, 213, 218, 219, 225, 231, 232, 237, 247, 250, 258, 260, 262, 265, 269, 272, 283, 284, 288, 293, 294, 300, 303, 305, 307 | 3, 8, 9, 10, 12, 18, 22, 29, 32, 34, 35, 40, 43, 45, 50, 51, 52, 55, 57, 86, 96, 118, 120, 135, 145, 146, 160, 165, 203, 207, 209, 210, 211, 217, 222, 234, 238, 241, 245, 248, 254, 259, 264, 297 | 1, 2, 5, 6, 7, 11, 13, 14, 17, 19, 23, 24, 25, 26, 27, 28, 30, 31, 33, 37, 38, 39, 41, 42, 44, 46, 47, 48, 53, 58, 59, 63, 64, 65, 66, 133, 148, 149, 150, 151, 166, 184, 185, 187, 199, 208, 214, 215, 216, 220, 223, 224, 226, 227, 228, 242, 246, 302, 304 |

What is claimed is:
1. A compound of Formula (II):

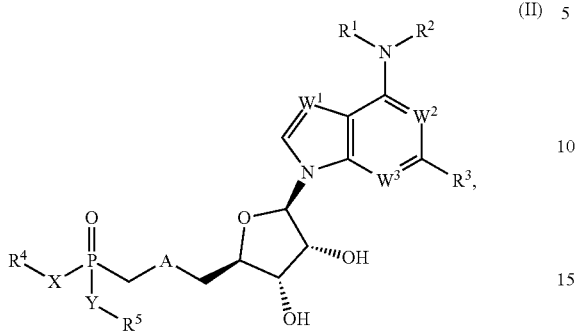

or a pharmaceutically acceptable salt thereof, wherein:
$W^1$, $W^2$ and $W^3$ are each independently selected from N and $CR^6$, wherein at least one of $W^1$, $W^2$ and $W^3$ is N;
$R^1$ is selected from hydrogen; and $C_{1-6}$ alkyl and $C_{3-12}$ carbocycle, each of which is optionally substituted with one or more $R^7$;
$R^2$ is selected from $C_{1-6}$ alkyl, $C_{3-12}$ carbocycle, 3- to 12-membered heterocycle and benzyl, each of which is optionally substituted with one or more $R^7$; or
$R^1$ and $R^2$ are taken together with the nitrogen atom to which they are attached to form a 3- to 12-membered heterocycle, optionally substituted with one or more $R^7$;
$R^3$ is selected from hydrogen, halogen and cyano; and $C_{1-6}$ alkyl, $C_{3-12}$ carbocycle, 3- to 12-membered heterocycle and benzyl, each of which is optionally substituted with one or more $R^7$;
A is selected from —S(=O)- and —S(=O)$_2$-;
X and Y are independently selected from —O— and —NR$^8$—;
$R^4$ and $R^5$ are independently selected from:
hydrogen; and
$C_{1-6}$ alkyl and phenyl, each of which is independently optionally substituted at each occurrence with one or more substituents selected from halogen, —NO$_2$, —CN, —OR$^8$, —SR$^8$, —N(R$^8$)$_2$, —NR$^9$R$^{10}$, —S(=O)R$^8$, —S(=O)$_2$R$^8$, —S(=O)$_2$N(R$^8$)$_2$, —S(=O)$_2$NR$^9$R$^{10}$, —NR$^8$S(=O)$_2$R$^8$, —NR$^8$S(=O)$_2$N(R$^8$)$_2$, —NR$^8$S(=O)$_2$NR$^9$R$^{10}$, —S—S—R$^8$, —S—C(O)R$^8$, —C(O)R$^8$, —C(O)OR$^8$, —OC(O)R$^8$, —OC(O)OR$^8$, —OC(O)N(R$^8$)$_2$, —OC(O)NR$^9$R$^{10}$, —NR$^8$C(O)R$^8$, —NR$^8$C(O)OR$^8$, —NR$^8$C(O)N(R$^8$)$_2$, —NR$^8$C(O)NR$^9$R$^{10}$, —C(O)N(R$^8$)$_2$, —C(O)NR$^9$R$^{10}$, —P(O)(OR$^8$)$_2$, —P(O)(R$^8$)$_2$, —OP(O)(OR$^8$)$_2$, =O, =S, =N(R$^8$), $C_{3-12}$ carbocycle, and 3- to 12-membered heterocycle;
$R^6$ is selected from hydrogen, halogen and cyano; and $C_{1-6}$ alkyl, optionally substituted with one or more $R^7$;
$R^7$ is independently selected at each occurrence from:
halogen, —NO$_2$, —CN, —OR$^8$, —SR$^8$, —N(R$^8$)$_2$, —NR$^9$R$^{10}$, —S(=O)R$^8$, —S(=O)$_2$R$^8$, —S(=O)$_2$N(R$^8$)$_2$, —S(=O)$_2$NR$^9$R$^{10}$, —NR$^8$S(=O)$_2$R$^8$, —NR$^8$S(=O)$_2$N(R$^8$)$_2$, —NR$^8$S(=O)$_2$NR$^9$R$^{10}$, —C(O)R$^8$, —C(O)OR$^8$, —OC(O)R$^8$, —OC(O)OR$^8$, —OC(O)N(R$^8$)$_2$, —OC(O)NR$^9$R$^{10}$, —NR$^8$C(O)R$^8$, —NR$^8$C(O)OR$^8$, —NR$^8$C(O)N(R$^8$)$_2$, —NR$^8$C(O)NR$^9$R$^{10}$, —C(O)N(R$^8$)$_2$, —C(O)NR$^9$R$^{10}$, —P(O)(OR$^8$)$_2$, —P(O)(R$^8$)$_2$, =O, =S, and =N(R$^8$);
$C_{1-10}$ alkyl, $C_{2-10}$ alkenyl, and $C_{2-10}$ alkynyl, each of which is independently optionally substituted at each occurrence with one or more substituents selected from halogen, —NO$_2$, —CN, —OR$^8$, —SR$^8$, —N(R$^8$)$_2$, —NR$^9$R$^{10}$, —S(=O)R$^8$, —S(=O)$_2$R$^8$, —S(=O)$_2$N(R$^8$)$_2$, —S(=O)$_2$NR$^9$R$^{10}$, —NR$^8$S(=O)$_2$R$^8$, —NR$^8$S(=O)$_2$N(R$^8$)$_2$, —NR$^8$S(=O)$_2$NR$^9$R$^{10}$, —C(O)R$^8$, —C(O)OR$^8$, —OC(O)R$^8$, —OC(O)OR$^8$, —OC(O)N(R$^8$)$_2$, —OC(O)NR$^9$R$^{10}$, —NR$^8$C(O)R$^8$, —NR$^8$C(O)OR$^8$, —NR$^8$C(O)N(R$^8$)$_2$, —NR$^8$C(O)NR$^9$R$^{10}$, —C(O)N(R$^8$)$_2$, —C(O)NR$^9$R$^{10}$, —P(O)(OR$^8$)$_2$, —P(O)(R$^8$)$_2$, =O, =S, =N(R$^8$), $C_{3-12}$ carbocycle, and 3- to 12-membered heterocycle; and
$C_{3-12}$ carbocycle and 3- to 12-membered heterocycle, wherein each $C_{3-12}$ carbocycle and 3- to 12-membered heterocycle in $R^7$ is independently optionally substituted with one or more substituents selected from halogen, —NO$_2$, —CN, —OR$^8$, —SR$^8$, —N(R$^8$)$_2$, —NR$^9$R$^{10}$, —S(=O)R$^8$, —S(=O)$_2$R$^8$, —S(=O)$_2$N(R$^8$)$_2$, —S(=O)$_2$NR$^9$R$^{10}$, —NR$^8$S(=O)$_2$R$^8$, —NR$^8$S(=O)$_2$N(R$^8$)$_2$, —NR$^8$S(=O)$_2$NR$^9$R$^{10}$, —C(O)R$^8$, —C(O)OR$^8$, —OC(O)R$^8$, —OC(O)OR$^8$, —OC(O)N(R$^8$)$_2$, —OC(O)NR$^9$R$^{10}$, —NR$^8$C(O)R$^8$, —NR$^8$C(O)OR$^8$, —NR$^8$C(O)N(R$^8$)$_2$, —NR$^8$C(O)NR$^9$R$^{10}$, —C(O)N(R$^8$)$_2$, —C(O)NR$^9$R$^{10}$, —P(O)(OR$^8$)$_2$, —P(O)(R$^8$)$_2$, =O, =S, =N(R$^8$), $C_{1-6}$ alkyl, $C_{1-6}$ haloalkyl, $C_{2-6}$ alkenyl, and $C_{2-6}$ alkynyl;
$R^8$ is independently selected at each occurrence from hydrogen; and $C_{1-20}$ alkyl, $C_{2-20}$ alkenyl, $C_{2-20}$ alkynyl, 1- to 6-membered heteroalkyl, $C_{3-12}$ carbocycle, and 3- to 12-membered heterocycle, each of which is optionally substituted by halogen, —CN, —NO$_2$, —NH$_2$, —NHCH$_3$, —NHCH$_2$CH$_3$, =O, —OH, —OCH$_3$, —OCH$_2$CH$_3$, $C_{3-12}$ carbocycle, or 3- to 6-membered heterocycle; and
$R^9$ and $R^{10}$ are taken together with the nitrogen atom to which they are attached to form a heterocycle, optionally substituted with one or more $R^7$.

2. The compound of claim 1, wherein $R^1$ and $R^2$ are taken together with the nitrogen atom to which they are attached to form a 3- to 12-membered heterocycle, optionally substituted with one or more $R^7$.

3. The compound of claim 2, wherein $R^1$ and $R^2$ are taken together with the nitrogen atom to which they are attached to form a 3- to 12-membered heterocycle, optionally substituted with one or more substituents independently selected from halogen, —CN, $C_{1-4}$ alkyl, $C_{1-3}$ haloalkyl, —OH and —NH$_2$.

4. The compound of claim 1, wherein $R^1$ and $R^2$ are taken together with the nitrogen atom to which they are attached to form optionally substituted 3- to 7-membered monocyclic heterocycloalkyl or optionally substituted 5- to 12-membered fused bicyclic heterocycloalkyl.

5. The compound of claim 1, wherein $R^2$ is selected from $C_{1-6}$ alkyl, $C_{3-12}$ carbocycle, 3- to 12-membered heterocycle and benzyl, each of which is optionally substituted with one or more substituents independently selected from halogen, —CN, $C_{1-4}$ alkyl, $C_{1-3}$ haloalkyl, —OH and —NH$_2$.

6. The compound of claim 1, wherein $R^2$ is benzyl, optionally substituted with one or more $R^7$.

7. The compound of claim 6, wherein $R^2$ is benzyl, optionally substituted with one or more substituents independently selected from halogen, —CN, $C_{1-4}$ alkyl, $C_{1-3}$ haloalkyl, —OH and —NH$_2$.

8. The compound of claim 1, represented by Formula (II-A) or (II-B):

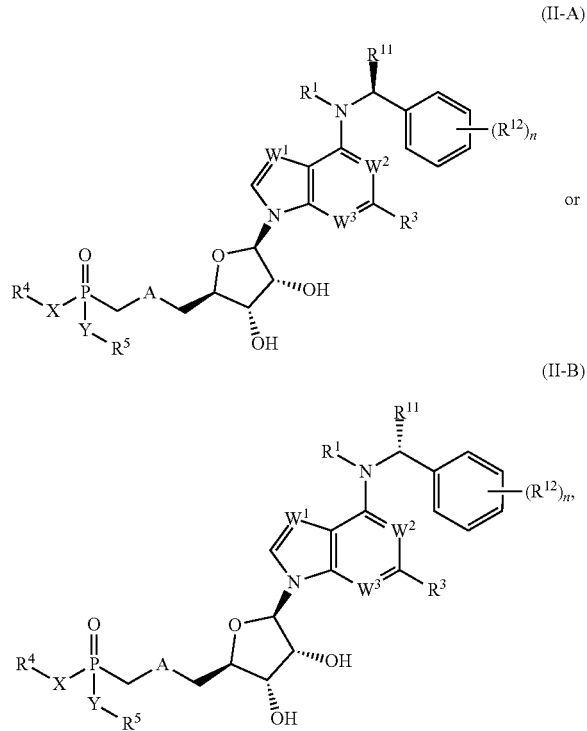

or a pharmaceutically acceptable salt thereof, wherein:
$R^{11}$ is selected from $C_{1-6}$ alkyl and $C_{3-12}$ carbocycle, each of which is optionally substituted with one or more $R^7$;
$R^{12}$ is independently selected at each occurrence from $R^7$; and
n is an integer from 0 to 3.

9. The compound of claim 8, wherein $R^{11}$ is $C_{1-4}$ alkyl.

10. The compound of claim 9, wherein $R^{11}$ is selected from methyl, ethyl, iso-propyl and tert-butyl.

11. The compound of claim 8, wherein $R^{11}$ is selected from $C_{1-4}$ alkyl and $C_{3-12}$ cycloalkyl, each of which is optionally substituted with one or more $R^7$.

12. The compound of claim 8, wherein $R^{12}$ is independently selected at each occurrence from F, —CN, —CH$_3$ and —CF$_3$.

13. The compound of claim 1, represented by Formula (II-C):

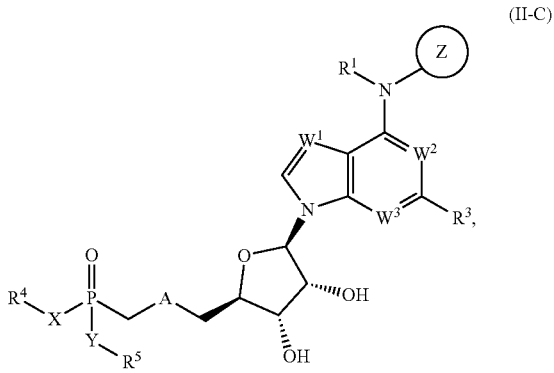

or a pharmaceutically acceptable salt thereof, wherein:
Z is selected from $C_{3-12}$ cycloalkyl and 3- to 12-membered heterocycloalkyl, each of which is optionally substituted with one or more $R^7$.

14. The compound of claim 13, wherein Z is substituted with one or more substituents independently selected from halogen, —CN, $C_{1-4}$ alkyl and $C_{1-3}$ haloalkyl.

15. The compound of claim 1, wherein $R^1$ is selected from hydrogen and —CH$_3$.

16. The compound of claim 1, wherein $W^3$ is N.

17. The compound of claim 1, wherein $W^2$ is N.

18. The compound of claim 1, wherein $W^1$ is N or CH.

19. The compound of claim 1, wherein $W^1$ is N or CH, $W^2$ is N and $W^3$ is N.

20. The compound of claim 1, wherein $R^3$ is selected from —Cl and —CN.

21. The compound of claim 1, wherein at least one of $R^4$ and $R^5$ is $C_{1-6}$ alkyl, optionally substituted at each occurrence with one or more substituents selected from halogen, —OR$^8$, —S—S—R$^8$, —S-C(O)R$^8$, —OC(O)R$^8$, —OC(O)OR$^8$ and —P(O)(OR$^8$)$_2$.

22. The compound of claim 1, wherein X and Y are each —O—.

23. The compound of claim 1, wherein —X—$R^4$ and —Y—$R^5$ are each —OH.

24. A compound selected from:
[(2S,3S,4R,5R)-5-[6-(benzylamino)purin-9-yl]-3,4-dihydroxy-tetrahydrofuran-2-yl]methylsulfonylmethylphosphonic acid;
[[(2S,3S,5R)-5-[6-(benzylamino)purin-9-yl]-3,4-dihydroxy-tetrahydrofuran-2-yl]methylsulfonyl-phenyl-methyl]phosphonic acid;
[(2S,3S,4R,5R)-5-[2-chloro-6-[[(1S)-1-phenylethyl]amino]purin-9-yl]-3,4-dihydroxy-tetrahydrofuran-2-yl]methylsulfonylmethylphosphonic acid;
[(2S,3S,4R,5R)-5-[2-chloro-4-[[(1S)-1-phenylethyl]amino]pyrrolo[2,3-d]pyrimidin-7-yl]-3,4-dihydroxy-tetrahydrofuran-2-yl]methylsulfonylmethylphosphonic acid;
[(2S,3S,4R,5R)-5-[2-chloro-4-[[(1R)-1-phenylethyl]amino]pyrrolo[2,3-d]pyrimidin-7-yl]-3,4-dihydroxy-tetrahydrofuran-2-yl]methylsulfonylmethylphosphonic acid;
[(2S,3S,4R,5R)-5-[2-chloro-4-(cyclopentylamino)pyrrolo[2,3-d]pyrimidin-7-yl]-3,4-dihydroxy-tetrahydrofuran-2-yl]methylsulfonylmethylphosphonic acid;
[(2S,3S,4R,5R)-5-[4-(3,3a,4,5,6,6a-hexahydro-1H-cyclopenta[c]pyrrol-2-yl)-2-chloro-pyrrolo[2,3-d]pyrimidin-7-yl]-3,4-dihydroxy-tetrahydrofuran-2-yl]methylsulfonylmethylphosphonic acid;
[(2S,3S,4R,5R)-5-[2-chloro-4-[methyl-[(1R)-1-phenylethyl]amino]pyrrolo[2,3-d]pyrimidin-7-yl]-3,4-dihydroxy-tetrahydrofuran-2-yl]methylsulfonylmethylphosphonic acid;
[(2S,3S,4R,5R)-5-[4-(3,3a,4,5,6,6a-hexahydro-1H-cyclopenta[c]pyrrol-2-yl)-2-cyano-pyrrolo[2,3-d]pyrimidin-7-yl]-3,4-dihydroxy-tetrahydrofuran-2-yl]methylsulfonylmethylphosphonic acid;
[(2S,3S,4R,5R)-5-[4-(3-bicyclo[3.1.0]hexanylamino)-2-chloro-pyrrolo[2,3-d]pyrimidin-7-yl]-3,4-dihydroxy-tetrahydrofuran-2-yl]methylsulfonylmethylphosphonic acid;
[(2S,3S,4R,5R)-5-[2-chloro-4-(cyclopentylamino)pyrrolo[2,3-d]pyrimidin-7-yl]-3,4-dihydroxy-tetrahydrofuran-2-yl]methylsulfonylmethyl-isopropoxy-phosphinic acid;

[(2S,3S,4R,5R)-5-[2-chloro-4-(cyclopentylamino)pyrrolo[2,3-d]pyrimidin-7-yl]-3,4-dihydroxy-tetrahydrofuran-2-yl]methylsulfonylmethyl-(2,2-dimethylpropanoyloxymethoxy)phosphinic acid;

[(2S,3S,4R,5R)-542-chloro-4-(isopropylamino)pyrrolo[2,3-d]pyrimidin-7-yl]-3,4-dihydroxy-tetrahydrofuran-2-yl]methylsulfonylmethylphosphonic acid;

[(2S,3S,4R,5R)-5-(2-chloro-4-pyrrolidin-1-yl-pyrrolo[2,3-d]pyrimidin-7-yl)-3,4-dihydroxy-tetrahydrofuran-2-yl]methylsulfonylmethylphosphonic acid;

[(2S,3S,4R,5R)-5-[2-chloro-4-(3,3-difluoropyrrolidin-1-yl)pyrrolo[2,3-d]pyrimidin-7-yl]-3,4-dihydroxy-tetrahydrofuran-2-yl]methylsulfonylmethylphosphonic acid;

[[(2S,3S,4R,5R)-542-chloro-4-(cyclopentylamino)pyrrolo[2,3-d]pyrimidin-7-yl]-3,4-dihydroxy-tetrahydrofuran-2-yl]methylsulfonylmethyl-(2,2-dimethylpropanoyloxymethoxy)phosphoryl]oxymethyl 2,2-dimethylpropanoate;

[[(2S,3S,4R,5R)-542-chloro-4-(cyclopentylamino)pyrrolo[2,3-d]pyrimidin-7-yl]-3,4-dihydroxy-tetrahydrofuran-2-yl]methylsulfinylmethyl-(2,2-dimethylpropanoyloxymethoxy)phosphoryl]oxymethyl 2,2-dimethylpropanoate;

[(2S,3S,4R,5R)-5-[2-chloro-4-]](1R)-1-(4-fluorophenyl)ethyl]amino]pyrrolo[2,3-d]pyrimidin-7-yl]-3,4-dihydroxy-tetrahydrofuran-2-yl]methylsulfonylmethylphosphonic acid;

[(2S,3S,4R,5R)-5-[2-chloro-4-]](1R)-1-(2-fluorophenyl)ethyl]amino]pyrrolo[2,3-d]pyrimidin-7-yl]-3,4-dihydroxy-tetrahydrofuran-2-yl]methylsulfonylmethylphosphonic acid;

[(2S,3S,4R,5R)-5-]2-chloro-4-]](1R)-1-(p-tolyl)ethyl]amino]pyrrolo[2,3-d]pyrimidin-7-yl]-3,4-dihydroxy-tetrahydrofuran-2-yl]methylsulfonylmethylphosphonic acid;

[(2S,3S,4R,5R)-5-]2-chloro-4-]](1S)-1-(p-tolyl)ethyl]amino]pyrrolo[2,3-d]pyrimidin-7-yl]-3,4-dihydroxy-tetrahydrofuran-2-yl]methylsulfonylmethylphosphonic acid;

[(2S,3S,4R,5R)-5-[2-chloro-4-[(3,3-difluorocyclopentyl)amino]pyrrolo[2,3-d]pyrimidin-7-yl]-3,4-dihydroxy-tetrahydrofuran-2-yl]methylsulfonylmethylphosphonic acid;

[(2S,3S,4R,5R)-5-[2-chloro-4-(cyclobutylamino)pyrrolo[2,3-d]pyrimidin-7-yl]-3,4-dihydroxy-tetrahydrofuran-2-yl]methylsulfonylmethylphosphonic acid;

[(2S,3S,4R,5R)-5-[2-chloro-4-[(3,3-difluorocyclobutyl)amino]pyrrolo[2,3-d]pyrimidin-7-yl]-3,4-dihydroxy-tetrahydrofuran-2-yl]methylsulfonylmethylphosphonic acid;

[(2S,3S,4R,5R)-5-[2-chloro-4-(cyclohexylamino)pyrrolo[2,3-d]pyrimidin-7-yl]-3,4-dihydroxy-tetrahydrofuran-2-yl]methylsulfonylmethylphosphonic acid;

[(2S,3S,4R,5R)-5-[4-(3-azabicyclo[3.1.0]hexan-3-yl)-2-chloro-pyrrolo[2,3-d]pyrimidin-7-yl]-3,4-dihydroxy-tetrahydrofuran-2-yl]methylsulfonylmethylphosphonic acid;

[(2S,3S,4R,5R)-5-[2-chloro-4-(ethylamino)pyrrolo[2,3-d]pyrimidin-7-yl]-3,4-dihydroxy-tetrahydrofuran-2-yl]methylsulfonylmethylphosphonic acid;

[(2S,3S,4R,5R)-542-chloro-4-[isopropyl(methyl)amino]pyrrolo[2,3-d]pyrimidin-7-yl]-3,4-dihydroxy-tetrahydrofuran-2-yl]methylsulfonylmethylphosphonic acid;

[(2S,3S,4R,5R)-5-[2-chloro-4-[[(1R)-1-(2,4-difluorophenyl)ethyl]amino]pyrrolo[2,3-d]pyrimidin-7-yl]-3,4-dihydroxy-tetrahydrofuran-2-yl]methylsulfonylmethylphosphonic acid;

[(2S,3S,4R,5R)-5-[2-chloro-4-[[(1R)-1-(4-chlorophenyl)ethyl]amino]pyrrolo[2,3-d]pyrimidin-7-yl]-3,4-dihydroxy-tetrahydrofuran-2-yl]methylsulfonylmethylphosphonic acid;

[(2S,3S,4R,5R)-5-[2-chloro-4-[[(1R)-1-(3-cyanophenyl)ethyl]amino]pyrrolo[2,3-d]pyrimidin-7-yl]-3,4-dihydroxy-tetrahydrofuran-2-yl]methylsulfonylmethylphosphonic acid;

[(2S,3S,4R,5R)-5-[2-chloro-4-[[(1S)-1-(4-cyanophenyl)ethyl]amino]pyrrolo[2,3-d]pyrimidin-7-yl]-3,4-dihydroxy-tetrahydrofuran-2-yl]methylsulfonylmethylphosphonic acid;

[(2S,3S,4R,5R)-5-[2-chloro-4-[(4,4-difluorocyclohexyl)amino]pyrrolo[2,3-d]pyrimidin-7-yl]-3,4-dihydroxy-tetrahydrofuran-2-yl]methylsulfonylmethylphosphonic acid; and

[(2S,3S,4R,5R)-5-[2-chloro-4-[[(1S)-1-(2,4-difluorophenyl)ethyl]amino]pyrrolo[2,3-d]pyrimidin-7-yl]-3,4-dihydroxy-tetrahydrofuran-2-yl]methylsulfonylmethylphosphonic acid; or a pharmaceutically salt thereof.

25. A pharmaceutical composition comprising the compound or pharmaceutically acceptable salt of claim 1 and a pharmaceutically acceptable carrier or diluent.

\* \* \* \* \*